(12) United States Patent
Madsen et al.

(10) Patent No.: US 9,708,383 B2
(45) Date of Patent: Jul. 18, 2017

(54) DOUBLE-ACYLATED GLP-1 DERIVATIVES

(75) Inventors: Alice Ravn Madsen, Roedovre (DK); Birgit Wieczorek, Koebenhavn N (DK); Jacob Kofoed, Vaerloese (DK); Jesper Lau, Farum (DK); Jane Spetzler, Broenshoej (DK); Janos Tibor Kodra, Koebenhavn Oe (DK); Lars Linderoth, Alleroed (DK); Patrick William Garibay, Holte (DK); Per Sauerberg, Farum (DK); Thomas Kruse, Herlev (DK)

(73) Assignee: Novo Nordisk A/S, Bagsvaerd (DK)

( * ) Notice: Subject to any disclaimer, the term of this patent is extended or adjusted under 35 U.S.C. 154(b) by 831 days.

(21) Appl. No.: 13/882,947

(22) PCT Filed: Nov. 9, 2011

(86) PCT No.: PCT/EP2011/069738
§ 371 (c)(1),
(2), (4) Date: Jul. 16, 2013

(87) PCT Pub. No.: WO2012/062803
PCT Pub. Date: May 18, 2012

(65) Prior Publication Data
US 2013/0288960 A1    Oct. 31, 2013

Related U.S. Application Data

(60) Provisional application No. 61/414,221, filed on Nov. 16, 2010, provisional application No. 61/497,123, filed on Jun. 15, 2011.

(30) Foreign Application Priority Data

Nov. 9, 2010  (EP) ..................... 10190515
Jun. 9, 2011  (EP) ..................... 11169276

(51) Int. Cl.
*A61K 38/00* (2006.01)
*C07K 14/605* (2006.01)
*A61K 47/48* (2006.01)

(52) U.S. Cl.
CPC ...... *C07K 14/605* (2013.01); *A61K 47/48038* (2013.01)

(58) Field of Classification Search
None
See application file for complete search history.

(56) References Cited

U.S. PATENT DOCUMENTS 5,417,662 A * 5/1995 Hjertman ............... A61M 5/46
                                                       604/117

FOREIGN PATENT DOCUMENTS

| WO | 98/08871 | | 3/1998 |
|---|---|---|---|
| WO | 99/43706 | A1 | 9/1999 |
| WO | WO99/43706 | * | 9/1999 |
| WO | 2005/027978 | A2 | 3/2005 |
| WO | 2006/097537 | A2 | 9/2006 |
| WO | 2009/030738 | A1 | 3/2009 |
| WO | 2009/030771 | A1 | 3/2009 |
| WO | 2009/083549 | A1 | 7/2009 |
| WO | WO2009/083549 | * | 7/2009 |
| WO | 2010/029159 | A1 | 3/2010 |
| WO | 2011/080103 | A1 | 7/2011 |

OTHER PUBLICATIONS

Chae, S. et al. "The fatty acid conjugated exendin-4 analogs for type 2 antidiabetic therapeutics" Journal of Controlled Release (2010) vol. 144: 10-16.
Christoph E. Dumelin et al., Angewandte Chemie (International Ed. In English), A Portable Albumin Binder From A DNA-Encoded Chemical Library, 2008, vol. 47, No. 17, pp. 3196-3201.
Lotte B. Knudsen et al., Journal of Medicinal Chemistry, Potent Derivatives of Glucagon-Like Peptide-1 With Pharmacokinetic Properties Suitable For Once Daily Administration, 2000, vol. 43, No. 9, pp. 1664-1669.

* cited by examiner

*Primary Examiner* — Jeanette Lieb
(74) *Attorney, Agent, or Firm* — Richard W. Bork

(57) ABSTRACT

The invention relates to a derivative of a GLP-1 analog, which analog comprises a first K residue at a position corresponding to position 18 of GLP-1(7-37) (SEQ ID NO: 1), a second K residue at another position, and a maximum of twelve amino acid changes as compared to GLP-1(7-37); which derivative comprises two protracting moieties attached to said first and second K residue, respectively, via a linker, wherein the protracting moiety is selected from Chem. 1, Chem. 2, and Chem. 3:

HOOC—(CH$_2$)$_x$—CO—*            Chem. 1:

HOOC—C$_6$H$_4$—O—(CH$_2$)$_y$—CO—*        Chem. 2:

R$^2$—C$_6$H$_4$—(CH$_2$)$_z$—CO—*,          Chem. 3:

in which x is an integer in the range of 6-18, y is an integer in the range of 3-17, z is an integer in the range of 1-5, and R$^2$ is a group having a molar mass not higher than 150 Da; and the linker comprises

*—NH—(CH$_2$)$_2$—(O—(CH$_2$)$_2$)$_k$—O—(CH$_2$)$_n$—CO—*.    Chem. 4:

wherein k is an integer in the range of 1-5, and n is an integer in the range of 1-5; or a pharmaceutically acceptable salt, amide, or ester thereof.
The invention also relates to the pharmaceutical use thereof, for example in the treatment and/or prevention of all forms of diabetes and related diseases, as well as to corresponding novel peptides and side chain intermediates. The derivatives are suitable for oral administration.

16 Claims, No Drawings

SEQUENCE LISTING

```
<160> NUMBER OF SEQ ID NOS: 65

<210> SEQ ID NO 1
<211> LENGTH: 31
<212> TYPE: PRT
<213> ORGANISM: Homo sapiens

<400> SEQUENCE: 1

His Ala Glu Gly Thr Phe Thr Ser Asp Val Ser Ser Tyr Leu Glu Gly
1               5                   10                  15

Gln Ala Ala Lys Glu Phe Ile Ala Trp Leu Val Lys Gly Arg Gly
            20                  25                  30

<210> SEQ ID NO 2
<211> LENGTH: 28
<212> TYPE: PRT
<213> ORGANISM: Artificial Sequence
<220> FEATURE:
<223> OTHER INFORMATION: SYNTHETIC
```

<400> SEQUENCE: 2

His Ala Glu His Thr Gly Thr Ser Asp Val Ser Lys Tyr Leu Glu Glu
1               5                   10                  15

Gln Ala Ala Arg Lys Phe Ile Ala His Leu Val Gly
            20                  25

<210> SEQ ID NO 3
<211> LENGTH: 32
<212> TYPE: PRT
<213> ORGANISM: Artificial Sequence
<220> FEATURE:
<223> OTHER INFORMATION: SYNTHETIC
<220> FEATURE:
<221> NAME/KEY: MISC_FEATURE
<222> LOCATION: (1)..(1)
<223> OTHER INFORMATION: Xaa = His or desamino-histidine
      (imdazopropionyl)
<220> FEATURE:
<221> NAME/KEY: MISC_FEATURE
<222> LOCATION: (2)..(2)
<223> OTHER INFORMATION: Xaa = Aib
<220> FEATURE:
<221> NAME/KEY: MISC_FEATURE
<222> LOCATION: (6)..(6)
<223> OTHER INFORMATION: Xaa = Phe or Leu
<220> FEATURE:
<221> NAME/KEY: MISC_FEATURE
<222> LOCATION: (10)..(10)
<223> OTHER INFORMATION: Xaa = Val
<220> FEATURE:
<221> NAME/KEY: MISC_FEATURE
<222> LOCATION: (13)..(13)
<223> OTHER INFORMATION: Xaa = Tyr
<220> FEATURE:
<221> NAME/KEY: MISC_FEATURE
<222> LOCATION: (14)..(14)
<223> OTHER INFORMATION: Xaa = Leu
<220> FEATURE:
<221> NAME/KEY: MISC_FEATURE
<222> LOCATION: (16)..(16)
<223> OTHER INFORMATION: Xaa = Glu
<220> FEATURE:
<221> NAME/KEY: MISC_FEATURE
<222> LOCATION: (17)..(17)
<223> OTHER INFORMATION: Xaa = Gln, Glu or Arg
<220> FEATURE:
<221> NAME/KEY: MISC_FEATURE
<222> LOCATION: (19)..(19)
<223> OTHER INFORMATION: Xaa = Ala or Val
<220> FEATURE:
<221> NAME/KEY: MISC_FEATURE
<222> LOCATION: (20)..(20)
<223> OTHER INFORMATION: Xaa = Lys
<220> FEATURE:
<221> NAME/KEY: MISC_FEATURE
<222> LOCATION: (21)..(21)
<223> OTHER INFORMATION: Xaa = Glu, His, Leu or Lys
<220> FEATURE:
<221> NAME/KEY: MISC_FEATURE
<222> LOCATION: (24)..(24)
<223> OTHER INFORMATION: Xaa = Ala, Glu or Lys
<220> FEATURE:
<221> NAME/KEY: MISC_FEATURE
<222> LOCATION: (25)..(25)
<223> OTHER INFORMATION: Xaa = Trp, Lys or His
<220> FEATURE:
<221> NAME/KEY: MISC_FEATURE
<222> LOCATION: (27)..(27)
<223> OTHER INFORMATION: Xaa = Val
<220> FEATURE:
<221> NAME/KEY: MISC_FEATURE
<222> LOCATION: (28)..(28)
<223> OTHER INFORMATION: Xaa = Gln
<220> FEATURE:
<221> NAME/KEY: MISC_FEATURE
<222> LOCATION: (29)..(29)

```
<223> OTHER INFORMATION: Xaa = Gly or absent
<220> FEATURE:
<221> NAME/KEY: MISC_FEATURE
<222> LOCATION: (30)..(30)
<223> OTHER INFORMATION: Xaa = Arg or absent
<220> FEATURE:
<221> NAME/KEY: MISC_FEATURE
<222> LOCATION: (31)..(31)
<223> OTHER INFORMATION: Xaa = Gly, Lys or absent
<220> FEATURE:
<221> NAME/KEY: MISC_FEATURE
<222> LOCATION: (32)..(32)
<223> OTHER INFORMATION: Xaa = absent

<400> SEQUENCE: 3

Xaa Xaa Glu Gly Thr Xaa Thr Ser Asp Xaa Ser Lys Xaa Xaa Glu Xaa
1               5                   10                  15

Xaa Ala Xaa Xaa Xaa Phe Ile Xaa Xaa Leu Xaa Xaa Xaa Xaa Xaa Xaa
            20                  25                  30

<210> SEQ ID NO 4
<211> LENGTH: 32
<212> TYPE: PRT
<213> ORGANISM: Artificial Sequence
<220> FEATURE:
<223> OTHER INFORMATION: SYNTHETIC
<220> FEATURE:
<221> NAME/KEY: MISC_FEATURE
<222> LOCATION: (1)..(1)
<223> OTHER INFORMATION: Xaa = His
<220> FEATURE:
<221> NAME/KEY: MISC_FEATURE
<222> LOCATION: (6)..(6)
<223> OTHER INFORMATION: Xaa = Phe
<220> FEATURE:
<221> NAME/KEY: MISC_FEATURE
<222> LOCATION: (10)..(10)
<223> OTHER INFORMATION: Xaa = Val
<220> FEATURE:
<221> NAME/KEY: MISC_FEATURE
<222> LOCATION: (13)..(13)
<223> OTHER INFORMATION: Xaa = Tyr
<220> FEATURE:
<221> NAME/KEY: MISC_FEATURE
<222> LOCATION: (14)..(14)
<223> OTHER INFORMATION: Xaa = Leu
<220> FEATURE:
<221> NAME/KEY: MISC_FEATURE
<222> LOCATION: (16)..(16)
<223> OTHER INFORMATION: Xaa = Glu
<220> FEATURE:
<221> NAME/KEY: MISC_FEATURE
<222> LOCATION: (17)..(17)
<223> OTHER INFORMATION: Xaa = Gln
<220> FEATURE:
<221> NAME/KEY: MISC_FEATURE
<222> LOCATION: (19)..(19)
<223> OTHER INFORMATION: Xaa = Ala
<220> FEATURE:
<221> NAME/KEY: MISC_FEATURE
<222> LOCATION: (20)..(20)
<223> OTHER INFORMATION: Xaa = Lys
<220> FEATURE:
<221> NAME/KEY: MISC_FEATURE
<222> LOCATION: (21)..(21)
<223> OTHER INFORMATION: Xaa = Glu
<220> FEATURE:
<221> NAME/KEY: MISC_FEATURE
<222> LOCATION: (24)..(24)
<223> OTHER INFORMATION: Xaa = Ala
<220> FEATURE:
<221> NAME/KEY: MISC_FEATURE
<222> LOCATION: (25)..(25)
<223> OTHER INFORMATION: Xaa = Trp
<220> FEATURE:
<221> NAME/KEY: MISC_FEATURE
```

```
<222> LOCATION: (27)..(27)
<223> OTHER INFORMATION: Xaa = Val
<220> FEATURE:
<221> NAME/KEY: MISC_FEATURE
<222> LOCATION: (28)..(28)
<223> OTHER INFORMATION: Xaa = Gln
<220> FEATURE:
<221> NAME/KEY: MISC_FEATURE
<222> LOCATION: (29)..(29)
<223> OTHER INFORMATION: Xaa = Gly
<220> FEATURE:
<221> NAME/KEY: MISC_FEATURE
<222> LOCATION: (30)..(30)
<223> OTHER INFORMATION: Xaa = Arg
<220> FEATURE:
<221> NAME/KEY: MISC_FEATURE
<222> LOCATION: (31)..(31)
<223> OTHER INFORMATION: Xaa = Gly
<220> FEATURE:
<221> NAME/KEY: MISC_FEATURE
<222> LOCATION: (32)..(32)
<223> OTHER INFORMATION: Xaa = Absent

<400> SEQUENCE: 4

Xaa Ala Glu Gly Thr Xaa Thr Ser Asp Xaa Ser Ser Xaa Xaa Glu Xaa
 1               5                  10                  15

Xaa Ala Xaa Xaa Xaa Phe Ile Xaa Xaa Leu Xaa Xaa Xaa Xaa Xaa Xaa
            20                  25                  30

<210> SEQ ID NO 5
<211> LENGTH: 32
<212> TYPE: PRT
<213> ORGANISM: Artificial Sequence
<220> FEATURE:
<223> OTHER INFORMATION: SYNTHETIC
<220> FEATURE:
<221> NAME/KEY: MISC_FEATURE
<222> LOCATION: (1)..(1)
<223> OTHER INFORMATION: Xaa = L-histidine, imidazopropionyl,
      alpha-hydroxy-histidine, D-histidine, desamino-histidine,
      2-amino-histidine, beta-hydroxy-histidine, homohistidine,
      Nalpha-acetyl-histidine, Nalpha-formyl-histidine,
      alpha-fluoromethyl-histidine,
<220> FEATURE:
<221> NAME/KEY: MISC_FEATURE
<222> LOCATION: (2)..(2)
<223> OTHER INFORMATION: Xaa = Ala, Gly, Val, Leu, Ile, Thr, Ser, Lys,
      Aib, (1-aminocyclopropyl) carboxylic acid, (1-aminocyclobutyl)
      carboxylic acid, (1-aminocyclopentyl) carboxylic acid,
      (1-aminocyclohexyl) carboxylic acid, (1-aminocycloheptyl)
<220> FEATURE:
<221> NAME/KEY: MISC_FEATURE
<222> LOCATION: (6)..(6)
<223> OTHER INFORMATION: Xaa = Phe or Leu
<220> FEATURE:
<221> NAME/KEY: MISC_FEATURE
<222> LOCATION: (10)..(10)
<223> OTHER INFORMATION: Xaa = Val or Leu
<220> FEATURE:
<221> NAME/KEY: MISC_FEATURE
<222> LOCATION: (13)..(13)
<223> OTHER INFORMATION: Xaa = Tyr or Gln
<220> FEATURE:
<221> NAME/KEY: MISC_FEATURE
<222> LOCATION: (14)..(14)
<223> OTHER INFORMATION: Xaa = Leu or Met
<220> FEATURE:
<221> NAME/KEY: MISC_FEATURE
<222> LOCATION: (16)..(16)
<223> OTHER INFORMATION: Xaa = Gly, Glu, Lys or Aib
<220> FEATURE:
<221> NAME/KEY: MISC_FEATURE
<222> LOCATION: (17)..(17)
<223> OTHER INFORMATION: Xaa = Gln, Glu or Arg
<220> FEATURE:
<221> NAME/KEY: MISC_FEATURE
```

```
<222> LOCATION: (19)..(19)
<223> OTHER INFORMATION: Xaa = Ala or Val
<220> FEATURE:
<221> NAME/KEY: MISC_FEATURE
<222> LOCATION: (20)..(20)
<223> OTHER INFORMATION: Xaa = Val, His, Lys, or Arg
<220> FEATURE:
<221> NAME/KEY: MISC_FEATURE
<222> LOCATION: (21)..(21)
<223> OTHER INFORMATION: Xaa = Glu, His, Leu or Lys
<220> FEATURE:
<221> NAME/KEY: MISC_FEATURE
<222> LOCATION: (24)..(24)
<223> OTHER INFORMATION: Xaa = Ala, Glu, Lys or Arg
<220> FEATURE:
<221> NAME/KEY: MISC_FEATURE
<222> LOCATION: (25)..(25)
<223> OTHER INFORMATION: Xaa = Trp, Lys or His
<220> FEATURE:
<221> NAME/KEY: MISC_FEATURE
<222> LOCATION: (27)..(27)
<223> OTHER INFORMATION: Xaa = Val or Lys
<220> FEATURE:
<221> NAME/KEY: MISC_FEATURE
<222> LOCATION: (28)..(28)
<223> OTHER INFORMATION: Xaa = Lys, Glu, Asn, Gly, Gln, Arg, His or
      absent
<220> FEATURE:
<221> NAME/KEY: MISC_FEATURE
<222> LOCATION: (29)..(29)
<223> OTHER INFORMATION: Xaa = Gly, Aib or absent
<220> FEATURE:
<221> NAME/KEY: MISC_FEATURE
<222> LOCATION: (30)..(30)
<223> OTHER INFORMATION: Xaa = Arg, Gly, Lys or absent
<220> FEATURE:
<221> NAME/KEY: MISC_FEATURE
<222> LOCATION: (31)..(31)
<223> OTHER INFORMATION: Xaa = Gly, Ala, Glu, Pro, Lys, Arg or absent
<220> FEATURE:
<221> NAME/KEY: MISC_FEATURE
<222> LOCATION: (32)..(32)
<223> OTHER INFORMATION: Xaa = Ser, Gly, Ala, Glu, Pro, Lys, Arg, or
      absent

<400> SEQUENCE: 5

Xaa Xaa Glu Gly Thr Xaa Thr Ser Asp Xaa Ser Lys Xaa Xaa Glu Xaa
1               5                   10                  15

Xaa Ala Xaa Xaa Xaa Phe Ile Xaa Xaa Leu Xaa Xaa Xaa Xaa Xaa Xaa
            20                  25                  30

<210> SEQ ID NO 6
<211> LENGTH: 31
<212> TYPE: PRT
<213> ORGANISM: Artificial Sequence
<220> FEATURE:
<223> OTHER INFORMATION: SYNTHETIC
<220> FEATURE:
<221> NAME/KEY: MISC_FEATURE
<222> LOCATION: (2)..(2)
<223> OTHER INFORMATION: Xaa = Aib

<400> SEQUENCE: 6

His Xaa Glu Gly Thr Phe Thr Ser Asp Val Ser Lys Tyr Leu Glu Gly
1               5                   10                  15

Gln Ala Ala Val Lys Phe Ile Ala Trp Leu Val Arg Gly Arg Gly
            20                  25                  30

<210> SEQ ID NO 7
<211> LENGTH: 31
<212> TYPE: PRT
<213> ORGANISM: Artificial Sequence
<220> FEATURE:
```

<223> OTHER INFORMATION: SYNTHETIC
<220> FEATURE:
<221> NAME/KEY: MISC_FEATURE
<222> LOCATION: (2)..(2)
<223> OTHER INFORMATION: Xaa = Aib

<400> SEQUENCE: 7

His Xaa Glu Gly Thr Phe Thr Ser Asp Val Ser Lys Tyr Leu Glu Glu
1               5                   10                  15
Gln Ala Ala Lys Glu Phe Ile Ala Trp Leu Val Gln Gly Arg Gly
            20                  25                  30

<210> SEQ ID NO 8
<211> LENGTH: 31
<212> TYPE: PRT
<213> ORGANISM: Artificial Sequence
<220> FEATURE:
<223> OTHER INFORMATION: SYNTHETIC
<220> FEATURE:
<221> NAME/KEY: MISC_FEATURE
<222> LOCATION: (2)..(2)
<223> OTHER INFORMATION: Xaa = Aib

<400> SEQUENCE: 8

His Xaa Glu Gly Thr Phe Thr Ser Asp Val Ser Lys Tyr Leu Glu Glu
1               5                   10                  15
Gln Ala Ala Arg Glu Phe Ile Ala Lys Leu Val Arg Gly Arg Gly
            20                  25                  30

<210> SEQ ID NO 9
<211> LENGTH: 31
<212> TYPE: PRT
<213> ORGANISM: Artificial Sequence
<220> FEATURE:
<223> OTHER INFORMATION: SYNTHETIC
<220> FEATURE:
<221> NAME/KEY: MISC_FEATURE
<222> LOCATION: (2)..(2)
<223> OTHER INFORMATION: Xaa = Aib

<400> SEQUENCE: 9

His Xaa Glu Gly Thr Phe Thr Ser Asp Val Ser Lys Tyr Leu Glu Glu
1               5                   10                  15
Gln Ala Val Arg Glu Phe Ile Ala Lys Leu Val Gly Gly Arg Gly
            20                  25                  30

<210> SEQ ID NO 10
<211> LENGTH: 31
<212> TYPE: PRT
<213> ORGANISM: Artificial Sequence
<220> FEATURE:
<223> OTHER INFORMATION: SYNTHETIC

<400> SEQUENCE: 10

His Ala Glu Gly Thr Phe Thr Ser Asp Val Ser Lys Tyr Leu Glu Glu
1               5                   10                  15
Gln Ala Val Arg Glu Phe Ile Ala Lys Leu Val Arg Gly Arg Gly
            20                  25                  30

<210> SEQ ID NO 11
<211> LENGTH: 31
<212> TYPE: PRT
<213> ORGANISM: Artificial Sequence
<220> FEATURE:
<223> OTHER INFORMATION: SYNTHETIC

<400> SEQUENCE: 11

```
His Ala Glu Gly Thr Phe Thr Ser Asp Val Ser Lys Tyr Leu Glu Glu
1               5                   10                  15

Gln Ala Val Arg Glu Phe Ile Ala Lys Leu Val Gln Gly Arg Gly
                20                  25                  30
```

<210> SEQ ID NO 12
<211> LENGTH: 31
<212> TYPE: PRT
<213> ORGANISM: Artificial Sequence
<220> FEATURE:
<223> OTHER INFORMATION: SYNTHETIC
<220> FEATURE:
<221> NAME/KEY: MISC_FEATURE
<222> LOCATION: (2)..(2)
<223> OTHER INFORMATION: Xaa = Aib

<400> SEQUENCE: 12

```
His Xaa Glu Gly Thr Phe Thr Ser Asp Val Ser Lys Tyr Leu Glu Glu
1               5                   10                  15

Gln Ala Val Arg Glu Phe Ile Ala Lys Leu Val Arg Gly Arg Gly
                20                  25                  30
```

<210> SEQ ID NO 13
<211> LENGTH: 31
<212> TYPE: PRT
<213> ORGANISM: Artificial Sequence
<220> FEATURE:
<223> OTHER INFORMATION: SYNTHETIC
<220> FEATURE:
<221> NAME/KEY: MISC_FEATURE
<222> LOCATION: (2)..(2)
<223> OTHER INFORMATION: Xaa = Aib

<400> SEQUENCE: 13

```
His Xaa Glu Gly Thr Phe Thr Ser Asp Val Ser Lys Tyr Leu Glu Glu
1               5                   10                  15

Gln Ala Ala Arg Glu Phe Ile Ala Trp Leu Val Arg Gly Arg Lys
                20                  25                  30
```

<210> SEQ ID NO 14
<211> LENGTH: 31
<212> TYPE: PRT
<213> ORGANISM: Artificial Sequence
<220> FEATURE:
<223> OTHER INFORMATION: SYNTHETIC
<220> FEATURE:
<221> NAME/KEY: MISC_FEATURE
<222> LOCATION: (1)..(1)
<223> OTHER INFORMATION: Xaa = Imp

<400> SEQUENCE: 14

```
Xaa Ala Glu Gly Thr Phe Thr Ser Asp Val Ser Lys Tyr Leu Glu Glu
1               5                   10                  15

Gln Ala Ala Arg Glu Phe Ile Ala Trp Leu Val Arg Gly Arg Lys
                20                  25                  30
```

<210> SEQ ID NO 15
<211> LENGTH: 31
<212> TYPE: PRT
<213> ORGANISM: Artificial Sequence
<220> FEATURE:
<223> OTHER INFORMATION: SYNTHETIC
<220> FEATURE:
<221> NAME/KEY: MISC_FEATURE
<222> LOCATION: (2)..(2)
<223> OTHER INFORMATION: Xaa = Aib

```
<400> SEQUENCE: 15

His Xaa Glu Gly Thr Phe Thr Ser Asp Val Ser Lys Tyr Leu Glu Glu
1               5                   10                  15

Gln Ala Val Arg Glu Phe Ile Glu Lys Leu Val Gly Gly Arg Gly
            20                  25                  30

<210> SEQ ID NO 16
<211> LENGTH: 31
<212> TYPE: PRT
<213> ORGANISM: Artificial Sequence
<220> FEATURE:
<223> OTHER INFORMATION: SYNTHETIC
<220> FEATURE:
<221> NAME/KEY: MISC_FEATURE
<222> LOCATION: (2)..(2)
<223> OTHER INFORMATION: Xaa = Aib

<400> SEQUENCE: 16

His Xaa Glu Gly Thr Phe Thr Ser Asp Val Ser Lys Tyr Leu Glu Glu
1               5                   10                  15

Gln Ala Val His Glu Phe Ile Ala Lys Leu Val Gly Gly Arg Gly
            20                  25                  30

<210> SEQ ID NO 17
<211> LENGTH: 31
<212> TYPE: PRT
<213> ORGANISM: Artificial Sequence
<220> FEATURE:
<223> OTHER INFORMATION: SYNTHETIC
<220> FEATURE:
<221> NAME/KEY: MISC_FEATURE
<222> LOCATION: (2)..(2)
<223> OTHER INFORMATION: Xaa = Aib

<400> SEQUENCE: 17

His Xaa Glu Gly Thr Phe Thr Ser Asp Val Ser Lys Tyr Leu Glu Glu
1               5                   10                  15

Gln Ala Ala Arg Lys Phe Ile Ala His Leu Val Arg Gly Arg Gly
            20                  25                  30

<210> SEQ ID NO 18
<211> LENGTH: 31
<212> TYPE: PRT
<213> ORGANISM: Artificial Sequence
<220> FEATURE:
<223> OTHER INFORMATION: SYNTHETIC

<400> SEQUENCE: 18

His Ala Glu Gly Thr Phe Thr Ser Asp Val Ser Lys Tyr Leu Glu Glu
1               5                   10                  15

Gln Ala Val Arg Glu Phe Ile Ala Lys Leu Val Gly Gly Arg Gly
            20                  25                  30

<210> SEQ ID NO 19
<211> LENGTH: 31
<212> TYPE: PRT
<213> ORGANISM: Artificial Sequence
<220> FEATURE:
<223> OTHER INFORMATION: SYNTHETIC
<220> FEATURE:
<221> NAME/KEY: MISC_FEATURE
<222> LOCATION: (1)..(1)
<223> OTHER INFORMATION: Xaa = Imp

<400> SEQUENCE: 19

Xaa Ala Glu Gly Thr Phe Thr Ser Asp Val Ser Lys Tyr Leu Glu Glu
```

-continued

```
                1               5                  10                  15
Gln Ala Val Arg Glu Phe Ile Ala Lys Leu Val Gly Gly Arg Gly
            20                  25                  30

<210> SEQ ID NO 20
<211> LENGTH: 31
<212> TYPE: PRT
<213> ORGANISM: Artificial Sequence
<220> FEATURE:
<223> OTHER INFORMATION: SYNTHETIC

<400> SEQUENCE: 20

His Ser Glu Gly Thr Phe Thr Ser Asp Val Ser Lys Tyr Leu Glu Glu
1               5                  10                  15

Gln Ala Val Arg Glu Phe Ile Ala Lys Leu Val Gly Gly Arg Gly
            20                  25                  30

<210> SEQ ID NO 21
<211> LENGTH: 31
<212> TYPE: PRT
<213> ORGANISM: Artificial Sequence
<220> FEATURE:
<223> OTHER INFORMATION: SYNTHETIC

<400> SEQUENCE: 21

His Ala Glu Gly Thr Phe Thr Ser Asp Val Ser Lys Tyr Leu Glu Glu
1               5                  10                  15

Gln Ala Ala Arg Glu Phe Ile Ala Lys Leu Val Gly Gly Arg Gly
            20                  25                  30

<210> SEQ ID NO 22
<211> LENGTH: 31
<212> TYPE: PRT
<213> ORGANISM: Artificial Sequence
<220> FEATURE:
<223> OTHER INFORMATION: SYNTHETIC
<220> FEATURE:
<221> NAME/KEY: MISC_FEATURE
<222> LOCATION: (2)..(2)
<223> OTHER INFORMATION: Xaa = Aib

<400> SEQUENCE: 22

His Xaa Glu Gly Thr Phe Thr Ser Asp Val Ser Lys Tyr Leu Glu Glu
1               5                  10                  15

Gln Ala Ala Arg Glu Phe Ile Ala Lys Leu Val Gly Gly Arg Gly
            20                  25                  30

<210> SEQ ID NO 23
<211> LENGTH: 31
<212> TYPE: PRT
<213> ORGANISM: Artificial Sequence
<220> FEATURE:
<223> OTHER INFORMATION: SYNTHETIC
<220> FEATURE:
<221> NAME/KEY: MISC_FEATURE
<222> LOCATION: (2)..(2)
<223> OTHER INFORMATION: Xaa = Aib

<400> SEQUENCE: 23

His Xaa Glu Gly Thr Phe Thr Ser Asp Val Ser Lys Tyr Leu Glu Glu
1               5                  10                  15

Arg Ala Val Arg Glu Phe Ile Ala Lys Leu Val Gly Gly Arg Gly
            20                  25                  30

<210> SEQ ID NO 24
```

```
<211> LENGTH: 31
<212> TYPE: PRT
<213> ORGANISM: Artificial Sequence
<220> FEATURE:
<223> OTHER INFORMATION: SYNTHETIC
<220> FEATURE:
<221> NAME/KEY: MISC_FEATURE
<222> LOCATION: (2)..(2)
<223> OTHER INFORMATION: Xaa = Aib

<400> SEQUENCE: 24

His Xaa Glu Gly Thr Phe Thr Ser Asp Val Ser Lys Tyr Leu Glu Glu
1               5                   10                  15

Gln Ala Val Arg His Phe Ile Ala Lys Leu Val Gly Gly Arg Gly
            20                  25                  30

<210> SEQ ID NO 25
<211> LENGTH: 31
<212> TYPE: PRT
<213> ORGANISM: Artificial Sequence
<220> FEATURE:
<223> OTHER INFORMATION: SYNTHETIC
<220> FEATURE:
<221> NAME/KEY: MISC_FEATURE
<222> LOCATION: (1)..(1)
<223> OTHER INFORMATION: Xaa = Imp
<220> FEATURE:
<221> NAME/KEY: MISC_FEATURE
<222> LOCATION: (2)..(2)
<223> OTHER INFORMATION: Xaa = Aib

<400> SEQUENCE: 25

Xaa Xaa Glu Gly Thr Phe Thr Ser Asp Val Ser Lys Tyr Leu Glu Glu
1               5                   10                  15

Gln Ala Val Arg Glu Phe Ile Ala Lys Leu Val Gly Gly Arg Gly
            20                  25                  30

<210> SEQ ID NO 26
<211> LENGTH: 31
<212> TYPE: PRT
<213> ORGANISM: Artificial Sequence
<220> FEATURE:
<223> OTHER INFORMATION: SYNTHETIC
<220> FEATURE:
<221> NAME/KEY: MISC_FEATURE
<222> LOCATION: (2)..(2)
<223> OTHER INFORMATION: Xaa = Aib

<400> SEQUENCE: 26

His Xaa Glu Gly Thr Phe Thr Ser Asp Val Ser Lys Tyr Leu Glu Glu
1               5                   10                  15

Gln Ala Val Arg Lys Phe Ile Ala His Leu Val Gly Gly Arg Gly
            20                  25                  30

<210> SEQ ID NO 27
<211> LENGTH: 31
<212> TYPE: PRT
<213> ORGANISM: Artificial Sequence
<220> FEATURE:
<223> OTHER INFORMATION: SYNTHETIC

<400> SEQUENCE: 27

His Ala Glu Gly Thr Phe Thr Ser Asp Val Ser Lys Tyr Leu Glu Glu
1               5                   10                  15

Gln Ala Ala Arg Lys Phe Ile Ala His Leu Val Gly Gly Arg Gly
            20                  25                  30
```

<210> SEQ ID NO 28
<211> LENGTH: 31
<212> TYPE: PRT
<213> ORGANISM: Artificial Sequence
<220> FEATURE:
<223> OTHER INFORMATION: SYNTHETIC
<220> FEATURE:
<221> NAME/KEY: MISC_FEATURE
<222> LOCATION: (1)..(1)
<223> OTHER INFORMATION: Xaa = Imp

<400> SEQUENCE: 28

Xaa Ala Glu Gly Thr Phe Thr Ser Asp Val Ser Lys Tyr Leu Glu Glu
1               5                   10                  15
Gln Ala Ala Arg Lys Phe Ile Ala His Leu Val Gly Gly Arg Gly
            20                  25                  30

<210> SEQ ID NO 29
<211> LENGTH: 31
<212> TYPE: PRT
<213> ORGANISM: Artificial Sequence
<220> FEATURE:
<223> OTHER INFORMATION: SYNTHETIC

<400> SEQUENCE: 29

His Ala Glu Gly Thr Phe Thr Ser Asp Val Ser Lys Tyr Leu Glu Gly
1               5                   10                  15
Gln Ala Ala Lys Glu Phe Ile Ala Trp Leu Val Gln Gly Arg Gly
            20                  25                  30

<210> SEQ ID NO 30
<211> LENGTH: 31
<212> TYPE: PRT
<213> ORGANISM: Artificial Sequence
<220> FEATURE:
<223> OTHER INFORMATION: SYNTHETIC

<400> SEQUENCE: 30

His Ala Glu Gly Thr Phe Thr Ser Asp Val Ser Lys Tyr Leu Glu Glu
1               5                   10                  15
Gln Ala Ala His Lys Phe Ile Ala Trp Leu Val Gln Gly Arg Gly
            20                  25                  30

<210> SEQ ID NO 31
<211> LENGTH: 31
<212> TYPE: PRT
<213> ORGANISM: Artificial Sequence
<220> FEATURE:
<223> OTHER INFORMATION: SYNTHETIC
<220> FEATURE:
<221> NAME/KEY: MISC_FEATURE
<222> LOCATION: (2)..(2)
<223> OTHER INFORMATION: Xaa = Aib

<400> SEQUENCE: 31

His Xaa Glu Gly Thr Phe Thr Ser Asp Val Ser Lys Tyr Leu Glu Glu
1               5                   10                  15
Gln Ala Val Arg Glu Phe Ile Ala Lys Leu Val Lys Gly Arg Gly
            20                  25                  30

<210> SEQ ID NO 32
<211> LENGTH: 31
<212> TYPE: PRT
<213> ORGANISM: Artificial Sequence
<220> FEATURE:
<223> OTHER INFORMATION: SYNTHETIC

```
<400> SEQUENCE: 32

His Ala Glu Gly Thr Phe Thr Ser Asp Val Ser Lys Tyr Leu Glu Glu
1               5                   10                  15

Gln Ala Ala Lys Glu Phe Ile Ala Trp Leu Val Gln Gly Arg Gly
            20                  25                  30

<210> SEQ ID NO 33
<211> LENGTH: 31
<212> TYPE: PRT
<213> ORGANISM: Artificial Sequence
<220> FEATURE:
<223> OTHER INFORMATION: SYNTHETIC
<220> FEATURE:
<221> NAME/KEY: MISC_FEATURE
<222> LOCATION: (2)..(2)
<223> OTHER INFORMATION: Xaa = Aib

<400> SEQUENCE: 33

His Xaa Glu Gly Thr Phe Thr Ser Asp Val Ser Lys Tyr Leu Glu Glu
1               5                   10                  15

Gln Ala Val Arg Lys Phe Ile Ala Trp Leu Val Gln Gly Arg Gly
            20                  25                  30

<210> SEQ ID NO 34
<211> LENGTH: 31
<212> TYPE: PRT
<213> ORGANISM: Artificial Sequence
<220> FEATURE:
<223> OTHER INFORMATION: SYNTHETIC

<400> SEQUENCE: 34

His Ala Glu Gly Thr Phe Thr Ser Asp Val Ser Lys Tyr Leu Glu Glu
1               5                   10                  15

Gln Ala Val Arg Lys Phe Ile Ala Trp Leu Val Gln Gly Arg Gly
            20                  25                  30

<210> SEQ ID NO 35
<211> LENGTH: 31
<212> TYPE: PRT
<213> ORGANISM: Artificial Sequence
<220> FEATURE:
<223> OTHER INFORMATION: SYNTHETIC

<400> SEQUENCE: 35

His Ala Glu Gly Thr Phe Thr Ser Asp Val Ser Lys Tyr Leu Glu Glu
1               5                   10                  15

Gln Ala Val Arg Lys Phe Ile Ala Trp Leu Val Arg Gly Arg Gly
            20                  25                  30

<210> SEQ ID NO 36
<211> LENGTH: 31
<212> TYPE: PRT
<213> ORGANISM: Artificial Sequence
<220> FEATURE:
<223> OTHER INFORMATION: SYNTHETIC

<400> SEQUENCE: 36

His Ala Glu Gly Thr Phe Thr Ser Asp Val Ser Lys Tyr Leu Glu Glu
1               5                   10                  15

Gln Ala Val Arg Lys Phe Ile Ala His Leu Val Arg Gly Arg Gly
            20                  25                  30

<210> SEQ ID NO 37
<211> LENGTH: 31
```

```
<212> TYPE: PRT
<213> ORGANISM: Artificial Sequence
<220> FEATURE:
<223> OTHER INFORMATION: SYNTHETIC

<400> SEQUENCE: 37

His Ala Glu Gly Thr Phe Thr Ser Asp Val Ser Lys Tyr Leu Glu Glu
1               5                   10                  15

Gln Ala Val Arg Glu Phe Ile Lys Trp Leu Val Gly Gly Arg Gly
            20                  25                  30

<210> SEQ ID NO 38
<211> LENGTH: 31
<212> TYPE: PRT
<213> ORGANISM: Artificial Sequence
<220> FEATURE:
<223> OTHER INFORMATION: SYNTHETIC
<220> FEATURE:
<221> NAME/KEY: MISC_FEATURE
<222> LOCATION: (2)..(2)
<223> OTHER INFORMATION: Xaa = Aib

<400> SEQUENCE: 38

His Xaa Glu Gly Thr Phe Thr Ser Asp Val Ser Lys Tyr Leu Glu Glu
1               5                   10                  15

Gln Ala Ala Arg Glu Phe Ile Lys Trp Leu Val Arg Gly Arg Gly
            20                  25                  30

<210> SEQ ID NO 39
<211> LENGTH: 31
<212> TYPE: PRT
<213> ORGANISM: Artificial Sequence
<220> FEATURE:
<223> OTHER INFORMATION: SYNTHETIC

<400> SEQUENCE: 39

His Ala Glu Gly Thr Phe Thr Ser Asp Val Ser Lys Tyr Leu Glu Glu
1               5                   10                  15

Gln Ala Val Arg Glu Phe Ile Lys His Leu Val Gly Gly Arg Gly
            20                  25                  30

<210> SEQ ID NO 40
<211> LENGTH: 31
<212> TYPE: PRT
<213> ORGANISM: Artificial Sequence
<220> FEATURE:
<223> OTHER INFORMATION: SYNTHETIC

<400> SEQUENCE: 40

His Ala Glu Gly Thr Phe Thr Ser Asp Val Ser Lys Tyr Leu Glu Glu
1               5                   10                  15

Gln Ala Val Arg Leu Phe Ile Lys Trp Leu Val Gly Gly Arg Gly
            20                  25                  30

<210> SEQ ID NO 41
<211> LENGTH: 31
<212> TYPE: PRT
<213> ORGANISM: Artificial Sequence
<220> FEATURE:
<223> OTHER INFORMATION: SYNTHETIC

<400> SEQUENCE: 41

His Ala Glu Gly Thr Phe Thr Ser Asp Val Ser Lys Tyr Leu Glu Glu
1               5                   10                  15

Glu Ala Val Arg Lys Phe Ile Ala Trp Leu Val Arg Gly Arg Gly
```

<210> SEQ ID NO 42
<211> LENGTH: 31
<212> TYPE: PRT
<213> ORGANISM: Artificial Sequence
<220> FEATURE:
<223> OTHER INFORMATION: SYNTHETIC

<400> SEQUENCE: 42

His Ala Glu Gly Thr Phe Thr Ser Asp Val Ser Lys Tyr Leu Glu Glu
1               5                   10                  15

Glu Ala Val Arg Lys Phe Ile Ala Trp Leu Val Gln Gly Arg Gly
            20                  25                  30

<210> SEQ ID NO 43
<211> LENGTH: 31
<212> TYPE: PRT
<213> ORGANISM: Artificial Sequence
<220> FEATURE:
<223> OTHER INFORMATION: SYNTHETIC

<400> SEQUENCE: 43

His Ala Glu Gly Thr Phe Thr Ser Asp Val Ser Lys Tyr Leu Glu Glu
1               5                   10                  15

Gln Ala Ala His Lys Phe Ile Ala Trp Leu Val Arg Gly Arg Gly
            20                  25                  30

<210> SEQ ID NO 44
<211> LENGTH: 31
<212> TYPE: PRT
<213> ORGANISM: Artificial Sequence
<220> FEATURE:
<223> OTHER INFORMATION: SYNTHETIC

<400> SEQUENCE: 44

His Ala Glu Gly Thr Phe Thr Ser Asp Val Ser Lys Tyr Leu Glu Glu
1               5                   10                  15

Gln Ala Ala His Lys Phe Ile Ala His Leu Val Arg Gly Arg Gly
            20                  25                  30

<210> SEQ ID NO 45
<211> LENGTH: 31
<212> TYPE: PRT
<213> ORGANISM: Artificial Sequence
<220> FEATURE:
<223> OTHER INFORMATION: SYNTHETIC
<220> FEATURE:
<221> NAME/KEY: MISC_FEATURE
<222> LOCATION: (2)..(2)
<223> OTHER INFORMATION: Xaa = Aib

<400> SEQUENCE: 45

His Xaa Glu Gly Thr Phe Thr Ser Asp Val Ser Lys Tyr Leu Glu Glu
1               5                   10                  15

Gln Ala Val Arg Leu Phe Ile Ala Trp Leu Val Lys Gly Arg Gly
            20                  25                  30

<210> SEQ ID NO 46
<211> LENGTH: 31
<212> TYPE: PRT
<213> ORGANISM: Artificial Sequence
<220> FEATURE:
<223> OTHER INFORMATION: SYNTHETIC

<400> SEQUENCE: 46

His Ala Glu Gly Thr Phe Thr Ser Asp Val Ser Lys Tyr Leu Glu Glu
1               5                   10                  15

Gln Ala Val Arg Glu Phe Ile Ala His Leu Val Lys Gly Arg Gly
            20                  25                  30

<210> SEQ ID NO 47
<211> LENGTH: 31
<212> TYPE: PRT
<213> ORGANISM: Artificial Sequence
<220> FEATURE:
<223> OTHER INFORMATION: SYNTHETIC

<400> SEQUENCE: 47

His Ala Glu Gly Thr Phe Thr Ser Asp Val Ser Lys Tyr Leu Glu Gly
1               5                   10                  15

Gln Ala Ala His Lys Phe Ile Ala Trp Leu Val Gln Gly Arg Gly
            20                  25                  30

<210> SEQ ID NO 48
<211> LENGTH: 31
<212> TYPE: PRT
<213> ORGANISM: Artificial Sequence
<220> FEATURE:
<223> OTHER INFORMATION: SYNTHETIC

<400> SEQUENCE: 48

His Ala Glu Gly Thr Phe Thr Ser Asp Val Ser Lys Tyr Leu Glu Gly
1               5                   10                  15

Gln Ala Ala Arg Glu Phe Ile Ala Lys Leu Val Arg Gly Arg Gly
            20                  25                  30

<210> SEQ ID NO 49
<211> LENGTH: 31
<212> TYPE: PRT
<213> ORGANISM: Artificial Sequence
<220> FEATURE:
<223> OTHER INFORMATION: SYNTHETIC

<400> SEQUENCE: 49

His Ala Glu Gly Thr Phe Thr Ser Asp Val Ser Lys Tyr Leu Glu Gly
1               5                   10                  15

Gln Ala Val Arg Glu Phe Ile Ala Lys Leu Val Arg Gly Arg Gly
            20                  25                  30

<210> SEQ ID NO 50
<211> LENGTH: 31
<212> TYPE: PRT
<213> ORGANISM: Artificial Sequence
<220> FEATURE:
<223> OTHER INFORMATION: SYNTHETIC

<400> SEQUENCE: 50

His Ala Glu Gly Thr Phe Thr Ser Asp Val Ser Lys Tyr Leu Glu Glu
1               5                   10                  15

Gln Ala Ala Arg Glu Phe Ile Ala Lys Leu Val Arg Gly Arg Gly
            20                  25                  30

<210> SEQ ID NO 51
<211> LENGTH: 31
<212> TYPE: PRT
<213> ORGANISM: Artificial Sequence
<220> FEATURE:
<223> OTHER INFORMATION: SYNTHETIC
<220> FEATURE:

<221> NAME/KEY: MISC_FEATURE
<222> LOCATION: (2)..(2)
<223> OTHER INFORMATION: Xaa = Aib

<400> SEQUENCE: 51

His Xaa Glu Gly Thr Phe Thr Ser Asp Val Ser Lys Tyr Leu Glu Gly
1               5                   10                  15

Gln Ala Ala His Glu Phe Ile Lys Trp Leu Val Arg Gly Arg Gly
            20                  25                  30

<210> SEQ ID NO 52
<211> LENGTH: 31
<212> TYPE: PRT
<213> ORGANISM: Artificial Sequence
<220> FEATURE:
<223> OTHER INFORMATION: SYNTHETIC
<220> FEATURE:
<221> NAME/KEY: MISC_FEATURE
<222> LOCATION: (2)..(2)
<223> OTHER INFORMATION: Xaa = Aib

<400> SEQUENCE: 52

His Xaa Glu Gly Thr Phe Thr Ser Asp Val Ser Lys Tyr Leu Glu Glu
1               5                   10                  15

Gln Ala Ala Lys Glu Phe Ile Ala Trp Leu Val Gln Gly Arg Gly
            20                  25                  30

<210> SEQ ID NO 53
<211> LENGTH: 31
<212> TYPE: PRT
<213> ORGANISM: Artificial Sequence
<220> FEATURE:
<223> OTHER INFORMATION: SYNTHETIC
<220> FEATURE:
<221> NAME/KEY: MISC_FEATURE
<222> LOCATION: (2)..(2)
<223> OTHER INFORMATION: Xaa = Aib

<400> SEQUENCE: 53

His Xaa Glu Gly Thr Phe Thr Ser Asp Val Ser Lys Tyr Leu Glu Glu
1               5                   10                  15

Gln Ala Ala Lys Glu Phe Ile Ala Trp Leu Val Arg Gly Arg Gly
            20                  25                  30

<210> SEQ ID NO 54
<211> LENGTH: 31
<212> TYPE: PRT
<213> ORGANISM: Artificial Sequence
<220> FEATURE:
<223> OTHER INFORMATION: SYNTHETIC
<220> FEATURE:
<221> NAME/KEY: MISC_FEATURE
<222> LOCATION: (2)..(2)
<223> OTHER INFORMATION: Xaa = Aib

<400> SEQUENCE: 54

His Xaa Glu Gly Thr Phe Thr Ser Asp Val Ser Lys Tyr Leu Glu Gly
1               5                   10                  15

Gln Ala Ala Lys Glu Phe Ile Ala Trp Leu Val Gln Gly Arg Gly
            20                  25                  30

<210> SEQ ID NO 55
<211> LENGTH: 31
<212> TYPE: PRT
<213> ORGANISM: Artificial Sequence
<220> FEATURE:
<223> OTHER INFORMATION: SYNTHETIC

```
<220> FEATURE:
<221> NAME/KEY: MISC_FEATURE
<222> LOCATION: (2)..(2)
<223> OTHER INFORMATION: Xaa = Aib

<400> SEQUENCE: 55

His Xaa Glu Gly Thr Phe Thr Ser Asp Val Ser Lys Tyr Leu Glu Gly
1               5                   10                  15

Gln Ala Ala Lys Glu Phe Ile Ala Trp Leu Val Arg Gly Arg Gly
            20                  25                  30

<210> SEQ ID NO 56
<211> LENGTH: 31
<212> TYPE: PRT
<213> ORGANISM: Artificial Sequence
<220> FEATURE:
<223> OTHER INFORMATION: SYNTHETIC

<400> SEQUENCE: 56

His Ala Glu Gly Thr Phe Thr Ser Asp Val Ser Lys Tyr Leu Glu Glu
1               5                   10                  15

Gln Ala Ala Lys Glu Phe Ile Ala Trp Leu Val Arg Gly Arg Gly
            20                  25                  30

<210> SEQ ID NO 57
<211> LENGTH: 31
<212> TYPE: PRT
<213> ORGANISM: Artificial Sequence
<220> FEATURE:
<223> OTHER INFORMATION: SYNTHETIC

<400> SEQUENCE: 57

His Ala Glu Gly Thr Phe Thr Ser Asp Val Ser Lys Tyr Leu Glu Gly
1               5                   10                  15

Gln Ala Ala Lys Glu Phe Ile Ala Trp Leu Val Arg Gly Arg Gly
            20                  25                  30

<210> SEQ ID NO 58
<211> LENGTH: 31
<212> TYPE: PRT
<213> ORGANISM: Artificial Sequence
<220> FEATURE:
<223> OTHER INFORMATION: SYNTHETIC
<220> FEATURE:
<221> NAME/KEY: MISC_FEATURE
<222> LOCATION: (2)..(2)
<223> OTHER INFORMATION: Xaa = Aib

<400> SEQUENCE: 58

His Xaa Glu Gly Thr Phe Thr Ser Asp Val Ser Lys Tyr Leu Glu Gly
1               5                   10                  15

Gln Ala Val Arg Glu Phe Ile Ala Lys Leu Val Arg Gly Arg Gly
            20                  25                  30

<210> SEQ ID NO 59
<211> LENGTH: 31
<212> TYPE: PRT
<213> ORGANISM: Artificial Sequence
<220> FEATURE:
<223> OTHER INFORMATION: SYNTHETIC

<400> SEQUENCE: 59

His Ala Glu Gly Thr Phe Thr Ser Asp Val Ser Lys Tyr Leu Glu Glu
1               5                   10                  15

Gln Ala Val Arg Lys Phe Ile Ala His Leu Val Gln Gly Arg Gly
```

20                  25                  30

<210> SEQ ID NO 60
<211> LENGTH: 31
<212> TYPE: PRT
<213> ORGANISM: Artificial Sequence
<220> FEATURE:
<223> OTHER INFORMATION: SYNTHETIC

<400> SEQUENCE: 60

His Ala Glu Gly Thr Phe Thr Ser Asp Val Ser Lys Tyr Leu Glu Glu
1               5                   10                  15

Gln Ala Ala His Lys Phe Ile Ala His Leu Val Gln Gly Arg Gly
            20                  25                  30

<210> SEQ ID NO 61
<211> LENGTH: 31
<212> TYPE: PRT
<213> ORGANISM: Artificial Sequence
<220> FEATURE:
<223> OTHER INFORMATION: SYNTHETIC

<400> SEQUENCE: 61

His Ala Glu Gly Thr Phe Thr Ser Asp Val Ser Lys Tyr Leu Glu Lys
1               5                   10                  15

Gln Ala Ala Arg Glu Phe Ile Ala Trp Leu Val Gln Gly Arg Gly
            20                  25                  30

<210> SEQ ID NO 62
<211> LENGTH: 31
<212> TYPE: PRT
<213> ORGANISM: Artificial Sequence
<220> FEATURE:
<223> OTHER INFORMATION: SYNTHETIC
<220> FEATURE:
<221> NAME/KEY: MISC_FEATURE
<222> LOCATION: (1)..(1)
<223> OTHER INFORMATION: Xaa = Imp

<400> SEQUENCE: 62

Xaa Ala Glu Gly Thr Phe Thr Ser Asp Val Ser Lys Tyr Leu Glu Glu
1               5                   10                  15

Gln Ala Ala Lys Glu Phe Ile Ala Trp Leu Val Gln Gly Arg Gly
            20                  25                  30

<210> SEQ ID NO 63
<211> LENGTH: 31
<212> TYPE: PRT
<213> ORGANISM: Artificial Sequence
<220> FEATURE:
<223> OTHER INFORMATION: SYNTHETIC
<220> FEATURE:
<221> NAME/KEY: MISC_FEATURE
<222> LOCATION: (2)..(2)
<223> OTHER INFORMATION: Xaa = Aib

<400> SEQUENCE: 63

His Xaa Glu Gly Thr Leu Thr Ser Asp Val Ser Lys Tyr Leu Glu Gly
1               5                   10                  15

Gln Ala Ala Lys Glu Phe Ile Ala Trp Leu Val Gln Gly Arg Gly
            20                  25                  30

<210> SEQ ID NO 64
<211> LENGTH: 31
<212> TYPE: PRT
<213> ORGANISM: Artificial Sequence

```
<220> FEATURE:
<223> OTHER INFORMATION: SYNTHETIC
<220> FEATURE:
<221> NAME/KEY: MISC_FEATURE
<222> LOCATION: (2)..(2)
<223> OTHER INFORMATION: Xaa = Aib

<400> SEQUENCE: 64

His Xaa Glu Gly Thr Phe Thr Ser Asp Val Ser Lys Tyr Leu Glu Gly
1               5                   10                  15

Gln Ala Ala Lys Glu Phe Ile Ala Trp Leu Val His Gly Arg Gly
            20                  25                  30

<210> SEQ ID NO 65
<211> LENGTH: 31
<212> TYPE: PRT
<213> ORGANISM: Artificial Sequence
<220> FEATURE:
<223> OTHER INFORMATION: SYNTHETIC
<220> FEATURE:
<221> NAME/KEY: MISC_FEATURE
<222> LOCATION: (1)..(1)
<223> OTHER INFORMATION: Xaa = Imp

<400> SEQUENCE: 65

Xaa Ala Glu Gly Thr Phe Thr Ser Asp Val Ser Lys Tyr Leu Glu Glu
1               5                   10                  15

Gln Ala Ala Arg Lys Phe Ile Ala Trp Leu Val Gln Gly Arg Gly
            20                  25                  30
```

DOUBLE-ACYLATED GLP-1 DERIVATIVES

CROSS-REFERENCE TO RELATED APPLICATIONS

This application is a 35 U.S.C. §371 National Stage application of International Application PCT/EP2011/069738 (WO 2012/062803 A1), filed Nov. 9, 2011, which claimed priority of European Patent Application 10190515.6, filed Nov. 9, 2010 and European Patent Application 11169276.0, filed Jun. 9, 2011; this application claims priority under 35 U.S.C. §119 of U.S. Provisional Application 61/414,221, filed Nov. 16, 2010 and U.S. Provisional Application 61/497,123, filed Jun. 15, 2011; all hereby incorporated by reference.

TECHNICAL FIELD

The present invention relates to derivatives of analogues of Glucagon-Like Peptide 1 (GLP-1), more in particular to double-acylated GLP-1 derivatives acylated at $K^{18}$ and at another K residue of the peptide, and their pharmaceutical use.

INCORPORATION-BY-REFERENCE OF THE SEQUENCE LISTING

The Sequence Listing, entitled "SEQUENCE LISTING", is 30,882 bytes, was created on 9 Jun. 2011, and is incorporated herein by reference.

In accordance with 37 C.F.R. §1.52(e)(5), Applicants enclose herewith the Sequence Listing for the above-captioned application entitled "SEQUENCE LISTING", created on Mar. 20, 2013. The Sequence Listing is made up of 627 bytes, and the information contained in the attached "SEQUENCE LISTING" is identical to the information in the specification as originally filed. No new matter is added.

BACKGROUND

WO 99/43706 discloses a number of mono- and double-acylated GLP-1 derivatives including some $K^{18,26}$ and $K^{18,34}$ derivatives.

WO 2011/080103 which published after the priority dates of the present application discloses a number of GLP-1 derivatives that are double-acylated at $K^{26,37}$. WO 06/097537 discloses a number of GLP-1 derivatives including semaglutide (Example 4), a mono-acylated GLP-1 derivative for once weekly administration which is under development by Novo Nordisk A/S.

Angewandte Chemie International Edition 2008, vol. 47, p. 3196-3201 reports the discovery and characterisation of a class of 4-(p-iodophenyl)butyric acid derivatives which purportedly display a stable noncovalent binding interaction with both mouse serum albumin (MSA) and human serum albumin (HSA).

SUMMARY

The invention relates to derivatives of GLP-1 peptides.

The derivatives are acylated at a lysine substituted for the native serine at position 18, as well as at another lysine residue. The other lysine residue may be a native lysine, or a lysine substituted for another amino acid residue. The side chains are albumin binding moieties. They comprise a protracting moiety, preferably selected from fatty diacids, and fatty acids with a terminal, or distal, phenyl or phenoxy group, both optionally substituted. A carboxy group of the fatty acid or fatty diacid is acylated, optionally via a linker, to a lysine residue of the GLP-1 peptide, preferably at the epsilon-amino group thereof. The GLP-1 peptide may be an analogue of GLP-1 (7-37) (SEQ ID NO: 1) having a total of up to twelve amino acid differences as compared to GLP-1 (7-37), for example one or more additions, one or more deletions, and/or one or more substitutions. The protracting moiety is attached to the peptide via a linker. The linker may comprise one or more ethylene glycol units that may be sequentially linked together as mono or oligo ethylene glycol units.

More in particular, the invention relates to a derivative of a GLP-1 analogue, which analogue comprises a first K residue at a position corresponding to position 18 of GLP-1(7-37) (SEQ ID NO: 1), a second K residue at another position, and a maximum of twelve amino acid changes as compared to GLP-1 (7-37); which derivative comprises two protracting moieties attached to said first and second K residue, respectively, each via a linker, wherein each protracting moiety is selected from Chem. 1, Chem. 2, and Chem. 3:

Chem. 1:

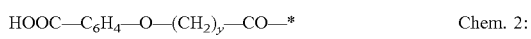

Chem. 2:

Chem. 3:

in which x is an integer in the range of 6-18, y is an integer in the range of 3-17, z is an integer in the range of 1-5, and $R^2$ is a group having a molar mass not higher than 150 Da; and the linker comprises

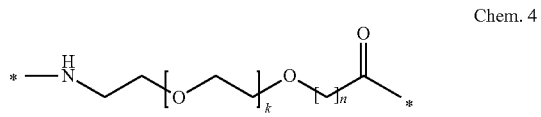

Chem. 4 wherein k is an integer in the range of 1-5, and n is an integer in the range of 1-5; or a pharmaceutically acceptable salt, amide, or ester thereof.

The invention also relates to such derivative for use as a medicament, in particular for use in the treatment and/or prevention of all forms of diabetes and related diseases, such as eating disorders, cardiovascular diseases, gastrointestinal diseases, diabetic complications, critical illness, and/or polycystic ovary syndrome; and/or for improving lipid parameters, improving β-cell function, and/or for delaying or preventing diabetic disease progression.

The invention furthermore relates to intermediate products in the form of corresponding GLP-1 peptides and side chains.

The derivatives of the invention are biologically active. Also, or alternatively, they have a protracted pharmacokinetic profile. Also, or alternatively, they have a high oral bioavailability. Also, or alternatively, they have good biophysical properties. These properties are of importance in the development of next generation GLP-1 compounds for subcutaneous, intravenous, and/or in particular oral administration.

DESCRIPTION

In what follows, Greek letters may be represented by their symbol or the corresponding written name, for example:

α=alpha; β=beta; ε=epsilon; γ=gamma; ω=omega; etc. Also, the greek letter of μ may be represented by "u", e.g. in μl=ul, or in μM=uM.

An asterisk (*) in a chemical formula designates i) a point of attachment, ii) a radical, and/or iii) an unshared electron.

The invention relates to a derivative of a GLP-1 analogue, which analogue comprises a first K residue at a position corresponding to position 18 of GLP-1(7-37) (SEQ ID NO: 1), a second K residue at another position, and a maximum of twelve amino acid changes as compared to GLP-1(7-37); which derivative comprises two protracting moieties attached to said first and second K residue, respectively, via a linker, wherein the protracting moiety is selected from Chem. 1, Chem. 2, and Chem. 3:

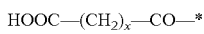  Chem. 1:

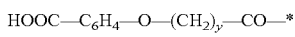  Chem. 2:

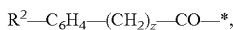  Chem. 3:

in which x is an integer in the range of 6-18, y is an integer in the range of 3-17, z is an integer in the range of 1-5, and $R^2$ is a group having a molar mass not higher than 150 Da; and the linker comprises Chem. 4

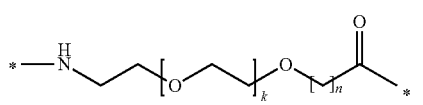

wherein k is an integer in the range of 1-5, and n is an integer in the range of 1-5; or a pharmaceutically acceptable salt, amide, or ester thereof.

GLP-1 Analogues

The term "GLP-1 analogue" or "analogue of GLP-1" as used herein refers to a peptide, or a compound, which is a variant of the human Glucagon-Like Peptide-1 (GLP-1(7-37)), the sequence of which is included in the sequence listing as SEQ ID NO: 1. The peptide having the sequence of SEQ ID NO: 1 may also be designated native GLP-1.

In the sequence listing, the first amino acid residue of SEQ ID NO: 1 (histidine) is assigned no. 1. However, in what follows—according to established practice in the art—this histidine residue is referred to as no. 7, and subsequent amino acid residues are numbered accordingly, ending with glycine no. 37. Therefore, generally, any reference herein to an amino acid residue number or a position number of the GLP-1 (7-37) sequence is to the sequence starting with His at position 7 and ending with Gly at position 37.

GLP-1 analogues of the derivatives of the invention may be described by reference to i) the number of the amino acid residue in native GLP-1(7-37) which corresponds to the amino acid residue which is changed (i.e., the corresponding position in native GLP-1), and to ii) the actual change.

The GLP-1 analogue of the derivative of the invention comprises a first lysine residue at a position corresponding to position 18 of GLP-1(7-37). If the amino acid sequence of this analogue is otherwise identical to that of native GLP-1, such analogue may be designated $K^{18}$-GLP-1(7-37). This designation accordingly represents the amino acid sequence of native GLP-1 where serine at position 18 has been substituted with lysine. As an added remark, this analogue comprises a second Lys residue at position 26, and a third Lys residue at position 34 (viz. the native lysines of GLP-1(7-37)).

The GLP-1 analogue of the derivative of the invention furthermore comprises a second lysine residue at another position, which position may be designated "T". T accordingly represents any other position than position 18.

For example, T may represent 26, in which case the analogue, in addition to the lysine at position 18, comprises a lysine at a position corresponding to position 26 in native GLP-1. Such analogue would still be designated $K^{18}$-GLP-1(7-37), provided that, except for the $K^{18}$-substitution, its amino acid sequence would be identical to that of native GLP-1.

As another example, T may represent 34, in which case the analogue, in addition to the lysine at position 18, comprises a lysine at a position corresponding to position 34 in native GLP-1. Such analogue would also still be designated $K^{18}$-GLP-1(7-37), provided that, except for the $K^{18}$-substitution, its amino acid sequence would be identical to that of native GLP-1.

But T may also represent a number in the range of 7-37 other than 18, 26, or 34. Such analogue would be designated $K^{18},K^T$-GLP-1(7-37), provided that, except for the $K^{18}$- and the $K^T$-substitutions, its amino acid sequence is identical to that of native GLP-1.

The GLP-1 analogue forming part of the derivative of the invention comprises, preferably has, a maximum of twelve amino acid changes when compared with native GLP-1 (SEQ ID NO: 1)—in other words, it is a GLP-1 peptide in which a number of amino acid residues have been changed when compared to native GLP-1(7-37) (SEQ ID NO: 1). These changes may represent, independently, one or more amino acid substitutions, additions, and/or deletions.

The following are non-limiting examples of appropriate analogue nomenclature.

For example, the analogue [Aib8,Lys18,Glu22,Arg26, Arg34,Lys37]-GLP-1-(7-37) designates a GLP-1(7-37) peptide which, when compared to native GLP-1, is changed by the following substitutions: Substitution of alanine at position 8 with Aib (α-aminoisobutyric acid), of serine at position 18 with lysine, of glycine at position 22 with glutamic acid, of lysine at position 26 with arginine, of lysine at position 34 with arginine, and of glycine at position 37 with lysine. This analogue may also be briefly designated (8Aib, 18K, 22E, 26R, 34R, 37K).

As another example, the analogue [Lys18,Glu22,Arg26, Lys27,His31,Gly34]-GLP-1-(7-34) designates a GLP-1(7-37) peptide, which, when compared to native GLP-1, is changed by substitution of serine at position 18 with lysine, substitution of glycine at position 22 with glutamic acid, substitution of lysine at position 26 with arginine, substitution of glutamic acid at position 27 with lysine, substitution of tryptophan at position 31 with histidine, substitution of lysine at position 34 with glycine, and by deletion of the C-terminus of glycine-arginine-glycine at position 35-36-37. This analogue may also be briefly designated (18K, 22E, 26R, 27K, 31H, 34G, des35-37), where reference to GLP-1(7-37) is implied, and "des" represents a deletion.

As a still further example, an analogue comprising $Imp^7$, and/or ($Aib^8$ or $S^8$) refers to a GLP-1(7-37) peptide, which, when compared to native GLP-1, comprises a substitution of histidine at position 7 with imidazopropionic acid (Imp); and/or a substitution of alanine at position 8 with α-aminoisobutyric acid (Aib), or with serine. This analogue may comprise further changes as compared to SEQ ID NO: 1.

As is apparent from the above examples, amino acid residues may be identified by their full name, their one-letter code, and/or their three-letter code. These three ways are fully equivalent.

The expressions "a position equivalent to" or "corresponding position" may be used to characterise the site of change in a GLP-1 sequence by reference to native GLP-1 (7-37) (SEQ ID NO: 1). Equivalent or corresponding positions are easily deduced, e.g. by simple handwriting and eyeballing; and/or a standard protein or peptide alignment program may be used, such as "align" which is a Needleman-Wunsch alignment. The algorithm is described in Needleman, S. B. and Wunsch, C. D., (1970), Journal of Molecular Biology, 48: 443-453, and the align program by Myers and W. Miller in "Optimal Alignments in Linear Space" CABIOS (computer applications in the biosciences) (1988) 4:11-17. For the alignment, the default scoring matrix BLOSUM62 and the default identity matrix may be used, and the penalty for the first residue in a gap may be set at −10 (minus 10) and the penalties for additional residues in a gap at −0.5 (minus 0.5).

An example of such alignment is inserted hereinbelow, in which sequence no. 1 is SEQ ID NO: 1, and sequence no. 2 is the analogue (18K, 22E, 26R, 27K, 31H, 34G, des35-37) thereof:

```
# 1: GLP-1 (7-37)
# 2: GLP-1 (7-37)_ANALOGUE
# Matrix: EBLOSUM62
# Gap_penalty: 10.0
# Extend_penalty: 0.5
# Length: 31
# Identity: 22/31 (71.0%)
# Similarity: 24/31 (77.4%)
# Gaps: 3/31 (9.7%)
# Score: 105.0

1    1 HAEGTFTSDVSSYLEGQAAKEFIAWLVKGRG 31 (SEQ ID NO: 1)
       ||||||||||.|||.|||::|||.||.
2    1 HAEGTFTSDVSKYLEEQAARKFIAHLVG--- 28 (SEQ ID NO: 2)
```

In case of non-natural amino acids such as Imp and/or Aib being included in the sequence, they may, for alignment purposes, be replaced with X. If desired, X can later be manually corrected.

The term "peptide", as e.g. used in the context of the GLP-1 analogues of the derivatives of the invention, refers to a compound which comprises a series of amino acids interconnected by amide (or peptide) bonds.

The peptides of the invention comprise at least five constituent amino acids connected by peptide bonds. In particular embodiments the peptide comprises at least 10, preferably at least 15, more preferably at least 20, even more preferably at least 25, or most preferably at least 27 amino acids.

In particular embodiments, the peptide is composed of at least five constituent amino acids, preferably composed of at least 10, at least 15, at least 20, at least 25, or most preferably composed of at least 27 amino acids. In still further particular embodiments the peptide is composed of at least 28, at least 29, at least 30, at least 31, or at least 32 amino acids.

In a still further particular embodiment the peptide consists of amino acids interconnected by peptide bonds.

Amino acids are molecules containing an amine group and a carboxylic acid group, and, optionally, one or more additional groups, often referred to as the amino acid side chain.

The term "amino acid" includes proteogenic amino acids (encoded by the genetic code, including natural amino acids, and standard amino acids), as well as non-proteogenic (not found in proteins, and/or not coded for in the standard genetic code), and synthetic amino acids. Thus, the amino acids may be selected from the group of proteinogenic amino acids, non-proteinogenic amino acids, and/or synthetic amino acids.

Non-limiting examples of amino acids which are not encoded by the genetic code are gamma-carboxyglutamate, ornithine, and phosphoserine. Non-limiting examples of synthetic amino acids are the D-isomers of the amino acids such as D-alanine and D-leucine, Aib (α-aminoisobutyric acid), β-alanine, and des-amino-histidine (desH, alternative name imidazopropionic acid, abbreviated Imp).

In what follows, all amino acids for which the optical isomer is not stated is to be understood to mean the L-isomer (unless otherwise specified).

The GLP-1 derivatives and analogues of the invention have GLP-1 activity. This term refers to the ability to bind to the GLP-1 receptor and initiate a signal transduction pathway resulting in insulinotropic action or other physiological effects as is known in the art. For example, the analogues and derivatives of the invention may suitably be tested for GLP-1 activity using the in vitro potency assay described in Example 148 herein.

GLP-1 Derivatives

The term "derivative" as used herein in the context of a GLP-1 peptide or analogue means a chemically modified GLP-1 peptide or analogue, in which one or more substituents have been covalently attached to the peptide. The substituent may also be referred to as a side chain.

In a particular embodiment, the side chain is capable of forming non-covalent aggregates with albumin, thereby promoting the circulation of the derivative with the blood stream, and also having the effect of protracting the time of action of the derivative, due to the fact that the aggregate of the GLP-1-derivative and albumin is only slowly disintegrated to release the active pharmaceutical ingredient. Thus, the substituent, or side chain, as a whole may be referred to as an albumin binding moiety.

In another particular embodiment the albumin binding moiety comprises a portion which is particularly relevant for the albumin binding and thereby the protraction, which portion may accordingly be referred to as a protracting moiety. The protracting moiety may be at, or near, the opposite end of the albumin binding moiety, relative to its point of attachment to the peptide.

In a still further particular embodiment the albumin binding moiety comprises a portion inbetween the protracting moiety and the point of attachment to the peptide, which portion may be referred to as a linker, a linker moiety, a spacer, or the like.

In particular embodiments, the protracting moiety is lipophilic, and/or negatively charged at physiological pH (7.4).

The albumin binding moiety, the protracting moiety, or the linker may be covalently attached to a lysine residue of the GLP-1 peptide by acylation.

In a preferred embodiment, an active ester of the albumin binding moiety, preferably comprising a protracting moiety and a linker, is covalently linked to an amino group of a lysine residue, preferably the epsilon amino group thereof, under formation of an amide bond (this process being referred to as acylation).

Unless otherwise stated, when reference is made to an acylation of a lysine residue, it is understood to be to the epsilon-amino group thereof.

A derivative comprising two protracting moieties attached to a first and a second K residue (e.g., to $K^{18}$ and $K^T$) via a linker may be referred to as a derivative which has been acylated twice, double-acylated, or dual acylated at the epsilon-amino groups of the first and second lysine residues, e.g. at position 18 and T, respectively, of the GLP-1 peptide.

For the present purposes, the terms "albumin binding moiety", "protracting moiety", and "linker" include the molecule itself as well as radicals thereof. Whether or not one or the other form is meant is clear from the context in which the term is used. In a preferred embodiment, these terms refer to radicals. The radicals are preferably suitable for forming one or more amide bonds, i.e. with one or two unshared electrons (*) in connection with a carbonyl group and/or an amino group. Examples of such radicals are Chem. 1-Chem. 3, the structures of which are shown in the following.

In one aspect, each protracting moiety comprises, or consists of, a protracting moiety, independently selected from Chem. 1, Chem. 2, and Chem. 3:

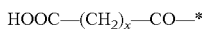  Chem. 1:

HOOC—(CH$_2$)$_x$—CO—*

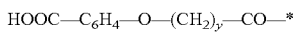  Chem. 2:

HOOC—C$_6$H$_4$—O—(CH$_2$)$_y$—CO—*

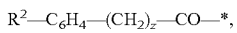  Chem. 3:

R$^2$—C$_6$H$_4$—(CH$_2$)$_z$—CO—*, in which x is an integer in the range of 6-18, y is an integer in the range of 3-17, z is an integer in the range of 1-5, and R$^2$ is a group having a molar mass not higher than 150 Da.

In one embodiment, *—(CH$_2$)$_x$—* refers to straight or branched, preferably straight, alkylene in which x is an integer in the range of 6-18.

In another embodiment, *—(CH$_2$)$_y$—* refers to straight or branched, preferably straight, alkylene in which y is an integer in the range of 3-11.

In a still further embodiment, *—(CH$_2$)$_z$—* refers to straight or branched, preferably straight, alkylene in which z is an integer in the range of 1-5.

In a still further embodiment *—(CH$_2$)$_z$—* refers to cyclic alkylene in which z is an integer in the range of 1-5, preferably 3.

The nomenclature is as is usual in the art, for example in the above formulas *—COOH refers to carboxy, *—C$_6$H$_4$—* to phenylene, and *—CO—* to carbonyl (O═C<**). In particular embodiments, the aromatics, such as the phenoxy, and the phenylene radicals, may be, independently, ortho, meta, or para.

The molar mass (M) of a chemical substance (such as the group R$^2$) is the mass of one mole of the substance. The molar mass is quoted in dalton, symbol Da, with the definition 1 Da=1 g/mol.

Molar mass may be calculated from standard atomic weights, and is often listed in chemical catalogues. The molar mass of a compound is given by the sum of the standard atomic weights of the atoms which form the compound multiplied by the molar mass constant, M$_u$ which equals 1 g/mol. As an example, the molar mass of tert. butyl (C$_4$H$_9$) is M(C$_4$H$_9$)=([4×12.01]+[9×1.008])×1 g/mol=57 Da.

Standard atomic weights are published by the International Union of Pure and Applied Chemistry (IUPAC), and also reprinted in a wide variety of textbooks, commercial catalogues, wallcharts etc.

For the present purposes, the molar mass of a compound is calculated using the exact mass of the most abundant isotope of each constituent atom of the compound. The exact mass is based on the Carbon 12 standard. The exact mass of each constituent atom is rounded to an integer before calculating the molar mass of the compound.

For example, for CF$_3$ (one example of a R$^2$ substituent of the invention) the molar mass is calculated as follows: The exact mass of the most abundant Carbon isotope (C12), rounded to an integer, is 12. The exact mass of the most abundant Fluorine atom (F19), rounded to an integer, is 19. Accordingly, the molar mass of CF$_3$ is (12+3×19)×1 g/mol=69 Da. As explained above, the GLP-1 derivatives of the present invention are double-acylated, i.e. two albumin binding moieties are covalently attached to the GLP-1 peptide.

In a particular embodiment, the two albumin binding moieties (i.e. the entire side chains) are similar, preferably substantially identical, or, most preferably, identical.

In another particular embodiment, the two protracting moieties are similar, preferably substantially identical, or, most preferably, identical.

In a still further particular embodiment, the two linkers are similar, preferably substantially identical, or, most preferably identical.

The term "substantially identical" includes differences from identity which are due to formation of one or more salts, esters, and/or amides; preferably formation of one or more salts, methyl esters, and simple amides; more preferably formation of no more than two salts, methyl esters, and/or simple amides; even more preferably formation of no more than one salt, methyl ester, and/or simple amide; or most preferably formation of no more than one salt.

In the context of chemical compounds such as albumin binding moieties, protracting moieties, and linkers, similarity and/or identity may be determined using any suitable computer program and/or algorithm known in the art.

For example, the similarity of two protracting moieties, two linkers, and/or two entire side chains may suitably be determined using molecular fingerprints. Fingerprints is a mathematical method of representing a chemical structure (see e.g. Chemoinformatics: A textbook, Johann Gasteiger and Thomas Engel (Eds), Wiley-VCH Verlag, 2003).

Examples of suitable fingerprints include, without limitation, UNITY fingerprints, MDL fingerprints, and/or ECFP fingerprints, such as ECFP_6 fingerprints (ECFP stands for extended-connectivity fingerprints).

In particular embodiments, the two protracting moieties, the two linkers, and/or the two entire side chains are represented as a) ECFP_6 fingerprints; b) UNITY fingerprints; and/or c) MDL fingerprints.

The Tanimoto coefficient is preferably used for calculating the similarity of the two fingerprints, whether a), b) or c) is used.

In particular embodiments, whether a), b) or c) is used, the two protracting moieties, the two linkers, and/or the two entire side chains, respectively, have a similarity of at least 0.5 (50%); preferably at least 0.6 (60%); more preferably at least 0.7 (70%), or at least 0.8 (80%); even more preferably at least 0.9 (90%); or most preferably at least 0.99 (99%), such as a similarity of 1.0 (100%).

UNITY fingerprints may be calculated using the programme SYBYL (available from Tripos, 1699 South Hanley Road, St. Louis, Mo. 63144-2319 USA). ECFP_6 and MDL fingerprints may be calculated using the programme Pipeline Pilot (available from Accelrys Inc., 10188 Telesis Court, Suite 100, San Diego, Calif. 92121, USA).

For more details, see for example J. Chem. Inf. Model. 2008, 48, 542-549; J. Chem. Inf. Comput. Sci. 2004, 44, 170-178; J. Med. Chem. 2004, 47, 2743-2749; J. Chem. Inf. Model. 2010, 50, 742-754; as well as SciTegic Pipeline Pilot Chemistry Collection: Basic Chemistry User Guide, March 2008, SciTegic Pipeline Pilot Data Modeling Collection, 2008—both from Accelrys Software Inc., San Diego, US, and the guides http://www.tripos.com/tripos_resources/fileroot/pdfs/Unity_111408.pdf, and http://www.tripos.com/data/SYBYL/SYBYL_072505.pdf.

An example of a similarity calculation is inserted hereinbelow, in which the entire side chain of Chem. 36 was compared with a methyl ester thereof (Chem 36a):

Chem. 36a

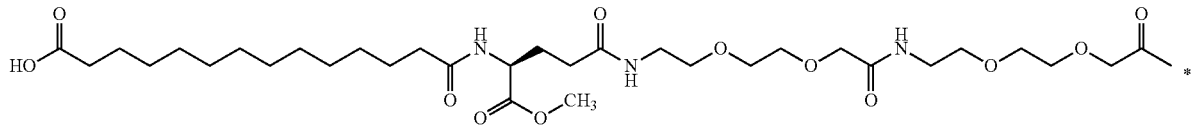

Using a) ECFP_6 fingerprints the similarity is 0.798, using b) UNITY fingerprints the similarity is 0.957; and using MDL fingerprints the similarity is 0.905.

In case of two identical side chains (albumin binding moieties) the derivative may be designated symmetrical.

Each of the two linkers of the derivative of the invention comprises the following first linker element:

Chem. 4

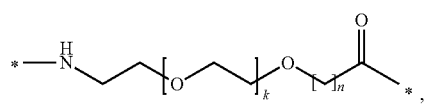

wherein k is an integer in the range of 1-5, and n is an integer in the range of 1-5.

In a particular embodiment, when k=1 and n=1, this linker element may be designated OEG, or 8-amino-3,6-dioxaoctanic acid, and/or it may be represented by the following formula:

*—NH—(CH$_2$)$_2$—O—(CH$_2$)$_2$—O—CH$_2$—CO—*.   Chem. 4a:

In another particular embodiment, each linker of the derivative of the invention may further comprise, independently, the following second linker element:

Chem. 5

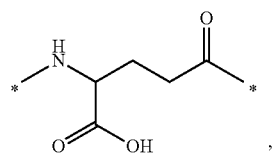

that may be included p times, where p is an integer in the range of 1-3. This second linker element may also be referred to as gamma-Glu, or briefly gGlu, due to the fact that it is the gamma carboxy group of the amino acid glutamic acid which is here used for connection to another linker element, or to the epsilon-amino group of lysine. The structure of Chem. 5 covers the L-form, as well as the D-form of Glu. In particular embodiments, Chem. 5 is a) in the L-form, or b) in the D-form.

In another particular embodiment, each linker of the derivative of the invention may further comprise, independently, the following third linker element:

*—NH—(CH$_2$)$_q$—CHR$^3$—CO—*,   Chem. 6:

in which q is an integer in the range of 2-12, and R$^3$ is hydrogen (H). In Chem. 6, the group *—(CH$_2$)$_q$—* may represent straight or branched, preferably straight, alkylene, wherein q is an integer in the range of 2-12.

In still further particular embodiments the linker has a) from 6 to 41 C-atoms; and/or b) from 4 to 28 hetero atoms.

Particular and non-limiting examples of hetero atoms are N—, and O-atoms. H-atoms are not hetero atoms.

In a particular embodiment, each linker consists of one time Chem. 5 and two times Chem. 4, interconnected via amide bonds and in the sequence indicated, the thus formed (combined/aggregated) linker being connected at its free amino (HN—*) end to the free carbonyl (CO—*) group of the protracting moiety, and at its free carbonyl (CO—*) end to the epsilon amino group of the first or the second K residue of the GLP-1 analogue, respectively.

In another particular embodiment, each linker consists of two times Chem. 4 and one time Chem. 5, interconnected via amide bonds and in the sequence indicated, the thus formed (combined/aggregated) linker being connected at its free amino (HN—*) end to the free carbonyl (CO—*) group of the protracting moiety, and at its free carbonyl (CO—*) end to the epsilon amino group of the first or the second K residue of the GLP-1 analogue, respectively.

Needless to say, just for the sake of good order: Here and in the following the phrase "in the sequence indicated" means, that the *—NH end of the first-mentioned linker element (here the first one of the two times Chem. 4) is connected to the *—CO end of the protractor, and the *—CO end of the last-mentioned linker element (here Chem. 5) is connected to the epsilon amino group of the K residue in question of the GLP-1 analogue.

In still further particular embodiments, the invention relates to:

(a) A derivative of a GLP-1 analogue, which analogue comprises a first K residue at a position corresponding to position 18 of GLP-1(7-37) (SEQ ID NO: 1), a second K residue at position 26 of GLP-1(7-37) (SEQ ID NO: 1), and a maximum of four amino acid changes as compared to GLP-1(7-37), which derivative comprises two protracting moieties attached to said first and second K residue, respectively, via a linker, wherein the protracting moiety is Chem. 1:

HOOC—(CH$_2$)$_x$—CO—*, in which x is 12; and the linker comprises Chem. 4:

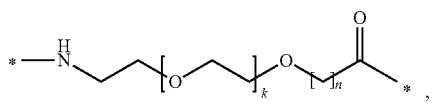

wherein k is 1, and n is 1; or a pharmaceutically acceptable salt, amide, or ester thereof.

(b) A derivative of a GLP-1 analogue, which analogue comprises a first K residue at a position corresponding to position 18 of GLP-1(7-37) (SEQ ID NO: 1), a second K residue at position 26 of GLP-1(7-37) (SEQ ID NO: 1), and a maximum of four amino acid changes as compared to GLP-1(7-37), which derivative comprises two protracting moieties attached to said first and second K residue, respectively, via a linker, wherein the protracting moiety is Chem. 2:

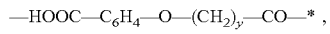

in which y is 9; and the linker comprises Chem. 4:

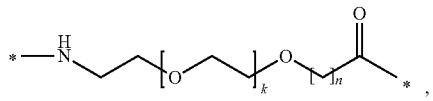

wherein k is 1, and n is 1; or a pharmaceutically acceptable salt, amide, or ester thereof.
(c) A derivative of (a) or (b), wherein the linker consists of two times Chem. 4, interconnected via an amide bond, the linker being connected at its *—NH end to the *—CO end of the protracting moiety, and at its *—CO end to the epsilon amino group of the first or the second K residue of the GLP-1 analogue.
(d) A derivative of (a) or (b), wherein the linker consists of one time Chem. 4, one time Chem. 5a, and one time Chem. 4, interconnected via amide bonds and in the sequence indicated, the linker being connected at its *—NH end to the *—CO end of the protracting moiety, and at its *—CO end to the epsilon amino group of the first or the second K residue of the GLP-1 analogue.
(e) The derivative of any of (a), (b), (c), or (d), wherein the analogue, in addition to the change $K^{18}$, further comprises $Q^{34}$.
(f) The derivative of any of (a), (b), (c), (d), or (e), wherein the analogue comprises $Aib^8$.
(g) The derivative of any of (a), (b), (c), (d), (e), or (f), wherein the analogue comprises $E^{22}$.
(h) The derivative of any of (a), (b), (c), (d), (e), (f), or (g), wherein the analogue comprises, preferably has, Formula I:
Xaa$_7$-Xaa$_8$-Glu-Gly-Thr-Xaa$_{12}$-Thr-Ser-Asp-Xaa$_{16}$-Ser-Lys-Xaa$_{19}$-Xaa$_{20}$-Glu-Xaa$_{22}$-Xaa$_{23}$-Ala-Xaa$_{25}$-Xaa$_{26}$-Xaa$_{27}$-Phe-Ile-Xaa$_{30}$-Xaa$_{31}$-Leu-Xaa$_{33}$-Xaa$_{34}$-Xaa$_{35}$-Xaa$_{36}$-Xaa$_{37}$-Xaa$_{38}$, (SEQ ID NO: 3) wherein
Xaa$_7$ is His or desamino-histidine (imidazopropionyl); Xaa$_8$ is Aib; Xaa$_{12}$- is Phe or Leu; Xaa$_{16}$ is Val; Xaa$_{19}$ is Tyr; Xaa$_{20}$ is Leu; Xaa$_{22}$ is Glu; Xaa$_{23}$ is Gln, Glu, or Arg; Xaa$_{25}$ is Ala or Val; Xaa$_{26}$ is Lys; Xaa$_{27}$ is Glu, His, Leu, or Lys; Xaa$_{30}$ is Ala, Glu, or Lys; Xaa$_{31}$ is Trp, Lys, or His; Xaa$_{33}$ is Val; Xaa$_{34}$ is Gln; Xaa$_{35}$ is Gly or absent; Xaa$_{36}$ is Arg or absent; Xaa$_{37}$ is Gly, Lys, or absent; and Xaa$_{38}$ is absent.
(i) The derivative of (h) (SEQ ID NO: 4), wherein Xaa$_7$ is His; Xaa$_{12}$- is Phe; Xaa$_{16}$ is Val; Xaa$_{19}$ is Tyr; Xaa$_{20}$ is Leu; Xaa$_{22}$ is Glu; Xaa$_{23}$ is Gln; Xaa$_{25}$ is Ala; Xaa$_{26}$ is Lys; Xaa$_{27}$ is Glu; Xaa$_{30}$ is Ala; Xaa$_{31}$ is Trp; Xaa$_{33}$ is Val; Xaa$_{34}$ is Gln; Xaa$_{35}$ is Gly; Xaa$_{36}$ is Arg; Xaa$_{37}$ is Gly; and Xaa$_{38}$ is absent.
(j) The derivative of any of (a), (b), (c), (d), (e), (f), (g), (h), or (i), wherein the analogue comprises, preferably has, the following amino acid changes, as compared to GLP-1(7-37) (SEQ ID NO: 1): 8Aib, 18K, 22E, 34Q.
(k) A compound selected from Chem. 21, Chem. 57, Chem. 101, Chem. 103, Chem. 104, Chem. 105, Chem. 107, and Chem. 109; or a pharmaceutically acceptable salt, amide, or ester thereof.
(l) A compound characterised by its name, and selected from a listing of each of the names of the compounds of Example 2, 38, 82, 84, 85, 86, 88, and 90; or a pharmaceutically acceptable salt, amide, or ester thereof.
(m) The derivative of any of embodiments (a), (b), (c), (d), (e), (f), (g), (h), (i), (j), (k), or (l), which has a potency corresponding to an $EC_{50}$ below 500 pM, preferably below 400 pM, more preferably below 300 pM, even more preferably below 200 pM, or most preferably below 100 pM; wherein the potency is determined as $EC_{50}$ for stimulation of the formation of cAMP in a medium containing the human GLP-1 receptor, using a stable transfected cell-line such as BHK467-12A (tk-ts13); and wherein cAMP is determined using a functional receptor assay, e.g. based on competition between endogenously formed cAMP and exogenously added biotin-labelled cAMP, and e.g. capturing cAMP using a specific antibody, such as the AlphaScreen cAMP Assay, e.g. as described in Example 148.
(n) The derivative of any of embodiments (a), (b), (c), (d), (e), (f), (g), (h), (i), (j), (k), (l), or (m), for which the GLP-1 receptor binding affinity ($IC_{50}$) in the presence of 0.005% HSA (low albumin) is below 10 nM, preferably below 8.0 nM, still more preferably below 6.0 nM, even more preferably below 4.0 nM, or most preferably below 2.00 nM; wherein the binding affinity to the GLP-1 receptor is measured by way of displacement of $^{125}I$-GLP-1 from the receptor, for example using a SPA binding assay; and wherein the GLP-1 receptor is prepared using a stable, transfected baby hamster kidney cell line, such as BHK tk-ts13; and wherein the $IC_{50}$ value is determined as the concentration which displaces 50% of $^{125}I$-GLP-1 from the receptor.
(o) The derivative of any of embodiments (a), (b), (c), (d), (e), (f), (g), (h), (i), (j), (k), (l), (m), or (n), wherein the terminal half-life (T ½) after i.v. administration in rat is at least three times the terminal half-life of semaglutide; wherein the half-life is determined in in vivo pharmacokinetic studies in rat, for example as described in Example 154.

The derivatives of the invention may exist in different stereoisomeric forms having the same molecular formula and sequence of bonded atoms, but differing only in the three-dimensional orientation of their atoms in space. The stereoisomerism of the exemplified derivatives of the invention is indicated in the experimental section, in the names as well as the structures, using standard nomenclature. Unless otherwise stated the invention relates to all stereoisomeric forms of the claimed derivative.

The concentration in plasma of the GLP-1 derivatives of the invention may be determined using any suitable method. For example, LC-MS (Liquid Chromatography Mass Spectroscopy) may be used, or immunoassays such as RIA (Radio Immuno Assay), ELISA (Enzyme-Linked Immuno Sorbent Assay), and LOCI (Luminescence Oxygen Channeling Immunoasssay). General protocols for suitable RIA and ELISA assays are found in, e.g., WO09/030738 on p. 116-118. A preferred assay is the LOCI assay described in 150 herein.

Intermediate Products

One type of intermediate product of the invention takes the form of a GLP-1 analogue which comprises the following changes as compared to GLP-1(7-37) (SEQ ID NO: 1): (i) 8Aib, 18K, 34R; (ii) 8Aib, 18K, 34Q; (iii) 8Aib, 18K, 22E, 34R; (iv) 8Aib, 18K, 22E, 34Q; (v) 8Aib, 12L, 18K, 34Q; (vi) 7Imp, 18K, 22E, 34Q; (vii) 18K, 34R; (iix) 18K, 34Q; (ix) 18K, 22E, 34R; (x) 18K, 22E, 34Q; (xi) 18K, 26R, 31K, 34R; (xii) 18K, 26H, 31K, 34R; (xiii) 18K, 26H, 27K, 34Q; (xiv) 18K, 22K, 26R, 34Q; (xv) 18K, 25V, 26R, 31K, 34R; (xvi) 18K, 22E, 26R, 31K, 34R; (xvii) 18K, 22E, 26H, 27K, 34R; (iixx) 18K, 22E, 26H, 27K, 34Q; (ixx) 18K, 22E, 26H, 27K, 31H, 34R; (xx) 18K, 22E, 26H, 27K, 31H, 34Q; (xxi) 18K, 22E, 25V, 26R, 31K, 34R; (xxii) 18K, 22E, 25V, 26R, 31K, 34Q; (xxiii) 18K, 22E, 25V, 26R, 31K, 34G; (xxiv) 18K, 22E, 25V, 26R, 27K, 34R; (xxv) 18K, 22E, 25V, 26R, 27K, 34Q; (xxvi) 18K, 22E, 25V, 26R, 27K, 31H, 34R; (xxvii) 18K, 22E, 25V, 26R, 27K, 31H, 34Q; (iixxx) 18K, 22E, 23E, 25V, 26R, 27K, 34R; (ixxx) 18K, 22E, 23E, 25V, 26R, 27K, 34Q; (xxx) 18K, 22E, 25V, 26R, 31K, 34G, des35-37; (xxxi) 18K, 22E, 25V, 26R, 31H, des35-37; (xxxii) 18K, 22E, 25V, 26R, 30K, 34G, des35-37; (xxxiii) 18K, 22E, 25V, 26R, 30K, 31H, 34G, des35-37; (xxxiv) 18K, 22E, 25V, 26R, 27L, 30K, 34G, des35-37); (xxxv) 18K, 22E, 26R, 31K, 34G, des35-37; (xxxvi) 18K, 22E, 26R, 27K, 31H, 34G, des35-37; (xxxvii) 71mp, 18K, 22E, 26R, 34R, 37K; (iixxxx) 71mp, 18K, 22E, 26R, 27K, 31H, 34G, des35-37; (ixxxx) 71mp, 18K, 22E, 25V, 26R, 31K, 34G, des35-37; (xxxx) 71mp, 8Aib, 18K, 22E, 25V, 26R, 31K, 34G, des35-37; (xxxxi) 8S, 18K, 22E, 25V, 26R, 31K, 34G, des35-37; (xxxxii) 8Aib, 18K, 26V, 27K, 34R; (xxxxiii) 8Aib, 18K, 26H, 30K, 34R, des36-37; (xxxxiv) 8Aib, 18K, 25V, 26R, 31K, 34R; (xxxxv) 8Aib, 18K, 22E, 34R, des36-37; (xxxxvi) 8Aib, 18K, 22E, 26R, 34R, 37K; (xxxxvii) 8Aib, 18K, 22E, 26R, 31K, 34R; (iixxxxx) 8Aib, 18K, 22E, 26R, 31K, 34G, des35-37; (ixxxxx) 8Aib, 18K, 22E, 26R, 30K, 34R, des36-37; (xxxxx) 8Aib, 18K, 22E, 26R, 30K, 34R; (xxxxxi) 8Aib, 18K, 22E, 26R, 27K, 31H, 34R, des36-37; (xxxxxii) 8Aib, 18K, 22E, 25V, 26R, 31K, des34-37; (xxxxxiii) 8Aib, 18K, 22E, 25V, 26R, 31K, 34R; (xxxxxiv) 8Aib, 18K, 22E, 25V, 26R, 31K, 34G, des35-37; (xxxxxv) 8Aib, 18K, 22E, 25V, 26R, 30E, 31K, 34G, des35-37; (xxxxxvi) 8Aib, 18K, 22E, 25V, 26R, 27L, des35-37; (xxxxxvii) 8Aib, 18K, 22E, 25V, 26R, 27K, 34Q; (iixxxxxx) 8Aib, 18K, 22E, 25V, 26R, 27K, 31H, 34G, des35-37; (ixxxxxx) 8Aib, 18K, 22E, 25V, 26R, 27H, 31K, 34G, des35-37; (xxxxxx) 8Aib, 18K, 22E, 25V, 26H, 31K, 34G, des35-37; (xxxxxxi) 8Aib, 18K, 22E, 23R, 25V, 26R, 31K, 34G, des35-37; (xxxxxxii) 18K, 22E, 25V, 26R, 27L, 30K, 34G, des35-37; (xxxxxxiii) 71mp, 18K, 22E, 26R, 27K, 34Q; (xxxxxxiv) 34H; and (xxxxxxv) 8Aib, 18K, 34H; or a pharmaceutically acceptable salt, amide, or ester of any of the analogues of (i)-(xxxxxxv).

Another type of intermediate product of the invention takes the form of an albumin binding moiety, or a side chain intermediate, selected from Chem. 137-160, and Chem. 184-188, wherein R and PG are protecting groups; or a pharmaceutically acceptable salt, amide, or ester thereof.

In a particular embodiment, the protection group is a group that reversibly renders the compound unreactive, and that can be removed selectively.

Non-limiting examples of protecting groups are groups functionalised as an activated ester, for example, without limitation, OPfp, OPnp, and OSuc.

Other suitable activated esters may be selected, e.g., according to the teaching of M. Bodanszky, "Principles of Peptide Synthesis", 2nd ed., Springer Verlag, 1993.

Pharmaceutically Acceptable Salt, Amide, or Ester

The derivatives of the invention may be in the form of a pharmaceutically acceptable salt, amide, or ester.

Salts are e.g. formed by a chemical reaction between a base and an acid, e.g.: $2\ NH_3 + H_2SO_4 \rightarrow (NH_4)_2SO_4$.

The salt may be a basic salt, an acid salt, or it may be neither nor (i.e. a neutral salt). Basic salts produce hydroxide ions and acid salts hydronium ions in water.

The salts of the derivatives of the invention may be formed with added cations or anions that react with anionic or cationic groups, respectively. These groups may be situated in the peptide moiety, and/or in the side chain of the derivatives of the invention.

Non-limiting examples of anionic groups of the derivatives of the invention include free carboxylic groups in the side chain, if any, as well as in the peptide moiety. The peptide moiety often includes a free carboxylic acid group at the C-terminus, and it may also include free carboxylic groups at internal acid amino acid residues such as Asp and Glu.

Non-limiting examples of cationic groups in the peptide moiety include the free amino group at the N-terminus, if present, as well as any free amino group of internal basic amino acid residues such as His, Arg, and Lys.

The ester of the derivatives of the invention may, e.g., be formed by the reaction of a free carboxylic acid group with an alcohol or a phenol, which leads to replacement of at least one hydroxyl group by an alkoxy or aryloxy group The ester formation may involve the free carboxylic group at the C-terminus of the peptide, and/or any free carboxylic group in the side chain.

The amide of the derivatives of the invention may, e.g., be formed by the reaction of an activated form of a free carboxylic acid group with an amine or a substituted amine, or by reaction of a free or substituted amino group with an activated form of a carboxylic acid.

The amide formation may involve the free carboxylic group at the C-terminus of the peptide, any free carboxylic group in the side chain, the free amino group at the N-terminus of the peptide, and/or any free or substituted amino group of the peptide in the peptide and/or the side chain.

In a particular embodiment, the peptide or derivative is in the form of a pharmaceutically acceptable salt. In another particular embodiment, the derivative is in the form of a pharmaceutically acceptable amide, preferably with an amide group at the C-terminus of the peptide. In a still further particular embodiment, the peptide or derivative is in the form a pharmaceutically acceptable ester.

Functional Properties

In a first aspect, the derivatives of the invention have a good potency. Also, or alternatively, in a second aspect, they have a protracted pharmacokinetic profile. Also, or alternatively, in a third aspect, they have a high oral bioavailability. Also, or alternatively, in a fourth aspect, they have good biophysical properties.

Biological Activity (Potency)

According to the first aspect, the derivatives of the invention, as well as the constituent GLP-1 peptides as such (such as $K^{18}$-GLP-1(7-37) or analogues thereof), are biologically active, or potent.

In a particular embodiment, potency and/or activity refers to in vitro potency, i.e. performance in a functional GLP-1 receptor assay, more in particular to the capability of stimulating cAMP formation in a cell line expressing the cloned human GLP-1 receptor.

The stimulation of the formation of cAMP in a medium containing the human GLP-1 receptor may preferably be determined using a stable transfected cell-line such as BHK467-12A (tk-ts13), and/or using for the determination of cAMP a functional receptor assay, e.g. based on competition between endogenously formed cAMP and exogenously added biotin-labelled cAMP, in which assay cAMP is more preferably captured using a specific antibody, and/or wherein an even more preferred assay is the AlphaScreen cAMP Assay, most preferably the one described in Example 148.

The term half maximal effective concentration ($EC_{50}$) generally refers to the concentration which induces a response halfway between the baseline and maximum, by reference to the dose response curve. $EC_{50}$ is used as a measure of the potency of a compound and represents the concentration where 50% of its maximal effect is observed.

The in vitro potency of the derivatives of the invention may be determined as described above, and the $EC_{50}$ of the derivative in question determined. The lower the $EC_{50}$, the better the potency.

In a particular embodiment, the medium has the following composition (final in-assay concentrations): 50 mM TRIS-HCl; 5 mM HEPES; 10 mM $MgCl_2$, $6H_2O$; 150 mM NaCl; 0.01% Tween; 0.1% BSA; 0.5 mM IBMX; 1 mM ATP; 1 uM GTP. A first alternative medium is: 50 mM TRIS-HCl; 5 mM HEPES; 10 mM $MgCl_2$, $6H_2O$; 150 mM NaCl; 0.01% Tween. A second alternative medium is: 50 mM Tris-HCl, 1 mM EGTA, 1.5 mM $MgSO_4$, 1.7 mM ATP, 20 mM GTP, 2 mM 3-isobutyl-1-methylxanthine (IBMX), 0.01% Tween-20, pH 7.4.

In a further particular embodiment, the derivative of the invention has an in vitro potency corresponding to an $EC_{50}$ at or below 10000 pM, more preferably below 5000 pM, even more preferably below 1000 pM, or most preferably below 500 pM.

The ability of the derivatives of the invention to bind to the GLP-1 receptor may also be used as a measure of the GLP-1 activity (receptor affinity). This ability may be determined as described in Example 149. Generally, the binding to the GLP-1 receptor at low albumin concentration should be as good as possible, corresponding to a low $IC_{50}$ value.

In another particular embodiment the derivatives of the invention are potent in vivo, which may be determined as is known in the art in any suitable animal model, as well as in clinical trials.

The diabetic db/db mouse is one example of a suitable animal model, and the blood glucose lowering effect, as well as the body weight lowering effect may be determined in such mice in vivo, e.g. as described in Example 151.

Also, or alternatively, the effect on food (or feed) intake in vivo may be determined in pharmacodynamic studies in pigs, e.g. as described in Example 153.

Protraction—Receptor Binding/Low and High Albumin

According to the second aspect, the derivatives of the invention are protracted.

The ability of the derivatives of the invention to bind to the GLP-1 receptor in the presence of a low and a high concentration of albumin, respectively, may be determined as described in Example 149.

Generally, the binding to the GLP-1 receptor at low albumin concentration should be as good as possible, corresponding to a low $IC_{50}$ value.

The $IC_{50}$ value at high albumin concentration is a measure of the influence of albumin on the binding of the derivative to the GLP-1 receptor. As is known, the GLP-1 derivatives also bind to albumin. This is a generally desirable effect, which extends their lifetime in plasma. Therefore, the $IC_{50}$ value at high albumin will generally be higher than the $IC_{50}$ value at low albumin, corresponding to a reduced binding to the GLP-1 receptor, caused by albumin binding competing with the binding to the GLP-1 receptor.

A high ratio ($IC_{50}$ value (high albumin)/$IC_{50}$ value (low albumin)) may therefore be taken as an indication that the derivative in question binds well to albumin (may have a long half-life), and also per se binds well to the GLP-1 receptor (the $IC_{50}$ value (high albumin) is high, and the $IC_{50}$ value (low albumin) is low). On the other hand, albumin binding may not always be desirable, or the binding to albumin may become too strong. Therefore, the desirable ranges for $IC_{50}$ (low albumin), $IC_{50}$ (high albumin) 1, and the ratio high/low may vary from compound to compound, depending on the intended use and the circumstances surrounding such use, and on other compound properties of potential interest.

As an example, in one particular embodiment, the ratio (hi/lo), vis. [GLP-1 receptor binding affinity ($IC_{50}$) in the presence of 2.0% human serum albumin (HSA), divided by GLP-1 receptor binding affinity ($IC_{50}$) in the presence of 0.005% HSA], is at least 1, preferably at least 10, more preferably at least 20, even more preferably at least 30, or most preferably at least 50.

Protraction—Half Life In Vivo in Minipigs

According to the second aspect, the derivatives of the invention are protracted.

Protraction may be determined as terminal half-life (T %) in vivo in rats after i.v. administration, as described in Example 154. In particular embodiments, the half-life in rat is at least 7 hours, preferably at least 10 hours, even more preferably at least 20 hours, or most preferably at least 30 hours.

Or, protraction may be determined in another animal species, for example as terminal half-life ($T_{1/2}$) in vivo in minipigs after i.v. administration, as described in Example 152. In particular embodiments, the terminal half-life is at least 8 hours, preferably at least 24 hours, even more preferably at least 40 hours, or most preferably at least 60 hours.

Surprisingly, the present inventors identified a novel class of GLP-1 derivatives, object of the present invention, which have a high potency, and at the same time preferably a good half-life.

Oral Bioavailability

According to the third aspect, the derivatives of the invention have a high oral bioavailability.

The oral bioavailability of commercial GLP-1 derivatives is very low. The oral bioavailability of GLP-1 derivatives under development for i.v. or s.c. administration is also low.

Accordingly, there is a need in the art for GLP-1 derivatives of an improved oral bioavailability. Such derivatives could be suitable candidates for oral administration, as long as mainly their potency is generally satisfactory, and/or as long as their half-life is also generally satisfactory.

Surprisingly, the present inventors identified a novel class of GLP-1 derivatives, object of the present invention, which have a surprisingly high oral bioavailability, and at the same time a satisfactory potency, and/or half-life.

Generally, the term bioavailability refers to the fraction of an administered dose of an active pharmaceutical ingredient (API), such as a derivative of the invention that reaches the systemic circulation unchanged. By definition, when an API is administered intravenously, its bioavailability is 100%. However, when it is administered via other routes (such as orally), its bioavailability decreases (due to incomplete absorption and first-pass metabolism).

Knowledge about bioavailability is important when calculating dosages for non-intravenous routes of administration.

Absolute oral bioavailability compares the bioavailability (estimated as the area under the curve, or AUC) of the API in systemic circulation following oral administration, with the bioavailability of the same API following intravenous administration. It is the fraction of the API absorbed through non-intravenous administration compared with the corresponding intravenous administration of the same API. The comparison must be dose normalised if different doses are used; consequently, each AUC is corrected by dividing by the corresponding dose administered.

A plasma API concentration vs time plot is made after both oral and intravenous administration. The absolute bioavailability (F) is the dose-corrected AUC-oral divided by AUC-intravenous.

In a particular embodiment, the derivative of the invention has an absolute oral bioavailability which is higher than that of semaglutide, preferably at least 10% higher, more preferably at least 20% higher, even more preferably at least 30% higher, or most preferably at least 40% higher. In additional particular embodiments, it has an absolute oral bioavailability which is at least 1.5 times that of semaglutide, preferably at least 2.0 times, more preferably at least 3.0 times, even more preferably at least 4.0 times, or most preferably at least 5.0 times that of semaglutide.

Before testing oral bioavailability the derivatives of the invention may suitably be formulated as is known in the art of oral formulations of insulinotropic compounds, e.g. using any one or more of the formulations described in WO 2008/145728.

A test has been developed, described in Example 150, which was found to give an acceptable prediction of oral bioavailability. According to this test, after direct injection of the GLP-1 derivative into the intestinal lumen of rats, the concentration (exposure) thereof in plasma is determined, and the ratio of plasma concentration (pmol/l) divided by the concentration of the dosing solution (umol/l) is calculated for t=30 min. This ratio is a measure of intestinal bioavailability, and it is expected to correlate with actual oral bioavailability data.

Biophysical Properties

According to the fourth aspect, the peptides/derivatives of the invention have good biophysical properties. These properties include but are not limited to physical stability and/or solubility. These and other biophysical properties may be measured using standard methods known in the art of protein chemistry. In a particular embodiment, these properties are improved as compared to native GLP-1 (SEQ ID NO: 1). Changed oligomeric properties of the peptides/derivatives may be at least partly responsible for the improved biophysical properties.

Additional particular embodiments of the derivatives of the invention are described in the sections headed "particular embodiments" and "additional particular embodiments" before the experimental section.

Production Processes

The production of peptides like GLP-1(7-37) and GLP-1 analogues is well known in the art.

The GLP-1 moiety of the derivatives of the invention, viz. $K^{18}$-GLP-1(7-37) or an analogue thereof, may for instance be produced by classical peptide synthesis, e.g., solid phase peptide synthesis using t-Boc or Fmoc chemistry or other well established techniques, see, e.g., Greene and Wuts, "Protective Groups in Organic Synthesis", John Wiley & Sons, 1999, Florencio Zaragoza Dörwald, "Organic Synthesis on solid Phase", Wiley-VCH Verlag GmbH, 2000, and "Fmoc Solid Phase Peptide Synthesis", Edited by W. C. Chan and P. D. White, Oxford University Press, 2000.

Also, or alternatively, they may be produced by recombinant methods, viz. by culturing a host cell containing a DNA sequence encoding the analogue and capable of expressing the peptide in a suitable nutrient medium under conditions permitting the expression of the peptide. Non-limiting examples of host cells suitable for expression of these peptides are: *Escherichia coli, Saccharomyces cerevisiae*, as well as mammalian BHK or CHO cell lines.

Those derivatives of the invention which include non-natural amino acids and/or a covalently attached N-terminal mono- or dipeptide mimetic may e.g. be produced as described in the experimental part. Or see e.g., Hodgson et al: "The synthesis of peptides and proteins containing non-natural amino acids", Chemical Society Reviews, vol. 33, no. 7 (2004), p. 422-430; and WO 2009/083549 A1 entitled "Semi-recombinant preparation of GLP-1 analogues".

Specific examples of methods of preparing a number of the derivatives of the invention are included in the experimental part.

Pharmaceutical Compositions

Pharmaceutical composition comprising a derivative of the invention or a pharmaceutically acceptable salt, amide, or ester thereof, and a pharmaceutically acceptable excipient may be prepared as is known in the art.

The term "excipient" broadly refers to any component other than the active therapeutic ingredient(s). The excipient may be an inert substance, an inactive substance, and/or a not medicinally active substance.

The excipient may serve various purposes, e.g. as a carrier, vehicle, diluent, tablet aid, and/or to improve administration, and/or absorption of the active substance.

The formulation of pharmaceutically active ingredients with various excipients is known in the art, see e.g. Remington: The Science and Practice of Pharmacy (e.g. $19^{th}$ edition (1995), and any later editions).

Non-limiting examples of excipients are: Solvents, diluents, buffers, preservatives, tonicity regulating agents, chelating agents, and stabilisers.

Examples of formulations include liquid formulations, i.e. aqueous formulations, i.e. formulations comprising water. A liquid formulation may be a solution, or a suspension. An aqueous formulation typically comprises at least 50% w/w water, or at least 60%, 70%, 80%, or even at least 90% w/w of water.

Alternatively a pharmaceutical composition may be a solid formulation, e.g. a freeze-dried or spray-dried composition, which may be used as is, or whereto the physician or the patient adds solvents, and/or diluents prior to use.

The pH in an aqueous formulation may be anything between pH 3 and pH 10, for example from about 7.0 to about 9.5; or from about 3.0 to about 7.0.

A pharmaceutical composition may comprise a buffer. The buffer may e.g. be selected from the group consisting of sodium acetate, sodium carbonate, citrate, glycylglycine, histidine, glycine, lysine, arginine, sodium dihydrogen phosphate, disodium hydrogen phosphate, sodium phosphate, and tris(hydroxymethyl)-aminomethan, bicine, tricine, malic acid, succinate, maleic acid, fumaric acid, tartaric acid, aspartic acid, and mixtures thereof.

A pharmaceutical composition may comprise a preservative. The preservative may e.g. be selected from the group consisting of phenol, o-cresol, m-cresol, p-cresol, methyl p-hydroxybenzoate, propyl p-hydroxybenzoate, 2-phenoxyethanol, butyl p-hydroxybenzoate, 2-phenylethanol, benzyl alcohol, chlorobutanol, and thiomerosal, bronopol, benzoic acid, imidurea, chlorohexidine, sodium dehydroacetate, chlorocresol, ethyl p-hydroxybenzoate, benzethonium chloride, chlorphenesine (3p-chlorphenoxypropane-1,2-diol), and mixtures thereof. The preservative may be present in a concentration from 0.1 mg/ml to 20 mg/ml.

A pharmaceutical composition may comprise an isotonic agent. The isotonic agent may e.g. be selected from the group consisting of a salt (e.g. sodium chloride), a sugar or sugar alcohol, an amino acid (e.g. glycine, histidine, arginine, lysine, isoleucine, aspartic acid, tryptophan, threonine), an alditol (e.g. glycerol (glycerine), 1,2-propanediol (propyleneglycol), 1,3-propanediol, 1,3-butanediol) polyethyleneglycol (e.g. PEG400), and mixtures thereof. Any sugar such as mono-, di-, or polysaccharides, or water-soluble glucans, including for example fructose, glucose, mannose, sorbose, xylose, maltose, lactose, sucrose, trehalose, dextran, pullulan, dextrin, cyclodextrin, alfa and beta HPCD, soluble starch, hydroxyethyl starch and carboxymethylcellulose-Na may be used. Sugar alcohol is defined as a C4-C8 hydrocarbon having at least one —OH group and includes, for example, mannitol, sorbitol, inositol, galactitol, dulcitol, xylitol, and arabitol.

A pharmaceutical composition may comprise a chelating agent. The chelating agent may e.g. be selected from salts of ethylenediaminetetraacetic acid (EDTA), citric acid, and aspartic acid, and mixtures thereof.

A pharmaceutical composition may comprise a stabiliser. The stabiliser may e.g. be one or more oxidation inhibitors, aggregation inhibitors, surfactants, and/or one or more protease inhibitors.

The term "aggregate formation" refers to a physical interaction between the polypeptide molecules resulting in formation of oligomers, which may remain soluble, or large visible aggregates that precipitate from the solution. Aggregate formation by a polypeptide during storage of a liquid pharmaceutical composition can adversely affect biological activity of that polypeptide, resulting in loss of therapeutic efficacy of the pharmaceutical composition. Furthermore, aggregate formation may cause other problems such as blockage of tubing, membranes, or pumps when the polypeptide-containing pharmaceutical composition is administered using an infusion system.

A pharmaceutical composition may comprise an amount of an amino acid base sufficient to decrease aggregate formation of the peptide during storage of the composition. The term "amino acid base" refers to one or more amino acids (such as methionine, histidine, imidazole, arginine, lysine, isoleucine, aspartic acid, tryptophan, threonine), or analogues thereof. Any amino acid may be present either in its free base form or in its salt form. Any stereoisomer (i.e., L, D, or a mixture thereof) of the amino acid base may be present.

Methionine (or other sulphuric amino acids or amino acid analogues) may be added to inhibit oxidation of methionine residues to methionine sulfoxide when the peptide is a polypeptide comprising at least one methionine residue susceptible to such oxidation. Any stereoisomer of methionine (L or D) or combinations thereof can be used.

A pharmaceutical composition may comprise a stabiliser selected from the group of high molecular weight polymers or low molecular compounds. The stabiliser may e.g. be selected from polyethylene glycol (e.g. PEG 3350), polyvinyl alcohol (PVA), polyvinylpyrrolidone, carboxy-/hydroxycellulose or derivates thereof (e.g. HPC, HPC-SL, HPC-L and HPMC), cyclodextrins, sulphur-containing substances as monothioglycerol, thioglycolic acid and 2-methylthioethanol, and different salts (e.g. sodium chloride).

A pharmaceutical composition may comprise additional stabilising agents such as, but not limited to, methionine and EDTA, which protect the polypeptide against methionine oxidation, and a nonionic surfactant, which protects the polypeptide against aggregation associated with freeze-thawing or mechanical shearing.

A pharmaceutical composition may comprise one or more surfactants, for example a surfactant, at least one surfactant, or two different surfactants. The term "surfactant" refers to any molecules or ions that are comprised of a water-soluble (hydrophilic) part, and a fat-soluble (lipophilic) part. The surfactant may e.g. be selected from the group consisting of anionic surfactants, cationic surfactants, nonionic surfactants, and/or zwitterionic surfactants.

A pharmaceutical composition may comprise one or more protease inhibitors, such as, e.g., EDTA (ethylenediamine tetraacetic acid), and/or benzamidineHCl.

Additional, optional, ingredients of a pharmaceutical composition include, e.g., wetting agents, emulsifiers, antioxidants, bulking agents, metal ions, oily vehicles, proteins (e.g., human serum albumin, gelatine), and/or a zwitterion (e.g., an amino acid such as betaine, taurine, arginine, glycine, lysine and histidine).

Still further, a pharmaceutical composition may be formulated as is known in the art of oral formulations of insulinotropic compounds, e.g. using any one or more of the formulations described in WO 2008/145728.

An administered dose may contain from 0.01 mg-100 mg of the derivative, or from 0.01-50 mg, or from 0.01-20 mg, or from 0.01 mg-10 mg of the derivative.

The derivative may be administered in the form of a pharmaceutical composition. It may be administered to a patient in need thereof at several sites, for example, at topical sites such as skin or mucosal sites; at sites which bypass absorption such as in an artery, in a vein, or in the heart; and at sites which involve absorption, such as in the skin, under the skin, in a muscle, or in the abdomen.

The route of administration may be, for example, lingual; sublingual; buccal; in the mouth; oral; in the stomach; in the intestine; nasal; pulmonary, such as through the bronchioles, the alveoli, or a combination thereof; parenteral, epidermal; dermal; transdermal; conjunctival; uretal; vaginal; rectal; and/or ocular. In a particular embodiment the route of administration is per oral.

A composition may be administered in several dosage forms, for example as a solution; a suspension; an emulsion; a microemulsion; multiple emulsions; a foam; a salve; a paste; a plaster; an ointment; a tablet; a coated tablet; a chewing gum; a rinse; a capsule such as hard or soft gelatine capsules; a suppositorium; a rectal capsule; drops; a gel; a spray; a powder; an aerosol; an inhalant; eye drops; an ophthalmic ointment; an ophthalmic rinse; a vaginal pessary; a vaginal ring; a vaginal ointment; an injection solution; an in situ transforming solution such as in situ gelling, setting, precipitating, and in situ crystallisation; an infusion solution; or as an implant. A composition may further be compounded in a drug carrier or drug delivery system, e.g. in order to improve stability, bioavailability, and/or solubility. A composition may be attached to such system through covalent, hydrophobic, and/or electrostatic interactions. The purpose of such compounding may be, e.g., to decrease adverse effects, achieve chronotherapy, and/or increase patient compliance.

A composition may also be used in the formulation of controlled, sustained, protracting, retarded, and/or slow release drug delivery systems.

Parenteral administration may be performed by subcutaneous, intramuscular, intraperitoneal, or intravenous injection by means of a syringe, optionally a pen-like syringe, or by means of an infusion pump.

A composition may be administered nasally in the form of a solution, a suspension, or a powder; or it may be administered pulmonally in the form of a liquid or powder spray.

Transdermal administration is a still further option, e.g. by needle-free injection, from a patch such as an iontophoretic patch, or via a transmucosal route, e.g. buccally.

A composition may be a stabilised formulation. The term "stabilised formulation" refers to a formulation with increased physical and/or chemical stability, preferably both. In general, a formulation must be stable during use and storage (in compliance with recommended use and storage conditions) until the expiration date is reached.

The term "physical stability" refers to the tendency of the polypeptide to form biologically inactive and/or insoluble aggregates as a result of exposure to thermo-mechanical stress, and/or interaction with destabilising interfaces and surfaces (such as hydrophobic surfaces). The physical stability of an aqueous polypeptide formulation may be evaluated by means of visual inspection, and/or by turbidity measurements after exposure to mechanical/physical stress (e.g. agitation) at different temperatures for various time periods. Alternatively, the physical stability may be evaluated using a spectroscopic agent or probe of the conformational status of the polypeptide such as e.g. Thioflavin T or "hydrophobic patch" probes.

The term "chemical stability" refers to chemical (in particular covalent) changes in the polypeptide structure leading to formation of chemical degradation products potentially having a reduced biological potency, and/or increased immunogenic effect as compared to the intact polypeptide. The chemical stability can be evaluated by measuring the amount of chemical degradation products at various time-points after exposure to different environmental conditions, e.g. by SEC-HPLC, and/or RP-HPLC.

The treatment with a derivative according to the present invention may also be combined with one or more additional pharmacologically active substances, e.g. selected from antidiabetic agents, antiobesity agents, appetite regulating agents, antihypertensive agents, agents for the treatment and/or prevention of complications resulting from or associated with diabetes and agents for the treatment and/or prevention of complications and disorders resulting from or associated with obesity. Examples of these pharmacologically active substances are: Insulin, sulphonylureas, biguanides, meglitinides, glucosidase inhibitors, glucagon antagonists, DPP-IV (dipeptidyl peptidase-IV) inhibitors, inhibitors of hepatic enzymes involved in stimulation of gluconeogenesis and/or glycogenolysis, glucose uptake modulators, compounds modifying the lipid metabolism such as antihyperlipidemic agents as HMG CoA inhibitors (statins), Gastric Inhibitory Polypeptides (GIP analogs), compounds lowering food intake, RXR agonists and agents acting on the ATP-dependent potassium channel of the β-cells; Cholestyramine, colestipol, clofibrate, gemfibrozil, lovastatin, pravastatin, simvastatin, probucol, dextrothyroxine, neteglinide, repaglinide; β-blockers such as alprenolol, atenolol, timolol, pindolol, propranolol and metoprolol, ACE (angiotensin converting enzyme) inhibitors such as benazepril, captopril, enalapril, fosinopril, lisinopril, alatriopril, quinapril and ramipril, calcium channel blockers such as nifedipine, felodipine, nicardipine, isradipine, nimodipine, diltiazem and verapamil, and α-blockers such as doxazosin, urapidil, prazosin and terazosin; CART (cocaine amphetamine regulated transcript) agonists, NPY (neuropeptide Y) antagonists, PYY agonists, Y2 receptor agonists, Y4 receptor agonits, mixed Y2/Y4 receptor agonists, MC4 (melanocortin 4) agonists, orexin antagonists, TNF (tumor necrosis factor) agonists, CRF (corticotropin releasing factor) agonists, CRF BP (corticotropin releasing factor binding protein) antagonists, urocortin agonists, β3 agonists, oxyntomodulin and analogues, MSH (melanocyte-stimulating hormone) agonists, MCH (melanocyte-concentrating hormone) antagonists, CCK (cholecystokinin) agonists, serotonin re-uptake inhibitors, serotonin and noradrenaline re-uptake inhibitors, mixed serotonin and noradrenergic compounds, 5HT (serotonin) agonists, bombesin agonists, galanin antagonists, growth hormone, growth hormone releasing compounds, TRH (thyreotropin releasing hormone) agonists, UCP 2 or 3 (uncoupling protein 2 or 3) modulators, leptin agonists, DA agonists (bromocriptin, doprexin), lipase/amylase inhibitors, RXR (retinoid X receptor) modulators, TR β agonists; histamine $H_3$ antagonists, Gastric Inhibitory Polypeptide agonists or antagonists (GIP analogs), gastrin and gastrin analogs.

The treatment with a derivative according to this invention may also be combined with a surgery that influences the glucose levels, and/or lipid homeostasis such as gastric banding or gastric bypass.

Pharmaceutical Indications

The present invention also relates to a derivative of the invention for use as a medicament.

In particular embodiments, the derivative of the invention may be used for the following medical treatments, all preferably relating one way or the other to diabetes:

(i) prevention and/or treatment of all forms of diabetes, such as hyperglycemia, type 2 diabetes, impaired glucose tolerance, type 1 diabetes, non-insulin dependent diabetes, MODY (maturity onset diabetes of the young), gestational diabetes, and/or for reduction of HbA1C;

(ii) delaying or preventing diabetic disease progression, such as progression in type 2 diabetes, delaying the progression of impaired glucose tolerance (IGT) to insulin requiring type 2 diabetes, and/or delaying the progression of non-insulin requiring type 2 diabetes to insulin requiring type 2 diabetes;

(iii) improving β-cell function, such as decreasing β-cell apoptosis, increasing β-cell function and/or β-cell mass, and/or for restoring glucose sensitivity to β-cells;

(iv) prevention and/or treatment of cognitive disorders;

(v) prevention and/or treatment of eating disorders, such as obesity, e.g. by decreasing food intake, reducing body weight, suppressing appetite, inducing satiety; treating or preventing binge eating disorder, bulimia nervosa, and/or obesity induced by administration of an antipsychotic or a steroid; reduction of gastric motility; and/or delaying gastric emptying;

(vi) prevention and/or treatment of diabetic complications, such as neuropathy, including peripheral neuropathy; nephropathy; or retinopathy;

(vii) improving lipid parameters, such as prevention and/or treatment of dyslipidemia, lowering total serum lipids; lowering HDL; lowering small, dense LDL; lowering VLDL: lowering triglycerides; lowering cholesterol; increasing HDL; lowering plasma levels of lipoprotein a (Lp(a)) in a human; inhibiting generation of apolipoprotein a (apo(a)) in vitro and/or in vivo;

(iix) prevention and/or treatment of cardiovascular diseases, such as syndrome X; atherosclerosis; myocardial infarction; coronary heart disease; stroke, cerebral ischemia; an early cardiac or early cardiovascular disease, such as left ventricular hypertrophy; coronary artery disease; essential hypertension; acute hypertensive emergency; cardiomyopathy; heart insufficiency; exercise tolerance; chronic heart failure; arrhythmia; cardiac dysrhythmia; syncopy; atheroschlerosis; mild chronic heart failure; angina pectoris; cardiac bypass reocclusion; intermittent claudication (atheroschlerosis oblitterens); diastolic dysfunction; and/or systolic dysfunction;

(ix) prevention and/or treatment of gastrointestinal diseases, such as inflammatory bowel syndrome; small bowel syndrome, or Crohn's disease; dyspepsia; and/or gastric ulcers;

(x) prevention and/or treatment of critical illness, such as treatment of a critically ill patient, a critical illness polynephropathy (CIPNP) patient, and/or a potential CIPNP patient; prevention of critical illness or development of CIPNP; prevention, treatment and/or cure of systemic inflammatory response syndrome (SIRS) in a patient; and/or for the prevention or reduction of the likelihood of a patient suffering from bacteraemia, septicaemia, and/or septic shock during hospitalisation; and/or (xi) prevention and/or treatment of polycystic ovary syndrome (PCOS).

In a particular embodiment, the indication is selected from the group consisting of (i)-(iii) and (v)-(iix), such as indications (i), (ii), and/or (iii); or indication (v), indication (vi), indication (vii), and/or indication (iix).

In another particular embodiment, the indication is (i). In a further particular embodiment the indication is (v). In a still further particular embodiment the indication is (iix).

The following indications are particularly preferred: Type 2 diabetes, and/or obesity.

PARTICULAR EMBODIMENTS

The following are particular embodiments of the invention:
1. A derivative of a GLP-1 analogue,
which analogue comprises a first K residue at a position corresponding to position 18 of GLP-1(7-37) (SEQ ID NO: 1), a second K residue at another position, and a maximum of twelve amino acid changes as compared to GLP-1 (7-37), which derivative comprises two albumin binding moieties attached to said first and second K residue, respectively, wherein
the albumin binding moiety comprises a protracting moiety selected from Chem. 1, Chem. 2, and Chem. 3:

HOOC—(CH$_2$)$_x$—CO—*    Chem. 1:

HOOC—C$_6$H$_4$—O—(CH$_2$)$_y$—CO—*    Chem. 2:
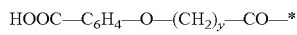

R$^2$—C$_6$H$_4$—(CH$_2$)$_z$—CO—*,    Chem. 3:
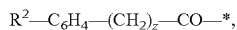

in which x is an integer in the range of 6-18, y is an integer in the range of 3-17, z is an integer in the range of 1-5, and R$^2$ is a group having a molar mass not higher than 150 Da;
with the proviso that when the protracting moiety is Chem. 1, the albumin binding moiety further comprises a linker of formula Chem. 4:

Chem. 4
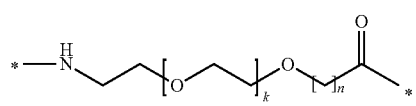

wherein k is an integer in the range of 1-5, and n is an integer in the range of 1-5; or a pharmaceutically acceptable salt, amide, or ester thereof.

2. A derivative of a GLP-1 analogue,
which analogue comprises a first K residue at a position corresponding to position 18 of GLP-1(7-37) (SEQ ID NO: 1), a second K residue at another position, and a maximum of twelve amino acid changes as compared to GLP-1(7-37), which derivative comprises two albumin binding moieties attached to said first and second K residue, respectively, wherein
the albumin binding moiety comprises a protracting moiety, wherein
the protracting moiety is Chem. 2:

HOOC—C$_6$H$_4$—O—(CH$_2$)$_y$—CO—*    Chem. 2:
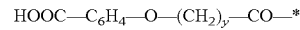

in which y is an integer in the range of 3-17;
or a pharmaceutically acceptable salt, amide, or ester thereof.

3. A derivative of a GLP-1 analogue,
which analogue comprises a first K residue at a position corresponding to position 18 of GLP-1(7-37) (SEQ ID NO: 1), a second K residue at another position, and a maximum of twelve amino acid changes as compared to GLP-1 (7-37), which derivative comprises two albumin binding moieties attached to said first and second K residue, respectively, wherein
the albumin binding moiety comprises a protracting moiety, wherein
the protracting moiety is Chem. 3:

R$^2$—C$_6$H$_4$—(CH$_2$)$_z$—CO—*,    Chem. 3:
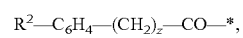

in which z is an integer in the range of 1-5, and R$^2$ is a group having a molar mass not higher than 150 Da;
or a pharmaceutically acceptable salt, amide, or ester thereof.

4. The derivative of any of embodiments 2-3, wherein the albumin binding moiety further comprises a linker.

5. The derivative of embodiment 4, wherein the linker comprises i) a Glu di-radical; and/or ii) a linker of formula Chem. 4:

Chem. 4
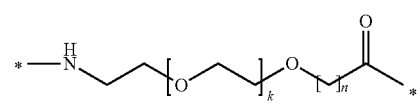

wherein k is an integer in the range of 1-5, and n is an integer in the range of 1-5.

6. The derivative of embodiment 5, wherein the Glu di-radical is selected from Chem. 5a, and/or Chem. 5b:

Chem. 5a
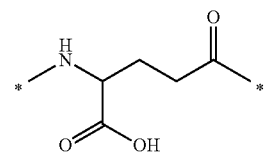

Chem. 5b
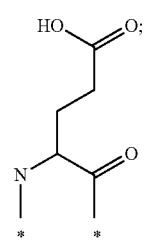

preferably Chem. 5a.

7. A derivative of a GLP-1 analogue,
which analogue comprises a first K residue at a position corresponding to position 18 of GLP-1(7-37) (SEQ ID NO: 1), a second K residue at another position, and a maximum of twelve amino acid changes as compared to GLP-1 (7-37), which derivative comprises two albumin binding moieties attached to said first and second K residue, respectively, via a linker, wherein the albumin binding moiety comprises i) a protracting moiety of formula Chem. 1:

    Chem. 1:

in which x is an integer in the range of 6-18; and
ii) a linker comprising Chem. 4:

    Chem. 4 wherein k is an integer in the range of 1-5, and n is an integer in the range of 1-5; or a pharmaceutically acceptable salt, amide, or ester thereof.

8. A derivative of a GLP-1 analogue,
which analogue comprises a first K residue at a position corresponding to position 18 of GLP-1(7-37) (SEQ ID NO: 1), a second K residue at another position, and a maximum of twelve amino acid changes as compared to GLP-1 (7-37),
which derivative comprises two protracting moieties attached to said first and second K residue, respectively, via a linker, wherein
the protracting moiety is selected from Chem. 1, Chem. 2, and Chem. 3:

    Chem. 1:

    Chem. 2:

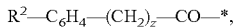    Chem. 3:

in which x is an integer in the range of 6-18, y is an integer in the range of 3-17, z is an integer in the range of 1-5, and $R^2$ is a group having a molar mass not higher than 150 Da; and
the linker comprises

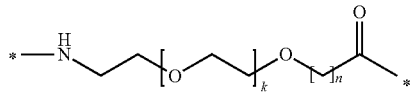    Chem. 4 wherein k is an integer in the range of 1-5, and n is an integer in the range of 1-5;
or a pharmaceutically acceptable salt, amide, or ester thereof.

9. The derivative of any of embodiments 1, and -8, wherein Chem. 4 is a first linker element.
10. The derivative of embodiment 9, wherein k is 1.
11. The derivative of any of embodiments 9-10, wherein n is 1.
12. The derivative of any of embodiments 9-11, wherein Chem. 4 is included m times, wherein m is an integer in the range of 1-10.
13. The derivative of embodiment 12, wherein m is an integer in the range of 1-6.
14. The derivative of any of embodiments 12-13, wherein m is 1, 2, 4, or 6.
15. The derivative of any of embodiments 12-14, wherein m is 1.
16. The derivative of any of embodiments 12-14, wherein m is 2.
17. The derivative of any of embodiments 12-14, wherein m is 4.
18. The derivative of any of embodiments 12-14, wherein m is 6.
19. The derivative of any of embodiments 12-14, and 16-18, wherein, when m is different from 1, the Chem. 4 elements are interconnected via amide bond(s).
20. The derivative of any of embodiments 8-19, wherein the linker comprises a second, optional, linker element.
21. The derivative of embodiment 20, wherein the second linker element is selected from Chem. 5a and Chem. 5b:

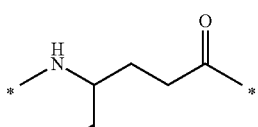    Chem. 5a

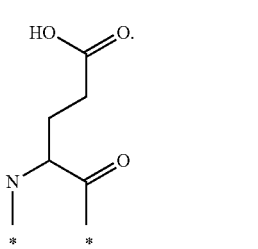    Chem. 5b

22. The derivative of any of embodiments 20-21, wherein the second linker element is Chem. 5a.
23. The derivative of embodiment 22, wherein Chem. 5a is included p times, wherein p is 0, or an integer in the range of 1-3.
24. The derivative of embodiment 23, wherein p is 0.
25. The derivative of embodiment 23, wherein p is 1.
26. The derivative of embodiment 23, wherein p is 2.
27. The derivative of embodiment 23, wherein p is 3.
28. The derivative any of embodiments 21-27, wherein Chem. 5a is a di-radical of L-Glu or D-Glu.
29. The derivative of embodiment 28, wherein Chem. 5a is a di-radical of L-Glu.
30. The derivative of any of embodiments 23-29, wherein, when p is different from 0 and different from 1, the Chem. 5a elements are interconnected via amide bond(s).
31. The derivative of any of embodiments 23-30, wherein the linker comprises a third, optional, linker element.
32. The derivative of embodiment 31, wherein the third linker element is

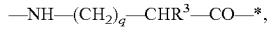    Chem. 6:

in which q is an integer in the range of 2-12, and $R^3$ is hydrogen (H).
33. The derivative of embodiment 32, wherein q is 4.
34. The derivative of embodiment 32, wherein q is 6.
35. The derivative of embodiment 32, wherein q is 10.
36. The derivative of any of embodiments 32-35, wherein $R^3$ is hydrogen (H).
37. The derivative of any of embodiments 32-36, wherein Chem. 6 is a di-radical of amino hexanoic acid, amino octanoic acid, or amino dodecanoic acid.
38. The derivative of any of embodiments 23-30, wherein the linker consists of m times Chem. 4 and p times Chem. 5a.

39. The derivative of embodiment 38, wherein (m,p) is (2,0); (2,2); (2,1); (2,3); (4,0); (4,1); (6,1); (1,1); or (1,2).
40. The derivative of any of embodiments 38-39, wherein (m,p) is (2,0).
41. The derivative of any of embodiments 38-39, wherein (m,p) is (2,2).
42. The derivative of any of embodiments 38-39, wherein (m,p) is (2,1).
43. The derivative of any of embodiments 38-39, wherein (m,p) is (2,3).
44. The derivative of any of embodiments 38-39, wherein (m,p) is (4,0).
45. The derivative of any of embodiments 38-39, wherein (m,p) is (4,1).
46. The derivative of any of embodiments 38-39, wherein (m,p) is (6,1).
47. The derivative of any of embodiments 38-39, wherein (m,p) is (1,1).
48. The derivative of any of embodiments 38-39, wherein (m,p) is (1,2).
49. The derivative of any of embodiments 38-39-48, wherein the m Chem. 4 elements and the p Chem. 5a elements are interconnected via amide bonds.
50. The derivative of any of embodiments 32-37, wherein the linker consists of m times Chem. 4, p times Chem. 5a, and Chem. 6.
51. The derivative of embodiment 50, wherein the m Chem. 4 elements, the p Chem. 5a elements, and the Chem. 6 element are interconnected via amide bonds.
52. The derivative of any of embodiments 1, 4-7, and 8-51, wherein the linker and the protracting moiety are interconnected via an amide bond.
53. The derivative of any of embodiments 1, 4-7, and 8-52, wherein the linker and the GLP-1 analogue are interconnected via an amide bond.
54. The derivative of any of embodiments 1, 4-7, and 8-53, wherein the linker is attached to the epsilon-amino group of the first or the second K residue.
55. The derivative of any of embodiments 1, 4-7, and 8-54, wherein the linker has from 6 to 41 C-atoms.
56. The derivative of any of embodiments 1, 4-7, and 8-55, wherein the linker has 11C-atoms.
57. The derivative of any of embodiments 1, 4-7, and 8-55, wherein the linker has 12 C-atoms.
58. The derivative of any of embodiments 1, 4-7, and 8-55, wherein the linker has 16 C-atoms.
59. The derivative of any of embodiments 1, 4-7, and 8-555, wherein the linker has 17 C-atoms.
60. The derivative of any of embodiments 1, 4-7, and 8-55, wherein the linker has 22 C-atoms.
61. The derivative of any of embodiments 1, 4-7, and 8-55, wherein the linker has 24 C-atoms.
62. The derivative of any of embodiments 1, 4-7, and 8-55, wherein the linker has 27 C-atoms.
63. The derivative of any of embodiments 1, 4-7, and 8-55, wherein the linker has 28 C-atoms.
64. The derivative of any of embodiments 1, 4-7, and 8-55, wherein the linker has 29 C-atoms.
65. The derivative of any of embodiments 1, 4-7, and 8-55, wherein the linker has 30 C-atoms.
66. The derivative of any of embodiments 1, 4-7, and 8-55, wherein the linker has 34 C-atoms.
67. The derivative of any of embodiments 1, 4-7, and 8-55, wherein the linker has 41 C-atoms.
68. The derivative of any of embodiments 1, 4-7, and 8-67, wherein the linker has from 4 to 28 hetero atoms; preferably from 8 to 28 hetero atoms; such as 8, 11, 12, 16, 17, 18, 20, or 28 hetero atoms.
69. The derivative of any of embodiments 1, 4-7, and 8-67, wherein the linker has 8 hetero atoms.
70. The derivative of any of embodiments 1, 4-7, and 8-67, wherein the linker has 11 hetero atoms.
71. The derivative of any of embodiments 1, 4-7, and 8-67, wherein the linker has 12 hetero atoms.
72. The derivative of any of embodiments 1, 4-7, and 8-67, wherein the linker has 16 hetero atoms.
73. The derivative of any of embodiments 1, 4-7, and 8-67, wherein the linker has 17 hetero atoms.
74. The derivative of any of embodiments 1, 4-7, and 8-67, wherein the linker has 18 hetero atoms.
75. The derivative of any of embodiments 1, 4-7, and 8-67, wherein the linker has hetero atoms.
76. The derivative of any of embodiments 1, 4-7, and 8-67, wherein the linker has 28 hetero atoms.
77. The derivative of any of embodiments 1, 4-7, and 8-67, wherein the hetero atoms are N—, and/or O-atoms.
78. The derivative of any of embodiments 1, 4-7, and 8-77, wherein the linker has from 1 to 7 N-atoms.
79. The derivative of any of embodiments 1, 4-7, and 8-78, wherein the linker has 2, 3, 4, 5, or 7 N-atoms.
80. The derivative of any of embodiments 1, 4-7, and 8-78, wherein the linker has 2 N-atoms.
81. The derivative of any of embodiments 1, 4-7, and 8-78, wherein the linker has 3 N-atoms.
82. The derivative of any of embodiments 1, 4-7, and 8-78, wherein the linker has 4 N-atoms.
83. The derivative of any of embodiments 1, 4-7, and 8-78, wherein the linker has 5 N-atoms.
84. The derivative of any of embodiments 1, 4-7, and 8-78, wherein the linker has 7 N-atoms.
85. The derivative of any of embodiments 1, 4-7, and 8-84, wherein the linker has from 3 to 21 O-atoms; preferably from 6 to 21 O-atoms; such as 6, 7, 9, 12, 13, 15, or 21 O-atoms.
86. The derivative of any of embodiments 1, 4-7, and 8-85, wherein the linker has 6 O-atoms.
87. The derivative of any of embodiments 1, 4-7, and 8-85, wherein the linker has 7 O-atoms.
88. The derivative of any of embodiments 1, 4-7, and 8-85, wherein the linker has 9 O-atoms.
89. The derivative of any of embodiments 1, 4-7, and 8-85, wherein the linker has 12 O-atoms.
90. The derivative of any of embodiments 1, 4-7, and 8-85, wherein the linker has 13 O-atoms.
91. The derivative of any of embodiments 1, 4-7, and 8-85, wherein the linker has 15 O-atoms.
92. The derivative of any of embodiments 1, 4-7, and 8-85, wherein the linker has 21 O-atoms.
93. The derivative of any of embodiments 1, 4-7, 8-14, 16, 19, 20-24, 39-41, 50, 53-56, 58, 68-69, 77-80, and 85-86, wherein the linker consists of two times Chem. 4, interconnected via an amide bond, the linker being connected at its *—NH end to the *—CO end of the protracting moiety, and at its *—CO end to the epsilon amino group of the first or the second K residue of the GLP-1 analogue.
94. The derivative of any of the embodiments 1, 4-7, 8-14, 17, 20-24, 38-39, 44, 49, 52-55, 61, 68, 73, 77-79, 83, 85, and 89, wherein the linker consists of four times Chem. 4, interconnected via amide bonds, the linker being connected at its *—NH end to the *—CO end of the protracting moiety, and at its *—CO end to the epsilon amino group of the first or the second K residue of the GLP-1 analogue.

95. The derivative of any of the embodiments 1, 4-7, 8-14, 16, 19, 20-23, 26, 28-30, 38-39, 41, 49, 52-55, 60, 68, 72, 77-79, 82, and 89, wherein the linker consists of two times Chem. 5a and two times Chem. 4, interconnected via amide bonds and in the sequence indicated, the linker being connected at its *—NH end to the *—CO end of the protracting moiety, and at its *—CO end to the epsilon amino group of the first or the second K residue of the GLP-1 analogue.

96. The derivative of any of the embodiments 1, 4-7, 8-14, 16, 19, 20-23, 25, 28-30, 38-39, 48, 49, 52-55, 59, 68, 71, 77-79, 81, 85, and 88, wherein the linker consists of two times Chem. 4 and one time Chem. 5a, interconnected via amide bonds and in the sequence indicated, the linker being connected at its *—NH end to the *—CO end of the protracting moiety, and at its *—CO end to the epsilon amino group of the first or the second K residue of the GLP-1 analogue.

97. The derivative of any of the embodiments 1, 4-7, 8-14, 16, 19, 20-23, 27, 28-30, 38-39, 43, 49, 52-55, 62, 68, 75, 77-79, 83, 85, and 91, wherein the linker consists of three times Chem. 5a and two times Chem. 4, interconnected amide bonds and in the sequence indicated, the linker being connected at its *—NH end to the *—CO end of the protracting moiety, and at its *—CO end to the epsilon amino group of the first or the second K residue of the GLP-1 analogue.

98. The derivative of any of the embodiments 1, 4-7, 8-14, 16, 19, 20-23, 25, 28-30, 38-39, 42, 49, 52-55, 59, 68, 71, 77-79, 81, 85, and 88, wherein the linker consists of one time Chem. 5a and two times Chem. 4, interconnected via amide bonds and in the sequence indicated, the linker being connected at its *—NH end to the *—CO end of the protracting moiety, and at its *—CO end to the epsilon amino group of the first or the second K residue of the GLP-1 analogue.

99. The derivative of any of the embodiments 1, 4-7, 8-14, 16, 19, 20-23, 26, 28-30, 38-39, 41, 49, 52-55, 60, 68, 72, 77-79, 82, 85, and 89, wherein the linker consists of one time Chem. 5a, two times Chem. 4, and one time Chem. 5a, interconnected via amide bonds and in the sequence indicated, the linker being connected at its *—NH end to the *—CO end of the protracting moiety, and at its *—CO end to the epsilon amino group of the first or the second K residue of the GLP-1 analogue.

100. The derivative of any of the embodiments 1, 4-7, 8-14, 17, 19, 20-23, 25, 38-39, 45, 49, 52-55, 64, 68, 75, 77-79, 83, 85, and 91, wherein the linker consists of one time Chem. 5a and four times Chem. 4, interconnected via amide bonds and in the sequence indicated, the linker being connected at its *—NH end to the *—CO end of the protracting moiety, and at its *—CO end to the epsilon amino group of the first or the second K residue of the GLP-1 analogue.

101. The derivative of any of the embodiments 1, 4-7, 8-14, 18-19, 20-23, 25, 28-29, 38-39, 46, 49, 52-55, 67, 68, 76, 77-79, 84, 85, and 92, wherein the linker consists of one time Chem. 5a and six times Chem. 4, interconnected via amide bonds and in the sequence indicated, the linker being connected at its *—NH end to the *—CO end of the protracting moiety, and at its *—CO end to the epsilon amino group of the first or the second K residue of the GLP-1 analogue.

102. The derivative of any of the embodiments 1, 4-7, 8-15, 20-23, 25, 28-29, 38-39, 47, 49, 52-55, 57, 68-69, 77-80, and 85-86, wherein the linker consists of one time Chem. 5a and one time Chem. 4, interconnected via amide bonds and in the sequence indicated, the linker being connected at its *—NH end to the *—CO end of the protracting moiety, and at its *—CO end to the epsilon amino group of the first or the second K residue of the GLP-1 analogue.

103. The derivative of any of embodiments 1, 4-7, 8-14, 16, 19, 20-23, 25, 28-29, 38-39, 42, 49, 52-55, 59, 68, 71, 77-79, 81, 85, and 88, wherein the linker consists of one time Chem. 4, one time Chem. 5a, and one time Chem. 4, interconnected via amide bonds and in the sequence indicated, the linker being connected at its *—NH end to the *—CO end of the protracting moiety, and at its *—CO end to the epsilon amino group of the first or the second K residue of the GLP-1 analogue.

104. The derivative of any of embodiments 1, 4-7, 8-15, 20-23, 26, 28-30, 38-39, 41, 49, 52-55, 58, 68, 71, 77-79, 81, 85, and 88, wherein the linker consists of one time Chem. 5a, one time Chem. 4, and one time Chem. 5a, interconnected via amide bonds and in the sequence indicated, the linker being connected at its *—NH end to the *—CO end of the protracting moiety, and at its *—CO end to the epsilon amino group of the first or the second K residue of the GLP-1 analogue.

105. The derivative of any of embodiments 1, 4-7, 8-14, 16, 19, 20-23, 26, 28-32, 35-36, 37, 50-55, 66, 68, 74, 77-79, 83, 85, and 90, wherein the linker consists of one time Chem. 5a, one time Chem. 6, in which q is 10 and $R^3$ is H, one time Chem. 5a, and two times Chem. 4, interconnected via amide bonds and in the sequence indicated, the linker being connected at its *—NH end to the *—CO end of the protracting moiety, and at its *—CO end to the epsilon amino group of the first or the second K residue of the GLP-1 analogue.

106. The derivative of any of embodiments 1, 4-7, 8-14, 16, 19, 20-23, 26, 28-33, 36, 37, 50-55, 63, 68, 74, 77-79, 83, 85, and 90, wherein the linker consists of one time Chem. 5a, one time Chem. 6, in which q is 4 and $R^3$ is H, one time Chem. 5a, and two times Chem. 4, interconnected via amide bonds and in the sequence indicated, the linker being connected at its *—NH end to the *—CO end of the protracting moiety, and at its *—CO end to the epsilon amino group of the first or the second K residue of the GLP-1 analogue.

107. The derivative of any of embodiments 1, 4-7, 8-14, 16, 19, 20-23, 26, 28-32, 34, 36, 37, 50-55, 65, 68, 74, 77-79, 83, 85, and 90, wherein the linker consists of one time Chem. 5a, one time Chem. 6, in which q is 6 and $R^3$ is H, one time Chem. 5a, and two times Chem. 4, interconnected via amide bonds and in the sequence indicated, the linker being connected at its *—NH end to the *—CO end of the protracting moiety, and at its *—CO end to the epsilon amino group of the first or the second K residue of the GLP-1 analogue.

108. The derivative of any of embodiments 1, 7, and 8-107, wherein the protracting moiety is Chem. 1.

109. The derivative of embodiment 108, wherein x is an even number.

110. The derivative of any of embodiments 108-109, wherein x is an integer in the range of 10-16.

111. The derivative of any of embodiments 108-110, wherein x is 10.

112. The derivative of any of embodiments 108-110, wherein x is 12.

113. The derivative of any of embodiments 108-110, wherein x is 14.

114. The derivative of any of embodiments 108-110, wherein x is 16.

115. The derivative of any of embodiments 1-107, wherein the protracting moiety is Chem. 2.

116. The derivative of embodiment 115, wherein y is an odd number.

117. The derivative of any of embodiments 115-116, wherein y is an integer in the range of 7-11.

118. The derivative of any of embodiments 115-118, wherein y is an integer in the range of 7-9.
119. The derivative of any of embodiments 115-118, wherein y is 7.
120. The derivative of any of embodiments 115-118, wherein y is 8.
121. The derivative of any of embodiments 115-118, wherein y is 9.
122. The derivative of any of embodiments 1-107, wherein the protracting moiety is Chem. 3.
123. The derivative of embodiment 122, wherein z is an odd number.
124. The derivative of any of embodiments 122-123, wherein z is 1.
125. The derivative of any of embodiments 122-123, wherein z is 3.
126. The derivative of any of embodiments 122-123, wherein z is 5.
127. The derivative of any of embodiments 122-126, wherein *—$(CH_2)_z$—* refers to linear alkylene.
128. The derivative of any of embodiments 122-126, wherein *—$(CH_2)_z$—* refers to cyclic alkylene.
129. The derivative of any of embodiments 122-128, wherein $R^2$ is a group having a molar mass not higher than 127 Da.
130. The derivative of any of embodiments 122-129, wherein $R^2$ is a group having a molar mass in the range of 1-127 Da (both inclusive).
131. The derivative of any of embodiments 122-130, wherein $R^2$ is a group having a molar mass in the range of 1-111 Da (both inclusive).
132. The derivative of any of embodiments 122-130, wherein $R^2$ is a group having a molar mass in the range of 1-69 Da (both inclusive).
133. The derivative of any of embodiments 122-130, wherein $R^2$ is a group having a molar mass in the range of 1-46 Da (both inclusive).
134. The derivative of any of embodiments 122-130, wherein $R^2$ is a group having a molar mass in the range of 1-35 Da (both inclusive).
135. The derivative of any of embodiments 122-134, wherein $R^2$ is *—H.
136. The derivative of any of embodiments 122-133, wherein $R^2$ is *—$NO_2$.
137. The derivative of any of embodiments 122-132, wherein $R^2$ comprises a halogen atom.
138. The derivative of any of embodiments 122-132, and 137, wherein $R^2$ is *—$CF_3$.
139. The derivative of any of embodiments 122-131, and 137, wherein $R^2$ is *—O—$(C_6H_4)$—F.
140. The derivative of any of embodiments 122-131, 137, and 139, wherein $R^2$ is 4-fluorophenoxy.
141. The derivative of any of embodiments 122-134, and 137, wherein $R^2$ is a halogen radical.
142. The derivative of any of embodiments 122-130, 137, and 141, wherein $R^2$ is *—I.
143. The derivative of any of embodiments 122-134, 137, and 141, wherein $R^2$ is *—Cl.
144. The derivative of any of embodiments 1, 7, and 8-114, wherein Chem. 1 is represented by Chem. 1a:

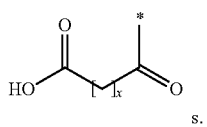

Chem. 1a

145. The derivative of embodiments 1-107, and 115-121, wherein Chem. 2 is represented by Chem. 2a:

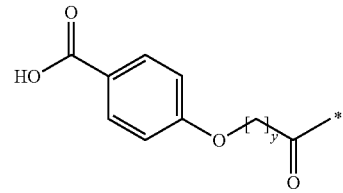

Chem. 2a

146. The derivative of any of embodiments 1-107, and 122-143, wherein Chem. 3 is represented by Chem 3a:

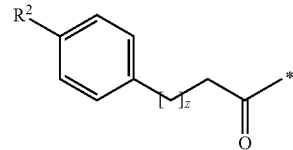

Chem. 3a

147. The derivative of any of embodiments 1-146, wherein the two protracting moieties are substantially identical.
148. The derivative of any of embodiments 1-147, wherein the two protracting moieties have a similarity of at least 0.5; preferably at least 0.6; more preferably at least 0.7, or at least 0.8; even more preferably at least 0.9; or most preferably at least 0.99, such as a similarity of 1.0.
149. The derivative of any of embodiments 1-148, wherein the two linkers are substantially identical.
150. The derivative of any of embodiments 1-149, wherein the two linkers have a similarity of at least 0.5; preferably at least 0.6; more preferably at least 0.7, or at least 0.8; even more preferably at least 0.9; or most preferably at least 0.99, such as a similarity of 1.0.
151. The derivative of any of embodiments 1-150, wherein the two side chains consisting of protracting moiety and linker are substantially identical.
152. The derivative of any of embodiments 1-151, wherein the two side chains consisting of protracting moiety and linker have a similarity of at least 0.5; preferably at least 0.6; more preferably at least 0.7, or at least 0.8; even more preferably at least 0.9; or most preferably at least 0.99, such as a similarity of 1.0.
153. The derivative of any of embodiments 147-152, wherein the two chemical structures to be compared are represented as fingerprints, such as a) ECFP_6 fingerprints; b) UNITY fingerprints; and/or c) MDL fingerprints; and wherein for each of a), b) and c) the Tanimoto coefficient is preferably used for calculating the similarity of the two fingerprints.
154. The derivative of any of embodiments 1-153, wherein the first K residue is designated $K^{18}$.
155. The derivative of any of embodiments 1-154, wherein the second K residue is at a position corresponding to position T of GLP-1 (7-37) (SEQ ID NO: 1).
156. The derivative of any of embodiments 1-155, wherein the second K residue is designated $K^T$.
157. The derivative of any of embodiments 155-156, wherein T is an integer selected from the range of 7-17 or from the range of 19-37.

158. The derivative of any of embodiments 155-157, wherein T is an integer selected from the range of 12-17.
159. The derivative of any of embodiments 155-157, wherein T is selected from the range of 19-37.
160. The derivative of any of embodiments 155-157, and 159, wherein T is selected from the group consisting of 22, 26, 27, 30, 31, 34, and 37.
161. The derivative of any of embodiments 155-157, and 159-160, wherein T=22.
162. The derivative of any of embodiments 155-157, and 159-160, wherein T=26.
163. The derivative of any of embodiments 155-157, and 159-160, wherein T=27.
164. The derivative of any of embodiments 155-157, and 159-160, wherein T=30.
165. The derivative of any of embodiments 155-157, and 159-160, wherein T=31.
166. The derivative of any of embodiments 155-157, and 159-160, wherein T=34.
167. The derivative of any of embodiments 155-157, and 159-160, wherein T=37.
168. The derivative of any of embodiments 1-167, wherein the position corresponding to position 18 of GLP-1 (7-37) (SEQ ID NO: 1) is identified by handwriting and eyeballing.
169. The derivative of any of embodiments 155-168, wherein the position corresponding to position T of GLP-1 (7-37) (SEQ ID NO: 1) is identified by handwriting and eyeballing.
170. The derivative of any of embodiments 1-169, wherein the number of amino acid changes as compared to GLP-1 (7-37) (SEQ ID NO: 1) are identified by handwriting and eyeballing.
171. The derivative of any of embodiments 1-170, wherein the position corresponding to position 18 of GLP-1(7-37) (SEQ ID NO: 1) is identified by use of a standard protein or peptide alignment program.
172. The derivative of any of embodiments 155-171, wherein the position corresponding to position T of GLP-1 (7-37) (SEQ ID NO: 1) is identified by use of a standard protein or peptide alignment program.
173. The derivative of any of embodiments 1-172, wherein the number of amino acid changes as compared to GLP-1 (7-37) (SEQ ID NO: 1) are identified by use of a standard protein or peptide alignment program.
174. The derivative of any of embodiments 171-173, wherein the alignment program is a Needleman-Wunsch alignment.
175. The derivative of any of embodiments 171-174, wherein the default scoring matrix and the default identity matrix is used.
176. The derivative of any of embodiments 171-174, wherein the scoring matrix is BLOSUM62.
177. The derivative of any of embodiments 171-174, wherein the penalty for the first residue in a gap is −10 (minus ten).
178. The derivative of any of embodiments 171-174, wherein the penalties for additional residues in a gap is −0.5 (minus point five).
179. The derivative of any of embodiments 1-178, wherein the analogue comprises no K residues other than the first and the second K residue.
180. The derivative of any of embodiments 1-179, wherein the maximum twelve amino acid change(s) is (are) at one or more positions corresponding to the following positions in GLP-1(7-37) (SEQ ID NO: 1): 7, 8, 12, 18, 22, 23, 25, 26, 27, 30, 31, 34, 35, 36, and 37.
181. The derivative of any of embodiments 1-179, wherein the maximum twelve amino acid change(s) is (are) at one or more positions corresponding to the following positions in GLP-1(7-37) (SEQ ID NO: 1): 7, 8, 18, 22, 23, 25, 26, 27, 30, 31, 34, 35, 36, and 37.
182. The derivative of any of embodiments 1-181, wherein the analogue comprises $K^{18}$.
183. The derivative of any of embodiments 1-180, and 182, wherein the analogue comprises at least one of the following changes: $Imp^7$, $Aib^8$ or $S^8$, $L^{12}$, $K^{22}$ or $E^{22}$, $R^{23}$ or $E^{23}$, $V^{25}$, $R^{26}$ or $H^{26}$ or $V^{26}$, $K^{27}$ or $L^{27}$ or $H^{27}$, $K^{30}$ or $E^{30}$, $K^{31}$ or $H^{31}$, $G^{34}$ or $R^{34}$ or $Q^{34}$ or $Des^{34}$ or $H^{34}$, $Des^{35}$, $Des^{36}$, $K^{37}$ or $Des^{37}$.
184. The derivative of any of embodiments 1-183, wherein the second K residue is $K^{22}$, and wherein the analogue, in addition to the change $K^{18}$, further comprises i) a change selected from $Des^{34}$, $G^{34}$, $R^{34}$, and $Q^{34}$, and ii) a change selected from $R^{26}$, $H^{26}$, and $V^{26}$.
185. The derivative of any of embodiments 1-184, wherein the second K residue is $K^{22}$, and wherein the analogue, in addition to the change $K^{18}$, further comprises $Q^{34}$, and $R^{26}$.
186. The derivative of any of embodiments 1-183, wherein the second K residue is $K^{26}$, and wherein the analogue, in addition to the change $K^{18}$, further comprises a change selected from $G^{34}$, $R^{34}$, $H^{34}$, and $Q^{34}$.
187. The derivative of any of embodiments 1-183, and 186, wherein the second K residue is $K^{26}$, and wherein the analogue, in addition to the change $K^{18}$, further comprises $R^{34}$.
188. The derivative of any of embodiments 1-183, and 186, wherein the second K residue is $K^{26}$, and wherein the analogue, in addition to the change $K^{18}$, further comprises $Q^{34}$.
189. The derivative of any of embodiments 1-183, and 186, wherein the second K residue is $K^{26}$, and wherein the analogue, in addition to the change $K^{18}$, further comprises $H^{34}$.
190. The derivative of any of embodiments 1-183, wherein the second K residue is $K^{27}$, and wherein the analogue, in addition to the change $K^{18}$, further comprises i) a change selected from $Des^{34}$, $G^{34}$, $R^{34}$, and $Q^{34}$, and ii) a change selected from $R^{26}$, $H^{26}$, and $V^{26}$.
191. The derivative of any of embodiments 1-183, and 190, wherein the second K residue is $K^{27}$, and wherein the analogue, in addition to the change $K^{18}$, further comprises $Q^{34}$ and $R^{26}$.
192. The derivative of any of embodiments 1-183, and 190, wherein the second K residue is $K^{27}$, and wherein the analogue, in addition to the change $K^{18}$, further comprises $R^{34}$ and $R^{26}$.
193. The derivative of any of embodiments 1-183, and 190, wherein the second K residue is $K^{27}$, and wherein the analogue, in addition to the change $K^{18}$, further comprises $G^{34}$ and $R^{26}$.
194. The derivative of any of embodiments 1-183, and 190, wherein the second K residue is $K^{27}$, and wherein the analogue, in addition to the change $K^{18}$, further comprises $Q^{34}$ and $H^{26}$.
195. The derivative of any of embodiments 1-183, and 190, wherein the second K residue is $K^{27}$, and wherein the analogue, in addition to the change $K^{18}$, further comprises $R^{34}$ and $H^{26}$.
196. The derivative of any of embodiments 1-183, and 190, wherein the second K residue is $K^{27}$, and wherein the analogue, in addition to the change $K^{18}$, further comprises $R^{34}$ and $V^{26}$.

197. The derivative of any of embodiments 1-183, wherein the second K residue is $K^{30}$ and wherein the analogue, in addition to the change $K^{18}$, further comprises i) a change selected from $Des^{34}$, $G^{34}$, $R^{34}$, and $Q^{34}$, and ii) a change selected from $R^{26}$, $H^{26}$, and $V^{26}$.

198. The derivative of any of embodiments 1-183, and 197, wherein the second K residue is $K^{30}$, and wherein the analogue, in addition to the change $K^{18}$, further comprises $R^{34}$ and $R^{26}$.

199. The derivative of any of embodiments 1-183, and 197, wherein the second K residue is $K^{30}$, and wherein the analogue, in addition to the change $K^{18}$, further comprises $G^{34}$ and $R^{26}$.

200. The derivative of any of embodiments 1-183, and 197, wherein the second K residue is $K^{30}$, and wherein the analogue, in addition to the change $K^{18}$, further comprises $R^{34}$ and $H^{26}$.

201. The derivative of any of embodiments 1-183, wherein the second K residue is $K^{31}$ and wherein the analogue, in addition to the change $K^{18}$, further comprises i) a change selected from $Des^{34}$, $G^{34}$, $R^{34}$, and $Q^{34}$, and ii) a change selected from $R^{26}$, $H^{26}$, and $V^{26}$.

202. The derivative of any of embodiments 1-183, and 201, wherein the second K residue is $K^{31}$, and wherein the analogue, in addition to the change $K^{18}$, further comprises $Des^{34}$ and $R^{26}$.

203. The derivative of any of embodiments 1-183, and 201, wherein the second K residue is $K^{31}$, and wherein the analogue, in addition to the change $K^{18}$, further comprises $Q^{34}$ and $R^{26}$.

204. The derivative of any of embodiments 1-183, and 201, wherein the second K residue is $K^{31}$, and wherein the analogue, in addition to the change $K^{18}$, further comprises $R^{34}$ and $R^{26}$.

205. The derivative of any of embodiments 1-183, and 201, wherein the second K residue is $K^{31}$, and wherein the analogue, in addition to the change $K^{18}$, further comprises $G^{34}$ and $R^{26}$.

206. The derivative of any of embodiments 1-183, and 201, wherein the second K residue is $K^{31}$, and wherein the analogue, in addition to the change $K^{18}$, further comprises $R^{34}$ and $H^{26}$.

207. The derivative of any of embodiments 1-183, and 201, wherein the second K residue is $K^{31}$, and wherein the analogue, in addition to the change $K^{18}$, further comprises $G^{34}$ and $H^{26}$.

208. The derivative of any of embodiments 1-183, wherein the second K residue is $K^{34}$ and wherein the analogue, in addition to the change $K^{18}$, further comprises a change selected from $R^{26}$, $H^{26}$, and $V^{26}$.

209. The derivative of any of embodiments 1-183, and 208, wherein the second K residue is $K^{34}$, and wherein the analogue, in addition to the change $K^{18}$, further comprises $R^{26}$.

210. The derivative of any of embodiments 1-183, wherein the second K residue is $K^{37}$, and wherein the analogue, in addition to the change $K^{18}$, further comprises i) a change selected from $Des^{34}$, $G^{34}$, $R^{34}$, and $Q^{34}$, and ii) a change selected from $R^{26}$, $H^{26}$, and $V^{26}$.

211. The derivative of any of embodiments 1-183, and 210, wherein the second K residue is $K^{37}$, and wherein the analogue, in addition to the change $K^{18}$, further comprises $R^{34}$ and $R^{26}$.

212. The derivative of any of embodiments 1-211, wherein the analogue comprises at least one of the following changes: $Imp^7$, $Aib^8$ or $S^8$, $L^{12}$, $E^{22}$, $R^{23}$ or $E^{23}$, $V^{25}$, $L^{27}$ or $H^{27}$, $E^{30}$, $H^{31}$, $Des^{34}$, $Des^{35}$, $Des^{36}$, or $Des^{37}$.

213. The derivative of any of embodiments 1-212, wherein the analogue comprises at least one of the following changes: $Imp^7$, $Aib^8$, $E^{22}$, $R^{23}$ or $E^{23}$, $V^{25}$, $L^{27}$ or $H^{27}$, $E^{30}$, $H^{31}$, $Des^{34}$, $Des^{35}$, $Des^{36}$, or $Des^{37}$.

214. The derivative of any of embodiments 183-213, wherein if the amino acid residue at the position corresponding to position 34 is deleted ($Des^{34}$), then the amino acid residues at the positions corresponding to positions 35-37 are also deleted ($Des^{35}$, $Des^{36}$, and $Des^{37}$).

215. The derivative of any of embodiments 183-213, wherein if the amino acid residue at the position corresponding to position 35 is deleted ($Des^{35}$), then the amino acid residues at the positions corresponding to positions 36-37 are also deleted ($Des^{36}$ and $Des^{37}$).

216. The derivative of any of embodiments 183-213, wherein if the amino acid residue at the position corresponding to position 36 is deleted ($Des^{36}$), then the amino acid residue at the position corresponding to position 37 is also deleted ($Des^{37}$).

217. The derivative of any of embodiments 1-216, wherein the analogue comprises $Imp^7$.

218. The derivative of any of embodiments 1-217, wherein the analogue comprises $Aib^8$.

219. The derivative of any of embodiments 1-212, and 214-218, wherein the analogue comprises $S^8$.

220. The derivative of any of embodiments 1-212, and 214-219, wherein the analogue comprises $L^{12}$.

221. The derivative of any of embodiments 1-183, and 187-220, wherein the analogue comprises $E^{22}$.

222. The derivative of any of embodiments 1-221, wherein the analogue comprises $R^{23}$.

223. The derivative of any of embodiments 1-221, wherein the analogue comprises $E^{23}$.

224. The derivative of any of embodiments 1-223, wherein the analogue comprises $V^{25}$.

225. The derivative of any of embodiments 1-188, and 197-224, wherein the analogue comprises $L^{27}$.

226. The derivative of any of embodiments 1-188, and 197-224, wherein the analogue comprises $H^{27}$.

227. The derivative of any of embodiments 1-196, and 201-226, wherein the analogue comprises $E^{30}$.

228. The derivative of any of embodiments 1-200, and 208-227, wherein the analogue comprises $H^{31}$.

229. The derivative of any of embodiments 1-228, wherein the analogue comprises $Imp^7$, and/or ($Aib^8$ or $S^8$).

230. The derivative of any of embodiments 1-229, wherein the analogue comprises $Imp^7$, and/or $Aib^8$.

231. The derivative of any of embodiments 1-186, 189-191, 194, 197, 201, 203, 210, and 217-230, wherein the analogue comprises $Q^{34}$.

232. The derivative of any of embodiments 1-184, 186-187, 190, 192, 195-198, 200-201, 204, 206, 210-211, and 217-230, wherein the analogue comprises $R^{34}$.

233. The derivative of any of embodiments 1-184, 186, 190, 193, 197, 199, 201, 205, 207, 210, and 217-230, wherein the analogue comprises $G^{34}$.

234. The derivative of any of embodiments 1-184, 186, 190, 193, 197, 199, 201, 205, 207, 210, and 217-230, wherein the analogue comprises $H^{34}$.

235. The derivative of any of embodiments 1-185, 190-193, 197-199, 201-205, 208-234, wherein the analogue comprises $R^{26}$.

236. The derivative of any of embodiments 1-184, 190, 194-195, 197, 200, 201, 206-208, 210, and 212-233, wherein the analogue comprises $H^{26}$.

237. The derivative of any of embodiments 1-184, 190, 196-197, 201, 208, 210, and 212-233, wherein the analogue comprises $V^{26}$.
238. The derivative of any of embodiments 1-209, and 212-237, wherein the analogue comprises $Des^{37}$.
239. The derivative of any of embodiments 1-208, and 212-238, wherein the analogue comprises $Des^{37}$ and $Des^{36}$.
240. The derivative of any of embodiments 1-208, and 212-239, wherein the analogue comprises $Des^{37}$, $Des^{36}$, and $Des^{35}$.
241. The derivative of any of embodiments 1-184, 190, 197, 201-202, 210, and 212-240, wherein the analogue comprises $Des^{37}$, $Des^{36}$, $Des^{35}$, and $Des^{34}$.
242. The derivative of any of embodiments 1-241, wherein, for determination of the changes in the analogue, the amino acid sequence of the analogue is compared to the amino acid sequence of native GLP-1 (7-37) (SEQ ID NO: 1).
243. The derivative of any of embodiments 1-242, wherein, for determination of a position in an analogue which corresponds to a specified position in native GLP-1 (7-37) (SEQ ID NO: 1), the amino acid sequence of the analogue is compared to the amino acid sequence of native GLP-1(7-37) (SEQ ID NO: 1).
244. The derivative of any of embodiments 1-243, wherein the comparison of the amino acid sequence of the analogue with that of GLP-1(7-37) (SEQ ID NO: 1) is done by handwriting and eyeballing.
245. The derivative of any of embodiments 1-244, wherein the comparison of the amino acid sequence of the analogue with that of GLP-1 (7-37) (SEQ ID NO: 1) is done by use of a standard protein or peptide alignment program.
246. The derivative of embodiment 245, wherein the alignment program is a Needleman-Wunsch alignment.
247. The derivative of any of embodiments 245-246, wherein the default scoring matrix and the default identity matrix is used.
248. The derivative of any of embodiments 245-246, wherein the scoring matrix is BLOSUM62.
249. The derivative of any of embodiments 245-248, wherein the penalty for the first residue in a gap is −10 (minus ten).
250. The derivative of any of embodiments 245-249, wherein the penalties for additional residues in a gap is −0.5 (minus point five).
251. The derivative of any of embodiments 1-250, wherein the position corresponding to any of the indicated positions of GLP-1 (7-37) (SEQ ID NO: 1) is identified by handwriting and eyeballing.
252. The derivative of any of embodiments 1-251, wherein the position corresponding to any of the indicated positions of GLP-1(7-37) (SEQ ID NO: 1) is identified as described for position 18 and position T in any of embodiments 171-172, and 174-178.
253. The derivative of any of embodiments 1-184, 190, 197, 20-202, 210, and 212-252, which is a derivative of GLP-1 (7-33) (amino acids 1-27 of SEQ ID NO: 1).
254. The derivative of any of embodiments 1-252, which is a derivative of GLP-1(7-34) (amino acids 1-28 of SEQ ID NO: 1).
255. The derivative of any of embodiments 1-252, which is a derivative of GLP-1(7-35) (amino acids 1-29 of SEQ ID NO: 1).
256. The derivative of any of embodiments 1-255, wherein the analogue has a maximum of eleven amino acid changes, preferably a maximum of ten amino acid changes.
257. The derivative of any of embodiments 1-255, wherein the analogue has a maximum of nine amino acid changes.
258. The derivative of any of embodiments 1-255, wherein the analogue has a maximum of eight amino acid changes.
259. The derivative of any of embodiment 1-255, wherein the analogue has a maximum of seven amino acid changes.
260. The derivative of any of embodiments 1-255, wherein the analogue has a maximum of six amino acid changes.
261. The derivative of any of embodiment 1-255, wherein the analogue has a maximum of five amino acid changes.
262. The derivative of any of embodiment 1-255, wherein the analogue has a maximum of four amino acid changes.
263. The derivative of any of embodiment 1-255, wherein the analogue has a maximum of three amino acid changes.
264. The derivative of any of embodiment 1-255, wherein the analogue has a maximum of two amino acid changes.
265. The derivative of any of embodiments 1-255, wherein the analogue has a minimum of one amino acid modification.
266. The derivative of any of embodiments 1-255, wherein the analogue has a minimum of two amino acid changes.
267. The derivative of any of embodiments 1-255, wherein the analogue has a minimum of three amino acid changes.
268. The derivative of any of embodiments 1-255, wherein the analogue has a minimum of four amino acid changes.
269. The derivative of any of embodiments 1-255, wherein the analogue has a minimum of five amino acid changes.
270. The derivative of any of embodiments 1-255, wherein the analogue has a minimum of six amino acid changes.
271. The derivative of any of embodiments 1-255, wherein the analogue has a minimum of seven amino acid changes.
272. The derivative of any of embodiments 1-255, wherein the analogue has a minimum of eight amino acid changes.
273. The derivative of any of embodiments 1-255, wherein the analogue has a minimum of nine amino acid changes.
274. The derivative of any of embodiments 1-255, wherein the analogue has a minimum of ten amino acid changes.
275. The derivative of any of embodiments 1-255, wherein the analogue has a minimum of eleven amino acid changes.
276. The derivative of any of embodiments 1-255, wherein the analogue has one amino acid changes.
277. The derivative of any of embodiments 1-255, wherein the analogue has two amino acid changes.
278. The derivative of any of embodiments 1-255, wherein the analogue has three amino acid changes.
279. The derivative of any of embodiments 1-255, wherein the analogue has four amino acid changes.
280. The derivative of any of embodiments 1-255, wherein the analogue has five amino acid changes.
281. The derivative of any of embodiments 1-255, wherein the analogue has six amino acid changes.
282. The derivative of any of embodiments 1-255, wherein the analogue has seven amino acid changes.
283. The derivative of any of embodiments 1-255, wherein the analogue has eight amino acid changes.
284. The derivative of any of embodiments 1-255, wherein the analogue has nine amino acid changes.
285. The derivative of any of embodiments 1-255, wherein the analogue has ten amino acid changes.
286. The derivative of any of embodiments 1-255, wherein the analogue has eleven amino acid changes.
287. The derivative of any of embodiments 1-286, wherein the changes are, independently, substitutions, additions, and/or deletions.
288. The derivative of any of embodiments 1-287, wherein the changes are, independently, substitutions, and/or deletions.
289. The derivative of any of embodiments 1-288, wherein the changes are substitutions.

290. The derivative of any of embodiments 1-287, wherein the changes are deletions.

291. The derivative of any of embodiments 1-286, wherein the analogue a) comprises a GLP-1 analogue of Formula I; and/or b) is a GLP-1 analogue of Formula I:

$Xaa_7$-$Xaa_8$-Glu-Gly-Thr-$Xaa_{12}$-Thr-Ser-Asp-$Xaa_{16}$-Ser-Lys-$Xaa_{19}$-$Xaa_{20}$-Glu-$Xaa_{22}$-$Xaa_{23}$-Ala-$Xaa_{25}$-$Xaa_{26}$-$Xaa_{27}$-Phe-Ile-$Xaa_{30}$-$Xaa_{31}$-Leu-$Xaa_{33}$-$Xaa_{34}$-$Xaa_{35}$-$Xaa_{36}$-$Xaa_{37}$-$Xaa_{38}$, wherein Formula I (SEQ ID NO: 5):

$Xaa_7$ is L-histidine, imidazopropionyl, α-hydroxy-histidine, D-histidine, desamino-histidine, 2-amino-histidine, β-hydroxy-histidine, homohistidine, N$^α$-acetyl-histidine, N$^α$-formyl-histidine, α-fluoromethyl-histidine, α-methyl-histidine, β-pyridylalanine, 2-pyridylalanine, or 4-pyridylalanine;

$Xaa_8$ is Ala, Gly, Val, Leu, Ile, Thr, Ser, Lys, Aib, (1-aminocyclopropyl) carboxylic acid, (1-aminocyclobutyl) carboxylic acid, (1-aminocyclopentyl) carboxylic acid, (1-aminocyclohexyl) carboxylic acid, (1-aminocycloheptyl) carboxylic acid, or (1-aminocyclooctyl) carboxylic acid;

$Xaa_{12}$- is Phe or Leu;
$Xaa_{16}$ is Val or Leu;
$Xaa_{19}$ is Tyr or Gln;
$Xaa_{20}$ is Leu or Met;
$Xaa_{22}$ is Gly, Glu, Lys, or Aib;
$Xaa_{23}$ is Gln, Glu, or Arg;
$Xaa_{25}$ is Ala or Val;
$Xaa_{26}$ is Val, His, Lys, or Arg;
$Xaa_{27}$ is Glu, His, Leu, or Lys;
$Xaa_{30}$ is Ala, Glu, Lys, or Arg;
$Xaa_{31}$ is Trp, Lys, or His
$Xaa_{33}$ is Val or Lys;
$Xaa_{34}$ is Lys, Glu, Asn, Gly, Gln, Arg, His, or absent;
$Xaa_{35}$ is Gly, Aib, or absent;
$Xaa_{36}$ is Arg, Gly, Lys, or absent;
$Xaa_{37}$ is Gly, Ala, Glu, Pro, Lys, Arg, or absent; and
$Xaa_{38}$ is Ser, Gly, Ala, Glu, Pro, Lys, Arg, or absent.

292. The derivative of embodiment 291, wherein the peptide of Formula I is an analogue of GLP-1 (7-37) (SEQ ID NO: 1).

293. The derivative of any of embodiments 291-292, wherein if $Xaa_{37}$ is absent, then $Xaa_{38}$ is also absent.

294. The derivative of any of embodiments 291-293, wherein if $Xaa_{36}$ is absent, then $Xaa_{37}$, and $Xaa_{38}$ are also absent.

295. The derivative of any of embodiments 291-294, wherein if $Xaa_{35}$ is absent, then $Xaa_{36}$, $Xaa_{37}$, and $Xaa_{38}$ are also absent.

296. The derivative of any of embodiments 291-295, wherein if $Xaa_{34}$ is absent, then $Xaa_{35}$, $Xaa_{36}$, $Xaa_{37}$, and $Xaa_{38}$ are also absent.

297. The derivative of any of embodiments 291-296, wherein $Xaa_7$ is His or desamino-histidine (imidazopropionyl); $Xaa_8$ is Ala, Ser, or Aib; $Xaa_{12}$- is Phe or Leu; $Xaa_{16}$ is Val; $Xaa_{19}$ is Tyr; $Xaa_{20}$ is Leu; $Xaa_{22}$ is Gly, Glu, or Lys; $Xaa_{23}$ is Gln, Glu, or Arg; $Xaa_{25}$ is Ala or Val; $Xaa_{26}$ is Val, His, Lys, or Arg; $Xaa_{27}$ is Glu, His, Leu, or Lys; $Xaa_{30}$ is Ala, Glu, or Lys; $Xaa_{31}$ is Trp, Lys, or His; $Xaa_{33}$ is Val; $Xaa_{34}$ is Lys, Gly, Gln, Arg, His, or absent; $Xaa_{35}$ is Gly or absent; $Xaa_{36}$ is Arg or absent; $Xaa_{37}$ is Gly, Lys, or absent; and $Xaa_{38}$ is absent.

298. The derivative of any of embodiments 291-297, wherein $Xaa_7$ is His or desamino-histidine; $Xaa_8$ is Ala or Aib; $Xaa_{12}$- is Phe; $Xaa_{16}$ is Val; $Xaa_{19}$ is Tyr; $Xaa_{20}$ is Leu; $Xaa_{22}$ is Gly, Glu, or Lys; $Xaa_{23}$ is Gln, Glu, or Arg; $Xaa_{25}$ is Ala or Val; $Xaa_{26}$ is Val, His, Lys, or Arg; $Xaa_{27}$ is Glu, His, Leu, or Lys; $Xaa_{30}$ is Ala, Glu, or Lys; $Xaa_{31}$ is Trp, Lys, or His; $Xaa_{33}$ is Val; $Xaa_{34}$ is Lys, Gly, Gln, Arg, His, or absent; $Xaa_{35}$ is Gly or absent; $Xaa_{36}$ is Arg or absent; $Xaa_{37}$ is Gly, Lys, or absent; and $Xaa_{38}$ is absent.

299. The derivative of any of embodiments 291-298, wherein $Xaa_7$ is His.

300. The derivative of any of embodiments 291-298, wherein $Xaa_7$ is desamino-histidine (imidazopropionyl).

301. The derivative of any of embodiments 291-300, wherein $Xaa_8$ is Ala.

302. The derivative of any of embodiments 291-300, wherein $Xaa_8$ is Ser.

303. The derivative of any of embodiments 291-300, wherein $Xaa_8$ is Aib.

304. The derivative of any of embodiments 291-303, wherein $Xaa_{12}$ is Phe.

305. The derivative of any of embodiments 291-303, wherein $Xaa_{12}$ is Leu.

306. The derivative of any of embodiments 291-305, wherein $Xaa_{16}$ is Val.

307. The derivative of any of embodiments 291-306, wherein $Xaa_{19}$ is Tyr.

308. The derivative of any of embodiments 291-307, wherein $Xaa_{20}$ is Leu.

309. The derivative of any of embodiments 291-308, wherein $Xaa_{22}$ is Gly.

310. The derivative of any of embodiments 291-308, wherein $Xaa_{22}$ is Glu.

311. The derivative of any of embodiments 291-308, wherein $Xaa_{22}$ is Lys.

312. The derivative of any of embodiments 291-311, wherein $Xaa_{23}$ is Gln.

313. The derivative of any of embodiments 291-311, wherein $Xaa_{23}$ is Glu.

314. The derivative of any of embodiments 291-311, wherein $Xaa_{23}$ is Arg.

315. The derivative of any of embodiments 291-314, wherein $Xaa_{25}$ is Ala.

316. The derivative of any of embodiments 291-314, wherein $Xaa_{25}$ is Val.

317. The derivative of any of embodiments 291-316, wherein $Xaa_{26}$ is His.

318. The derivative of any of embodiments 291-316, wherein $Xaa_{26}$ is Lys.

319. The derivative of any of embodiments 291-316, wherein $Xaa_{26}$ is Arg.

320. The derivative of any of embodiments 291-319, wherein $Xaa_{27}$ is Glu.

321. The derivative of any of embodiments 291-319, wherein $Xaa_{27}$ is His.

322. The derivative of any of embodiments 291-319, wherein $Xaa_{27}$ is Leu.

323. The derivative of any of embodiments 291-319, wherein $Xaa_{27}$ is Lys.

324. The derivative of any of embodiments 291-323, wherein $Xaa_{30}$ is Ala.

325. The derivative of any of embodiments 291-323, wherein $Xaa_{30}$ is Glu.

326. The derivative of any of embodiments 291-323, wherein $Xaa_{30}$ is Lys.

327. The derivative of any of embodiments 291-326, wherein $Xaa_{31}$ is Trp.

328. The derivative of any of embodiments 291-326, wherein $Xaa_{31}$ is Lys.

329. The derivative of any of embodiments 291-326, wherein $Xaa_{31}$ is His.

330. The derivative of any of embodiments 291-329, wherein $Xaa_{33}$ is Val.

331. The derivative of any of embodiments 291-330, wherein $Xaa_{34}$ is Lys.
332. The derivative of any of embodiments 291-330, wherein $Xaa_{34}$ is Gly.
333. The derivative of any of embodiments 291-330, wherein $Xaa_{34}$ is Gln.
334. The derivative of any of embodiments 291-330, wherein $Xaa_{34}$ is Arg.
335. The derivative of any of embodiments 291-330, wherein $Xaa_{34}$ is His.
336. The derivative of any of embodiments 291-330, wherein $Xaa_{34}$ absent.
337. The derivative of any of embodiments 291-336, wherein $Xaa_{35}$ is Gly.
338. The derivative of any of embodiments 291-336, wherein $Xaa_{35}$ is absent.
339. The derivative of any of embodiments 291-338, wherein $Xaa_{36}$ is Arg.
340. The derivative of any of embodiments 291-338, wherein $Xaa_{36}$ is absent.
341. The derivative of any of embodiments 291-340, wherein $Xaa_{37}$ is Gly.
342. The derivative of any of embodiments 291-340, wherein $Xaa_{37}$ is Lys.
343. The derivative of any of embodiments 291-340, wherein $Xaa_{37}$ is absent.
344. The derivative of any of embodiments 291-343, wherein $Xaa_{38}$ is absent.
345. The derivative of any of embodiments 1-183, 242-252, and 291-298, wherein the analogue comprises the following amino acid changes, as compared to GLP-1(7-37) (SEQ ID NO: 1):
(i) 8Aib, 18K, 34R; (ii) 8Aib, 18K, 34Q; (iii) 8Aib, 18K, 22E, 34R; (iv) 8Aib, 18K, 22E, 34Q; (v) 8Aib, 12L, 18K, 34Q; (vi) 7Imp, 18K, 22E, 34Q; (vii) 18K, 34R; (iix) 18K, 34Q; (ix) 18K, 22E, 34R; (x) 18K, 22E, 34Q; (xi) 18K, 26R, 31K, 34R; (xii) 18K, 26H, 31K, 34R; (xiii) 18K, 26H, 27K, 34Q; (xiv) 18K, 22K, 26R, 34Q; (xv) 18K, 25V, 26R, 31K, 34R; (xvi) 18K, 22E, 26R, 31K, 34R; (xvii) 18K, 22E, 26H, 27K, 34R; (iixx) 18K, 22E, 26H, 27K, 34Q; (ixx) 18K, 22E, 26H, 27K, 31H, 34R; (xx) 18K, 22E, 26H, 27K, 31H, 34Q; (xxi) 18K, 22E, 25V, 26R, 31K, 34R; (xxii) 18K, 22E, 25V, 26R, 31K, 34Q; (xxiii) 18K, 22E, 25V, 26R, 31K, 34G; (xxiv) 18K, 22E, 25V, 26R, 27K, 34R; (xxv) 18K, 22E, 25V, 26R, 27K, 34Q; (xxvi) 18K, 22E, 25V, 26R, 27K, 31H, 34R; (xxvii) 18K, 22E, 25V, 26R, 27K, 31H, 34Q; (iixxx) 18K, 22E, 23E, 25V, 26R, 27K, 34R; (ixxx) 18K, 22E, 23E, 25V, 26R, 27K, 34Q; (xxx) 18K, 22E, 25V, 26R, 31K, 34G, des35-37; (xxxi) 18K, 22E, 25V, 26R, 31H, des35-37; (xxxii) 18K, 22E, 25V, 26R, 30K, 34G, des35-37; (xxxiii) 18K, 22E, 25V, 26R, 30K, 31H, 34G, des35-37; (xxxiv) 18K, 22E, 25V, 26R, 27L, 30K, 34G, des35-37); (xxxv) 18K, 22E, 26R, 31K, 34G, des35-37; (xxxvi) 18K, 22E, 26R, 27K, 31H, 34G, des35-37; (xxxvii) 7Imp, 18K, 22E, 26R, 34R, 37K; (iixxxx) 7Imp, 18K, 22E, 26R, 27K, 31H, 34G, des35-37; (ixxxx) 7Imp, 18K, 22E, 25V, 26R, 31K, 34G, des35-37; (xxxx) 7Imp, 8Aib, 18K, 22E, 25V, 26R, 31K, 34G, des35-37; (xxxxi) 8S, 18K, 22E, 25V, 26R, 31K, 34G, des35-37; (xxxxii) 8Aib, 18K, 26V, 27K, 34R; (xxxxiii) 8Aib, 18K, 26H, 30K, 34R, des36-37; (xxxxiv) 8Aib, 18K, 25V, 26R, 31K, 34R; (xxxxv) 8Aib, 18K, 22E, 34R, des36-37; (xxxxvi) 8Aib, 18K, 22E, 26R, 34R, 37K; (xxxxvii) 8Aib, 18K, 22E, 26R, 31K, 34R; (iixxxxx) 8Aib, 18K, 22E, 26R, 31K, 34G, des35-37; (ixxxxx) 8Aib, 18K, 22E, 26R, 30K, 34R, des36-37; (xxxxx) 8Aib, 18K, 22E, 26R, 30K, 34R; (xxxxxi) 8Aib, 18K, 22E, 26R, 27K, 31H, 34R, des36-37; (xxxxxii) 8Aib, 18K, 22E, 25V, 26R, des34-37; (xxxxxiii) 8Aib, 18K, 22E, 25V, 26R, 31K, 34R; (xxxxxiv) 8Aib, 18K, 22E, 25V, 26R, 31K, 34G, des35-37; (xxxxxv) 8Aib, 18K, 22E, 25V, 26R, 30E, 31K, 34G, des35-37; (xxxxxvi) 8Aib, 18K, 22E, 25V, 26R, 27L, des35-37; (xxxxxvii) 8Aib, 18K, 22E, 25V, 26R, 27K, 34Q; (iixxxxxx) 8Aib, 18K, 22E, 25V, 26R, 27K, 31H, 34G, des35-37; (ixxxxxx) 8Aib, 18K, 22E, 25V, 26R, 27H, 31K, 34G, des35-37; (xxxxxx) 8Aib, 18K, 22E, 25V, 26H, 31K, 34G, des35-37; (xxxxxxi) 8Aib, 18K, 22E, 23R, 25V, 26R, 31K, 34G, des35-37; (xxxxxxii) 18K, 22E, 25V, 26R, 27L, 30K, 34G, des35-37; (xxxxxxiii) 7Imp, 18K, 22E, 26R, 27K, 34Q; or (xxxxxxiv) 8Aib, 18K, 34H.

346. The derivative of any of embodiments 1-183, 242-252, and 291-298, wherein the analogue has the following amino acid changes, as compared to GLP-1(7-37) (SEQ ID NO: 1):
(i) 8Aib, 18K, 34R; (ii) 8Aib, 18K, 34Q; (iii) 8Aib, 18K, 22E, 34R; (iv) 8Aib, 18K, 22E, 34Q; (v) 8Aib, 12L, 18K, 34Q; (vi) 7Imp, 18K, 22E, 34Q; (vii) 18K, 34R; (iix) 18K, 34Q; (ix) 18K, 22E, 34R; (x) 18K, 22E, 34Q; (xi) 18K, 26R, 31K, 34R; (xii) 18K, 26H, 31K, 34R; (xiii) 18K, 26H, 27K, 34Q; (xiv) 18K, 22K, 26R, 34Q; (xv) 18K, 25V, 26R, 31K, 34R; (xvi) 18K, 22E, 26R, 31K, 34R; (xvii) 18K, 22E, 26H, 27K, 34R; (iixx) 18K, 22E, 26H, 27K, 34Q; (ixx) 18K, 22E, 26H, 27K, 31H, 34R; (xx) 18K, 22E, 26H, 27K, 31H, 34Q; (xxi) 18K, 22E, 25V, 26R, 31K, 34R; (xxii) 18K, 22E, 25V, 26R, 31K, 34Q; (xxiii) 18K, 22E, 25V, 26R, 31K, 34G; (xxiv) 18K, 22E, 25V, 26R, 27K, 34R; (xxv) 18K, 22E, 25V, 26R, 27K, 34Q; (xxvi) 18K, 22E, 25V, 26R, 27K, 31H, 34R; (xxvii) 18K, 22E, 25V, 26R, 27K, 31H, 34Q; (iixxx) 18K, 22E, 23E, 25V, 26R, 27K, 34R; (ixxx) 18K, 22E, 23E, 25V, 26R, 27K, 34Q; (xxx) 18K, 22E, 25V, 26R, 31K, 34G, des35-37; (xxxi) 18K, 22E, 25V, 26R, 31H, des35-37; (xxxii) 18K, 22E, 25V, 26R, 30K, 34G, des35-37; (xxxiii) 18K, 22E, 25V, 26R, 30K, 31H, 34G, des35-37; (xxxiv) 18K, 22E, 25V, 26R, 27L, 30K, 34G, des35-37); (xxxv) 18K, 22E, 26R, 31K, 34G, des35-37; (xxxvi) 18K, 22E, 26R, 27K, 31H, 34G, des35-37; (xxxvii) 7Imp, 18K, 22E, 26R, 34R, 37K; (iixxxx) 7Imp, 18K, 22E, 26R, 27K, 31H, 34G, des35-37; (ixxxx) 7Imp, 18K, 22E, 25V, 26R, 31K, 34G, des35-37; (xxxx) 7Imp, 8Aib, 18K, 22E, 25V, 26R, 31K, 34G, des35-37; (xxxxi) 8S, 18K, 22E, 25V, 26R, 31K, 34G, des35-37; (xxxxii) 8Aib, 18K, 26V, 27K, 34R; (xxxxiii) 8Aib, 18K, 26H, 30K, 34R, des36-37; (xxxxiv) 8Aib, 18K, 25V, 26R, 31K, 34R; (xxxxv) 8Aib, 18K, 22E, 34R, des36-37; (xxxxvi) 8Aib, 18K, 22E, 26R, 34R, 37K; (xxxxvii) 8Aib, 18K, 22E, 26R, 31K, 34R; (iixxxxx) 8Aib, 18K, 22E, 26R, 31K, 34G, des35-37; (ixxxxx) 8Aib, 18K, 22E, 26R, 30K, 34R, des36-37; (xxxxx) 8Aib, 18K, 22E, 26R, 30K, 34R; (xxxxxi) 8Aib, 18K, 22E, 26R, 27K, 31H, 34R, des36-37; (xxxxxii) 8Aib, 18K, 22E, 25V, 26R, des34-37; (xxxxxiii) 8Aib, 18K, 22E, 25V, 26R, 31K, 34R; (xxxxxiv) 8Aib, 18K, 22E, 25V, 26R, 31K, 34G, des35-37; (xxxxxv) 8Aib, 18K, 22E, 25V, 26R, 30E, 31K, 34G, des35-37; (xxxxxvi) 8Aib, 18K, 22E, 25V, 26R, 27L, des35-37; (xxxxxvii) 8Aib, 18K, 22E, 25V, 26R, 27K, 34Q; (iixxxxxx) 8Aib, 18K, 22E, 25V, 26R, 27K, 31H, 34G, des35-37; (ixxxxxx) 8Aib, 18K, 22E, 25V, 26R, 27H, 31K, 34G, des35-37; (xxxxxx) 8Aib, 18K, 22E, 25V, 26H, 31K, 34G, des35-37; (xxxxxxi) 8Aib, 18K, 22E, 23R, 25V, 26R, 31K, 34G, des35-37; (xxxxxxii) 18K, 22E, 25V, 26R, 27L, 30K, 34G, des35-37; (xxxxxxiii) 7Imp, 18K, 22E, 26R, 27K, 34Q; or (xxxxxxiv) 8Aib, 18K, 34H.

347. The derivative of any of embodiments 1-346, wherein the analogue is modified so as to comprise a C-terminal amide.

348. The derivative of any of embodiments 1-347, wherein a carboxylic acid group of the C-terminal amino acid of the analogue is converted into carboxylic acid amide.
349. The derivative of embodiment 347, wherein the carboxylic acid group which is converted into carboxylic acid amide is not in the side chain of the C-terminal amino acid.
350. The derivative of any of embodiments 1-346, wherein the analogue has a C-terminal carboxylic acid.
351. A compound, preferably according to any of embodiments 1-350, selected from the following: Chem. 20, Chem. 21, Chem. 22, Chem. 23, Chem. 24, Chem. 25, Chem. 26, Chem. 27, Chem. 28, Chem. 29, Chem. 30, Chem. 31, Chem. 32, Chem. 33, Chem. 34, Chem. 35, Chem. 36, Chem. 37, Chem. 38, Chem. 39, Chem. 40, Chem. 41, Chem. 42, Chem. 43, Chem. 44, Chem. 45, Chem. 46, Chem. 47, Chem. 48, Chem. 49, Chem. 50, Chem. 51, Chem. 52, Chem. 53, Chem. 54, Chem. 55, Chem. 56, Chem. 57, Chem. 58, Chem. 59, Chem. 60, Chem. 61, Chem. 62, Chem. 63, Chem. 64, Chem. 65, Chem. 66, Chem. 67, Chem. 68, Chem. 69, Chem. 70, Chem. 71, Chem. 72, Chem. 73, Chem. 74, Chem. 75, Chem. 76, Chem. 77, Chem. 78, Chem. 79, Chem. 80, Chem. 81, Chem. 82, Chem. 83, Chem. 84, Chem. 85, Chem. 86, Chem. 87, Chem. 88, Chem. 89, Chem. 90, Chem. 91, Chem. 92, Chem. 93, Chem. 94, Chem. 95, Chem. 96, Chem. 97, Chem. 98, Chem. 99, Chem. 100, Chem. 101, Chem. 102, Chem. 103, Chem. 104, Chem. 105, Chem. 106, Chem. 107, Chem. 108, Chem. 109, Chem. 110, Chem. 111, Chem. 112, Chem. 113, Chem. 114, Chem. 115, Chem. 116, Chem. 117, Chem. 118, Chem. 119, Chem. 120, Chem. 121, Chem. 122, Chem. 123, Chem. 124, Chem. 125, Chem. 126, Chem. 127, Chem. 128, Chem. 129, Chem. 130, Chem. 131, Chem. 132, Chem. 133, Chem. 134, Chem. 135, Chem. 161, Chem. 162, Chem. 163, Chem. 164, Chem. 165, Chem. 166, Chem. 167, Chem. 168, Chem. 169, Chem. 170, Chem. 171, Chem. 172, Chem. 173, Chem. 174, Chem. 175, Chem. 176, Chem. 177, Chem. 178, Chem. 179, Chem. 180, Chem. 181, Chem. 182, Chem. 183, Chem. 189, Chem. 190, Chem. 191, Chem. 192, Chem. 193, Chem. 194, and Chem. 195; or a pharmaceutically acceptable salt, amide, or ester of any of Chem. 20-135, Chem. 161-183, and Chem. 189-195.
352. A compound characterised by its name, and selected from a listing of each of the names of the compounds of Examples 1-116, 118-140, and 141-147 herein; or a pharmaceutically acceptable salt, amide, or ester thereof.
353. The compound of embodiment 352, which is a compound of embodiment 351.
354. The derivative of any of embodiments 1-353, which has GLP-1 activity.
355. The derivative of embodiment 354, wherein GLP-1 activity refers to the capability of activating the human GLP-1 receptor.
356. The derivative of embodiment 355, wherein activation of the human GLP-1 receptor is measured in an in vitro assay, as the potency of cAMP production.
357. The derivative of any of embodiments 1-356, which has a potency corresponding to an $EC_{50}$
a) below 18000 pM, preferably below 10000 pM, more preferably below 5000 pM, even more preferably below 4000 pM, or most preferably below 3000 pM;
b) below 2000 pM, preferably below 1200 pM, more preferably below 1000 pM, even more preferably below 800 pM, or most preferably below 600 pM;
c) below 400 pM, preferably below 300 pM, more preferably below 200 pM, even more preferably below 150 pM, or most preferably below 100 pM; or
d) below 80 pM, preferably below 60 pM, more preferably below 50 pM, even more preferably below 40 pM, or most preferably below 30 pM.
358. The derivative of embodiment 357, wherein the potency is determined as $EC_{50}$ for stimulation of the formation of cAMP in a medium containing the human GLP-1 receptor, preferably using a stable transfected cell-line such as BHK467-12A (tk-ts13), and/or using for the determination of cAMP a functional receptor assay, e.g. based on competition between endogenously formed cAMP and exogenously added biotin-labelled cAMP, in which assay cAMP is more preferably captured using a specific antibody, and/or wherein an even more preferred assay is the AlphaScreen cAMP Assay, most preferably the one described in Example 148.
359. The derivative of any of embodiments 1-358, for which the ratio [GLP-1 receptor binding affinity ($IC_{50}$ in nM) in the presence of 2.0% HSA (high albumin), divided by GLP-1 receptor binding affinity ($IC_{50}$ in nM) in the presence of 0.005% HSA (low albumin)] is:
a) at least 1, preferably at least 10, more preferably at least 20, even more preferably at least 30, or most preferably at least 40;
b) at least 50, preferably at least 60, more preferably at least 70, even more preferably at least 80, or most preferably at least 90;
c) at least 100, preferably at least 200, more preferably at least 300, still more preferably at least 400, even more preferably at least 500, or most preferably at least 600; or
d) at least 700, preferably at least 800, more preferably at least 900, still more preferably at least 1000, even more preferably at least 1200, or most preferably at least 1400.
360. The derivative of any of embodiments 1-359, for which the GLP-1 receptor binding affinity ($IC_{50}$) in the presence of 0.005% HSA (low albumin) is
a) below 1000 nM, preferably below 500 nM, more preferably below 100 nM, or most preferably below 50 nM;
b) below 10 nM, preferably below 8.0 nM, still more preferably below 6.0 nM, even more preferably below 5.0 nM, or most preferably below 2.00 nM; or
c) below 1.00 nM, preferably below 0.50 nM, even more preferably below 0.25 nM, or most preferably below 0.15 nM.
361. The derivative of any of embodiments 1-360, for which the GLP-1 receptor binding affinity ($IC_{50}$) in the presence of 2.0% HSA (high albumin) is
a) below 1000 nM;
b) below 800 nM, preferably below 700 nM, more preferably below 500 nM; or
c) below 300 nM, preferably below 200 nM, even more preferably below 100 nM, or most preferably below 50 nM.
362. The derivative of any of embodiments 359-361, wherein the binding affinity to the GLP-1 receptor is measured by way of displacement of $^{125}$I-GLP-1 from the receptor, preferably using a SPA binding assay.
363. The derivative of embodiment 362, wherein the GLP-1 receptor is prepared using a stable, transfected cell line, preferably a hamster cell line, more preferably a baby hamster kidney cell line, such as BHK tk-ts13.
364. The derivative of any of embodiments 359-363, wherein the $IC_{50}$ value is determined as the concentration which displaces 50% of $^{125}$I-GLP-1 from the receptor.
365. The derivative of any of embodiments 1-364, which has an oral bioavailability, preferably an absolute oral bioavailability, which is higher than that of semaglutide.

366. The derivative of any of embodiments 1-365, which has an oral bioavailability, preferably an absolute oral bioavailability, which is higher than that of liraglutide.

367. The derivative of any of embodiments 365-366, wherein oral bioavailability is measured in vivo in rats, as exposure in plasma after direct injection into the intestinal lumen.

368. The derivative of any of embodiments 1-367, for which the plasma concentration (pM) of the derivative, determined 30 minutes after injection of a solution of the derivative in the jejunum of rat, divided by the concentration (pM) of the injected solution (dose-corrected exposure at 30 min) is a) at least 20, preferably at least 40, more preferably at least 45, even more preferably at least 50, or most preferably at least 60; or b) at least 70, preferably at least 80, or most preferably at least 100.

369. The derivative of any of embodiments 1-367, for which the plasma concentration (pM) of the derivative, determined 30 minutes after injection of a solution of the derivative in the jejunum of rat, divided by the concentration (pM) of the injected solution (dose-corrected exposure at 30 min) is at least 110, preferably at least 120, more preferably at least 130, still more preferably at least 140, even more preferably at least 150, or most preferably at least 160.

370. The derivative of any of embodiments 1-367, for which the plasma concentration (pM) of the derivative, determined 30 minutes after injection of a solution of the derivative in the jejunum of rat, divided by the concentration (pM) of the injected solution (dose-corrected exposure at 30 min) is at least 180, preferably at least 190, more preferably at least 200, still more preferably at least 210, even more preferably at least 220, or most preferably at least 230.

371. The derivative of any of embodiments 1-367, for which the plasma concentration (pM) of the derivative, determined 30 minutes after injection of a solution of the derivative in the jejunum of rat, divided by the concentration (pM) of the injected solution (dose-corrected exposure at 30 min) is at least 240, preferably at least 250, more preferably at least 260, or most preferably at least 270.

372. The derivative of any of embodiments 368-371, wherein the GLP-1 derivative is tested in a concentration of 1000 uM in a solution of 55 mg/ml sodium caprate.

373. The derivative of any of embodiments 368-372, wherein male Sprague Dawley rats are used, preferably with a body weight upon arrival of approximately 240 g.

374. The derivative of any of embodiments 368-373, wherein the rats are fasted for approximately 18 hours before the experiment.

375. The derivative of any of embodiments 368-374, wherein the rats are and taken into general anaesthesia after having fasted and before the injection of the derivative in the jejunum.

376. The derivative of any of embodiments 368-375, wherein the derivative is administered in the proximal part of the jejunum (10 cm distal for the duodenum) or in the mid-intestine (50 cm proximal for the cecum).

377. The derivative of any of embodiments 368-376, wherein 100 µl of the derivative is injected into the jejunal lumen through a catheter with a 1 ml syringe, and subsequently 200 µl of air is pushed into the jejunal lumen with another syringe, which is then left connected to the catheter to prevent flow back into the catheter.

378. The derivative of any of embodiments 368-377, wherein blood samples (200 ul) are collected into EDTA tubes from the tail vein at desired intervals, such as at times 0, 10, 30, 60, 120 and 240 min, and centrifuged 5 minutes, 10000G, at 4° C. within 20 minutes.

379. The derivative of any of embodiments 368-378, wherein plasma (e.g. 75 ul) is separated, immediately frozen, and kept at −20° C. until analyzed for plasma concentration of the derivative.

380. The derivative of any of embodiments 368-379, wherein LOCI (Luminescent Oxygen Channeling Immunoassay) is used for analyzing the plasma concentration of the derivative.

381. The derivative of any of embodiments 1-380, wherein the derivative is effective at lowering blood glucose in vivo in db/db mice.

382. The derivative of any of embodiments 1-380, wherein the derivative is effective at lowering body weight in vivo in db/db mice.

383. The derivative of any of embodiments 381-382, wherein db/db mice are treated, s.c., with a suitable range of doses of the GLP-1 derivative, and blood glucose and/or bodyweight is/are determined at appropriate intervals.

384. The derivative of any of embodiments 381-383, wherein the dose of the GLP-1 derivative is 0.3 nmol/kg, 1.0 nmol/kg, 3.0 nmol/kg, 10 nmol/kg, 30 nmol/kg, and 100 nmol/kg, wherein kg refers to the body weight of the mouse.

385. The derivative of any of embodiments 381-384, wherein a control group is treated with vehicle, s.c., preferably the medium in which the GLP-1 derivative is dissolved, e.g. with the following composition: 50 mM sodium phosphate, 145 mM sodium chloride, 0.05% tween 80, pH 7.4.

386. The derivative of any of embodiments 381-385, wherein blood glucose is determined, and/or the mice are weighed, at time −½ h (half an hour prior to dosing (t=0)), and at times 1, 2, 4, and 8 h.

387. The derivative of any of embodiments 381-386, wherein the glucose concentration is measured using the glucose oxidase method. 388. The derivative of any of embodiments 381-387, wherein (i) $ED_{50}$ (body weight (BW)) is calculated as the dose giving rise to half-maximum effect on delta (e.g., decrease) BW 8 hours following the subcutaneous administration of the derivative; and/or (ii) $ED_{50}$ (blood glucose (BG)) is calculated as the dose giving rise to half-maximum effect on AUC (Area Under the Curve) delta (e.g., decrease) BG 8 hours and/or 24 hours following the subcutaneous administration of the analogue.

389. The derivative of any of embodiments 381-388, wherein a sigmoidal dose-response relationship exists, preferably with a clear definition of the maximum response.

390. The derivative of any of embodiments 381-389, wherein $ED_{50}$ (BG) 8 hours is below 5.0 nmol/kg, preferably below 4.0 nmol/kg, more preferably below 3.0 nmol/kg, even more preferably below 2.0 nmol/kg, or most preferably below 1.0 nmol/kg.

391. The derivative of any of embodiments 381-390, wherein $ED_{50}$ (BW) 8 hours is a) below 10, nmol/kg, preferably below 8 nmol/kg, even more preferably below 6.0 nmol/kg, or most preferably below 5.0 nmol/kg; or b) below 4.0 nmol/kg, preferably below 3.0 nmol/kg, even more preferably below 2.0 nmol/kg, or most preferably below 1.0 nmol/kg.

392. The derivative of any of embodiments 1-391, which has a more protracted profile of action than liraglutide.

393. The derivative of embodiment 392, wherein protraction means half-life in vivo in a relevant animal species, such as db/db mice, rat, pig, and/or, preferably, minipig; wherein the derivative is administered i) s.c., and/or, ii) i.v.; preferably ii) i.v.

394. The derivative of any of embodiments 1-393, wherein the terminal half-life (T ½) after i.v. administration in rat is higher than that of semaglutide.

395. The derivative of any of embodiments 1-394, wherein the terminal half-life (T ½) after i.v. administration in rat is at least twice the terminal half-life of semaglutide.

396. The derivative of any of embodiments 1-395, wherein the terminal half-life (T ½) after i.v. administration in rat is at least three times the terminal half-life of semaglutide.

397. The derivative of any of embodiments 1-396, wherein the terminal half-life (T ½) after i.v. administration in rat is at least four times the terminal half-life of semaglutide.

398. The derivative of any of embodiments 1-397, wherein the terminal half-life (T ½) after i.v. administration in rat is at least five times the terminal half-life of semaglutide.

399. The derivative of any of embodiments 1-398, wherein the half-life is determined in in vivo pharmacokinetic studies in rat, for example as described in Example 154.

400. The derivative of any of embodiments 1-399, wherein the terminal half-life (T ½) after i.v. administration in minipigs is
a) at least 8 hours, preferably at least 16 hours, more preferably at least 24 hours, even more preferably at least 32 hours, or most preferably at least 40 hours; or
b) at least 50 hours, preferably at least 58 hours, more preferably at least 70 hours, even more preferably at least 80 hours, or most preferably at least 84 hours.

401. The derivative of any of embodiments 393-400, wherein the minipigs are male Göttingen minipigs.

402. The derivative of any of embodiments 393-401, wherein the minipigs are 7-14 months of age, and preferably weighing from 16-35 kg.

403. The derivative of any of embodiments 393-402, wherein the minipigs are housed individually, and fed once or twice daily, preferably with SDS minipig diet.

404. The derivative of any of embodiments 393-403, wherein the derivative is dosed, i.v., after at least 2 weeks of acclimatisation.

405. The derivative of any of embodiments 393-404, wherein the animals are fasted for approximately 18 h before dosing and for at least 4 h after dosing, and have ad libitum access to water during the whole period.

406. The derivative of any of embodiments 393-405, wherein the GLP-1 derivative is dissolved in 50 mM sodium phosphate, 145 mM sodium chloride, 0.05% tween 80, pH 7.4 to a suitable concentration, preferably from 20-60 nmol/ml.

407. The derivative of any of embodiments 393-406, wherein intravenous injections of the derivative are given in a volume corresponding to 1-2 nmol/kg.

408. The derivative of any of embodiments 1-407, which causes a reduced food intake in pigs relative to a control (preferably vehicle-treated, or untreated);
optionally the food intake (0-24 h) may be 90% or lower relative to the vehicle-treated control, preferably 80% or lower, more preferably 70% or lower, even more preferably 60% or lower, or most preferably 50% or lower;
wherein food intake (0-24 h) refers to the first 24 hours after administration of the derivative or vehicle.

409. The derivative of embodiment 408, wherein the pigs are female Landrace Yorkshire Duroc (LYD) pigs.

410. The derivative of any of embodiments 408-409, wherein the LYD pigs are 3 months of age, and preferably have a weight of 30-35 kg.

411. The derivative of any of embodiments 408-410, where the animals are housed in a group for 1-2 weeks for acclimatisation.

412. The derivative of any of embodiments 408-411, wherein during the experimental period the animals are placed in individual pens from Monday morning to Friday afternoon for measurement of individual food intake.

413. The derivative of any of embodiments 408-412, wherein the animals are fed ad libitum with pig fodder (such as Svinefoder, Antonio).

414. The derivative of any of embodiments 408-413, wherein food intake is monitored on line by logging the weight of fodder every 15 minutes, preferably using the Mpigwin system.

415. The derivative of any of embodiments 408-414, which is dosed 0.3, 1.0, 3.0, 10, or nmol/kg, preferably dissolved in a phosphate buffer (50 mM phosphate, 145 mM sodium chloride, 0.05% tween 80, pH 8), more preferably at concentrations of 12, 40, 120, 400, or 1200 nmol/ml.

416. The derivative of any of embodiments 408-415, wherein the phosphate buffer serves as vehicle.

417. The derivative of any of embodiments 408-416, wherein the animals are dosed with a single subcutaneous dose of the derivative, or vehicle (preferably with a dose volume of 0.025 ml/kg), on the morning of day 1, and food intake is measured for 4 days after dosing.

418. An intermediate product in the form of a GLP-1 analogue which comprises the following changes as compared to GLP-1(7-37) (SEQ ID NO: 1): (i) 8Aib, 18K, 34R; (ii) 8Aib, 18K, 34Q; (iii) 8Aib, 18K, 22E, 34R; (iv) 8Aib, 18K, 22E, 34Q; (v) 8Aib, 12L, 18K, 34Q; (vi) 71mp, 18K, 22E, 34Q; (vii) 18K, 34R; (iix) 18K, 34Q; (ix) 18K, 22E, 34R; (x) 18K, 22E, 34Q; (xi) 18K, 26R, 31K, 34R; (xii) 18K, 26H, 31K, 34R; (xiii) 18K, 26H, 27K, 34Q; (xiv) 18K, 22K, 26R, 34Q; (xv) 18K, 25V, 26R, 31K, 34R; (xvi) 18K, 22E, 26R, 31K, 34R; (xvii) 18K, 22E, 26H, 27K, 34R; (iixx) 18K, 22E, 26H, 27K, 34Q; (ixx) 18K, 22E, 26H, 27K, 31H, 34R; (xx) 18K, 22E, 26H, 27K, 31H, 34Q; (xxi) 18K, 22E, 25V, 26R, 31K, 34R; (xxii) 18K, 22E, 25V, 26R, 31K, 34Q; (xxiii) 18K, 22E, 25V, 26R, 31K, 34G; (xxiv) 18K, 22E, 25V, 26R, 27K, 34R; (xxv) 18K, 22E, 25V, 26R, 27K, 34Q; (xxvi) 18K, 22E, 25V, 26R, 27K, 31H, 34R; (xxvii) 18K, 22E, 25V, 26R, 27K, 31H, 34Q; (iixxx) 18K, 22E, 23E, 25V, 26R, 27K, 34R; (ixxx) 18K, 22E, 23E, 25V, 26R, 27K, 34Q; (xxx) 18K, 22E, 25V, 26R, 31K, 34G, des35-37; (xxxi) 18K, 22E, 25V, 26R, 31H, des35-37; (xxxii) 18K, 22E, 25V, 26R, 30K, 34G, des35-37; (xxxiii) 18K, 22E, 25V, 26R, 30K, 31H, 34G, des35-37; (xxxiv) 18K, 22E, 25V, 26R, 27L, 30K, 34G, des35-37); (xxxv) 18K, 22E, 26R, 31K, 34G, des35-37; (xxxvi) 18K, 22E, 26R, 27K, 31H, 34G, des35-37; (xxxvii) 71mp, 18K, 22E, 26R, 34R, 37K; (iixxxx) 71mp, 18K, 22E, 26R, 27K, 31H, 34G, des35-37; (ixxxx) 71mp, 18K, 22E, 25V, 26R, 31K, 34G, des35-37; (xxxx) 71mp, 8Aib, 18K, 22E, 25V, 26R, 31K, 34G, des35-37; (xxxxi) 8S, 18K, 22E, 25V, 26R, 31K, 34G, des35-37; (xxxxii) 8Aib, 18K, 26V, 27K, 34R; (xxxxiii) 8Aib, 18K, 26H, 30K, 34R, des36-37; (xxxxiv) 8Aib, 18K, 25V, 26R, 31K, 34R; (xxxxv) 8Aib, 18K, 22E, 34R, des36-37; (xxxxvi) 8Aib, 18K, 22E, 26R, 34R, 37K; (xxxxvii) 8Aib, 18K, 22E, 26R, 31K, 34R; (iixxxxx) 8Aib, 18K, 22E, 26R, 31K, 34G, des35-37; (ixxxxx) 8Aib, 18K, 22E, 26R, 30K, 34R, des36-37; (xxxxx) 8Aib, 18K, 22E, 26R, 30K, 34R; (xxxxxi) 8Aib, 18K, 22E, 26R, 27K, 31H, 34R, des36-37; (xxxxxii) 8Aib, 18K, 22E, 25V, 26R, 31K, des34-37; (xxxxxiii) 8Aib, 18K, 22E, 25V, 26R, 31K, 34R; (xxxxxiv) 8Aib, 18K, 22E, 25V, 26R, 31K, 34G, des35-37; (xxxxxv) 8Aib, 18K, 22E, 25V, 26R, 30E, 31K, 34G, des35-37; (xxxxxvi) 8Aib, 18K, 22E, 25V, 26R, 27L, des35-37; (xxxxxvii) 8Aib, 18K, 22E, 25V, 26R, 27K, 34Q; (iixxxxxx) 8Aib, 18K, 22E, 25V, 26R, 27K, 31H, 34G, des35-37; (ixxxxxx) 8Aib, 18K, 22E, 25V, 26R, 27H, 31K, 34G, des35-37; (xxxxxx) 8Aib, 18K, 22E, 25V, 26H, 31K, 34G, des35-37; (xxxxxxi) 8Aib, 18K, 22E, 23E, 25V, 26R, 31K, 34G, des35-37; (xxxxxxii) 18K, 22E, 25V, 26R, 27L, 30K, 34G, des35-37; (xxxxxxiii) 71mp, 18K, 22E, 26R, 27K, 34Q; (xxxxxxiv) 34H; or (xxxxxxv) 8Aib, 18K, 34H; or a pharmaceutically acceptable salt, amide, or ester of any of the analogues of (i)-(xxxxxxv).

419. An intermediate product in the form of a GLP-1 analogue selected from the following analogues of GLP-1 (7-37) (SEQ ID NO: 1): (i) 8Aib, 18K, 34R; (ii) 8Aib, 18K, 34Q; (iii) 8Aib, 18K, 22E, 34R; (iv) 8Aib, 18K, 22E, 34Q; (v) 8Aib, 12L, 18K, 34Q; (vi) 71mp, 18K, 22E, 34Q; (vii) 18K, 34R; (iix) 18K, 34Q; (ix) 18K, 22E, 34R; (x) 18K, 22E, 34Q; (xi) 18K, 26R, 31K, 34R; (xii) 18K, 26H, 31K, 34R; (xiii) 18K, 26H, 27K, 34Q; (xiv) 18K, 22K, 26R, 34Q; (xv) 18K, 25V, 26R, 31K, 34R; (xvi) 18K, 22E, 26R, 31K, 34R; (xvii) 18K, 22E, 26H, 27K, 34R; (iixx) 18K, 22E, 26H, 27K, 34Q; (ixx) 18K, 22E, 26H, 27K, 31H, 34R; (xx) 18K, 22E, 26H, 27K, 31H, 34Q; (xxi) 18K, 22E, 25V, 26R, 31K, 34R; (xxii) 18K, 22E, 25V, 26R, 31K, 34Q; (xxiii) 18K, 22E, 25V, 26R, 31K, 34G; (xxiv) 18K, 22E, 25V, 26R, 27K, 34R; (xxv) 18K, 22E, 25V, 26R, 27K, 34Q; (xxvi) 18K, 22E, 25V, 26R, 27K, 31H, 34R; (xxvii) 18K, 22E, 25V, 26R, 27K, 31H, 34Q; (iixxx) 18K, 22E, 23E, 25V, 26R, 27K, 34R; (ixxx) 18K, 22E, 23E, 25V, 26R, 27K, 34Q; (xxx) 18K, 22E, 25V, 26R, 31K, 34G, des35-37; (xxxi) 18K, 22E, 25V, 26R, 31H, des35-37; (xxxii) 18K, 22E, 25V, 26R, 30K, 34G, des35-37; (xxxiii) 18K, 22E, 25V, 26R, 30K, 31H, 34G, des35-37; (xxxiv) 18K, 22E, 25V, 26R, 27L, 30K, 34G, des35-37); (xxxv) 18K, 22E, 26R, 31K, 34G, des35-37; (xxxvi) 18K, 22E, 26R, 27K, 31H, 34G, des35-37; (xxxvii) 71mp, 18K, 22E, 26R, 34R, 37K; (iixxxx) 71mp, 18K, 22E, 26R, 27K, 31H, 34G, des35-37; (ixxxx) 71mp, 18K, 22E, 25V, 26R, 31K, 34G, des35-37; (xxxx) 71mp, 8Aib, 18K, 22E, 25V, 26R, 31K, 34G, des35-37; (xxxxi) 8S, 18K, 22E, 25V, 26R, 31K, 34G, des35-37; (xxxxii) 8Aib, 18K, 26V, 27K, 34R; (xxxxiii) 8Aib, 18K, 26H, 30K, 34R, des36-37; (xxxxiv) 8Aib, 18K, 25V, 26R, 31K, 34R; (xxxxv) 8Aib, 18K, 22E, 34R, des36-37; (xxxxvi) 8Aib, 18K, 22E, 26R, 34R, 37K; (xxxxvii) 8Aib, 18K, 22E, 26R, 31K, 34R; (iixxxxx) 8Aib, 18K, 22E, 26R, 31K, 34G, des35-37; (ixxxxx) 8Aib, 18K, 22E, 26R, 30K, 34R, des36-37; (xxxxx) 8Aib, 18K, 22E, 26R, 30K, 34R; (xxxxxi) 8Aib, 18K, 22E, 26R, 27K, 31H, 34R, des36-37; (xxxxxii) 8Aib, 18K, 22E, 25V, 26R, 31K, des34-37; (xxxxxiii) 8Aib, 18K, 22E, 25V, 26R, 31K, 34R; (xxxxxiv) 8Aib, 18K, 22E, 25V, 26R, 31K, 34G, des35-37; (xxxxxv) 8Aib, 18K, 22E, 25V, 26R, 30E, 31K, 34G, des35-37; (xxxxxvi) 8Aib, 18K, 22E, 25V, 26R, 27L, des35-37; (xxxxxvii) 8Aib, 18K, 22E, 25V, 26R, 27K, 34Q; (iixxxxxx) 8Aib, 18K, 22E, 25V, 26R, 27K, 31H, 34G, des35-37; (ixxxxxx) 8Aib, 18K, 22E, 25V, 26R, 27H, 31K, 34G, des35-37; (xxxxxx) 8Aib, 18K, 22E, 25V, 26H, 31K, 34G, des35-37; (xxxxxxi) 8Aib, 18K, 22E, 23R, 25V, 26R, 31K, 34G, des35-37; (xxxxxxii) 18K, 22E, 25V, 26R, 27L, 30K, 34G, des35-37; (xxxxxxiii) 71mp, 18K, 22E, 26R, 27K, 34Q; (xxxxxxiv) 34H; and (xxxxxxv) 8Aib, 18K, 34H; or a pharmaceutically acceptable salt, amide, or ester of any of the analogues of (i)-(xxxxxxv).

420. The analogue of any of embodiments 418-419, which comprises a C-terminal amide.

421. The analogue of any of embodiments 418-420, wherein a carboxylic acid group of the C-terminal amino acid of the analogue is converted into carboxylic acid amide.

422. The analogue of embodiment 421, wherein the carboxylic acid group which is converted into carboxylic acid amide is not in the side chain of the C-terminal amino acid.

423. The analogue of any of embodiments 418-419, which comprises a C-terminal carboxylic acid.

42417. The analogue of any of embodiments 418-420, wherein the comparison with GLP-1(7-37) (SEQ ID NO: 1) is made by handwriting and eyeballing.

425. The analogue of any of embodiments 418-424, wherein the comparison with GLP-1(7-37) (SEQ ID NO: 1) is made by use of a standard protein or peptide alignment program.

426. The analogue of embodiment 425, wherein the alignment program is a Needleman-Wunsch alignment.

427. The analogue of any of embodiments 425-426, wherein the default scoring matrix and the default identity matrix is used.

428. The analogue of any of embodiments 425-427, wherein the scoring matrix is BLOSUM62.

429. The analogue of any of embodiments 425-428, wherein the penalty for the first residue in a gap is −10 (minus ten).

430. The analogue of any of embodiments 425-429, wherein the penalties for additional residues in a gap is −0.5 (minus point five).

431. An intermediate product selected from the following: $N^{\epsilon 18}$-[2-[2-[2-[[2-[2-[2-[[(4S)-4-amino-4-carboxybutanoyl] amino]ethoxy]ethoxy]acetyl]amino]ethoxy]ethoxy] acetyl], $N^{\epsilon 27}$-[2-[2-[2-[[2-[2-[2-[[(4S)-4-amino-4-carboxybutanoyl]amino]ethoxy]ethoxy]acetyl]amino] ethoxy]ethoxy]acetyl]-[Aib$^8$,Lys$^{18}$,Val$^{26}$,Lys$^{27}$,Arg$^{34}$]-GLP-1-(7-37)-peptide (SEQ ID NO: 6);

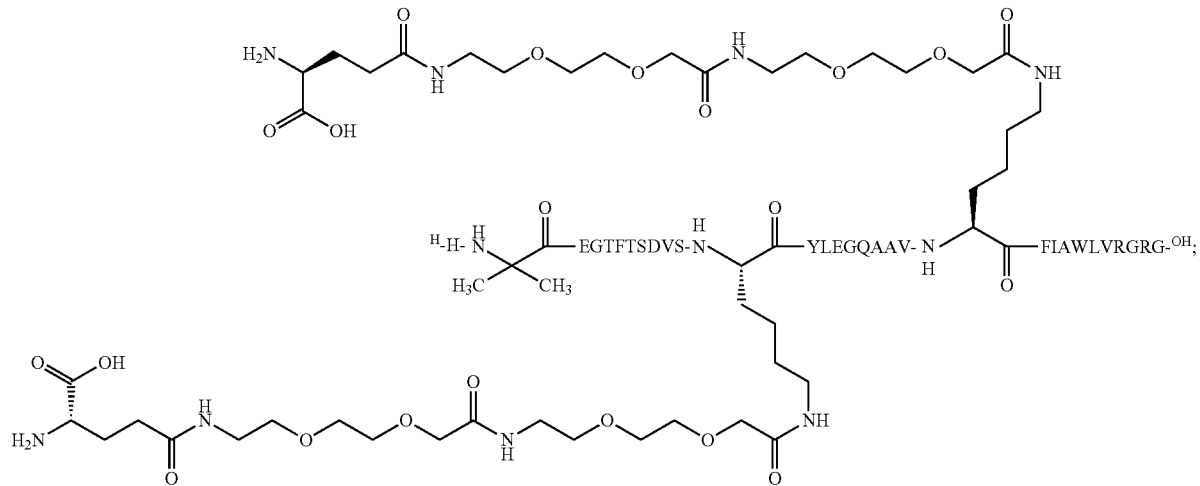

Chem. 137

Chem. 138
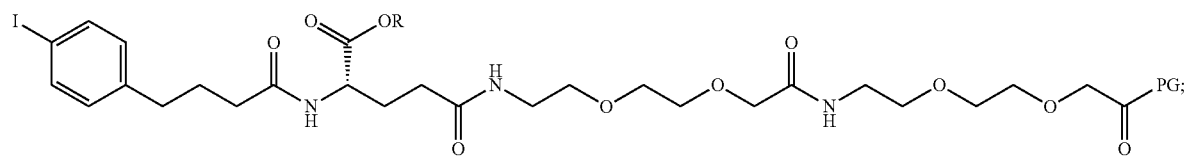
Chem. 139
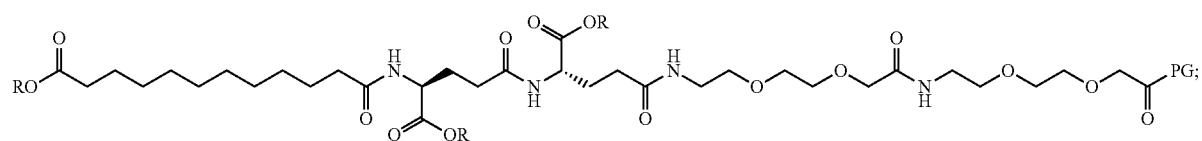
Chem. 140
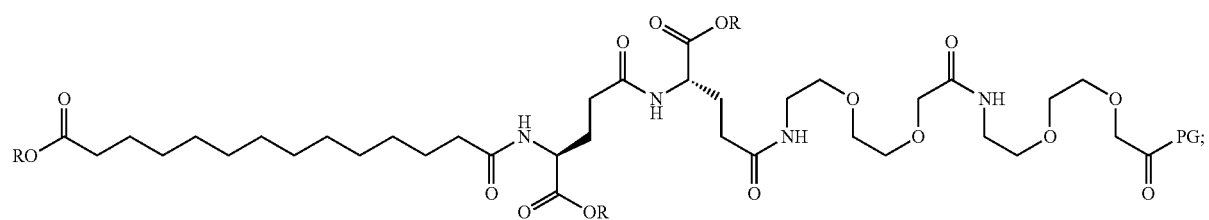
Chem. 141
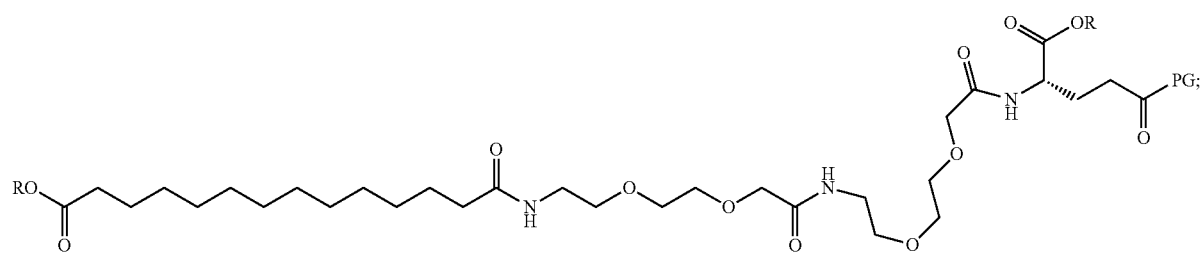
Chem. 142
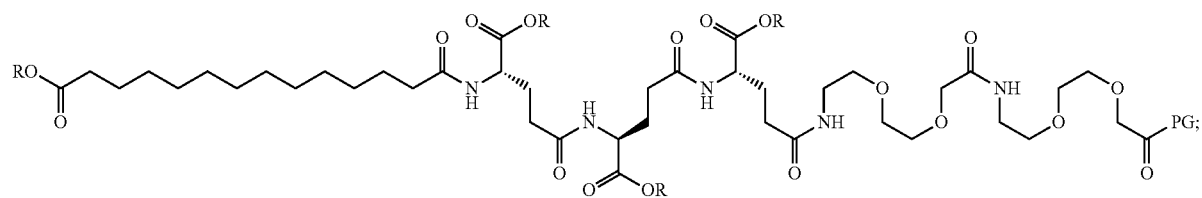
Chem. 143
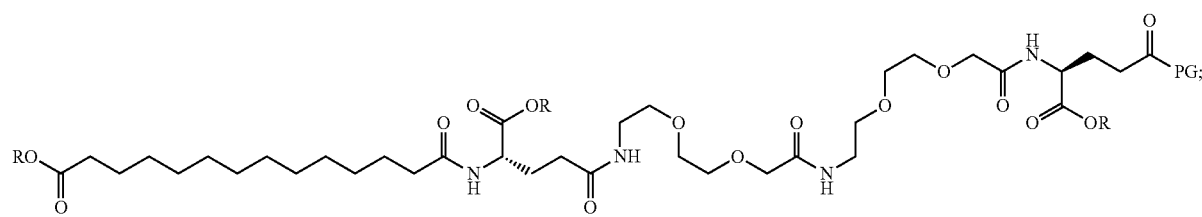

-continued
Chem. 144
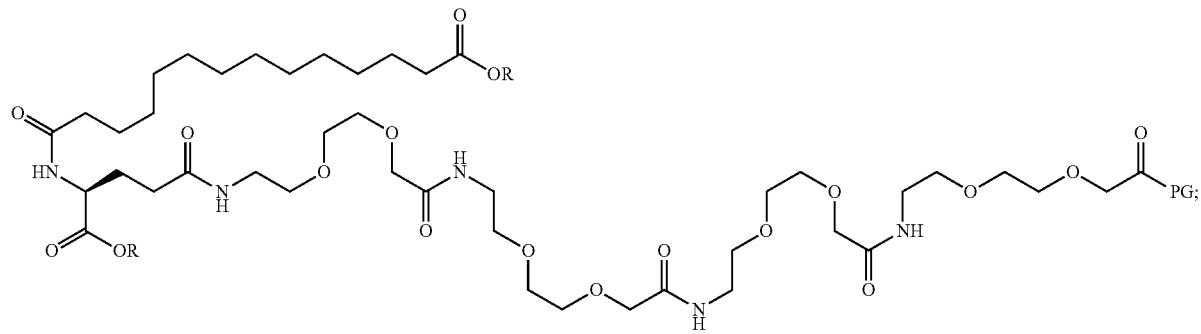
Chem. 145
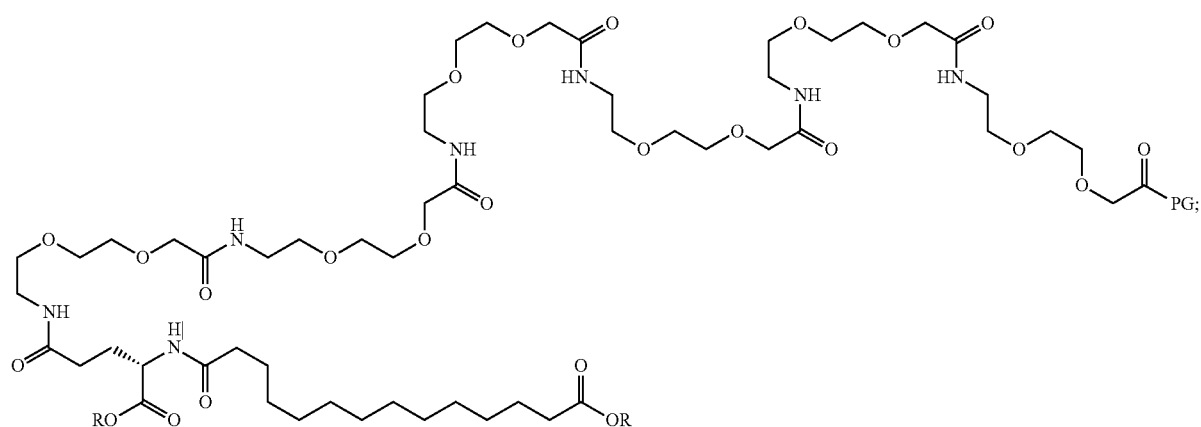
Chem. 146
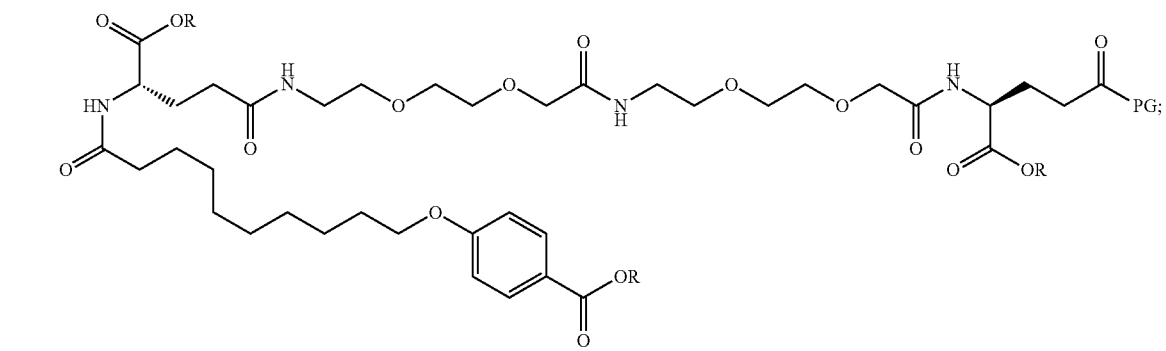
Chem. 147
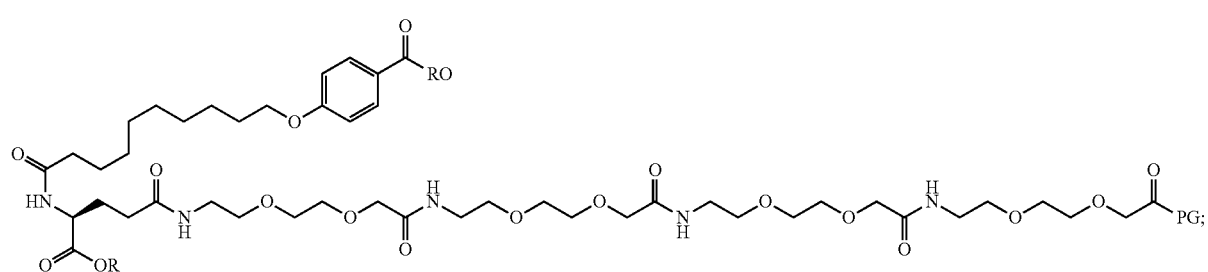
Chem. 148
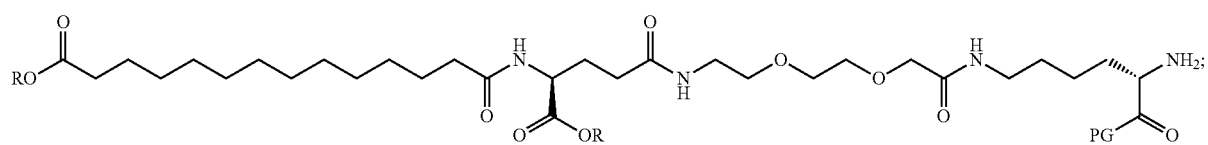

Chem. 149
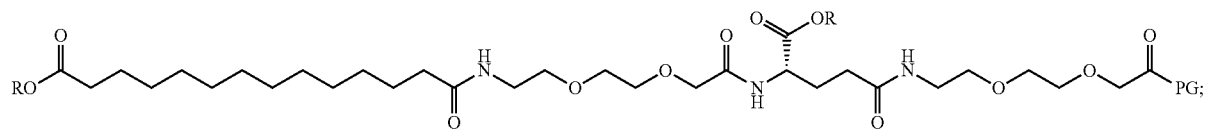
Chem. 150
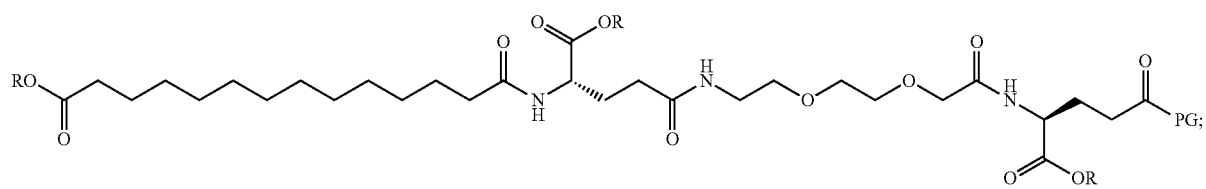
Chem. 151
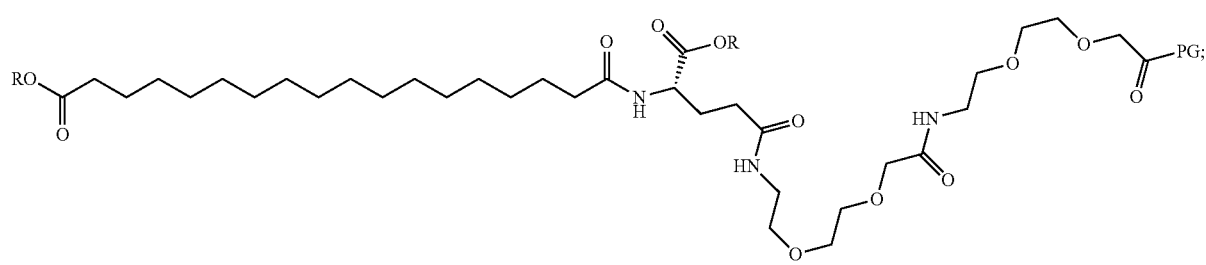
Chem. 152
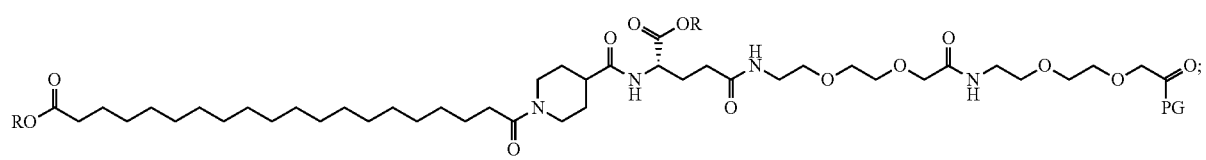
Chem. 153
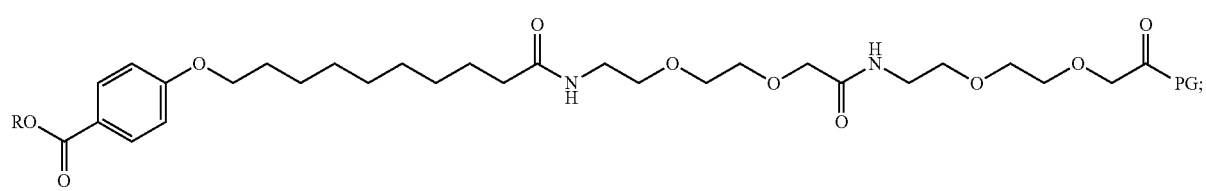
Chem. 154
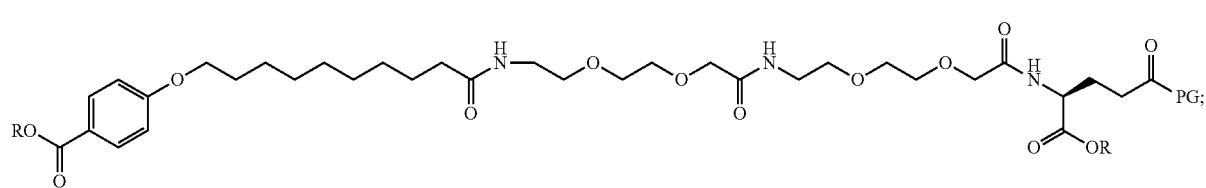
Chem. 155
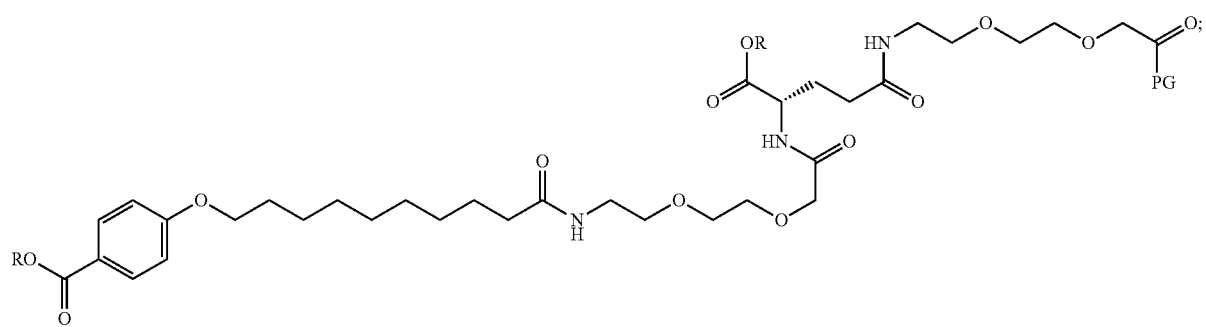

Chem. 156
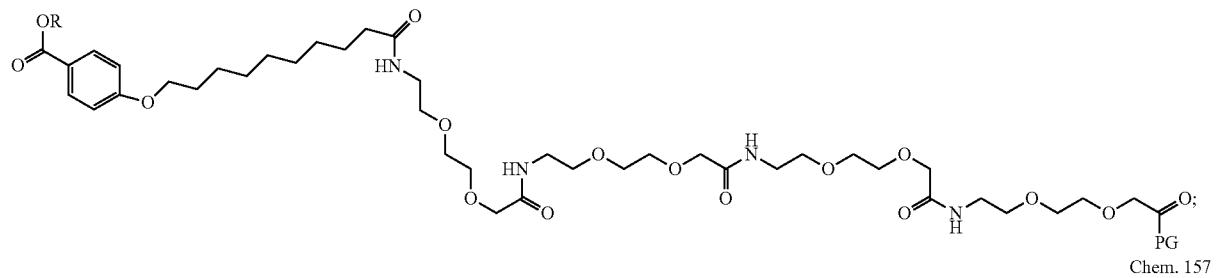
Chem. 157
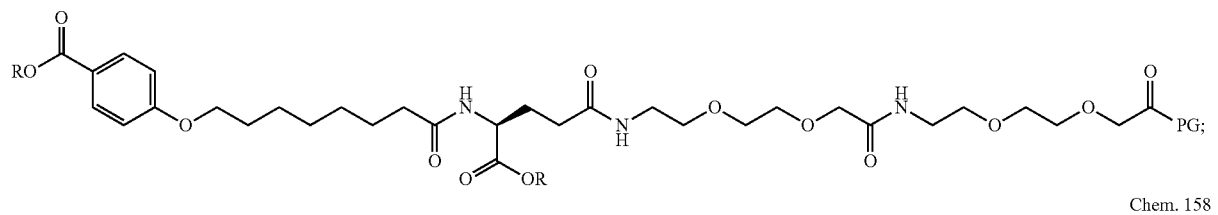
Chem. 158
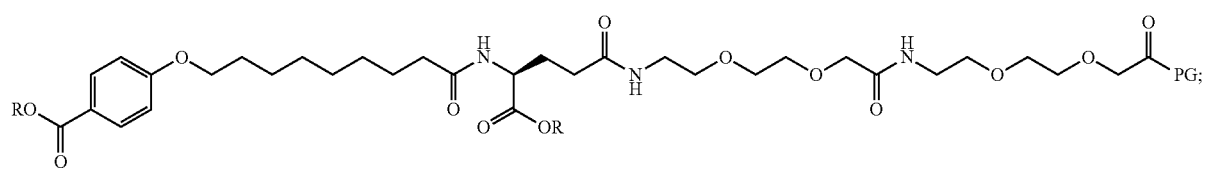
Chem. 159
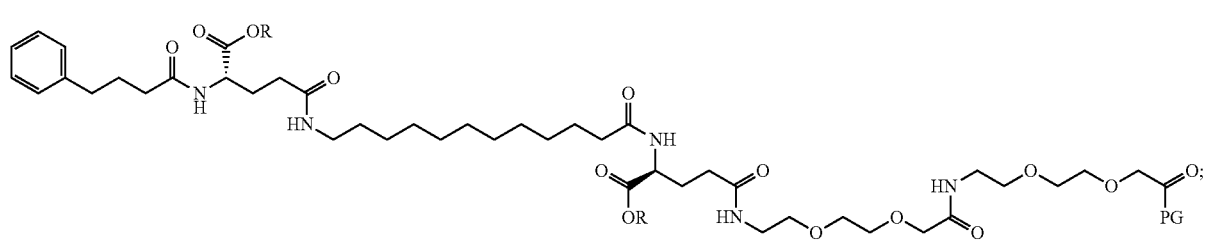
Chem. 160
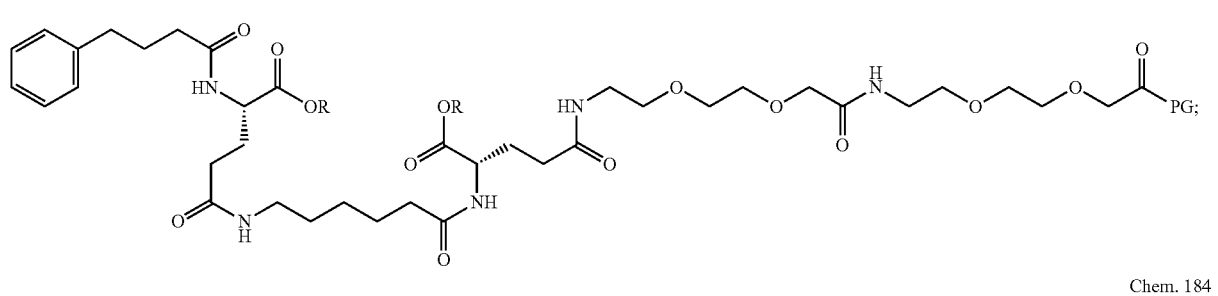
Chem. 184
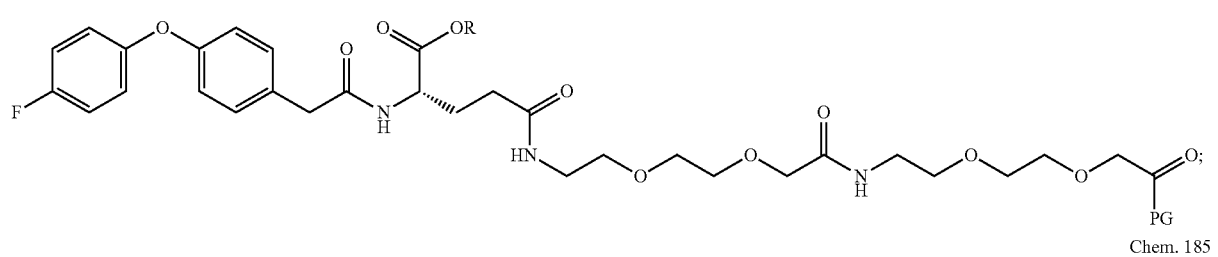
Chem. 185
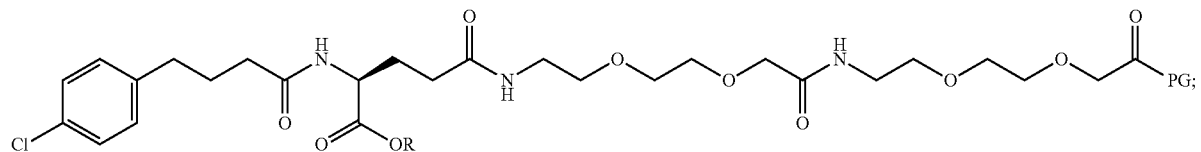

-continued

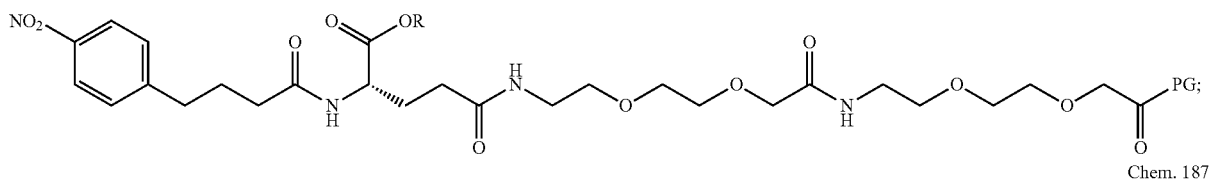

Chem. 186

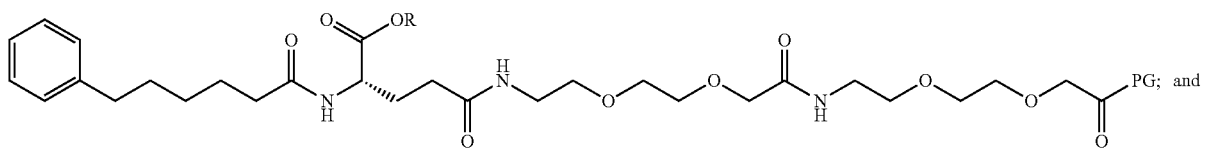

Chem. 187

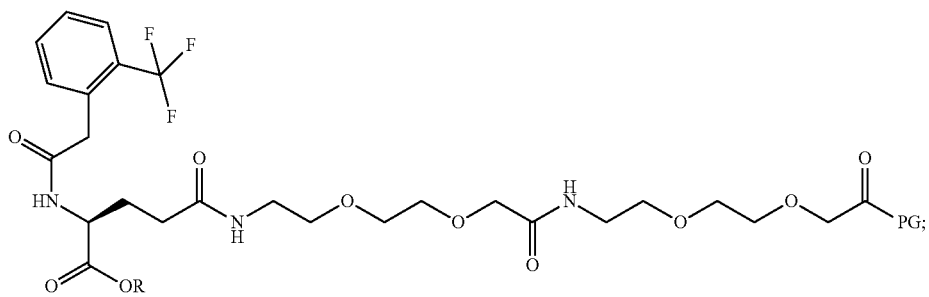

Chem. 188 wherein R and PG are protecting groups;
or a pharmaceutically acceptable salt, amide, or ester of any of Chem. 137-160, and Chem. 184-188.

432. The intermediate product of embodiment 431, wherein R is hydrogen, lower alkyl, or aralkyl of lower alkyl.

433. The intermediate product of any of embodiments 431-432, wherein R is hydrogen.

434. The intermediate product of any of embodiments 431-432, wherein R is lower alkyl.

435. The intermediate product of any of embodiments 431-432, wherein R is aralkyl of lower alkyl.

436. The intermediate product of any of embodiments 431-432, and 434-435, wherein the lower alkyl is linear, cyclic, or branched C1-C6 alkyl, preferably branched C3-C6 alkyl.

437. The intermediate product of any of embodiments 431-432, 434-436, wherein the lower alkyl is linear, cyclic, or branched C1-C4 alkyl, preferably branched C3-C4 alkyl.

438. The intermediate product of any of embodiments 431-432, and 434-437, wherein the lower alkyl is methyl.

439. The intermediate product of any of embodiments 431-432, and 434-438, wherein the aralkyl comprises (preferably has) from 1 to 3 aromatic groups.

440. The intermediate product of any of embodiments 431-432, 434-439, wherein R is tert. butyl, benzyl, or trityl.

441. The intermediate product of any of embodiments 431-440, wherein *—CO-PG is *—CO—OH or an activated ester.

442. The intermediate product of any of embodiments 431-441, preferably according to any of embodiments 434-440, wherein *—CO-PG is *—CO—OH, 443. The intermediate product of any of embodiments 431-441, preferably according to any of embodiments 432-440, wherein *—CO-PG is an activated ester 444. The intermediate product of any of embodiments 441-443, wherein the activated ester is an ester of p-nitrophenol; 2,4,5-trichlorophenol; N-hydroxysuccinimide; N-hydroxysulfosuccinimide; 3,4-dihydro-3-hydroxy-1,2,3-benzotriazine-4-one; 5-chloro-8-hydroxyquinoline; N-hydroxy-5-norbornene-2,3-dicarboxylic acid imide; pentafluorophenol; p-sulfotetrafluorophenol; N-hydroxyphthalimide; 1-hydroxybenzotriazole; 1-hydroxy-7-azabenzotriazole; N-hydroxymaleimide; 4-hydroxy-3-nitrobenzene sulfonic acid; or any other activated ester known in the art.

445. A derivative according to any of embodiments 1-417, for use as a medicament.

446. A derivative according to any of embodiments 1-417, for use in the treatment and/or prevention of all forms of diabetes and related diseases, such as eating disorders, cardiovascular diseases, gastrointestinal diseases, diabetic complications, critical illness, and/or polycystic ovary syndrome; and/or for improving lipid parameters, improving 1-cell function, and/or for delaying or preventing diabetic disease progression.

447. Use of a derivative according to any of embodiments 1-417 in the manufacture of a medicament for the treatment and/or prevention of all forms of diabetes and related diseases, such as eating disorders, cardiovascular diseases, gastrointestinal diseases, diabetic complications, critical illness, and/or polycystic ovary syndrome; and/or for improving lipid parameters, improving 1-cell function, and/or for delaying or preventing diabetic disease progression.

448. A method for treating or preventing all forms of diabetes and related diseases, such as eating disorders, cardiovascular diseases, gastrointestinal diseases, diabetic complications, critical illness, and/or polycystic ovary syndrome; and/or for improving lipid parameters, improving 1-cell function, and/or for delaying or preventing diabetic disease progression—by administering a pharmaceutically active amount of a derivative according to any of embodiments 1-417.

ADDITIONAL PARTICULAR EMBODIMENTS

The following are additional particular embodiments of the invention:

1. A derivative of a GLP-1 analogue,
which analogue comprises a first K residue at a position corresponding to position 18 of GLP-1(7-37) (SEQ ID NO: 1), a second K residue at another position, and a maximum of twelve amino acid modifications as compared to GLP-1 (7-37),
which derivative comprises two protracting moieties attached to said first and second K residue, respectively, via a linker, wherein
the protracting moiety is selected from Chem. 1, Chem. 2, and Chem. 3:

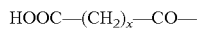  Chem. 1:

  Chem. 2:

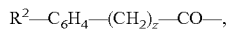  Chem. 3:

in which x is an integer in the range of 6-18, y is an integer in the range of 3-11, z is an integer in the range of 1-5, $R^1$— is —OH, and $R^2$ is a group having a molar mass not higher than 150 Da; and
the linker comprises

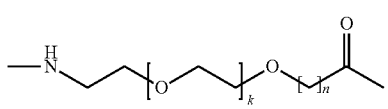  Chem. 4 wherein k is an integer in the range of 1-5, and n is an integer in the range of 1-5;
or a pharmaceutically acceptable salt, amide, or ester thereof.

2. The derivative of embodiment 1, wherein Chem. 4 is a first linker element.
3. The derivative of any one of embodiments 1-2, wherein k is 1.
4. The derivative of any one of embodiments 1-3, wherein n is 1.
5. The derivative of any one of embodiments 1-4, wherein Chem. 4 is included m times, wherein m is an integer in the range of 1-10.
6. The derivative of embodiment 5, wherein m is an integer in the range of 1-6; preferably m is 1, 2, 4, or 6; more preferably m is 1, 2, or 4; even more preferably m is 1 or 4; or most preferably m is 2.
7. The derivative of any one of embodiments 5-6, wherein, when m is different from 1, the Chem. 4 elements are interconnected via amide bond(s).
8. The derivative of any one of embodiments 1-7, wherein the linker further comprises a second linker element.
9. The derivative of embodiment 8, wherein the second linker element is

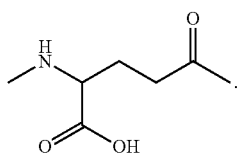  Chem. 5

10. The derivative of embodiment 9, wherein Chem. 5 is included p times, wherein p is an integer in the range of 1-3.
11. The derivative of embodiment 10, wherein p is 1, 2, or 3; preferably 2 or 3, or most preferably 1.

12. The derivative of any one of embodiments 9-11, wherein Chem. 5 is a radical of L-Glu or D-Glu, preferably of L-Glu.
13. The derivative of any one of embodiments 10-12, wherein, when p is different from 1, the Chem. 5 elements are interconnected via amide bond(s).
14. The derivative of any one of embodiments 1-13, wherein the linker further comprises a third linker element.
15. The derivative of embodiment 14, wherein the third linker element is —NH—(CH$_2$)$_q$—CHR$^3$—CO—,  Chem. 6:

in which q is an integer in the range of 2-12, and $R^3$ is hydrogen (H).
16. The derivative of embodiment 15, wherein q is 4, 6, or 10.
17. The derivative of any one of embodiments 15-16, wherein Chem. 6 is a radical of amino hexanoic acid, amino octanoic acid, or amino dodecanoic acid.
18. The derivative of embodiment 17, wherein the radical-ised amino group is at the epsilon position.
19. The derivative of any one of embodiments 10-12, wherein the linker consists of m times Chem. 4 and p times Chem. 5.
20. The derivative of embodiment 19, wherein (m,p) is (2,2), (2,1), (2,3), (4,1), (6,1), (1,1), or (1,2); preferably (2,1), (2,2), (1,2), or (2,3); or most preferably (2,1).
21. The derivative of any one of embodiments 19-20, wherein the m Chem. 4 elements and the p Chem. 5 elements are interconnected via amide bonds.
22. The derivative of any one of embodiments 15-18, wherein the linker consists of m times Chem. 4, p times Chem. 5, and Chem. 6.
23. The derivative of embodiment 22, wherein (m,p) is (2,1), or (1,1); preferably (2,1).
24. The derivative of any one of embodiments 22-23, wherein the m Chem. 4 elements, the p Chem. 5 elements, and the Chem. 6 element are interconnected via amide bonds.
25. The derivative of any one of embodiments 1-24, wherein the linker and the protracting moiety are interconnected via an amide bond.
26. The derivative of any one of embodiments 1-25, wherein the linker and the GLP-1 analogue are interconnected via an amide bond.
27. The derivative of embodiment 26, wherein the linker is attached to the epsilon-amino group of the first or the second K residue.
28. The derivative of any one of embodiments 1-27, wherein the linker has from 6 to 41 C-atoms; preferably from 11 to 41 C-atoms; such as 11, 12, 17, 22, 24, 27, 28, 29, 30, 34, or 41 C-atoms; more preferably 12, 17, 22, 27, or 29 C-atoms; or 11, 24, 28, 30, 34, or 41 C-atoms; even more preferably 12, 17, or 22 C-atoms; or most preferably 17 C-atoms.
29. The derivative of any one of embodiments 1-28, wherein the linker has from 4 to 28 hetero atoms; preferably from 8 to 28 hetero atoms; such as 8, 11, 12, 16, 17, 18, 20, or 28 hetero atoms; more preferably 8, 12, 16, 18, or 20 hetero atoms; even more preferably 8, 16, 18, or 20 hetero atoms; or most preferably 12 hetero atoms.
30. The derivative of embodiment 29, wherein the hetero atoms are N—, and/or O-atoms.
31. The derivative of any one of embodiments 28-30, wherein the linker has from 1 to 7 N-atoms; preferably from 2 to 7 N-atoms; such as 2, 3, 4, 5, or 7 N-atoms; preferably 2, 3, 4, or 5 N-atoms; even more preferably 3, 4, or 5 N-atoms; for example 4 or 5 N-atoms; or most preferably 3 N-atoms.

32. The derivative of any one of embodiments 28-31, wherein the linker has from 3 to 21 O-atoms; preferably from 6 to 21 O-atoms; such as 6, 7, 9, 12, 13, 15, or 21 O-atoms; preferably 6, 9, 12, 13, or 15 O-atoms; for example 6, 12, 13, or 15 O-atoms; or most preferably 9 O-atoms.

33. The derivative of any one of embodiments 1-7, wherein the linker consists of two times Chem. 4, interconnected via an amide bond, and being connected at its free amino end to the free carbonyl group of the protracting moiety, and at its free carbonyl end to the epsilon amino group of the first or the second K residue of the GLP-1 analogue.

34. The derivative of any one of embodiments 1-7, wherein the linker consists of four times Chem. 4, interconnected via amide bonds, and connected at its free amino end to the free carbonyl group of the protracting moiety, and at its free carbonyl end to the epsilon amino group of the first or the second K residue of the GLP-1 analogue.

35. The derivative of any one of embodiments 9-13, wherein the linker consists of two times Chem. 5 and two times Chem. 4, interconnected via amide bonds and in the sequence indicated, the linker being connected at its free amino end to the free carbonyl group of the protracting moiety, and at its free carbonyl end to the epsilon amino group of the first or the second K residue of the GLP-1 analogue.

36. The derivative of any one of embodiments 9-13, wherein the linker consists of two times Chem. 4 and one time Chem. 5, interconnected via amide bonds and in the sequence indicated, the linker being connected at its free amino end to the free carbonyl group of the protracting moiety, and at its free carbonyl end to the epsilon amino group of the first or the second K residue of the GLP-1 analogue.

37. The derivative of any one of embodiments 9-13, wherein the linker consists of three times Chem. 5 and two times Chem. 4, interconnected via amide bonds and in the sequence indicated, the linker being connected at its free amino end to the free carbonyl group of the protracting moiety, and at its free carbonyl end to the epsilon amino group of the first or the second K residue of the GLP-1 analogue.

38. The derivative of any one of embodiments 9-13, wherein the linker consists of one time Chem. 5 and two times Chem. 4, interconnected via amide bonds and in the sequence indicated, the linker being connected at its free amino end to the free carbonyl group of the protracting moiety, and at its free carbonyl end to the epsilon amino group of the first or the second K residue of the GLP-1 analogue.

39. The derivative of any one of embodiments 9-13, wherein the linker consists of one time Chem. 5, two times Chem. 4, and one time Chem. 5, interconnected via amide bonds and in the sequence indicated, the linker being connected at its free amino end to the free carbonyl group of the protracting moiety, and at its free carbonyl end to the epsilon amino group of the first or the second K residue of the GLP-1 analogue.

40. The derivative of any one of embodiments 9-13, wherein the linker consists of one time Chem. 5 and four times Chem. 4, interconnected via amide bonds and in the sequence indicated, the linker being connected at its free amino end to the free carbonyl group of the protracting moiety, and at its free carbonyl end to the epsilon amino group of the first or the second K residue of the GLP-1 analogue.

41. The derivative of any one of embodiments 9-13, wherein the linker consists of one time Chem. 5 and six times Chem. 4, interconnected via amide bonds and in the sequence indicated, the linker being connected at its free amino end to the free carbonyl group of the protracting moiety and at its free carbonyl end to the epsilon amino group of the first or the second K residue of the GLP-1 analogue.

42. The derivative of any one of embodiments 9-13, wherein the linker consists of one time Chem. 5 and one time Chem. 4, interconnected via amide bonds and in the sequence indicated, the linker being connected at its free amino end to the free carbonyl group of the protracting moiety, and at its free carbonyl end to the epsilon amino group of the first or the second K residue of the GLP-1 analogue.

43. The derivative of any one of embodiments 9-13, wherein the linker consists of one time Chem. 4, one time Chem. 5, and one time Chem. 4, interconnected via amide bonds and in the sequence indicated, the linker being connected at its free amino end to the free carbonyl group of the protracting moiety, and at its free carbonyl end to the epsilon amino group of the first or the second K residue of the GLP-1 analogue.

44. The derivative of any one of embodiments 15-18, wherein the linker consists of one time Chem. 5, one time Chem. 6, in which preferably q is 10 and $R^3$ is H, one time Chem. 5, and two times Chem. 4, interconnected via amide bonds and in the sequence indicated, the linker being connected at its free amino end to the free carbonyl group of the protracting moiety, and at its free carbonyl end to the epsilon amino group of the first or the second K residue of the GLP-1 analogue.

45. The derivative of any one of embodiments 15-18, wherein the linker consists of one time Chem. 5, one time Chem. 6, in which preferably q is 4 and $R^3$ is H, one time Chem. 5, and two times Chem. 4, interconnected via amide bonds and in the sequence indicated, the linker being connected at its free amino end to the free carbonyl group of the protracting moiety, and at its free carbonyl end to the epsilon amino group of the first or the second K residue of the GLP-1 analogue.

46. The derivative of any one of embodiments 15-18, wherein the linker consists of one time Chem. 5, one time Chem. 6, in which preferably q is 6 and $R^3$ is H, one time Chem. 5, and two times Chem. 4, interconnected via amide bonds and in the sequence indicated, the linker being connected at its free amino end to the free carbonyl group of the protracting moiety, and at its free carbonyl end to the epsilon amino group of the first or the second K residue of the GLP-1 analogue.

48. The derivative of any one of embodiments 1-46, wherein the protracting moiety is Chem. 3.

49. The derivative of any one of embodiments 1-46, wherein the protracting moiety is Chem. 1 or Chem. 2.

50. The derivative of embodiment 49, wherein the protracting moiety is Chem. 2.

51. The derivative of embodiment 49, wherein the protracting moiety is Chem. 1.

52. The derivative of any one of embodiments 1-46, 49, and 51, wherein x is an even number.

53. The derivative of any one of embodiments 1-46, 49, and 51-52, wherein x is an integer in the range of 10-16.

54. The derivative of embodiment 53, wherein x is 16.

55. The derivative of embodiment 53, wherein x is 10 or 12.

56. The derivative of embodiment 55, wherein x is 10.

57. The derivative of embodiment 55, wherein x is 12.

58. The derivative of any one of embodiments 1-46, and 49-50, wherein y is an odd number.

59. The derivative of any one of embodiments 1-46, 49-50, and 58, wherein y is an integer in the range of 7-9.
60. The derivative of embodiment 59, wherein y is 7 or 8.
61. The derivative of embodiment 60, wherein y is 8.
62. The derivative of embodiment 59, wherein y is 7 or 9
63. The derivative of embodiment 62, wherein y is 7.
64. The derivative of embodiment 62, wherein y is 9.
65. The derivative of any one of embodiments 1-48, wherein z is 3.
66. The derivative of any one of embodiments 1-48 and 65, wherein $R^2$ is a group having a molar mass not higher than 127 Da.
67. The derivative of embodiment 66, wherein $R^2$ is a group having a molar mass in the range of 1-127 Da.
68. The derivative of embodiment 67, wherein $R^2$ is —H.
69. The derivative of embodiment 67, wherein $R^2$ is a halogen radical.
70. The derivative of embodiment 69, wherein $R^2$ is —I.
71. The derivative of any one of embodiments 1-46, 49, and 51-57, wherein Chem. 1 is represented by Chem. 1a:

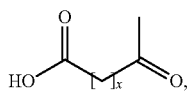

Chem. 1a where x is as defined in any one of embodiments 1 and 52-57.
72. The derivative of any one of embodiments 1-46, 49-50, and 58-64, wherein Chem. 2 is represented by Chem. 2a:

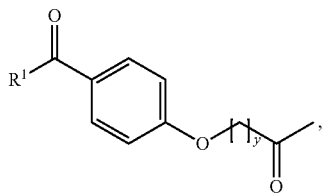

Chem 2a where $R^1$ and y are as defined in any one of embodiments 1, and 58-64.
73. The derivative of any one of embodiments 1-48, and 65-70, wherein Chem. 3 is represented by Chem 3a:

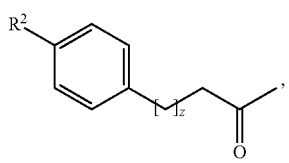

Chem. 3a where $R^2$ and z are as defined in any one of embodiments 1 and 65-70.
74. The derivative of any one of embodiments 1-73, wherein the two protracting moieties are substantially identical.
75. The derivative of any one of embodiments 1-74, wherein the two protracting moieties have a similarity of at least 0.5; preferably at least 0.6; more preferably at least 0.7, or at least 0.8; even more preferably at least 0.9; or most preferably at least 0.99, such as a similarity of 1.0.
76. The derivative of any one of embodiments 1-75, wherein the two linkers are substantially identical.
77. The derivative of any one of embodiments 1-76, wherein the two linkers have a similarity of at least 0.5; preferably at least 0.6; more preferably at least 0.7, or at least 0.8; even more preferably at least 0.9; or most preferably at least 0.99, such as a similarity of 1.0.
78. The derivative of any one of embodiments 1-77, wherein the two side chains consisting of protracting moiety and linker are substantially identical.
79. The derivative of any one of embodiments 1-78, wherein the two side chains consisting of protracting moiety and linker have a similarity of at least 0.5; preferably at least 0.6; more preferably at least 0.7, or at least 0.8; even more preferably at least 0.9; or most preferably at least 0.99, such as a similarity of 1.0.
80. The derivative of any one of embodiments 75, 77, and 79, wherein the two chemical structures to be compared are represented as fingerprints, such as a) ECFP_6 fingerprints; b) UNITY fingerprints; and/or c) MDL fingerprints; and wherein for each of a), b) and c) the Tanimoto coefficient is preferably used for calculating the similarity of the two fingerprints.
81. The derivative of any one of embodiments 1-80, wherein the first K residue is designated $K^{18}$.
82. The derivative of any one of embodiments 1-81, wherein the second K residue is at a position corresponding to position T of GLP-1 (7-37) (SEQ ID NO: 1).
83. The derivative of any one of embodiments 1-82, wherein the second K residue is designated $K^T$.
84. The derivative of any one of embodiments 82-83, wherein T is an integer selected from the range of 1-17, or from the range of 19-37.
85. The derivative of embodiment 84, wherein T is selected from the range of 19-37.
86. The derivative of embodiment 85, wherein T is selected from the group consisting of 26, 27, 30, 31, 34, and 37.
87. The derivative of embodiment 86, wherein T is selected from the group consisting of 26, 27, 30, and 31.
88. The derivative of embodiment 87, wherein T is selected from the group consisting of 26, 27, or 31.
89. The derivative of embodiment 88, wherein T is 26 or 27; 26 or 31; or 27 or 31.
90. The derivative of embodiment 86, wherein T=26.
91. The derivative of embodiment 86, wherein T=27.
92. The derivative of embodiment 86, wherein T=30.
93. The derivative of embodiment 86, wherein T=31.
94. The derivative of embodiment 86, wherein T=34.
95. The derivative of embodiment 86, wherein T=37.
96. The derivative of any one of embodiments 1-95, wherein the position corresponding to position 18 of GLP-1 (7-37) (SEQ ID NO: 1) is identified by handwriting and eyeballing.
97. The derivative of any one of embodiments 82-96, wherein the position corresponding to position T of GLP-1 (7-37) (SEQ ID NO: 1) is identified by handwriting and eyeballing.
98. The derivative of any one of embodiments 1-95, wherein the position corresponding to position 18 of GLP-1(7-37) (SEQ ID NO: 1) is identified by use of a standard protein or peptide alignment program.
99. The derivative of any one of embodiments 82-96, wherein the position corresponding to position T of GLP-1 (7-37) (SEQ ID NO: 1) is identified by use of a standard protein or peptide alignment program.
100. The derivative of any one of embodiments 98 and 99, wherein the alignment program is a Needleman-Wunsch alignment.

101. The derivative of any one of embodiments 98-100, wherein the default scoring matrix and the default identity matrix is used.

102. The derivative of embodiment 101, wherein the scoring matrix is BLOSUM62

103. The derivative of any one of embodiments 98-102, wherein the penalty for the first residue in a gap is −10 (minus ten).

104. The derivative of any one of embodiments 98-103, wherein the penalties for additional residues in a gap is −0.5 (minus point five).

105. The derivative of any one of embodiments 1-104, wherein the analogue comprises no K residues other than the first and the second K residue.

106. The derivative of any one of embodiments 1-105, wherein the maximum twelve amino acid modification(s) is (are) at one or more positions corresponding to the following positions in GLP-1(7-37) (SEQ ID NO: 1): 7, 8, 18, 22, 23, 25, 26, 27, 30, 31, 34, 35, 36, and 37.

107. The derivative of embodiment 106, wherein the position corresponding to any of the indicated positions of GLP-1 (7-37) (SEQ ID NO: 1) is identified by handwriting and eyeballing.

108. The derivative of embodiment 106, wherein the position corresponding to any of the indicated positions of GLP-1(7-37) (SEQ ID NO: 1) is identified as described for position 18 and position T in any one of embodiments 98-104.

109. The derivative of any one of embodiments 83-90 and 96-108, wherein the second K residue is $K^{26}$, and wherein the analogue, in addition to the modification $K^{18}$, further comprises a modification selected from $Des^{34}$, $G^{34}$, $Q^{34}$, and $R^{34}$; and still further, optionally, at least one of the following additional modifications: $Imp^7$, ($Aib^8$ or $S^8$), $E^{22}$, ($E^{23}$ or $R^{23}$), $V^{25}$, ($H^{27}$ or $L^{27}$), $E^{30}$, $Des^{35}$, $Des^{36}$, and/or $Des^{37}$, wherein in case of $Des^{35}$ and/or $Des^{36}$ being included they are preferably included in a combination selected from ($Des^{35}$, $Des^{36}$, and $Des^{37}$), and ($Des^{36}$, and $Des^{37}$).

110. The derivative of any one of embodiments 83-86, 94, and 96-108, wherein the second K residue is $K^{34}$, and wherein the analogue, in addition to the modification $K^{18}$, comprises a modification selected from $H^{26}$, $R^{26}$, $V^{26}$; and still further, optionally, at least one of the following additional modifications: $Imp^7$, ($Aib^8$ or $S^8$), $E^{22}$, ($E^{23}$ or $R^{23}$), $V^{25}$, ($H^{27}$ or $L^{27}$), $E^{30}$, $Des^{35}$, $Des^{36}$, and/or $Des^{37}$, wherein in case of $Des^{35}$ and/or $Des^{36}$ being included they are preferably included in a combination selected from ($Des^{35}$, $Des^{36}$, and $Des^{37}$), and ($Des^{36}$ and $Des^{37}$).

111. The derivative of any one of embodiments 83-89, 91, and 96-108, wherein the second K residue is $K^{27}$, and wherein the analogue, in addition to the modification $K^{18}$, comprises a modification selected from $H^{26}$, $R^{26}$, and $V^{26}$, as well as a modification selected from $Des^{34}$, $G^{34}$, $Q^{34}$, and $R^{34}$; and still further, optionally, at least one of the following additional modifications: $Imp^7$, ($Aib^8$ or $S^8$), $E^{22}$, ($E^{23}$ or $R^{23}$), $V^{25}$, $E^{30}$, $Des^{35}$, $Des^{36}$, and/or $Des^{37}$, wherein in case of $Des^{35}$ and/or $Des^{36}$ being included they are preferably included in a combination selected from ($Des^{35}$, $Des^{36}$, and $Des^{37}$), and ($Des^{36}$, and $Des^{37}$).

112. The derivative of any one of embodiments 83-873, 92, and 96-108, wherein the second K residue is $K^{30}$, and wherein the analogue, in addition to the modification $K^{18}$, comprises a modification selected from $H^{26}$, $R^{26}$, and $V^{26}$, as well as a modification selected from $Des^{34}$, $G^{34}$, $Q^{34}$, and $R^{34}$; and still further, optionally, at least one of the following additional modifications: $Imp^7$, ($Aib^8$ or $S^8$), $E^{22}$, ($E^{23}$ or $R^{23}$), $V^{25}$, ($H^{27}$ or $L^{27}$), $Des^{35}$, $Des^{36}$ and/or $Des^{37}$, wherein in case of $Des^{35}$ and/or $Des^{36}$ being included they are preferably included in a combination selected from ($Des^{35}$, $Des^{36}$, and $Des^{37}$), and ($Des^{36}$, and $Des^{37}$).

113. The derivative of any one of embodiments 83-89, 93, and 96-108, wherein the second K residue is $K^{31}$, and wherein the analogue, in addition to the modification $K^{18}$, comprises a modification selected from $H^{26}$, $R^{26}$, and $V^{26}$, as well as a modification selected from $Des^{34}$, $G^{34}$, $Q^{34}$, and $R^{34}$; and still further, optionally, at least one of the following additional modifications: $Imp^7$, ($Aib^8$ or $S^8$), $E^{22}$, ($E^{23}$ or $R^{23}$), $V^{25}$, ($H^{27}$ or $L^{27}$), $E^{30}$, $Des^{35}$, $Des^{36}$, and/or $Des^{37}$, wherein in case of $Des^{35}$ and/or $Des^{36}$ being included they are preferably included in a combination selected from ($Des^{35}$, $Des^{36}$, and $Des^{37}$), and ($Des^{36}$ and $Des^{37}$).

114. The derivative of any one of embodiments 83-86, 95, and 96-108, wherein the second K residue is $K^{37}$, and wherein the analogue, in addition to the modification $K^{18}$, comprises a modification selected from $H^{26}$, $R^{26}$, and $V^{26}$, as well as a modification selected from $Des^{34}$, $G^{34}$, $Q^{34}$, and $R^{34}$; and still further, optionally, at least one of the following additional modifications: $Imp^7$, ($Aib^8$ or $S^8$), $E^{22}$, ($E^{23}$ or $R^{23}$), $V^{25}$, ($H^{27}$ or $L^{27}$), $E^{30}$, $Des^{35}$ and/or $Des^{36}$, wherein in case of $Des^{35}$ being included it is preferably included in combination with $Des^{36}$; more preferably $Imp^7$, $Aib^8$, $S^8$, $E^{22}$, $E^{23}$, $R^{23}$, $V^{25}$, $H^{27}$, $L^{27}$, and/or $E^{30}$.

115. The derivative of embodiment any one of embodiments 1-114, wherein the analogue comprises $Imp^7$, and/or ($Aib^8$ or $S^8$).

116. The derivative of any one of embodiments 1-115, wherein the analogue comprises $Imp^7$, and/or $Aib^8$.

117. The derivative of any one of embodiments 1-116, wherein the analogue comprises $Aib^8$.

118. The derivative of any one of embodiments 1-117, wherein the analogue comprises $E^{22}$.

119. The derivative of any one of embodiments 1-118, wherein the analogue comprises $Q^{34}$, or $R^{34}$; preferably $R^{34}$.

120. The derivative of any one of embodiments 1-119, wherein the analogue comprises $V^{25}$.

121. The derivative of any one of embodiments 1-120, wherein the analogue comprises $R^{26}$.

122. The derivative of any one of embodiments 1-121, wherein the analogue comprises $Des^{37}$.

123. The derivative of any one of embodiments 1-122, wherein the analogue comprises $Des^{37}$ and $Des^{36}$.

124. The derivative of any one of embodiments 1-123, wherein the analogue comprises $Des^{37}$, $Des^{36}$, and $Des^{35}$.

125. The derivative of any one of embodiments 1-124, wherein the analogue comprises $Des^{37}$, $Des^{36}$, $Des^{35}$, and $Des^{34}$.

126. The derivative of any one of embodiments 1-125, which is a derivative of GLP-1(7-33) (amino acids 1-27 of SEQ ID NO: 1).

127. The derivative of any one of embodiments 1-126, which is a derivative of GLP-1(7-34) (amino acids 1-28 of SEQ ID NO: 1).

128. The derivative of any one of embodiments 1-127, which is a derivative of GLP-1(7-35) (amino acids 1-29 of SEQ ID NO: 1).

129. The derivative of any one of embodiments 1-128, wherein the analogue has a maximum of eleven amino acid modifications.

130. The derivative of any one of embodiments 1-129, wherein the analogue has a maximum of ten amino acid modifications.

131. The derivative of any one of embodiments 1-130, wherein the analogue has a maximum of nine amino acid modifications.

132. The derivative of any one of embodiments 1-131, wherein the analogue has a maximum of eight amino acid modifications.
133. The derivative of any one of embodiments 1-132, wherein the analogue has a maximum of seven amino acid modifications.
134. The derivative of any one of embodiments 1-133, wherein the analogue has a maximum of six amino acid modifications.
135. The derivative of any one of embodiments 1-134, wherein the analogue has a maximum of five amino acid modifications.
136. The derivative of any one of embodiments 1-135, wherein the analogue has a maximum of four amino acid modifications.
137. The derivative of any one of embodiments 1-136, wherein the analogue has a maximum of three amino acid modifications.
138. The derivative of any one of embodiments 1-137, wherein the analogue has a maximum of two amino acid modifications.
139. The derivative of any one of embodiments 1-138, wherein the analogue has a maximum of one amino acid modification.
140. The derivative of any one of embodiments 1-139, wherein the analogue has a minimum of one amino acid modification.
141. The derivative of any one of embodiments 1-140, wherein the analogue has a minimum of two amino acid modifications.
142. The derivative of any one of embodiments 1-141, wherein the analogue has a minimum of three amino acid modifications.
143. The derivative of any one of embodiments 1-142, wherein the analogue has a minimum of four amino acid modifications.
144. The derivative of any one of embodiments 1-143, wherein the analogue has a minimum of five amino acid modifications.
145. The derivative of any one of embodiments 1-144, wherein the analogue has a minimum of six amino acid modifications.
146. The derivative of any one of embodiments 1-145, wherein the analogue has a minimum of seven amino acid modifications.
147. The derivative of any one of embodiments 1-146, wherein the analogue has a minimum of eight amino acid modifications.
148. The derivative of any one of embodiments 1-147, wherein the analogue has a minimum of nine amino acid modifications.
149. The derivative of any one of embodiments 1-148, wherein the analogue has a minimum of ten amino acid modifications.
150. The derivative of any one of embodiments 1-149, wherein the analogue has one amino acid modification.
151. The derivative of any one of embodiments 1-150, wherein the analogue has two amino acid modifications.
152. The derivative of any one of embodiments 1-151, wherein the analogue has three amino acid modifications.
153. The derivative of any one of embodiments 1-152, wherein the analogue has four amino acid modifications.
154. The derivative of any one of embodiments 1-153, wherein the analogue has five amino acid modifications.
155. The derivative of any one of embodiments 1-154, wherein the analogue has six amino acid modifications.
156. The derivative of any one of embodiments 1-155, wherein the analogue has seven amino acid modifications.
157. The derivative of any one of embodiments 1-156, wherein the analogue has eight amino acid modifications.
158. The derivative of any one of embodiments 1-157, wherein the analogue has nine amino acid modifications.
159. The derivative of any one of embodiments 1-158, wherein the analogue has ten amino acid modifications.
160. The derivative of any one of embodiments 1-159, wherein the analogue has eleven amino acid modifications.
161. The derivative of any one of embodiments 1-160, wherein the modifications are, independently, substitutions, additions, and/or deletions.
162. The derivative of any one of embodiments 1-161, wherein the modifications are, independently, substitutions, and/or deletions.
163. The derivative of any one of embodiments 1-162, wherein the modifications are substitutions.
164. The derivative of any one of embodiments 1-163, wherein the modifications are deletions.
165. A compound selected from the following: Chem. 20, Chem. 21, Chem. 22, Chem. 23, Chem. 24, Chem. 25, Chem. 26, Chem. 27, Chem. 28, Chem. 29, Chem. 30, Chem. 31, Chem. 32, Chem. 33, Chem. 34, Chem. 35, Chem. 36, Chem. 37, Chem. 38, Chem. 39, Chem. 40, Chem. 41, Chem. 42, Chem. 43, Chem. 44, Chem. 45, Chem. 46, Chem. 47, Chem. 48, Chem. 49, Chem. 50, Chem. 51, Chem. 52, Chem. 53, Chem. 54, Chem. 55, Chem. 56, Chem. 57, Chem. 58, Chem. 59, Chem. 60, Chem. 61, Chem. 62, Chem. 63, Chem. 64, Chem. 65, Chem. 66, Chem. 67, Chem. 68, Chem. 69, Chem. 70, Chem. 71, Chem. 72, Chem. 73, Chem. 74, Chem. 75, Chem. 76, Chem. 77, Chem. 78, Chem. 79, Chem. 80, Chem. 81, Chem. 82, Chem. 83, Chem. 84, Chem. 85, Chem. 86, Chem. 87, Chem. 88, Chem. 89, Chem. 90, Chem. 91, Chem. 92, Chem. 93, Chem. 94, Chem. 95, Chem. 96, Chem. 97, Chem. 98, Chem. 100, Chem. 101, Chem. 102, Chem. 103, Chem. 104, Chem. 105, Chem. 106, Chem. 107, Chem. 108, Chem. 109, Chem. 110, Chem. 111, Chem. 112, Chem. 113, Chem. 114, Chem. 115, Chem. 116, Chem. 117, Chem. 118, Chem. 119, Chem. 120, Chem. 121, Chem. 122, Chem. 123, Chem. 124, Chem. 125, Chem. 126, Chem. 127, Chem. 128, Chem. 129, Chem. 130, Chem. 131, Chem. 132, Chem. 133, Chem. 134, and Chem. 135.
166. A compound characterised by its name, and selected from a listing of each of the names of the compounds of Examples 1-79, and 81-116 herein.
167. The compound of embodiment 166, which is a compound of embodiment 165.
168. The compound of any one of embodiments 165 and 166, which is a derivative according to any one of embodiments 1-164.
169. The derivative of any one of embodiments 1-168 which is selected from the following:

$N^{\epsilon 18}$-[2-[2-[2-[[2-[2-[2-[[(4S)-4-carboxy-4-[10-(4-carboxyphenoxy)decanoylamino]butanoyl]amino]ethoxy]ethoxy]acetyl]amino]ethoxy]ethoxy]acetyl], $N^{\epsilon 26}$-[2-[2-[2-[[2-[2-[2-[[(4S)-4-carboxy-4-[10-(4-carboxyphenoxy)decanoylamino]butanoyl]amino]ethoxy]ethoxy]acetyl]amino]eth oxy]ethoxy]acetyl]-[Aib8,Lys18,Glu22,Gln34]-GLP-1-(7-37)-peptide (SEQ ID NO: 7);

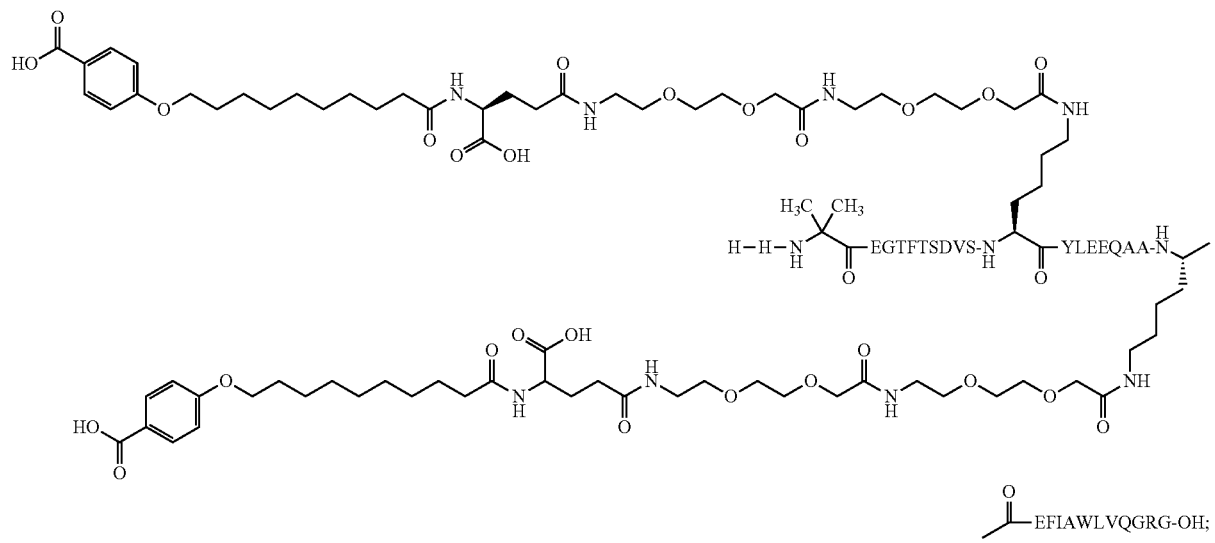

Chem. 21

$N^{\epsilon 18}$-[2-[2-[2-[[2-[2-[2-[[(4S)-4-carboxy-4-[10-(4-carboxy-phenoxy)decanoylamino]butanoyl]amino]ethoxy]ethoxy]acetyl]amino]ethoxy]ethoxy]acetyl], $N^{\epsilon 31}$-[2-[2-[2-[[2-[2-[2-[[(4S)-4-carboxy-4-[10-(4-carboxyphenoxy)decanoylamino]butanoyl]amino]ethoxy]ethoxy]acetyl]amino]ethoxy]ethoxy]acetyl]-[Aib8,Lys18,Glu22,Arg26,Lys31,Arg34]-GLP-1-(7-37)-peptide (SEQ ID NO: 8);

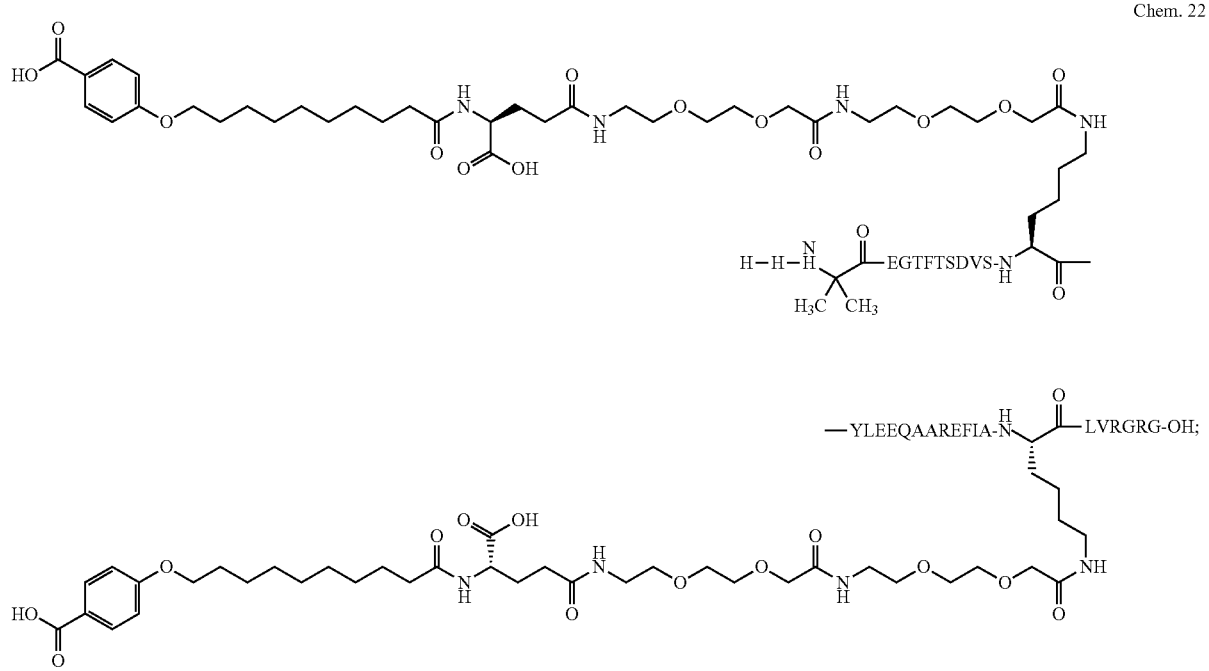

Chem. 22

$N^{\epsilon 18}$-[2-[2-[2-[[2-[2-[2-[[(4S)-4-carboxy-4-[10-(4-carboxy-phenoxy)decanoylamino]butanoyl]amino]ethoxy]ethoxy]acetyl], $N^{\epsilon 31}$-[2-[2-[2-[[2-[2-[2-[[(4S)-4-carboxy-4-[10-(4-carboxyphenoxy)decanoylamino]butanoyl]amino]ethoxy]ethoxy]acetyl]amino]ethoxy]ethoxy]acetyl]-[Aib8,Lys18,Glu22,Val25,Arg26,Lys31,Gly34]-GLP-1-(7-34)-peptide (SEQ ID NO: 9);

Chem. 38

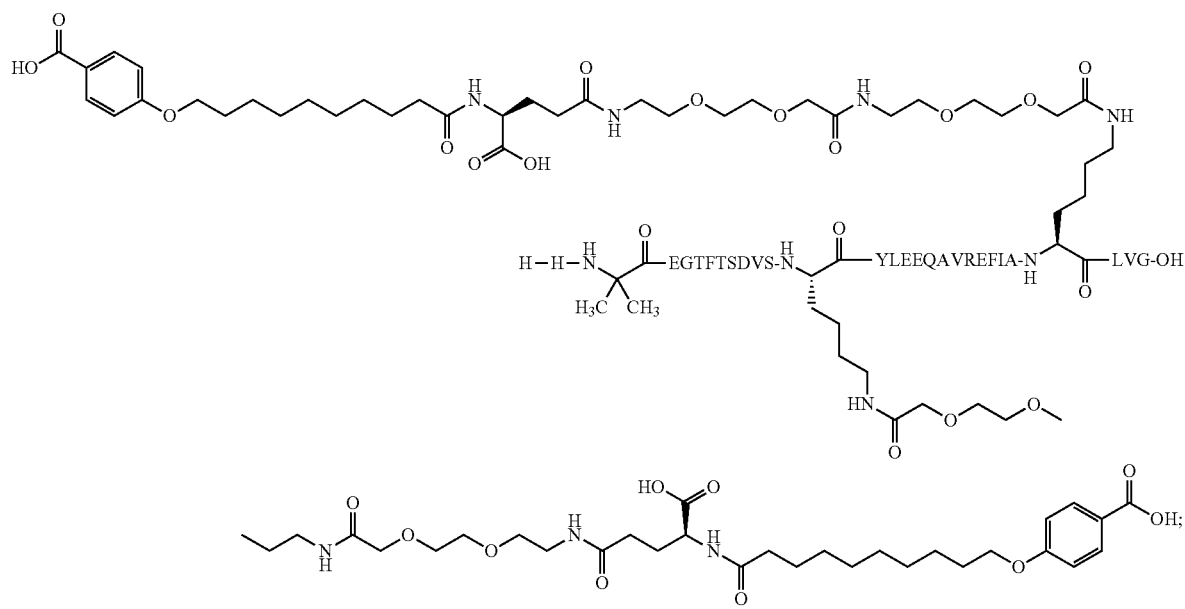

N^ε18-[2-[2-[2-[[2-[2-[2-[[(4S)-4-carboxy-4-(13-carboxytri-decanoylamino)butanoyl]amino]ethoxy]ethoxy]acetyl]amino]ethoxy]ethoxy]acetyl], N^ε31-[2-[2-[2-[[2-[2-[2-[[(4S)-4-carboxy-4-(13-carboxytridecanoylamino)butanoyl]amino]ethoxy]ethoxy]acetyl]amino]ethoxy]acetyl]-[Lys18,Glu22,Val25,Arg26,Lys31,Arg34]-GLP-1-(7-37)-peptide (SEQ ID NO: 10);

Chem. 62

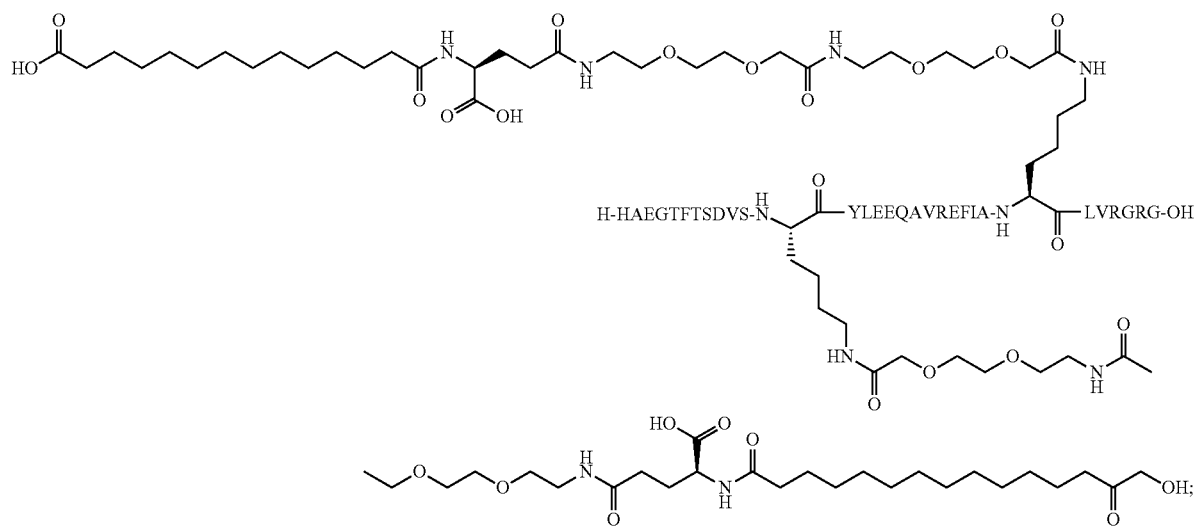

N^ε18-[2-[2-[2-[[2-[2-[2-[[(4S)-4-carboxy-4-(13-carboxytri-decanoylamino)butanoyl]amino]ethoxy]ethoxy]acetyl]amino]ethoxy]ethoxy]acetyl], N^ε31-[2-[2-[2-[[2-[2-[2-[[(4S)-4-carboxy-4-(13-carboxytridecanoylamino)butanoyl]amino]ethoxy]ethoxy]acetyl]amino]ethoxy]ethoxy]acetyl]-[Lys18,Glu22,Val25,Arg26,Lys31,Gln34]-GLP-1-(7-37)-peptide (SEQ ID NO: 11);

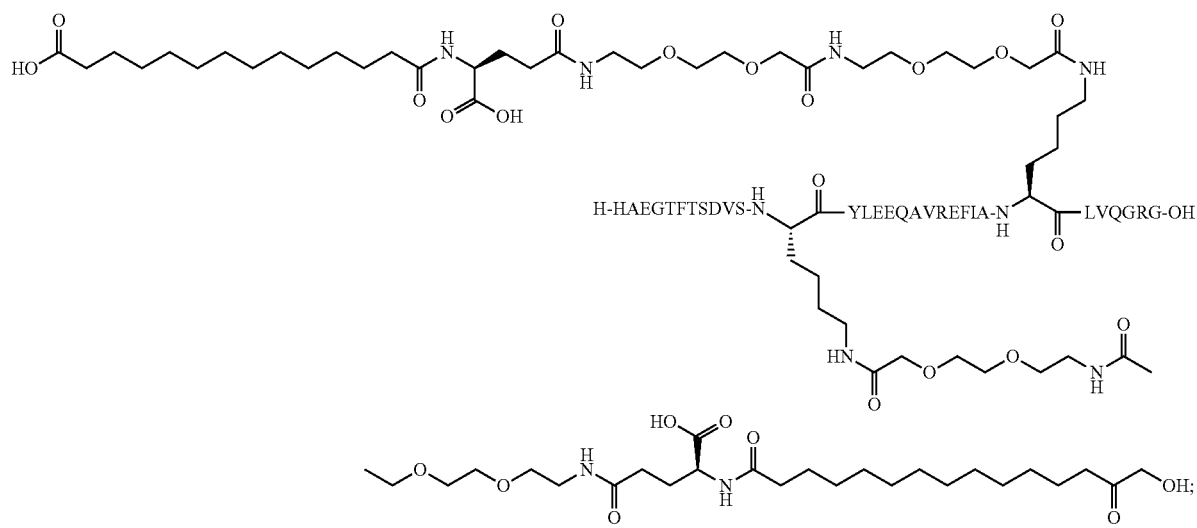

Chem. 63

$N^{\epsilon18}$-[2-[2-[2-[[2-[2-[2-[[(4S)-4-carboxy-4-(13-carboxytri-decanoylamino)butanoyl]amino]ethoxy]ethoxy]acetyl] amino]ethoxy]ethoxy]acetyl], $N^{\epsilon31}$-[2-[2-[2-[[2-[2-[2-[[(4S)-4-carboxy-4-(13-carboxytridecanoylamino) butanoyl]amino]ethoxy]ethoxy]acetyl]amino]ethoxy] ethoxy]acetyl]-[Aib8,Lys18,Glu22,Val25,Arg26,Lys31, Arg34]-GLP-1-(7-37)-peptide (SEQ ID NO: 12);

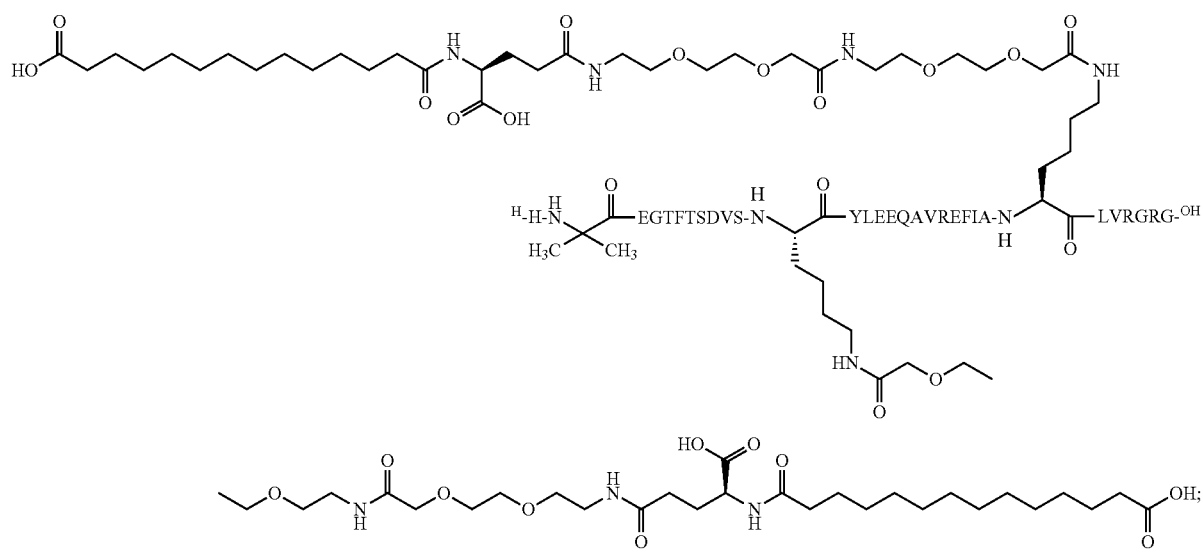

Chem. 93

$N^{\epsilon18}$-[2-[2-[2-[[2-[2-[2-[[(4S)-4-carboxy-4-[10-(4-carboxy-phenoxy)decanoylamino]butanoyl]amino]ethoxy]ethoxy] acetyl]amino]ethoxy]ethoxy]acetyl], $N^{\epsilon31}$-[2-[2-[2-[[2-[2-[2-[[(4S)-4-carboxy-4-[10-(4-carboxyphenoxy) decanoylamino]butanoyl]amino]ethoxy]ethoxy]acetyl] amino]ethoxy]ethoxy]acetyl]-[Lys18,Glu22,Val25, Arg26,Lys31,Arg34]-GLP-1-(7-37)-peptide (SEQ ID NO: 10);

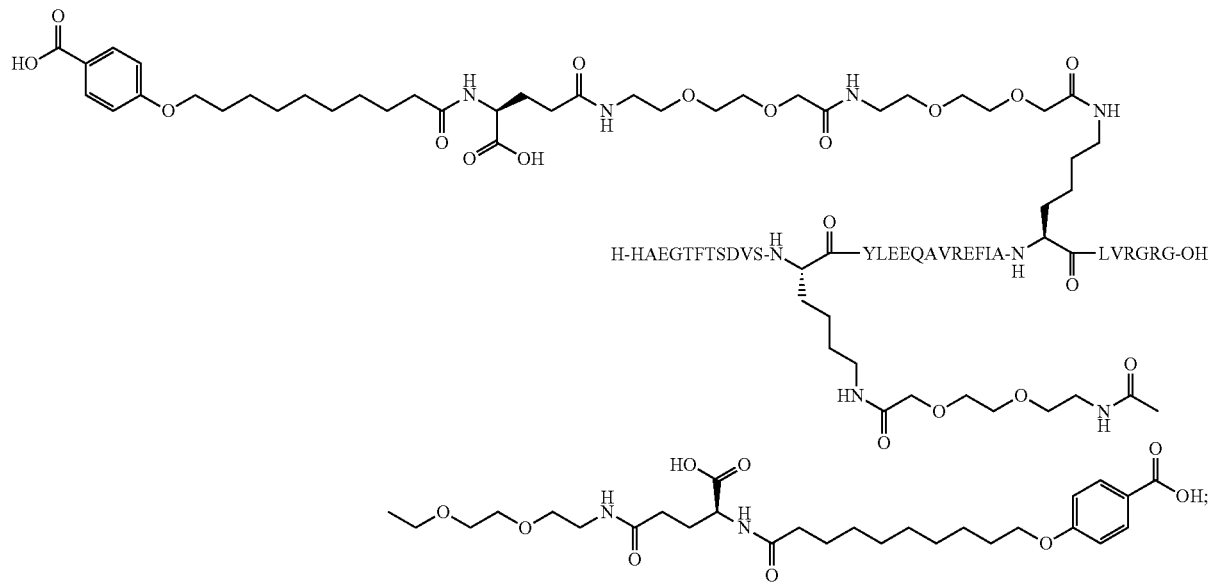

N^ε18-[2-[2-[2-[[2-[2-[2-[[(4S)-4-carboxy-4-[10-(4-carboxy-phenoxy)decanoylamino]butanoyl]amino]ethoxy]ethoxy]acetyl]amino]ethoxy]ethoxy]acetyl], N^ε31-[2-[2-[2-[[2-[2-[2-[[(4S)-4-carboxy-4-[10-(4-carboxyphenoxy)decanoylamino]butanoyl]amino]ethoxy]ethoxy]acetyl]amino]ethoxy]ethoxy]acetyl]-[Aib8,Lys18,Glu22,Val25,Arg26,Lys31,Arg34]-GLP-1-(7-37)-peptide (SEQ ID NO: 12);

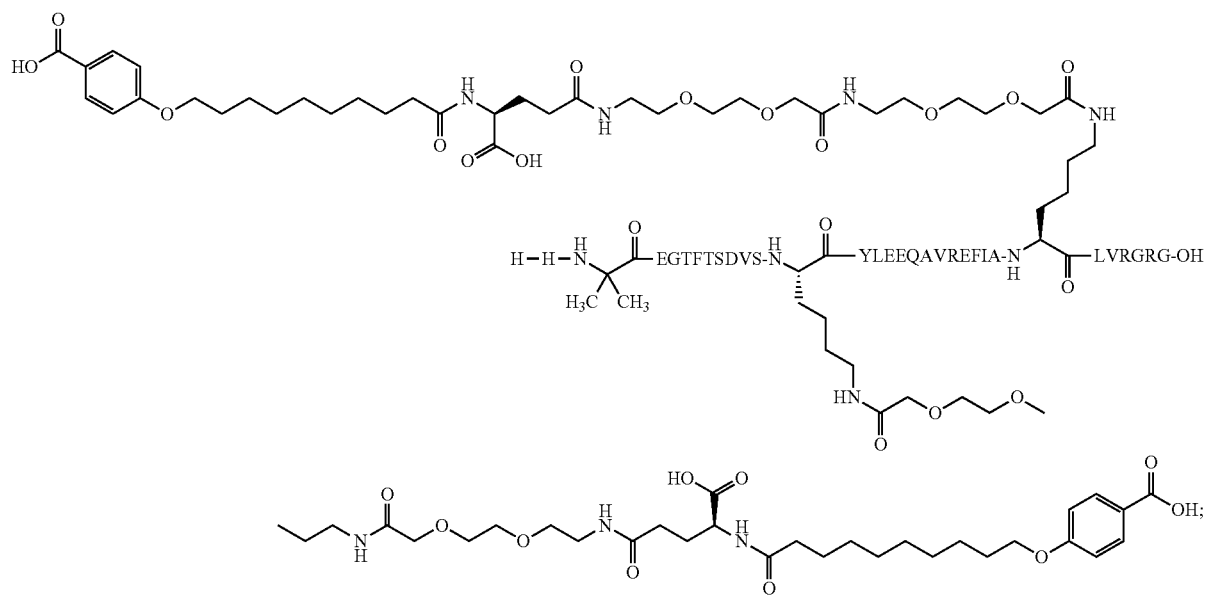

N^ε18-[(4S)-4-carboxy-4-[[2-[2-[2-[[2-[2-[2-[10-(4-carboxy-phenoxy)decanoylamino]ethoxy]ethoxy]acetyl]amino]ethoxy]ethoxy]acetyl]amino]butanoyl], N^ε26-[(4S)-4-carboxy-4-[[2-[2-[2-[[2-[2-[2-[10-(4-carboxyphenoxy)decanoylamino]ethoxy]ethoxy]acetyl]amino]ethoxy]ethoxy]acetyl]amino]butanoyl]-[Aib8,Lys18,Glu22,Gln34]-GLP-1-(7-37)-peptide (SEQ ID NO: 7);

Chem. 101

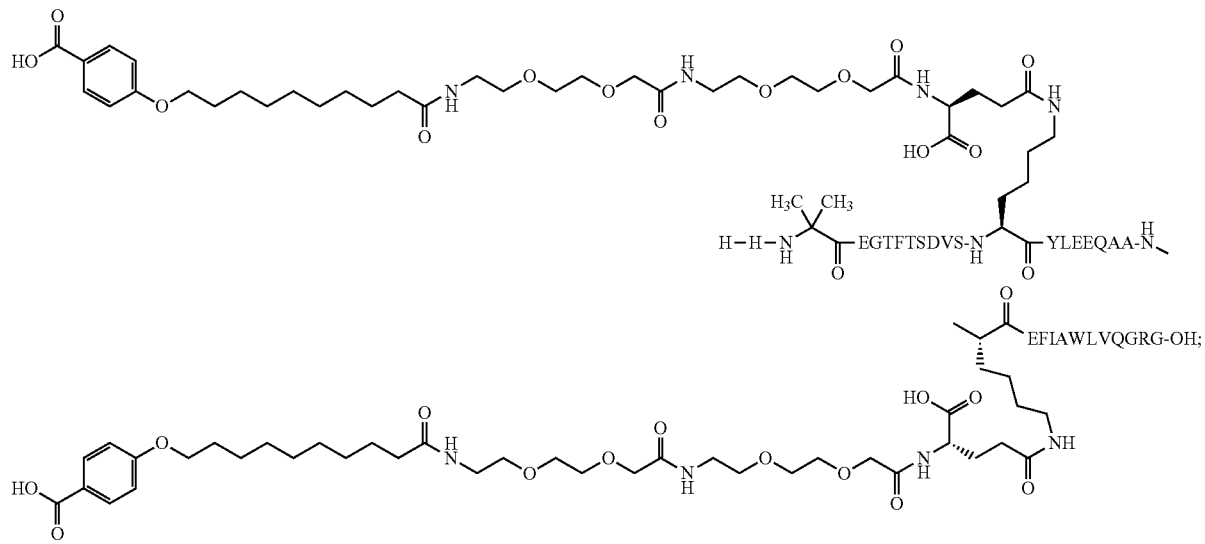

$N^{\epsilon 18}$-[(4S)-4-carboxy-4-[[2-[2-[2-[[2-[2-[2-[[(4S)-4-carboxy-4-(13-carboxytridecanoylamino)butanoyl]amino]ethoxy]ethoxy]acetyl]amino]ethoxy]ethoxy]acetyl]amino]butanoyl], $N^{\epsilon 31}$-[(4S)-4-carboxy-4-[[2-[2-[2-[[2-[2-[2-[[(4S)-4-carboxy-4-(13- carboxytridecanoylamino)butanoyl]amino]ethoxy]ethoxy]acetyl]amino]ethoxy]ethoxy]acetyl]amino]butanoyl]-[Lys18,Glu22,Val25,Arg26,Lys31,Arg34]-GLP-1-(7-37)-peptide (SEQ ID NO: 10); and 170. The derivative of any one of embodiments 1-169, which has a potency ($EC_{50}$)

a) at or below 10000 pM, preferably below 10000 pM, more preferably below 5000 pM, even more preferably below 4000 pM, or most preferably below 3000 pM;

b) below 2000 pM, preferably below 1000 pM, more preferably below 800 pM, even more preferably below 600 pM, or most preferably below 500 pM;

c) below 400 pM, preferably below 300 pM, more preferably below 200 pM, even more preferably below 150 pM, or most preferably below 100 pM; or d) below 80 pM, preferably below 60 pM, more preferably below 50 pM, even more preferably below 40 pM, or most preferably below 30 pM.

171. The derivative of any one of embodiments 1-170, wherein the potency is determined as stimulation of the formation of cAMP in a medium containing the human GLP-1 receptor, preferably using a stable transfected cell-line such as BHK467-12A (tk-ts13), and/or using for the determination of cAMP a functional receptor assay, e.g. based on competition between endogenously formed cAMP and exogenously added biotin-labelled cAMP, in which assay cAMP is more preferably captured using a specific antibody, and/or wherein an even more preferred assay is the AlphaScreen cAMP Assay, most preferably the one described in Example 148.

Chem. 130

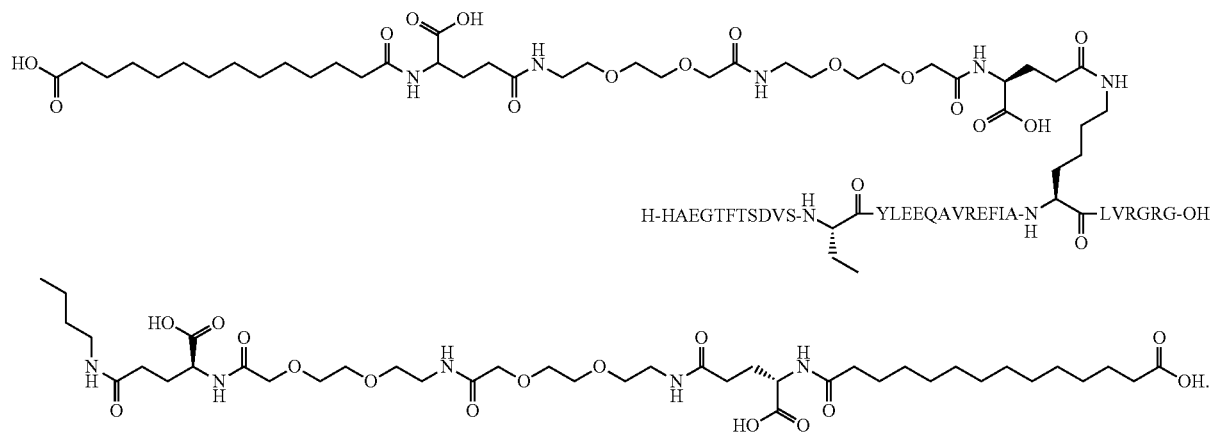

172. The derivative of any one of embodiments 1-171, for which the ratio [GLP-1 receptor binding affinity ($IC_{50}$) in the presence of 2.0% HSA (high albumin), divided by GLP-1 receptor binding affinity ($IC_{50}$) in the presence of 0.005% HSA (low albumin)] is:
a) at least 1, preferably at least 10, more preferably at least 20, even more preferably at least 30, or most preferably at least 40;
b) at least 50, preferably at least 60, more preferably at least 70, even more preferably at least 80, or most preferably at least 90; or
c) at least 100, preferably at least 200, more preferably at least 300, still more preferably at least 400, even more preferably at least 500, or most preferably at least 600.
173. The derivative of any one of embodiments 1-172, for which the GLP-1 receptor binding affinity ($IC_{50}$) in the presence of 0.005% HSA (low albumin) is
a) below 1000.00 nM, preferably below 500.00 nM, more preferably below 100.00 nM, or most preferably below 50.00 nM; or
b) below 10.00 nM, preferably below 5.00 nM, or more preferably below 1.00 nM.
174. The derivative of any one of embodiments 1-173, for which the GLP-1 receptor binding affinity ($IC_{50}$) in the presence of 2.0% HSA (high albumin) is
a) below 1000.00 nM; or
b) below 500.00 nM, preferably below 100.00 nM, or more preferably below 50.00 nM.
175. The derivative of any one of embodiments 172-174, wherein the binding affinity to the GLP-1 receptor is measured by way of displacement of $^{125}$I-GLP-1 from the receptor, preferably using a SPA binding assay.
176. The derivative of any one of embodiments 172-175, wherein the GLP-1 receptor is prepared using a stable, transfected cell line, preferably a hamster cell line, more preferably a baby hamster kidney cell line, such as BHK tk-ts13.
177. The derivative of any one of embodiments 172-176, wherein the $IC_{50}$ value is determined as the concentration which displaces 50% of $^{125}$I-GLP-1 from the receptor.
178. The derivative of any one of embodiments 1-177, for which the plasma concentration (pM) of the derivative, determined 30 minutes after injection of a solution of the derivative in the jejunum of rat, divided by the concentration (pM) of the injected solution (dose-corrected exposure at 30 min) is at least 40, preferably at least 50, more preferably at least 60, still more preferably at least 70, even more preferably at least 80, or most preferably at least 100.
179. The derivative of any one of embodiments 1-178, for which the plasma concentration (pM) of the derivative, determined 30 minutes after injection of a solution of the derivative in the jejunum of rat, divided by the concentration (pM) of the injected solution (dose-corrected exposure at 30 min) is at least 110, preferably at least 120, more preferably at least 130, still more preferably at least 140, even more preferably at least 150, or most preferably at least 160.
180. The derivative of any one of embodiments 1-179, for which the plasma concentration (pM) of the derivative, determined 30 minutes after injection of a solution of the derivative in the jejunum of rat, divided by the concentration (pM) of the injected solution (dose-corrected exposure at 30 min) is at least 180, preferably at least 190, more preferably at least 200, still more preferably at least 210, even more preferably at least 220, or most preferably at least 230.
181. The derivative of any one of embodiments 1-180, for which the plasma concentration (pM) of the derivative, determined 30 minutes after injection of a solution of the derivative in the jejunum of rat, divided by the concentration (pM) of the injected solution (dose-corrected exposure at 30 min) is at least 240, preferably at least 250, more preferably at least 260, or most preferably at least 270.
182. The derivative of any one of embodiments 178-181, wherein the GLP-1 derivative is tested in a concentration of 1000 uM in admixture with 55 mg/ml sodium caprate.
183. The derivative of any one of embodiments 178-182, wherein male Sprague Dawley rats are used, preferably with a body weight upon arrival of approximately 240 g.
184. The derivative of any one of embodiments 178-183, wherein the rats are fasted for approximately 18 hours before the experiment.
185. The derivative of any one of embodiments 178-184, wherein the rats are and taken into general anaesthesia after having fasted and before the injection of the derivative in the jejunum.
186. The derivative of any one of embodiments 178-185, wherein the derivative is administered in the proximal part of the jejunum (10 cm distal for the duodenum) or in the mid-intestine (50 cm proximal for the cecum).
187. The derivative of any one of embodiments 178-186, wherein 100 μl of the derivative is injected into the jejunal lumen through a catheter with a 1 ml syringe, and subsequently 200 μl of air is pushed into the jejunal lumen with another syringe, which is then left connected to the catheter to prevent flow back into the catheter.
188. The derivative of any one of embodiments 178-187, wherein blood samples (200 ul) are collected into EDTA tubes from the tail vein at desired intervals, such as at times 0, 10, 30, 60, 120 and 240 min, and centrifuged 5 minutes, 10000G, at 4° C. within 20 minutes.
189. The derivative of any one of embodiments 178-188, wherein plasma (75 ul) is separated, immediately frozen, and kept at −20° C. until analyzed for plasma concentration of the derivative.
190. The derivative of any one of embodiments 178-189, wherein LOCI (Luminescent Oxygen Channeling Immunoassay) is used for analyzing the plasma concentration of the derivative.
191. The derivative of any one of embodiments 1-190, wherein the derivative is effective at lowering blood glucose in vivo in db/db mice.
192. The derivative of any one of embodiments 1-191, wherein the derivative is effective at lowering body weight in vivo in db/db mice.
193. The derivative of any one of embodiments 191 and 192, wherein db/db mice are treated, s.c., with a suitable range of doses of the GLP-1 derivative, and blood glucose and/or bodyweight is/are determined at appropriate intervals.
194. The derivative of embodiment 193, wherein the dose of the GLP-1 derivative is 0.3 nmol/kg, 1.0 nmol/kg, 3.0 nmol/kg, 10 nmol/kg, 30 nmol/kg, and 100 nmol/kg, wherein kg refers to the body weight of the mouse.
195. The derivative of any one of embodiments 191-194, wherein a control group is treated with vehicle, s.c., preferably the medium in which the GLP-1 derivative is dissolved, e.g. with the following composition: 50 mM sodium phosphate, 145 mM sodium chloride, 0.05% tween 80, pH 7.4.
196. The derivative of any one of embodiments 191-195, wherein blood glucose is determined, and/or the mice are weighed, at time −½ h (half an hour prior to dosing (t=0)), and at times 1, 2, 4, 8, 24, 48, 72, and 96 h.
197. The derivative of any one of embodiments 191-196, wherein the glucose concentration is measured using the glucose oxidase method.

198. The derivative of any one of embodiments 191-197, wherein
  (i) $ED_{50}$ (body weight (BW)) is calculated as the dose giving rise to half-maximum effect on delta (e.g., decrease) BW 24 hours following the subcutaneous administration of the derivative; and/or
  (ii) $ED_{50}$ (blood glucose (BG)) is calculated as the dose giving rise to half-maximum effect on AUC (Area Under the Curve) delta (e.g., decrease) BG 8 hours following the subcutaneous administration of the analogue.

199. The derivative of any one of embodiments 191-198, wherein a sigmoidal dose-response relationship exists, preferably with a clear definition of the maximum response.

200. The derivative of any one of embodiments 191-199, wherein $ED_{50}$ (BG) is below 5.00 nmol/kg, preferably below 4.00 nmol/kg, more preferably below 3.00 nmol/kg, even more preferably below 2.00 nmol/kg, or most preferably below 1.00 nmol/kg.

201. The derivative of any one of embodiments 191-200, wherein $ED_{50}$ (BW) is below 5.00 nmol/kg, preferably below 4.00 nmol/kg, more preferably below 3.00 nmol/kg, even more preferably below 2.00 nmol/kg, or most preferably below 1.00 nmol/kg.

202. The derivative of any one of embodiments 1-201, wherein the terminal half-life ($T_{1/2}$) after i.v. administration in minipigs is
a) at least 8 hours, preferably at least 16 hours, more preferably at least 24 hours, even more preferably at least 32 hours, or most preferably at least 40 hours; or
b) at least 48 hours, preferably at least 60 hours, more preferably at least 72 hours, even more preferably at least 80 hours, or most preferably at least 84 hours.

203. The derivative of embodiment 202, wherein the minipigs are male Göttingen minipigs.

204. The derivative of any one of embodiments 202-203, wherein the minipigs are 7-14 months of age, and preferably weighing from 16-35 kg.

205. The derivative of any one of embodiments 202-204, wherein the minipigs are housed individually, and fed once or twice daily, preferably with SDS minipig diet.

206. The derivative of any one of embodiments 202-205, wherein the derivative is dosed, i.v., after at least 2 weeks of acclimatisation.

207. The derivative of any one of embodiments 202-206, wherein the animals are fasted for approximately 18 h before dosing and for at least 4 h after dosing, and have ad libitum access to water during the whole period.

208. The derivative of any one of embodiments 202-207, wherein the GLP-1 derivative is dissolved in 50 mM sodium phosphate, 145 mM sodium chloride, 0.05% tween 80, pH 7.4 to a suitable concentration, preferably from 20-60 nmol/ml.

209. The derivative of any one of embodiments 202-208, wherein intravenous injections of the derivative are given in a volume corresponding to 1-2 nmol/kg.

210. The derivative of any one of embodiments 1-209, which increases the glucose stimulated insulin secretion in minipigs.

211. The derivative of embodiment 210, wherein the minipigs are male Göttingen minipigs.

212. The derivative of any one of embodiments 210-211, wherein the minipigs are 7-14 months of age.

213. The derivative of any one of embodiments 210-212, wherein the minipigs are housed in single pens, and fed once or twice daily, preferably with SDS minipig fodder.

214. The derivative of any one of embodiments 202-213, wherein a single dose, optionally after a period with dose escalation, is given i.v., or s.c., in the thin skin behind the ear.

215. The derivative of any one of embodiments 202-214, wherein the animals are fasted for approximately 18 h before dosing.

216. The derivative of any one of embodiments 202-215, wherein a baseline group and a number of derivative dose groups corresponding to 2-6 different plasma concentration levels are tested, wherein the baseline group is a) vehicle treated, or b) untreated.

217. The derivative of any one of embodiments 202-216, wherein the plasma concentration level is 3000-80000 pM.

218. The derivative of any one of embodiments 202-217, wherein a 1 or 2 hour intravenous glucose tolerance test (IVGTT) is performed.

219. The derivative of any one of embodiments 202-218, wherein 0.3 g/kg glucose is given i.v. over a period of 30 seconds, and blood samples taken at suitable time points, such as the following time points (t=0 corresponds to the glucose bolus): −10, −5, 0, 2, 5, 10, 15, 20, 25, 30, 40, 50, 60, 70, 80, 90, 100, 110, 120 minutes.

220. The derivative of embodiment 219, wherein the concentration in plasma of the derivative, glucose, and insulin is determined.

221. The derivative of embodiment 220, wherein the derivative concentration is measured at t=0 min, and, optionally, at the end of the test (t=60 min, or t=120 min).

222. The derivative of any one of embodiments 202-221, wherein glucose is analyzed using the glucose oxidase method.

223. The derivative of any one of embodiments 202-222, wherein the area under the insulin curve (AUCinsulin) is calculated and used as a measure of insulin secretion.

224. The derivative of any one of embodiments 202-223, wherein for at least one concentration thereof, the AUCinsulin is higher than the baseline AUCinsulin, preferably at least 110% thereof, more preferably at least 120% thereof, even more preferably at least 130% thereof or most preferably at least 140% thereof.

225. The derivative of any one of embodiments 1-224, which causes a reduced feed intake in pigs relative to a control (preferably vehicle-treated, or untreated);
  optionally the feed intake (0-24 h) may be 90% or lower relative to the vehicle-treated control, preferably 80% or lower, more preferably 70% or lower, even more preferably 60% or lower, or most preferably 50% or lower;
  wherein feed intake (0-24 h) refers to the first 24 hours after administration of the derivative or vehicle.

226. The derivative of embodiment 225, wherein the pigs are female Landrace Yorkshire Duroc (LYD) pigs.

227. The derivative of embodiment 226, wherein the LYD pigs are 3 months of age, and preferably have a weight of 30-35 kg.

228. The derivative of any one of embodiments 225-227, where the animals are housed in a group for 1-2 weeks for acclimatisation.

229. The derivative of any one of embodiments 225-228, wherein during the experimental period the animals are placed in individual pens from Monday morning to Friday afternoon for measurement of individual food intake.

230. The derivative of any one of embodiments 225-229, wherein the animals are fed ad libitum with pig fodder (such as Svinefoder, Antonio).

231. The derivative of any one of embodiments 225-230, wherein food intake is monitored on line by logging the weight of fodder every 15 minutes, preferably using the Mpigwin system.

232. The derivative of any one of embodiments 225-231, which is dosed 0.3, 1.0, 3.0, 10, or 30 nmol/kg, preferably dissolved in a phosphate buffer (50 mM phosphate, 0.05% tween 80, pH 8), more preferably at concentrations of 12, 40, 120, 400, or 1200 nmol/ml.

233. The derivative of any one of embodiments 225-232, wherein the phosphate buffer serves as vehicle.

234. The derivative of any one of embodiments 225-233, wherein the animals are dosed with a single subcutaneous dose of the derivative, or vehicle (preferably with a dose volume of 0.025 ml/kg), on the morning of day 1, and food intake is measured for 4 days after dosing.

235. An intermediate product in the form of a GLP-1 analogue which comprises the following modifications as compared to GLP-1(7-37) (SEQ ID NO: 1):

(A) (i) (8Aib, 18K, 22E, 26R, 34R, 37K); (ii) (8Aib, 18K, 22E, 26R, 31K, 34R); (iii) (71mp, 18K, 22E, 26R, 34R, 37K); (iv) (8Aib, 18K, 22E, 25V, 26R, 31K, 34G, des35-37); (v) (8Aib, 18K, 22E, 25V, 26R, 30E, 31K, 34G, des35-37); (vi) (8Aib, 18K, 22E, 26R, 31H, 31K, 34G, des35-37); (vii) (8Aib, 18K, 22E, 26R, 27K, 31H, 34R, des36-37); (iix) (18K, 22E, 25V, 26R, 31K, 34G, des35-37); (ix) (18K, 22E, 25V, 26R, 31K, 34G, des35-37); (x) (71mp, 18K, 22E, 25V, 26R, 31K, 34G, des35-37); (xi) (8S, 18K, 22E, 25V, 26R, 31K, 34G, des35-37); (xii) (18K, 22E, 26R, 31K, 34G, des35-37); (xiii) (8Aib, 18K, 22E, 26R, 31K, 34G, des35-37); (xiv) (8Aib, 18K, 22E, 23R, 25V, 26R, 31K, 34G, des35-37); (xv) (8Aib, 18K, 22E, 25V, 26R, 27H, 31K, 34G, des35-37); (xvi) (71mp, 8Aib, 18K, 22E, 25V, 26R, 31K, 34G, des35-37); (xvii) (18K, 22E, 26R, 27K, 31H, 34G, des35-37); (iixx) (71mp, 18K, 22E, 26R, 27K, 31H, 34G, des35-37); (ixx) (18K, 34Q); (xx) (18K, 22E, 26H, 27K, 34Q); (xxi) (8Aib, 18K, 22E, 25V, 26R, 31K, des34-37); (xxii) (18K, 22E, 34Q) (xxiii); (8Aib, 18K, 22E, 25V, 26R, 27K, 34Q); (xxiv) (18K, 22E, 25V, 26R, 27K, 34Q); (xxv) (18K, 22E, 25V, 26R, 31K, 34R); (xxvi) (18K, 22E, 25V, 26R, 31K, 34Q); (xxvii) (18K, 22E, 25V, 26R, 31K, 34G); (iixxx) (18K, 22E, 25V, 26R, 27K, 34R); (ixxx) (18K, 22E, 25V, 26R, 27K, 31H, 34R); (xxx) (18K, 22E, 25V, 26R, 30K, 34G, des35-37); (xxxi) (8Aib, 18K, 22E, 26R, 30K, 34R); (xxxii) (18K, 22E, 25V, 26R, 30K, 31H, 34G, des35-37); (xxxiii) (18K, 22E, 25V, 26R, 27L, 30K, 34G, des35-37); (xxxiv) (18K, 22E, 23E, 25V, 26R, 27K, 34R); (xxxv) (18K, 22E, 23E, 25V, 26R, 27K, 34Q); (xxxvi) (18K, 22E, 26H, 27K, 34R); (xxxvii) (18K, 22E, 26H, 27K, 31H, 34R); (iixxxx) (8Aib, 18K, 22E, 25V, 26R, 27L, des35-37); (ixxxx) (18K, 22E, 25V, 26R, 31H, des35-37); (xxxx) (18K, 26H, 27K, 34Q); (xxxxi) (8Aib, 18K, 26V, 27K, 34R); (xxxxii) (18K, 26H, 31K, 34R); (xxxxiii) (8Aib, 18K, 22E, 25V, 26R, 31K, 34R); (xxxxiv) (18K, 25V, 26R, 31K, 34R); (xxxxv) (18K, 22E, 26R, 31K, 34R); (xxxxvi) (8Aib, 18K, 26H, 30K, 34R, des36-37); (xxxxvii) (8Aib, 18K, 22E, 26R, 30K, 34R, des36-37); (iixxxxx) (8Aib, 18K, 22E, 34R); (ixxxx) (8Aib, 18K, 34Q); (xxxxx) (8Aib, 18K, 22E, 34R); and (xxxxxi) (8Aib, 18K, 25V, 26R, 31K, 34R);

wherein the analogue is preferably selected from the following analogues of GLP-1(7-37) (SEQ ID NO: 1):

(B) (i-a) (8Aib, 18K, 22E, 26R, 34R, 37K); (ii-a) (8Aib, 18K, 22E, 26R, 31K, 34R); (iii-a) (71mp, 18K, 22E, 26R, 34R, 37K); (iv-a) (8Aib, 18K, 22E, 25V, 26R, 31K, 34G, des35-37); (v-a) (8Aib, 18K, 22E, 25V, 26R, 30E, 31K, 34G, des35-37); (vi-a) (8Aib, 18K, 22E, 25V, 26H, 31K, 34G, des35-37); (vii-a) (8Aib, 18K, 22E, 26R, 27K, 31H, 34R, des36-37); (iix-a) (18K, 22E, 25V, 26R, 31K, 34G, des35-37); (ix-a) (18K, 22E, 25V, 26R, 31K, 34G, des35-37); (x-a) (71mp, 18K, 22E, 25V, 26R, 31K, 34G, des35-37); (xi-a) (8S, 18K, 22E, 25V, 26R, 31K, 34G, des35-37); (xii-a) (18K, 22E, 26R, 31K, 34G, des35-37); (xiii-a) (8Aib, 18K, 22E, 26R, 31K, 34G, des35-37); (xiv-a) (8Aib, 18K, 22E, 23R, 25V, 26R, 31K, 34G, des35-37); (xv-a) (8Aib, 18K, 22E, 25V, 26R, 27H, 31K, 34G, des35-37); (xvi-a) (71mp, 8Aib, 18K, 22E, 25V, 26R, 31K, 34G, des35-37); (xvii-a) (18K, 22E, 26R, 27K, 31H, 34G, des35-37); (iixx-a) (71mp, 18K, 22E, 26R, 27K, 31H, 34G, des35-37); (ixx-a) (18K, 34Q); (xx-a) (18K, 22E, 26H, 27K, 34Q); (xxi-a) (8Aib, 18K, 22E, 25V, 26R, 31K, des34-37); (xxii-a) (18K, 22E, 34Q) (xxiii-a); (8Aib, 18K, 22E, 25V, 26R, 27K, 34Q); (xxiv-a) (18K, 22E, 25V, 26R, 27K, 34Q); (xxv-a) (18K, 22E, 25V, 26R, 31K, 34R); (xxvi-a) (18K, 22E, 25V, 26R, 31K, 34Q); (xxvii-a) (18K, 22E, 25V, 26R, 31K, 34G); (iixxx-a) (18K, 22E, 25V, 26R, 27K, 34R); (ixxx-a) (18K, 22E, 25V, 26R, 27K, 31H, 34R); (xxx-a) (18K, 22E, 25V, 26R, 30K, 34G, des35-37); (xxxi-a) (8Aib, 18K, 22E, 26R, 30K, 34R); (xxxii-a) (18K, 22E, 25V, 26R, 30K, 31H, 34G, des35-37); (xxxiii-a) (18K, 22E, 25V, 26R, 27L, 30K, 34G, des35-37); (xxxiv-a) (18K, 22E, 23E, 25V, 26R, 27K, 34R); (xxxv-a) (18K, 22E, 23E, 25V, 26R, 27K, 34Q); (xxxvi-a) (18K, 22E, 26H, 27K, 34R); (xxxvii-a) (18K, 22E, 26H, 27K, 31H, 34R); (iixxxx-a) (8Aib, 18K, 22E, 25V, 26R, 27L, des35-37); (ixxxx-a) (18K, 22E, 25V, 26R, 31H, des35-37-a); (xxxx-a) (18K, 26H, 27K, 34Q); (xxxxi-a) (8Aib, 18K, 26V, 27K, 34R); (xxxxii-a) (18K, 26H, 31K, 34R); (xxxxiii-a) (8Aib, 18K, 22E, 25V, 26R, 31K, 34R); (xxxxiv-a) (18K, 25V, 26R, 31K, 34R); (xxxxv-a) (18K, 22E, 26R, 31K, 34R); (xxxxvi-a) (8Aib, 18K, 26H, 30K, 34R, des36-37); (xxxxvii-a) (8Aib, 18K, 22E, 26R, 30K, 34R, des36-37); (iixxxxx-a) (8Aib, 18K, 22E, 34R); (ixxxx-a) (8Aib, 18K, 34Q); (xxxxx-a) (8Aib, 18K, 22E, 34R); (xxxxxi-a) (8Aib, 18K, 25V, 26R, 31K, 34R); (xxxxxii-a) (8Aib, 18K, 34R); and (xxxxxiii-a) (18K, 34R);

or a pharmaceutically acceptable salt, amide, or ester of any of the analogues of (A) or (B).

236. An intermediate product selected from the following:

$N^{\epsilon 18}$-[2-[2-[2-[[2-[2-[2-[[(4S)-4-amino-4-carboxybutanoyl]amino]ethoxy]ethoxy]acetyl]amino]ethoxy]ethoxy]acetyl], $N^{\epsilon 27}$ [2-[2-[2-[[2-[2-[2-[[(4S)-4-amino-4-carboxybutanoyl]amino]ethoxy]ethoxy]acetyl]amino]ethoxy]ethoxy]acetyl]-[Aib8,Lys18,Val26,Lys27,Arg34]-GLP-1-(7-37)-peptide (SEQ ID NO: 6);

Chem. 137
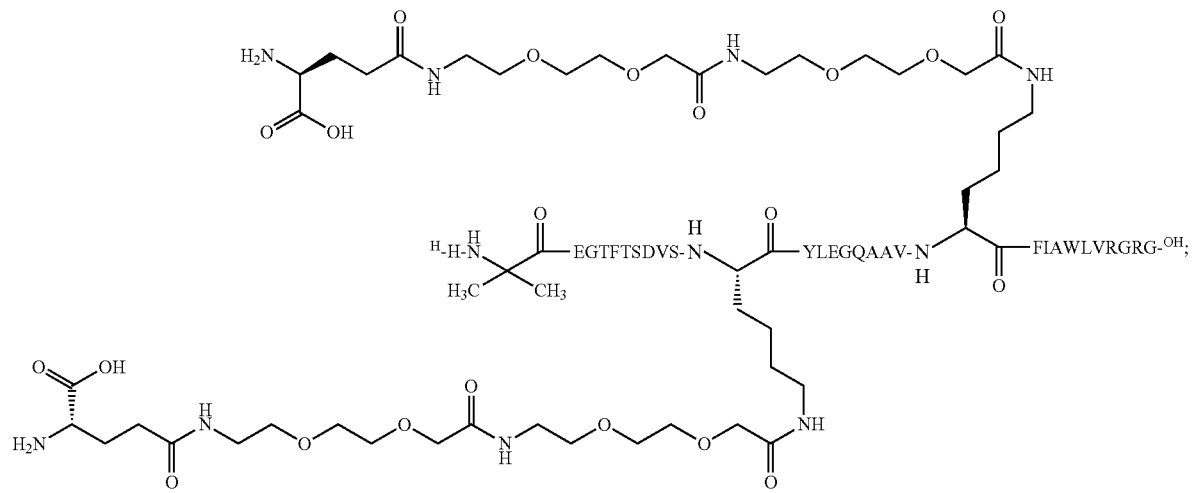
Chem. 138
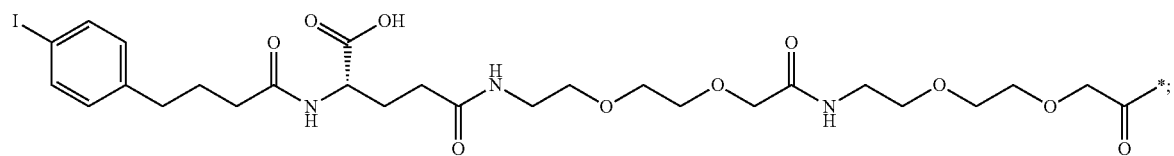
Chem. 139
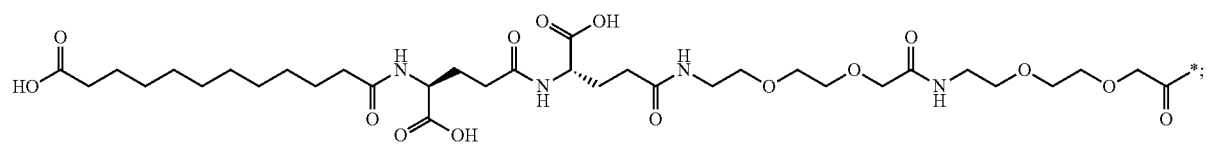
Chem. 140
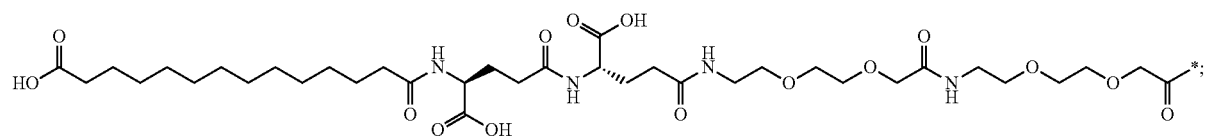
Chem. 141
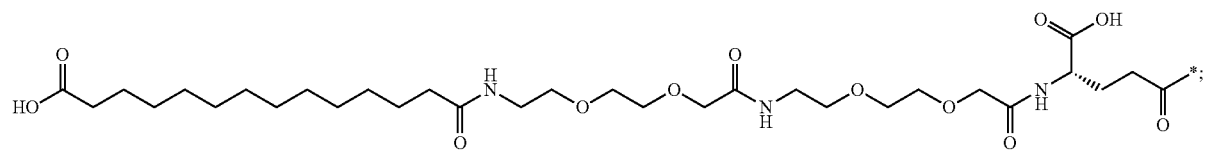
Chem. 142
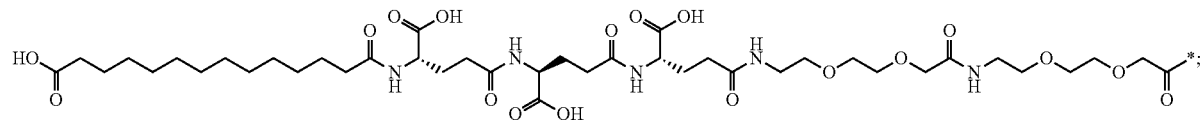
Chem. 143
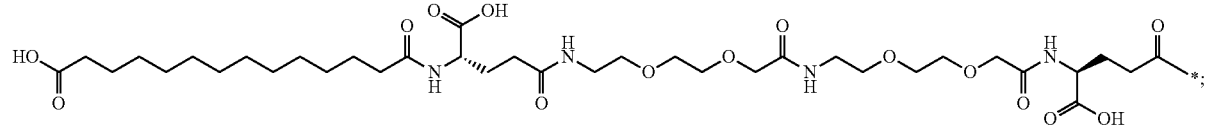

-continued
Chem. 144
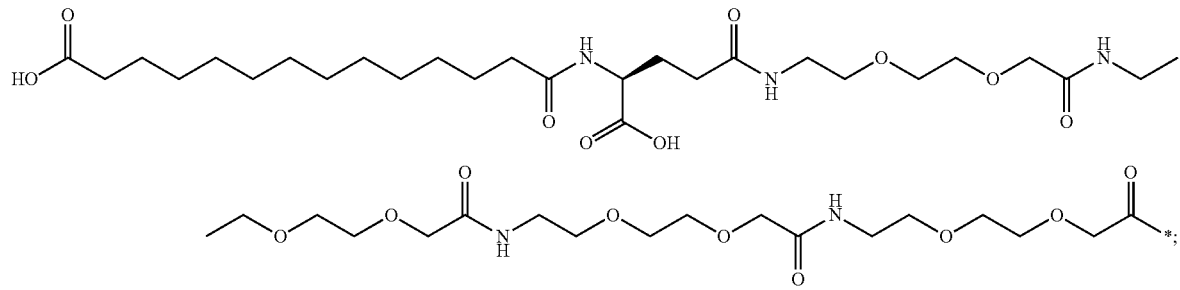
Chem. 145
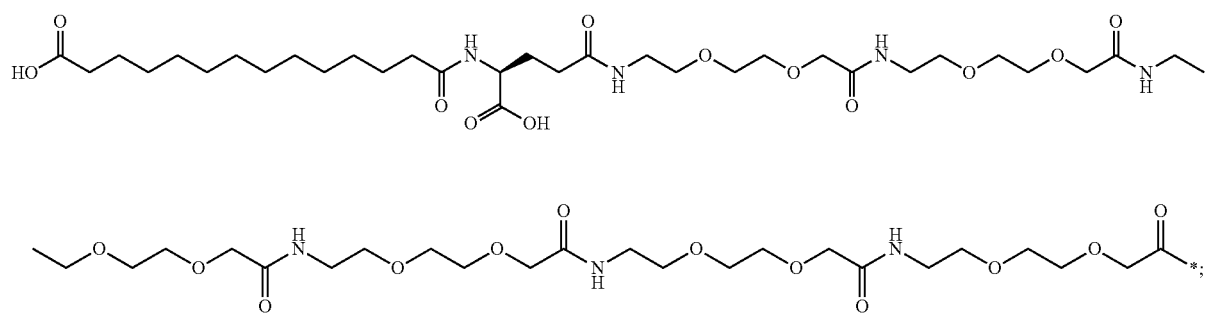
Chem. 146
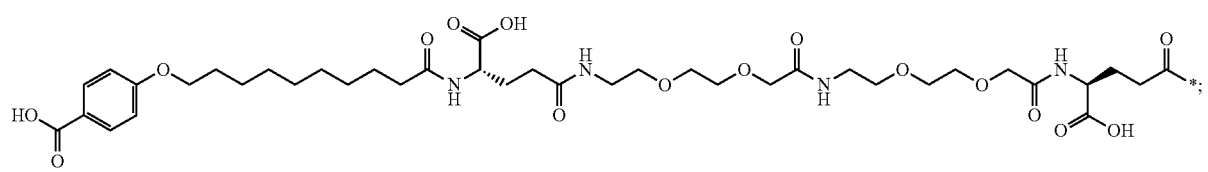
Chem. 147
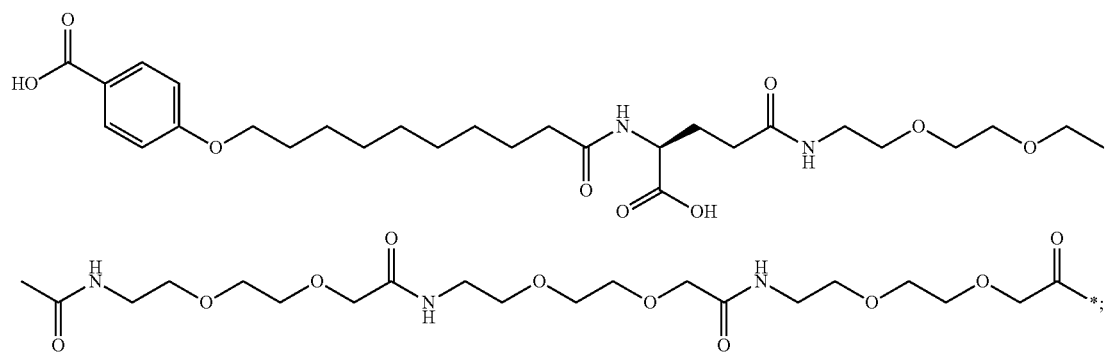
Chem. 148
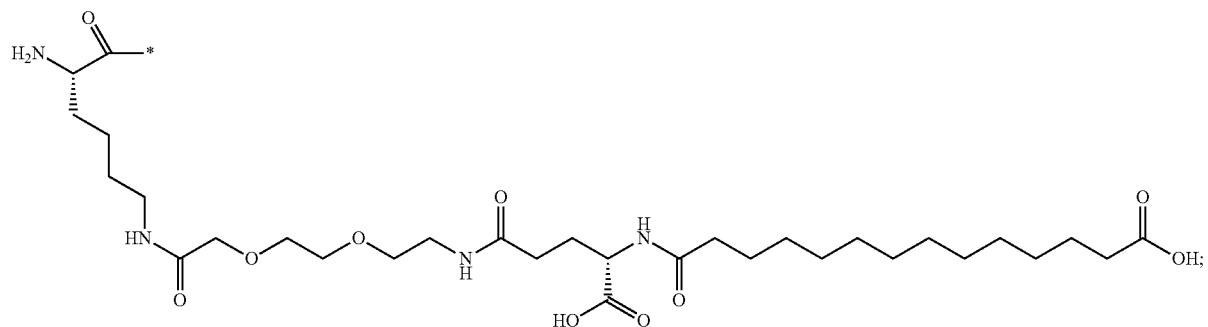

Chem. 149
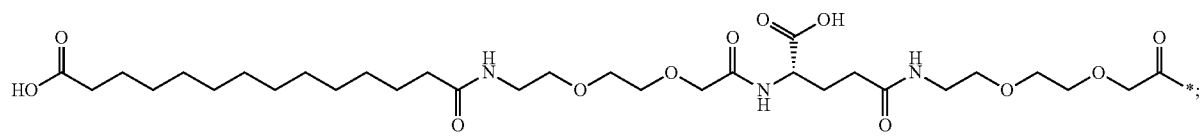
Chem. 150
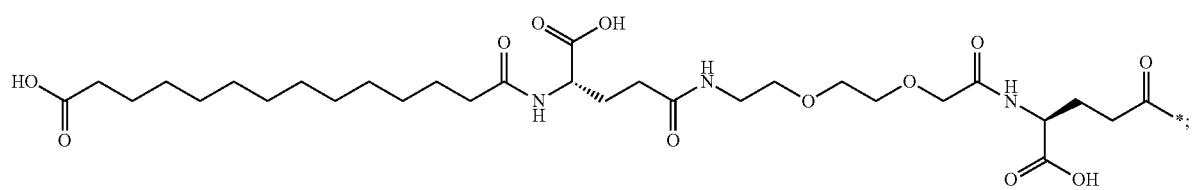
Chem. 151
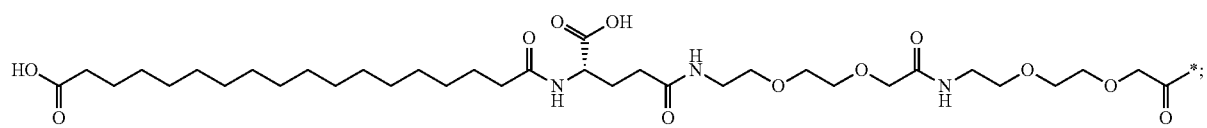
Chem. 152
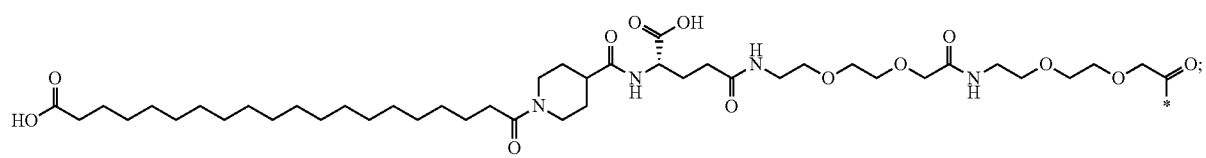
Chem. 153
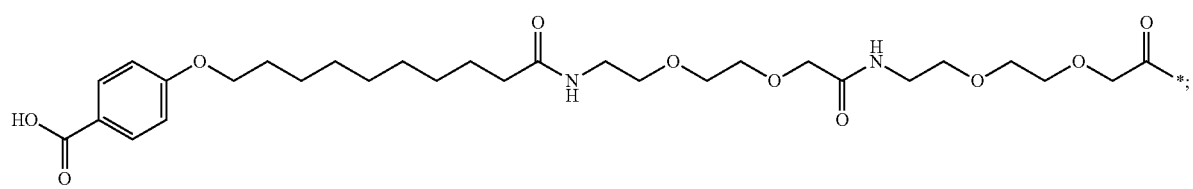
Chem. 154
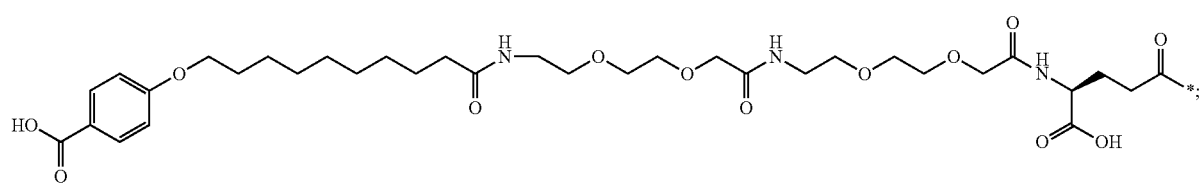
Chem. 155
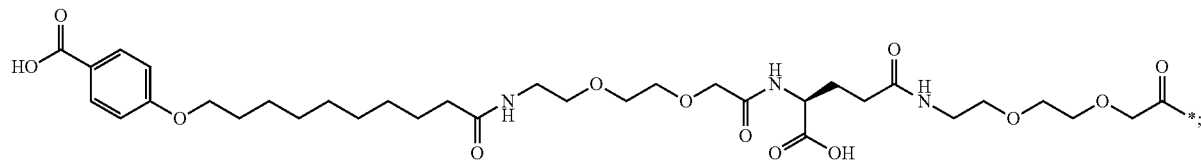
Chem. 156
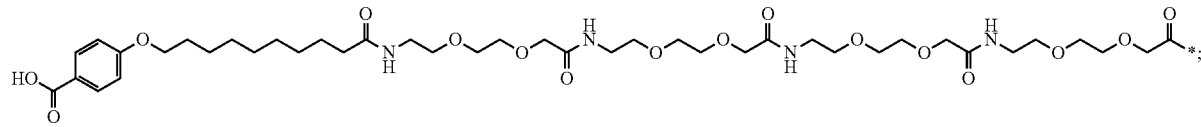

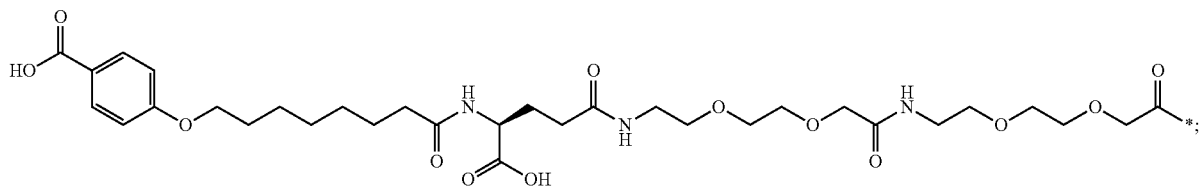

Chem. 157

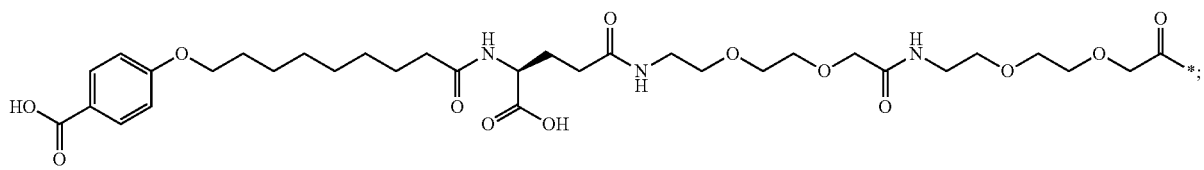

Chem. 158

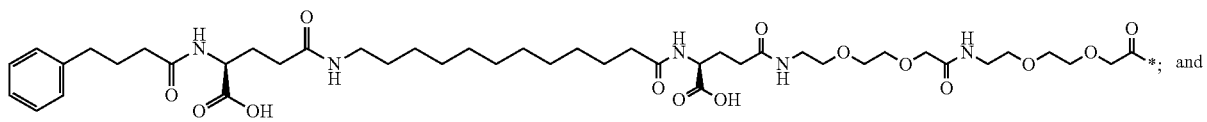

Chem. 159

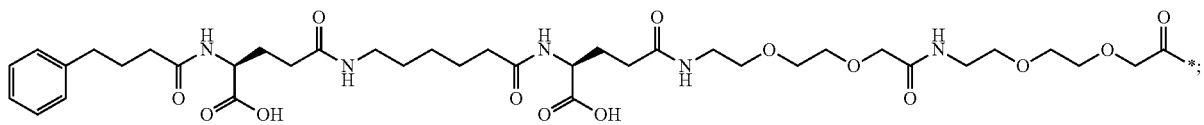

Chem. 160 where * represents a leaving group, such as i) —OH, or ii) an active ester, such as O-succinimidyl ester (OSu), or iii) the like—for potential later attachment to, e.g., an amino group of a lysine residue of peptide of interest;
or a pharmaceutically acceptable salt, amide, or ester thereof.

237. A derivative according to any one of embodiments 1-236, for use as a medicament.

238. A derivative according to any one of embodiments 1-236, for use in the treatment and/or prevention of all forms of diabetes and related diseases, such as eating disorders, cardiovascular diseases, gastrointestinal diseases, diabetic complications, critical illness, and/or polycystic ovary syndrome; and/or for improving lipid parameters, improving 1-cell function, and/or for delaying or preventing diabetic disease progression.

239. Use of a derivative according to any one of embodiments 1-236 in the manufacture of a medicament for the treatment and/or prevention of all forms of diabetes and related diseases, such as eating disorders, cardiovascular diseases, gastrointestinal diseases, diabetic complications, critical illness, and/or polycystic ovary syndrome; and/or for improving lipid parameters, improving β-cell function, and/or for delaying or preventing diabetic disease progression.

EXAMPLES

This experimental part starts with a list of abbreviations, and is followed by a section including general methods for synthesising and characterising analogues and derivatives of the invention. Then follows a number of examples which relate to the preparation of specific GLP-1 derivatives, and at the end a number of examples have been included relating to the activity and properties of these analogues and derivatives (section headed pharmacological methods).

The examples serve to illustrate the invention.

List of Abbreviations

Aib: α-aminoisobutyric acid
API: Active Pharmaceutical Ingredient
AUC: Area Under the Curve
BG: Blood Glucose
BHK Baby Hamster Kidney
BW: Body Weight
Boc: t-butyloxycarbonyl
Bom: benzyloxymethyl
BSA: Bovine serum albumin
Bzl: benzyl
CAS: Chemical Abstracts Service
Clt: 2-chlorotrityl
collidine: 2,4,6-trimethylpyridine
DCM: dichloromethane
Dde: 1-(4,4-dimethyl-2,6-dioxocyclohexylidene)ethyl
DesH: des-amino histidine (may also be referred to as imidazopropionic acid, Imp)
DIC: diisopropylcarbodiimide
DIPEA: diisopropylethylamine
DMEM: Dulbecco's Modified Eagle's Medium (DMEM)
EDTA: ethylenediaminetetraacetic acid
EGTA: ethylene glycol tetraacetic acid
FCS: Fetal Calf Serum Fmoc: 9-fluorenylmethyloxycarbonyl
HATU: (O-(7-azabenzotriazol-1-yl)-1,1,3,3-tetramethyluronium hexafluorophosphate)
HBTU: (2-(1H-benzotriazol-1-yl-)-1,1,3,3 tetramethyluronium hexafluorophosphate)
HEPES: 4-(2-hydroxyethyl)-1-piperazineethanesulfonic acid
HFIP 1,1,1,3,3,3-hexafluoro-2-propanol or hexafluoroisopropanol
HOAt: 1-hydroxy-7-azabenzotriazole
HOBt: 1-hydroxybenzotriazole
HPLC: High Performance Liquid Chromatography
HSA: Human Serum Albumin
IBMX: β-isobutyl-1-methylxanthine
Imp: Imidazopropionic acid (also referred to as des-amino histidine, DesH)
i.v. intravenously
ivDde: 1-(4,4-dimethyl-2,6-dioxocyclohexylidene)-3-methylbutyl
IVGTT: Intravenous Glucose Tolerance Test
LCMS: Liquid Chromatography Mass Spectroscopy
LYD: Landrace Yorkshire Duroc
MALDI-MS: See MALDI-TOF MS
MALDI-TOF MS: Matrix-Assisted Laser Desorption/Ionisation Time of Flight Mass Spectroscopy
MeOH: methanol
Mmt: 4-methoxytrityl
Mtt: 4-methyltrityl
NMP: N-methyl pyrrolidone
OBz: benzoyl ester
OEG: 8-amino-3,6-dioxaoctanic acid
OPfp: pentafluorophenoxy
OPnp: para-nitrophenoxy
OSu: O-succinimidyl esters (hydroxysuccinimide esters)
OtBu: tert butyl ester
Pbf: 2,2,4,6,7-pentamethyldihydrobenzofuran-5-sulfonyl
PBS: Phosphate Buffered Saline
PD: Pharmacodynamic
Pen/Strep: Pencillin/Streptomycin
PK: Pharmacokinetic
RP: Reverse Phase
RP-HPLC: Reverse Phase High Performance Liquid Chromatography
RT: Room Temperature
Rt: Retention time
s.c.: Subcutaneously
SD: Standard Deviation
SEC-HPLC: Size Exclusion High Performance Liquic Chromatography
SEM: Standard Error of Mean
SPA: Scintillation Proximity Assay
SPPS: Solid Phase Peptide Synthesis
tBu: tert. butyl
TFA: trifluoroacetic acid
TIS: triisopropylsilane
TLC: Thin Layer Chromatography
Tos: tosylate (or pare-toluenesulfonyl)
Tris: tris(hydroxymethyl)aminomethane or 2-amino-2-hydroxymethyl-propane-1,3-diol
Trt: triphenylmethyl (trityl)
Trx: tranexamic acid
UPLC: Ultra Performance Liquid Chromatography
Materials and Methods
Materials
N-α,N-β-Di-Fmoc-L-2,3-Diaminopropionic Acid (CAS 201473-90-7)
3,5-Di-tert-butyl-4-hydroxybenzoic acid (CAS 1421-49-4)
3,5-Di-tert-butylbenzoic Acid (CAS 16225-26-6)
Fmoc-8-amino-3,6-dioxaoctanoic acid (CAS 166108-71-0)
17-(9-Fluorenylmethyloxycarbonyl-amino)-9-aza-3,6,12,15-tetraoxa-10-on-heptadecanoic acid (IRIS Biotech GmbH)
Fmoc-L-Glutamic acid 1-tert-butyl ester (CAS 84793-07-7)
2-(2-Methoxyethoxy)acetic acid (CAS 16024-56-9)
N-α,N-ε-Bis(9-fluorenylmethyloxycarbonyl)-L-lysine (CAS 78081-87-5)
1-[(9H-fluoren-9-ylmethoxy)carbonyl]piperidine-4-carboxylic acid (CAS 148928-15-8)
FMOC-8-Aminocapryl acid (CAS 126631-93-4)
4-Phenylbutyric acid (CAS 1716-12-7)
4-(4-Nitrophenyl)butyric acid (CAS 5600-62-4)
4-(4-Chlorophenyl)butyric acid (CAS 4619-18-5)
FMOC-6-Aminohexanoic acid (CAS 88574-06-5)
FMOC-12-Aminododecanoic acid (CAS 128917-74-8)
4-(9-carboxy-nonyloxy)-benzoic acid tert-butyl ester (prepared as described in Example 25, step 1 and 2 of WO 2006/082204)
4-(8-Carboxy-octyloxy)-benzoic acid tert-butyl ester (M.p.: 71-72° C.
$^1$H NMR (300 MHz, CDCl$_3$, δ$_H$): 7.93 (d, J=8.9 Hz, 2H); 6.88 (d, J=8.9 Hz, 2H); 4.00 (t, J=6.4 Hz, 2H); 2.36 (t, J=7.4 Hz, 2H); 1.80 (m, 2H); 1.65 (m, 2H); 1.59 (s, 9H); 1.53-1.30 (m, 8H) (prepared as described in Example 25, step 1 and 2 of WO 2006/082204, replacing methyl 10-bromodecanoate with ethyl 9-Bromononanoate (CAS 28598-81-4)) 4-(7-Carboxy-heptyloxy)-benzoic acid tert-butyl ester ($^1$H NMR spectrum (300 MHz, CDCl$_3$, δ$_H$): 7.93 (d, J=9.0 Hz, 2H); 6.88 (d, J=9.0 Hz, 2H); 4.00 (t, J=6.5 Hz, 2H); 2.37 (t, J=7.4 Hz, 2H); 1.80 (m, 2H); 1.64 (m, 2H); 1.59 (s, 9H); 1.53-1.33 (m, 6H)) (prepared as described in Example 25, step 1 and 2 of WO 2006/082204, replacing methyl 10-bromodecanoate with ethyl 7-bromoheptanoate (CAS 29823-18-5))
Chemical Methods This section is divided in two: Section A relating to general methods (of preparation (A1); and of detection and characterisation (A2)), and section B, in which the preparation and characterisation of a number of specific example compounds is described.

A. General Methods

A1. Methods of Preparation

This section relates to methods for solid phase peptide synthesis (SPPS methods, including methods for de-protection of amino acids, methods for cleaving the peptide from the resin, and for its purification), as well as methods for detecting and characterising the resulting peptide (LCMS, MALDI, and UPLC methods). The solid phase synthesis of peptides may in some cases be improved by the use of di-peptides protected on the di-peptide amide bond with a group that can be cleaved under acidic conditions such as, but not limited to, 2-Fmoc-oxy-4-methoxybenzyl, or 2,4,6-trimethoxybenzyl. In cases where a serine or a threonine is present in the peptide, pseudoproline di-peptides may be used (available from, e.g., Novabiochem, see also W. R. Sampson (1999), J. Pep. Sci. 5, 403). The Fmoc-protected amino acid derivatives used were the standard recommended: Fmoc-Ala-OH, Fmoc-Arg(Pbf)-OH, Fmoc-Asn(Trt)-OH, Fmoc-Asp(OtBu)-OH, Fmoc-Cys(Trt)-OH, Fmoc-Gln(Trt)-OH, Fmoc-Glu(OtBu)-OH, Fmoc-Gly-OH, Fmoc-His(Trt)-OH, Fmoc-Ile-OH, Fmoc-Leu-OH, Fmoc-Lys(Boc)-OH, Fmoc-Met-OH, Fmoc-Phe-OH, Fmoc-Pro-OH, Fmoc-Ser(tBu)-OH, Fmoc-Thr(tBu)-OH, Fmoc-Trp(Boc)-OH, Fmoc-Tyr(tBu)-OH, or, Fmoc-Val-OH etc.

supplied from e.g. Anaspec, Bachem, Iris Biotech, or Novabiochem. Were nothing else is specified the natural L-form of the amino acids are used. The N-terminal amino acid was Boc protected at the alpha amino group (e.g. Boc-His(Boc)-OH, or Boc-His(Trt)-OH for peptides with His at the N-terminus). In case of modular albumin binding moiety attachment using SPPS the following suitably protected building blocks such as but not limited to Fmoc-8-amino-3,6-dioxaoctanoic acid, Fmoc-tranexamic acid, Fmoc-Glu-OtBu, octadecanedioic acid mono-tert-butyl ester, nonadecanedioic acid mono-tert-butyl ester, tetradecanedioic acid mono-tert-butyl ester, or 4-(9-carboxynonyloxy) benzoic acid tert-butyl ester were used. All operations stated below were performed at 250-µmol synthesis scale.

1. Synthesis of Resin Bound Protected Peptide Backbone
Method: SPPS_P

SPPS_P was performed on a Prelude Solid Phase Peptide Synthesizer from Protein Technologies (Tucson, Ariz. 85714 U.S.A.) at 250-µmol scale using six fold excess of Fmoc-amino acids (300 mM in NMP with 300 mM HOAt) relative to resin loading, e.g. low load Fmoc-Gly-Wang (0.35 mmol/g). Fmoc-deprotection was performed using 20% piperidine in NMP. Coupling was performed using 3:3:3:4 amino acid/HOAt/DIC/collidine in NMP. NMP and DCM top washes (7 ml, 0.5 min, 2×2 each) were performed between deprotection and coupling steps. Coupling times were generally 60 minutes. Some amino acids including, but not limited to Fmoc-Arg(Pbf)-OH, Fmoc-Aib-OH or Boc-His(Trt)-OH were "double coupled", meaning that after the first coupling (e.g. 60 min), the resin is drained and more reagents are added (amino acid, HOAt, DIC, and collidine), and the mixture allowed to react again (e.g. 60 min).
Method: SPPS_L SPPS_L was performed on a microwave-based Liberty peptide synthesiser from CEM Corp. (Matthews, N.C. 28106, U.S.A.) at 250-µmol or 100-µmol scale using six fold excess of Fmoc-amino acids (300 mM in NMP with 300 mM HOAt) relative to resin loading, e.g. low load Fmoc-Gly-Wang (0.35 mmol/g). Fmoc-deprotection was performed using 5% piperidine in NMP at up to 75° C. for 30 seconds where after the resin was drained and washed with NMP and the Fmoc-deprotection was repeated this time for 2 minutes at 75° C. Coupling was performed using 1:1:1 amino acid/HOAt/DIC in NMP. Coupling times and temperatures were generally 5 minutes at up to 75° C. Longer coupling times were used for larger scale reactions, for example 10 min. Histidine amino acids were double coupled at 50° C., or quadruple coupled if the previous amino acid was sterically hindered (e.g. Aib). Arginine amino acids were coupled at RT for 25 minutes and then heated to 75° C. for 5 min. Some amino acids such as but not limited to Aib, were "double coupled", meaning that after the first coupling (e.g. 5 min at 75° C.), the resin is drained and more reagents are added (amino acid, HOAt and DIC), and the mixture is heated again (e.g. 5 min at 75° C.). NMP washes (5×10 ml) were performed between deprotection and coupling steps.
Method: SPPS_A The protected peptidyl resin was synthesised according to the Fmoc strategy on an Applied Biosystems 433 peptide synthesiser in a 250-µmol or 1000 µmol scale with three or four fold excess of Fmoc-amino acids, using the manufacturer supplied FastMoc UV protocols which employ HBTU (2-(1H-Benzotriazol-1-yl-)-1,1,3,3 tetramethyluronium hexafluorophosphate) or HATU (O-(7-azabenzotriazol-1-yl)-1,1,3,3-tetramethyluronium hexafluorophosphate) mediated couplings in NMP and UV monitoring of the deprotection of the Fmoc protection group, in some cases double couplings were used, meaning that after the first coupling, the resin is drained and more Fmoc-amino acids and reagents are added. The starting resin used for the synthesis of the peptide amides was Rink-Amide resin and either preloaded Wang (e.g. low load Fmoc-Gly-Wang or Fmoc-Lys(Mtt)-wang) or chlorotrityl resin for peptides with a carboxy C-terminal. The protected amino acid derivatives used were standard Fmoc-amino acids (supplied from e.g. Anaspec, or Novabiochem) supplied in preweighed cartridges suitable for the AB1433A synthesiser with the exception of unnatural aminoacids such as Fmoc-Aib-OH (Fmoc-aminoisobutyric acid). The N terminal amino acid was Boc protected at the alpha amino group (e.g. Boc-His(Boc)-OH or Boc-His(Trt)-OH was used for peptides with His at the N-terminal). The epsilon amino group of lysines in the sequence were either protected with Mtt, Mmt, Dde, ivDde, or Boc, depending on the route for attachment of the albumin binding moiety and spacer. The synthesis of the peptides may in some cases be improved by the use of dipeptides protected on the dipeptide amide bond with a group that can be cleaved under acidic conditions such but not limited to 2-Fmoc-oxy-4-methoxybenzyl or 2,4,6-trimethoxybenzyl. In cases where a serine or a threonine is present in the peptide, the use of pseudoproline dipeptides may be used (see e.g. catalogue from Novobiochem 2009/2010 or newer version, or W. R. Sampson (1999), J. Pep. Sci. 5, 403).
Method: SPPS_M SPPS_M refers to synthesis of the protected peptidyl resin using manual Fmoc chemistry. The coupling chemistry was DIC/HOAt/collidine in NMP at a 4-10 fold molar excess. Coupling conditions were 1-6 h at room temperature. Fmoc-deprotection was performed with 20-25% piperidine in NMP (3×20 ml, each 10 min) followed by NMP washings (4×20 mL).

2. Synthesis of Side Chains
Mono Esters of Fatty Diacids

Overnight reflux of the C8, C10, C12, C14, C16 and C18 diacids with Boc-anhydride DMAP t-butanol in toluene gives predominately the t-butyl mono ester. Obtained is after work-up a mixture of mono acid, diacid and diester. Purification is carried out by washing, short plug silica filtration and crystallisation.
Synthesis of Intermediates
See Example 117.

3. Attachment of Side Chains to Resin Bound Protected Peptide Backbone

When an acylation is present on a lysine side chain, the epsilon amino group of lysine to be acylated was protected with either Mtt, Mmt, Dde, ivDde, or Boc, depending on the route for attachment of the protracting moiety and linker. Dde- or ivDde-deprotection was performed with 2% hydrazine in NMP (2×20 ml, each 10 min) followed by NMP washings (4×20 ml). Mtt- or Mmt-deprotection was performed with 2% TFA and 2-3% TIS in DCM (5×20 ml, each 10 min) followed by DCM (2×20 ml), 10% MeOH and 5% DIPEA in DCM (2×20 ml) and NMP (4×20 ml) washings, or by treatment with hexafluoroisopropanol/DCM (75:25, 5×20 ml, each 10 min) followed by washings as above. In some cases the Mtt group was removed by automated steps on the Liberty peptide synthesiser. Mtt deprotection was performed with hexafluoroisopropanol or hexafluoroisopropanol/DCM (75:25) at room temperature for 30 min followed by washing with DCM (7 ml×5), followed by NMP washings (7 ml×5). The protracting moiety and/or linker can be attached to the peptide either by acylation of the resin bound peptide or by acylation in solution of the unprotected peptide. In case of attachment of the protracting moiety and/or linker to the protected peptidyl resin the attachment can be modular using SPPS and suitably protected building blocks.

Method: SC_P

The N-ε-lysine protection group was removed as described above and the chemical modification of the lysine was performed by one or more automated steps on the Prelude peptide synthesiser using suitably protected building blocks as described above. Double couplings were performed as described in SPPS_P with 3 hours per coupling.

Method: SC_L

The N-ε-lysine protection group was removed as described above and the chemical modification of the lysine was performed by one or more automated steps on the Liberty peptide synthesiser using suitably protected building blocks as described above. Double couplings were performed as described in SPPS_L.

Method: SC_A

The N-ε-lysine protection group was removed as described above and the chemical modification of the lysine was performed by one or more automated steps on the ABI peptide synthesiser using suitably protected building blocks as described in SPPS_A.

Method: SC_M1

The N-ε-lysine protection group was removed as described above. Activated (active ester or symmetric anhydride) protracting moiety or linker such as octadecanedioic acid mono-(2,5-dioxo-pyrrolidin-1-yl) ester (Ebashi et al. EP511600, 4 molar equivalents relative to resin bound peptide) was dissolved in NMP (25 mL), added to the resin and shaken overnight at room temperature. The reaction mixture was filtered and the resin was washed extensively with NMP, DCM, 2-propanol, methanol and diethyl ether.

Method: SC_M2

The N-ε-lysine protection group was removed as described above. The protracting moiety was dissolved in NMP/DCM (1:1, 10 ml). The activating reagent such as HOBt (4 molar equivalents relative to resin) and DIC (4 molar equivalents relative to resin) was added and the solution was stirred for 15 min. The solution was added to the resin and DIPEA (4 molar equivalents relative to resin) was added. The resin was shaken 2 to 24 hours at room temperature. The resin was washed with NMP (2×20 ml), NMP/DCM (1:1, 2×20 ml) and DCM (2×20 ml).

Method: SC_M3

Activated (active ester or symmetric anhydride) protracting moiety or linker such as octadecanedioic acid mono-(2,5-dioxo-pyrrolidin-1-yl) ester (Ebashi et al. EP511600) 1-1.5 molar equivalents relative to the peptide was dissolved in an organic solvent such as acetonitrile, THF, DMF, DMSO or in a mixture of water/organic solvent (1-2 ml) and added to a solution of the peptide in water (10-20 ml) together with 10 molar equivalents of DIPEA. In case of protecting groups on the protracting moiety such as tert-butyl, the reaction mixture was lyophilised overnight and the isolated crude peptide deprotected afterwards. In case of tert-butyl protection groups the deprotection was performed by dissolving the peptide in a mixture of trifluoroacetic acid, water and triisopropylsilane (90:5:5). After 30 min the mixture was evaporated in vacuo and the crude peptide purified by preparative HPLC as described later.

4. Clevage of Resin Bound Peptide with or without Attached Side Chains and Purification Method: CP_M1

After synthesis the resin was washed with DCM, and the peptide was cleaved from the resin by a 2-3 hour treatment with TFA/TIS/water (95/2.5/2.5 or 92.5/5/2.5) followed by precipitation with diethylether. The peptide was dissolved in a suitable solvent (such as, e.g., 30% acetic acid) and purified by standard RP-HPLC on a C18, 5 pM column, using acetonitrile/water/TFA. The fractions were analysed by a combination of UPLC, MALDI and LCMS methods, and the appropriate fractions were pooled and lyophilised.

Method: CP_L1

After synthesis the resin was washed with DCM, and the peptide was cleaved from the resin by the use of a CEM Accent Microwave Cleavage System (CEM Corp., North Carolina). Cleavage from the resin was performed at 38° C. for 30 minutes by the treatment with TFA/TIS/water (95/2.5/2.5) followed by precipitation with diethylether. The peptide was dissolved in a suitable solvent (such as, e.g., 30% acetic acid) and purified by standard RP-HPLC on a C18, 5 pM column, using acetonitrile/water/TFA. The fractions were analysed by a combination of UPLC, MALDI and LCMS methods, and the appropriate fractions were pooled and lyophilized.

A2. General Methods for Detection and Characterisation

1. LC-MS Methods

Method: LCMS_1

An Agilent Technologies LC/MSD TOF (G1969A) mass spectrometer was used to identify the mass of the sample after elution from an Agilent 1200 series HPLC system. The de-convolution of the protein spectra was calculated with Agilent's protein confirmation software. Eluents: A: 0.1% Trifluoro acetic acid in water; B: 0.1% Trifluoro acetic acid in acetonitrile. Column: Zorbax 5u, 300SB-C3, 4.8×50 mm. Gradient: 25%-95% B over 15 min.

Method: LCMS_2

A Perkin Elmer Sciex API 3000 mass spectrometer was used to identify the mass of the sample after elution from a Perkin Elmer Series 200 HPLC system. Eluents: A: 0.05% Trifluoro acetic acid in water; B: 0.05% Trifluoro acetic acid in acetonitrile. Column: Waters Xterra MS C-18×3 mm id 5 µm. Gradient: 5%-90% B over 7.5 min at 1.5 ml/min.

Method: LCMS_3

A Waters Micromass ZQ mass spectrometer was used to identify the mass of the sample after elution from a Waters Alliance HT HPLC system. Eluents: A: 0.1% Trifluoro acetic acid in water; B: 0.1% Trifluoro acetic acid in acetonitrile. Column: Phenomenex, Jupiter C4 50×4.60 mm id 5 µm. Gradient: 10%-90% B over 7.5 min at 1.0 ml/min.

Method: LCMS_4

LCMS_4 was performed on a setup consisting of Waters Acquity UPLC system and LCT Premier XE mass spectrometer from Micromass. Eluents: A: 0.1% Formic acid in water B: 0.1% Formic acid in acetonitrile The analysis was performed at RT by injecting an appropriate volume of the sample (preferably 2-10 µl) onto the column which was eluted with a gradient of A and B. The UPLC conditions, detector settings and mass spectrometer settings were: Column: Waters Acquity UPLC BEH, C-18, 1.7 µm, 2.1 mm×50 mm. Gradient: Linear 5%-95% acetonitrile during 4.0 min (alternatively 8.0 min) at 0.4 ml/min. Detection: 214 nm (analogue output from TUV (Tunable UV detector)) MS ionisation mode: API-ES Scan: 100-2000 amu (alternatively 500-2000 amu), step 0.1 amu.

Method: LCMS_AP

A Micromass Quatro micro API mass spectrometer was used to identify the mass of the sample after elution from a HPLC system composed of Waters2525 binary gradient module, Waters2767 sample manager, Waters 2996 Photodiode Array Detector and Waters 2420 ELS Detector. Eluents: A: 0.1% Trifluoro acetic acid in water; B: 0.1% Trifluoro acetic acid in acetonitrile. Column: Phenomenex Synergi MAXRP, 4 um, 75×4.6 mm. Gradient: 5%-95% B over 7 min at 1.0 ml/min.

2. UPLC Methods

Method: 05_B5_1

The RP-analysis was performed using a Waters UPLC system fitted with a dual band detector. UV detections at 214 nm and 254 nm were collected using an ACQUITY UPLC BEH130, C18, 130 Å, 1.7 um, 2.1 mm×150 mm column, 40° C. The UPLC system was connected to two eluent reservoirs containing: A: 0.2 M $Na_2SO_4$, 0.04 M $H_3PO_4$, 10% $CH_3CN$ (pH 3.5); B: 70% $CH_3CN$, 30% $H_2O$. The following linear gradient was used: 60% A, 40% B to 30% A, 70% B over 8 minutes at a flow-rate of 0.40 ml/min.

Method: 05_B7_1

The RP-analysis was performed using a Waters UPLC system fitted with a dual band detector. UV detections at 214 nm and 254 nm were collected using an ACQUITY UPLC BEH130, C18, 130 Å, 1.7 um, 2.1 mm×150 mm column, 40° C. The UPLC system was connected to two eluent reservoirs containing: A: 0.2 M $Na_2SO_4$, 0.04 M $H_3PO_4$, 10% $CH_3CN$ (pH 3.5); B: 70% $CH_3CN$, 30% $H_2O$. The following linear gradient was used: 80% A, 20% B to 40% A, 60% B over 8 minutes at a flow-rate of 0.40 ml/min.

Method: 05_B9_1

The RP-analysis was performed using a Waters UPLC system fitted with a dual band detector. UV detections at 214 nm and 254 nm were collected using an ACQUITY UPLC BEH130, C18, 130 Å, 1.7 um, 2.1 mm×150 mm column, 40° C. The UPLC system was connected to two eluent reservoirs containing: A: 0.2 M $Na_2SO_4$, 0.04 M $H_3PO_4$, 10% $CH_3CN$ (pH 3.5); B: 70% $CH_3CN$, 30% $H_2O$. The following linear gradient was used: 70% A, 30% B to 20% A, 80% B over 8 minutes at a flow-rate of 0.40 ml/min.

Method: 04_A2_1

The RP-analysis was performed using a Waters UPLC system fitted with a dual band detector. UV detections at 214 nm and 254 nm were collected using an ACQUITY UPLC BEH130, C18, 130 Å, 1.7 um, 2.1 mm×150 mm column, 40° C. The UPLC system was connected to two eluent reservoirs containing: A: 90% $H_2O$, 10% $CH_3CN$, 0.25 M ammonium bicarbonate; B: 70% $CH_3CN$, 30% $H_2O$. The following linear gradient was used: 90% A, 10% B to 60% A, 40% B over 16 minutes at a flow-rate of 0.40 ml/min.

Method: 04_A3_1

The RP-analysis was performed using a Waters UPLC system fitted with a dual band detector. UV detections at 214 nm and 254 nm were collected using an ACQUITY UPLC BEH130, C18, 130 Å, 1.7 um, 2.1 mm×150 mm column, 40° C. The UPLC system was connected to two eluent reservoirs containing: A: 90% $H_2O$, 10% $CH_3CN$, 0.25 M ammonium bicarbonate; B: 70% $CH_3CN$, 30% $H_2O$. The following linear gradient was used: 75% A, 25% B to 45% A, 55% B over 16 minutes at a flow-rate of 0.40 ml/min.

Method: 04_A4_1

The RP-analysis was performed using a Waters UPLC system fitted with a dual band detector. UV detections at 214 nm and 254 nm were collected using an ACQUITY UPLC BEH130, C18, 130 Å, 1.7 um, 2.1 mm×150 mm column, 40° C. The UPLC system was connected to two eluent reservoirs containing: A: 90% $H_2O$, 10% $CH_3CN$, 0.25 M ammonium bicarbonate; B: 70% $CH_3CN$, 30% $H_2O$. The following linear gradient was used: 65% A, 35% B to 25% A, 65% B over 16 minutes at a flow-rate of 0.40 ml/min.

Method: 04_A6_1

The RP-analysis was performed using a Waters UPLC system fitted with a dual band detector. UV detections at 214 nm and 254 nm were collected using an ACQUITY UPLC BEH130, C18, 130 Å, 1.7 um, 2.1 mm×150 mm column, 40° C. The UPLC system was connected to two eluent reservoirs containing: A: 10 mM TRIS, 15 mM ammonium sulphate, 80% $H_2O$, 20% $CH_3CN$, pH 7.3; B: 80% $CH_3CN$, 20% $H_2O$. The following linear gradient was used: 95% A, 5% B to 10% A, 90% B over 16 minutes at a flow-rate of 0.35 ml/min.

Method: 04_A7_1

The RP-analysis was performed using a Waters UPLC system fitted with a dual band detector. UV detections at 214 nm and 254 nm were collected using an ACQUITY UPLC BEH130, C18, 130 Å, 1.7 um, 2.1 mm×150 mm column, 40° C. The UPLC system was connected to two eluent reservoirs containing: A: 10 mM TRIS, 15 mM ammonium sulphate, 80% $H_2O$, 20% $CH_3CN$, pH 7.3; B: 80% $CH_3CN$, 20% $H_2O$. The following linear gradient was used: 95% A, 5% B to 40% A, 60% B over 16 minutes at a flow-rate of 0.40 ml/min.

Method: B2_1

The RP-analysis was performed using a Waters UPLC system fitted with a dual band detector. UV detections at 214 nm and 254 nm were collected using an ACQUITY UPLC BEH130, C18, 130 Å, 1.7 um, 2.1 mm×150 mm column, 40° C. The UPLC system was connected to two eluent reservoirs containing: A: 99.95% $H_2O$, 0.05% TFA; B: 99.95% $CH_3CN$, 0.05% TFA. The following linear gradient was used: 95% A, 5% B to 40% A, 60% B over 16 minutes at a flow-rate of 0.40 ml/min.

Method: B4_1

The RP-analysis was performed using a Waters UPLC system fitted with a dual band detector. UV detections at 214 nm and 254 nm were collected using an ACQUITY UPLC BEH130, C18, 130 Å, 1.7 um, 2.1 mm×150 mm column, 40° C. The UPLC system was connected to two eluent reservoirs containing: A: 99.95% $H_2O$, 0.05% TFA; B: 99.95% $CH_3CN$, 0.05% TFA. The following linear gradient was used: 95% A, 5% B to 95% A, 5% B over 16 minutes at a flow-rate of 0.40 ml/min.

Method: 05_B10_1

The RP-analyses was performed using a Waters UPLC system fitted with a dual band detector. UV detections at 214 nm and 254 nm were collected using an ACQUITY UPLC BEH130, C18, 130 Å, 1.7 um, 2.1 mm×150 mm column, 40° C. The UPLC system was connected to two eluent reservoirs containing: A: 0.2 M $Na_2SO_4$, 0.04 M $H_3PO_4$, 10% $CH_3CN$ (pH 3.5); B: 70% $CH_3CN$, 30% $H_2O$. The following linear gradient was used: 40% A, 60% B to 20% A, 80% B over 8 minutes at a flow-rate of 0.40 ml/min.

Method: 10_B14_1

The RP-analyses was performed using a Waters UPLC system fitted with a dual band detector. UV detections at 214 nm and 254 nm were collected using an ACQUITY UPLC BEH ShieldRP18, 1.7 um, 2.1 mm×150 mm column, 50° C. The UPLC system was connected to two eluent reservoirs containing: A: 99.95% $H_2O$, 0.05% TFA; B: 99.95% $CH_3CN$, 0.05% TFA. The following linear gradient was used: 70% A, 30% B to 40% A, 60% B over 12 minutes at a flow-rate of 0.40 ml/min.

Method: 05_B8_1

The RP-analysis was performed using a Waters UPLC system fitted with a dual band detector. UV detections at 214 nm and 254 nm were collected using an ACQUITY UPLC BEH130, C18, 130 Å, 1.7 um, 2.1 mm×150 mm column, 40° C. The UPLC system was connected to two eluent reservoirs containing: A: 0.2 M $Na_2SO_4$, 0.04 M $H_3PO_4$, 10% $CH_3CN$ (pH 3.5); B: 70% $CH_3CN$, 30% $H_2O$. The following linear gradient was used: 50% A, 50% B to 20% A, 80% B over 8 minutes at a flow-rate of 0.40 ml/min.
Method: 08_B29_1

The RP-analysis was performed using a Waters UPLC system fitted with a dual band detector. UV detections at 215 nm and 254 nm were collected using an kinetex 1.7u C18, 100A 2.1×150 mm column, 60° C. The UPLC system was connected to two eluent reservoirs containing: A: 90% water and 10% $CH_3CN$ with 0.045M $(NH_4)_2HPO_4$, pH 3.6, B: 20% isopropanole, 20% water and 60% $CH_3CN$. The following step gradient was used: 35% B and 65% A over 2 minutes, then 35% B, 65% A to 65% B, 35% A over 15 minutes, then 65% B, 35% A to 80% B, 20% A over 3 minutes at a flowrate of 0.5 ml/min.
Method: 10_B29_1

The RP-analysis was performed using a Waters UPLC system fitted with a dual band detector. UV detections at 215 nm and 254 nm were collected using an kinetex 1.7u C18, 100A 2.1×150 mm column, 60° C. The UPLC system was connected to two eluent reservoirs containing: A: 90% water and 10% $CH_3CN$ with 0.045M $(NH_4)_2HPO_4$, pH 3.6, B: 20% isopropanole, 20% water and 60% $CH_3CN$. The following step gradient was used: 35% B and 65% A over 2 minutes, then 35% B, 65% A to 65% B, 35% A over 15 minutes, then 65% B, 35% A to 80% B, 20% A over 3 minutes at a flowrate of 0.5 ml/min.
Method: 10_B31_1

The RP-analysis was performed using a Waters UPLC system fitted with a dual band detector. UV detections at 215 nm and 254 nm were collected using an kinetex 1.7u C18, 100A 2.1×150 mm column, 60° C. The UPLC system was connected to two eluent reservoirs containing: A: 90% water and 10% MeCN with 0.045M $(NH_4)_2HPO_4$, pH 3.6, B: 20% isopropanole, 20% water and 60% $CH_3CN$. The following step gradient was used: 25% B and 75% A over 2 minutes, then 25% B, 75% A to 55% B, 45% A over 15 minutes, then 55% B, 45% A to 80% B, 20% A over 3 minutes at a flowrate of 0.5 ml/min.
Method: AP_B4_1

The RP-analysis was performed using a Waters UPLC system fitted with a dual band detector. UV detections at 214 nm and 254 nm were collected using an ACQUITY UPLC BEH130, C18, 130 Å, 1.7 um, 2.1 mm×150 mm column, 30° C. The UPLC system was connected to two eluent reservoirs containing: A: 99.95% $H_2O$, 0.05% TFA; B: 99.95% $CH_3CN$, 0.05% TFA. The following linear gradient was used: 95% A, 5% B to 5% A, 95% B over 16 minutes at a flow-rate of 0.30 ml/min.
Method: 04_A9_1

The RP-analysis was performed using a Waters UPLC system fitted with a dual band detector. UV detections at 214 nm and 254 nm were collected using an ACQUITY UPLC BEH Shield RP18, C18, 1.7 um, 2.1 mm×150 mm column, 60° C. The UPLC system was connected to two eluent reservoirs containing: A: 200 mM $Na_2SO_4$+20 mM $Na_2HPO_4$+20 mM $NaH_2PO_4$ in 90% $H_2O$/10% $CH_3CN$, pH 7.2; B: 70% $CH_3CN$, 30% $H_2O$. The following step gradient was used: 90% A, 10% B to 80% A, 20% B over 3 minutes, 80% A, 20% B to 50% A, 50% B over 17 minutes at a flow-rate of 0.40 ml/min.
Method: B2_1

The RP-analysis was performed using a Waters UPLC system fitted with a dual band detector. UV detections at 214 nm and 254 nm were collected using an ACQUITY UPLC BEH130, C18, 130 Å, 1.7 um, 2.1 mm×150 mm column, 40° C. The UPLC system was connected to two eluent reservoirs containing: A: 99.95% $H_2O$, 0.05% TFA; B: 99.95% $CH_3CN$, 0.05% TFA. The following linear gradient was used: 95% A, 5% B to 40% A, 60% B over 16 minutes at a flow-rate of 0.40 ml/min.

3. MALDI-MS Method
Method: MALDI_MS

Molecular weights were determined using matrix-assisted laser desorption and ionisation time-of-flight mass spectroscopy, recorded on a Microflex or Autoflex (Bruker). A matrix of alpha-cyano-4-hydroxy cinnamic acid was used.

B. Specific Example Compounds

Example 1

$N^{\epsilon 18}$-[2-[2-[2-[[2-[2-[2-[[(4S)-4-carboxy-4-[10-(4-carboxyphenoxy)decanoylamino]butanoyl]amino]ethoxy]ethoxy]acetyl]amino]ethoxy]ethoxy]acetyl],$N^{\epsilon 37}$-[2-[2-[2-[[2-[2-[2-[[(4S)-4-carboxy-4-[10-(4-carboxyphenoxy)decanoylamino]butanoyl]amino]ethoxy]ethoxy]acetyl]amino]ethoxy]ethoxy]acetyl]-[$Aib^8$,$Lys^{18}$,$Glu^{22}$,$Arg^{26}$,$Arg^{34}$,$Lys^{37}$]-GLP-1-(7-37)-peptide (SEQ ID NO: 13)

Chem. 20

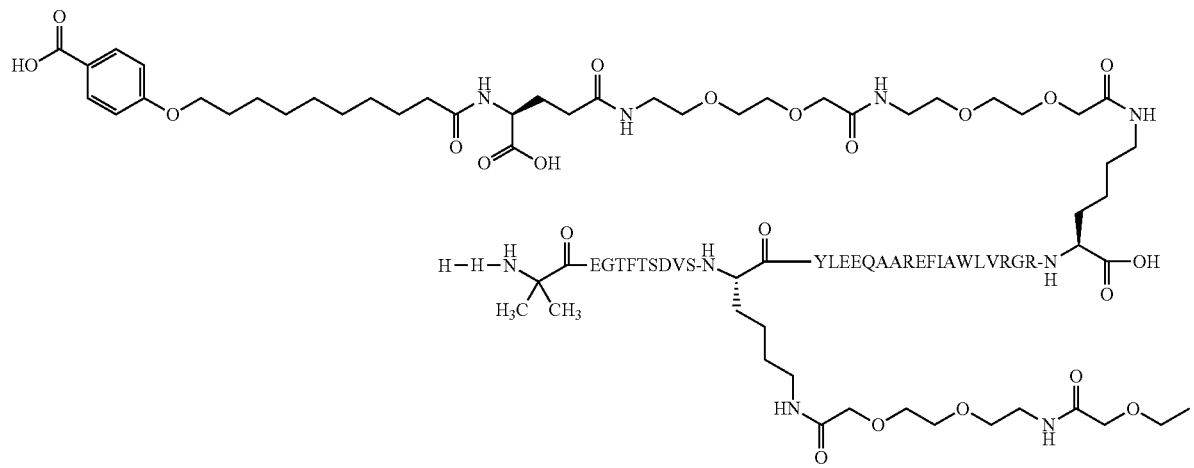

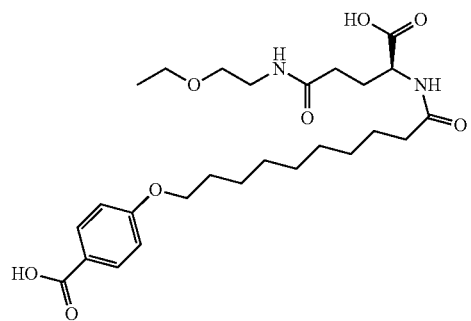

Preparation Method: SPPS_L; SC_L; CP_M1
LCMS Method: LCMS_4: Rt=2.15 min m/z: 5029.7; M/3: 1677 M/4: 1258; M/5: 1006
UPLC Method: B4_1: Rt=8.45 min
UPLC Method: 04_A3_1: Rt=8.55 min Example 2

$N^{\epsilon 18}$-[2-[2-[2-[[2-[2-[2-[[(4S)-4-carboxy-4-[10-(4-carboxyphenoxy)decanoylamino]butanoyl]amino]ethoxy]ethoxy]acetyl]amino]ethoxy]ethoxy]acetyl], $N^{\epsilon 26}$-[2-[2-[2-[[2-[2-[2-[[(4S)-4-carboxy-4-[10-(4-carboxyphenoxy)decanoylamino]butanoyl]amino]ethoxy]ethoxy]acetyl]amino]ethoxy]ethoxy]acetyl]-[Aib$^8$,Lys$^{18}$,Glu$^{22}$,Gln$^{34}$]-GLP-1-(7-37)-peptide (SEQ ID NO: 7)

Preparation Method: SPPS_L: SC_L: CP_M1
LCMS: Method: LCMS_4: Rt=2.29 min, m/z: 4902.3
UPLC Method: B4_1 Rt=8.83 min
UPLC Method: 04_A6_1: Rt=4.77 min Example 3

$N^{\epsilon 18}$-[2-[2-[2-[[2-[2-[2-[[(4S)-4-carboxy-4-[0-(4-carboxyphenoxy)decanoylamino]butanoyl]amino]ethoxy]ethoxy]acetyl]amino]ethoxy]ethoxy]acetyl], $N^{\epsilon 31}$-[2-[2-[2-[[2-[2-[2-[[(4S)-4-carboxy-4-[10-(4-carboxyphenoxy)decanoylamino]butanoyl]amino]ethoxy]ethoxy]acetyl]amino]ethoxy]ethoxy]acetyl]-[Aib$^8$,Lys$^{18}$,Glu$^{22}$,Arg$^{26}$,Lys$^{31}$,Arg$^{34}$]-GLP-1-(7-37)-peptide (SEQ ID NO: 8)

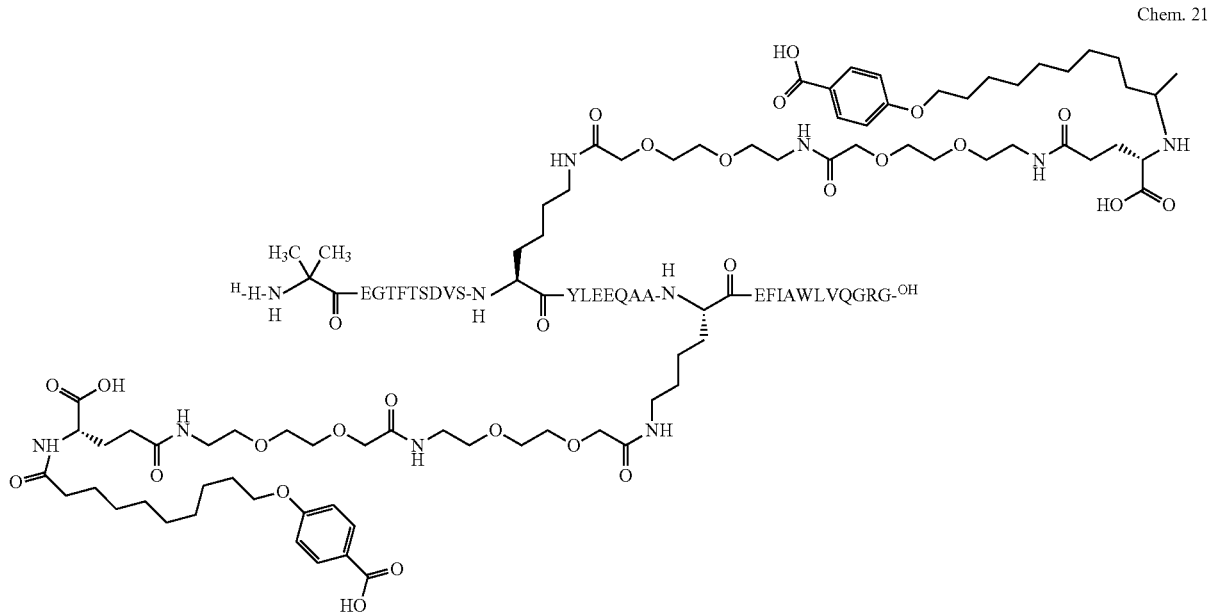

Chem. 21

Chem. 22

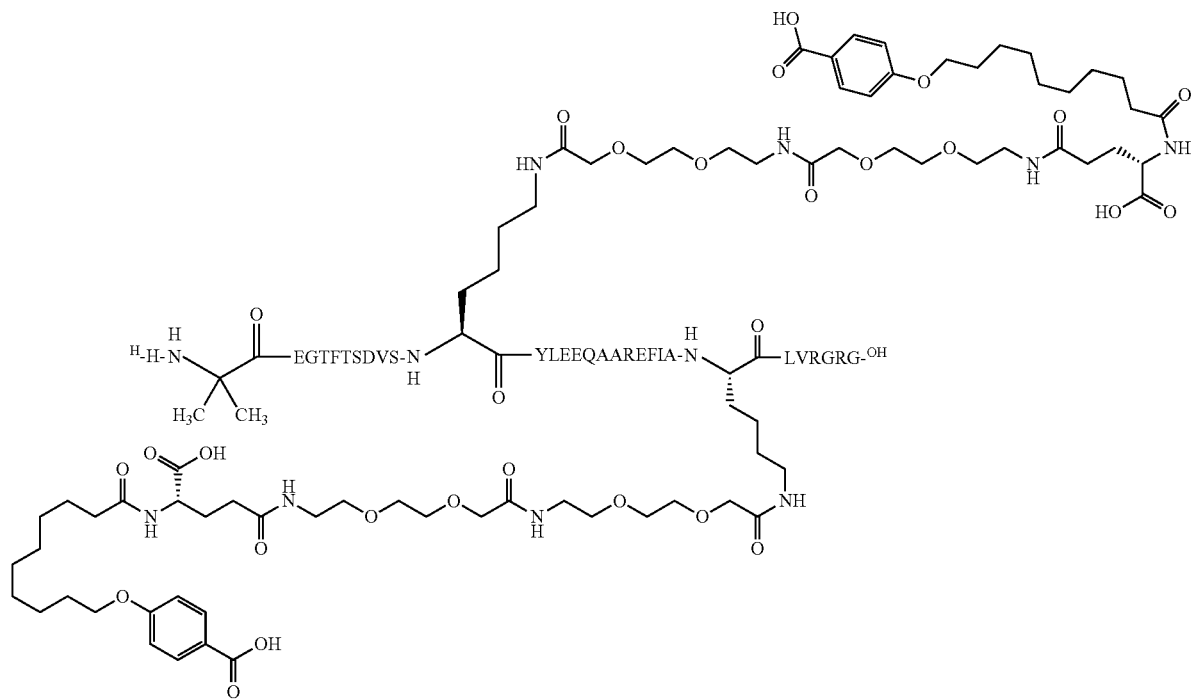

Preparation Method: SPPS_L; SC_L; CP_M1

LCMS: Method: LCMS_4: Rt=2.18 min m/z: 4900.5; M/3: 1634; M/4: 1226; M/5: 980

UPLC: Method: B4_1: Rt=7.90 min

UPLC: Method: 04_A3_1: Rt=5.68 min

Example 4

$N^{\epsilon 18}$-[2-[2-[2-[[2-[2-[2-[[(4S)-4-carboxy-4-[10-(4-carboxyphenoxy)decanoylamino]butanoyl]amino]ethoxy]ethoxy]acetyl]amino]ethoxy]ethoxy]acetyl], $N^{\epsilon 37}$-[2-[2-[2-[[2-[2-[2-[[(4S)-4-carboxy-4-[10-(4-carboxyphenoxy)decanoylamino]butanoyl]amino]ethoxy]ethoxy]acetyl]amino]ethoxy]ethoxy]acetyl]-[Imp$^7$,Lys$^{18}$,Glu$^{22}$,Arg$^{26}$,Arg$^{34}$,Lys$^{37}$]-GLP-1-(7-37)-peptide (SEQ ID NO: 14)

Chem. 23

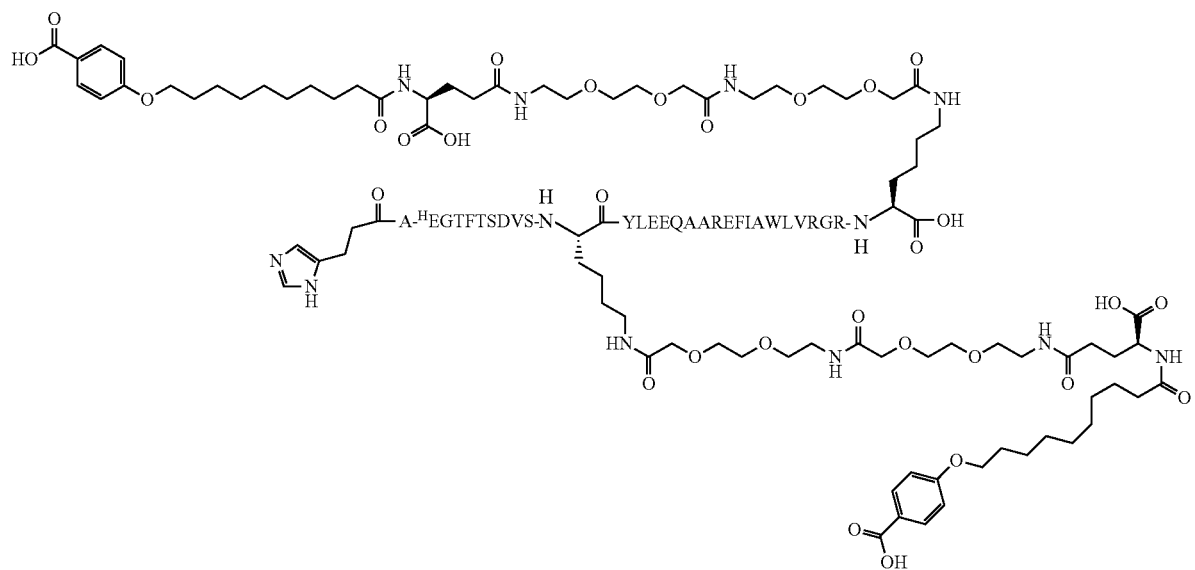

Preparation Method: SPPS_L; SC_L; CP_M1
LCMS: Method: LCMS_4: Rt=2.53 min m/z: 5000.6; M/5: 1001; M/4: 1250; M/3: 1667
UPLC: Method: B4_1: Rt=8.56 min
UPLC: Method: 04_A3_1, Rt=8.19 min Example 5

$N^{\epsilon 18}$-[2-[2-[2-[[2-[2-[2-[[(4S)-4-carboxy-4-(13-carboxytridecanoylamino)butanoyl]amino]ethoxy]ethoxy]acetyl]amino]ethoxy]ethoxy]acetyl]$N^{\epsilon 31}$-[2-[2-[2-[[2-[2-[2-[[(4S)-4-carboxy-4-(13-carboxytridecanoylamino)butanoyl]amino]ethoxy]ethoxy]acetyl]amino]ethoxy]ethoxy]acetyl]-[Aib$^8$,Lys$^{18}$,Glu$^{22}$,Val$^{25}$,Arg$^{26}$,Lys$^{31}$,Gly$^{34}$]-GLP-1-(7-34)-peptide (SEQ ID NO: 9)

Chem. 24

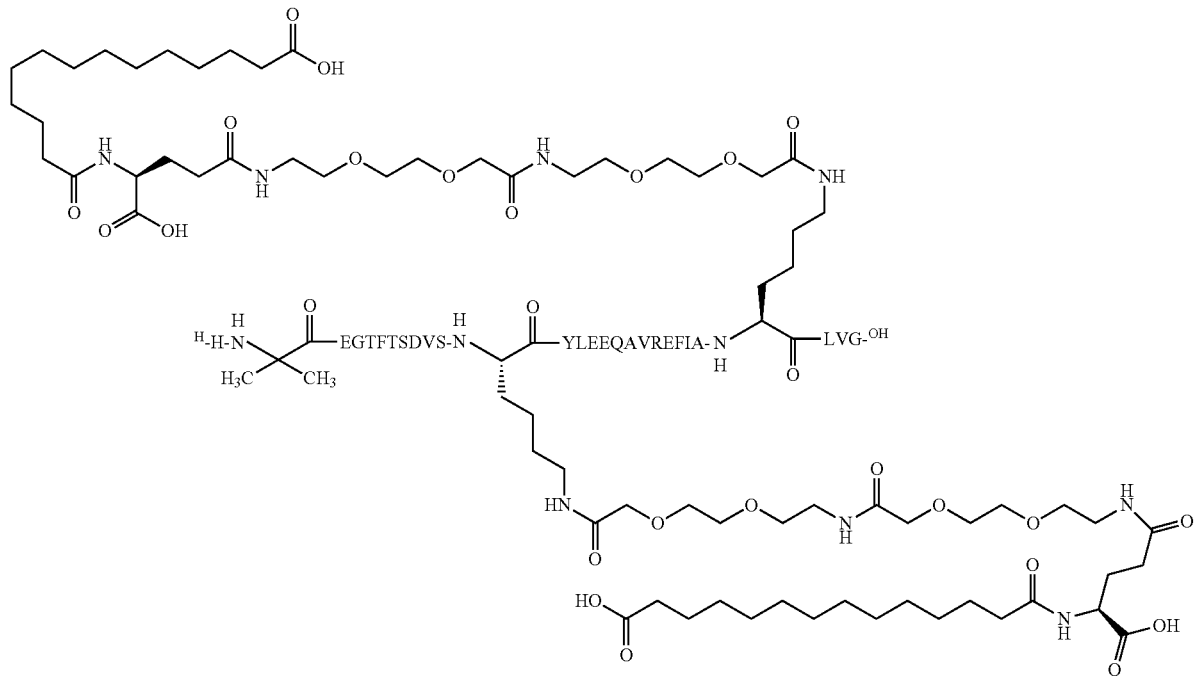

Preparation Method: SPPS_L: SC_L; CP_M1

The theoretical molecular mass of 4459.1 Da was confirmed by Method: MALDI_MS: m/z: 4457

UPLC Method: B4_1: Rt=9.1 min
UPLC Method: 04_A3_1 Rt=7.3 min

Example 6

$N^{\epsilon 18}$-[2-[2-[2-[[2-[2-[2-[[(4S)-4-carboxy-4-(13-carboxytridecanoylamino)butanoyl]amino]ethoxy]ethoxy]acetyl]amino]ethoxy]ethoxy]acetyl]$N^{\epsilon 31}$-[2-[2-[2-[[2-[2-[2-[[(4S)-4-carboxy-4-(13-carboxytridecanoylamino)butanoyl]amino]ethoxy]ethoxy]acetyl]amino]ethoxy]ethoxy]acetyl]-[Aib$^8$,Lys$^{18}$,Glu$^{22}$,Val$^{25}$,Arg$^{26}$,Glu$^{30}$,Lys$^{31}$,Gly$^{34}$]-GLP-1-(7-34)-peptide (SEQ ID NO: 15)

Chem. 25

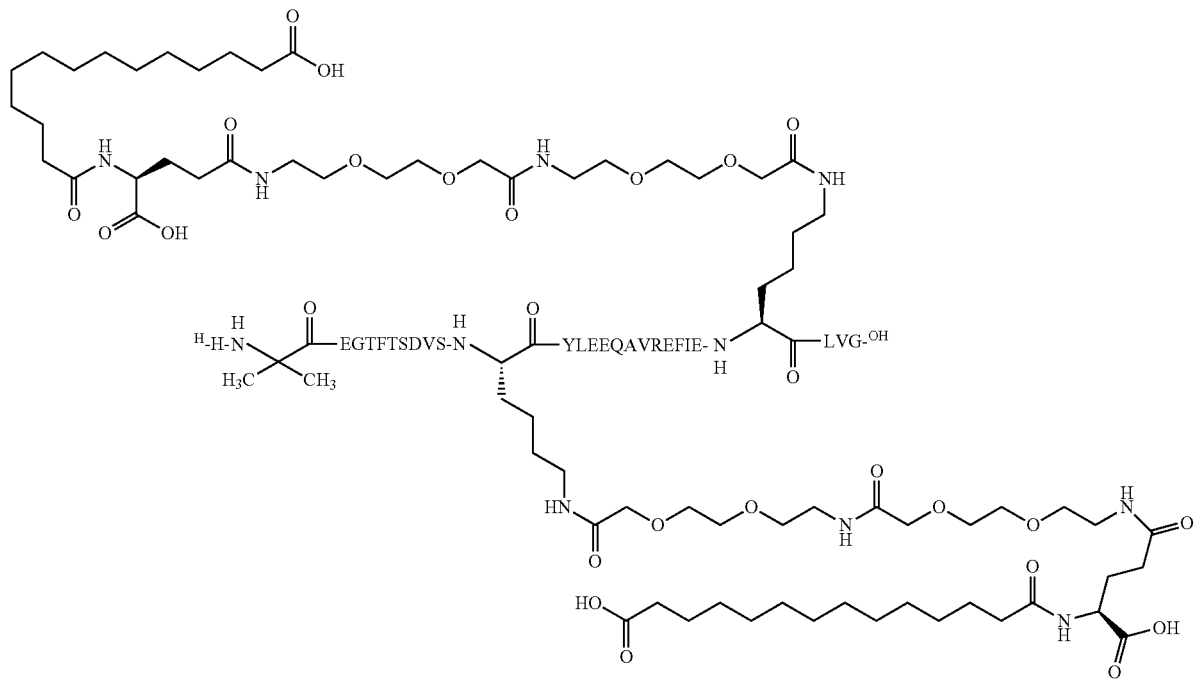

Preparation Method: SSPS_L: SC_L: CP_M1
LCMS: Method: LCMS_4: Rt=3.14 min, m/z: 4516.0
UPLC Method: B2_1: Rt=14.25 min
UPLC Method: 04_A3_1: Rt=6.20 min Example 7
N$^{\epsilon18}$-[2-[2-[2-[[2-[2-[2-[[(4S)-4-carboxy-4-(13-carboxytridecanoylamino)butanoyl]amino]ethoxy]ethoxy]acetyl]amino]ethoxy]ethoxy]acetyl]-N$^{\epsilon31}$-[2-[2-[2-[[2-[2-[2-[[(4S)-4-carboxy-4-(13-carboxytridecanoylamino)butanoyl]amino]ethoxy]ethoxy]acetyl]amino]ethoxy]ethoxy]acetyl]-[Aib$^8$,Lys$^{18}$,Glu$^{22}$,Val$^{25}$,His$^{26}$,Lys$^{31}$,Gly$^{34}$]-GLP-1-(7-34)-peptide (SEQ ID NO: 16)

Chem. 26

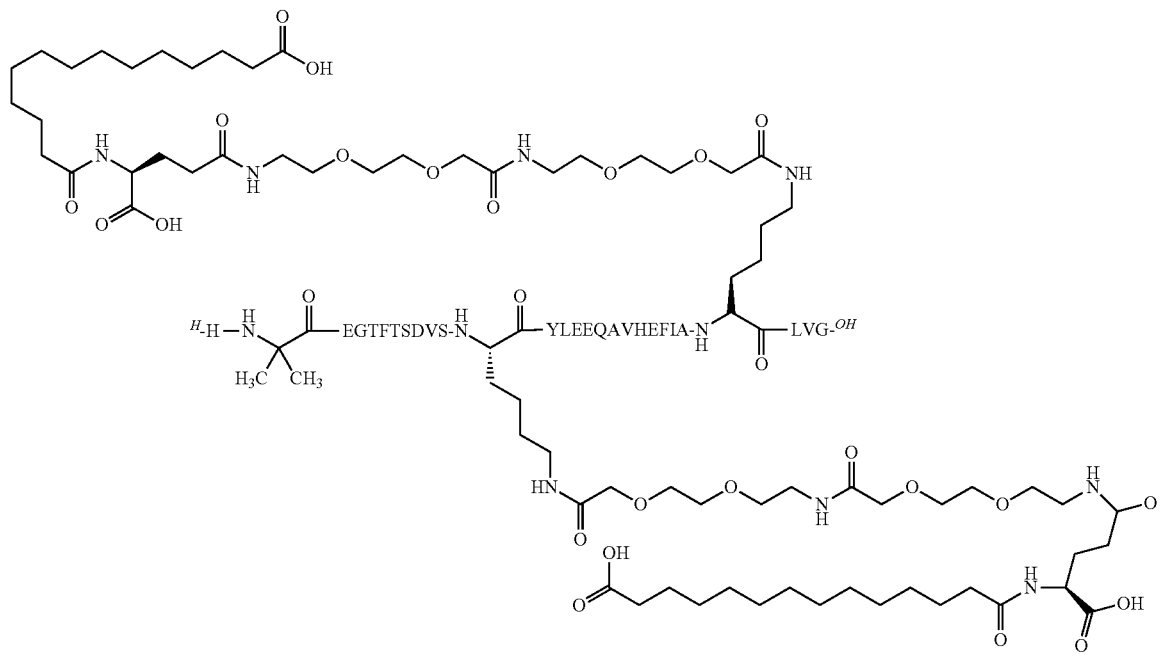

Preparation Method: SPPS_L: SC_L: CP_M1
LCMS: Method: LCMS_4: Rt=2.93 min, m/z: 4439.0
UPLC Method: B2_1: Rt=13.91 min
UPLC Method: 05_B5_1: Rt=6.67 min Example 8

$N^{\epsilon 18}$-[2-[2-[2-[[2-[2-[2-[[(4S)-4-carboxy-4-(11-carboxyundecanoylamino)butanoyl]amino]ethoxy]ethoxy]acetyl]amino]ethoxy]ethoxy]acetyl], $N^{\epsilon 31}$-[2-[2-[2-[[2-[2-[2-[[(4S)-4-carboxy-4-(11-carboxyundecanoylamino)butanoyl]amino]ethoxy]ethoxy]acetyl]amino]ethoxy]ethoxy]acetyl], [Aib$^8$,Lys$^{18}$,Glu$^{22}$,Val$^{25}$,Arg$^{26}$,Lys$^{31}$,Gly$^{34}$]-GLP-1-(7-34)-peptide (SEQ ID NO: 9)

Chem. 27
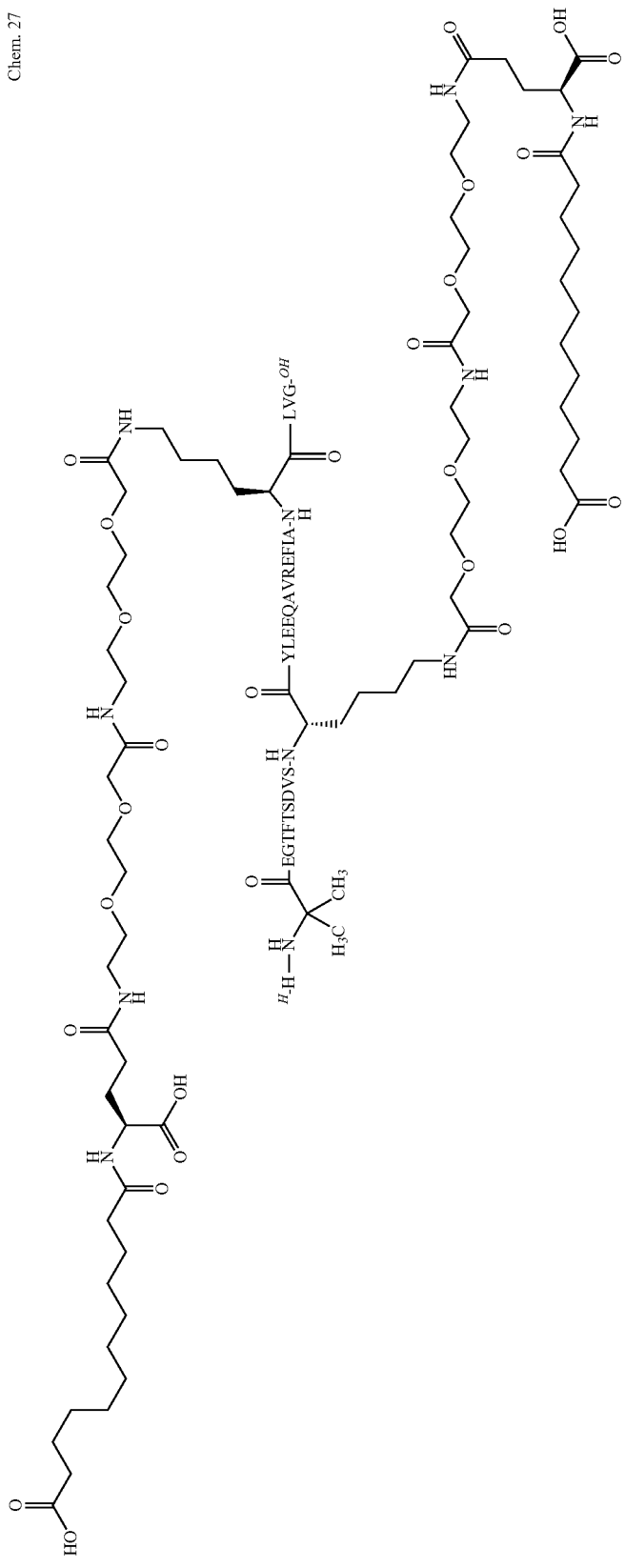

Preparation Method: SPPS_L: SC_L; CP_M1
LCMS: Method: LCMS_4: Rt=2.87 min m/z: 4401.8; M/3: 1468.07; M/4: 1101.3
UPLC Method: B4_1: Rt=8.4 min
UPLC Method: 04_A3_1: Rt=5.3 min Example 9

$N^{\epsilon 18}$-[2-[2-[2-[[2-[2-[2-[[(4S)-4-carboxy-4-(13-carboxytridecanoylamino)butanoyl]amino]ethoxy]ethoxy]acetyl]amino]ethoxy]ethoxy]acetyl], $N^{\epsilon 27}$-[2-[2-[2-[[2-[2-[2-[[(4S)-4-carboxy-4-(13-carboxytridecanoylamino)butanoyl]amino]ethoxy]ethoxy]acetyl]amino]ethoxy]ethoxy]acetyl], [Aib$^8$,Lys$^{18}$,Glu$^{22}$,Arg$^{26}$,Lys$^{27}$,His$^{31}$,Arg$^{34}$]-GLP-1-(7-35)-peptide (SEQ ID NO: 17)

Chem. 28
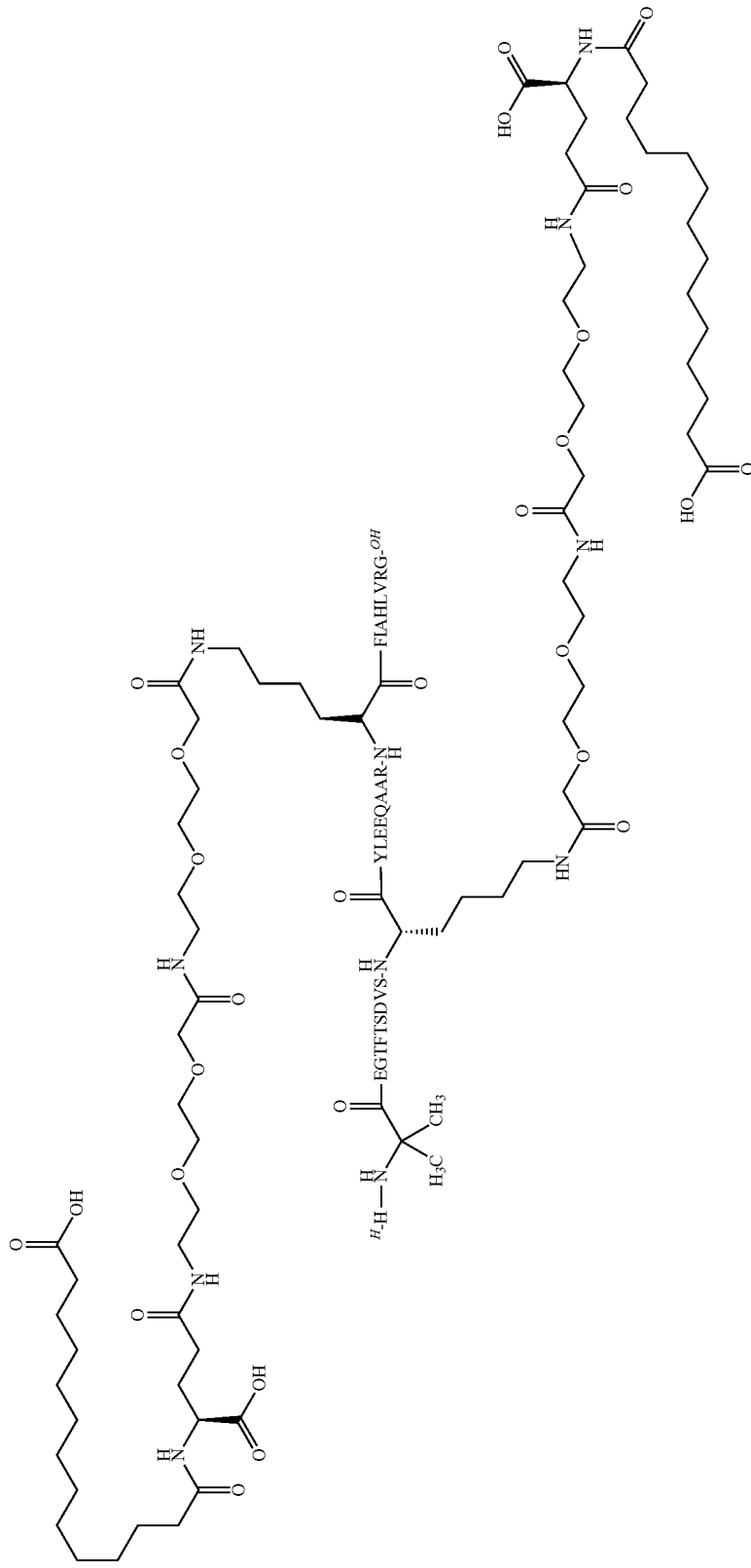

Preparation Method: SPPS_L: SC_L; CP_M1
LCMS: Method: LCMS_4: Rt=2.66 min m/z: 4594.3; M/3: 1532.1; M/4: 1149.33; M/5: 914.9
UPLC Method: B4_1: Rt=7.9 min
UPLC Method: 04_A3_1: Rt=5.5 min Example 10

$N^{\epsilon 18}$-[2-[2-[2-[[2-[2-[2-[[(4S)-4-carboxy-4-(13-carboxytridecanoylamino)butanoyl]amino]ethoxy]ethoxy]acetyl]amino]ethoxy]ethoxy]acetyl], $N^{\epsilon 31}$-[2-[2-[2-[[2-[2-[2-[[(4S)-4-carboxy-4-(13-carboxytridecanoylamino)butanoyl]amino]ethoxy]ethoxy]acetyl]amino]ethoxy]ethoxy]acetyl]-[Lys$^{18}$,Glu$^{22}$,Val$^{25}$,Arg$^{26}$,Lys$^{31}$,Gly$^{34}$]-GLP-1-(7-34)-peptide (SEQ ID NO: 18)

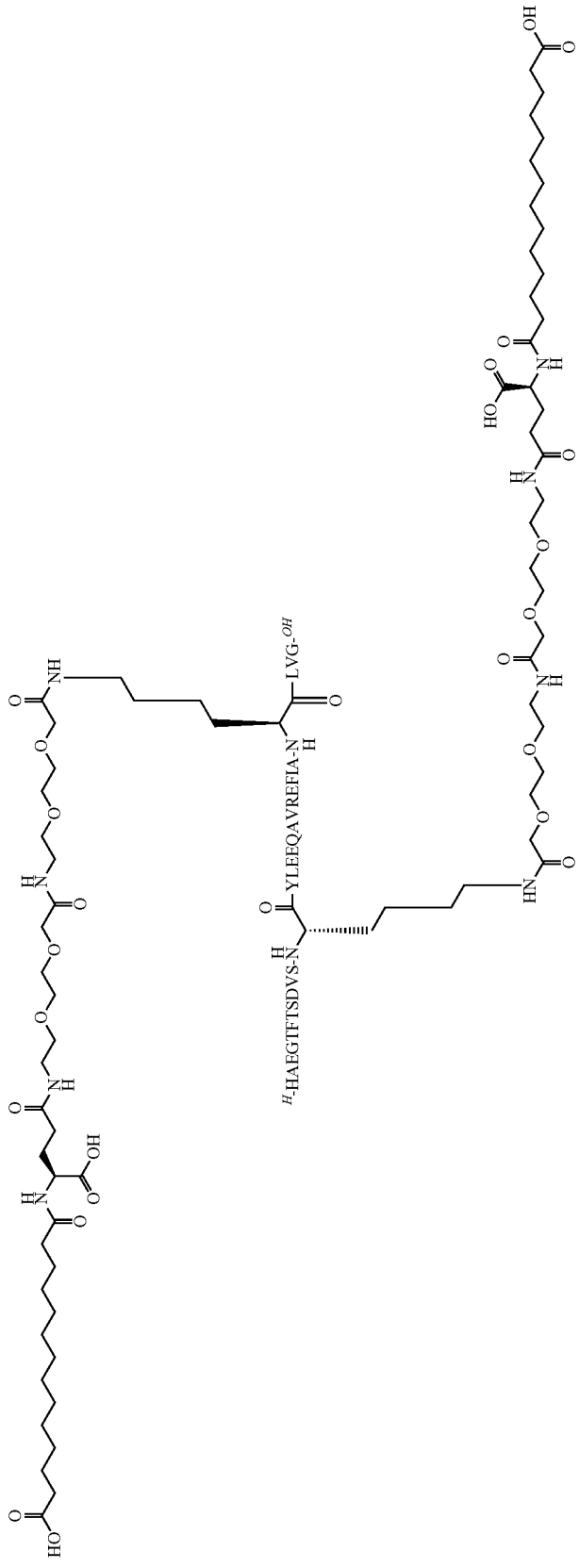
Chem. 29

Preparation Method: SPPS_L; SPPS_M; SC_L
LCMS: Method: LCMS_4: Rt=2.60 min m/3: 1481; m/4: 1111; m/5: 889
UPLC Method: B2_1: Rt=13.67 min
UPLC Method: 04_A2_1: Rt=14.96 min Example 11

$N^{\epsilon 18}$-[2-[2-[2-[[2-[2-[2-[[(4S)-4-carboxy-4-(11-carboxyundecanoylamino)butanoyl]amino]ethoxy]ethoxy]acetyl]amino]ethoxy]ethoxy]acetyl], $N^{\epsilon 31}$-[2-[2-[2-[[2-[2-[2-[[(4S)-4-carboxy-4-(11-carboxyundecanoylamino)butanoyl]amino]ethoxy]ethoxy]acetyl]amino]ethoxy]ethoxy]acetyl]-[Lys$^{18}$,Glu$^{22}$,Val$^{25}$,Arg$^{26}$,Lys$^{31}$,Gly$^{34}$]-GLP-1-(7-34)-peptide (SEQ ID NO: 18)

Chem. 30

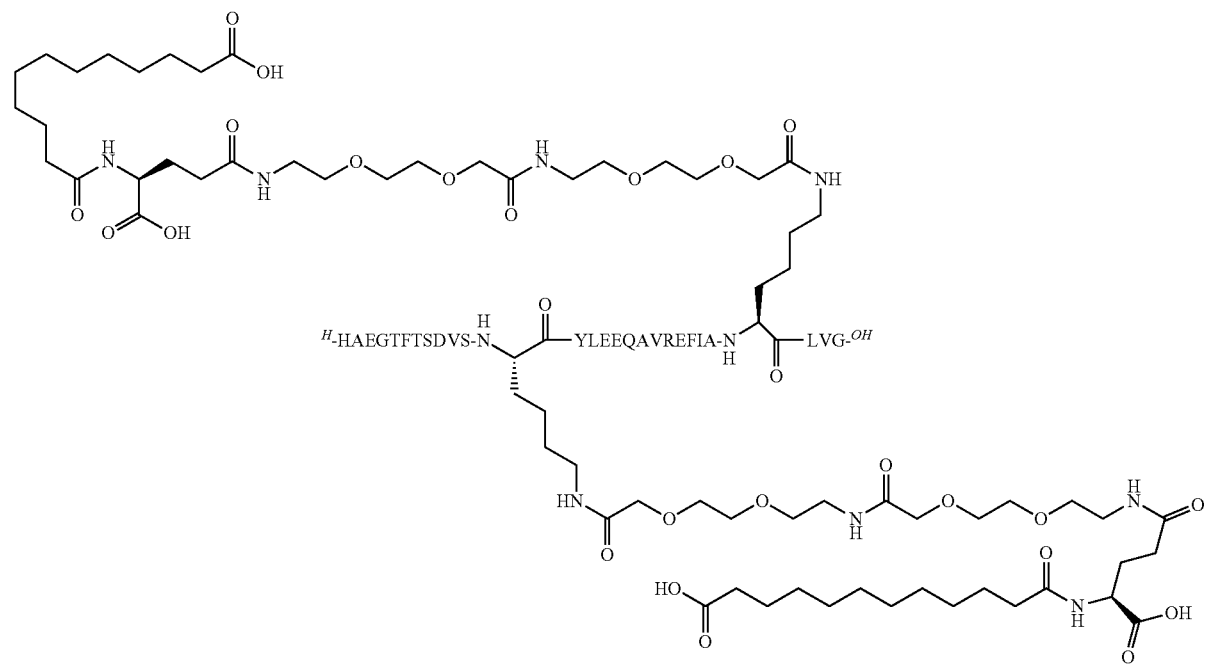

Preparation Method: SPPS_L; SPPS_M; SC_L; CP_M1
LCMS: Method: LCMS_4: Rt=2.60 min m/z: m/3: 1463; m/4: 1097; m/5: 877
UPLC Method: B2_1: Rt=12.64 min
UPLC Method: 04_A2_1: Rt=13.65 min Example 12

$N^{\epsilon 18}$-[2-[2-[2-[[2-[2-[2-[[(4S)-4-carboxy-4-(13-carboxytridecanoylamino)butanoyl]amino]ethoxy]ethoxy]acetyl]amino]ethoxy]ethoxy]acetyl], $N^{\epsilon 31}$-[2-[2-[2-[[2-[2-[2-[[(4S)-4-carboxy-4-(13-carboxytridecanoylamino)butanoyl]amino]ethoxy]ethoxy]acetyl]amino]ethoxy]acetyl]-[Imp$^7$,Lys$^{18}$,Glu$^{22}$,Val$^{25}$,Arg$^{26}$,Lys$^{31}$,Gly$^{34}$]-GLP-1-(7-34)-peptide (SEQ ID NO: 19)

Chem. 31
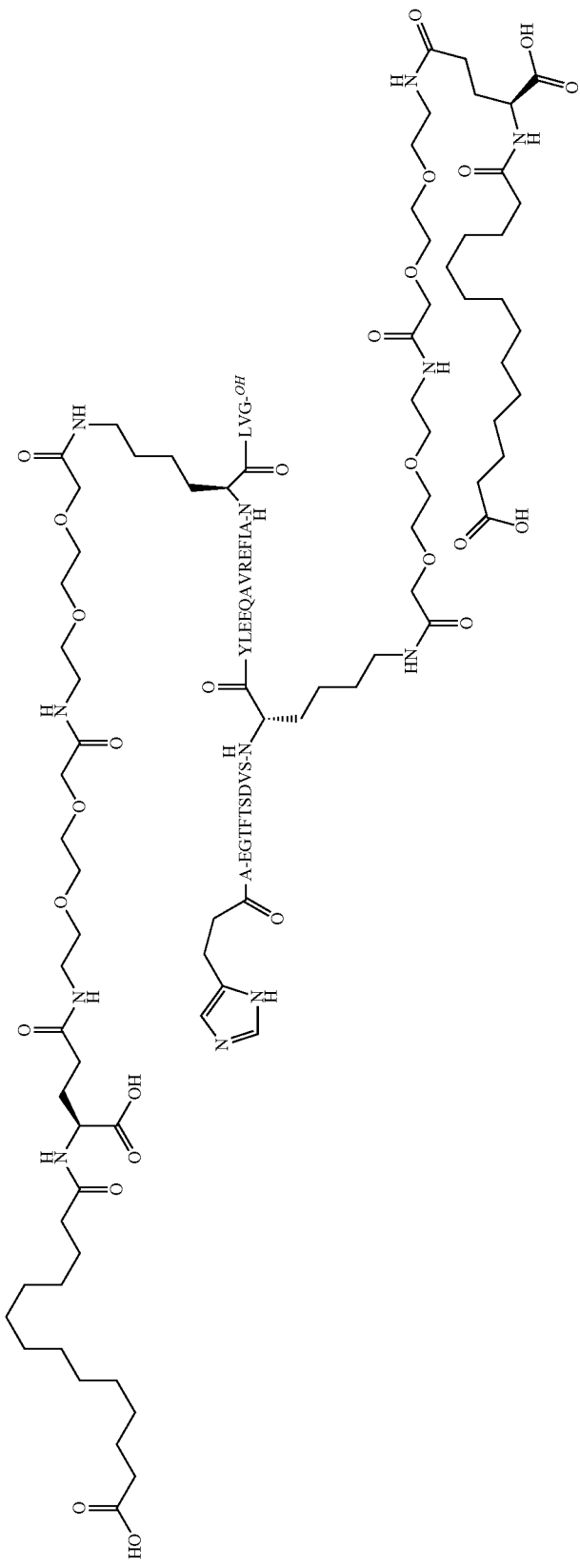

Preparation Method: SPPS_L; SPPS_M; SC_L; CP_M1
LCMS: Method: LCMS_4: Rt=2.65 min m/z: m/3: 1476; m/4: 1107 m/5: 886
UPLC Method: B2_1: Rt=14.11 min
UPLC Method: 04_A3_1: Rt=7.06 min Example 13

$N^{\epsilon 18}$-[2-[2-[2-[[2-[2-[2-[[(4S)-4-carboxy-4-(11-carboxyundecanoylamino)butanoyl]amino]ethoxy]ethoxy]acetyl]amino]ethoxy]ethoxy]acetyl]$N^{\epsilon 31}$-[2-[2-[2-[[2-[2-[2-[[(4S)-4-carboxy-4-(11-carboxyundecanoylamino)butanoyl]amino]ethoxy]ethoxy]acetyl]amino]ethoxy]ethoxy]acetyl]-[Imp$^7$,Lys$^{18}$,Glu$^{22}$,Val$^{25}$,Arg$^{26}$,Lys$^{31}$,Gly$^{34}$]-GLP-1-(7-34)-peptide (SEQ ID NO: 19)

Chem. 32
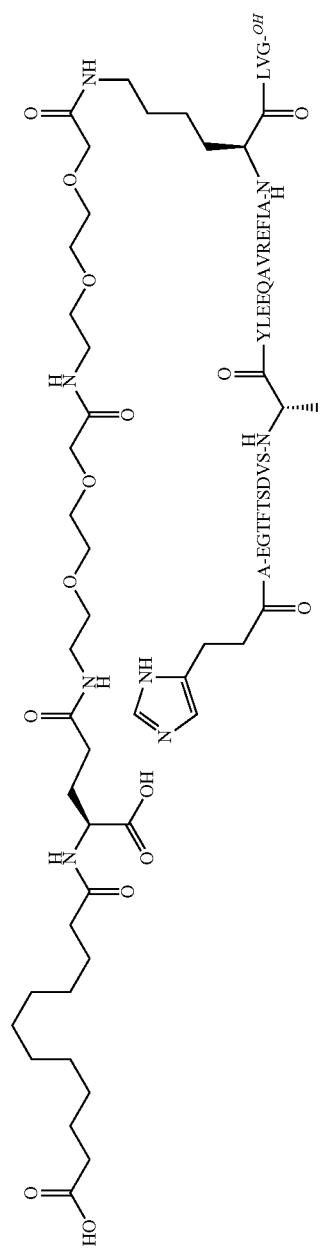
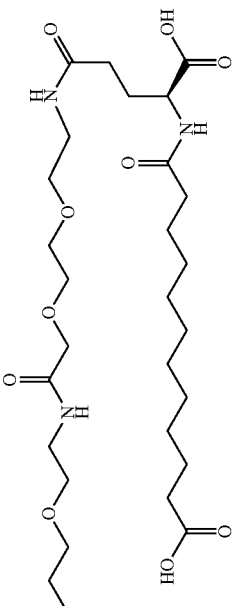

Preparation Method: SPPS_L; SPPS_M; SC_L; CP_M1
LCMS: Method: LCMS_4: Rt=2.53 min m/3=1458; m/4=1093; m/5=874
UPLC Method: B2_1: Rt=13.01 min Example 14

$N^{\epsilon18}$-[2-[2-[2-[[2-[2-[2-[[(4S)-4-carboxy-4-(13-carboxytridecanoylamino)butanoyl]amino]ethoxy]ethoxy]acetyl]amino]ethoxy]ethoxy]acetyl], $N^{\epsilon31}$-[2-[2-[2-[[2-[2-[2-[[(4S)-4-carboxy-4-(13-carboxytridecanoylamino)butanoyl]amino]ethoxy]ethoxy]acetyl]amino]ethoxy]ethoxy]acetyl]-[Ser$^8$,Lys$^{18}$,Glu$^{22}$,Val$^{25}$,Arg$^{26}$,Lys$^{31}$,Gly$^{34}$]-GLP-1-(7-34)-peptide (SEQ ID NO: 20)

Chem. 33

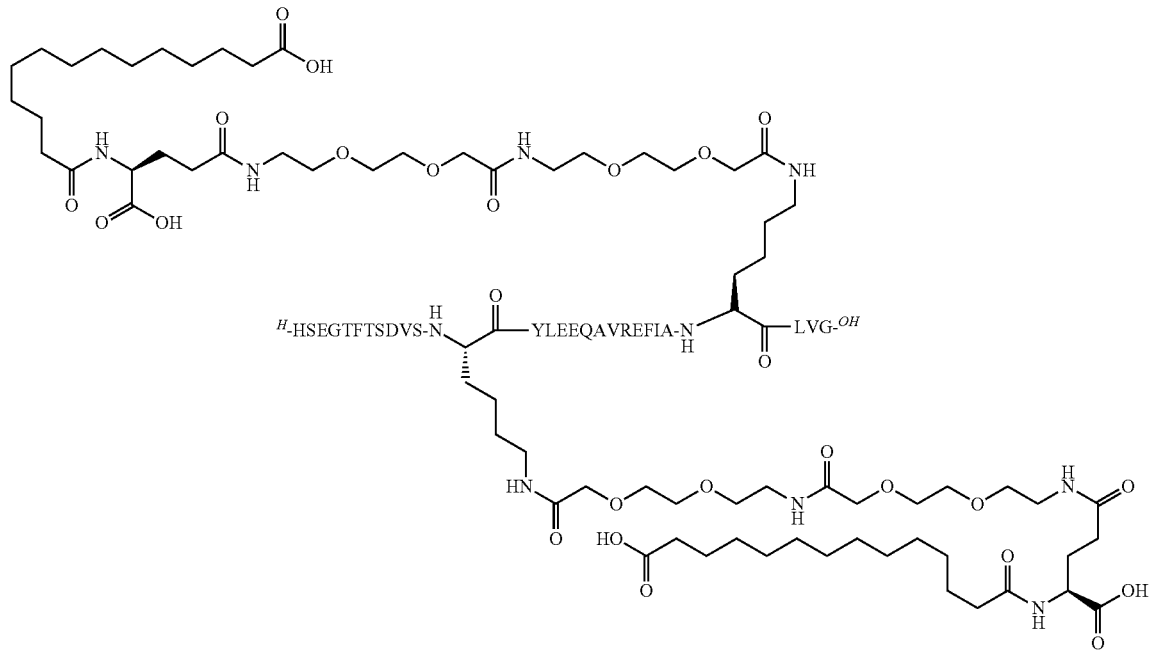

Preparation Method: SPPS_L; SC_L; CP_M1
LCMS: Method: LCMS_4: Rt=2.70 min m/z: m/3=1487 m/4=1115 m/5=892
UPLC Method: B2_1: Rt=13.92 min
UPLC Method: 05_B5_1: Rt=6.88 min Example 15

$N^{\epsilon18}$-[2-[2-[2-[[2-[2-[2-[[(4S)-4-carboxy-4-(13-carboxytridecanoylamino)butanoyl]amino]ethoxy]ethoxy]acetyl]amino]ethoxy]ethoxy]acetyl]$N^{\epsilon31}$-[2-[2-[2-[[2-[2-[2-[[(4S)-4-carboxy-4-(13-carboxytridecanoylamino)butanoyl]amino]ethoxy]ethoxy]acetyl]amino]ethoxy]ethoxy]acetyl]-[Lys8,Glu$^{22}$,Arg$^{26}$,Lys$^{31}$,Gly$^{34}$]-GLP-1-(7-34)-peptide (SEQ ID NO: 21)

Chem. 34
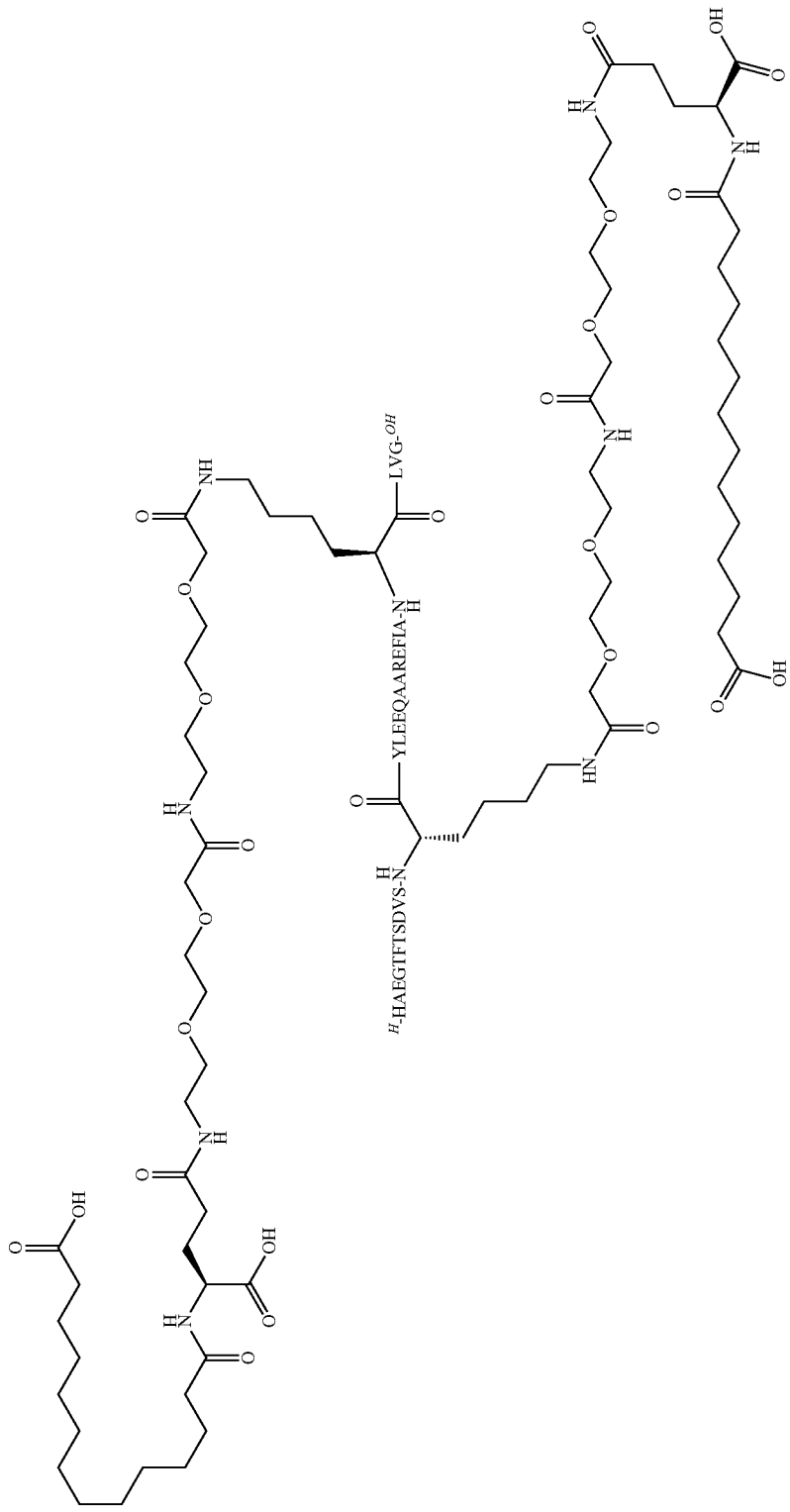

Preparation Method: SPPS_L; SC_L; CP_M1

LCMS: Method: LCMS_4: Rt=2.63 min: m/3=1472; m/4=1104; m/5=883

UPLC Method: B2_1: Rt=13.39 min

UPLC Method: 05_B5_1: Rt=5.95 min

Example 16

$N^{\epsilon 18}$-[2-[2-[2-[[2-[2-[2-[[(4S)-4-carboxy-4-(13-carboxytridecanoylamino)butanoyl]amino]ethoxy]ethoxy]acetyl]amino]ethoxy]ethoxy]acetyl], $N^{\epsilon 31}$-[2-[2-[2-[[2-[2-[2-[[(4S)-4-carboxy-4-(13-carboxytridecanoylamino)butanoyl]amino]ethoxy]ethoxy]acetyl]amino]ethoxy]ethoxy]acetyl]-[Aib$^8$,Lys$^{18}$,Glu$^{22}$,Arg$^{26}$,Lys$^{31}$,Gly$^{34}$]-GLP-1-(7-34)-peptide (SEQ ID NO: 22)

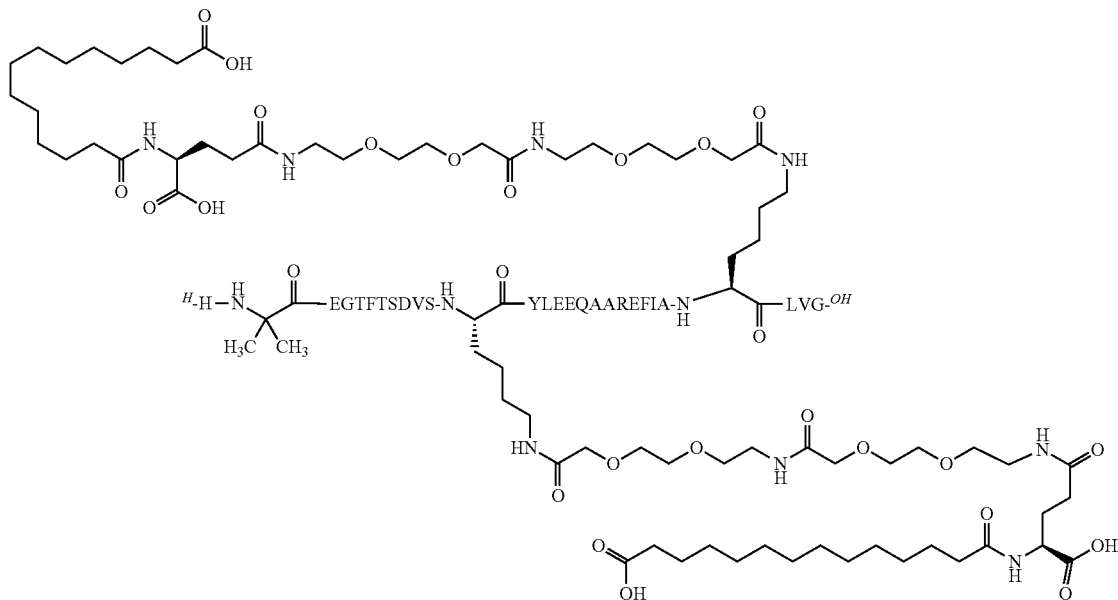

Chem. 35

Preparation Method: SPPS_L; SC_L; CP_M1

LCMS: Method: LCMS_4: Rt=2.67 min m/z: m/3=1477; m/4=1107; m/5=886

UPLC Method: B2_1: Rt=13.42 min

UPLC Method: 05_B5_1: Rt=6.10 min

Example 17

$N^{\epsilon 18}$-[2-[2-[2-[[2-[2-[2-[[(4S)-4-carboxy-4-(13-carboxytridecanoylamino)butanoyl]amino]ethoxy]ethoxy]acetyl]amino]ethoxy]ethoxy]acetyl], $N^{\epsilon 31}$-[2-[2-[2-[[2-[2-[2-[[(4S)-4-carboxy-4-(13-carboxytridecanoylamino)butanoyl]amino]ethoxy]ethoxy]acetyl]amino]ethoxy]ethoxy]acetyl]-[Aib$^8$,Lys$^{18}$,Glu$^{22}$,Arg$^{23}$,Val$^{25}$,Arg$^{26}$,Lys$^{31}$,Gly$^{34}$]-GLP-1-(7-34)-peptide (SEQ ID NO: 23)

Chem. 36

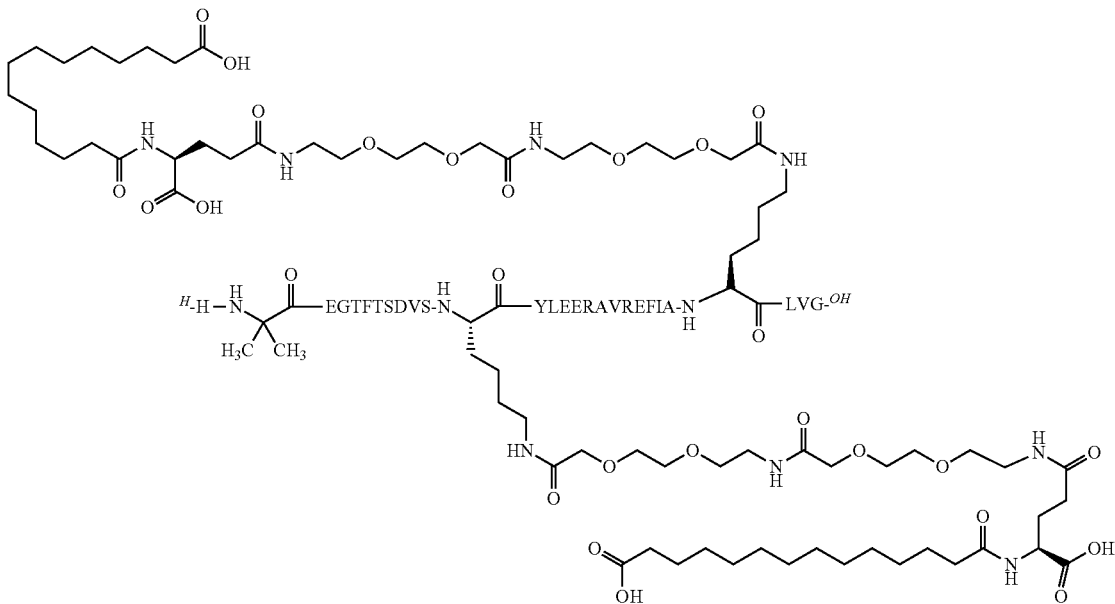

Preparation Method: SPPS_L: SC_L; CP_M1
LCMS: Method: LCMS_2: Rt=4.32 min m/z: m/3=1496
UPLC Method: B4_1: Rt=8.72 min
UPLC Method: 04_A3_1: Rt=7.96 min Example 18

$N^{\epsilon18}$-[2-[2-[2-[[2-[2-[2-[[(4S)-4-carboxy-4-(13-carboxytridecanoylamino)butanoyl]amino]ethoxy]ethoxy]acetyl]amino]ethoxy]ethoxy]acetyl], $N^{\epsilon31}$-[2-[2-[2-[[2-[2-[2-[[(4S)-4-carboxy-4-(13-carboxytridecanoylamino)butanoyl]amino]ethoxy]ethoxy]acetyl]amino]ethoxy]ethoxy]acetyl]-[Aib$^8$,Lys$^{18}$,Glu$^{22}$,Val$^{25}$,Arg$^{26}$,His$^{27}$,Lys$^{31}$,Gly$^{34}$]-GLP-1-(7-34)-peptide (SEQ ID NO: 24)

Chem 37

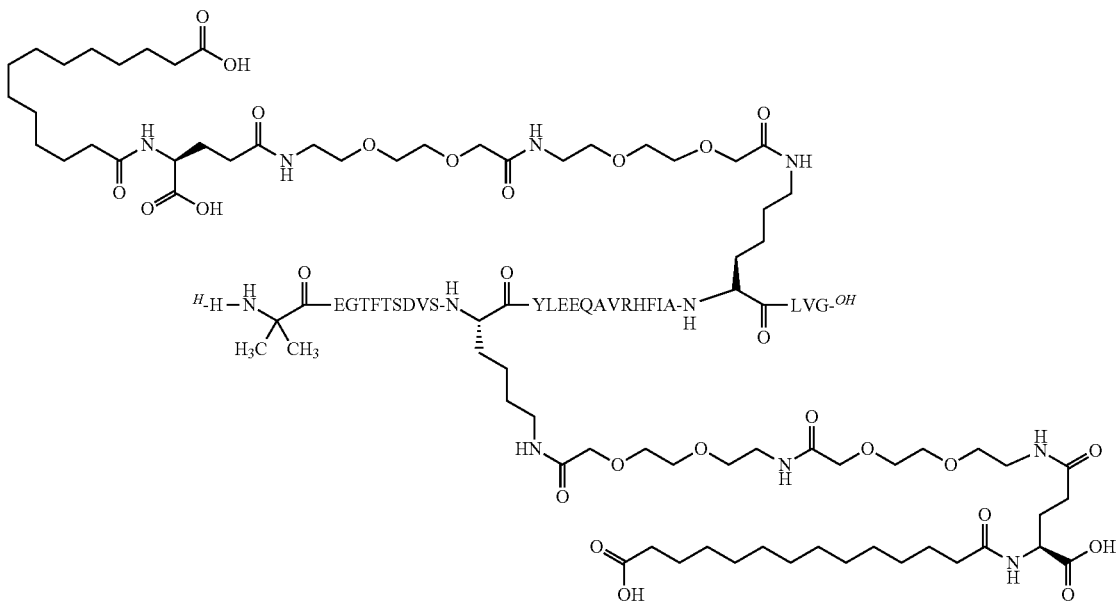

Preparation Method: SPPS_L: SC_L; CP_M1
LCMS: Method: LCMS_4: Rt=2.73 min; m/z: M/3: 1489.0; M/4: 1116.8
UPLC Method: B4_1: Rt=8.69 min
UPLC Method: 04_A3_1: Rt=7.95 min Example 19

$N^{\epsilon18}$-[2-[2-[2-[[2-[2-[2-[[(4S)-4-carboxy-4-[10-(4-carboxyphenoxy)decanoylamino]butanoyl]amino]ethoxy]ethoxy]acetyl]amino]ethoxy]ethoxy]acetyl], $N^{\epsilon31}$-[2-[2-[2-[[2-[2-[2-[[(4S)-4-carboxy-4-[10-(4-carboxyphenoxy)decanoylamino]butanoyl]amino]ethoxy]ethoxy]acetyl]amino]ethoxy]ethoxy]acetyl]-[Aib$^8$,Lys$^{18}$,Glu$^{22}$,Val$^{25}$,Arg$^{26}$,Lys$^{31}$,Gly$^{34}$]-GLP-1-(7-34)-peptide (SEQ ID NO: 9)

Chem. 38
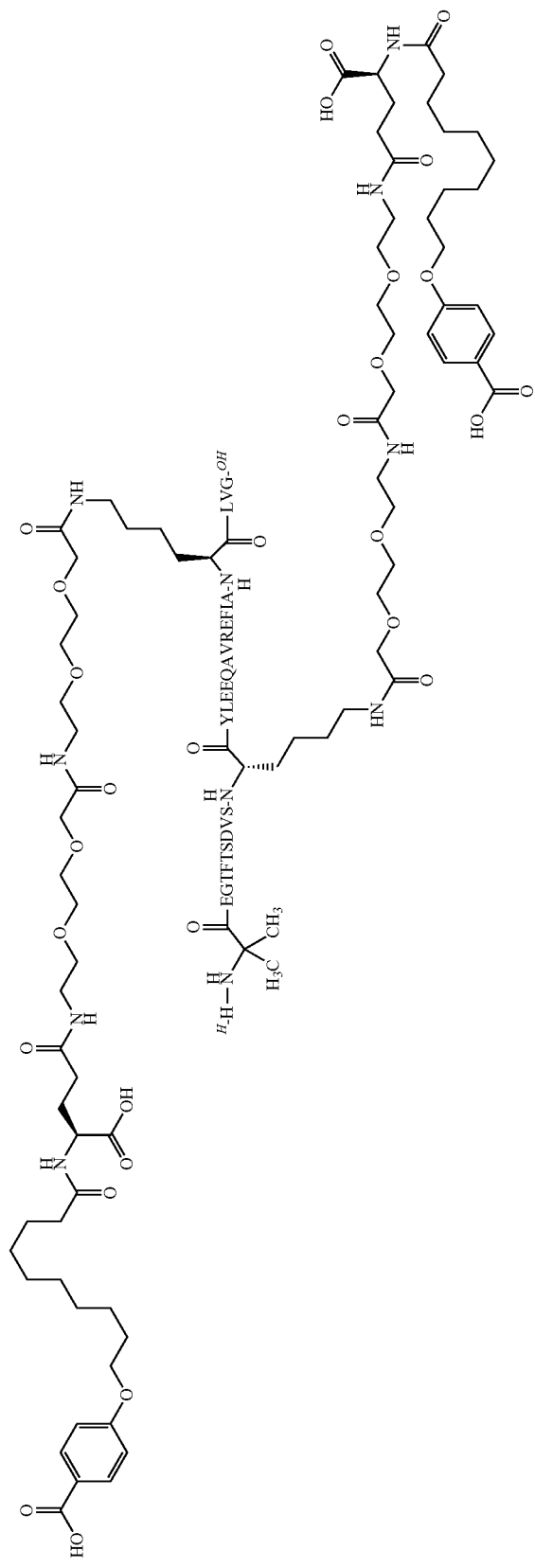

Preparation Method: SPPS_L: SC_L: CP_M1
LCMS: Method: LCMS_4: Rt=2.91 min, m/z: m/3=1520.0 m/4=1140.3 m/5=912.7
UPLC Method: B2_1: Rt=13.85 min
UPLC Method: 04_A3_1: Rt=7.68 min

Example 20

$N^{\epsilon18}$-[2-[2-[2-[[(4S)-4-carboxy-4-(13-carboxytridecanoylamino)butanoyl]amino]ethoxy]ethoxy]acetyl], $N^{\epsilon31}$-[2-[2-[2-[[(4S)-4-carboxy-4-(13-carboxytridecanoylamino)butanoyl]amino]ethoxy]ethoxy]acetyl]-[Aib$^8$,Lys$^{18}$, Glu$^{22}$,Val$^{25}$,Arg$^{26}$,Lys$^{31}$,Gly$^{34}$]-GLP-1-(7-34)-peptide (SEQ ID NO: 9)

Chem. 39

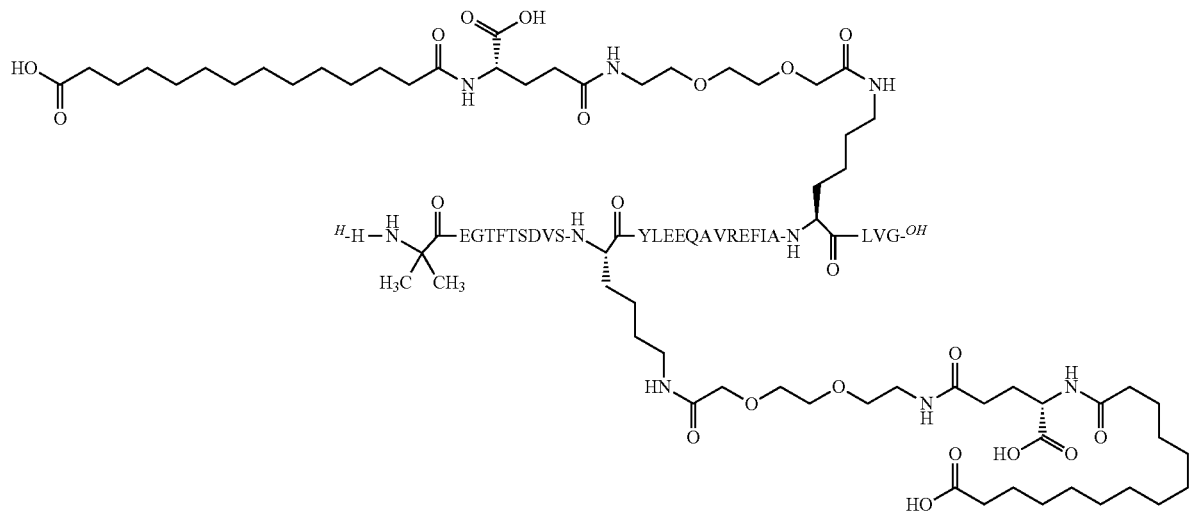

Preparation Method: SPPS_L; SC_L; CP_M1
LCMS: Method: LCMS_4: Rt=2.93 min; m/3: 1389; m/4: 1042; m/5: 833
UPLC Method: B2_1: Rt=14.07 min
UPLC Method: 05_B5_1: Rt=8.39 min

Example 21

$N^{\epsilon18}$-[2-[2-[2-[[2-[2-[2-[[(4S)-4-carboxy-4-(13-carboxytridecanoylamino)butanoyl]amino]ethoxy]ethoxy]acetyl]amino]ethoxy]ethoxy]acetyl], $N^3$-[2-[2-[2-[[2-[2-[2-[[(4S)-4-carboxy-4-(13-carboxytridecanoylamino)butanoyl]amino]ethoxy]ethoxy]acetyl]amino]ethoxy]ethoxy]acetyl]-[Imp$^7$,Aib$^8$,Lys$^{18}$,Glu$^{22}$,Val$^{25}$,Arg$^{26}$, Lys$^{31}$,Gly$^{34}$]-GLP-1-(7-34)-peptide (SEQ ID NO: 25)

Chem. 40

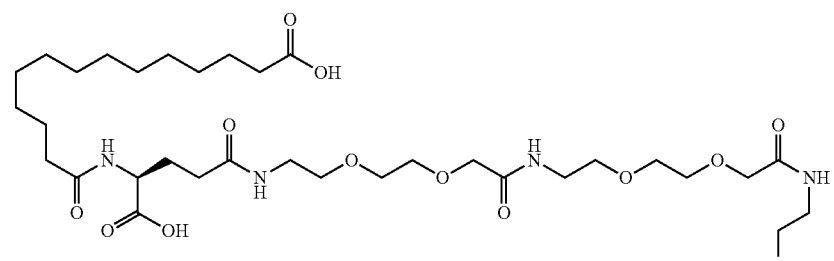

-continued

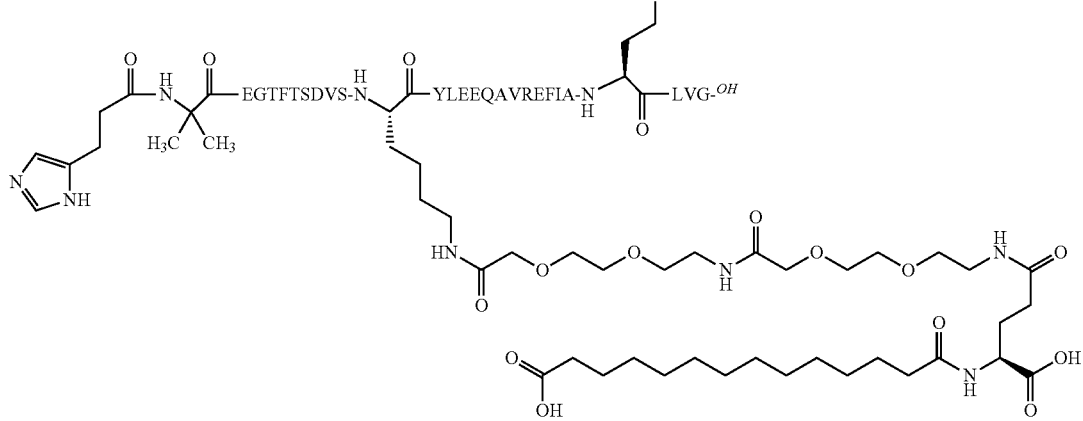

Preparation Method: SPPS_L: SC_L; CP_M1
LCMS: Method: LCMS_4: Rt=2.80 min; m/3: 1481; m/4: 1111; m/5: 888
UPLC Method: B2_1: Rt=14.32 min
UPLC Method: 05_B5_1: Rt=8.38 min Example 22

$N^{\epsilon 18}$-[2-[2-[2-[[2-[2-[2-[[(4S)-4-carboxy-4-(11-carboxyundecanoylamino)butanoyl]amino]ethoxy]ethoxy]acetyl]amino]ethoxy]ethoxy]acetyl]$N^{\epsilon 31}$-[2-[2-[2-[[2-[2-[2-[[(4S)-4-carboxy-4-(11-carboxyundecanoylamino)butanoyl]amino]ethoxy]ethoxy]acetyl]amino]ethoxy]ethoxy]acetyl]-[Imp$^7$,Aib$^8$,Lys$^{18}$,Glu$^{22}$,Val$^{25}$,Arg$^{26}$,Lys$^{31}$,Gly$^{34}$]-GLP-1-(7-34)-peptide (SEQ ID NO: 25)

Chem. 41
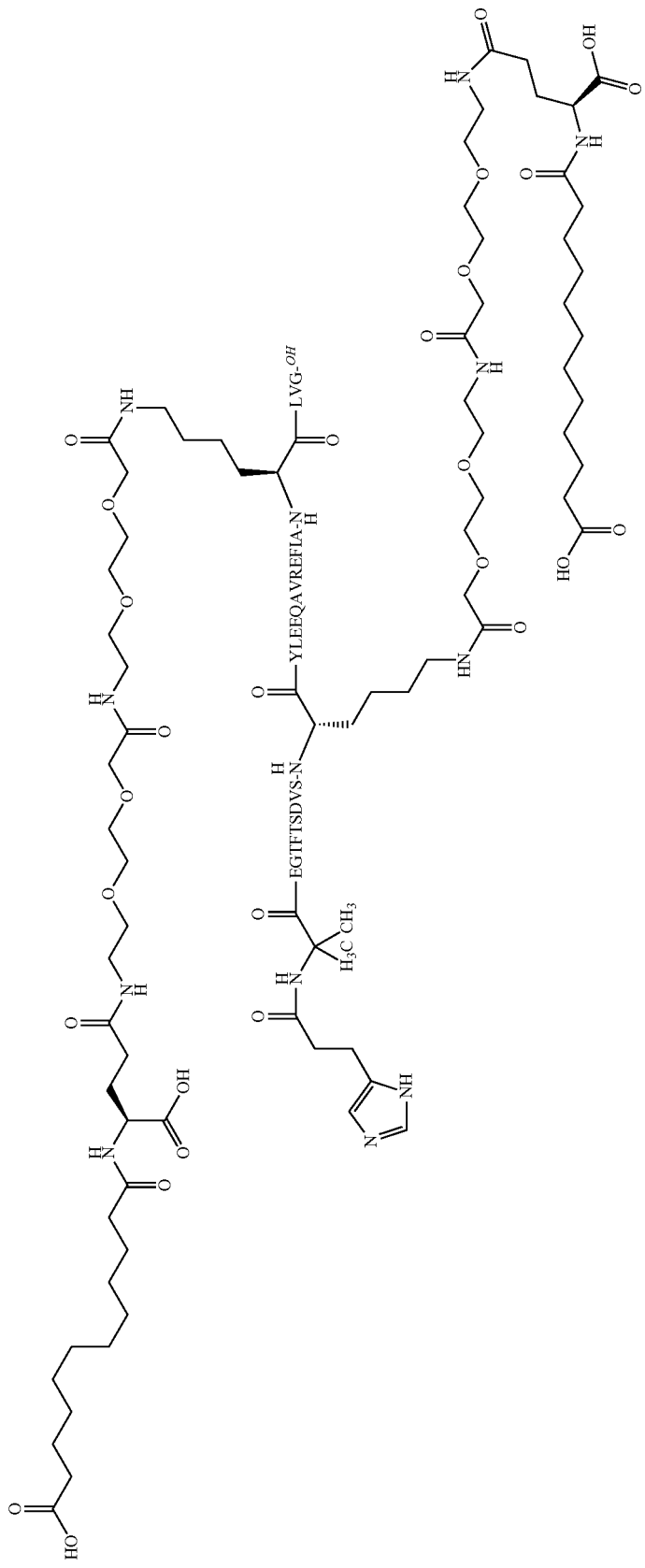

Preparation Method: SPPS_L; SC_L; CP_M1
LCMS: Method: LCMS_4: Rt=2.70 min; m/3=1462 m/4=1097 m/5=877
UPLC Method: B2_1: Rt=6.87 min
UPLC Method: 05_B5_1: Rt=13.30 min Example 23

$N^{\epsilon 18}$-[2-[2-[2-[[2-[2-[2-[[(4S)-4-carboxy-4-(17-carboxy-heptadecanoylamino)butanoyl]amino]ethoxy]ethoxy]acetyl]amino]ethoxy]ethoxy]acetyl], $N^{\epsilon 26}$-[2-[2-[2-[[2-[2-[2-[[(4S)-4-carboxy-4-(17-carboxyheptadecanoylamino)butanoyl]amino]ethoxy]ethoxy]acetyl]amino]ethoxy]ethoxy]acetyl]-[Aib$^8$,Lys$^{18}$,Glu$^{22}$,Gln$^{34}$]-GLP-1-(7-37)-peptide (SEQ ID NO: 7)

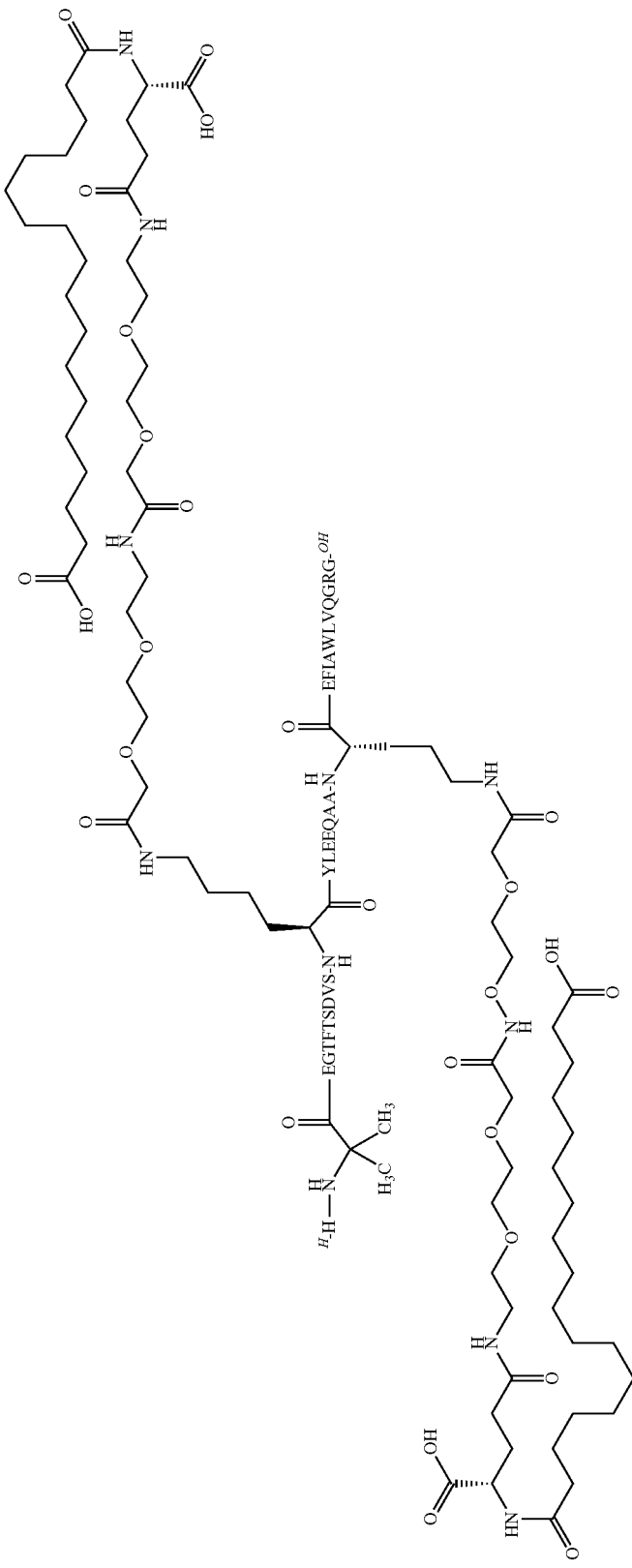
Chem. 42

Preparation Method: SPPS_L; SC_L; SC_M1

LCMS: Method: LCMS_4: Rt=2.78 min m/3: 1638; m/4: 1228; m/5: 983

UPLC Method: B4_1: Rt=10.40 min

UPLC Method: 04_A4_1: Rt=5.66 min

Example 24

$N^{\epsilon 18}$-[2-[2-[2-[[2-[2-[2-[[(4S)-4-carboxy-4-(11-carboxyundecanoylamino)butanoyl]amino]ethoxy]ethoxy]acetyl]amino]ethoxy]ethoxy]acetyl]$N^{\epsilon 27}$-[2-[2-[2-[[2-[2-[2-[[(4S)-4-carboxy-4-(11-carboxyundecanoylamino)butanoyl]amino]ethoxy]ethoxy]acetyl]amino]ethoxy]ethoxy]acetyl]-[Aib$^8$,Lys$^{18}$,Glu$^{22}$,Val$^{25}$,Arg$^{26}$,Lys$^{27}$,His$^{31}$,Gly$^{34}$]-GLP-1-(7-34)-peptide (SEQ ID NO: 26)

Chem. 43

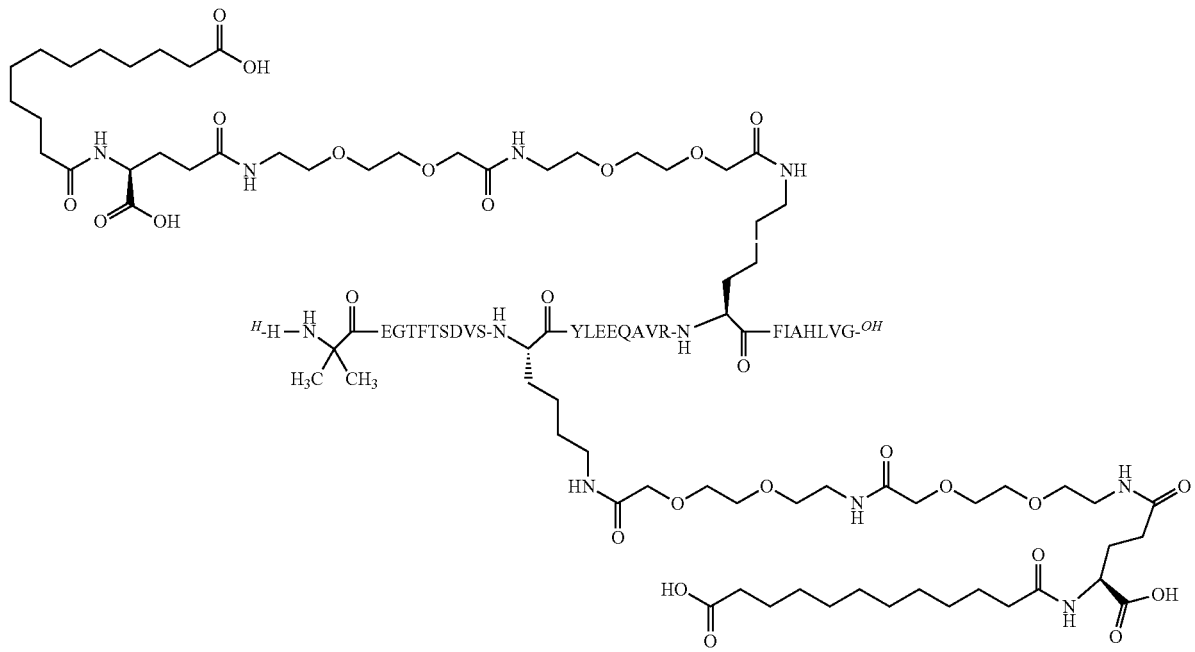

Preparation Method: SPPS_L: SC_L: CP_M1

LCMS: Method: LCMS_4: Rt=2.65 min, m/z: m/3=1470.7 m/4=1103.0 m/5=882.9

UPLC Method: B2_1: Rt=12.27 min

UPLC Method: 04_A3_1: Rt=6.50 min

Example 25

$N^{\epsilon 18}$-[2-[2-[2-[[2-[2-[2-[[(4S)-4-carboxy-4-(11-carboxyundecanoylamino)butanoyl]amino]ethoxy]ethoxy]acetyl]amino]ethoxy]ethoxy]acetyl], $N^{\epsilon 31}$-[2-[2-[2-[[2-[2-[2-[[(4S)-4-carboxy-4-(11-carboxyundecanoylamino)butanoyl]amino]ethoxy]ethoxy]acetyl]amino]ethoxy]ethoxy]acetyl]-[Ser$^8$,Lys$^{18}$,Glu$^{22}$,Val$^{25}$,Arg$^{26}$,Lys$^{31}$,Gly$^{34}$]-GLP-1-(7-34)-peptide (SEQ ID NO: 20)

Chem. 44

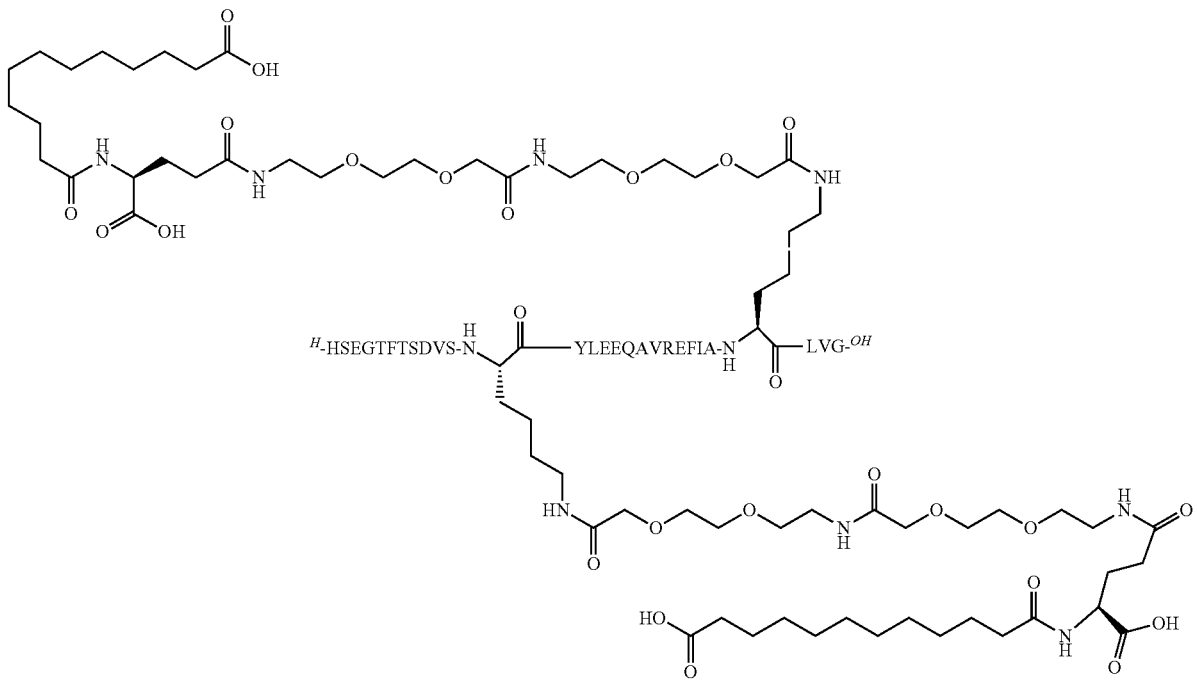

Preparation Method: SPPS_L: SC_L: CP_M1
LCMS: Method: LCMS_4: Rt=2.69 min, m/z: 1/3=1468.7 1/4=1101.8
UPLC Method: B2_1 Rt=12.80 min
UPLC Method: 04_A3_1 Rt=5.97 min Example 26

$N^{\varepsilon 18}$-[2-[2-[2-[[2-[2-[2-[[(4S)-4-carboxy-4-(13-carboxytridecanoylamino)butanoyl]amino]ethoxy]ethoxy]acetyl]amino]ethoxy]ethoxy]acetyl], $N^{\varepsilon 27}$-[2-[2-[2-[[2-[2-[2-[[(4S)-4-carboxy-4-(13-carboxytridecanoylamino)butanoyl]amino]ethoxy]ethoxy]acetyl]amino]ethoxy]ethoxy]acetyl]-[Aib$^8$,Lys$^{18}$,Glu$^{22}$,Val$^{25}$,Arg$^{26}$,Lys$^{27}$,His$^{31}$,Gly$^{34}$]-GLP-1-(7-34)-peptide (SEQ ID NO: 26)

Chem. 45

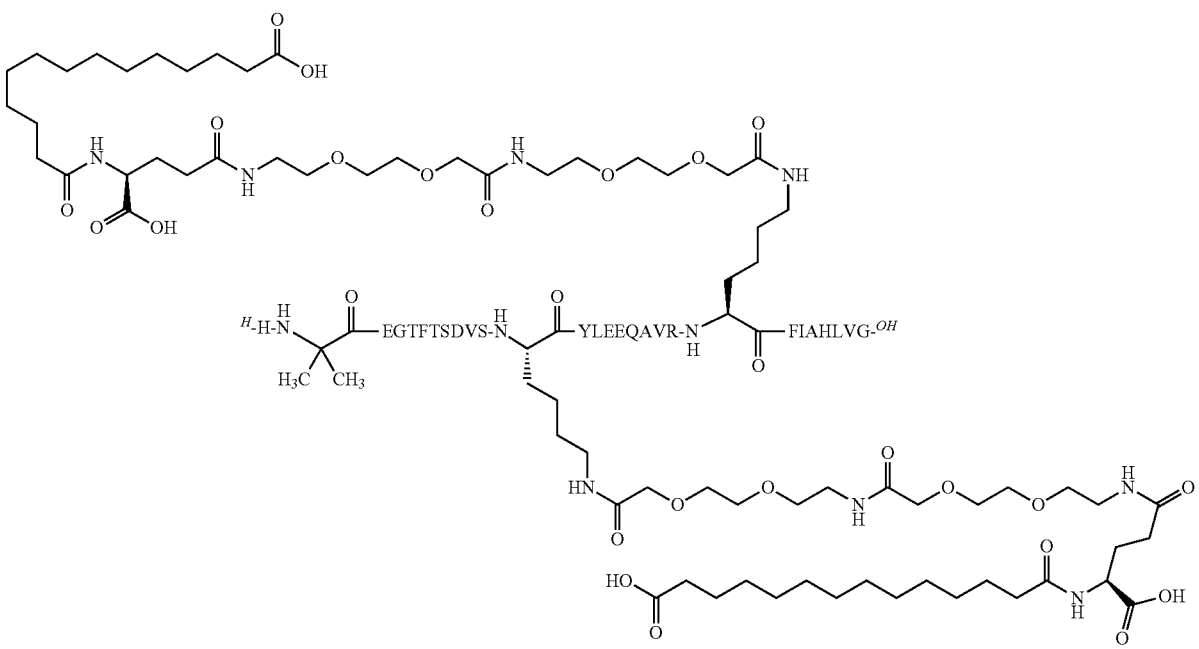

Preparation Method: SPPS_L: SC_L; CP_M1

The theoretical molecular mass of 4467.13 Da was confirmed by Method: MALDI_MS: m/z: 4466.3

UPLC Method: B4_1: Rt=8.52 min

UPLC Method: 04_A3_1: Rt=7.06 min

Example 27

$N^{\epsilon 18}$-[2-[2-[2-[[2-[2-[2-[[(4S)-4-carboxy-4-(11-carboxyundecanoylamino)butanoyl]amino]ethoxy]ethoxy]acetyl]amino]ethoxy]ethoxy]acetyl], $N^{\epsilon 31}$-[2-[2-[2-[[2-[2-[2-[[(4S)-4-carboxy-4-(11-carboxyundecanoylamino)butanoyl]amino]ethoxy]ethoxy]acetyl]amino]ethoxy]ethoxy]acetyl]-[Aib$^8$,Lys$^{18}$,Glu$^{22}$,Val$^{25}$,His$^{26}$,Lys$^{31}$,Gly$^{34}$]-GLP-1-(7-34)-peptide (SEQ ID NO: 16)

Chem. 46

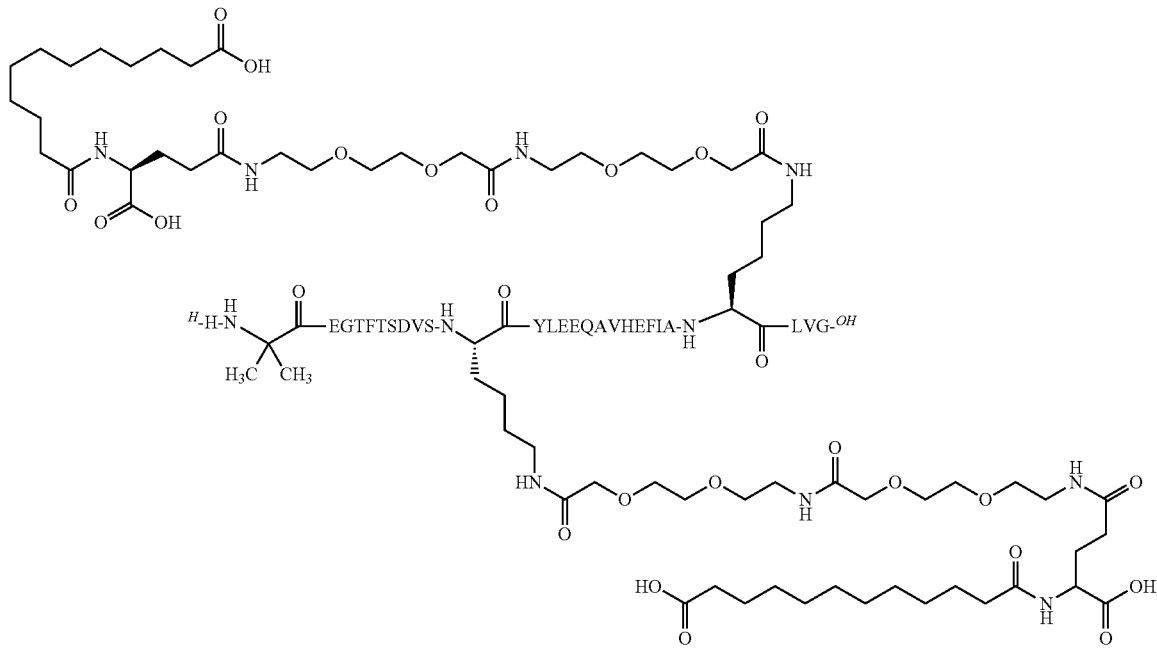

Preparation Method: SPPS_L: SC_L: CP_M1

The theoretical molecular mass of 4383.9 Da was confirmed by MALDI-MS (alpha-cyano); m/z: 4382.6

UPLC Method: B2_1: Rt=12.8 min

Example 28

$N^{\epsilon 18}$-[2-[2-[2-[[2-[2-[2-(13-carboxytridecanoylamino)ethoxy]ethoxy]acetyl]amino]ethoxy]ethoxy]acetyl], $N^{\epsilon 27}$-[2-[2-[2-[[2-[2-[2-(13-carboxytridecanoylamino)ethoxy]ethoxy]acetyl]amino]ethoxy]ethoxy]acetyl]-[Lys$^{18}$,Glu$^{22}$,Arg$^{26}$,Lys$^{27}$,His$^{31}$,Gly$^{34}$]-GLP-1-(7-34)-peptide (SEQ ID NO: 27)

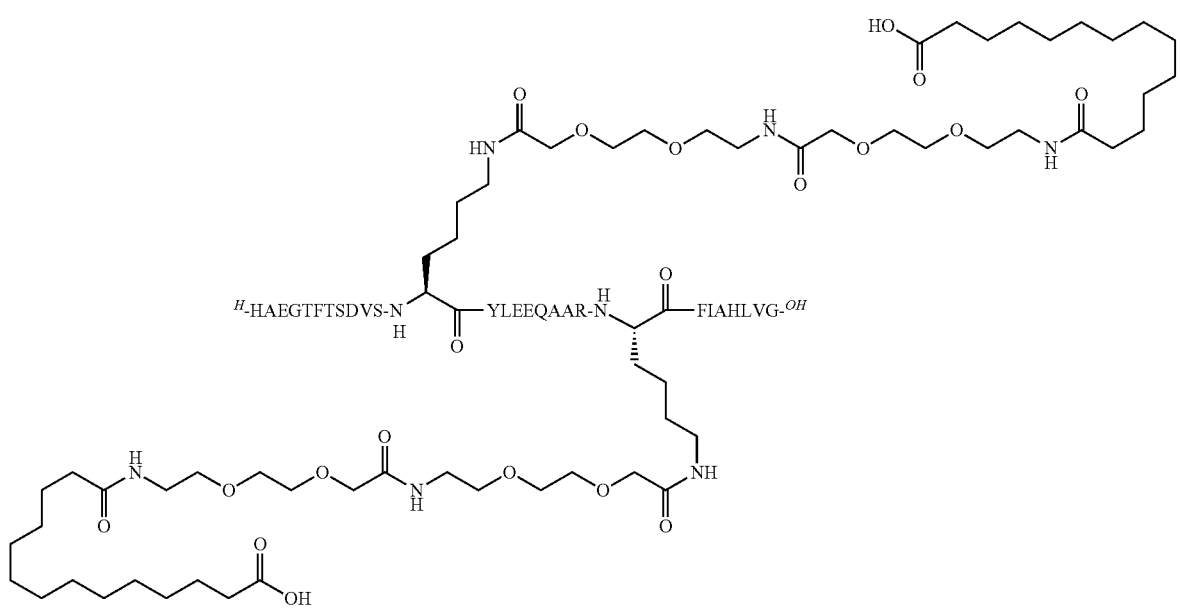

Chem. 47

Preparation Method: SPPS_L; SC_L; CP_M1
LCMS: Method: LCMS_2: Rt=4.22 min m/z: 4166.8; M/3: 1390; M/4: 1043
UPLC: Method: B4_1: Rt=8.81 min
UPLC: Method: 05_B8_1: Rt=4.64 min
UPLC: Method: 04_A3_1: Rt=8.52 min Example 29

$N^{\epsilon 18}$-[(4S)-4-carboxy-4-[[2-[2-[2-[2-[[2-[2-(13-carboxytridecanoylamino)ethoxy]ethoxy]acetyl]amino]ethoxy]ethoxy]acetyl]amino]butanoyl]$N^{\epsilon 27}$-[(4S)-4-carboxy-4-[[2-[2-[2-[[2-[2-[2-(13-carboxytridecanoylamino)ethoxy]ethoxy]acetyl]amino]ethoxy]ethoxy]acetyl]amino]butanoyl]-[Lys$^{18}$,Glu$^{22}$,Arg$^{26}$,Lys$^{27}$,His$^{31}$,Gly$^{34}$]-GLP-1-(7-34)-peptide (SEQ ID NO: 27)

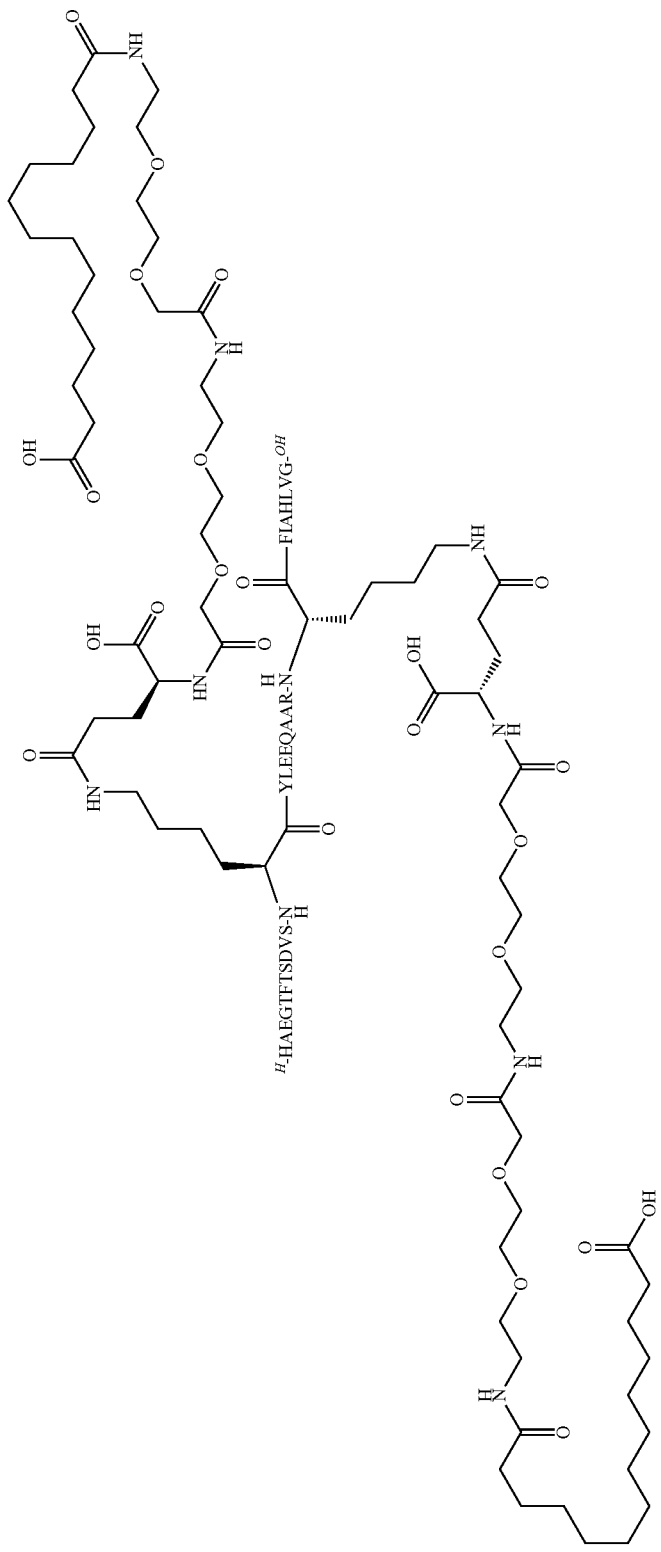

Preparation Method: SPPS_L; SC_L; CP_M1
LCMS: Method: LCMS_2: Rt=4.13 min m/z: 4425.0; M/3: 1476; M/4: 1108:
UPLC: Method: B4_1: Rt=8.43 min
UPLC: Method: 05_B8_1: Rt=4.20 min Example 30

$N^{\epsilon 18}$-[2-[2-[2-[[2-[2-[2-[[(4S)-4-carboxy-4-[10-(4-carboxyphenoxy)decanoylamino]butanoyl]amino]ethoxy]ethoxy]acetyl]amino]ethoxy]ethoxy]acetyl], $N^{\epsilon 27}$-[2-[2-[2-[[2-[2-[2-[[(4S)-4-carboxy-4-[10-(4-carboxyphenoxy)decanoylamino]butanoyl]amino]ethoxy]ethoxy]acetyl]amino]ethoxy]ethoxy]acetyl]-[Lys$^{18}$,Glu$^{22}$,Arg$^{26}$,Lys$^{27}$,His$^{31}$,Gly$^{34}$]-GLP-1-(7-34)-peptide (SEQ ID NO: 27)

Chem. 49
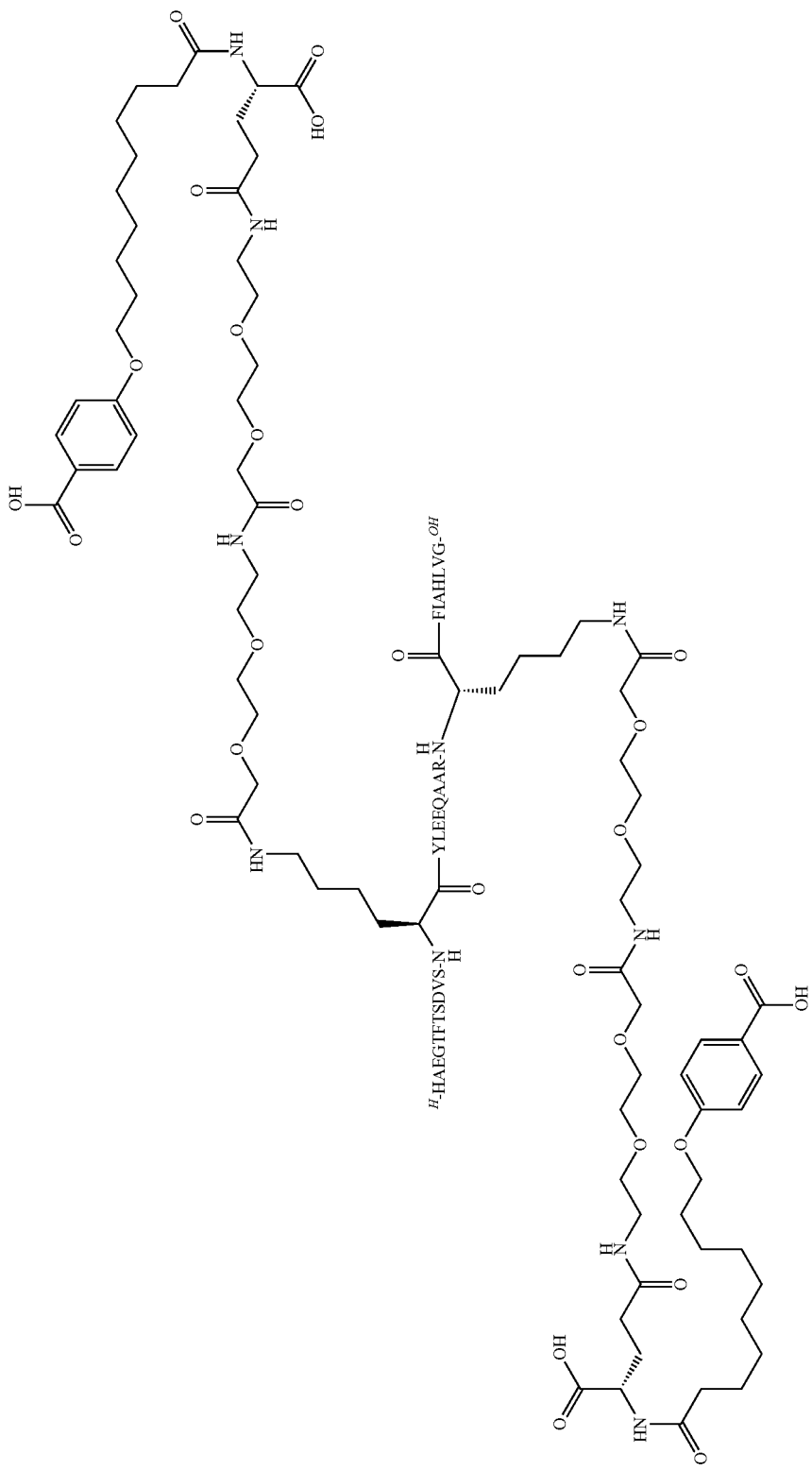

Preparation Method: SPPS_L; SC_L; CP_M1
LCMS: method LCMS_4: Rt=1.96 min m/z: 4525.1; M/3: 1509; M/4: 1132
UPLC: Method: 05_B5_1: Rt=5.29 min
UPLC: Method: B4_1: Rt=8.18 min

Example 31

$N^{\epsilon 18}$8-[2-[2-[2-[[2-[2-[2-(13-carboxytridecanoylamino)ethoxy]ethoxy]acetyl]amino]ethoxy]ethoxy]acetyl], $N^{\epsilon 27}$-[2-[2-[2-[[2-[2-[2-(13-carboxytridecanoylamino)ethoxy]ethoxy]acetyl]amino]ethoxy]ethoxy]acetyl]-[Imp$^7$,Lys$^{18}$,Glu$^{22}$,Arg$^{26}$,Lys$^{27}$,His$^{31}$,Gly$^{34}$]-GLP-1-(7-34)-peptide (SEQ ID NO: 28)

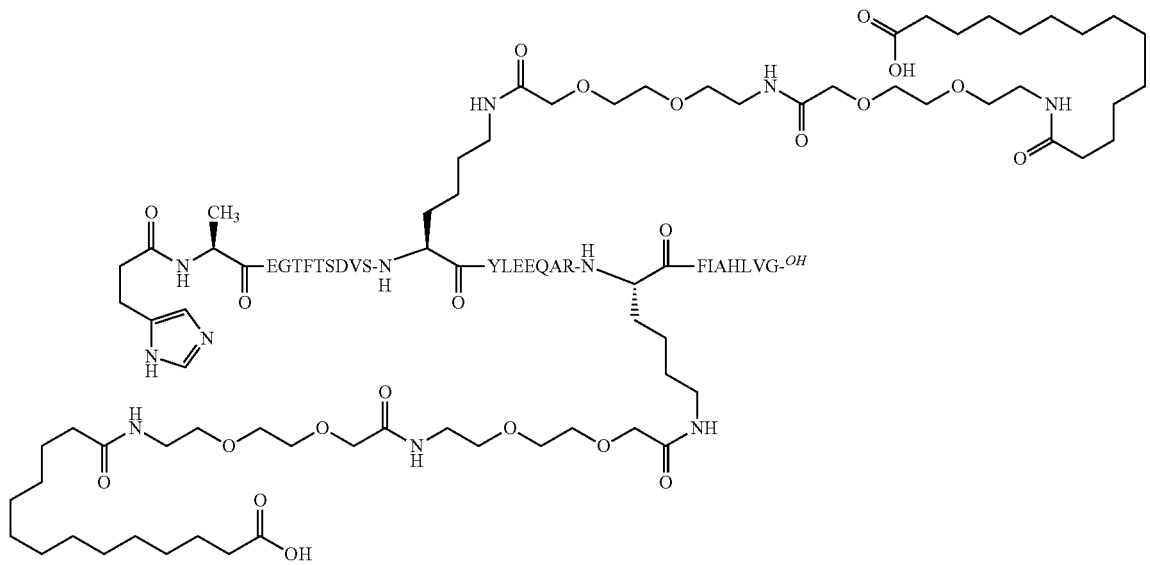

Chem. 50

Preparation Method: SPPS_L; SC_L; CP_M1
LCMS: Method: LCMS_4: Rt=2.17 min m/z: 4151.8; M/3: 1385; M/4: 1039
UPLC: Method: 05_B8_1: Rt=4.45 min
UPLC: Method: B4_1: Rt=8.88 min
UPLC: Method: 04_A3_1: Rt=8.96 min

Example 32

N$^{\epsilon 18}$-[(4S)-4-carboxy-4-[[2-[2-[2-[2-[[2-[2-(13-carboxytri-decanoylamino)ethoxy]ethoxy]acetyl]amino]ethoxy]ethoxy]acetyl]amino]butanoyl]N$^{\epsilon 27}$-[(4S)-4-carboxy-4-[[2-[2-[2-[[2-[2-[2-(13-carboxytridecanoylamino)ethoxy]ethoxy]acetyl]amino]ethoxy]ethoxy]acetyl]amino]butanoyl]-[Imp$^7$,Lys$^{18}$,Glu$^{22}$,Arg$^{26}$,Lys$^{27}$,His$^{31}$,Gly$^{34}$]-GLP-1-(7-34)-peptide (SEQ ID NO: 28)

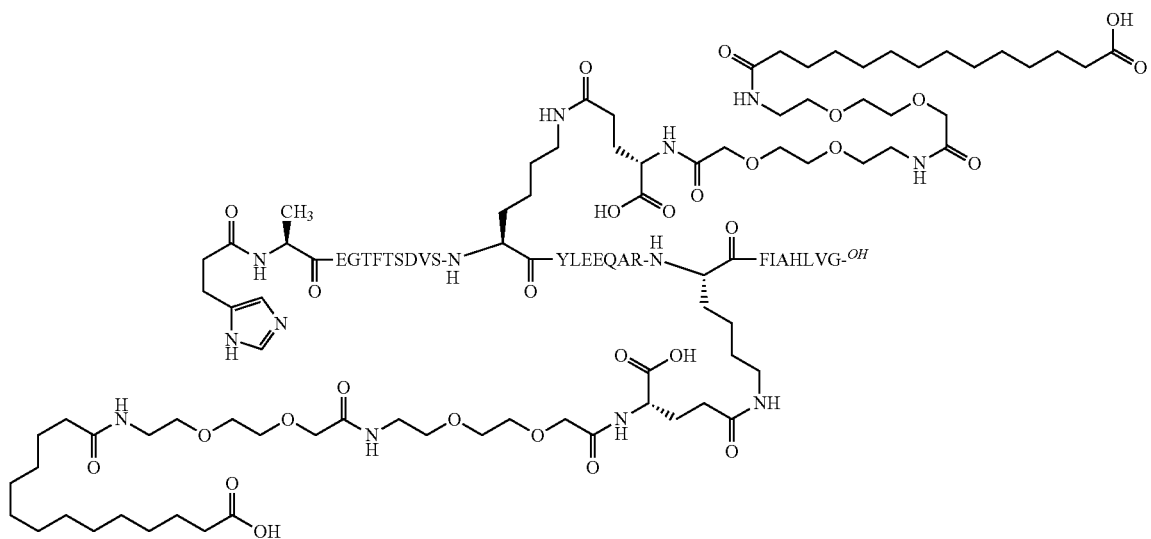

Chem. 51

Preparation Method: SPPS_L; SC_L; CP_M1
LC
MS: Method: LCMS_4: Rt=2.12 min m/z: 4410.0; M/3: 1470; M/4: 1103
UPLC: Method: 05_B5_1: Rt=6.57 min
UPLC: Method: 05_B8_1: Rt=3.81 min
UPLC: Method: B4_1: Rt=8.59 min
UPLC: Method: 04_A3_1: Rt=6.60 min

Example 33

$N^{\varepsilon 18}$-[2-[2-[2-[[2-[2-[2-[[(4S)-4-carboxy-4-[10-(4-carboxyphenoxy)decanoylamino]butanoyl]amino]ethoxy]ethoxy]acetyl]amino]ethoxy]ethoxy]acetyl], $N^{\varepsilon 27}$-[2-[2-[2-[[2-[2-[2-[[(4S)-4-carboxy-4-[10-(4-carboxyphenoxy)decanoylamino]butanoyl]amino]ethoxy]ethoxy]acetyl]amino]ethoxy]ethoxy]acetyl]-[Imp$^7$,Lys$^{18}$,Glu$^{22}$,Arg$^{26}$,Lys27,His$^{31}$,Gly$^{34}$]-GLP-1-(7-34)-peptide (SEQ ID NO: 28)

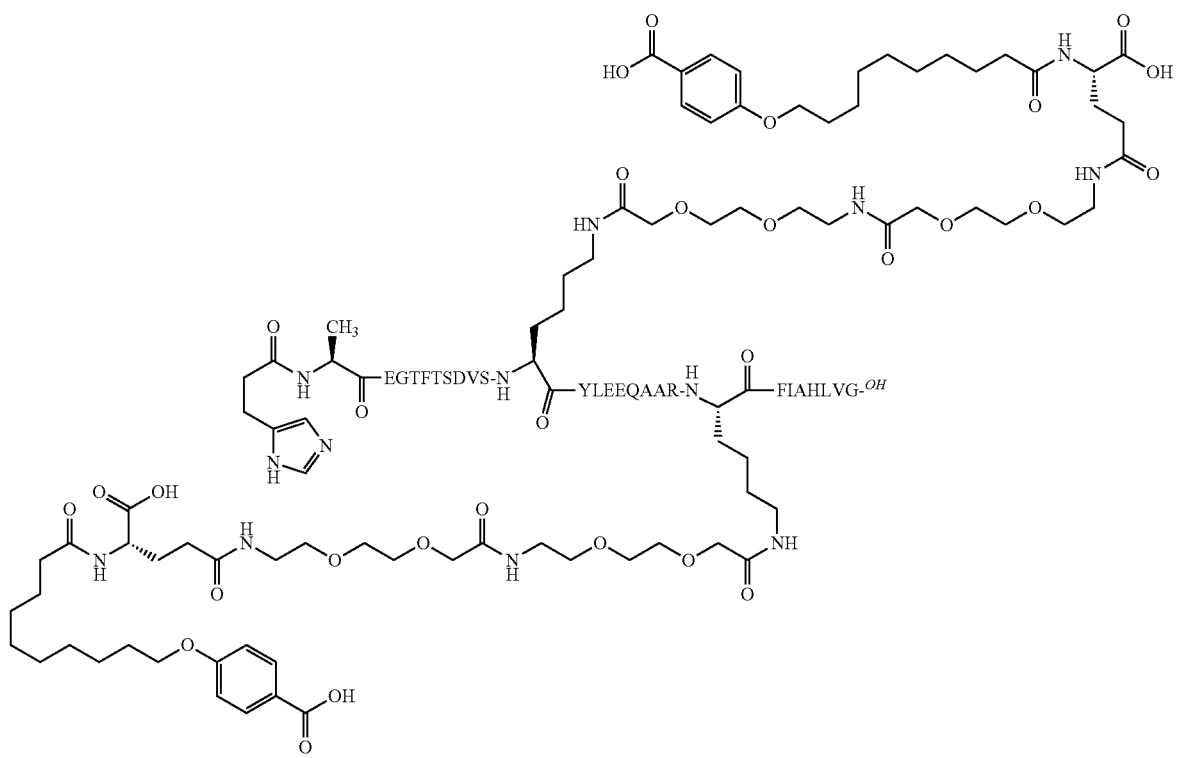

Chem. 52

Preparation Method: SPPS_L; SC_L; CP_M1
LCMS: Method: LCMS_4: Rt=2.04 min m/z: 4510.1; M/3: 1504; M/4: 1128
UPLC: Method: 05_B5_1: Rt=5.79 min
UPLC: Method: B4_1: Rt=8.36 min
UPLC: Method: 04_A3_1: Rt=5.57 min

Example 34

$N^{\varepsilon 18}$-[2-[2-[2-[[2-[2-[2-[[(4S)-4-carboxy-4-[10-(4-carboxyphenoxy)decanoylamino]butanoyl]amino]ethoxy]ethoxy]acetyl]amino]ethoxy]ethoxy]acetyl], $N^{\varepsilon 26}$-[2-[2-[2-[[2-[2-[2-[[(4S)-4-carboxy-4-[10-(4-carboxyphenoxy)decanoylamino]butanoyl]amino]ethoxy]ethoxy]acetyl]amino]ethoxy]ethoxy]acetyl]-[Lys$^{18}$,Gln$^{34}$]-GLP-1-(7-37)-peptide (SEQ ID NO: 29)

Chem. 53

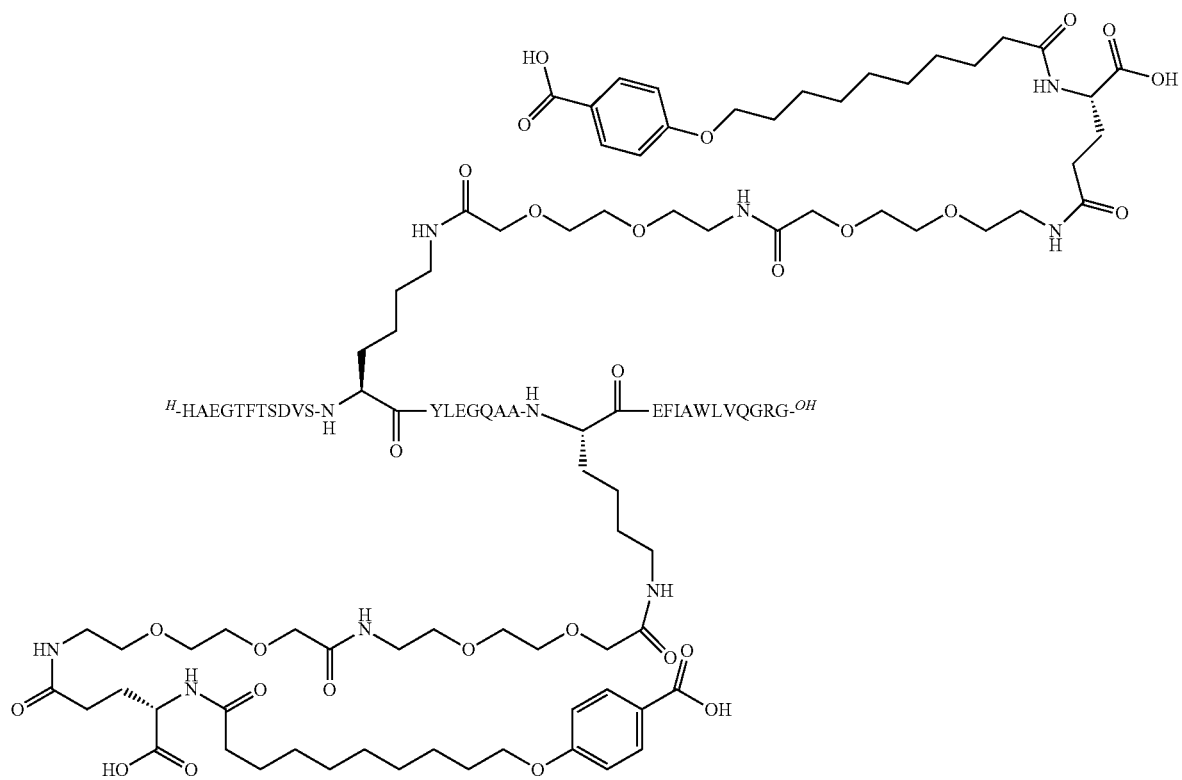

Preparation Method: SPPS_L: SC_L; CP_M1
The theoretical molecular mass of 4816.4 Da was confirmed by MALDI_MS: m/z: 4819.5
UPLC Method: B4_1: Rt=8.85 min
UPLC Method: 05_B8_1: Rt=3.42 min Example 35

$N^{\epsilon 18}$-[2-[2-[2-[[2-[2-[2-[[(4S)-4-carboxy-4-[10-(4-carboxyphenoxy)decanoylamino]butanoyl]amino]ethoxy]ethoxy]acetyl]amino]ethoxy]ethoxy]acetyl], $N^{\epsilon 27}$-[2-[2-[2-[[2-[2-[2-[[(4S)-4-carboxy-4-[10-(4-carboxyphenoxy)decanoylamino]butanoyl]amino]ethoxy]ethoxy]acetyl]amino]ethoxy]ethoxy]acetyl]-[Lys$^{18}$,Glu$^{22}$,His$^{26}$, Lys$^{27}$,Gln$^{34}$]-GLP-1-(7-37)-peptide (SEQ ID NO: 30)

Chem. 54
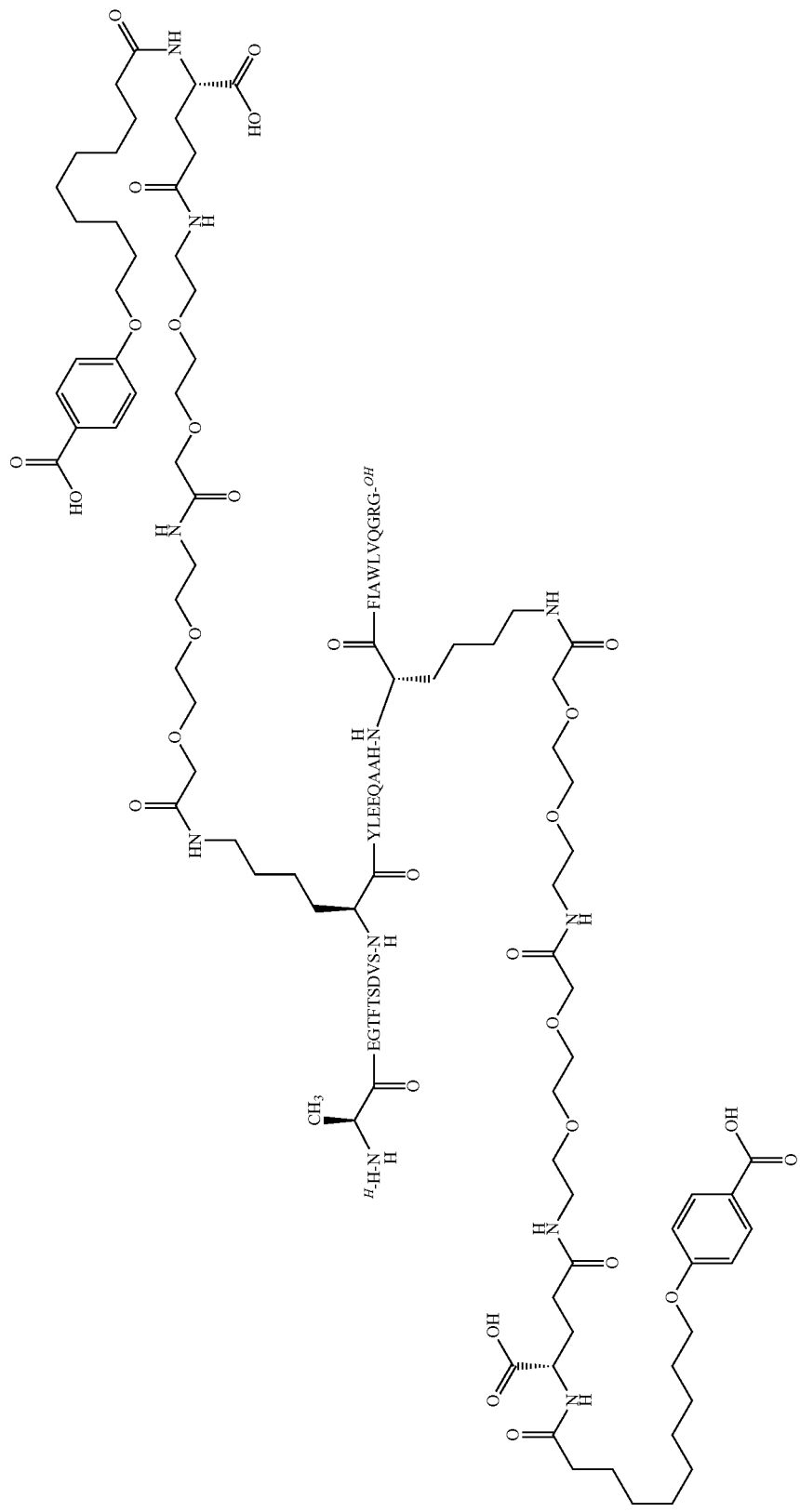

Preparation Method: SPPS_L: SC_L; CP_M1
The theoretical molecular mass of 4896.5 Da was confirmed by MALDI_MS: m/z: 4896
UPLC Method: B4_1: Rt=8.65 min
UPLC Method: 05_B8_1: Rt=2.98 min Example 36

$N^{\epsilon 18}$-[(4S)-4-carboxy-4-[[2-[2-[2-[2-[[2-[2-(13-carboxytridecanoylamino)ethoxy]ethoxy]acetyl]amino]ethoxy]ethoxy]acetyl]amino]butanoyl], $N^{\epsilon 31}$-[(4S)-4-carboxy-4-[[2-[2-[2-[[2-[2-[2-(13-carboxytridecanoylamino)ethoxy]ethoxy]acetyl]amino]ethoxy]ethoxy]acetyl]amino]butanoyl]-[Aib$^8$,Lys$^{18}$,Glu$^{22}$,Val$^{25}$,Arg$^{26}$,Lys$^{31}$,Gly$^{34}$]-GLP-1-(7-34)-peptide (SEQ ID NO: 9)

Chem. 55
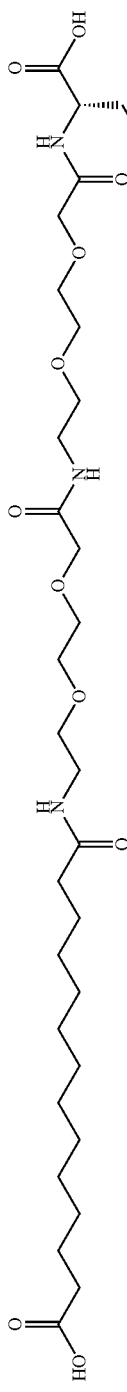
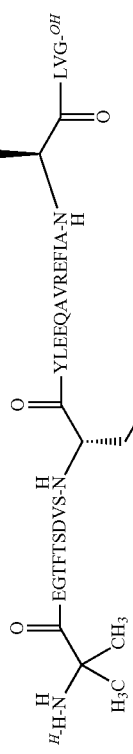
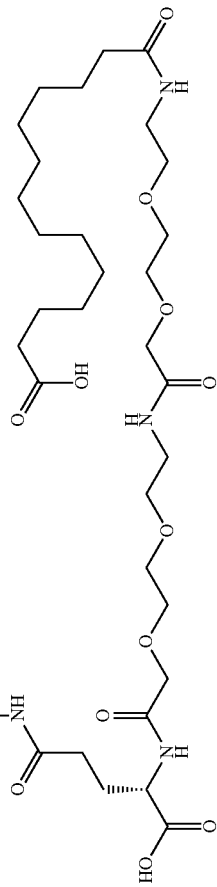

Preparation Method: SPPS_L: SC_L; CP_M1

The theoretical molecular mass of 4459.1 Da was confirmed by MALDI_MS: m/z: 4458.8

UPLC Method: B4_1 Rt=9.28 min

UPLC Method: 05_B8_1: Rt=5.6 min

Example 37

$N^{\epsilon 18}$-[2-[2-[2-[[2-[2-[2-[[(4S)-4-carboxy-4-(13-carboxytridecanoylamino)butanoyl]amino]ethoxy]ethoxy]acetyl]amino]ethoxy]ethoxy]acetyl]$N^{\epsilon}$-[2-[2-[2-[[2-[2-[2-[[(4S)-4-carboxy-4-(13-carboxytridecanoylamino)butanoyl]amino]ethoxy]ethoxy]acetyl]amino]ethoxy]ethoxy]acetyl][Aib$^8$,Lys$^{18}$,Glu$^{22}$,Val$^{25}$,Arg$^{26}$,Lys$^{31}$]-GLP-1-(7-33)-peptide amide (SEQ ID NO: 31)

Chem. 56
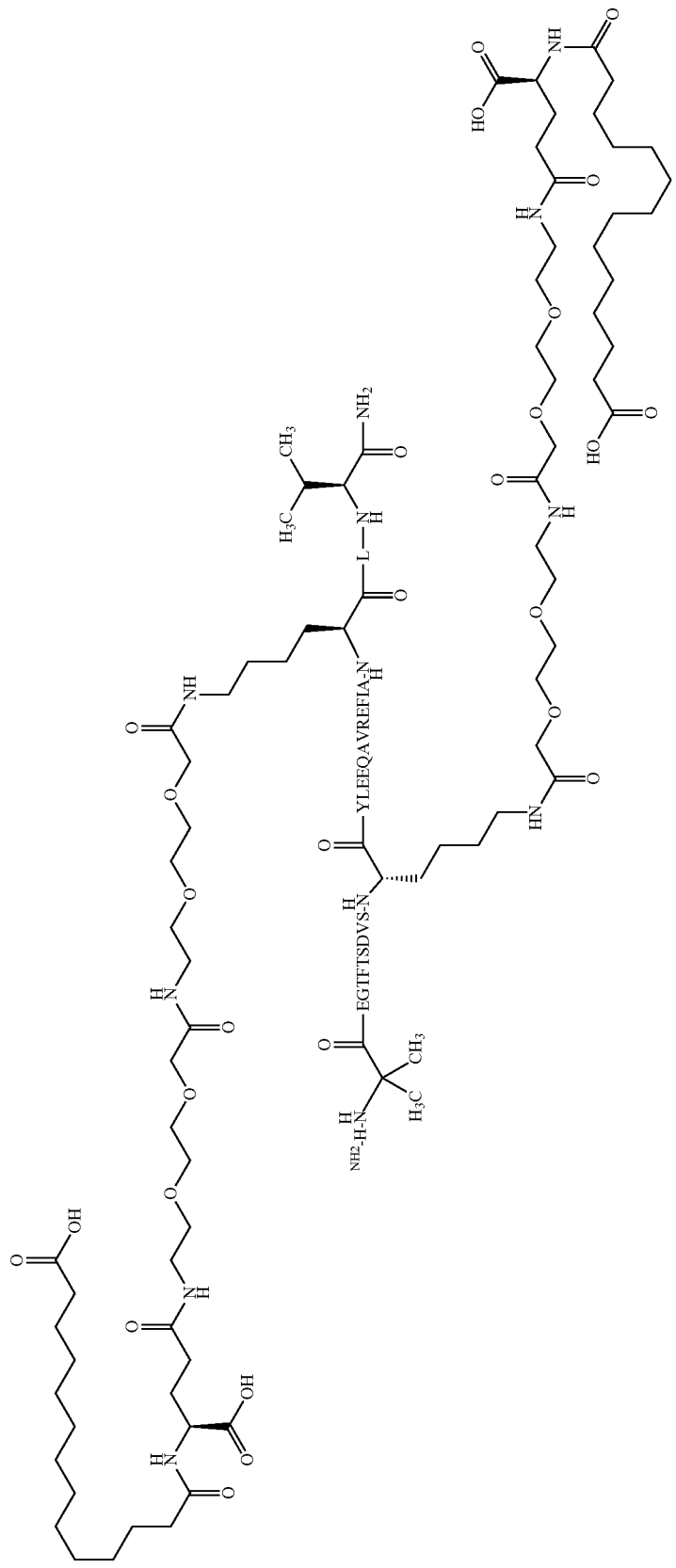

Preparation Method: SPPS_L: SC_L; CP_M1

The theoretical molecular mass of 4401.1 Da was confirmed by MALDI_MS: m/z: 4401.3

UPLC Method: B4_1: Rt=8.65 min

UPLC Method: 05_B8_1: Rt=4.47 min

Example 38

$N^{\epsilon 18}$-[2-[2-[2-[[2-[2-[2-[[(4S)-4-carboxy-4-[10-(4-carboxyphenoxy)decanoylamino]butanoyl]amino]ethoxy]ethoxy]acetyl]amino]ethoxy]ethoxy]acetyl], $N^{\epsilon 26}$-[2-[2-[2-[[2-[2-[2-[[(4S)-4-carboxy-4-[10-(4-carboxyphenoxy)decanoylamino]butanoyl]amino]ethoxy]ethoxy]acetyl]amino]ethoxy]ethoxy]acetyl]-[Lys$^{18}$,Glu$^{22}$,Gln$^{34}$]-GLP-1-(7-37)-peptide (SEQ ID NO: 32)

Chem. 57
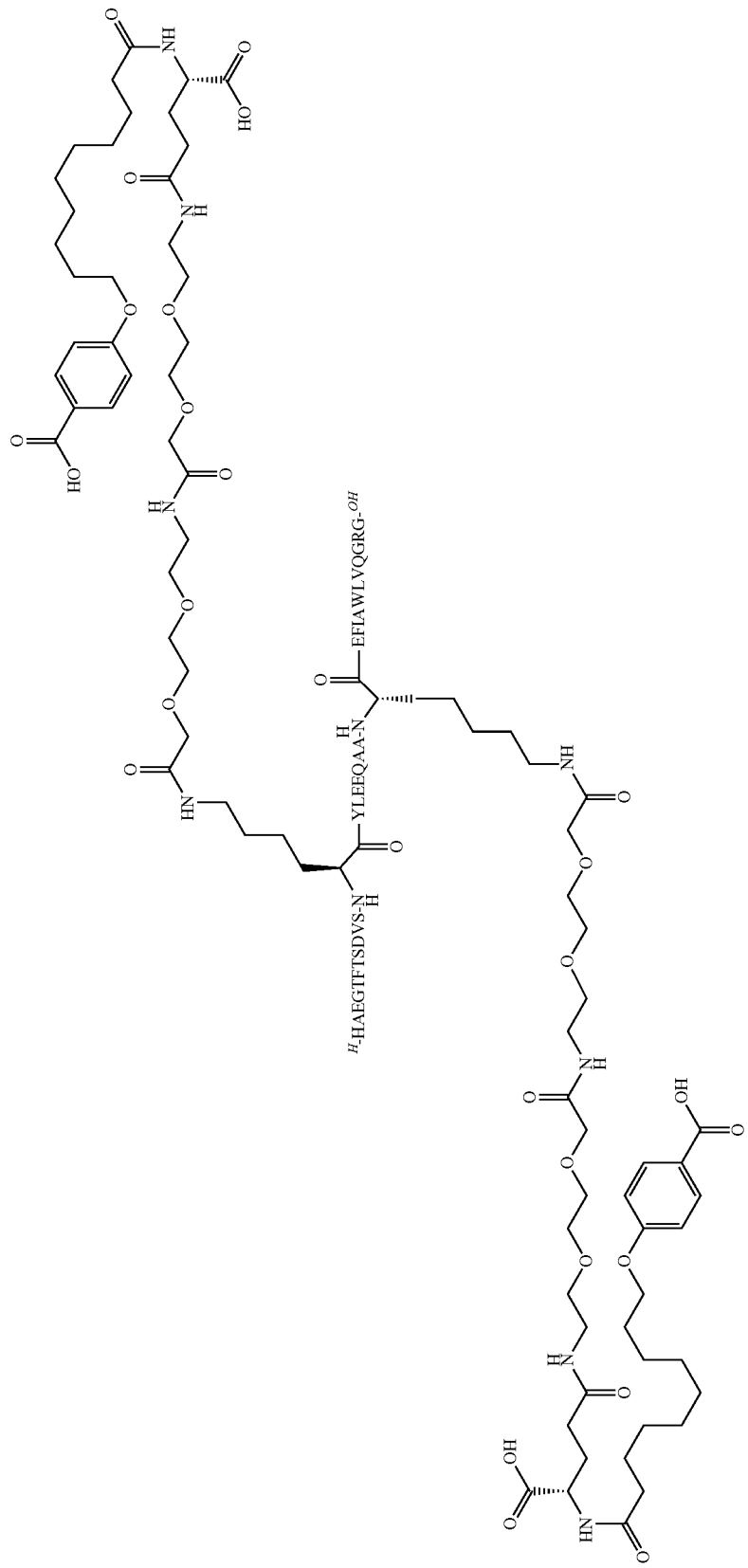

Preparation Method: SPPS_L: SC_L: CP_M1
LCMS: Method: LCMS_4: Rt=2.23 min, m/z: 4888.5
UPLC Method: B2_1: Rt=13.59 min
UPLC Method: 04_A7_1: Rt=5.03 min Example 39

$N^{\epsilon 18}$-[2-[2-[2-[[2-[2-[2-[[(4S)-4-carboxy-4-(11-carboxyundecanoylamino)butanoyl]amino]ethoxy]ethoxy]acetyl]amino]ethoxy]ethoxy]acetyl], $N^{\epsilon 26}$-[2-[2-[2-[[2-[2-[2-[[(4S)-4-carboxy-4-(11-carboxyundecanoylamino)butanoyl]amino]ethoxy]ethoxy]acetyl]amino]ethoxy]ethoxy]acetyl]-[Aib$^8$,Lys$^{18}$,Glu$^{22}$,Gln$^{34}$]-GLP-1-(7-37)-peptide (SEQ ID NO: 7)

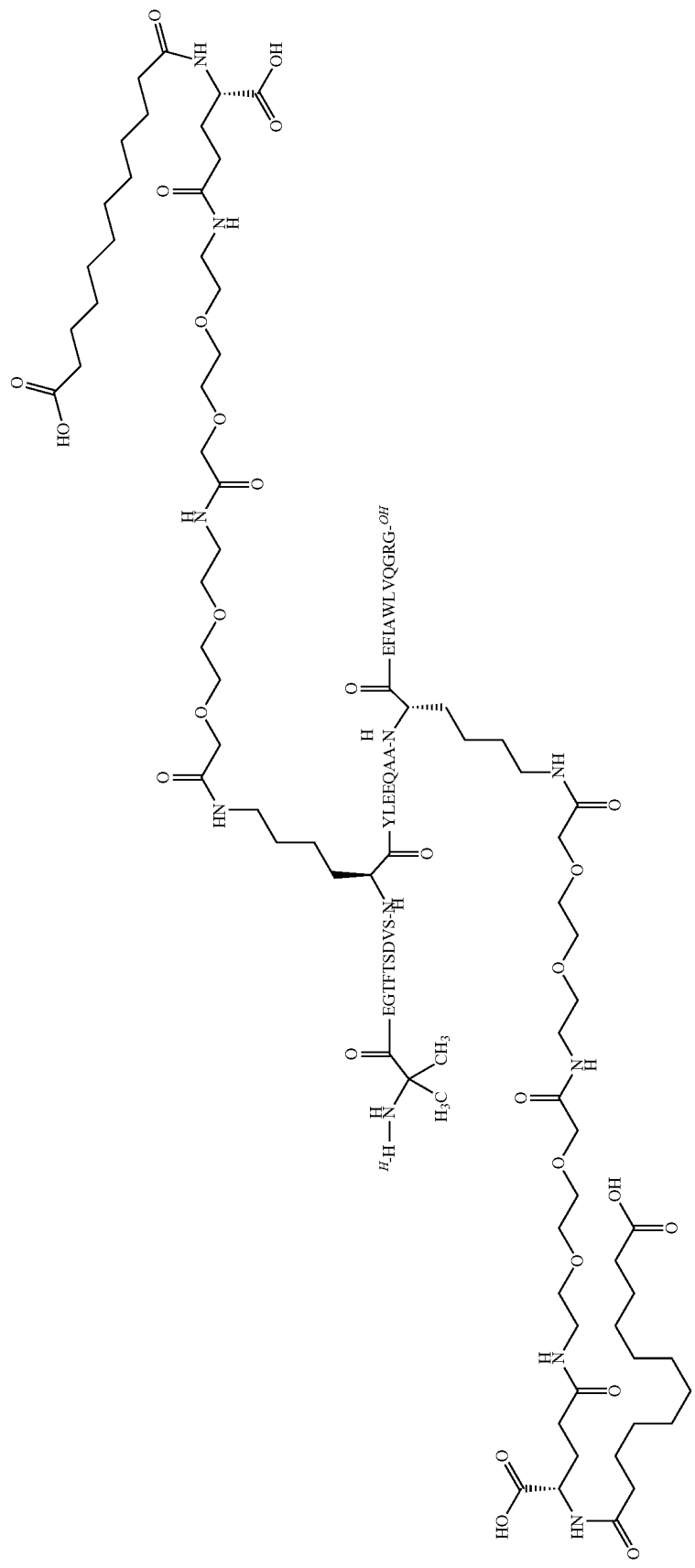
Chem. 58

Preparation Method: SPPS_L; SC_L
LCMS: Method: LCMS_4: Rt=2.03 min m/z: 4744.8; m/3: 1582; m/4: 1187; m/5: 950
UPLC Method: B2_1: Rt=12.80 min
UPLC Method: 05_B5_1: Rt=5.64 min Example 40

$N^{\epsilon18}$-[2-[2-[2-[[2-[2-[2-[[(4S)-4-carboxy-4-(11-carboxyundecanoylamino)butanoyl]amino]ethoxy]ethoxy]acetyl]amino]ethoxy]ethoxy]acetyl], $N^{\epsilon26}$-[2-[2-[2-[[2-[2-[2-[[(4S)-4-carboxy-4-(11-carboxyundecanoylamino)butanoyl]amino]ethoxy]ethoxy]acetyl]amino]ethoxy]ethoxy]acetyl]-[Lys$^{18}$,Glu$^{22}$,Gln$^{34}$]-GLP-1-(7-37)-peptide (SEQ ID NO: 32)

Chem. 59

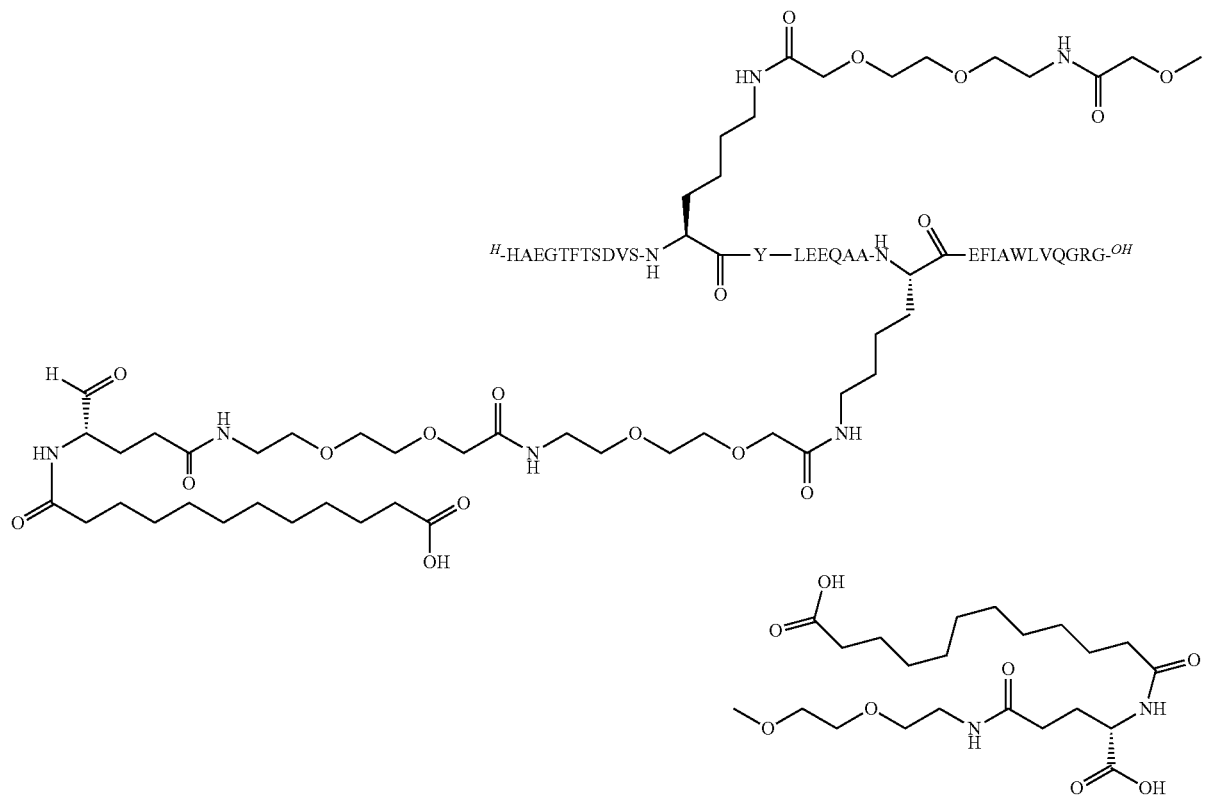

Preparation Method: SPPS_L; SC_L
LCMS: Method: LCMS_4: Rt=2.03 min; m/3: 1577; m/4: 1183; m/5: 946 (1A)
UPLC Method: B2_1: Rt=12.76 min
UPLC Method: 05_B5_1: Rt=5.54

Example 41

$N^{\epsilon18}$-[2-[2-[2-[[2-[2-[2-[[(4S)-4-carboxy-4-[10-(4-carboxyphenoxy)decanoylamino]butanoyl]amino]ethoxy]ethoxy]acetyl]amino]ethoxy]ethoxy]acetyl], $N^{\epsilon27}$-[2-[2-[2-[[2-[2-[2-[[(4S)-4-carboxy-4-[10-(4-carboxyphenoxy)decanoylamino]butanoyl]amino]ethoxy]ethoxy]acetyl]amino]ethoxy]ethoxy]acetyl]-[Aib$^8$,Lys$^{18}$,Glu$^{22}$,Val$^{25}$,Arg$^{26}$,Lys$^{27}$,Gln$^{34}$]-GLP-1-(7-37)-peptide (SEQ ID NO: 33)

Chem. 60

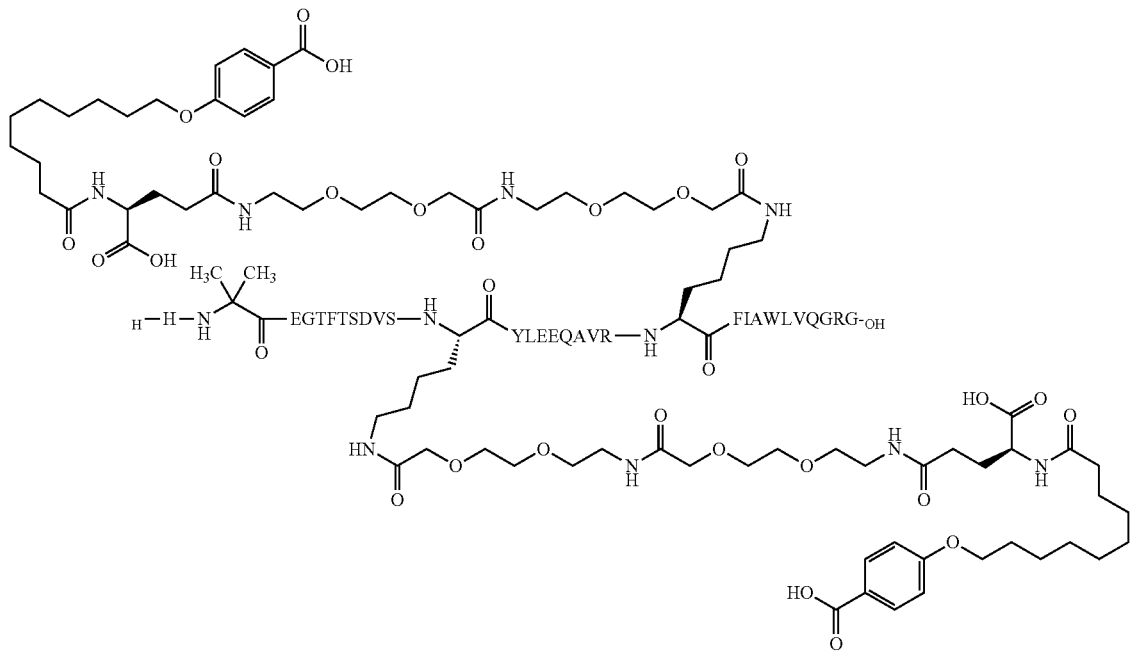

Preparation Method: SPPS_L: SC_L: CP_M1
LCMS: Method: LCMS_4: Rt=2.51 min, m/z: 4957.6
UPLC Method: B2_1: Rt=13.57 min
UPLC Method: 05_B5_1: Rt=6.50 min Example 42

$N^{\epsilon 18}$-[2-[2-[2-[[2-[2-[2-[[(4S)-4-carboxy-4-[0-(4-carboxyphenoxy)decanoylamino]butanoyl]amino]ethoxy]ethoxy]acetyl]amino]ethoxy]ethoxy]acetyl], $N^{\epsilon 27}$-[2-[2-[2-[[2-[2-[2-[[(4S)-4-carboxy-4-[10-(4-carboxyphenoxy)decanoylamino]butanoyl]amino]ethoxy]ethoxy]acetyl]amino]ethoxy]ethoxy]acetyl]-[Lys$^{18}$,Glu$^{22}$,Val$^{25}$,Arg$^{26}$, Lys$^{27}$,Gln$^{34}$]-GLP-1-(7-37)-peptide (SEQ ID NO: 34)

Chem. 61
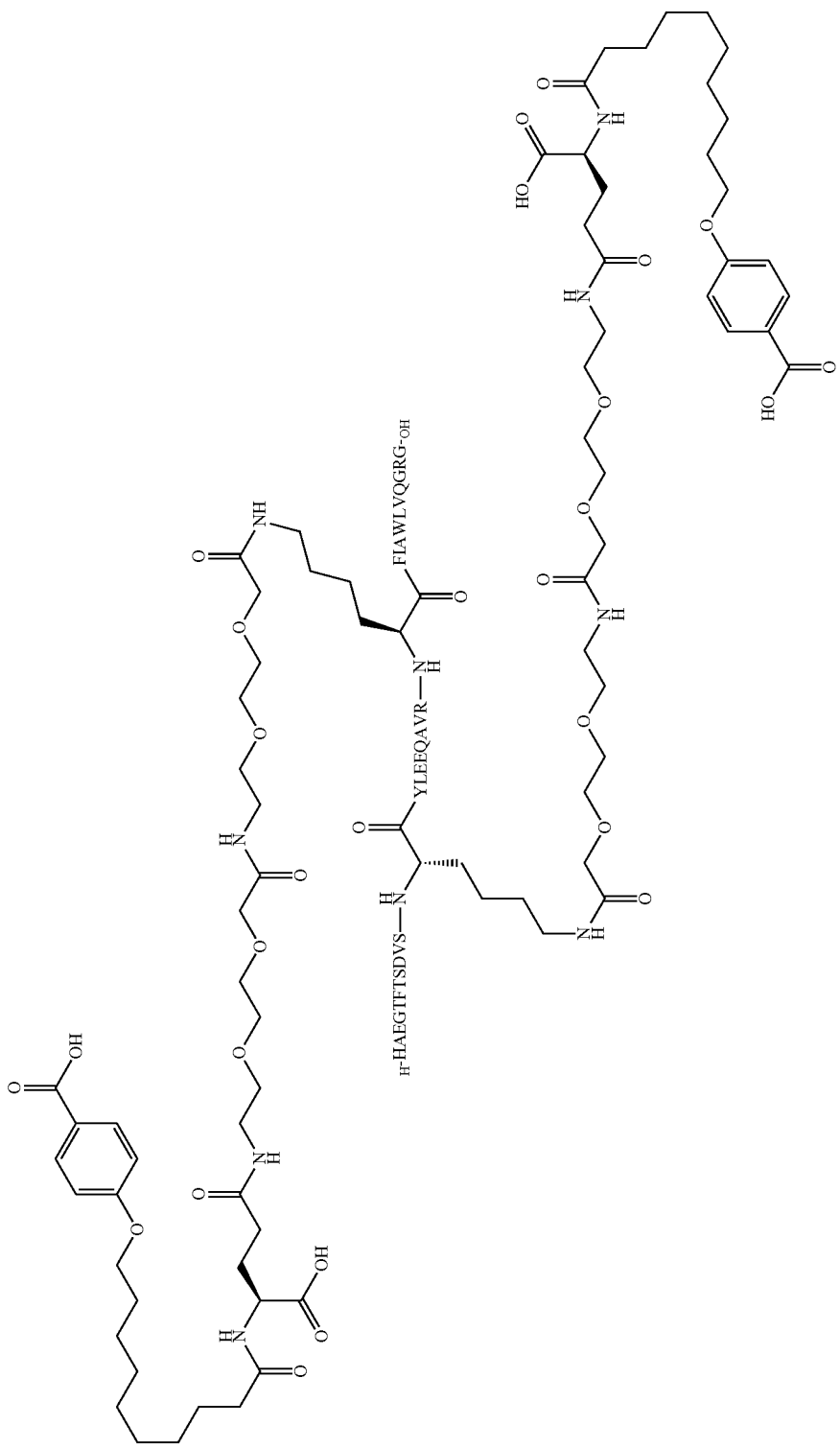

Preparation Method: SPPS_L: SC_L: CP_M1
LCMS: Method: LCMS_4: Rt=2.31 min, m/z: 4942.3
UPLC Method: B2_1: Rt=13.53 min
UPLC Method: 05_B5_1: Rt=6.34 min

Example 43

$N^{\epsilon 18}$-[2-[2-[2-[[2-[2-[2-[[(4S)-4-carboxy-4-(13-carboxytridecanoylamino)butanoyl]amino]ethoxy]ethoxy]acetyl]amino]ethoxy]ethoxy]acetyl], $N^{\epsilon 31}$-[2-[2-[2-[[2-[2-[2-[[(4S)-4-carboxy-4-(13-carboxytridecanoylamino)butanoyl]amino]ethoxy]ethoxy]acetyl]amino]ethoxy]ethoxy]acetyl]-[Lys$^{18}$,Glu$^{22}$,Val$^{25}$,Arg$^{26}$,Lys$^{31}$,Arg$^{34}$]-GLP-1-(7-37)-peptide (SEQ ID NO: 10)

Chem. 62
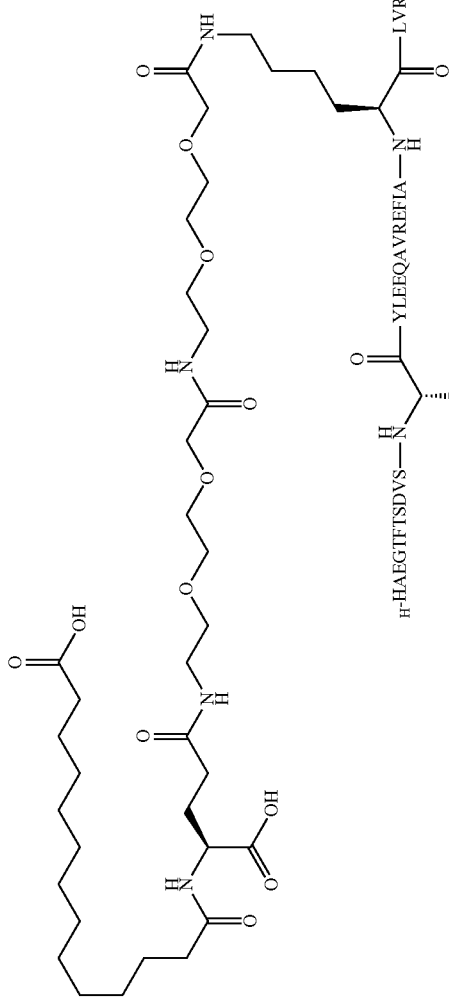
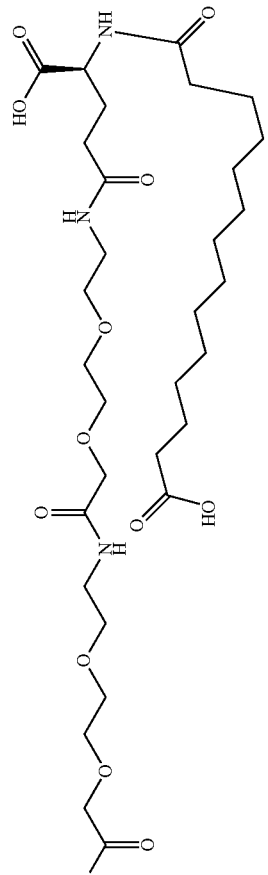

Preparation Method: SPPS_L; SC_L
LCMS: Method: LCMS_4: Rt=1.92 min m/z: 4815; m/3: 1605; m/4: 1204; m/5: 963
UPLC Method: B2_1: Rt=12.32 min
UPLC Method: 05_B5_1: Rt=5.28 min Example 44

$N^{\epsilon 18}$-[2-[2-[2-[[2-[2-[2-[[(4S)-4-carboxy-4-(13-carboxytridecanoylamino)butanoyl]amino]ethoxy]ethoxy]acetyl]amino]ethoxy]ethoxy]acetyl], $N^{\epsilon 31}$-[2-[2-[2-[[2-[2-[2-[[(4S)-4-carboxy-4-(13-carboxytridecanoylamino)butanoyl]amino]ethoxy]ethoxy]acetyl]amino]ethoxy]ethoxy]acetyl]-[Lys$^{18}$,Glu$^{22}$,Val$^{25}$,Arg$^{26}$,Lys$^{31}$,Gln$^{34}$]-GLP-1-(7-37)-peptide (SEQ ID NO: 11)

Chem. 63

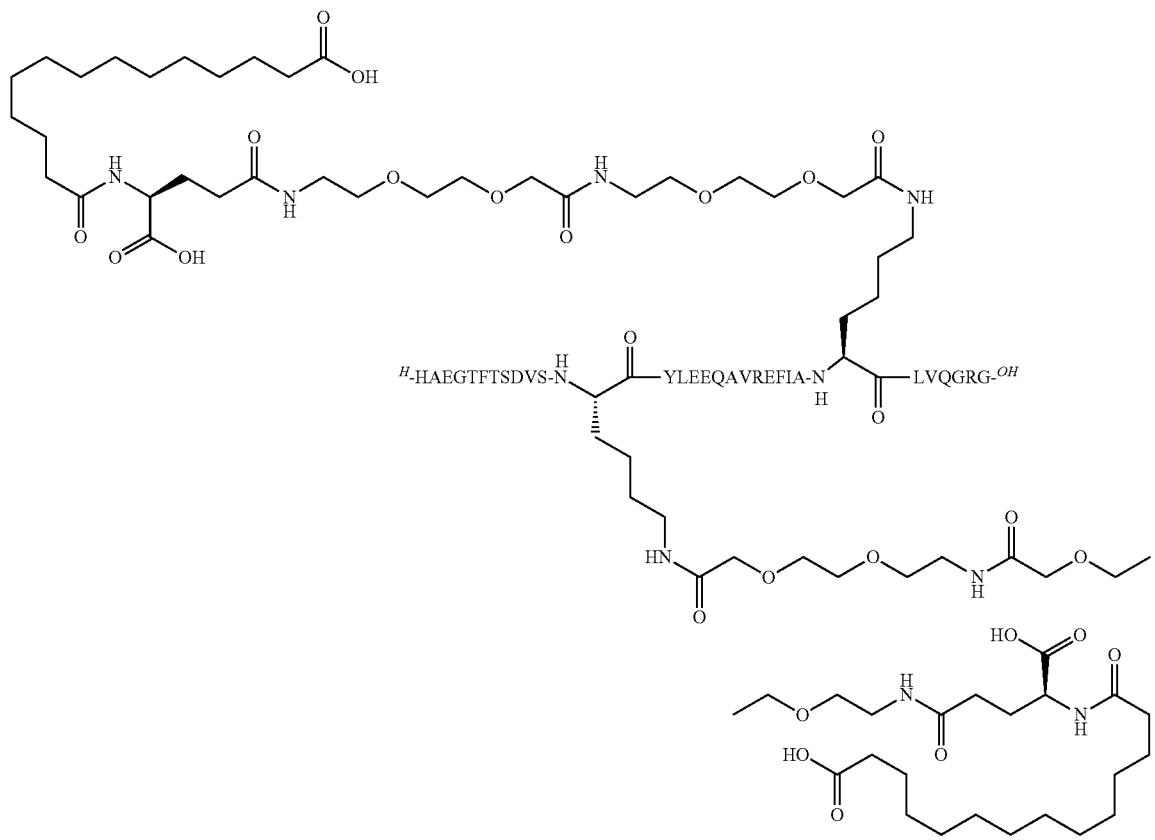

Preparation Method: SPPS_L; SC_L
LCMS: Method: LCMS_4: Rt=2.03 min; m/3: 1595; m/4: 1197; m/6: 957
UPLC Method: B2_1: Rt=12.99 min
UPLC Method: 05_B5_1: Rt=5.48 min Example 45

$N^{\epsilon 18}$-[2-[2-[2-[[2-[2-[2-[[(4S)-4-carboxy-4-(13-carboxytridecanoylamino)butanoyl]amino]ethoxy]ethoxy]acetyl]amino]ethoxy]ethoxy]acetyl]$N^{\epsilon 31}$-[2-[2-[2-[[2-[2-[2-[[(4S)-4-carboxy-4-(13-carboxytridecanoylamino)butanoyl]amino]ethoxy]ethoxy]acetyl]amino]ethoxy]ethoxy]acetyl]-[Lys$^{18}$,Glu$^{22}$,Val$^{25}$,Arg$^{26}$,Lys$^{31}$,Gly$^{34}$]-GLP-1-(7-37)-peptide (SEQ ID NO: 18)

Chem. 64

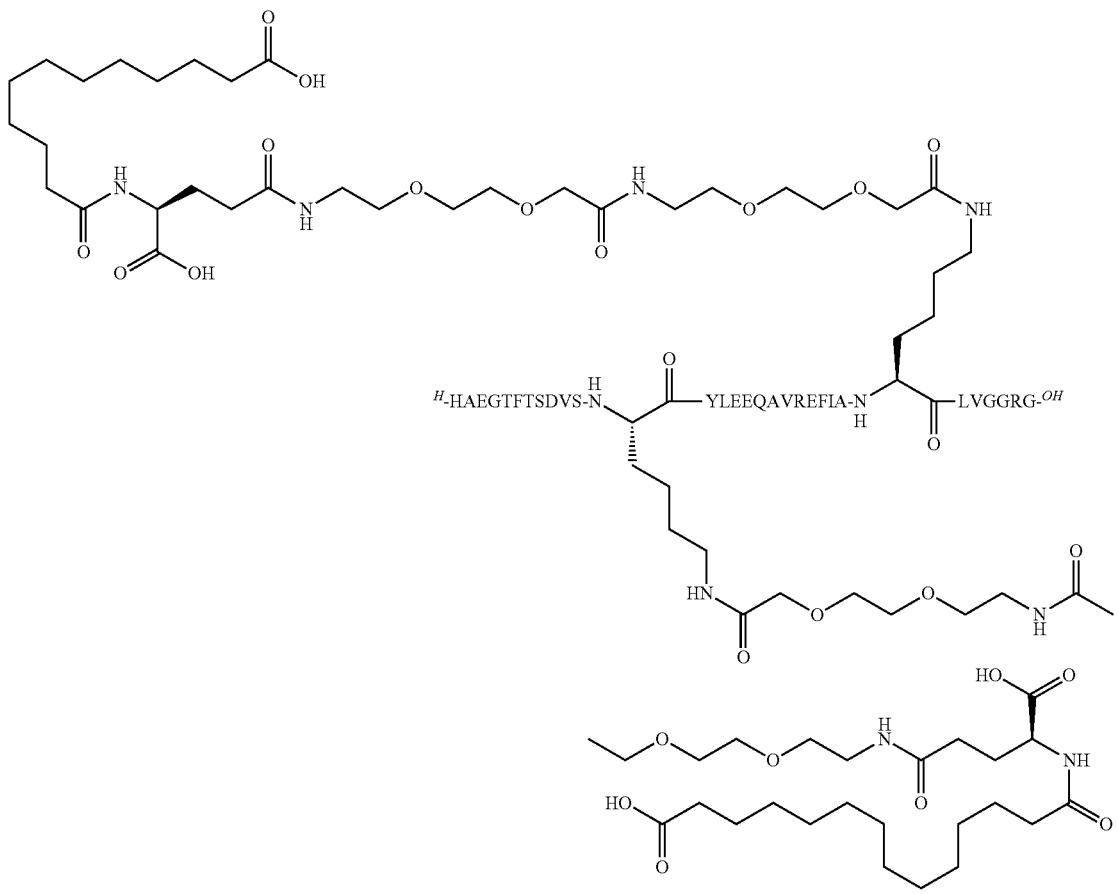

Preparation Method: SPPS_L; SC_L
LCMS: Method: LCMS_4: Rt=2.03 min; m/3=1572; m/4=1179; m/5=943;
UPLC Method: B2_1: Rt=13.19 min
UPLC Method: 05_B5_1: Rt=5.00 min Example 46

$N^{\epsilon 18}$-[2-[2-[2-[[2-[2-[2-[[(4S)-4-carboxy-4-(13-carboxytridecanoylamino)butanoyl]amino]ethoxy]ethoxy]acetyl]amino]ethoxy]ethoxy]acetyl]$N^{\epsilon 27}$-[2-[2-[2-[[2-[2-[2-[[(4S)-4-carboxy-4-(13-carboxytridecanoylamino)butanoyl]amino]ethoxy]ethoxy]acetyl]amino]ethoxy]ethoxy]acetyl]-[Lys$^{18}$,Glu$^{22}$,Val$^{25}$,Arg$^{26}$,Lys$^{27}$,Arg$^{34}$]-GLP-1-(7-37)-peptide (SEQ ID NO: 35)

Chem. 65
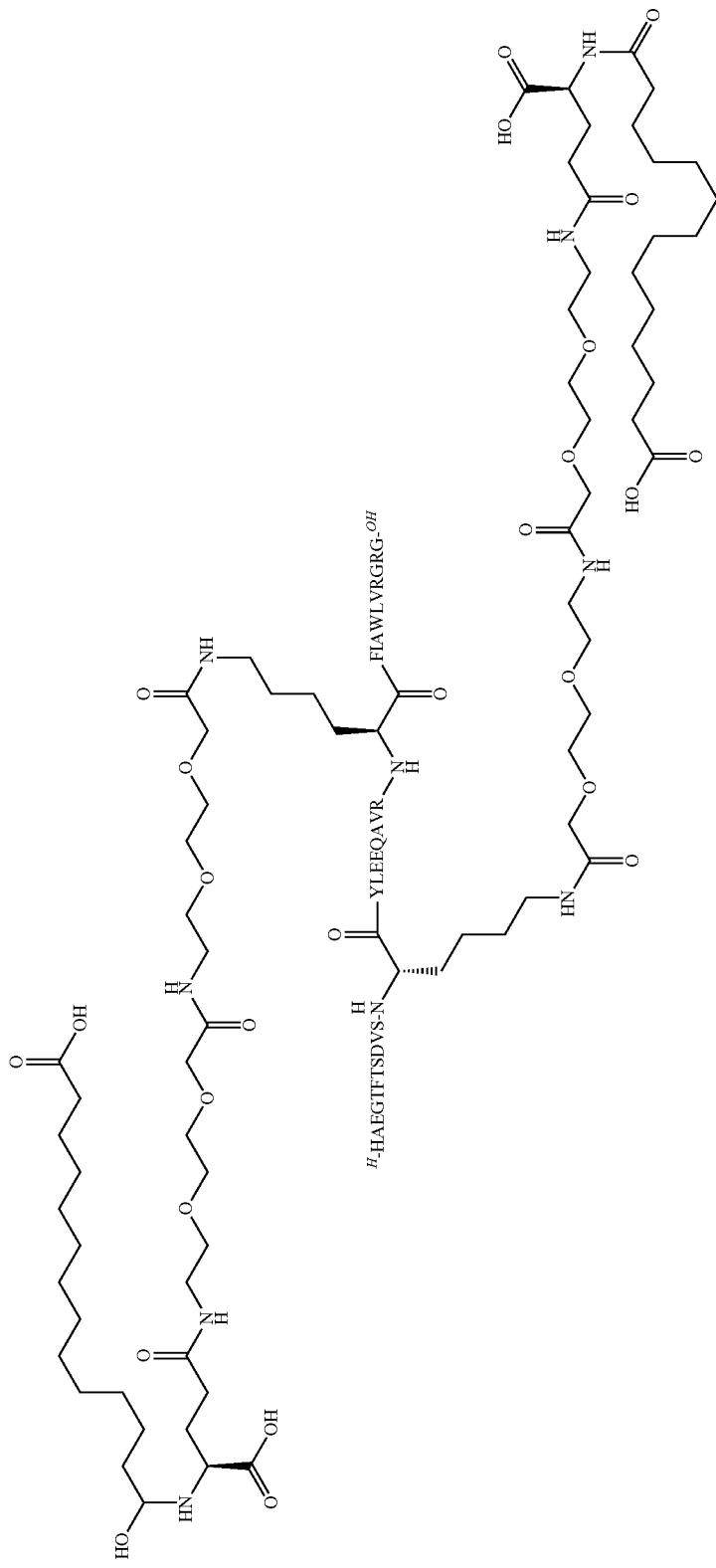

Preparation Method: SPPS_L) SC_L

LCMS: Method: LCMS_4: Rt=2.05 min; m/3: 1624; m/4: 1218; m/5: 975;

UPLC Method: B2_1: Rt=13.08 min

UPLC Method: 05_B51: Rt=6.32 min

Example 47

$N^{\epsilon 18}$-[2-[2-[2-[[2-[2-[2-[[(4S)-4-carboxy-4-(13-carboxytridecanoylamino)butanoyl]amino]ethoxy]ethoxy]acetyl]amino]ethoxy]ethoxy]acetyl]-[Lys$^{18}$,Glu$^{22}$,Val$^{25}$,Arg$^{26}$,Lys$^{27}$,His$^{31}$,Arg$^{34}$]-GLP-1-(7-37)-peptide (SEQ ID NO: 36)

Chem. 66
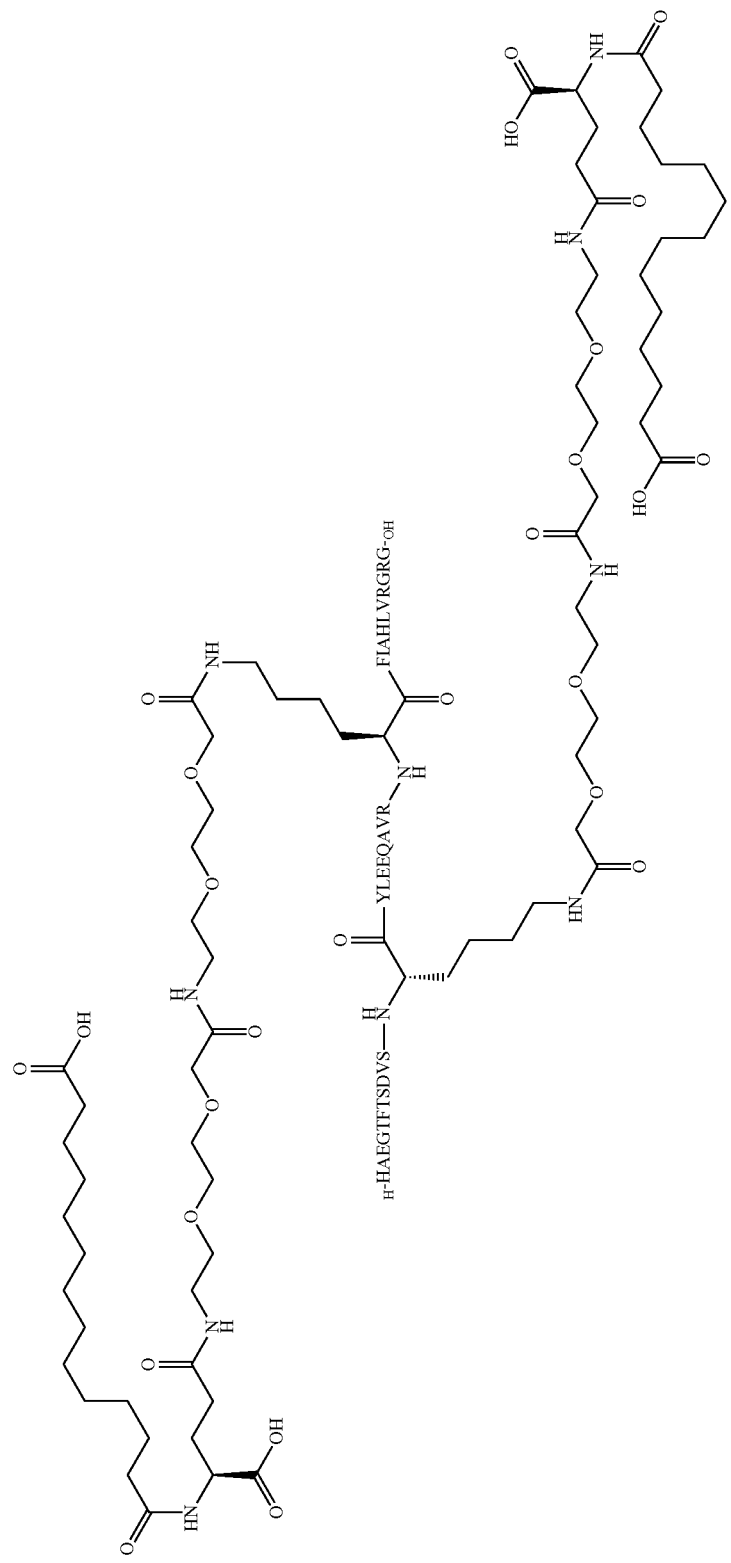

Preparation Method: SPPS_L; SC_L
LCMS: Method: LCMS_4: Rt=1.87 min; m/3: 1608; m/4: 1206; m/5: 965; m/6: 804
UPLC Method: B2_1: Rt=11.79 min
UPLC Method: 05_B9_1: Rt=7.23 min Example 48

$N^{\epsilon 18}$-[2-[2-[2-[[2-[2-[2-[[(4S)-4-carboxy-4-(13-carboxytridecanoylamino)butanoyl]amino]ethoxy]ethoxy]acetyl]amino]ethoxy]ethoxy]acetyl], $N^{\epsilon 27}$-[2-[2-[2-[[2-[2-[2-[[(4S)-4-carboxy-4-(13-carboxytridecanoylamino)butanoyl]amino]ethoxy]ethoxy]acetyl]amino]ethoxy]ethoxy]acetyl]-[Lys$^{18}$,Glu$^{22}$,Val$^{25}$,Arg$^{26}$,Lys$^{27}$,Gln$^{34}$]-GLP-1-(7-37)-peptide (SEQ ID NO: 34)

Chem. 67
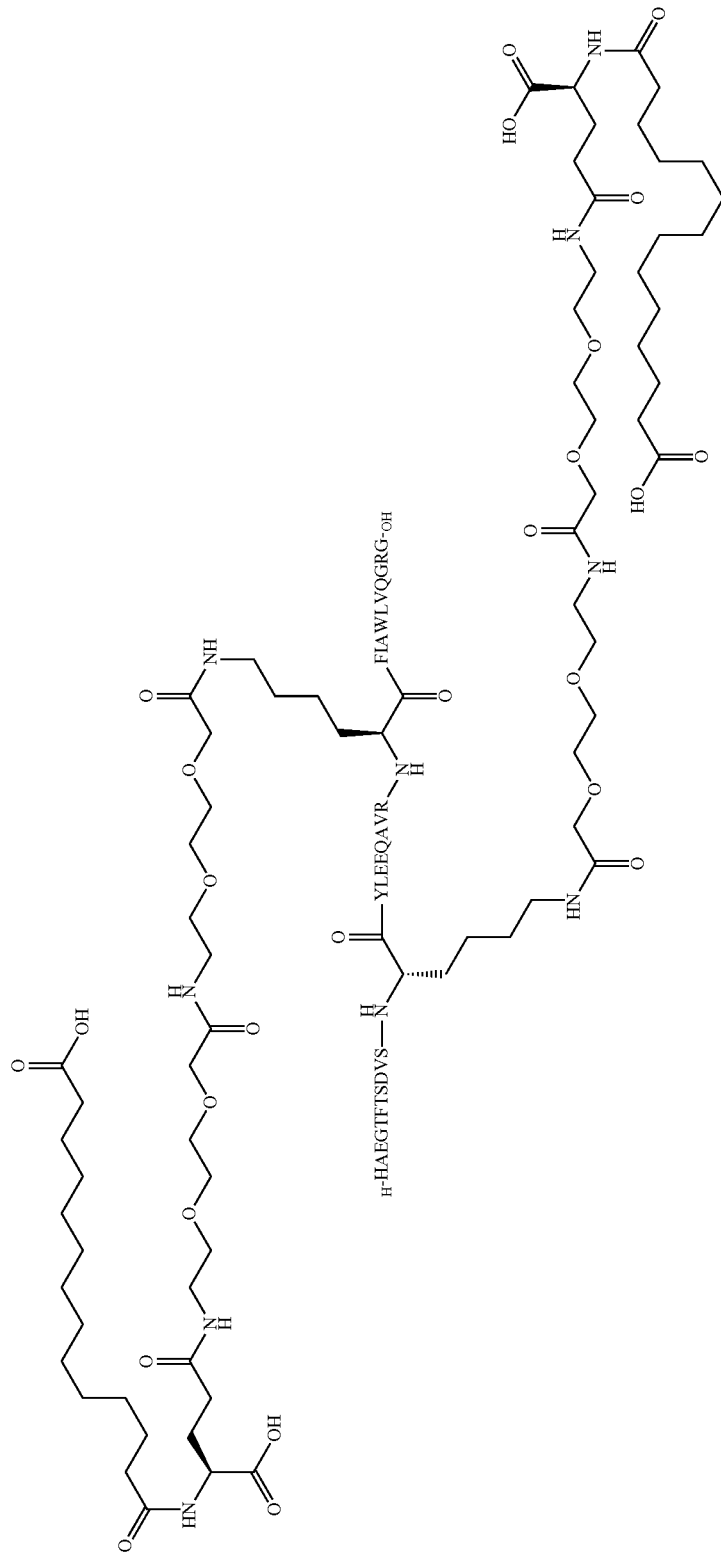

Preparation Method: SPPS_L; SC_L
LCMS: Method: LCMS_4: Rt=2.13 min; m/3: 1615; m/4: 1211; m/5: 969
UPLC Method: 05_B5_1: Rt=6.59 min
UPLC Method: B2_1: Rt=13.55 min Example 49

$N^{\epsilon 18}$-[(4S)-4-carboxy-4-[[2-[2-[2-[[2-[2-[2-[10-(4-carboxyphenoxy)decanoylamino]ethoxy]ethoxy]acetyl]amino]ethoxy]ethoxy]acetyl]amino]butanoyl], $N^{\epsilon 27}$-[(4S)-4-carboxy-4-[[2-[2-[2-[[2-[2-[2-[10-(4-carboxyphenoxy)decanoylamino]ethoxy]ethoxy]acetyl]amino]ethoxy]ethoxy]acetyl]amino]butanoyl]-[Lys$^{18}$,Glu$^{22}$,Arg$^{26}$,Lys$^{27}$,His$^{31}$,Gly$^{34}$]-GLP-1-(7-34)-peptide (SEQ ID NO: 27)

Chem. 68
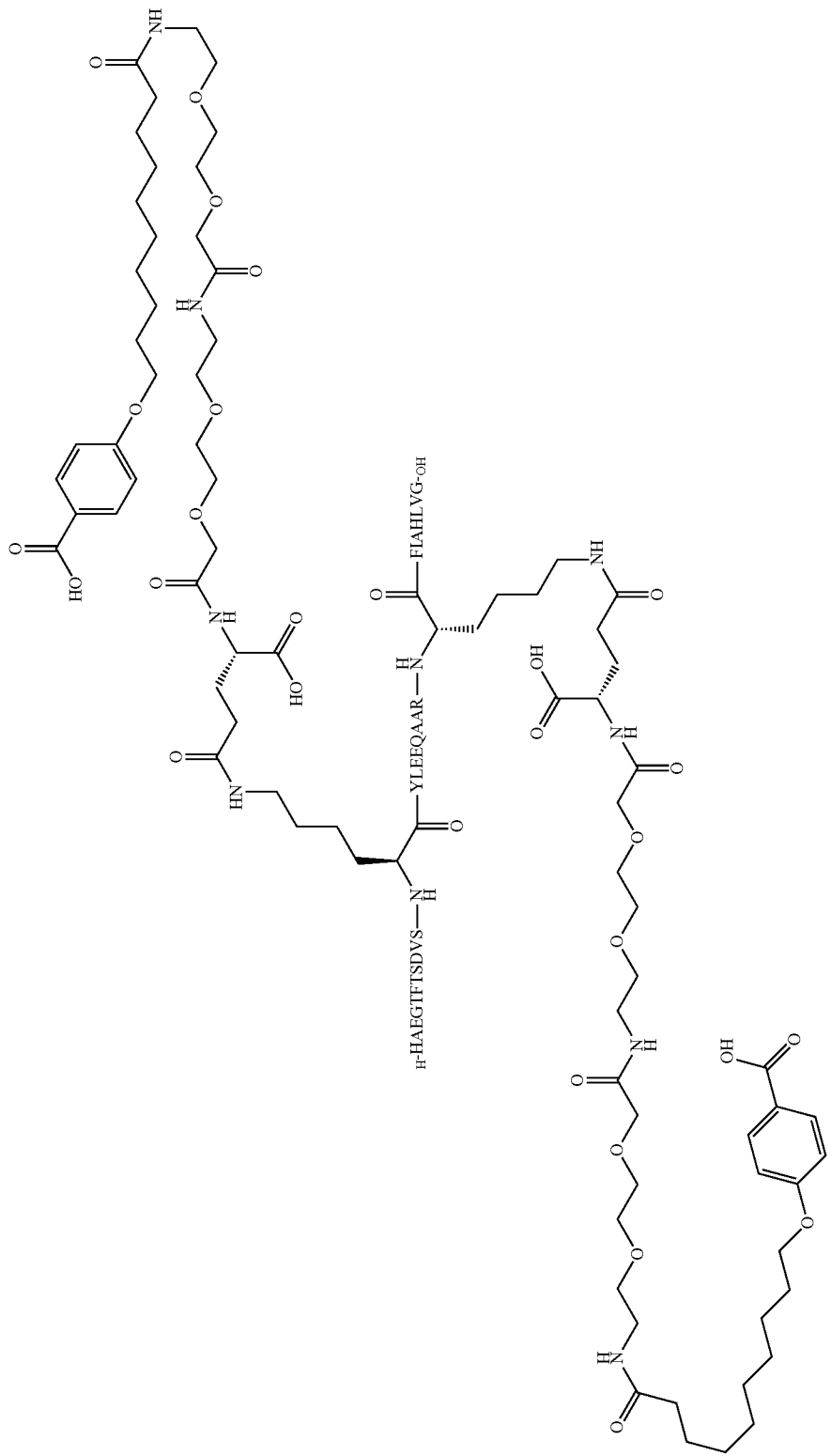

Preparation Method: SPPS_L; SC_L; CP_M1

LCMS: Method: LCMS_4: Rt=2.12 min m/z: 4525.1; M/3: 1509; M/4: 1132

UPLC: Method: 05_B5_1: Rt=5.54 min
UPLC: Method: B4_1: Rt=8.50 min
UPLC: Method: 04_A7_1: Rt=7.02 min
UPLC: Method: 04_A3_1: Rt=7.83 min Example 50

$N^{\epsilon 18}$-[2-[2-[2-[[2-[2-[2-[[(4S)-4-carboxy-4-(13-carboxytridecanoylamino)butanoyl]amino]ethoxy]ethoxy]acetyl]amino]ethoxy]ethoxy]acetyl]-$N^{\epsilon 30}$-[2-[2-[2-[[2-[2-[2-[[(4S)-4-carboxy-4-(13-carboxytridecanoylamino)butanoyl]amino]ethoxy]ethoxy]acetyl]amino]ethoxy]ethoxy]acetyl]-[Lys18,Glu22,Val25,Arg26,Lys30,Gly34]-GLP-1-(7-34)-peptide (SEQ ID NO: 37)

Chem. 69
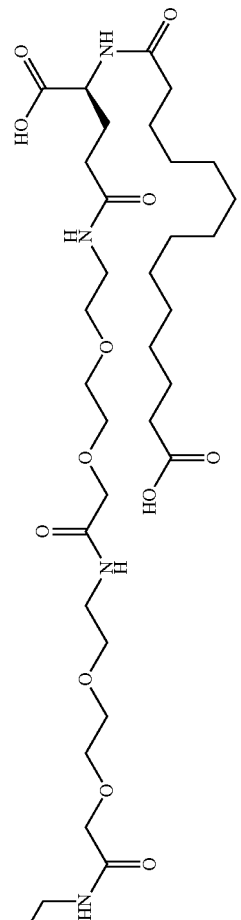
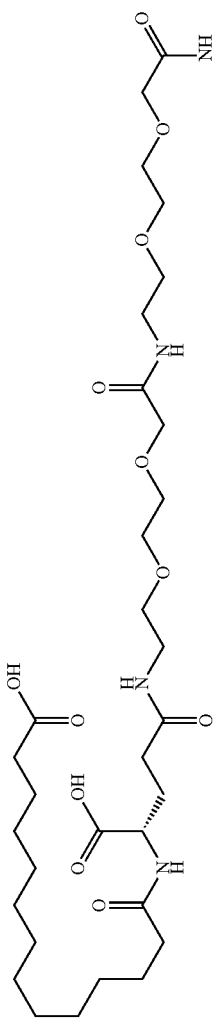

Preparation Method: SPPS_L: SC_L; CP_M1

The theoretical molecular mass of 4560.2 Da was confirmed by MALDI_MS: m/z: 4559

UPLC Method: B4_1: Rt=9.89 min

Example 51

$N^{\epsilon 18}$-[2-[2-[2-[[2-[2-[2-[[(4S)-4-carboxy-4-(13-carboxytridecanoylamino)butanoyl]amino]ethoxy]ethoxy]acetyl]amino]ethoxy]ethoxy]acetyl], $N^{\epsilon 30}$-[2-[2-[2-[[2-[2-[2-[[(4S)-4-carboxy-4-(13-carboxytridecanoylamino)butanoyl]amino]ethoxy]ethoxy]acetyl]amino]ethoxy]ethoxy]acetyl]-[Aib$^8$,Lys$^{18}$,Glu$^{22}$,Arg$^{26}$,Lys$^{30}$,Arg$^{34}$]-GLP-1-(7-37)-peptide (SEQ ID NO: 38)

Chem. 70
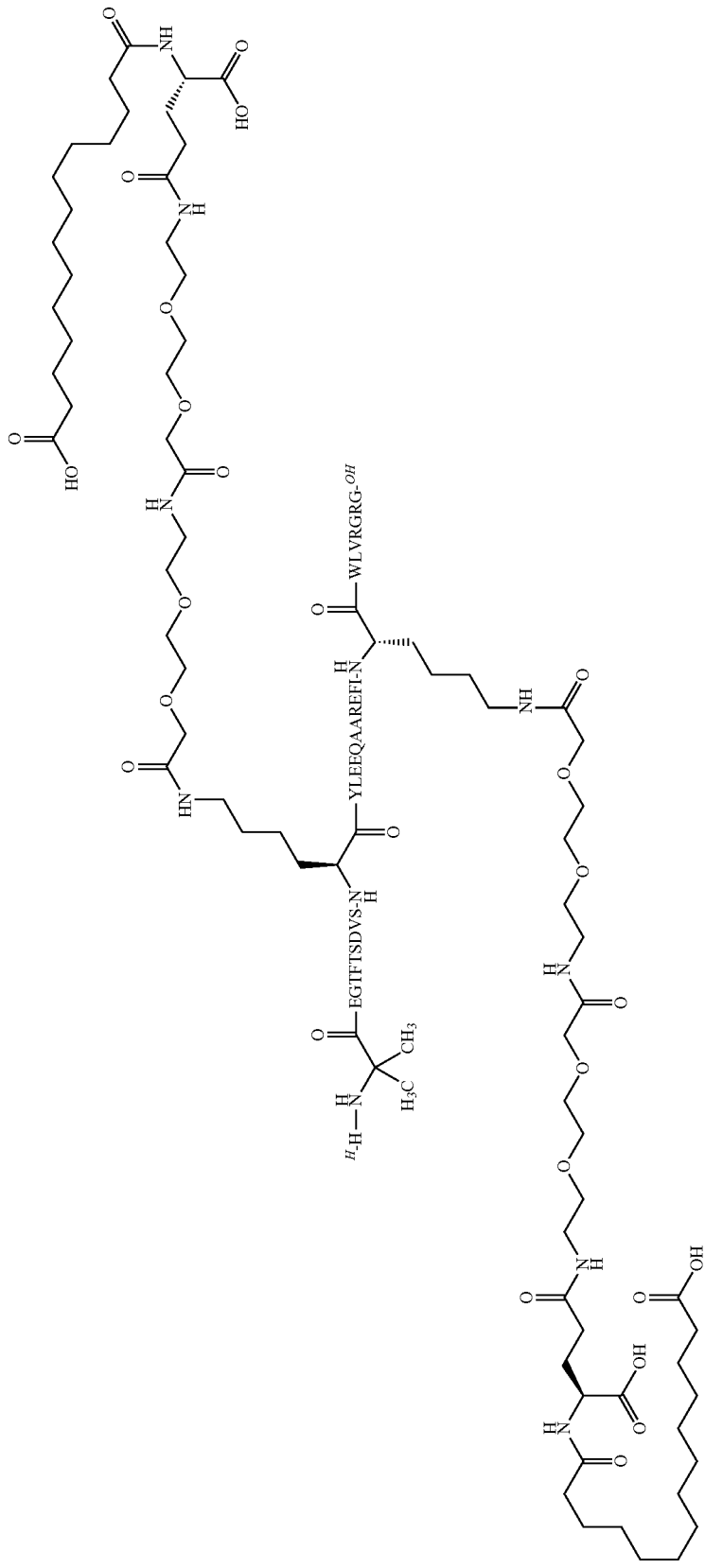

Preparation Method: SPPS_L: SC_L; CP_M1
LCMS: Method: LCMS_4: Rt=2.05 min m/z: 4916.5; M/3: 1639; M/4: 1229; M/5: 983
UPLC Method: B4_1: Rt=8.38 min Example 52

$N^{\epsilon 18}$-[2-[2-[2-[[2-[2-[2-[[(4S)-4-carboxy-4-(13-carboxytridecanoylamino)butanoyl]amino]ethoxy]ethoxy]acetyl]amino]ethoxy]ethoxy]acetyl], $N^{\epsilon 30}$-[2-[2-[2-[[2-[2-[2-[[(4S)-4-carboxy-4-(13-carboxytridecanoylamino)butanoyl]amino]ethoxy]ethoxy]acetyl]amino]ethoxy]ethoxy]acetyl]-[Lys$^{18}$,Glu$^{22}$,Val$^{25}$,Arg$^{26}$,Lys$^{30}$,His$^{31}$,Gly$^{34}$]-GLP-1-(7-34)-peptide (SEQ ID NO: 39)

Chem. 71

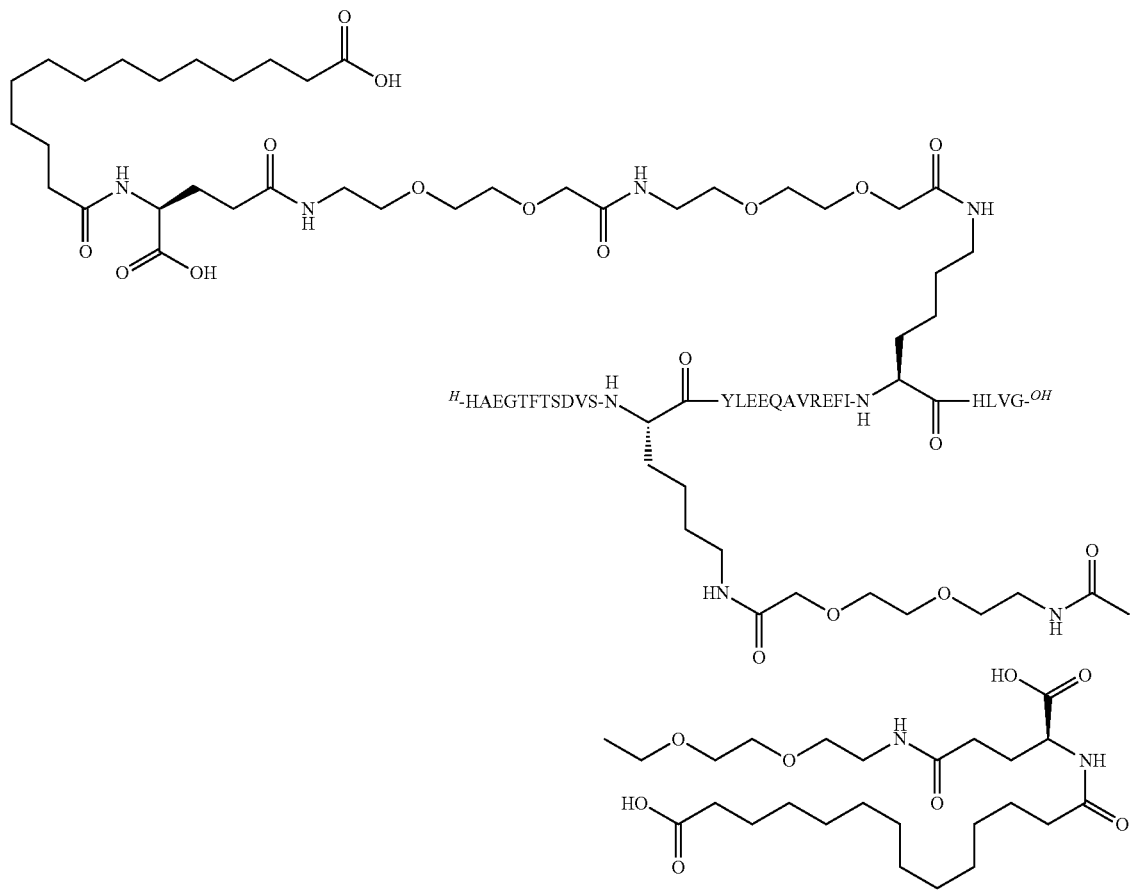

Preparation Method: SPPS_L: SC_L: CP_M1
LCMS: Method: LCMS_4: Rt=2.27 min, m/z: 4510.9
UPLC Method: B2_1: Rt=13.51 min
UPLC Method: 05_B9_1: Rt=7.42 min Example 53

$N^{\epsilon 18}$-[2-[2-[2-[[2-[2-[2-[[(4S)-4-carboxy-4-(13-carboxytridecanoylamino)butanoyl]amino]ethoxy]ethoxy]acetyl]amino]ethoxy]ethoxy]acetyl], $N^{\epsilon 30}$-[2-[2-[2-[[2-[2-[2-[[(4S)-4-carboxy-4-(13-carboxytridecanoylamino)butanoyl]amino]ethoxy]ethoxy]acetyl]amino]ethoxy]ethoxy]acetyl]-[Lys$^{18}$,Glu$^{22}$,Val$^{25}$,Arg$^{26}$,Leu$^{27}$,Lys$^{30}$,Gly$^{34}$]-GLP-1-(7-34)-peptide (SEQ ID NO: 40)

Chem. 72

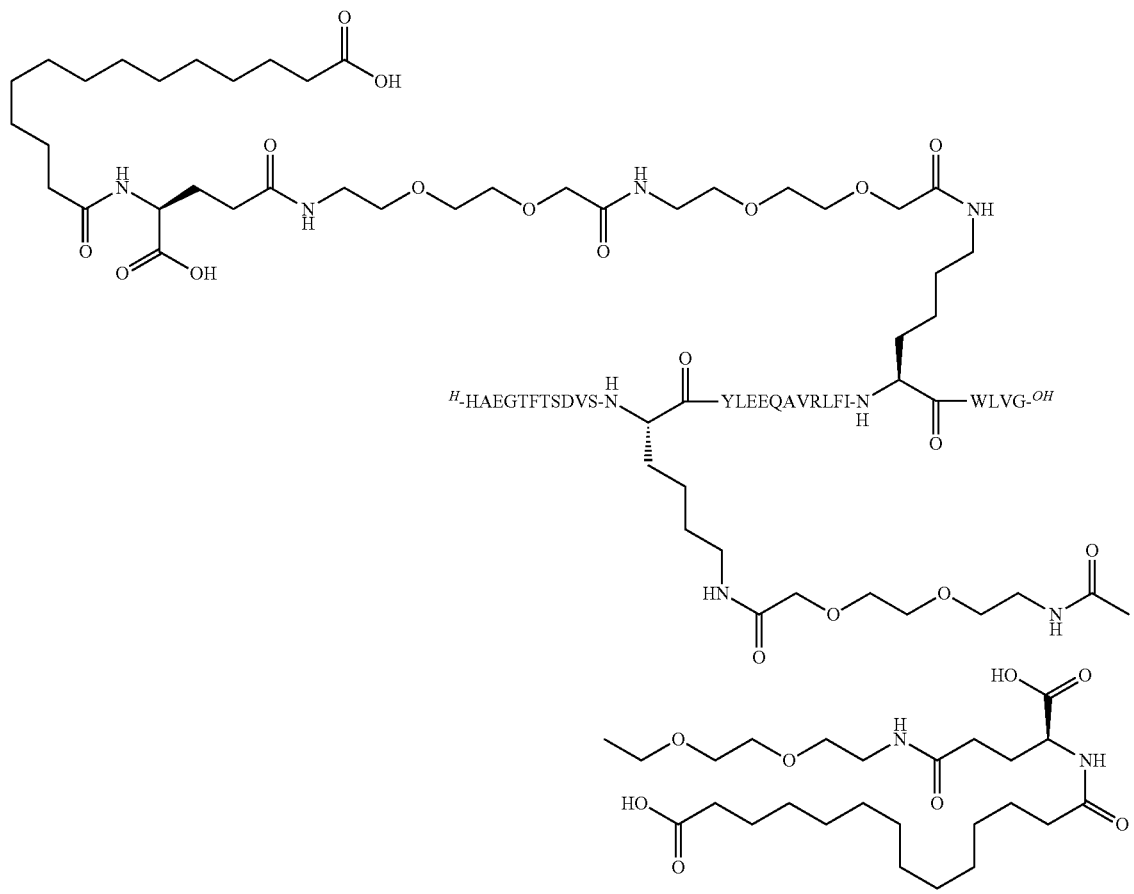

Preparation Method: SPPS_L: SC_L: CP_M1
LCMS: Method: LCMS_4: Rt=2.72 min, m/z: 4544.0
UPLC Method: B4_1: Rt=10.34 min
UPLC Method: 05_B9_1: Rt=10.24 min Example 54

$N^{\epsilon 18}$-[2-[2-[2-[[2-[2-[2-[[(4S)-4-carboxy-4-(13-carboxytridecanoylamino)butanoyl]amino]ethoxy]ethoxy]acetyl]amino]ethoxy]ethoxy]acetyl]-$N^{\epsilon 26}$-[2-[2-[2-[[2-[2-[2-[[(4S)-4-carboxy-4-(13-carboxytridecanoylamino)butanoyl]amino]ethoxy]ethoxy]acetyl]amino]ethoxy]ethoxy]acetyl]-[Lys$^{18}$,Glu$^{22}$,Gln$^{34}$]-GLP-1-(7-37)-peptide (SEQ ID NO: 32)

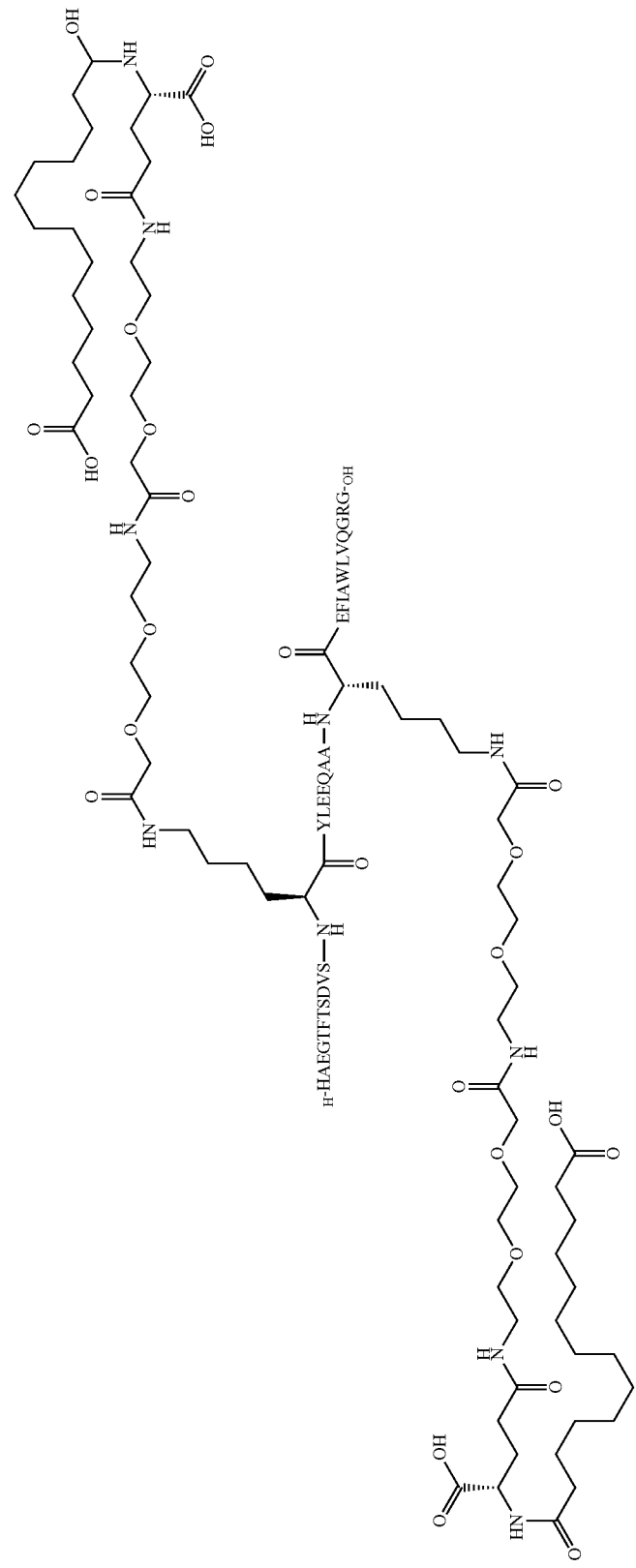
Chem. 73

Preparation Method: SPPS_L: SC_L: CP_M1
LCMS: Method: LCMS_4: Rt=2.29 min, m/z: 4788.1
UPLC Method: B4_1: Rt=8.98 min
UPLC Method: 05_B9_1: Rt=7.94 min

Example 55

$N^{\epsilon 18}$-[(4S)-4-carboxy-4-[[2-[2-[2-[[2-[2-[2-(13-carboxytridecanoylamino)ethoxy]ethoxy]acetyl]amino]ethoxy]ethoxy]acetyl]amino]butanoyl], $N^{\epsilon 31}$-[(4S)-4-carboxy-4-[[2-[2-[2-[[2-[2-[2-(13-carboxytridecanoylamino)ethoxy]ethoxy]acetyl]amino]ethoxy]ethoxy]acetyl]amino]butanoyl]-[Lys$^{18}$,Glu$^{22}$,Val$^{25}$,Arg$^{26}$,Lys$^{31}$,Arg$^{34}$]-GLP-1-(7-37)-peptide (SEQ ID NO: 10)

Chem. 74
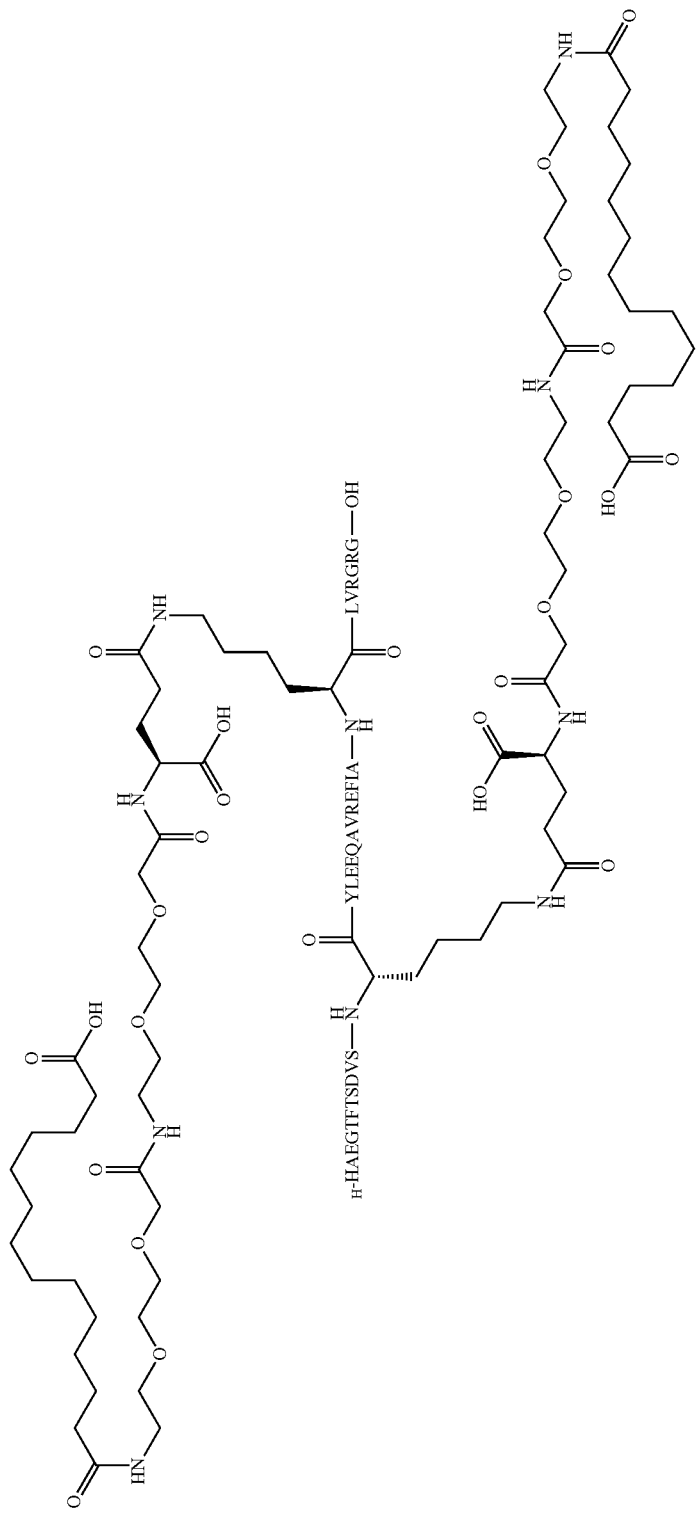

Preparation Method: SPPS_L; SC_L

LCMS: Method: LCMS_4: Rt=2.01 min m/z: m/3: 1605; m/4: 1204; m/5: 963

UPLC Method: B2_1: Rt=12.82 min
UPLC Method: 05_B7_1: Rt=9.18 min
UPLC Method: 05_B9_1: Rt=7.16 min Example 56

N$^{\epsilon 18}$-[(4S)-4-carboxy-4-[[2-[2-[2-[[2-[2-[2-(13-carboxytridecanoylamino)ethoxy]ethoxy]acetyl]amino]ethoxy]ethoxy]acetyl]amino]butanoyl], N$^{\epsilon 31}$-[(4S)-4-carboxy-4-[[2-[2-[2-[[2-[2-[2-(13-carboxytridecanoylamino)ethoxy]ethoxy]acetyl]amino]ethoxy]ethoxy]acetyl]amino]butanoyl]-[Lys$^{18}$,Glu$^{22}$,Val$^{25}$,Arg$^{26}$,Lys$^{31}$,Gln$^{34}$]-GLP-1-(7-37)-peptide (SEQ ID NO: 11)

Chem. 75

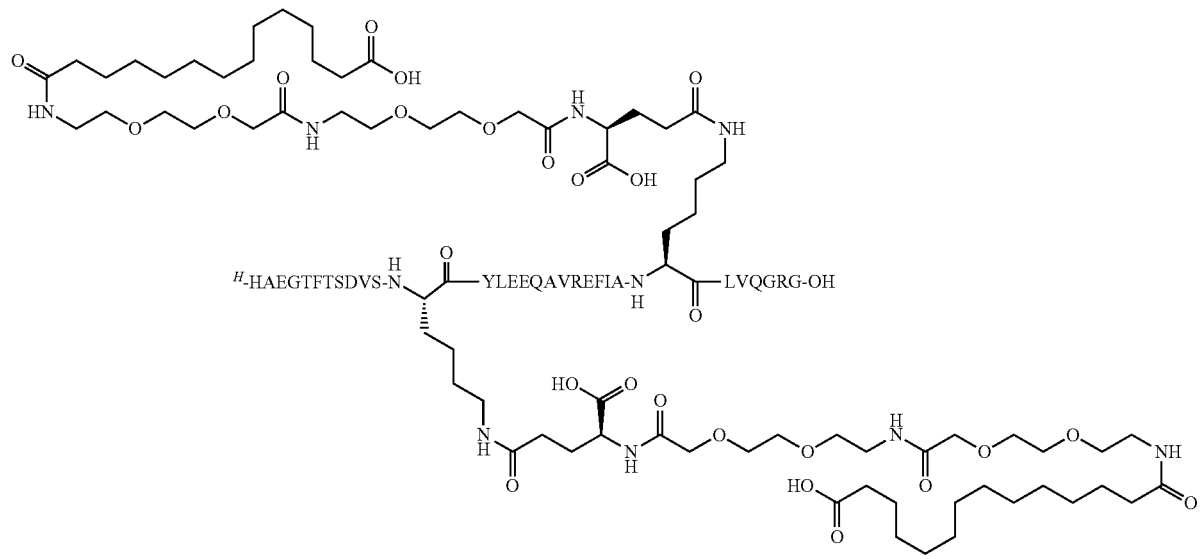

Preparation Method: SPPS_L; SC_L

LCMS: Method: LCMS_4: Rt=1.86 min m/z: 4785.6; m/3: 1596; m/4: 1197; m/5: 958

UPLC Method: B2_1: Rt=13.22 min
UPLC Method: 04_A7_1: Rt=7.05 min

Example 57

N$^{\epsilon 18}$-[2-[2-[2-[[2-[2-[2-[[(4S)-4-carboxy-4-(13-carboxytridecanoylamino)butanoyl]amino]ethoxy]ethoxy]acetyl]amino]ethoxy]ethoxy]acetyl], N$^{\epsilon 27}$-[2-[2-[2-[[2-[2-[2-[[(4S)-4-carboxy-4-(13-carboxytridecanoylamino)butanoyl]amino]ethoxy]ethoxy]acetyl]amino]ethoxy]acetyl]-[Lys$^{18}$,Glu$^{22}$,Glu$^{23}$,Val$^{25}$,Arg$^{26}$,Lys$^{27}$,Arg$^{34}$]-GLP-1-(7-37)-peptide (SEQ ID NO: 41)

Chem. 76

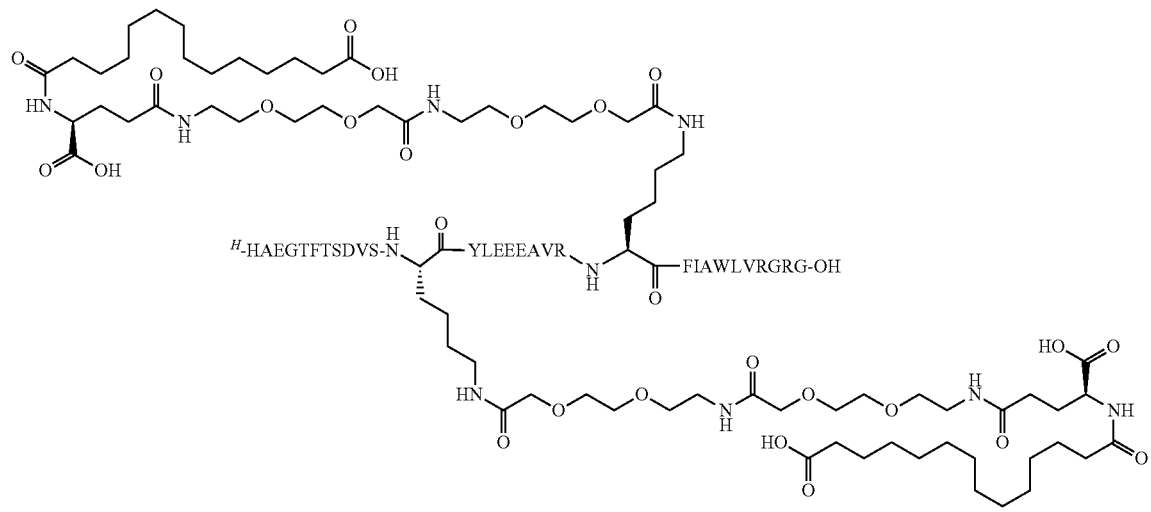

Preparation Method: SPPS_L; SC_L
LCMS: Method: LCMS_4: Rt=2.06 min m/3: 1624; m/4: 1218; m/5: 974
UPLC Method: B2_1: Rt=13.12 min Example 58

$N^{\epsilon18}$-[2-[2-[2-[[2-[2-[2-[[(4S)-4-carboxy-4-(13-carboxytridecanoylamino)butanoyl]amino]ethoxy]ethoxy]acetyl]amino]ethoxy]ethoxy]acetyl], $N^{\epsilon}27$-[2-[2-[2-[[2-[2-[2-[[(4S)-4-carboxy-4-(13-carboxytridecanoylamino)butanoyl]amino]ethoxy]ethoxy]acetyl]amino]ethoxy]ethoxy]acetyl]-[Lys$^{18}$,Glu$^{22}$,Glu$^{23}$,Val$^{25}$,Arg$^{26}$,Lys$^{27}$,Gln$^{34}$]-GLP-1-(7-37)-peptide (SEQ ID NO: 42)

Chem. 77

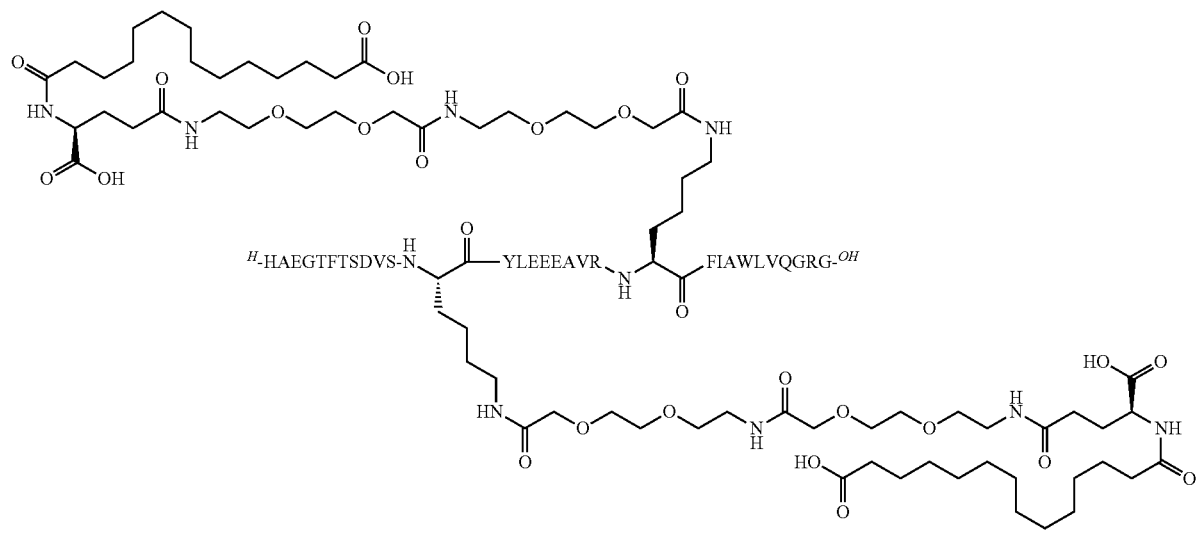

Preparation Method: SPPS_L; SC_L

LCMS: Method: LCMS_4: Rt=1.86 min m/3: 1614; m/4: 1211; m/5: 969

UPLC Method: B2_1: Rt=13.60 min

Example 59

$N^{\epsilon 18}$-[(4S)-4-carboxy-4-[[2-[2-[2-[[(4S)-4-carboxy-4-(13-carboxytridecanoylamino)butanoyl]amino]ethoxy]ethoxy]acetyl]amino]butanoyl], $N^{\epsilon 27}$-[(4S)-4-carboxy-4-[[2-[2-[2-[[(4S)-4-carboxy-4-(13-carboxytridecanoylamino)butanoyl]amino]ethoxy]ethoxy]acetyl]amino]butanoyl]-[Lys$^{18}$,Glu$^{22}$,Arg$^{26}$,Lys$^{27}$,His$^{31}$,Gly$^{34}$]-GLP-1-(7-34)-peptide (SEQ ID NO: 27)

Chem. 78

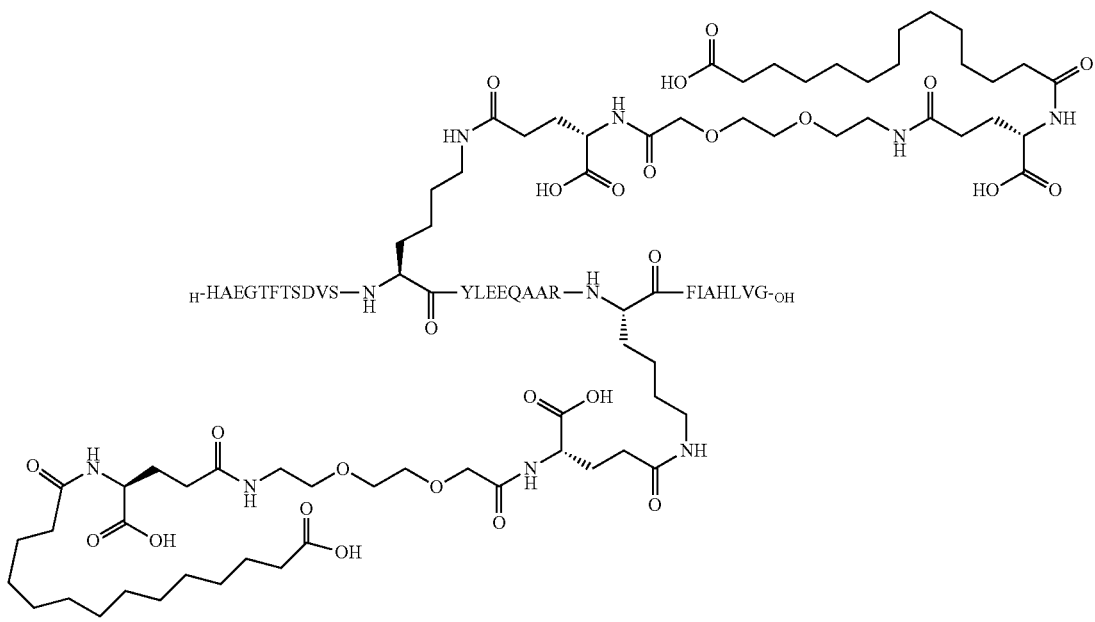

Preparation Method: SPPS_L; SC_L; CP_M1

LCMS: method LCMS_4: Rt=2.10 min m/z: 4393.0; M/3: 1465; M/4: 1099

UPLC: Method: B4_1: Rt=8.25 min

UPLC: Method: 05_B5_1: Rt=4.28 min

UPLC: Method: 04_A7_1: Rt=5.03 min

Example 60

$N^{\epsilon 18}$-[2-[2-[2-[[2-[2-[2-[[(4S)-4-carboxy-4-(13-carboxytridecanoylamino)butanoyl]amino]ethoxy]ethoxy]acetyl]amino]ethoxy]ethoxy]acetyl], $N^{\epsilon 27}$-[2-[2-[2-[[2-[2-[2-[[(4S)-4-carboxy-4-(13-carboxytridecanoylamino)butanoyl]amino]ethoxy]ethoxy]acetyl]amino]ethoxy]ethoxy]acetyl]-[Lys$^{18}$,Glu$^{22}$,His$^{26}$,Lys$^{27}$,Arg$^{34}$]-GLP-1-(7-37)-peptide (SEQ ID NO: 43)

Chem. 79

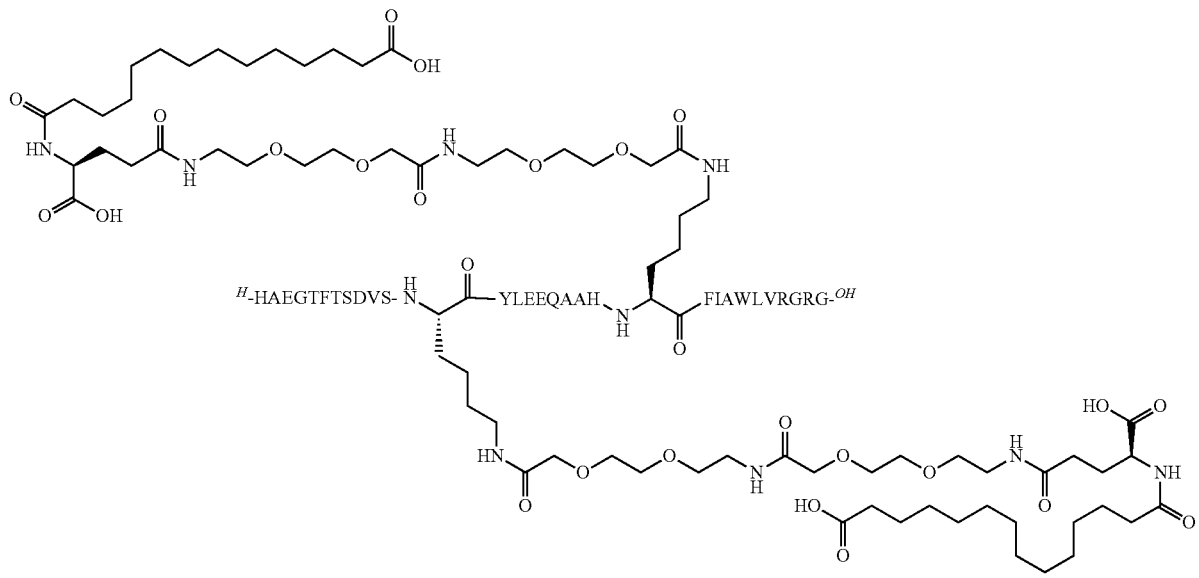

Preparation Method: SPPS_L; SC_L
LCMS: Method: LCMS_4: Rt=2.00 min; m/3: 1608; m/4: 1206; m/5: 965
UPLC method B2_1: Rt=12.62 min
UPLC method 05_B5_1: Rt=4.61 min Example 61

$N^{\epsilon 18}$-[2-[2-[2-[[2-[2-[2-[[(4S)-4-carboxy-4-(13-carboxytridecanoylamino)butanoyl]amino]ethoxy]ethoxy]acetyl]amino]ethoxy]ethoxy]acetyl], $N^{\epsilon 27}$-[2-[2-[2-[[2-[2-[2-[[(4S)-4-carboxy-4-(13-carboxytridecanoylamino)butanoyl]amino]ethoxy]ethoxy]acetyl]amino]ethoxy]ethoxy]acetyl]-[Lys$^{18}$,Glu$^{22}$,His$^{26}$,Lys$^{27}$,Gln$^{34}$]-GLP-1-(7-37)-peptide (SEQ ID NO: 30)

Chem. 80

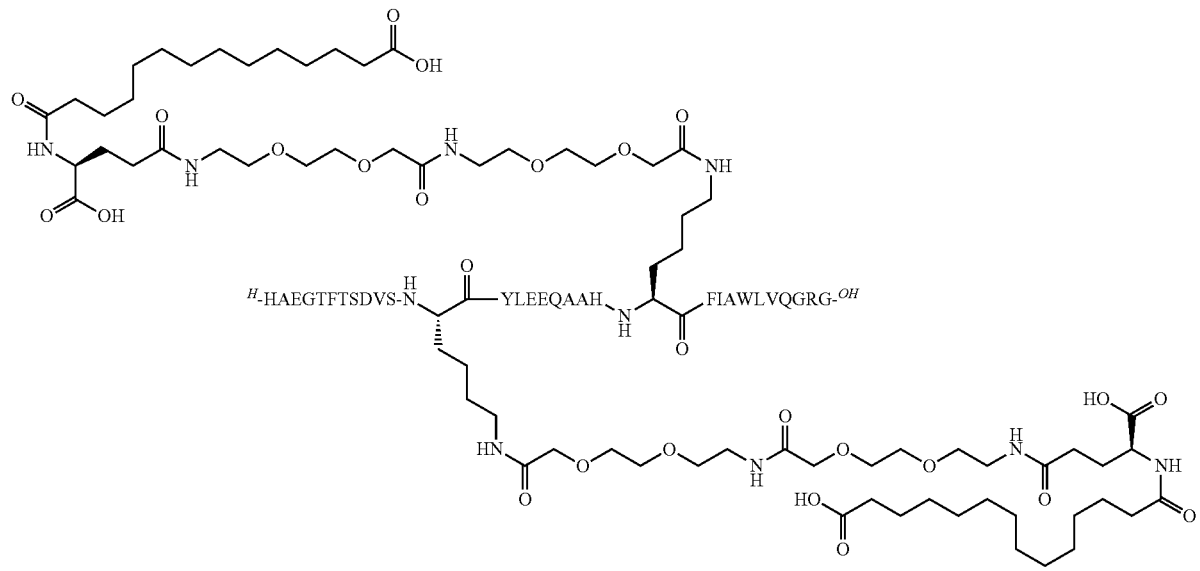

Preparation Method: SPPS_L; SC_L
LCMS: Method: LCMS_4: Rt=2.05 min; m/3: 1598; m/4: 1199; m/5: 960
UPLC method B2_1: Rt=12.98 min Example 62

$N^{\epsilon 18}$-[2-[2-[2-[[2-[2-[2-[[(4S)-4-carboxy-4-(13-carboxytridecanoylamino)butanoyl]amino]ethoxy]ethoxy]acetyl]amino]ethoxy]ethoxy]acetyl], $N^{\epsilon 27}$-[2-[2-[2-[[2-[2-[2-[[(4S)-4-carboxy-4-(13-carboxytridecanoylamino)butanoyl]amino]ethoxy]ethoxy]acetyl]amino]ethoxy]ethoxy]acetyl]-[Lys$^{18}$,Glu$^{22}$,His$^{26}$,Lys$^{27}$,His$^{31}$,Arg$^{34}$]-GLP-1-(7-37)-peptide (SEQ ID NO: 44)

Chem. 81

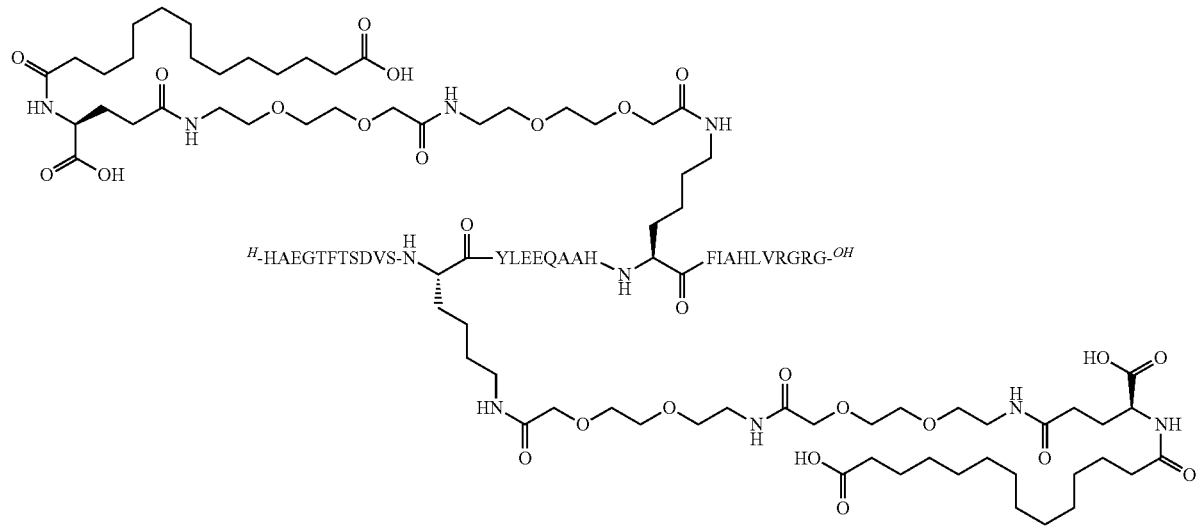

Preparation Method: SPPS_L; SC_L
LCMS: Method: LCMS_4: Rt=2.11 min m/3: 1592; m/4: 1194; m/5: 956
UPLC method B2_1: Rt=11.35 min Example 63

$N^{\epsilon 18}$-[2-[2-[2-[[2-[2-[2-[[(4S)-4-carboxy-4-(13-carboxytridecanoylamino)butanoyl]amino]ethoxy]ethoxy]acetyl]amino]ethoxy]ethoxy]acetyl], $N^{\epsilon 34}$-[2-[2-[2-[[2-[2-[2-[[(4S)-4-carboxy-4-(13-carboxytridecanoylamino)butanoyl]amino]ethoxy]ethoxy]acetyl]amino]ethoxy]ethoxy]acetyl]-[Aib$^{8}$,Lys$^{18}$,Glu$^{22}$,Val$^{25}$,Arg$^{26}$,Leu$^{27}$]-GLP-1-(7-34)-peptide (SEQ ID NO: 45)

Chem. 82

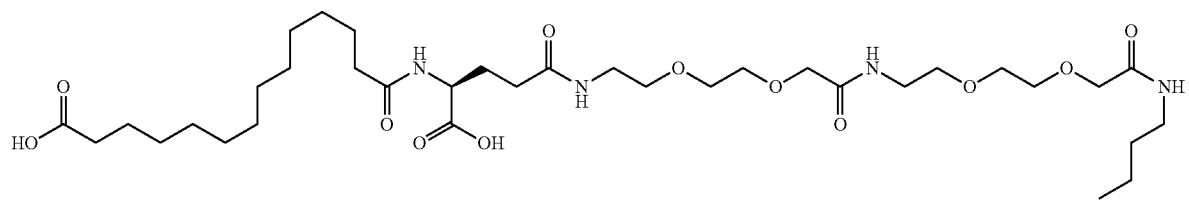

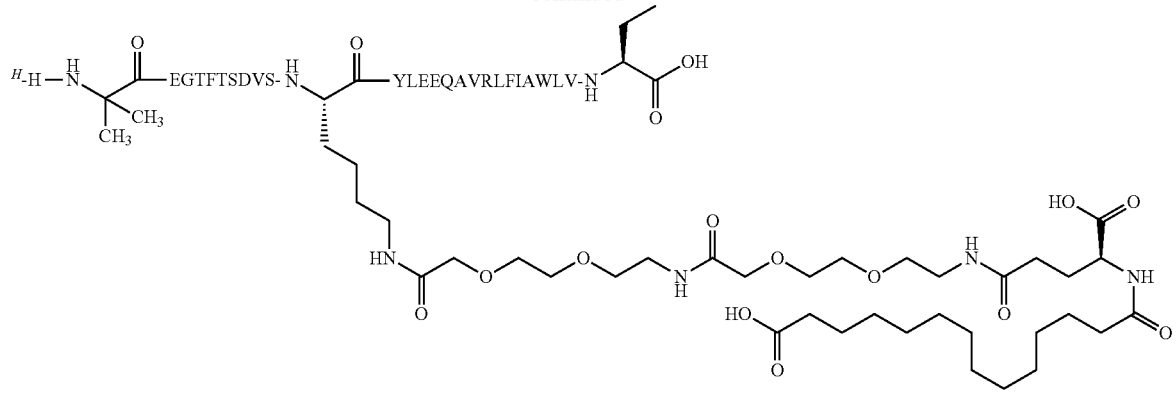

Preparation Method: SPPS_L: SC_L: CP_M1
LCMS: Method: LCMS_4: Rt=2.67 min, m/z: 4572.0
UPLC Method: B4$_{13}$ 1: Rt=10.23 min Example 64

N$^{\epsilon 18}$-[2-[2-[2-[[2-[2-[2-[[(4S)-4-carboxy-4-[9-(4-carboxy-phenoxy)nonanoylamino]butanoyl]amino]ethoxy]ethoxy]acetyl]amino]ethoxy]ethoxy]acetyl], N$^{\epsilon 27}$-[2-[2-[2-[[2-[2-[2-[[(4S)-4-carboxy-4-[9-(4-carboxyphenoxy)nonanoylamino]butanoyl]amino]ethoxy]ethoxy]acetyl]amino]ethoxy]ethoxy]acetyl]-[Lys$^{18}$,Glu$^{22}$,Arg$^{26}$,Lys$^{27}$,His$^{31}$,Gly$^{34}$]-GLP-1-(7-34)-peptide (SEQ ID NO: 27)

Chem. 83

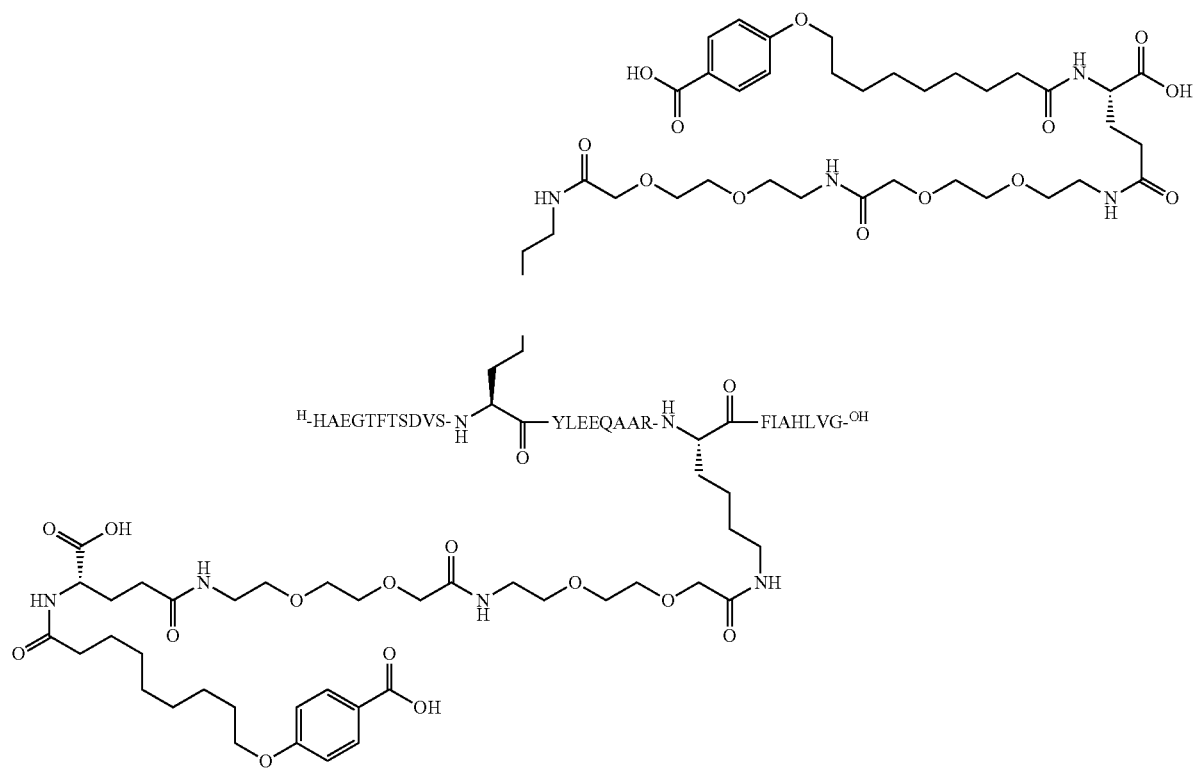

Preparation Method: SPPS_L; SC_L; CP_M1

LCMS: Method: LCMS_4: Rt=2.01 min m/z: 4497.0; M/3: 1500; M/4: 1125

UPLC: Method: B4_1: Rt=8.10 min
UPLC: Method: 05_B5_1: Rt=4.37 min
UPLC: Method: 04_A7_1: Rt=4.83 min

Example 65

$N^{\epsilon 18}$-[(4S)-4-carboxy-4-[[2-[2-[2-[2-[[2-[2-(13-carboxytridecanoylamino)ethoxy]ethoxy]acetyl]amino]ethoxy]ethoxy]acetyl]amino]butanoyl], $N^{\epsilon 26}$-[(4S)-4-carboxy-4-[[2-[2-[2-[[2-[2-[2-(13-carboxytridecanoylamino)ethoxy]ethoxy]acetyl]amino]ethoxy]ethoxy]acetyl]amino]butanoyl]-[Aib$^8$,Lys$^{18}$,Glu$^{22}$,Gln$^{34}$]-GLP-1-(7-37)-peptide (SEQ ID NO: 7)

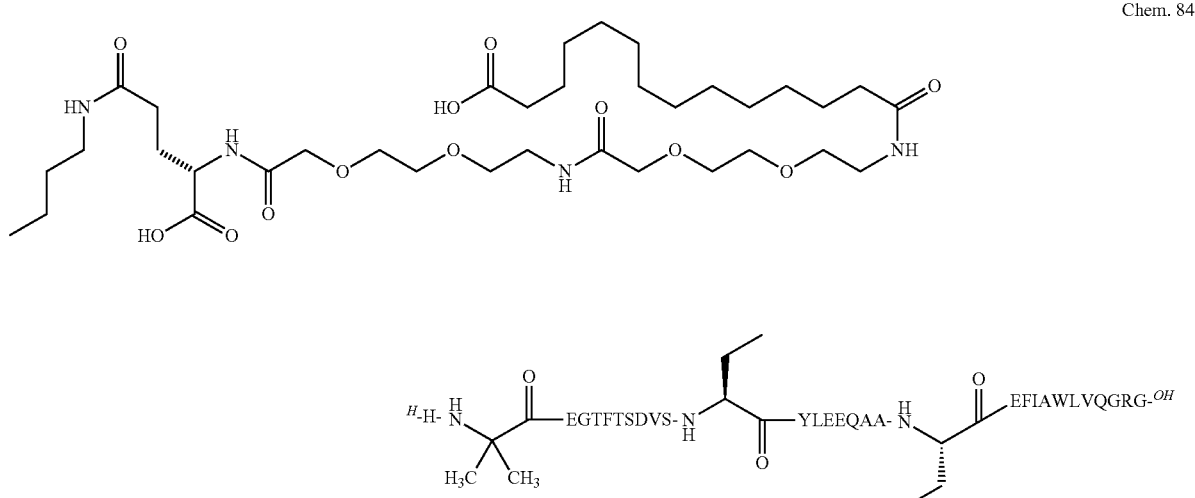

Chem. 84

Preparation Method: SPPS_L: SC_L; CP_M1

LCMS: Method LCMS_4: Rt=2.40 min m/z: 4802; M/3=1601; M/4=1201

UPLC Method: B4_1: Rt=9.11 min
UPLC Method: 04_A6_1: Rt=5.76 min

Example 66

$N^{\epsilon 18}$-[2-[2-[2-[[2-[2-[2-[[(4S)-4-carboxy-4-(11-carboxyundecanoylamino)butanoyl]amino]ethoxy]ethoxy]acetyl]amino]ethoxy]ethoxy]acetyl], $N^{\epsilon 34}$-[2-[2-[2-[[2-[2-[2-[[(4S)-4-carboxy-4-(11-carboxyundecanoylamino)butanoyl]amino]ethoxy]ethoxy]acetyl]amino]ethoxy]ethoxy]acetyl]-[Lys$^{18}$,Glu$^{22}$,Val$^{25}$,Arg$^{26}$,His$^{31}$]-GLP-1-(7-34)-peptide (SEQ ID NO: 46)

Chem. 85

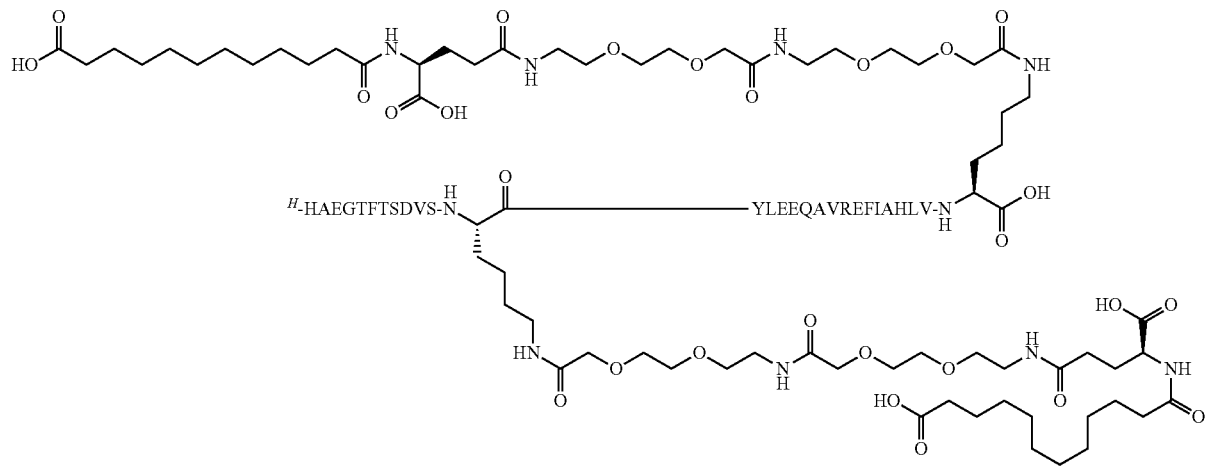

Preparation Method: SPPS_L: SC_L: CP_M1
LCMS: Method: LCMS_4: Rt=2.06 min, m/z: 4469.3
UPLC Method: B4_1: Rt=8.07 min
UPLC Method: 05_B9_1: Rt=6.40 min Example 67

$N^{\epsilon 18}$-[2-[2-[2-[[2-[2-[2-[[(4S)-4-carboxy-4-[10-(4-carboxyphenoxy)decanoylamino]butanoyl]amino]ethoxy]ethoxy]acetyl]amino]ethoxy]ethoxy]acetyl], $N^{\epsilon 27}$-[2-[2-[2-[[2-[2-[2-[[(4S)-4-carboxy-4-[10-(4-carboxyphenoxy)decanoylamino]butanoyl]amino]ethoxy]ethoxy]acetyl]amino]ethoxy]ethoxy]acetyl]-[Lys$^{18}$,His$^{26}$,Lys$^{27}$,Gln$^{34}$]-GLP-1-(7-37)-peptide (SEQ ID NO: 47)

Chem. 86

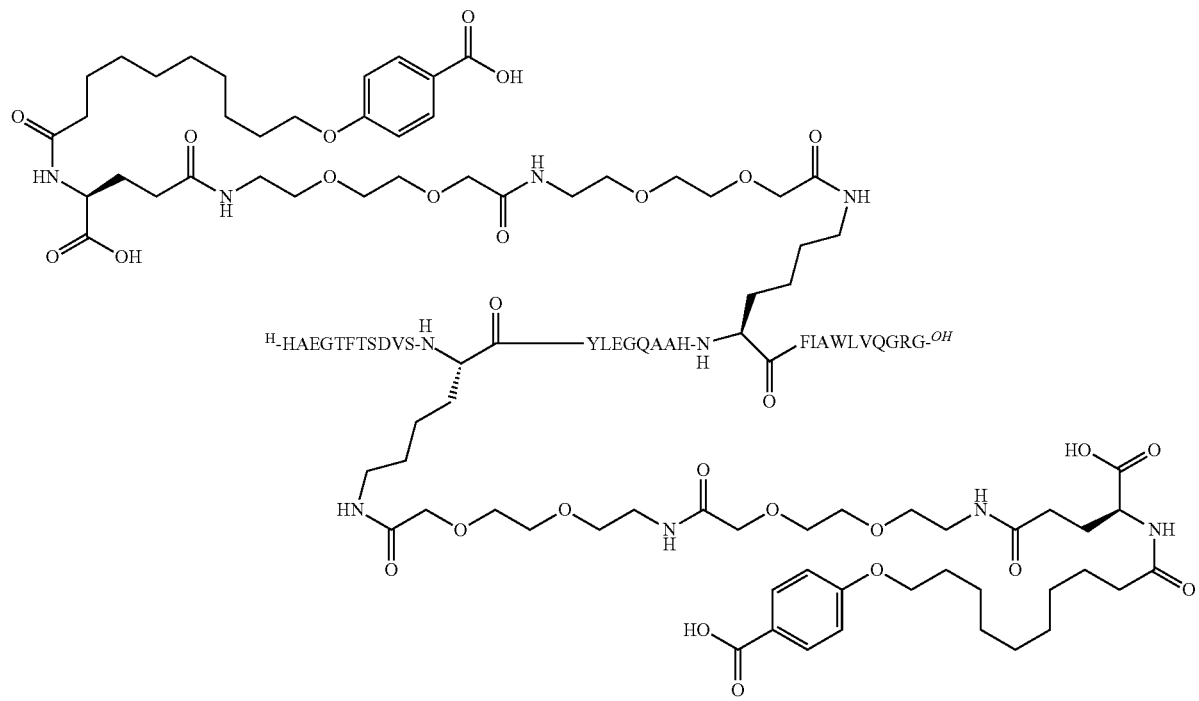

Preparation Method: SPPS_L: SC_L: CP_M1
LCMS: Method: LCMS_4: Rt=2.13 min, m/z: 4823.8
UPLC Method: B4_1: Rt=8.41 min Example 68

$N^{\epsilon 18}$-[2-[2-[2-[[2-[2-[2-[[(4S)-4-carboxy-4-[4-(4-iodophenyl)butanoylamino]butanoyl]amino]ethoxy]ethoxy]acetyl]amino]ethoxy]ethoxy]acetyl]$N^{\epsilon 27}$-[2-[2-[2-[[2-[2-[2-[[(4S)-4-carboxy-4-[4-(4-iodophenyl)butanoylamino]butanoyl]amino]ethoxy]ethoxy]acetyl]amino]ethoxy]ethoxy]acetyl]-[Aib$^8$,Lys$^{18}$,Val$^{26}$,Lys$^{27}$,Arg$^{34}$]-GLP-1-(7-37)-peptide (SEQ ID NO: 6)

Chem. 87

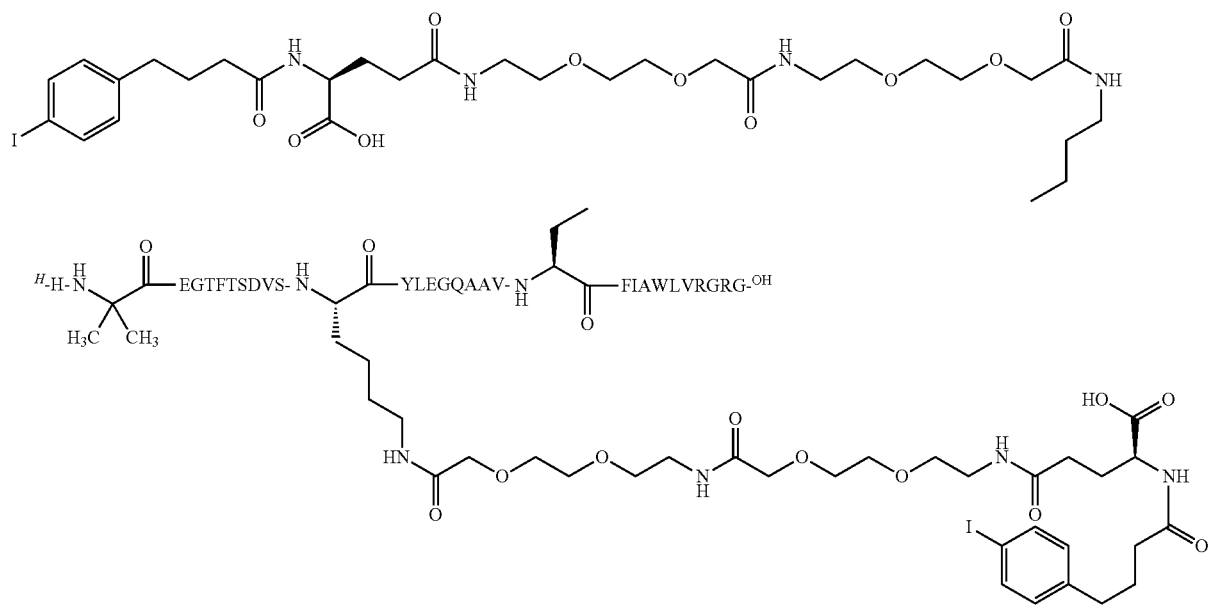

Preparation method: SPPS_L; SC_L; CP_M1
LCMS: Method: LCMS_4: Rt=2.22 min m/z: m/3 1597; m/4 1198; m/5 959
UPLC method B4_1: Rt=8.96
UPLC method: 05_B5_1: Rt=6.05

Example 69

$N^{\epsilon 18}$-[2-[2-[2-[[2-[2-[2-[[2-[2-[2-[[2-[2-[2-[[(4S)-4-carboxy-4-[10-(4-carboxyphenoxy)decanoylamino]butanoyl]amino]ethoxy]ethoxy]acetyl]amino]ethoxy]ethoxy]acetyl]amino]ethoxy]ethoxy]acetyl]amino]ethoxy]ethoxy]acetyl], $N^{\epsilon 26}$-[2-[2-[2-[[2-[2-[2-[[2-[2-[2-[[2-[2-[2-[[(4S)-4-carboxy-4-[10-(4-carboxyphenoxy)decanoylamino]butanoyl]amino]ethoxy]ethoxy]acetyl]amino]ethoxy]ethoxy]acetyl]amino]ethoxy]ethoxy]acetyl]amino]ethoxy]ethoxy]acetyl]-[Aib$^8$,Lys$^{18}$,Glu$^{22}$,Gln$^{34}$]-GLP-1-(7-37)-peptide (SEQ ID NO: 7)

Chem. 88

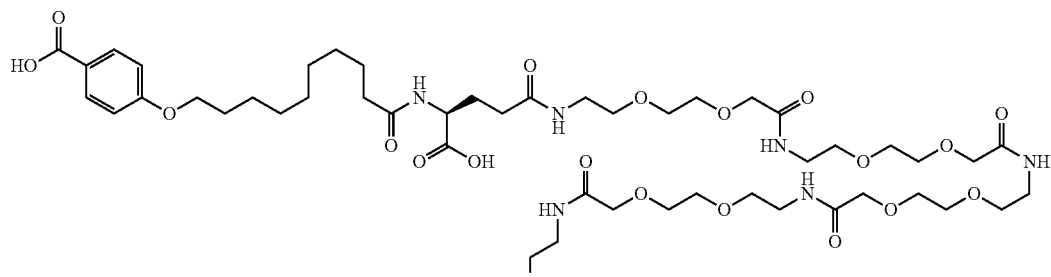

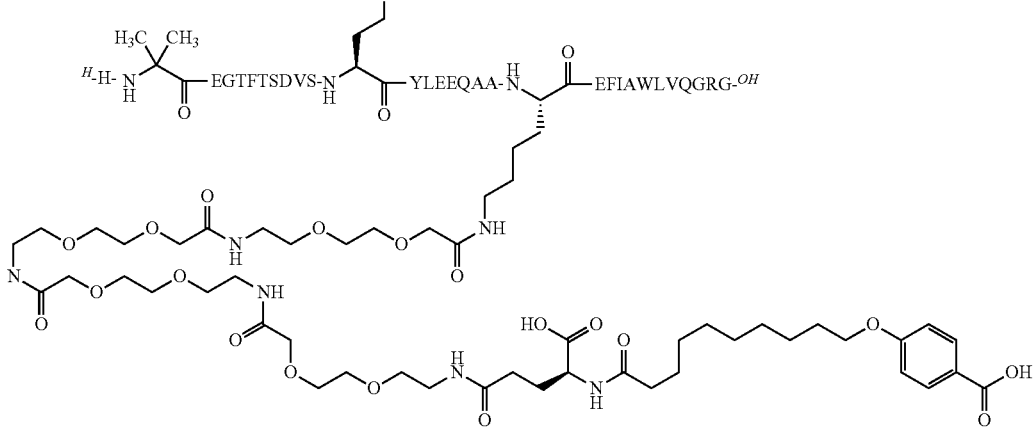

Preparation Method: SPPS_L: SC_L: CP_M1
LCMS: Method: LCMS_4: Rt=2.22 min, m/z: 5480.9
UPLC Method: B4_1: Rt=8.64 min
UPLC Method: 04_A6_1: Rt=4.22 min Example 70

$N^{\epsilon 18}$-[2-[2-[2-[[2-[2-[2-[[(4S)-4-carboxy-4-(13-carboxytridecanoylamino)butanoyl]amino]ethoxy]ethoxy]acetyl]amino]ethoxy]ethoxy]acetyl]$N^{\epsilon 31}$-[2-[2-[2-[[2-[2-[2-[[(4S)-4-carboxy-4-(13-carboxytridecanoylamino)butanoyl]amino]ethoxy]ethoxy]acetyl]amino]ethoxy]ethoxy]acetyl][Lys$^{18}$,Arg$^{26}$,Lys$^{31}$,Arg$^{34}$]-GLP-1-(7-37)-peptide (SEQ ID NO: 48)

Chem. 89

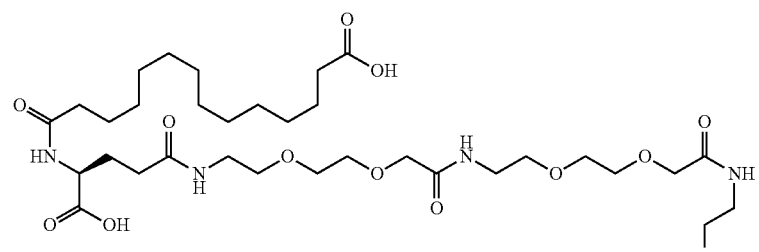

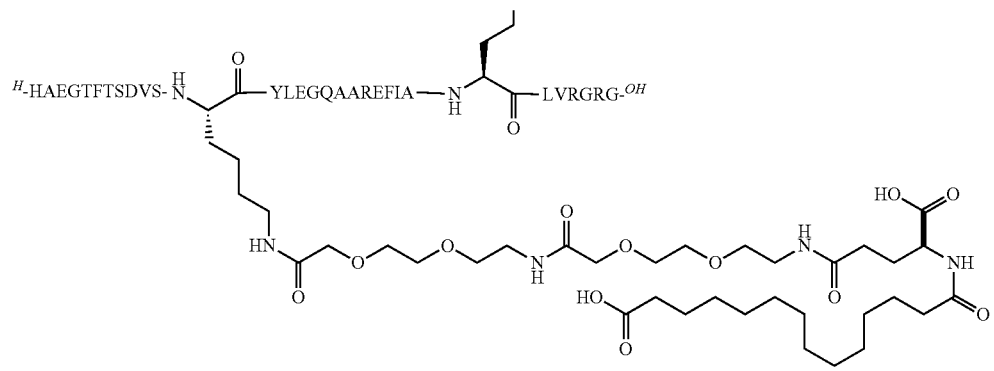

Preparation Method: SPPS_L: SC_L: CP_M1
LCMS: Method: LCMS_4: Rt=2.12 min, m/z: 4714.3
UPLC Method: B4_1: Rt=8.03 min
UPLC Method: 04_A7_1: Rt=6.61 min Example 71

$N^{\epsilon 18}$-[2-[2-[2-[[2-[2-[2-[[2-[2-[2-[[2-[2-[2-[10-(4-carboxyphenoxy)decanoylamino]ethoxy]ethoxy]acetyl]amino] ethoxy]ethoxy]acetyl]amino]ethoxy]ethoxy]acetyl] amino]ethoxy]ethoxy]acetyl], $N^{\epsilon 26}$-[2-[2-[2-[[2-[2-[2-[[2-[2-[2-[[2-[2-[2-[10-(4-carboxyphenoxy)decanoylamino]ethoxy]ethoxy]acetyl]amino]ethoxy] ethoxy]acetyl]amino]ethoxy]ethoxy]acetyl]amino] ethoxy]ethoxy]acetyl]-[Aib$^8$,Lys$^{18}$,Glu$^{22}$,Gln$^{34}$]-GLP-1-(7-37)-peptide (SEQ ID NO: 7)

Chem. 90

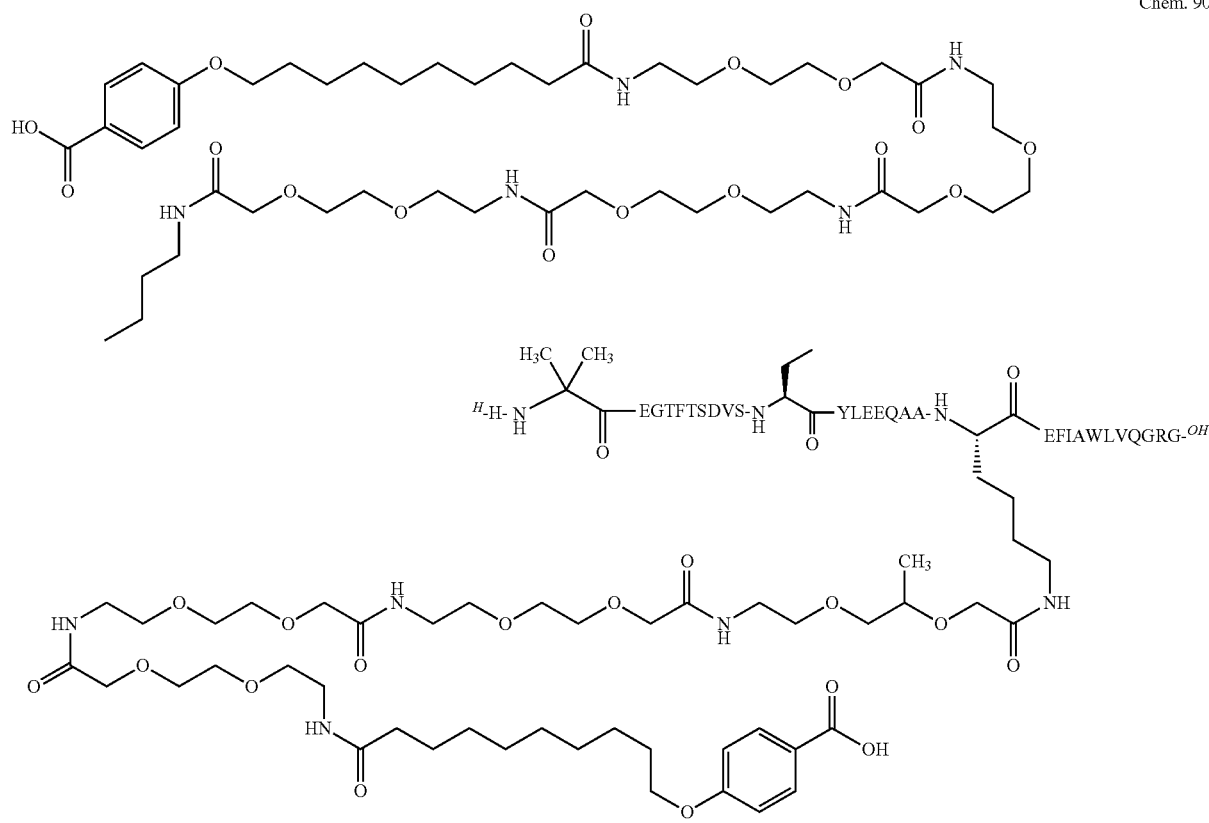

Preparation Method: SPPS_L: SC_L: CP_M1
LCMS: Method: LCMS_4: Rt=2.29 min, m/z: 5224.9
UPLC Method: B4_1: Rt=8.01 min
UPLC Method: 04_A6_1: Rt=5.48 min Example 72

$N^{\epsilon 18}$-[2-[2-[2-[[2-[2-[2-[[(4S)-4-carboxy-4-(13-carboxytridecanoylamino)butanoyl]amino]ethoxy]ethoxy]acetyl]amino]ethoxy]ethoxy]acetyl], $N^{\epsilon 31}$-[2-[2-[2-[[2-[2-[2-[[(4S)-4-carboxy-4-(13-carboxytridecanoylamino)butanoyl]amino]ethoxy]ethoxy]acetyl]amino]ethoxy] ethoxy]acetyl]-[Lys$^{18}$,His$^{26}$,Lys$^{31}$,Arg$^{34}$]-GLP-1-(7-37)-peptide (SEQ ID NO: 48)

Chem. 91

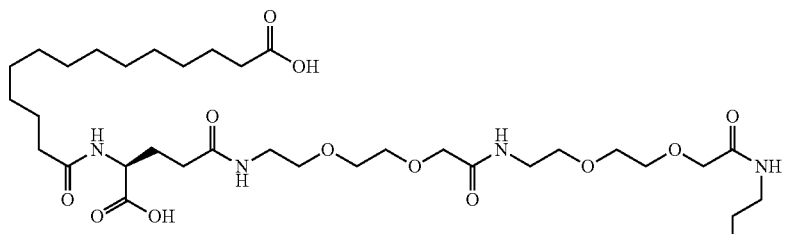

-continued

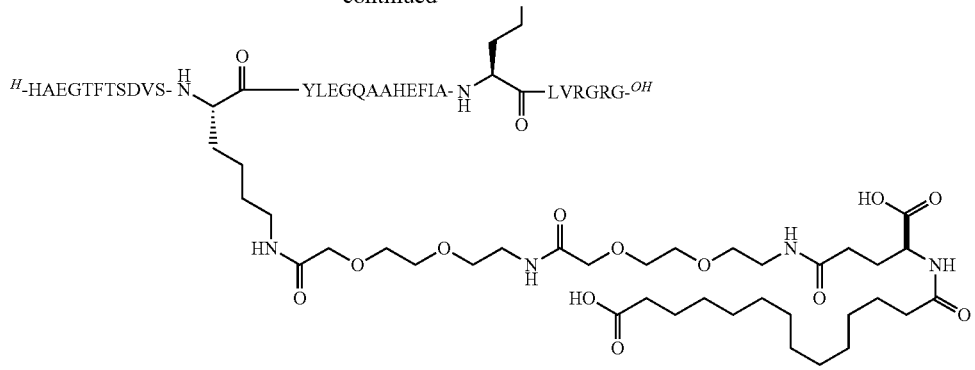

Preparation Method: SPPS_L: SC_L: CP_M1
LCMS: Method: LCMS_4: Rt=1.96 min, m/z: 4693.9
UPLC Method: B4_1: Rt=7.88 min
UPLC Method: 04_A6_1: Rt=4.90 min Example 73

$N^{\epsilon 18}$-[2-[2-[2-[[2-[2-[2-[[(4S)-4-carboxy-4-(13-carboxytridecanoylamino)butanoyl]amino]ethoxy]ethoxy]acetyl]amino]ethoxy]ethoxy]acetyl], $N^{\epsilon 31}$-[2-[2-[2-[[2-[2-[2-[[(4S)-4-carboxy-4-(13-carboxytridecanoylamino)butanoyl]amino]ethoxy]ethoxy]acetyl]amino]ethoxy]ethoxy]acetyl]-[Aib$^8$,Lys$^{18}$,Glu$^{22}$,Arg$^{26}$,Lys$^{31}$,Arg$^{34}$]-GLP-1-(7-37)-peptide (SEQ ID NO: 8)

Chem. 92

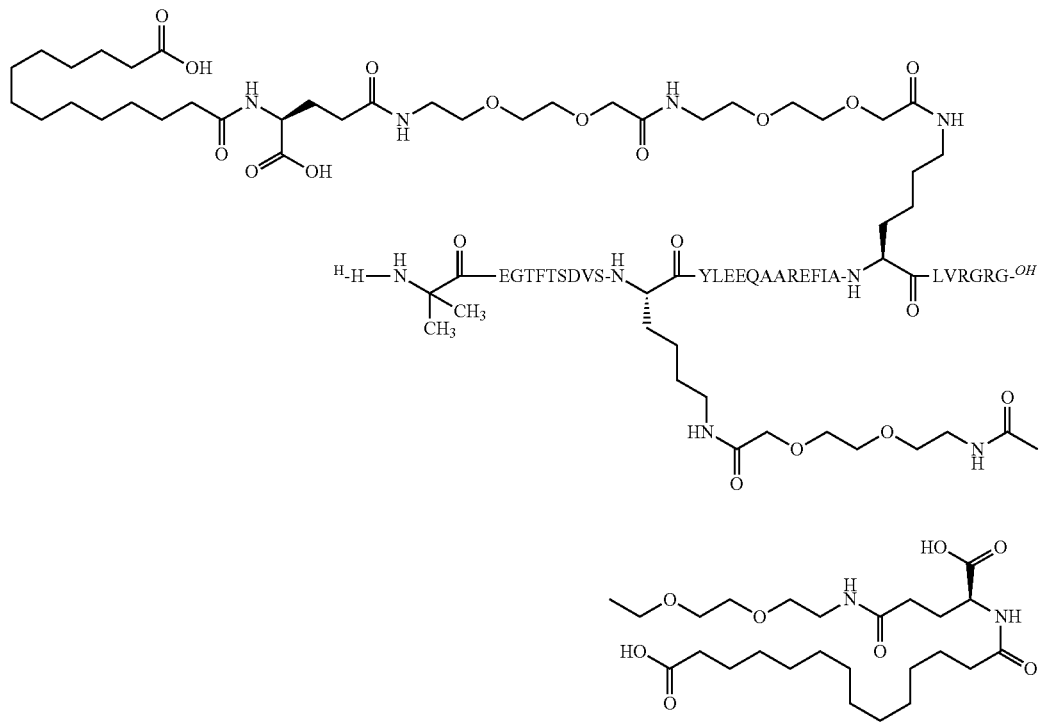

Preparation Method: SPPS_L; SC_L
LCMS: Method: LCMS_4: Rt=2.03 min m/z: 4800.48 m/3=1600 m/4=1200 m/5=960
UPLC Method: B2_1: Rt=12.785 min Example 74

N$^{\epsilon 18}$-[2-[2-[2-[[2-[2-[2-[[(4S)-4-carboxy-4-(13-carboxytridecanoylamino)butanoyl]amino]ethoxy]ethoxy]acetyl]amino]ethoxy]ethoxy]acetyl], N$^{\epsilon 31}$-[2-[2-[2-[[2-[2-[2-[[(4S)-4-carboxy-4-(13-carboxytridecanoylamino)butanoyl]amino]ethoxy]ethoxy]acetyl]amino]ethoxy]ethoxy]acetyl]-[Aib$^8$,Lys$^{18}$,Glu$^{22}$,Val$^{25}$,Arg$^{26}$,Lys$^{31}$,Arg$^{34}$]-GLP-1-(7-37)-peptide (SEQ ID NO: 12)

Chem. 93

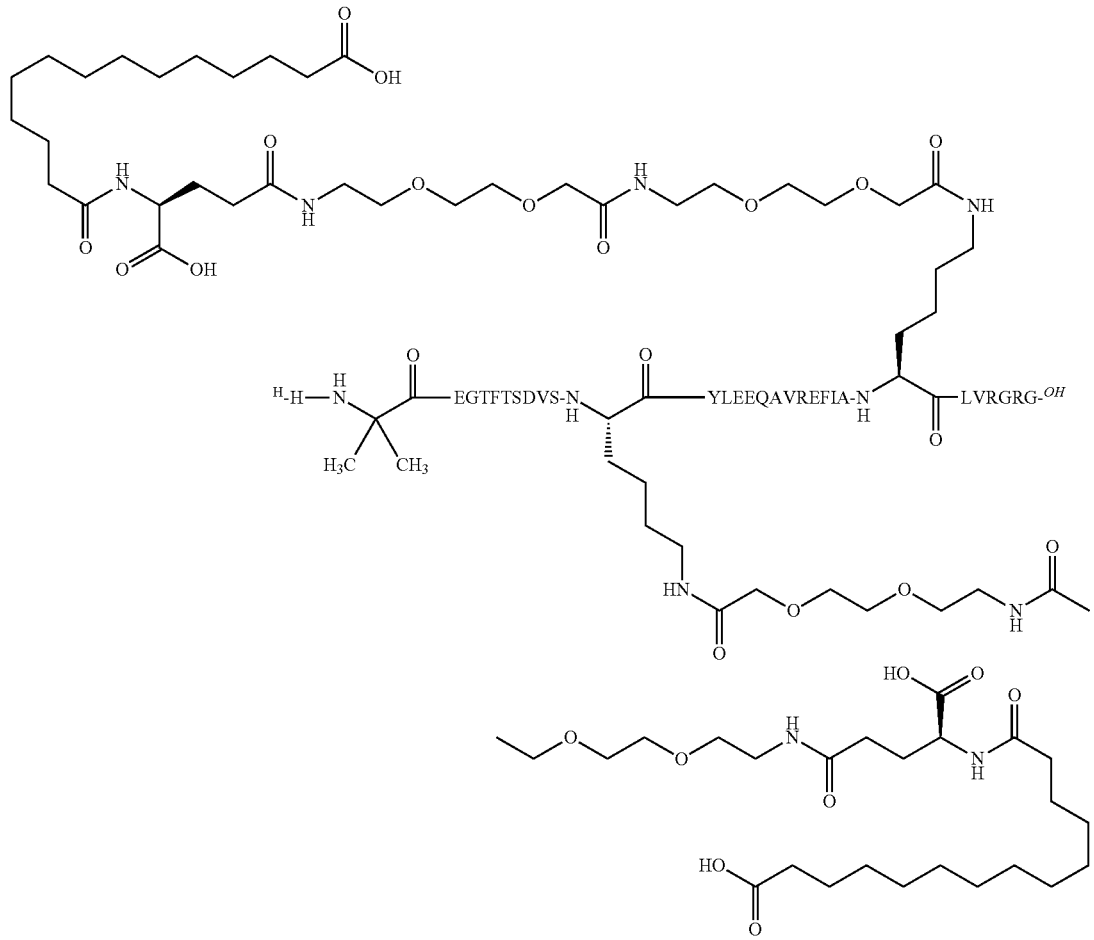

Preparation Method: SPPS_L; SC_L
LCMS: Method: LCMS_4: Rt=1.97 min; m/3: 1609; m/4: 1207; m/5: 965
UPLC Method: B2_1: Rt=12.45 min
UPLC Method: 04_A7_1: Rt=6.68 min Example 75

N$^{\epsilon 18}$-[2-[2-[2-[[2-[2-[2-[[(4S)-4-carboxy-4-[10-(4-carboxyphenoxy)decanoylamino]butanoyl]amino]ethoxy]ethoxy]acetyl]amino]ethoxy]ethoxy]acetyl], N$^{\epsilon 31}$-[2-[2-[2-[[2-[2-[2-[[(4S)-4-carboxy-4-[10-(4-carboxyphenoxy)decanoylamino]butanoyl]amino]ethoxy]ethoxy]acetyl]amino]ethoxy]ethoxy]acetyl]-[Lys$^{18}$,Glu$^{22}$,Val$^{25}$,Arg$^{26}$,Lys$^{31}$,Arg$^{34}$]-GLP-1-(7-37)-peptide (SEQ ID NO: 10)

Chem. 94

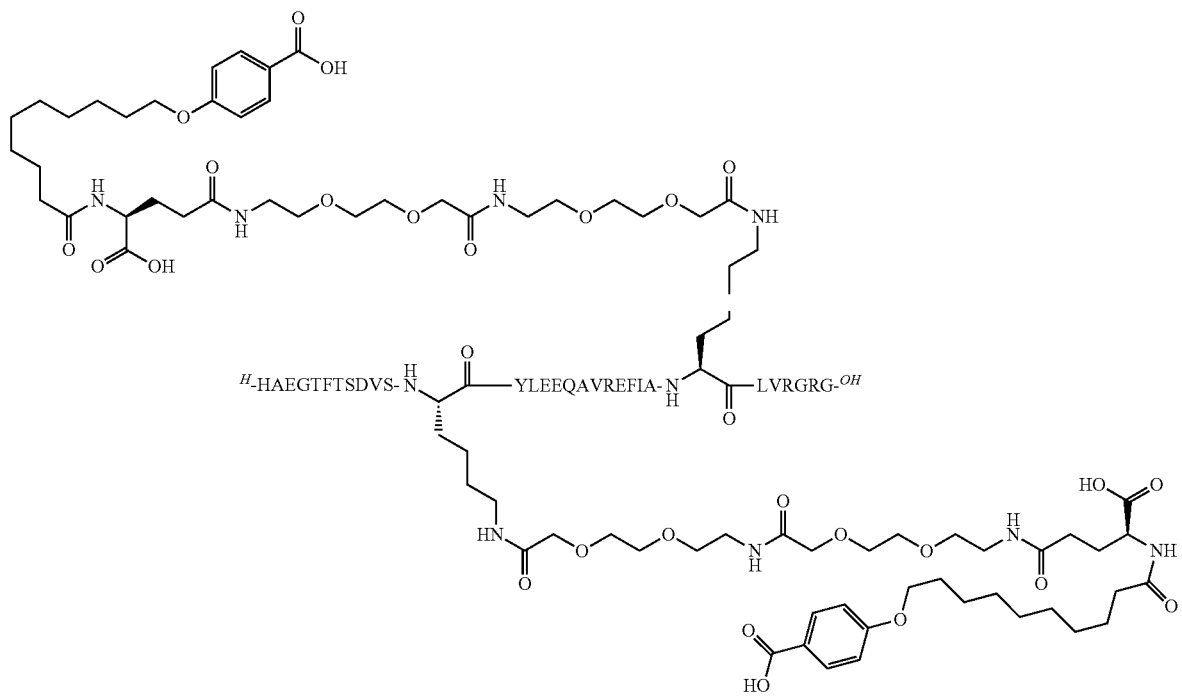

Preparation Method: SPPS_L; SC_L
LCMS: Method: LCMS_4: Rt=1.95 min; m/3: 1638; m/4: 1228; m/5: 983
UPLC Method: B2_1: Rt=12.45 min
UPLC Method: 04_A7_1: Rt=7.3 min Example 76

$N^{\epsilon 18}$-[2-[2-[2-[[2-[2-[2-[[(4S)-4-carboxy-4-[10-(4-carboxyphenoxy)decanoylamino]butanoyl]amino]ethoxy]ethoxy]acetyl]amino]ethoxy]ethoxy]acetyl], $N^{\epsilon 31}$-[2-[2-[2-[[2-[2-[2-[[(4S)-4-carboxy-4-[10-(4-carboxyphenoxy)decanoylamino]butanoyl]amino]ethoxy]ethoxy]acetyl]amino]ethoxy]ethoxy]acetyl]-[Aib$^8$,Lys$^{18}$,Glu$^{22}$,Val$^{25}$,Arg$^{26}$,Lys$^{31}$,Arg$^{34}$]-GLP-1-(7-37)-peptide (SEQ ID NO: 12)

Chem. 95

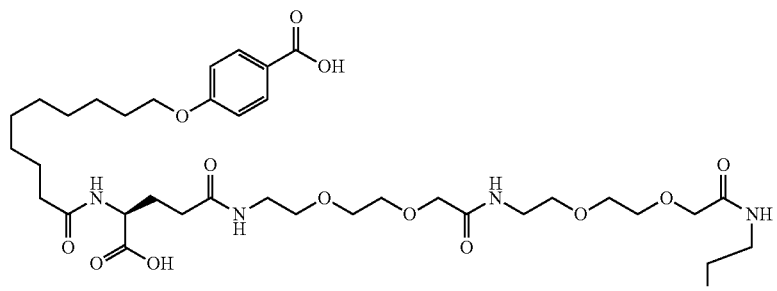

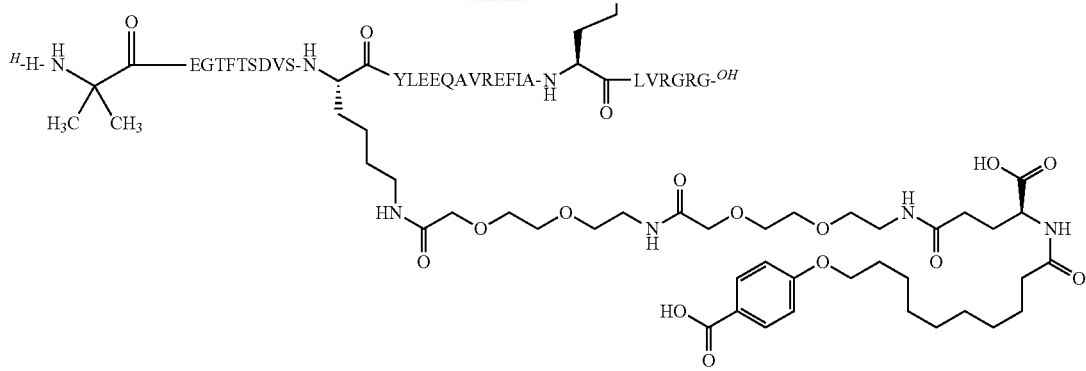

Preparation Method: SPPS_L; SC_L
LCMS: Method: LCMS_4: Rt=2.07 min; m/z=4928.0; m/3=1643; m/4=1232; m/5=986
UPLC Method: B2_1: Rt=12.45 min Example 77

$N^{\epsilon 18}$-[2-[2-[2-[[2-[2-[2-[[(4S)-4-carboxy-4-(13-carboxytridecanoylamino)butanoyl]amino]ethoxy]ethoxy]acetyl]amino]ethoxy]ethoxy]acetyl], $N^{\epsilon 31}$-[2-[2-[2-[[2-[2-[2-[[(4S)-4-carboxy-4-(13-carboxytridecanoylamino)butanoyl]amino]ethoxy]ethoxy]acetyl]amino]ethoxy]ethoxy]acetyl]-[Lys$^{18}$,Val$^{25}$,Arg$^{26}$,Lys$^{31}$,Arg$^{34}$]-GLP-1-(7-37)-peptide (SEQ ID NO: 49)

Chem. 96

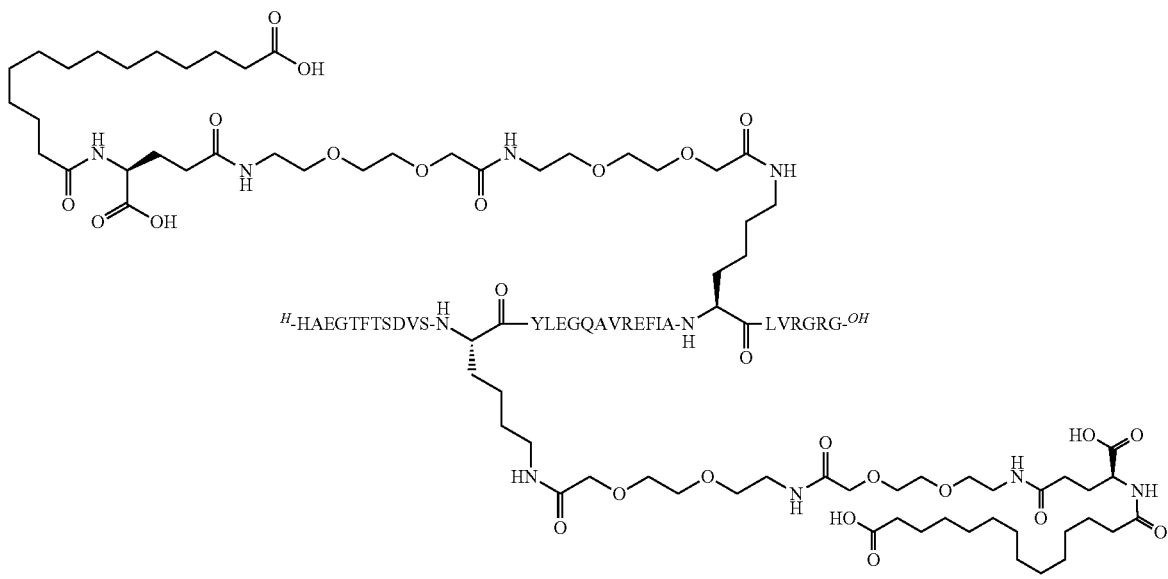

Preparation Method: SPPS_L: SC_L: CP_M1
LCMS: Method: LCMS_4: Rt=2.10 min, m/z: 4742.5
UPLC Method: B4_1: Rt=8.18 min
UPLC Method: 04_A6_1: Rt=5.57 min

Example 78

$N^{\epsilon 18}$-[2-[2-[2-[[2-[2-[2-[[(4S)-4-carboxy-4-(13-carboxytridecanoylamino)butanoyl]amino]ethoxy]ethoxy]acetyl]amino]ethoxy]ethoxy]acetyl], $N^{\epsilon 31}$-[2-[2-[2-[[2-[2-[2-[[(4S)-4-carboxy-4-(13-carboxytridecanoylamino)butanoyl]amino]ethoxy]ethoxy]acetyl]amino]ethoxy]ethoxy]acetyl]-[Lys$^{18}$,Glu$^{22}$,Arg$^{26}$,Lys$^{31}$,Arg$^{34}$]-GLP-1-(7-37)-peptide (SEQ ID NO: 50)

Chem. 97

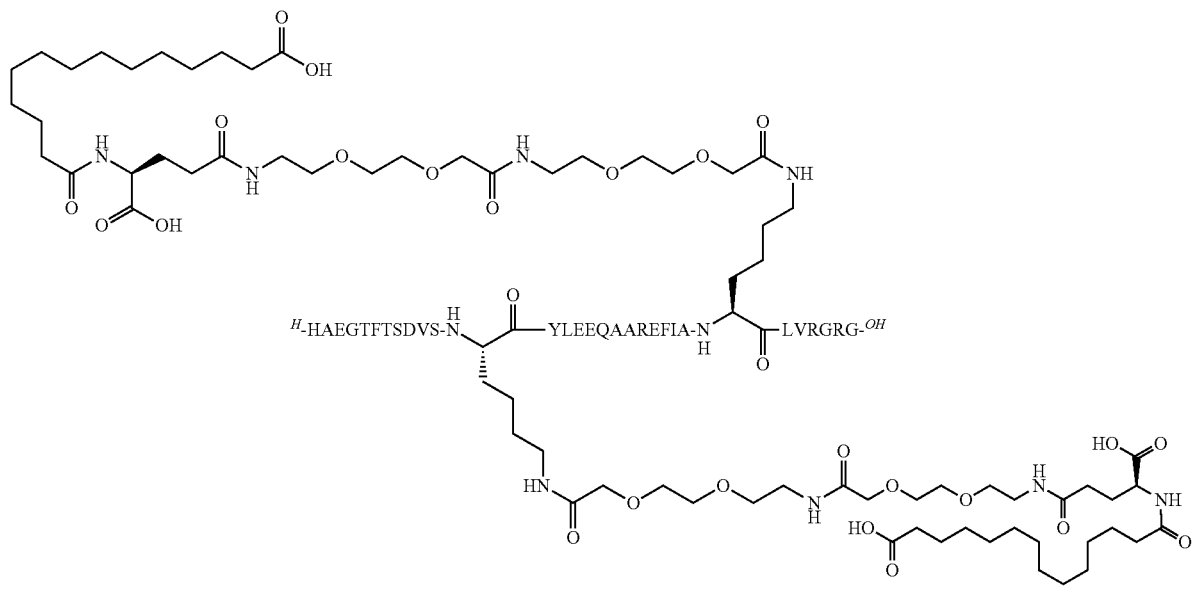

Preparation method: SPPS_L: SC_L: CP_M1
LCMS: Method: LCMS_4: Rt=1.80 min, m/z: 4785.9
UPLC Method: B4_1: Rt=7.90 min
UPLC Method: 04_A6_1: Rt=4.31 min

Example 79

$N^{\epsilon 18}$-[2-[2-[2-[[2-[2-[2-[[(4S)-4-carboxy-4-[(2-phenylcyclopropanecarbonyl)amino]butanoyl]amino]ethoxy]ethoxy]acetyl]amino]ethoxy]ethoxy]acetyl], $N^{\epsilon 26}$-[2-[2-[2-[[2-[2-[2-[[(4S)-4-carboxy-4-[(2-phenylcyclopropanecarbonyl)amino]butanoyl]amino]ethoxy]ethoxy]acetyl]amino]ethoxy]ethoxy]acetyl]-[Aib$^8$,Lys$^{18}$,Glu$^{22}$,Gln$^{34}$]-GLP-1-(7-37)-peptide (SEQ ID NO: 7)

Chem. 98

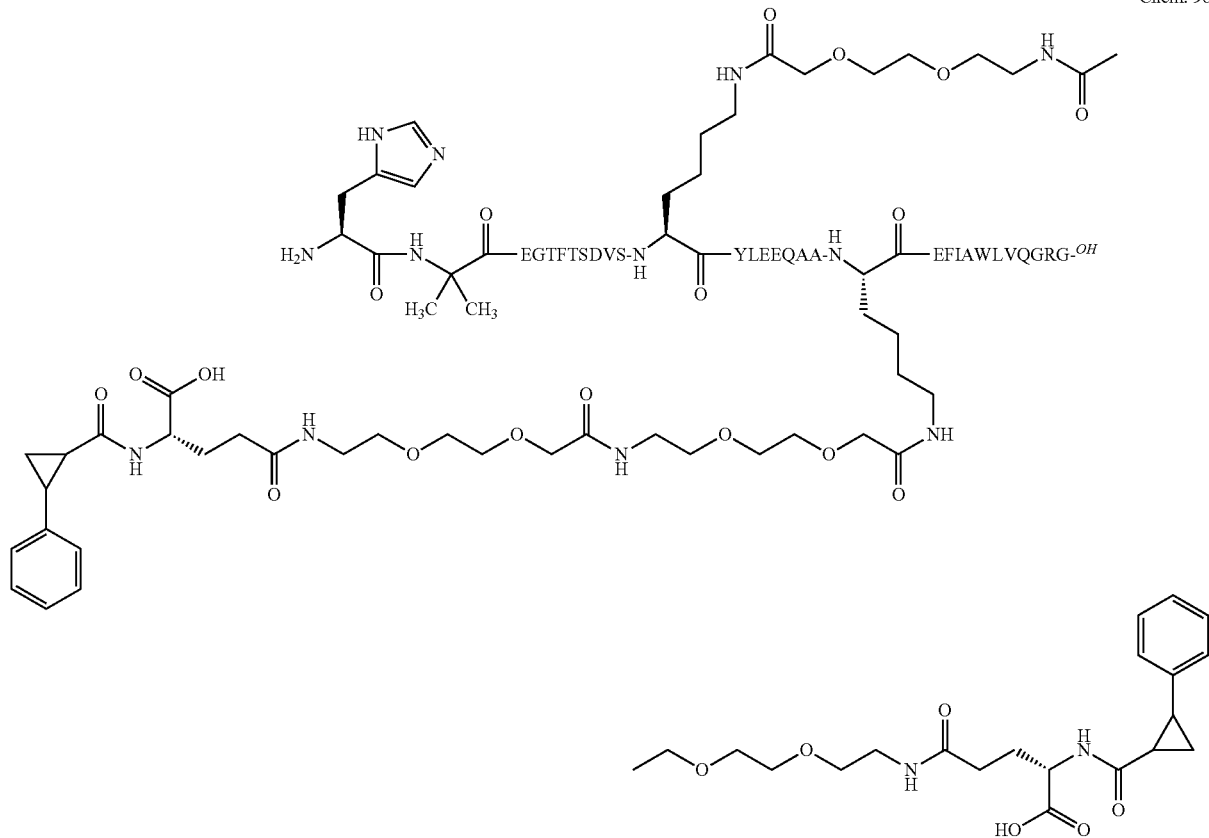

Example 80

Preparation method: SSPS_L: SC_L with trans-2-Phenyl-1-Cyclopropanecarboxylic acid attached as described in method SC_M2 with the modification that 8 eq. of HOBt/DIC and trans-2-Phenyl-1-Cyclopropanecarboxylic acid was used; CP_M1

LCMS: Method: LCMS_4: Rt=2.16 m/z: m/3 1537; m/4 1152; m/5 922

UPLC method: B4_1: Rt=8.37 min.
UPLC method: 05_B5_1: Rt=4.61 min.

$N^{\epsilon 18}$-[2-[2-[2-[[2-[2-[2-[[(4S)-4-carboxy-4-(13-carboxytridecanoylamino)butanoyl]amino]ethoxy]ethoxy]acetyl]amino]ethoxy]ethoxy]acetyl]$N^{\epsilon 26}$-[2-[2-[2-[[2-[2-[2-[[(4S)-4-carboxy-4-(13-carboxytridecanoylamino)butanoyl]amino]ethoxy]ethoxy]acetyl]amino]ethoxy]ethoxy]acetyl]-[Aib$^8$,Lys$^{18}$,Glu$^{22}$,Gln$^{34}$]-GLP-1-(7-37)-peptide (SEQ ID NO: 7)

Chem. 99

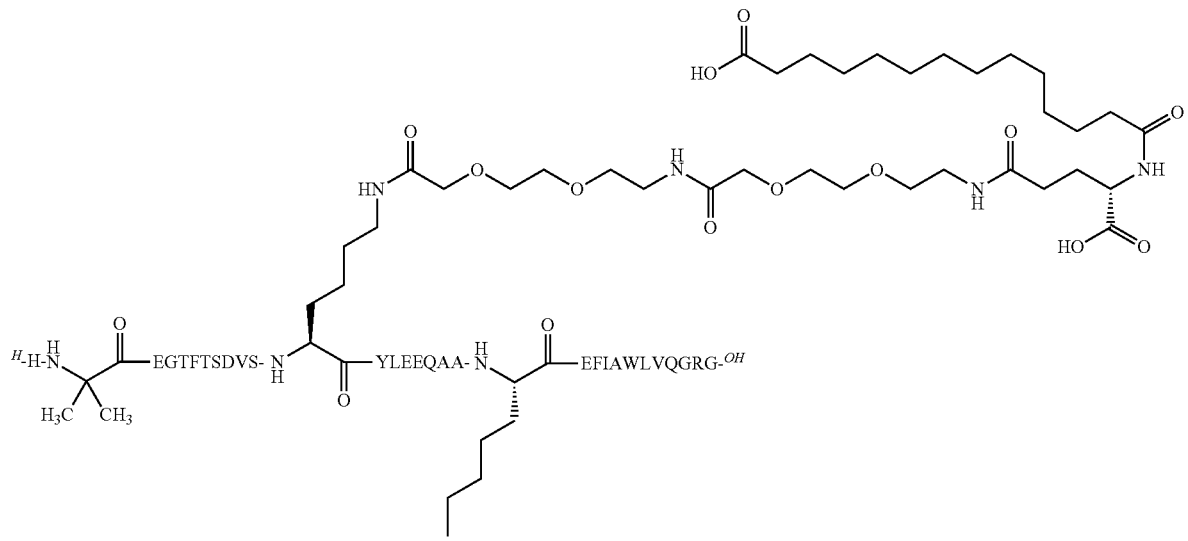

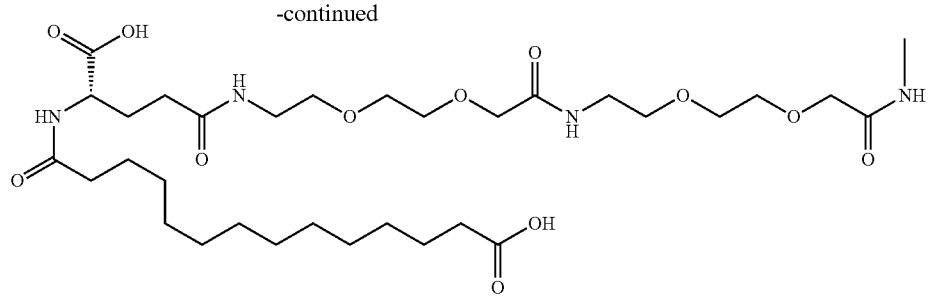

Preparation Method: SPPS_P; SC_L; CP_M1
UPLC method: B4_1: Rt=8.917 min
UPLC method: 04_A9_1: Rt=9.996 min
LCMS method: LCMS_2: Rt=6.99 min; m/3=1603, m/4=1202

Example 81

$N^{\epsilon 18}$-[2-[2-[2-[[2-[2-[2-[[(4S)-4-carboxy-4-(13-carboxytridecanoylamino)butanoyl]amino]ethoxy]ethoxy]acetyl]amino]ethoxy]ethoxy]acetyl], $N^{\epsilon 30}$-[2-[2-[2-[[2-[2-[2-[[(4S)-4-carboxy-4-(13-carboxytridecanoylamino)butanoyl]amino]ethoxy]ethoxy]acetyl]amino]ethoxy]ethoxy]acetyl]-[Aib$^8$,Lys$^{18}$,His$^{26}$,Lys$^{30}$,Arg$^{34}$]-GLP-1-(7-35)-peptide (SEQ ID NO: 51)

Chem. 100

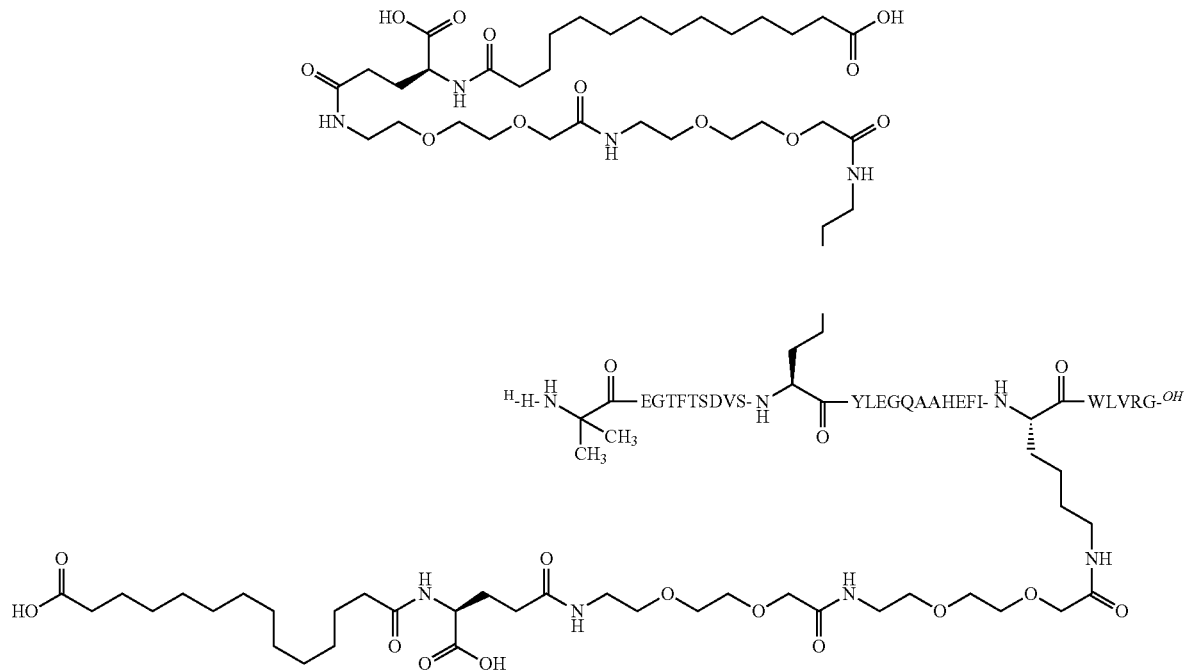

Preparation Method: SPPS_P, SC_P, CP_M1
The theoretical molecular mass of 4611 Da was confirmed by MALDI-MS (alpha-cyano); m/z: 4610
UPLC Method: B4_1: Rt=8.7 min
UPLC Method: 04_A6_1: Rt=5.7 min Example 82

$N^{\epsilon 18}$-[(4S)-4-carboxy-4-[[2-[2-[2-[[2-[2-[2-[10-(4-carboxyphenoxy)decanoylamino]ethoxy]ethoxy]acetyl]amino]ethoxy]ethoxy]acetyl]amino]butanoyl], $N^{\epsilon 26}$-[(4S)-4-carboxy-4-[[2-[2-[2-[[2-[2-[2-[10-(4-carboxyphenoxy)decanoylamino]ethoxy]ethoxy]acetyl]amino]ethoxy]ethoxy]acetyl]amino]butanoyl]-[Aib$^8$,Lys$^{18}$,Glu$^{22}$,Gln$^{34}$]-GLP-1-(7-37)-peptide (SEQ ID NO: 7)

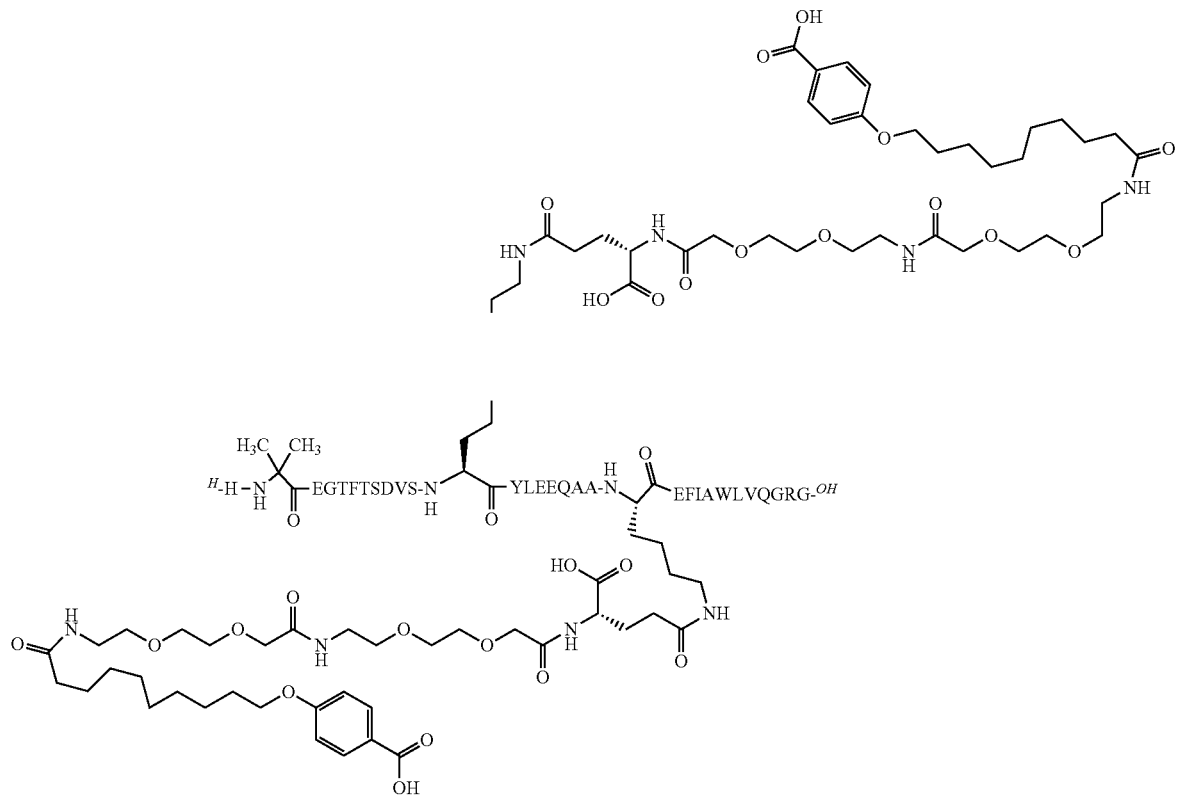

Chem. 101

Preparation Method: SPPS_L: SC_L: CP_M1
LCMS: Method LCMS_4: Rt=2.64 min, m/z: 4902.3
UPLC Method: B4_1: Rt=8.97 min
UPLC Method: 04_A6_1: Rt=5.01 min Example 83

$N^{\epsilon 18}$-[2-[2-[2-[[2-[2-[2-[[(4S)-4-carboxy-4-(13-carboxytridecanoylamino)butanoyl]amino]ethoxy]ethoxy]acetyl]amino]ethoxy]ethoxy]acetyl], $N^{\epsilon 30}$-[2-[2-[2-[[2-[2-[2-[[(4S)-4-carboxy-4-(13-carboxytridecanoylamino)butanoyl]amino]ethoxy]ethoxy]acetyl]amino]ethoxy]ethoxy]acetyl]-[Aib$^8$,Lys$^{18}$,Glu$^{22}$,Arg$^{26}$,Lys$^{30}$,Arg$^{34}$]-GLP-1-(7-35)-peptide (SEQ ID NO: 38)

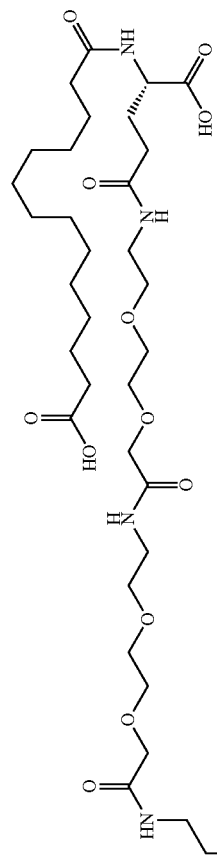
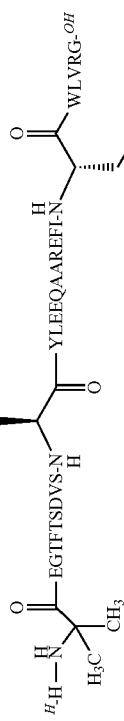
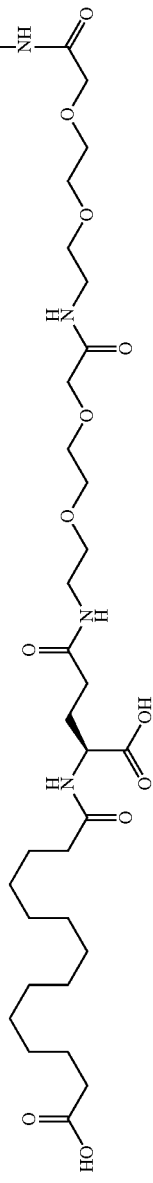
Chem. 102

Preparation Method: SPPS_P, SC_P, CP_M1

The theoretical molecular mass of 4702 Da was confirmed by MALDI_MS: m/z: 4701

UPLC Method: B4_1: Rt=9.0 min
UPLC Method: 04_A6_1: Rt=4.6 min

Example 84

$N^{\epsilon 18}$-[2-[2-[2-[[2-[2-[2-(13-carboxytridecanoylamino)ethoxy]ethoxy]acetyl]amino]ethoxy]ethoxy]acetyl], $N^{\epsilon 26}$-[2-[2-[2-[[2-[2-[2-(13-carboxytridecanoylamino)ethoxy]ethoxy]acetyl]amino]ethoxy]ethoxy]acetyl]-[Aib$^8$,Lys$^{18}$,Glu$^{22}$,Gln$^{34}$]-GLP-1-(7-37)-peptide (SEQ ID NO: 7)

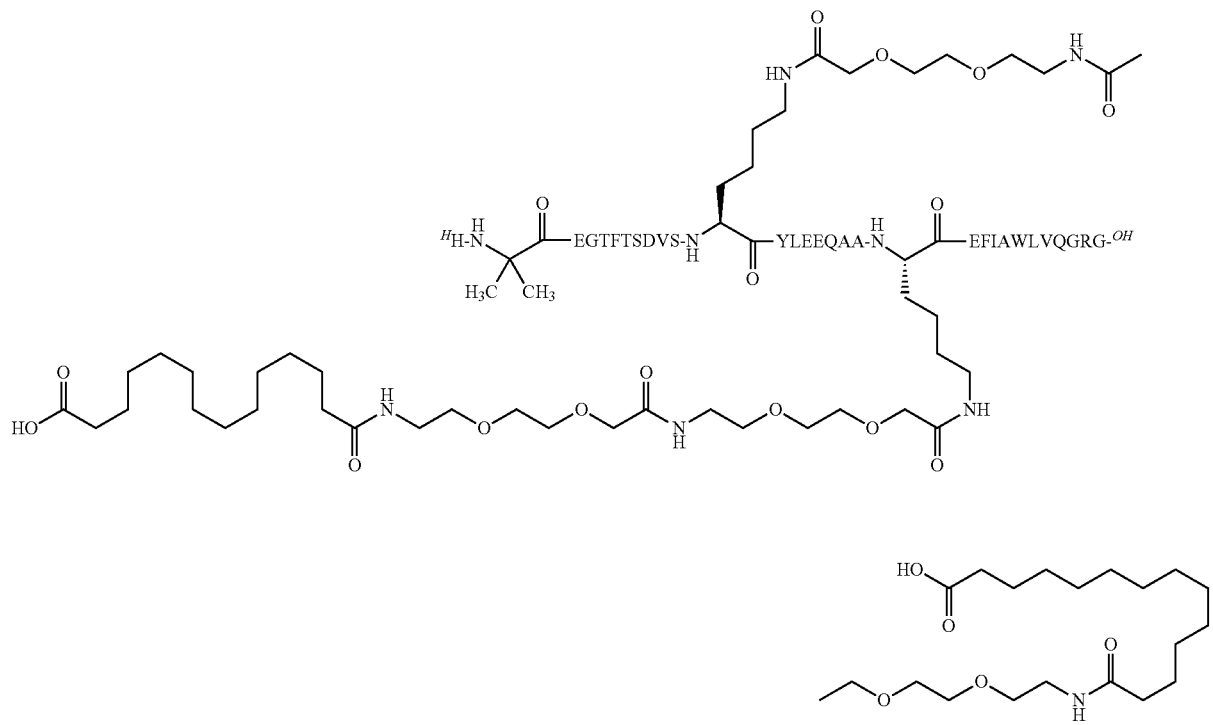

Chem. 103

Preparation Method: SPPS_L: SC_L; CP_M1

The theoretical molecular mass was confirmed by MALDI_MS: m/z: 4544

UPLC Method: B4_1: Rt=9.4 min
UPLC Method: 04_A6_1: Rt=6.2 min

Example 85

$N^{\epsilon 18}$-[2-[2-[2-[[2-[2-[2-[10-(4-carboxyphenoxy)decanoylamino]ethoxy]ethoxy]acetyl]amino]ethoxy]ethoxy]acetyl], $N^{\epsilon 26}$-[2-[2-[2-[[2-[2-[2-[10-(4-carboxyphenoxy)decanoylamino]ethoxy]ethoxy]acetyl]amino]ethoxy]ethoxy]acetyl]-[Aib$^8$,Lys$^{18}$,Glu$^{22}$,Lys$^{26}$,Gln$^{34}$]-GLP-1-(7-37)-peptide (SEQ ID NO: 52)

Chem. 104

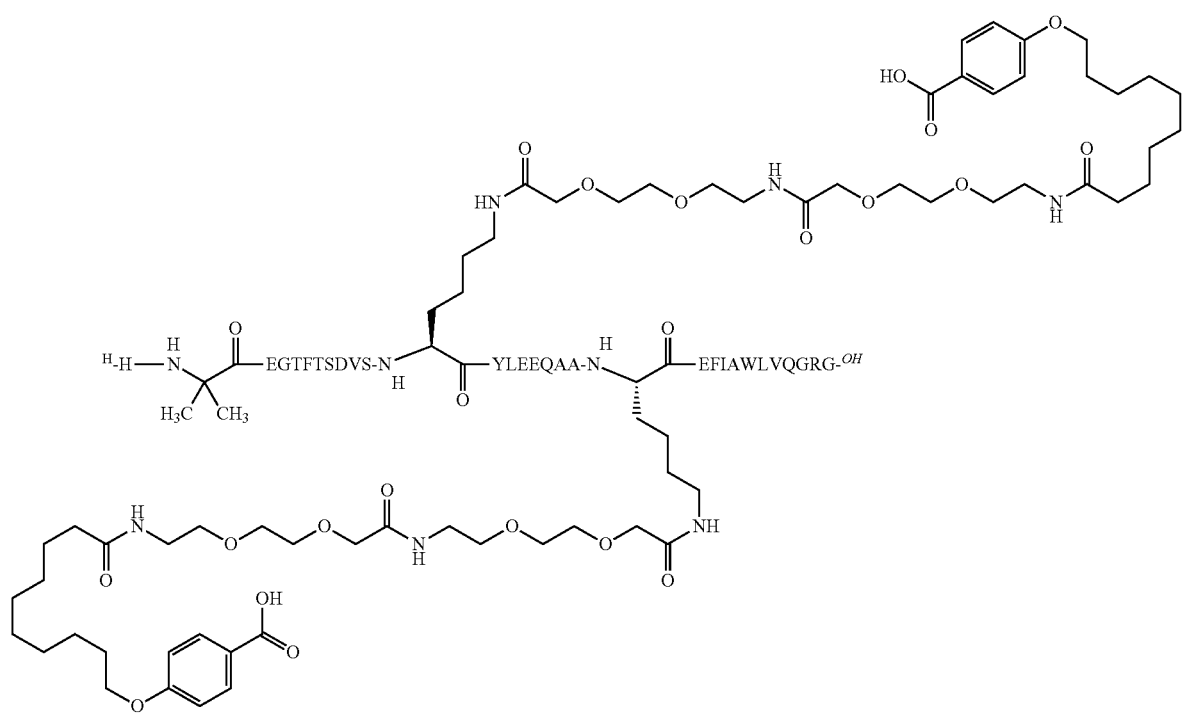

Preparation Method: SPPS_L: SC_L; CP_M1
LCMS: Method LCMS_4: Rt=2.33 min m/z: 4644: M/3=1549; M/4=1162;
UPLC Method: B4_1: Rt=9.31 min
UPLC Method: 04_A6_1: Rt=5.85 min Example 86

$N^{\epsilon 18}$-[2-[2-[2-[[(4S)-4-carboxy-4-[2-[[2-[2-(13-carboxytridecanoylamino)ethoxy]ethoxy]acetyl]amino]butanoyl]amino]ethoxy]ethoxy]acetyl], $N^{\epsilon 26}$-[2-[2-[2-[[(4S)-4-carboxy-4-[[2-[2-[2-(13-carboxytridecanoylamino)ethoxy]ethoxy]acetyl]amino]butanoyl]amino]ethoxy]ethoxy]acetyl]-[Aib$^8$,Lys$^{18}$,Glu$^{22}$,Gln$^{34}$]-GLP-1-(7-37)-peptide (SEQ ID NO: 7)

Chem. 105
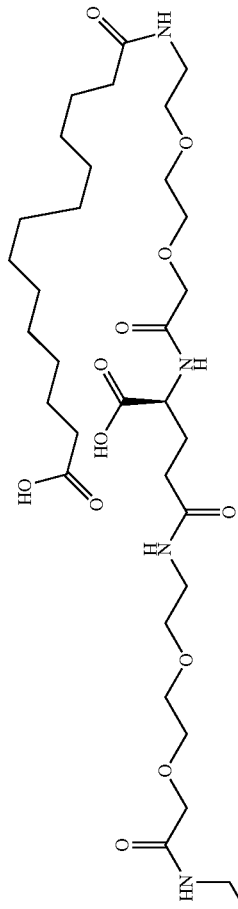
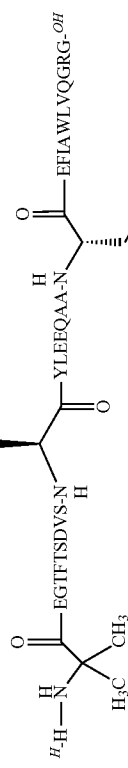
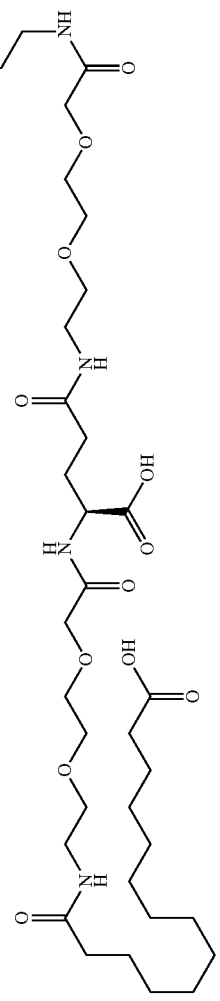

Preparation Method: SPPS_L: SC_L; CP_M1
LCMS: Method LCMS_4: Rt=2.27 min m/z: M/3=1601; M/4=1201;
UPLC Method: B4_1: Rt=9.01 min
UPLC Method: 04_A6_1: Rt=5.08 min Example 87

$N^{\epsilon18}$2-[2-[2-[[2-[2-[2-[[(4S)-4-carboxy-4-[8-(4-carboxy-phenoxy)octanoylamino]butanoyl]amino]ethoxy]ethoxy]acetyl]amino]ethoxy]ethoxy]acetyl], $N^{\epsilon26}$-[2-[2-[2-[[2-[2-[2-[[(4S)-4-carboxy-4-[8-(4-carboxyphenoxy)octanoylamino]butanoyl]amino]ethoxy]ethoxy]acetyl]amino]ethoxy]ethoxy]acetyl]-[Aib$^8$,Lys$^{18}$,Glu$^{22}$,Gln$^{34}$]-GLP-1-(7-37)-peptide (SEQ ID NO: 7)

Chem. 106

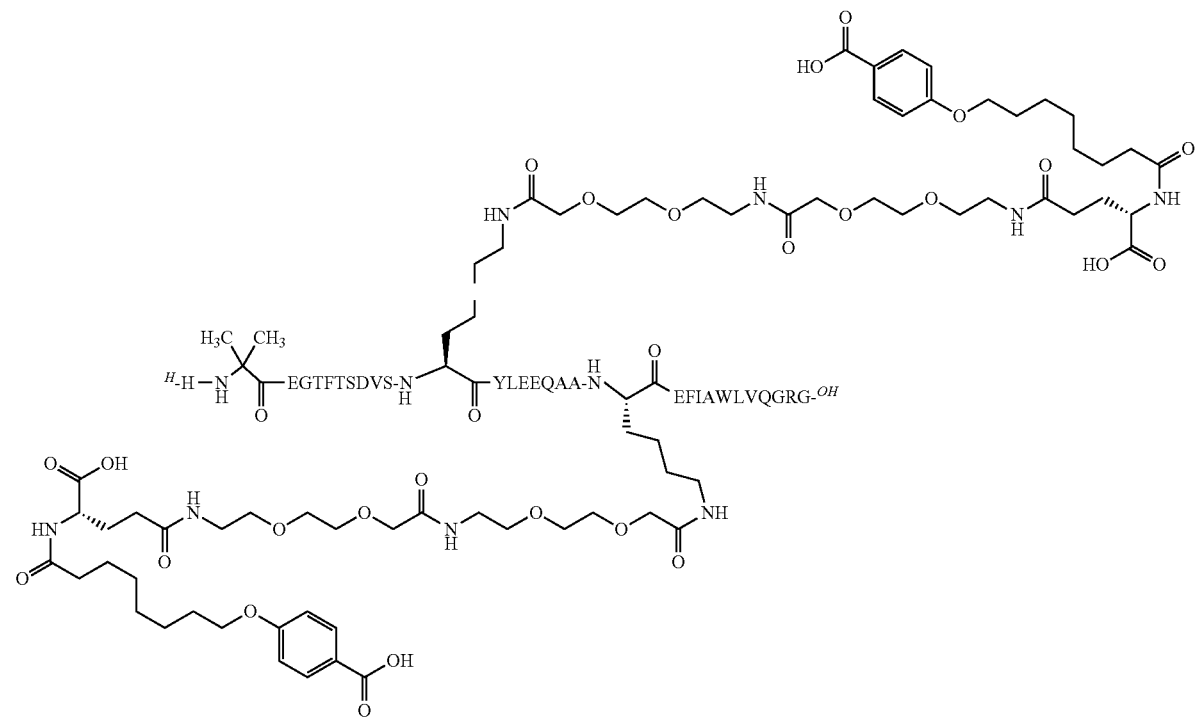

Preparation Method: SPPS_L: SC_L: CP_M1

The theoretical molecular mass of 4846.4 Da was confirmed by MALDI_MS: m/z: 4846.3

UPLC Method: B4_1: Rt=8.26 min
UPLC Method: 04_A6_1: Rt=3.93 min

Example 88

$N^{\epsilon18}$-[2-[2-[2-[[2-[2-[2-[[(4S)-4-carboxy-4-[10-(4-carboxy-phenoxy)decanoylamino]butanoyl]amino]ethoxy]ethoxy]acetyl]amino]ethoxy]ethoxy]acetyl], $N^{\epsilon26}$-[2-[2-[2-[[2-[2-[2-[[(4S)-4-carboxy-4-[10-(4-carboxyphenoxy)decanoylamino]butanoyl]amino]ethoxy]ethoxy]acetyl]amino]ethoxy]ethoxy]acetyl]-[Aib$^8$,Lys$^{18}$,Glu$^{22}$,Arg$^{34}$]-GLP-1-(7-37)-peptide (SEQ ID NO: 53)

Chem. 107

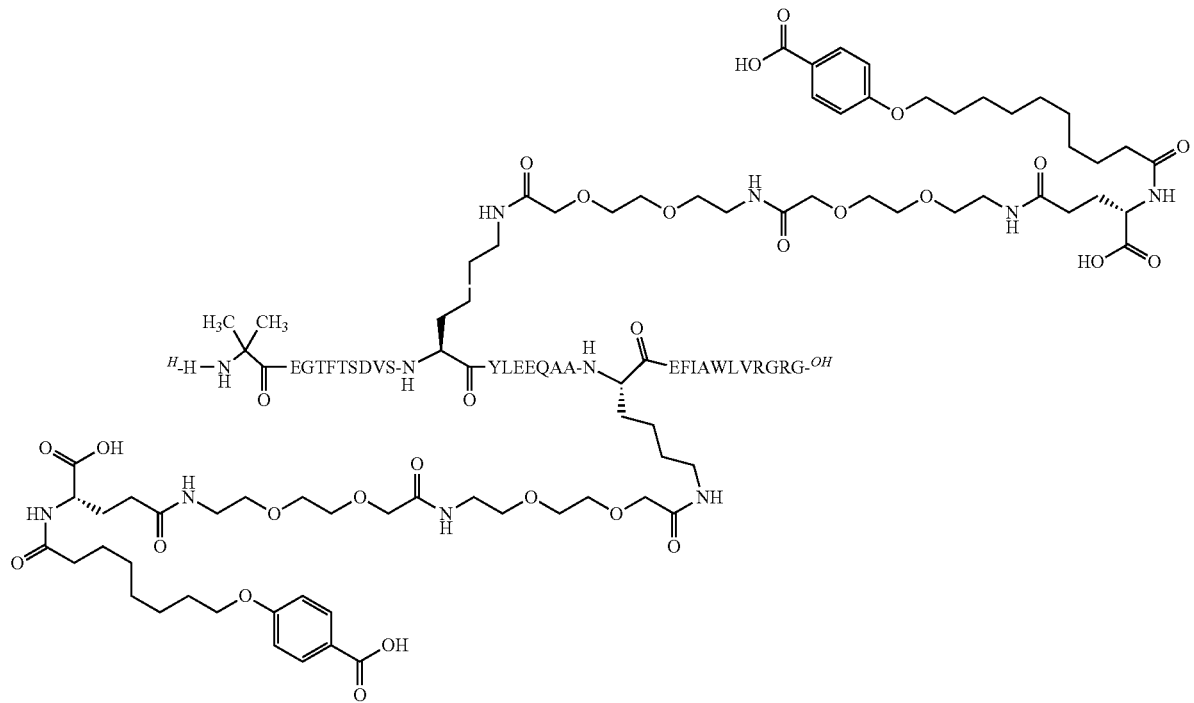

Preparation Method: SPPS_L: SC_L: CP_M1
LCMS: Method LCMS_4: Rt=2.03 min, m/z: 4930.6
UPLC Method: B4_1: Rt=8.63 min
UPLC Method: 04_A6_1: Rt=5.31 min Example 89

$N^{\epsilon18}$-[2-[2-[2-[[2-[2-[2-[[(4S)-4-carboxy-4-[8-(4-carboxyphenoxy)octanoylamino]butanoyl]amino]ethoxy]ethoxy]acetyl]amino]ethoxy]ethoxy]acetyl], $N^{\epsilon26}$-[2-[2-[2-[[2-[2-[2-[[(4S)-4-carboxy-4-[8-(4-carboxyphenoxy)octanoylamino]butanoyl]amino]ethoxy]ethoxy]acetyl]amino]ethoxy]ethoxy]acetyl]-[Lys$^{18}$,Glu$^{22}$,Gln$^{34}$]-GLP-1-(7-37)-peptide (SEQ ID NO: 32)

Chem. 108
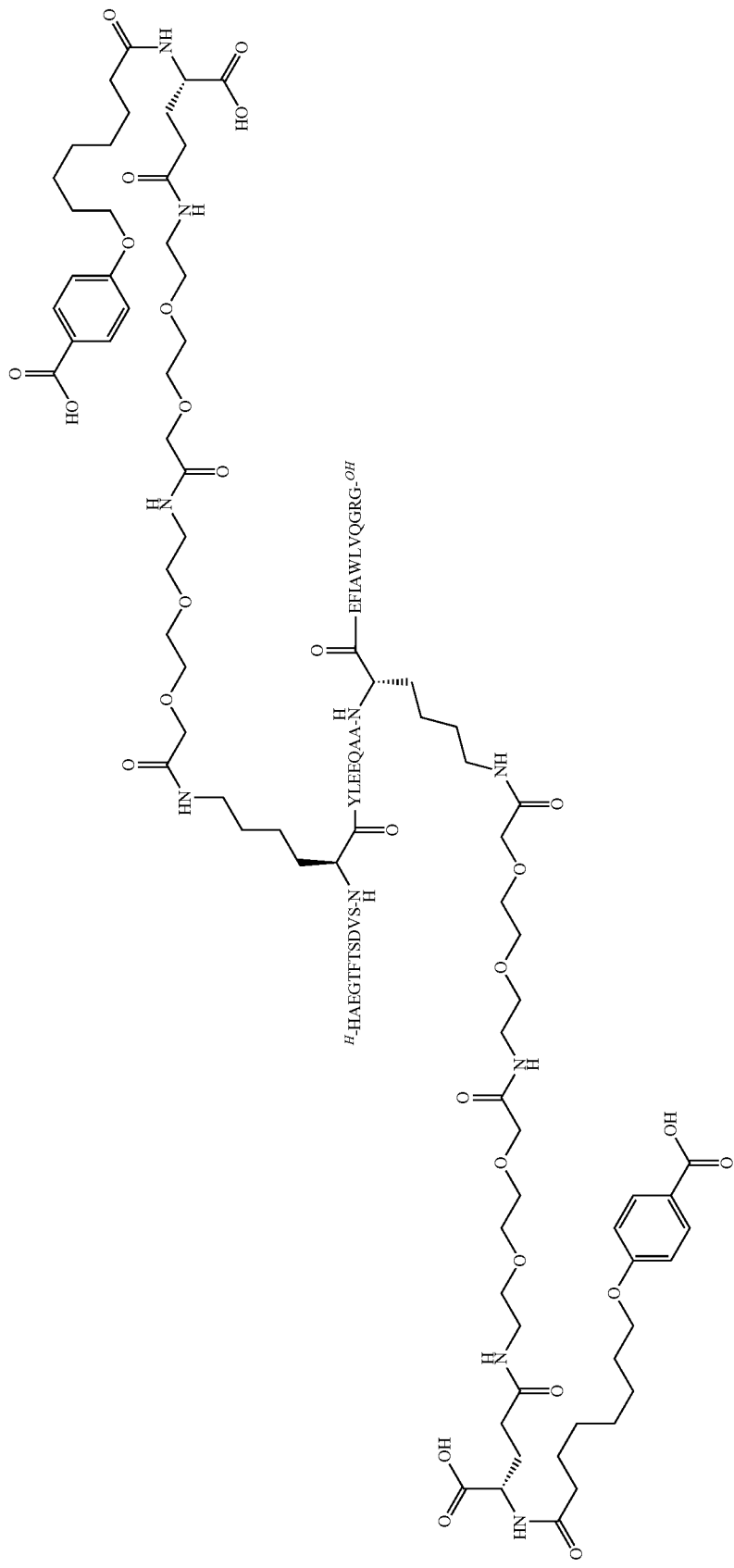

Preparation Method: SPPS_L; SC_L; CP_M1
LCMS: Method: LC/MS_4: Rt=2.13 min m/z: 4832.3; M/3: 1611; M/4: 1209
UPLC: Method: B4_1: Rt=8.23 min
UPLC: Method: 04_A6_1: Rt=3.77 min
UPLC: Method: 04_A7_1: Rt=4.90 min Example 90

$N^{\epsilon 18}$-[2-[2-[2-[[(4S)-4-carboxy-4-[[2-[2-[2-[10-(4-carboxyphenoxy)decanoylamino]ethoxy]ethoxy]acetyl]amino]butanoyl]amino]ethoxy]ethoxy]acetyl], $N^{\epsilon 26}$-[2-[2-[2-[[(4S)-4-carboxy-4-[[2-[2-[2-[10-(4-carboxyphenoxy)decanoylamino]ethoxy]ethoxy]acetyl]amino]butanoyl]amino]ethoxy]ethoxy]acetyl]-[Aib$^8$,Lys$^{18}$,Glu$^{22}$,Gln$^{34}$]-GLP-1-(7-37)-peptide (SEQ ID NO: 7)

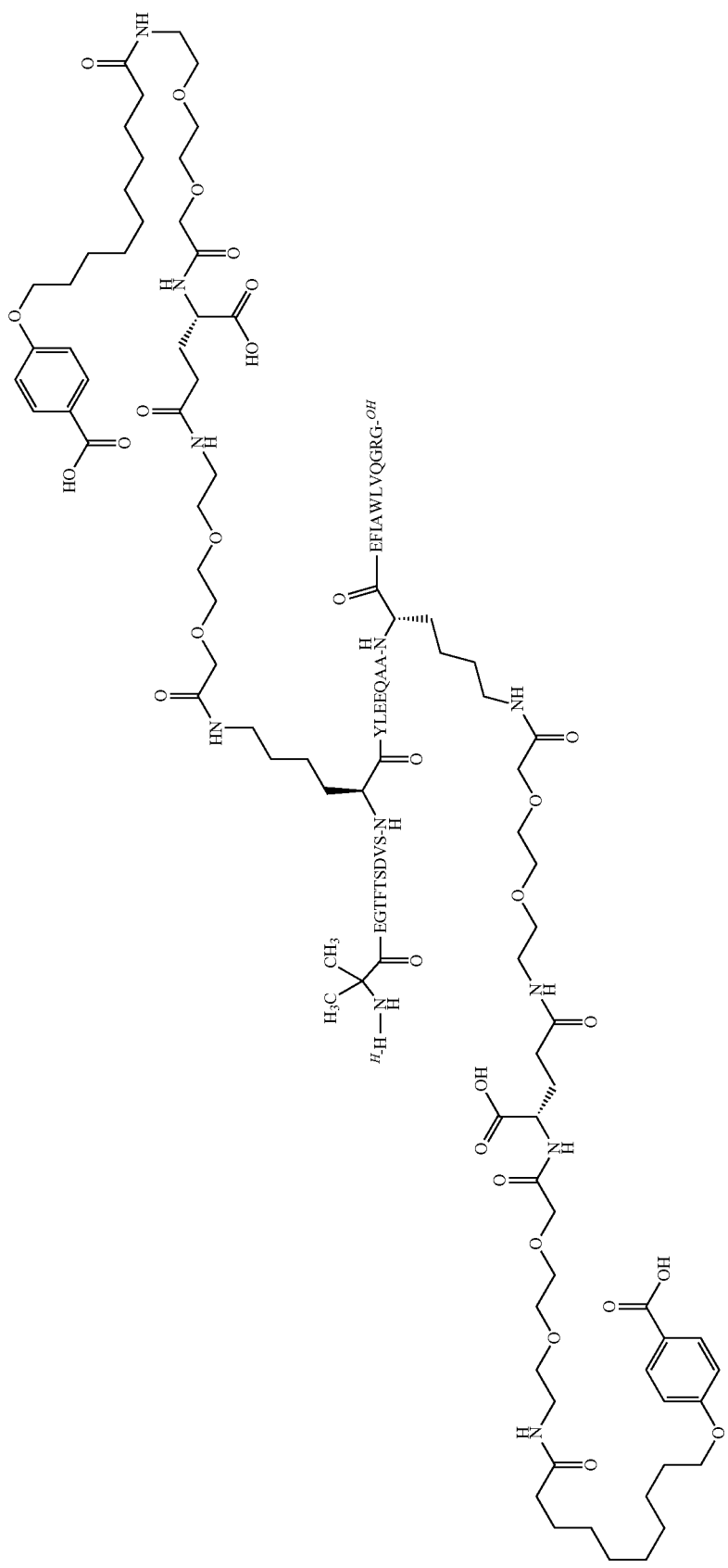
Chem. 109

Preparation Method: SPPS_L: SC_L: CP_M1
LCMS: Method: LCMS_4: Rt=2.32 min, m/z: 4902.4
UPLC Method: B4_1 Rt=8.95 min
UPLC Method: 04_A6_1 Rt=4.97 min Example 91

$N^{\epsilon 18}$-[2-[2-[2-[[2-[2-[2-[[(4S)-4-carboxy-4-[[(4S)-4-carboxy-4-[[(4S)-4-carboxy-4-(13-carboxytridecanoylamino)butanoyl]amino]butanoyl]amino]butanoyl]amino]ethoxy]ethoxy]acetyl], amino]ethoxy]ethoxy]acetyl], $N^{\epsilon 31}$-[2-[2-[2-[[2-[2-[2-[[(4S)-4-carboxy-4-[[(4S)-4-carboxy-4-[[(4S)-4-carboxy-4-(13-carboxytridecanoylamino)butanoyl]amino]butanoyl]amino]butanoyl]amino]ethoxy]ethoxy]acetyl], amino]ethoxy]ethoxy]acetyl]-[Lys$^{18}$,Arg$^{26}$,Lys$^{31}$,Arg$^{34}$]-GLP-1-(7-37)-peptide (SEQ ID NO: 48)

Chem. 110
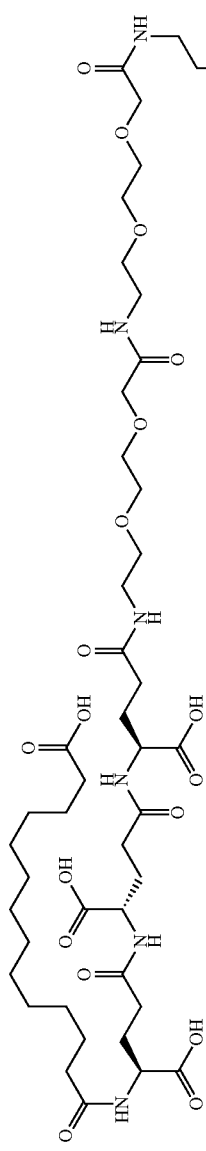
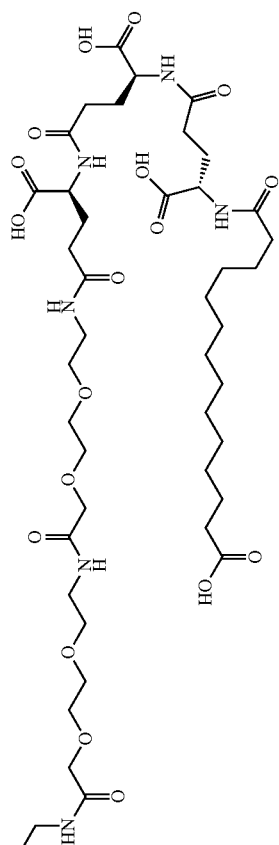

Preparation Method: SPPS_P, SC_P, CP_M1
The theoretical molecular mass of 5230 Da was confirmed by MALDI_MS: m/z: 5230
UPLC Method: B4_1: Rt=7.56 min
UPLC Method: 04_A6_1: Rt=3.9 min Example 92

$N^{\epsilon 18}$-[2-[2-[2-[[2-[2-[2-[[(4S)-4-carboxy-4-[10-(4-carboxyphenoxy)decanoylamino]butanoyl]amino]ethoxy]ethoxy]acetyl]amino]ethoxy]ethoxy]acetyl], $N^{\epsilon 26}$-[2-[2-[2-[[2-[2-[2-[[(4S)-4-carboxy-4-[10-(4-carboxyphenoxy)decanoylamino]butanoyl]amino]ethoxy]ethoxy]acetyl]amino]ethoxy]ethoxy]acetyl]-[Aib$^8$,Lys$^{18}$,Gln$^{34}$]-GLP-1-(7-37)-peptide (SEQ ID NO: 54)

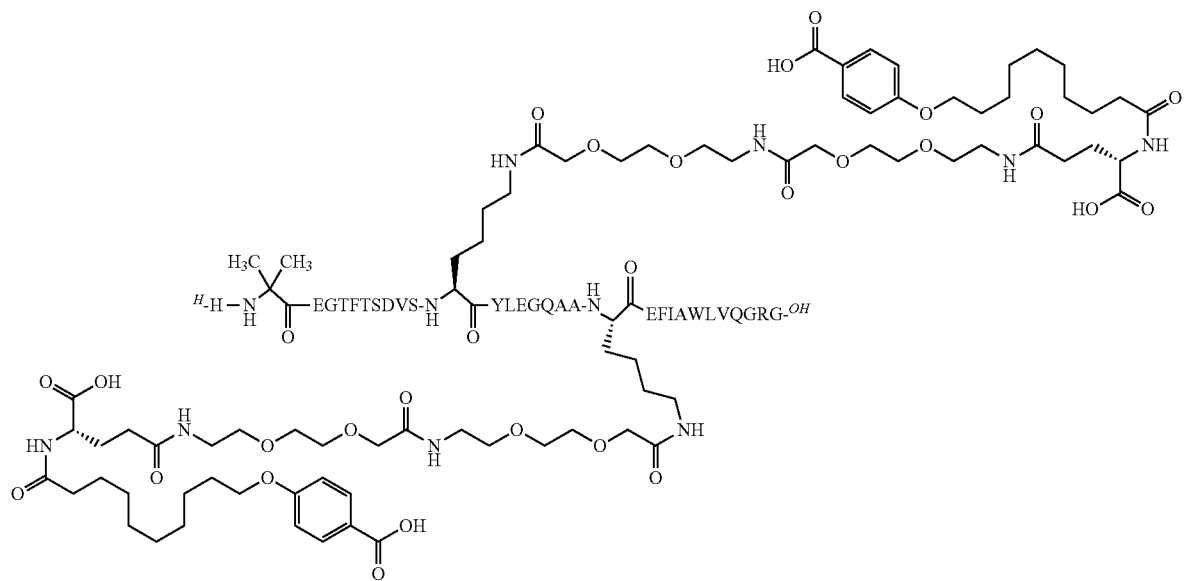

Chem. 111

Preparation Method: SPPS_L: SC_L: CP_M1
LCMS: Method LCMS_4: Rt=2.29 min, m/z: 4829.2
UPLC Method: B4$_{13}$_1: Rt=8.90 min
UPLC Method: 04_A6_1: Rt=5.39 min Example 93

$N^{\epsilon 18}$-[2-[2-[2-[[2-[2-[2-[[(4S)-4-carboxy-4-[10-(4-carboxyphenoxy)decanoylamino]butanoyl]amino]ethoxy]ethoxy]acetyl]amino]ethoxy]ethoxy]acetyl], $N^{\epsilon 26}$-[2-[2-[2-[[2-[2-[2-[[(4S)-4-carboxy-4-[10-(4-carboxyphenoxy)decanoylamino]butanoyl]amino]ethoxy]ethoxy]acetyl]amino]ethoxy]ethoxy]acetyl]-[Aib$^8$,Lys$^{18}$,Arg$^{34}$]-GLP-1-(7-37)-peptide (SEQ ID NO: 55)

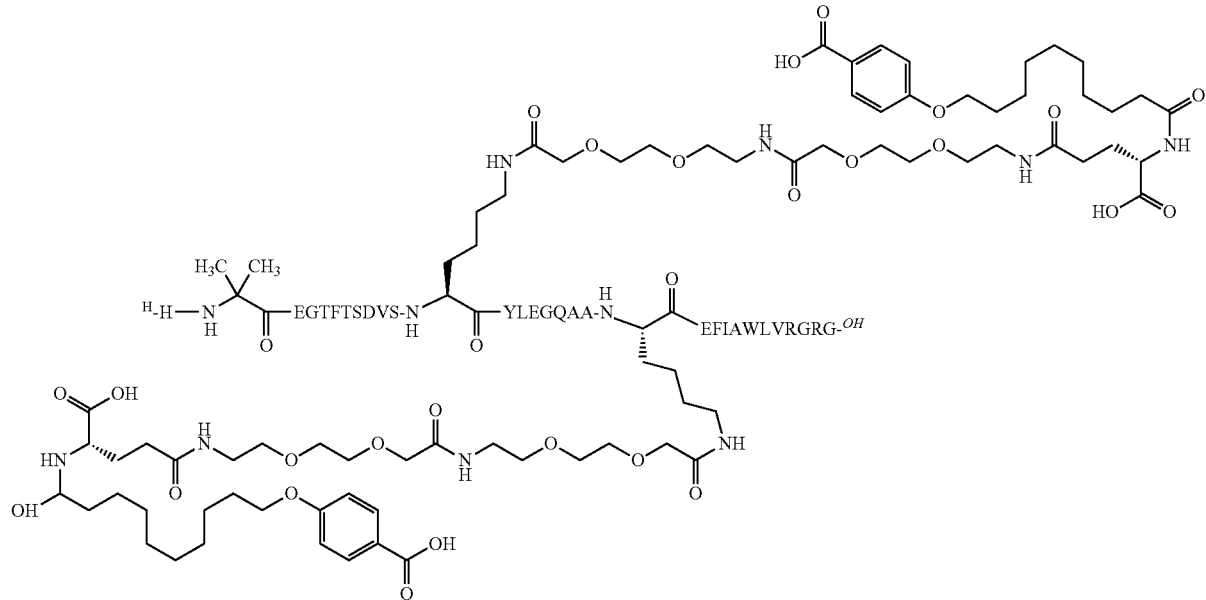

Preparation Method: SPPS_L: SC_L: CP_M1
LCMS: Method LCMS_4: Rt=2.18 min, m/z: 4858.4
UPLC Method: B4_1: Rt=8.56 min
UPLC Method: O4_A6_1: Rt=5.26 min Example 94

$N^{\epsilon 18}$-[2-[2-[2-[[2-[2-[2-[[(4S)-4-carboxy-4-[10-(4-carboxy-phenoxy)decanoylamino]butanoyl]amino]ethoxy]ethoxy]acetyl]amino]ethoxy]ethoxy]acetyl], $N^{\epsilon 26}$-[2-[2-[2-[[2-[2-[2-[[(4S)-4-carboxy-4-[10-(4-carboxyphenoxy)decanoylamino]butanoyl]amino]ethoxy]ethoxy]acetyl]amino]ethoxy]ethoxy]acetyl]-[Lys$^{18}$,Glu$^{22}$,Arg$^{34}$]-GLP-1-(7-37)-peptide (SEQ ID NO: 56)

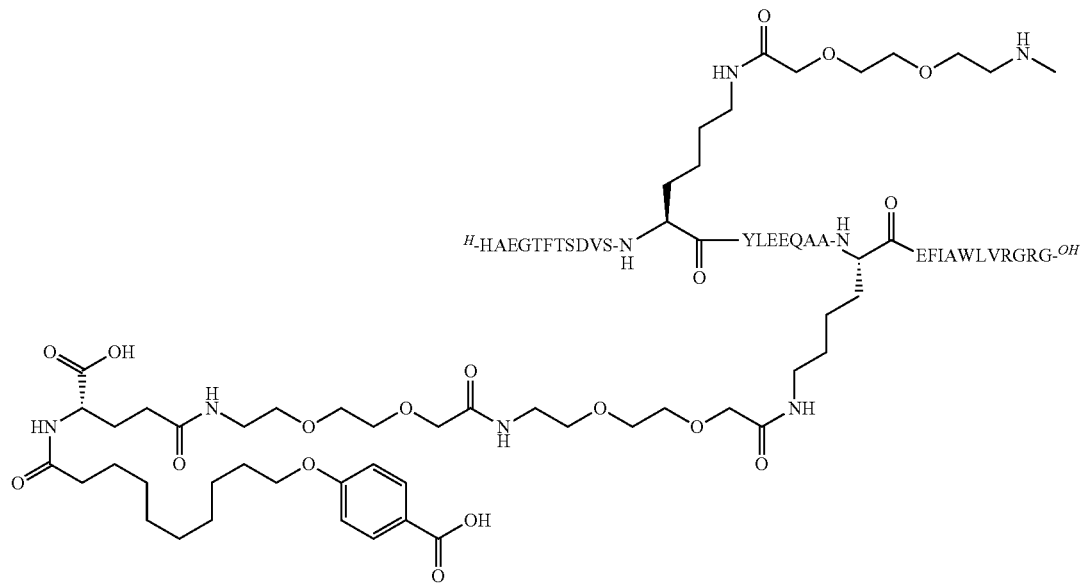

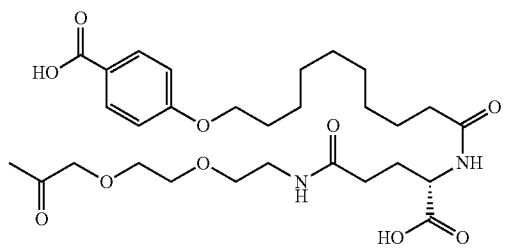

Preparation Method: SPPS_L: SC_L: CP_M1
LCMS: Method LCMS_4: Rt=2.17 min, m/z: 4916.5
UPLC Method: B4_1: Rt=8.51 min Example 95

$N^{\epsilon 18}$-[2-[2-[2-[[2-[2-[2-[[(4S)-4-carboxy-4-[10-(4-carboxyphenoxy)decanoylamino]butanoyl]amino]ethoxy]ethoxy]acetyl]amino]ethoxy]ethoxy]acetyl], $N^{\epsilon 26}$-[2-[2-[2-[[2-[2-[2-[[(4S)-4-carboxy-4-[10-(4-carboxyphenoxy)decanoylamino]butanoyl]amino]ethoxy]ethoxy]acetyl]amino]ethoxy]ethoxy]acetyl]-[Lys$^{18}$,Arg$^{34}$]-GLP-1-(7-37)-peptide (SEQ ID NO: 57)

Chem. 114

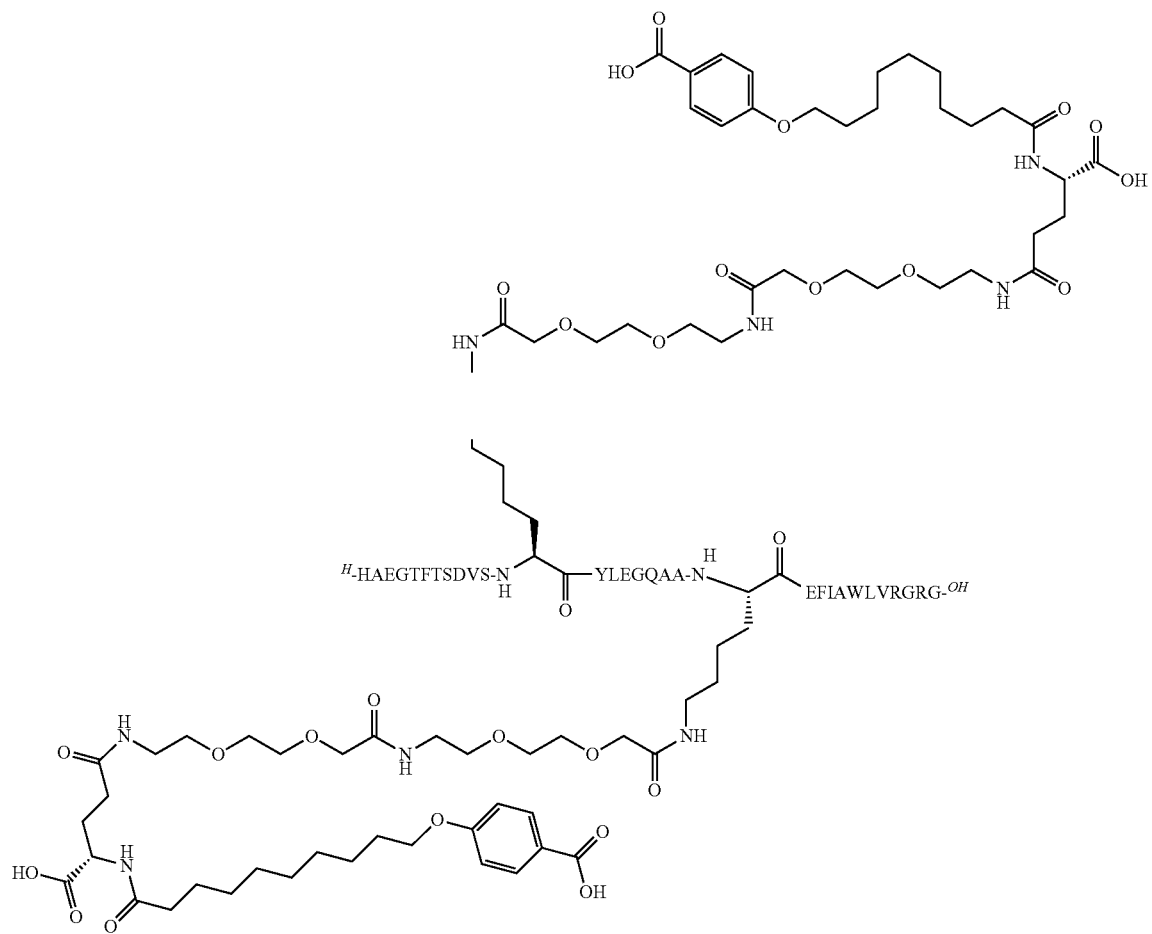

Preparation Method: SPPS_L: SC_L: CP_M1

The theoretical molecular mass of 4448.5 Da was confirmed by MALDI-MS (alpha-cyano): m/z: 4448.9

UPLC Method: B4_1: Rt=8.53 min

UPLC Method: 04_A6_1: Rt=5.73 min

Example 96

$N^{\epsilon 18}$-[2-[2-[2-[[2-[2-[2-[[(4S)-4-carboxy-4-(13-carboxytridecanoylamino)butanoyl]amino]ethoxy]ethoxy]acetyl]amino]ethoxy]ethoxy]acetyl], $N^{\epsilon 26}$-[2-[2-[2-[[2-[2-[2-[[(4S)-4-carboxy-4-(13-carboxytridecanoylamino)butanoyl]amino]ethoxy]ethoxy]acetyl]amino]ethoxy]ethoxy]acetyl]-[Lys$^{18}$,Glu$^{22}$,Arg$^{34}$]-GLP-1-(7-37)-peptide (SEQ ID NO: 56)

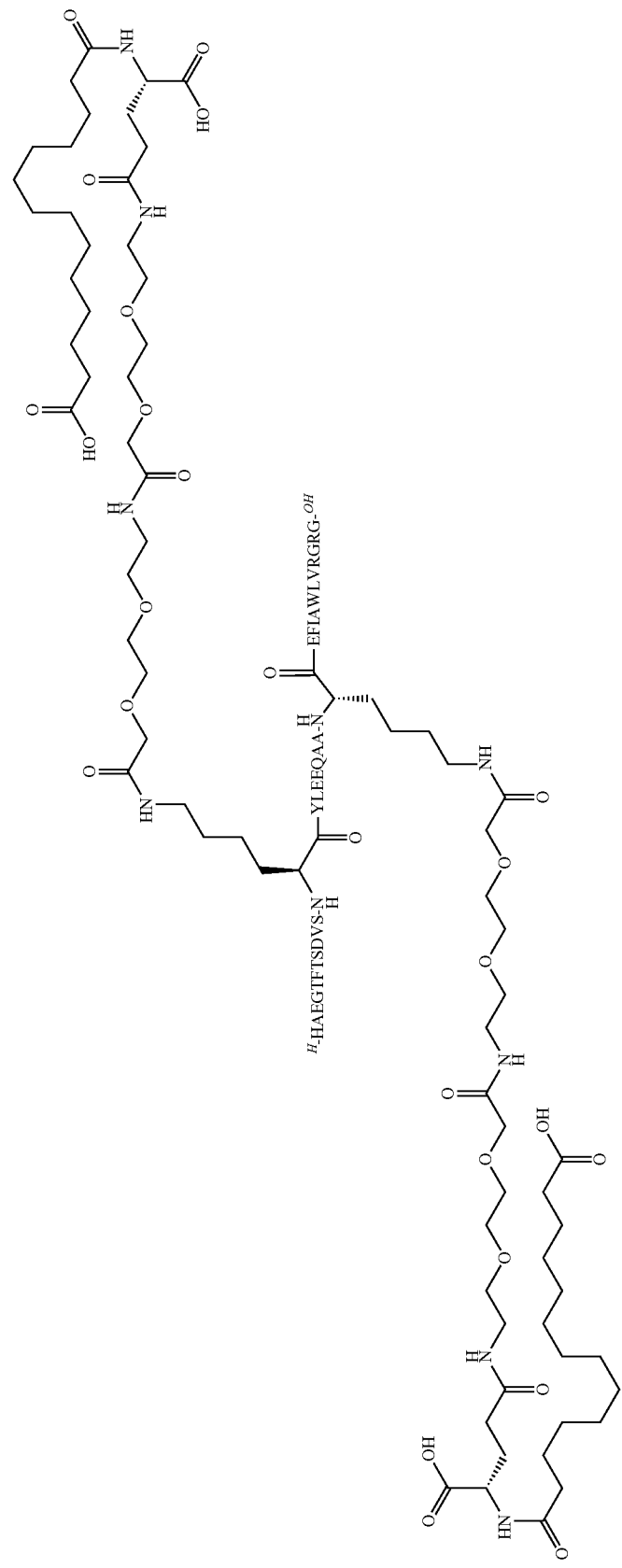

Preparation Method: SPPS_L, SC_L, CP_M1
LCMS: Method LC-MS_4: Rt=2.23 min m/z: 4816.10 (calc. 4816.4766 Da)
UPLC Method: 05_B5_1: Rt=5.803 min
UPLC Method: 04_A6_1: Rt=5.847 min

Example 97

$N^{\epsilon18}$-[2-[2-[2-[[2-[2-[2-[[(4S)-4-carboxy-4-[[(4S)-4-carboxy-4-(13-carboxytridecanoylamino)butanoyl]amino]butanoyl]amino]ethoxy]ethoxy]acetyl]amino]ethoxy]ethoxy]acetyl], $N^{\epsilon26}$-[2-[2-[2-[[2-[2-[2-[[(4S)-4-carboxy-4-[[(4S)-4-carboxy-4-(13-carboxytridecanoylamino)butanoyl]amino]butanoyl]amino]ethoxy]ethoxy]acetyl]amino]ethoxy]ethoxy]acetyl]-[Lys,Glu$^{22}$,Arg$^{34}$]-GLP-1-(7-37)-peptide (SEQ ID NO: 56)

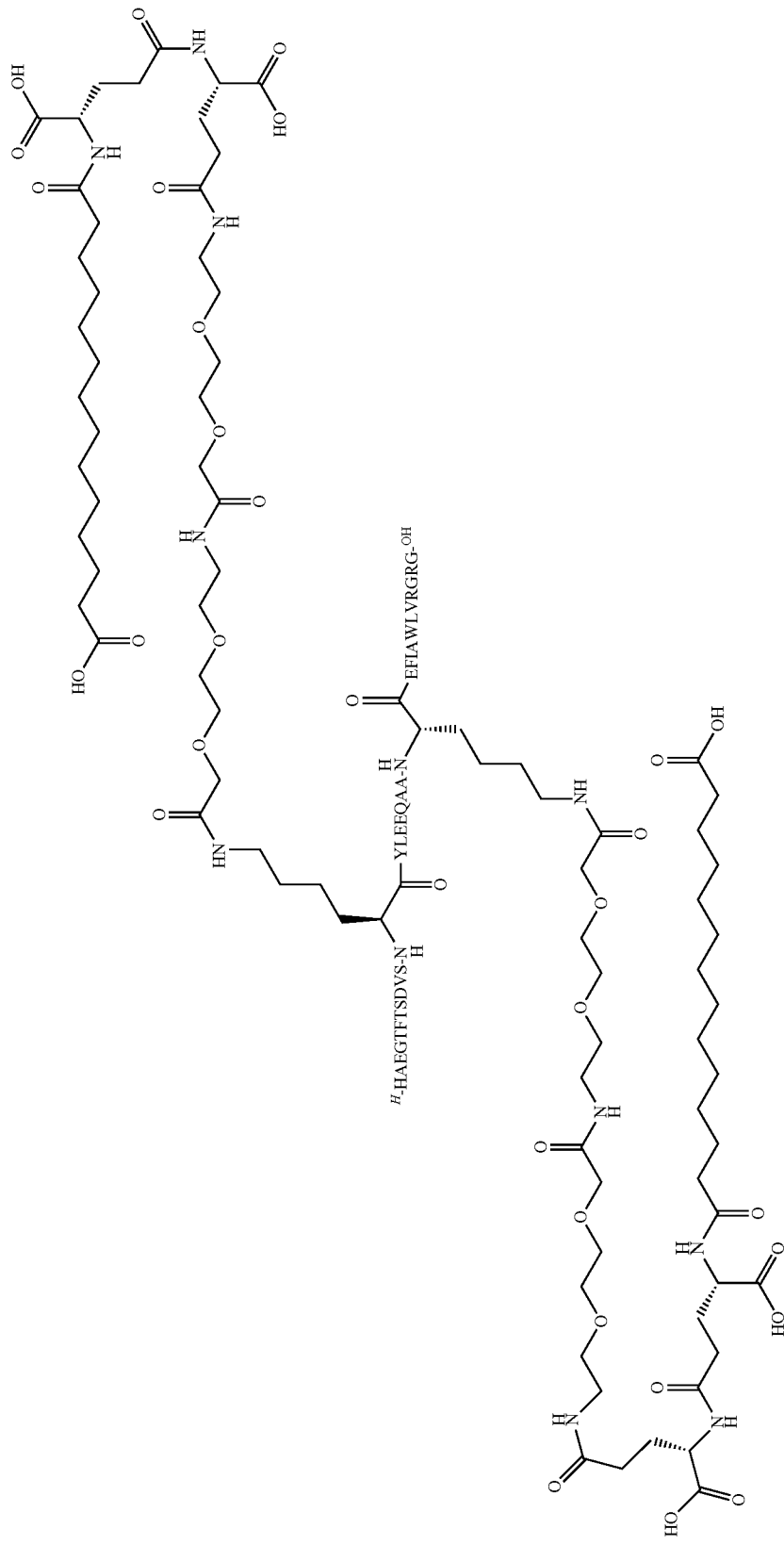
Chem. 116

Preparation Method: SPPS_L, SC_L, CP_M1
LCMS_4: Rt=2.22 min m/z: 5073.50,
　　UPLC Method: B4_13_1: Rt=11.06 min
　　UPLC Method: 05_B5_1: Rt=4.77 min

Example 98

$N^{\epsilon 18}$-[2-[2-[2-[[2-[2-[2-[[2-[2-[2-[[2-[2-[2-[[(4S)-4-carboxy-4-(13-carboxytridecanoylamino)butanoyl]amino]ethoxy]ethoxy]acetyl]amino]ethoxy]ethoxy]acetyl]amino]ethoxy]ethoxy]acetyl]amino]ethoxy]ethoxy]acetyl], $N^{\epsilon 31}$-[2-[2-[2-[[2-[2-[2-[[2-[2-[2-[[2-[2-[2-[[(4S)-4-carboxy-4-(13-carboxytridecanoylamino)butanoyl]amino]ethoxy]ethoxy]acetyl]amino]ethoxy]ethoxy]acetyl]amino]ethoxy]ethoxy]acetyl]amino]ethoxy]ethoxy]acetyl]-[Lys$^{18}$,Glu$^{22}$,Val$^{25}$,Arg$^{26}$,Lys$^{31}$,Arg$^{34}$]-GLP-1-(7-37)-peptide (SEQ ID NO: 10)

[Chem. 117]
317
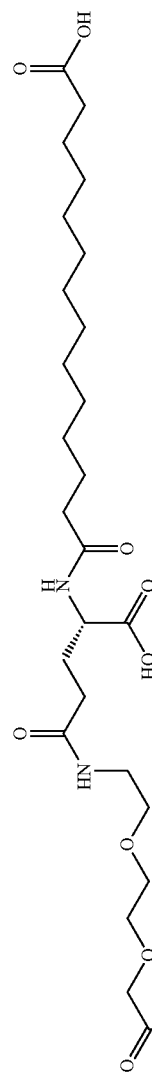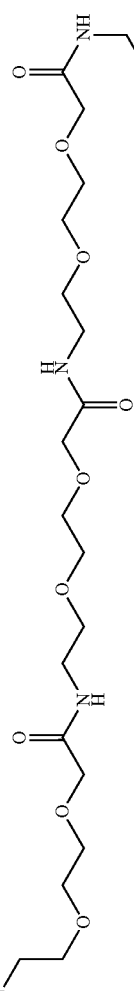
318
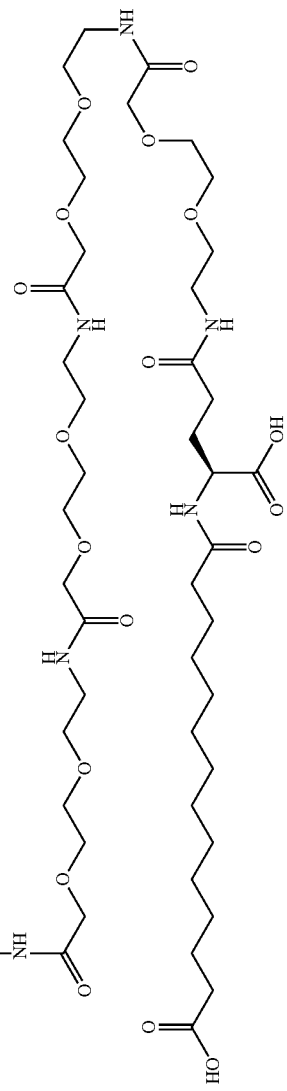

Preparation Method: SPPS_L: SC_L; CP_M1
LCMS: Method: LCMS_4: Rt=2.03 min m/z: 5395; M/4=1350; M/5=1080
UPLC Method: B4_1: Rt=8.08 min
UPLC Method: 04_A6_1: Rt=4.59 min Example 99

$N^{\epsilon 18}$-[2-[2-[2-[[2-[2-[2-[[2-[2-[2-[[2-[2-[2-[[2-[2-[[(4S)-4-carboxy-4-(13-carboxytridecanoylamino)butanoyl]amino]ethoxy]ethoxy]acetyl]amino]ethoxy]ethoxy]acetyl]amino]ethoxy]ethoxy]acetyl]amino]ethoxy]ethoxy]acetyl]amino]ethoxy]ethoxy]acetyl]amino]ethoxy]ethoxy]acetyl], $N^{\epsilon 31}$-[2-[2-[2-[[2-[2-[2-[[2-[2-[2-[[2-[2-[2-[[2-[2-[2-[[2-[2-[[(4S)-4-carboxy-4-(13-carboxytridecanoylamino)butanoyl]amino]ethoxy]ethoxy]acetyl]amino]ethoxy]ethoxy]acetyl]amino]ethoxy]ethoxy]acetyl]amino]ethoxy]ethoxy]acetyl]amino]ethoxy]ethoxy]acetyl]amino]ethoxy]ethoxy]acetyl]-[Lys$^{18}$,Glu$^{22}$,Val$^{25}$,Arg$^{26}$,Lys$^{31}$,Arg$^{34}$]-GLP-1-(7-37)-peptide (SEQ ID NO: 10)

Chem. 118
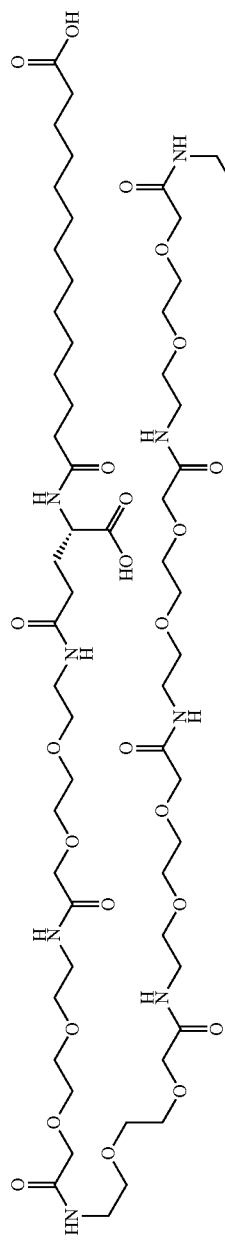
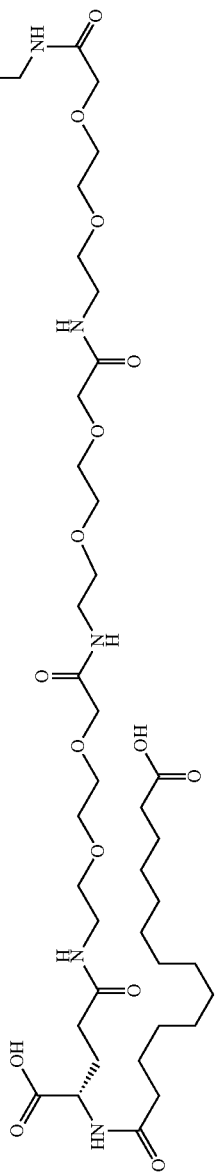

Preparation Method: SPPS_L: SC_L; CP_M1
LCMS: Method: LCMS_4: Rt=2.08 min m/z: 5975.8; M/4: 1494.5; M/5: 1195.6
UPLC: Method: B4_1: Rt=7.89 min
UPLC: Method: 04_A6_1: Rt=5.51 min Example 100

$N^{\epsilon 18}$-[2-[2-[2-[[2-[2-[2-[[(4S)-4-carboxy-4-(13-carboxytridecanoylamino)butanoyl]amino]ethoxy]ethoxy]acetyl]amino]ethoxy]ethoxy]acetyl],$N^{\epsilon 26}$-[2-[2-[2-[[2-[2-[2-[[(4S)-4-carboxy-4-(13-carboxytridecanoylamino)butanoyl]amino]ethoxy]ethoxy]acetyl]amino]ethoxy]ethoxy]acetyl], [Aib$^8$,Lys$^{18}$,Glu$^{22}$,Arg$^{34}$]-GLP-1-(7-37)-peptide (SEQ ID NO: 53)

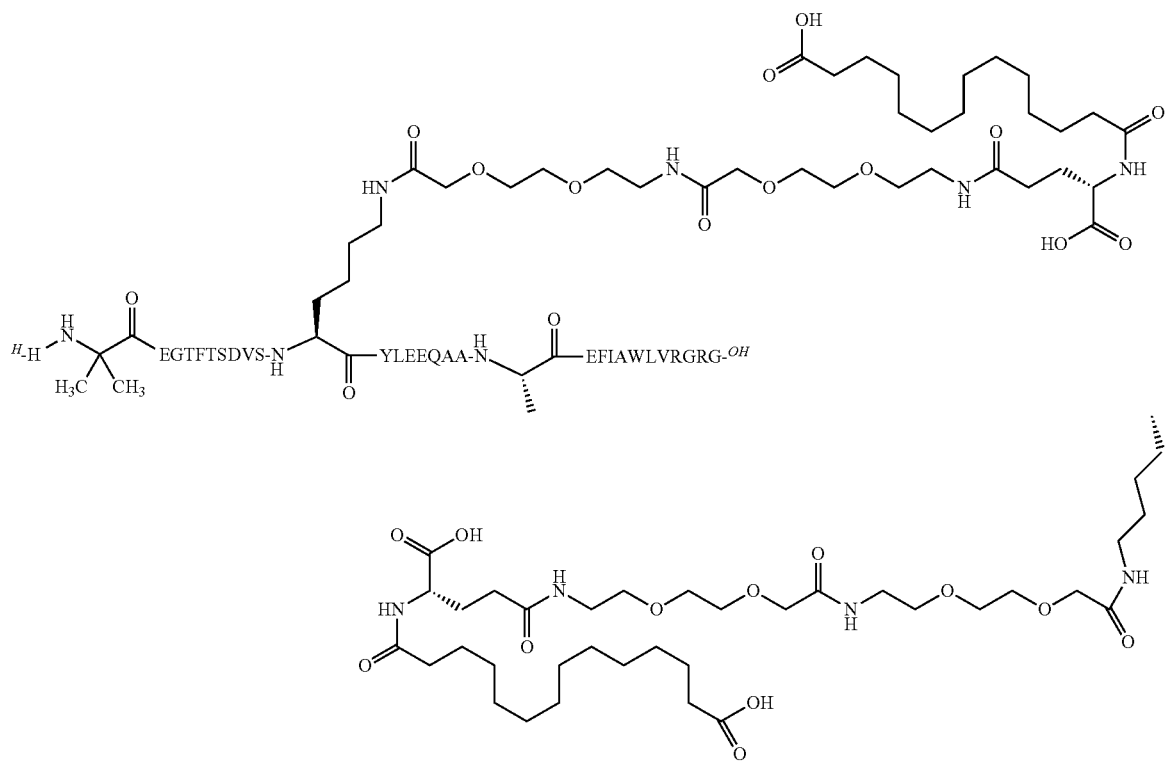

Chem. 119

Preparation Method: SPPS_L: SC_L; CP_M1 LCMS_4: Rt=5.8 min m/z: 1610 (M 3+), 1208 (M 4+) and 966 (M 5+)
UPLC method: 10_B14_1: Rt=6.653 min
UPLC method: B4_1: Rt=8.713 min Example 101

$N^{\epsilon 18}$-[2-[2-[2-[[2-[2-[2-[[(4S)-4-carboxy-4-[[(4S)-4-carboxy-4-[[(4S)-4-carboxy-4-(13-carboxytridecanoylamino)butanoyl]amino]butanoyl]amino]butanoyl]amino]ethoxy]ethoxy]acetyl]amino]ethoxy]ethoxy]acetyl], $N^{\epsilon 31}$-[2-[2-[2-[[2-[2-[2-[[(4S)-4-carboxy-4-[[(4S)-4-carboxy-4-[[(4S)-4-carboxy-4-(13-carboxytridecanoylamino)butanoyl]amino]butanoyl]amino]ethoxy]ethoxy]acetyl]amino]ethoxy]ethoxy]acetyl]-[Lys$^{18}$,Glu$^{22}$,Val$^{25}$,Arg$^{26}$,Lys$^{31}$,Arg$^{34}$]-GLP-1-(7-37)-peptide (SEQ ID NO: 10)

Chem. 120

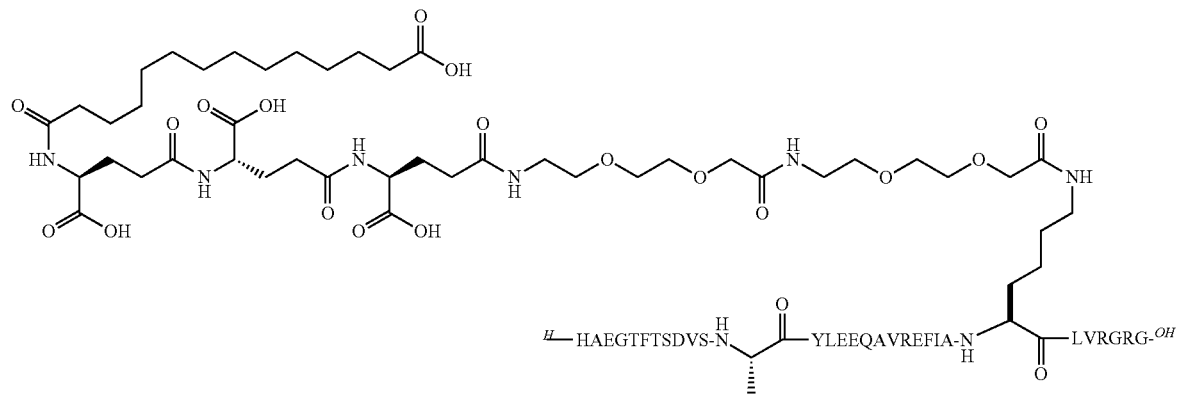

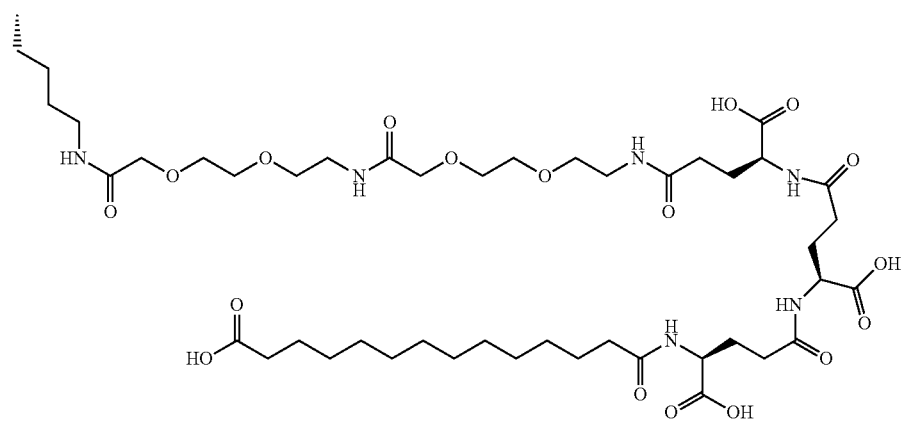

Preparation Method: SPPS_P, SC_P, CP_M1

The theoretical molecular mass of 5331 Da was confirmed by MALDI_MS; m/z: 5330

UPLC Method: B4_1: Rt=7.8 min

UPLC Method: 04_A6_1: Rt=4.03 min

Example 102

$N^{\epsilon 18}$-[2-[2-[2-[[2-[2-[2-[[(4S)-4-carboxy-4-[[(4S)-4-carboxy-4-[[(4S)-4-carboxy-4-(13-carboxytridecanoylamino)butanoyl]amino]butanoyl]amino]butanoyl]amino]ethoxy]ethoxy]acetyl]amino]ethoxy]ethoxy]acetyl], $N^{\epsilon 31}$-[2-[2-[2-[[2-[2-[2-[[(4S)-4-carboxy-4-[[(4S)-4-carboxy-4-[[(4S)-4-carboxy-4-(13-carboxytridecanoylamino)butanoyl]amino]butanoyl]amino]butanoyl]amino]ethoxy]ethoxy]acetyl]amino]ethoxy]ethoxy]acetyl]-[Aib$^8$,Lys$^{18}$,Glu$^{22}$,Val$^{25}$,Arg$^{26}$,Lys$^{31}$,Arg$^{34}$]-GLP-1-(7-37)-peptide (SEQ ID NO: 12)

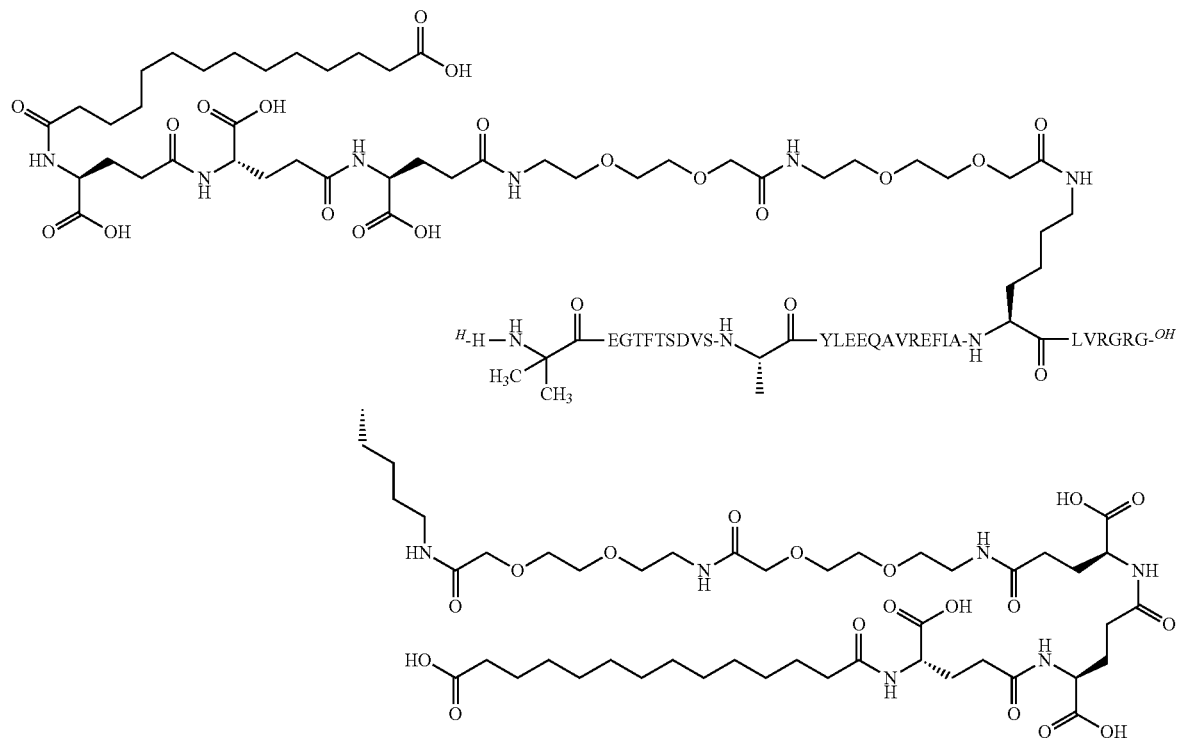

Preparation Method: SPPS_P, SC_P, CP_M1
The theoretical molecular mass of 5345 Da was confirmed by MALDI_MS: m/z: 5344
UPLC Method B4_1: Rt=7.8 min
UPLC Method 04_A6_1: Rt=4.1 min Example 103

$N^{\epsilon 18}$-[2-[2-[2-[[2-[2-[2-[[(4S)-4-carboxy-4-[[(4S)-4-carboxy-4-(13-carboxytridecanoylamino)butanoyl]amino]butanoyl]amino]ethoxy]ethoxy]acetyl]amino]ethoxy]ethoxy]acetyl], $N^{\epsilon 26}$-[2-[2-[2-[[2-[2-[2-[[(4S)-4-carboxy-4-[[(4S)-4-carboxy-4-(13-carboxytridecanoylamino)butanoyl]amino]butanoyl]amino]ethoxy]ethoxy]acetyl]amino]ethoxy]ethoxy]acetyl]-[Aib$^8$,Lys$^{18}$,Arg$^{34}$]-GLP-1-(7-37)-peptide (SEQ ID NO: 55)

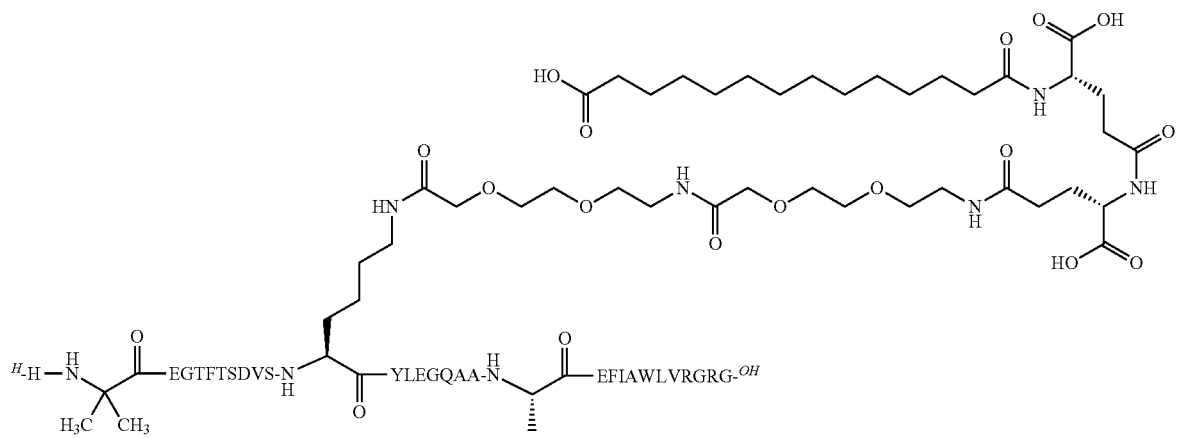

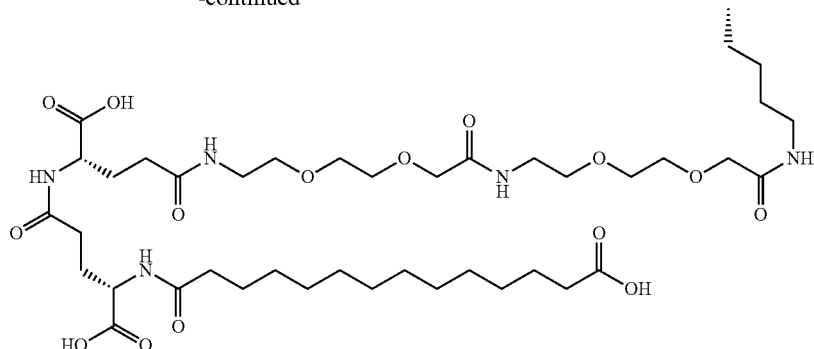

Preparation method: SPPS_Å, SC_Å, CP_M1
LCMS: method LCMS_4: Rt=2.22 min m/z: 5016, M/4: 1254.6; M/5: 1004.1
UPLC method: 10_B14_1: Rt=5.07 min
UPLC method: 04_A6_1: Rt=4.71 min Example 104

$N^{\epsilon 18}$-[(4S)-4-carboxy-4-[[2-[2-[2-[[2-[2-[2-(13-carboxytridecanoylamino)ethoxy]ethoxy]acetyl]amino]ethoxy]ethoxy]acetyl]amino]butanoyl], $N^{\epsilon 31}$-[(4S)-4-carboxy-4-[[2-[2-[2-[[2-[2-[2-(13-carboxytridecanoylamino)ethoxy]ethoxy]acetyl]amino]ethoxy]ethoxy]acetyl]amino]butanoyl]-[Lys$^{18}$,Val$^{25}$,Arg$^{26}$,Lys$^{31}$,Arg$^{34}$]-GLP-1-(7-37)-peptide (SEQ ID NO: 49)

Chem. 123

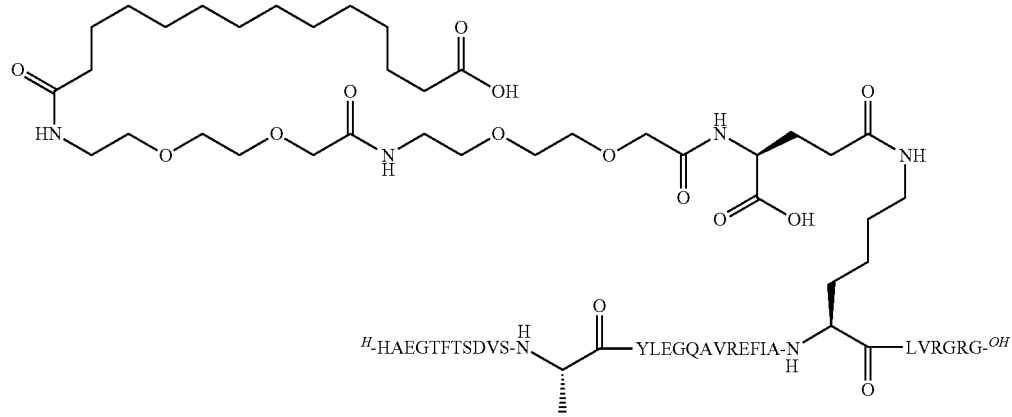

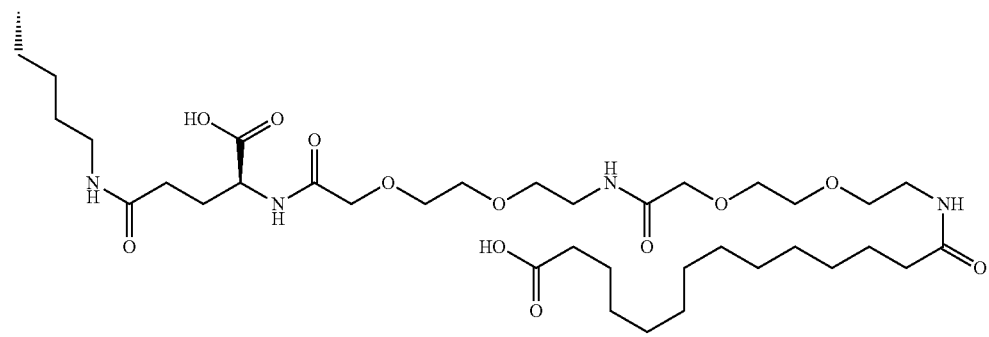

Preparation Method: SPPS_L: SC_L: CP_M1
LCMS: Method: LCMS_4: Rt=2.27 min, m/z: 4742.5
UPLC Method: B4_1: Rt=9.47 min
UPLC Method: 05_B9_1: Rt=8.19 min Example 105

$N^{\epsilon 18}$-[2-[2-[2-[[2-[2-[2-[[(4R)-4-carboxy-4-[[(4S)-4-carboxy-4-(13-carboxytridecanoylamino)butanoyl]amino]butanoyl]amino]ethoxy]ethoxy]acetyl]amino]ethoxy]ethoxy]acetyl], $N^{\epsilon 26}$-[2-[2-[2-[[2-[2-[2-[[(4R)-4-carboxy-4-[[(4S)-4-carboxy-4-(13-carboxytridecanoylamino)butanoyl]amino]butanoyl]amino]ethoxy]ethoxy]acetyl]amino]ethoxy]ethoxy]acetyl]-[Aib$^8$,Lys18,Glu22,Gln34]-GLP-1-(7-37)-peptide (SEQ ID NO: 7)

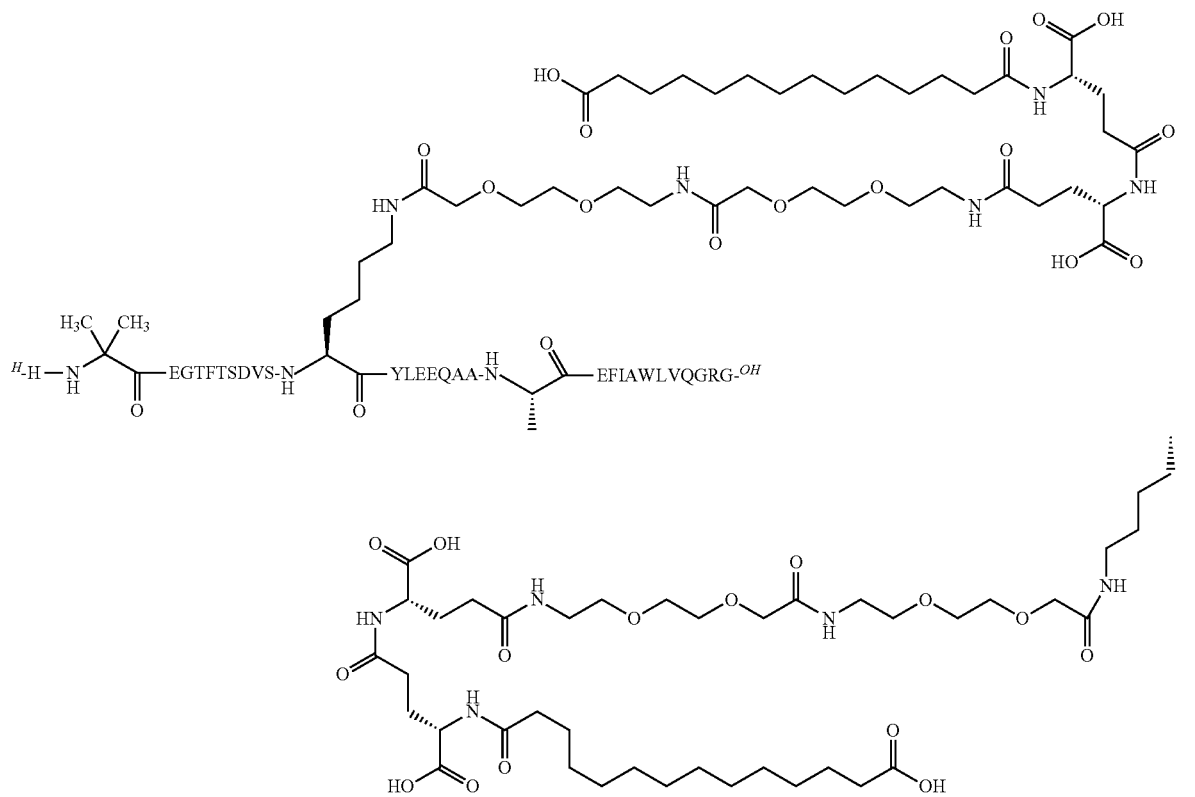

Chem. 124

Preparation Method: SPPS_L, SC-L, CP_M1

LCMS: Method LCMS_4: Rt=2.34 min m/z: m/z: 5060.27 (calc. 5060.6795)

UPLC Method: B4_1: Rt=8.811 min
UPLC Method: 05_B5_1: Rt=5.237 min

Example 106

$N^{\epsilon 18}$-[(4S)-4-carboxy-4-[[2-[2-[2-[[2-[2-[2-[10-(4-carboxyphenoxy)decanoylamino]ethoxy]ethoxy]acetyl]amino]ethoxy]ethoxy]acetyl]amino]butanoyl], $N^{\epsilon 26}$-[(4S)-4-carboxy-4-[[2-[2-[2-[[2-[2-[2-[10-(4-carboxyphenoxy)decanoylamino]ethoxy]ethoxy]acetyl]amino]ethoxy]ethoxy]acetyl]amino]butanoyl]-[Lys$^{18}$,Arg$^{34}$]-GLP-1-(7-37)-peptide (SEQ ID NO: 57)

Chem. 125

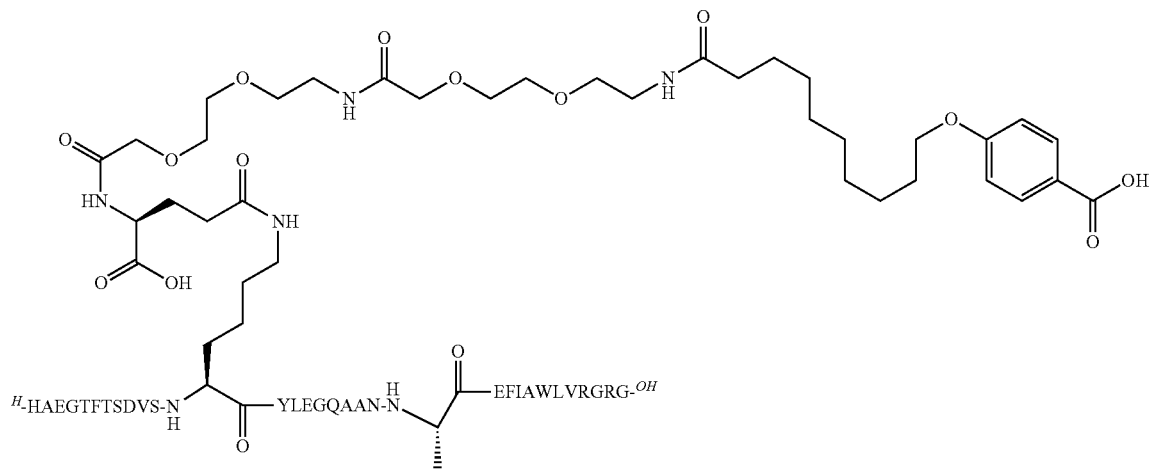

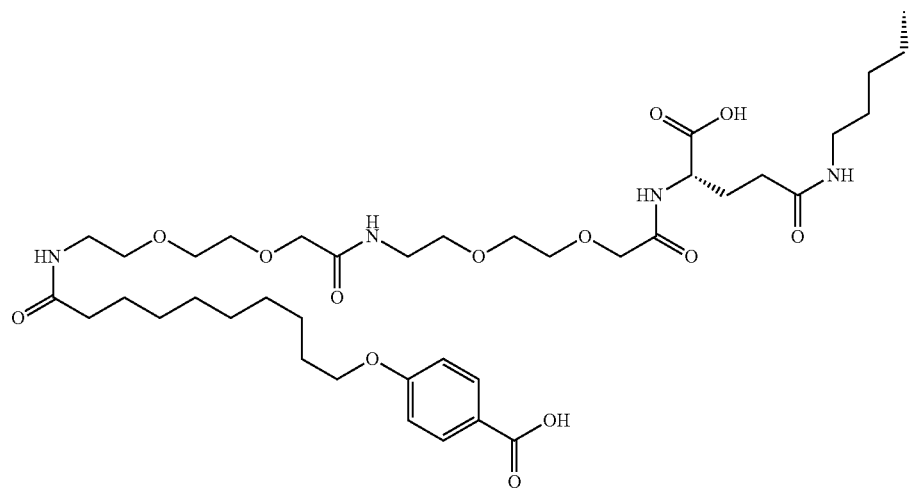

Preparation Method: SPPS_L: SC_L: CP_M1
LCMS: Method: LCMS_4: Rt=2.27 min, m/z: 4843.2
UPLC Method: B4_1: Rt=8.71 min Example 107

$N^{\epsilon 18}$-[2-[2-[2-[[2-[2-[2-[[(4S)-4-carboxy-4-[10-(4-carboxyphenoxy)decanoylamino]butanoyl]amino]ethoxy]ethoxy]acetyl]amino]ethoxy]ethoxy]acetyl], $N^{\epsilon 31}$-[2-[2-[2-[[2-[2-[2-[[(4S)-4-carboxy-4-[10-(4-carboxyphenoxy)decanoylamino]butanoyl]amino]ethoxy]ethoxy]acetyl]amino]ethoxy]ethoxy]acetyl]-[Lys$^{18}$,Val$^{25}$,Arg$^{26}$,Lys$^{31}$,Arg$^{34}$]-GLP-1-(7-37)-peptide (SEQ ID NO: 49)

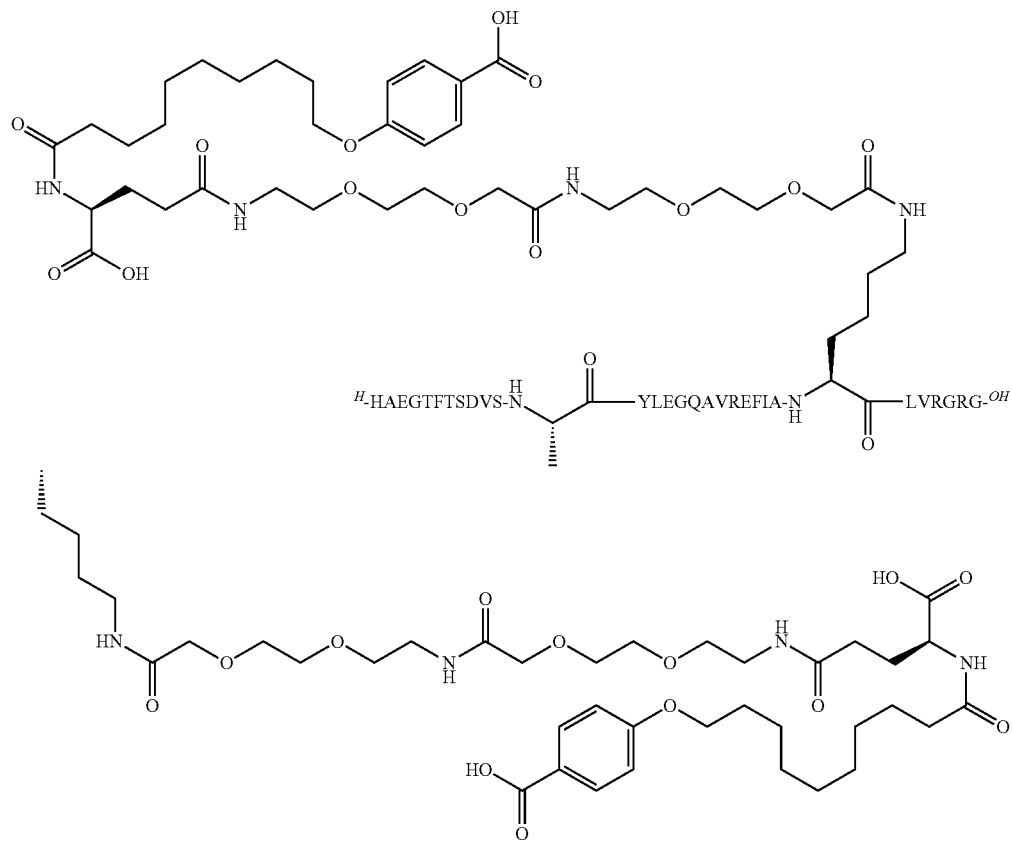

Chem. 126

Preparation Method: SPPS_L: SC_L: CP_M1
LCMS: Method: LCMS_4: Rt=2.13 min, m/z: 4841.6
UPLC Method: B4_1: Rt=8.42 min Example 108

N$^{\varepsilon 18}$-[2-[2-[2-[[2-[2-[2-[[(4S)-4-carboxy-4-[[(4S)-4-carboxy-4-(11-carboxyundecanoylamino)butanoyl]amino]butanoyl]amino]ethoxy]ethoxy]acetyl]amino]ethoxy]ethoxy]acetyl], N$^{\varepsilon 26}$-[2-[2-[2-[[2-[2-[2-[[(4S)-4-carboxy-4-[[(4S)-4-carboxy-4-(11-carboxyundecanoylamino)butanoyl]amino]butanoyl]amino]ethoxy]ethoxy]acetyl]amino]ethoxy]ethoxy]acetyl]-[Aib$^8$,Lys$^{18}$,Arg$^{34}$]-GLP-1-(7-37)-peptide (SEQ ID NO: 55)

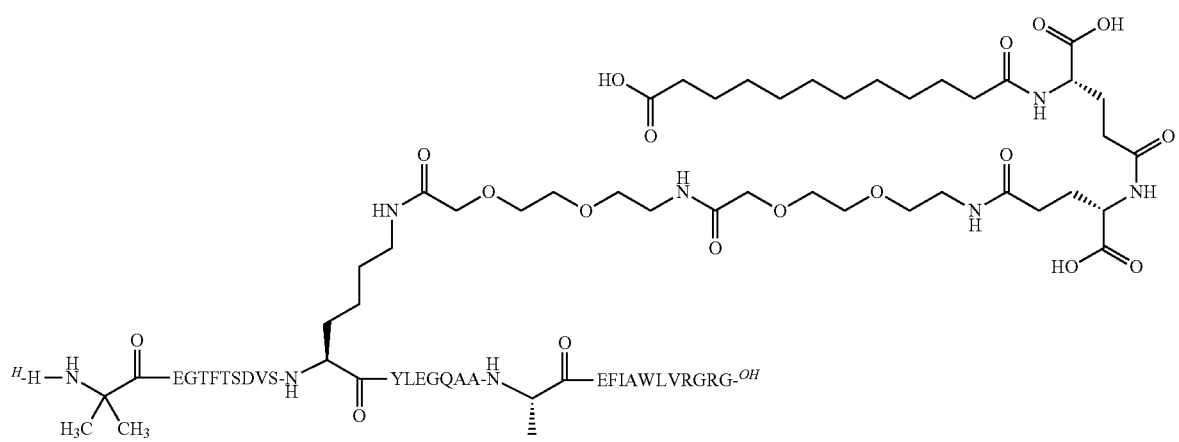

Chem. 127

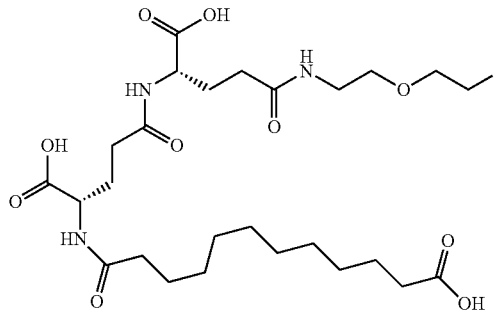

Preparation method: SPPS_Å, SC_Å, CP_M1
LCMS: method LCMS_4: Rt=2.10 min m/z: 4960.5, M/4: 1240.8; M/5: 992.9 (1A)
UPLC method: 10_B14_1: Rt=5.07 min
UPLC method: 04_A6_1: Rt=4.25 min Example 109

$N^{\epsilon18}$-[2-[2-[2-[[2-[2-[2-[[(4S)-4-carboxy-4-[8-[[(4S)-4-carboxy-4-(4-phenylbutanoylamino)butanoyl]amino]octanoylamino]butanoyl]amino]ethoxy]ethoxy]acetyl]amino]ethoxy]ethoxy]acetyl], $N^{\epsilon26}$-[2-[2-[2-[[2-[2-[2-[[(4S)-4-carboxy-4-[8-[[(4S)-4-carboxy-4-(4-phenylbutanoylamino)butanoyl]amino]octanoylamino]butanoyl]amino]ethoxy]ethoxy]acetyl]amino]ethoxy]ethoxy]acetyl]-[Aib$^8$,Lys$^{18}$,Glu$^{22}$,Gln$^{34}$]-GLP-1-(7-37)-peptide (SEQ ID NO: 7)

Chem. 128

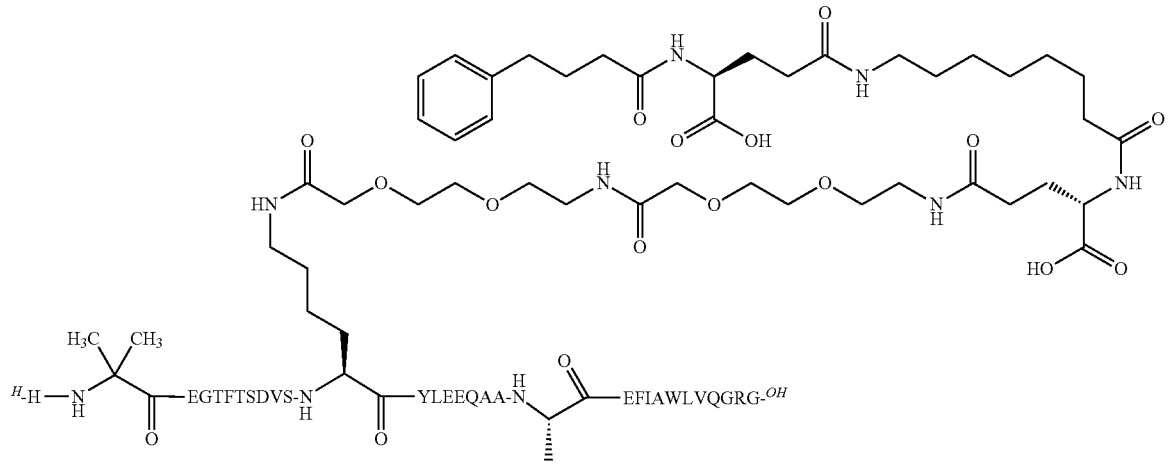

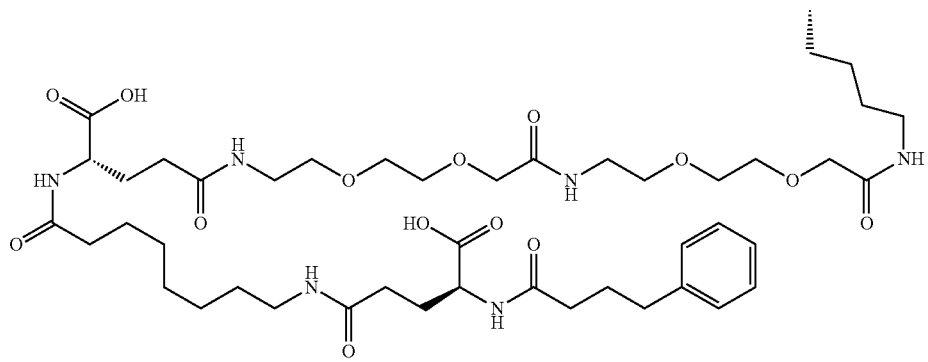

Preparation Method: SPPS_L: SC_L: CP_M1
LCMS: Method LCMS_4: Rt=2.27 min, m/z: 5154.6
UPLC: Method B4_1: Rt=10.11 min
UPLC: Method 05_B9_1: Rt=7.04 min

Example 110

$N^{\epsilon 18}$-[2-[2-[2-[[2-[2-[2-[[(4S)-4-carboxy-4-[6-[[(4S)-4-carboxy-4-(4-phenylbutanoylamino)butanoyl]amino]hexanoylamino]butanoyl]amino]ethoxy]ethoxy]acetyl]amino]ethoxy]ethoxy]acetyl], $N^{\epsilon 26}$-[2-[2-[2-[[2-[2-[2-[[(4S)-4-carboxy-4-[6-[[(4S)-4-carboxy-4-(4-phenylbutanoylamino)butanoyl]amino]hexanoylamino]butanoyl]amino]ethoxy]ethoxy]acetyl]amino]ethoxy]ethoxy]acetyl]-[Lys$^{18}$,Arg$^{34}$]-GLP-1-(7-37)-peptide (SEQ ID NO: 57)

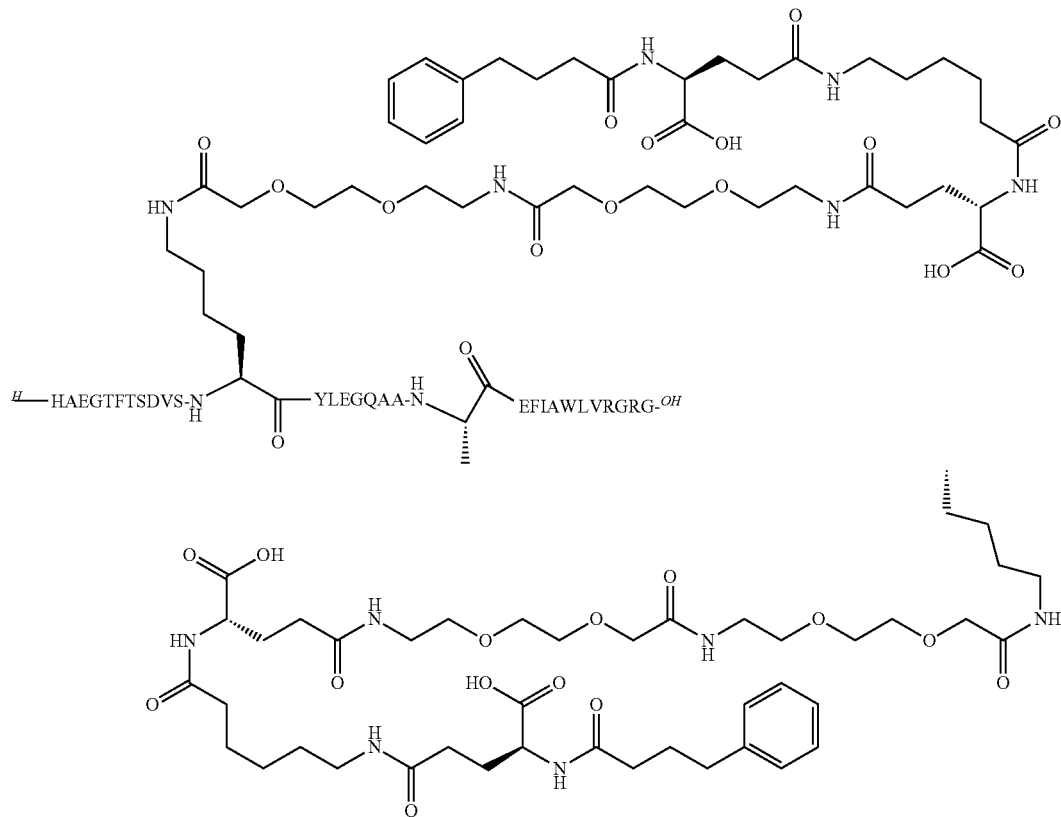

Chem. 129

Preparation Method: SPPS_L: SC_L: CP_M1
LCMS: Method: LCMS_4: Rt=2.12 min, m/z: 5039.7
UPLC Method: B4_1: Rt=9.45 min
UPLC Method: 05_B9_1 Rt=6.53 min

Example 111

$N^{\epsilon 118}$-[(4S)-4-carboxy-4-[[2-[2-[2-[[2-[2-[2-[[(4S)-4-carboxy-4-(13-carboxytridecanoylamino)butanoyl]amino]ethoxy]ethoxy]acetyl]amino]ethoxy]ethoxy]acetyl]amino]butanoyl], $N^{\epsilon 31}$-[(4S)-4-carboxy-4-[[2-[2-[2-[[2-[2-[2-[[(4S)-4-carboxy-4-(13-carboxytridecanoylamino)butanoyl]amino]ethoxy]ethoxy]acetyl]amino]ethoxy]ethoxy]acetyl]amino]butanoyl]-[Lys$^{18}$,Glu$^{22}$,Val$^{25}$,Arg$^{26}$,Lys$^{31}$,Arg$^{34}$]-GLP-1-(7-37)-peptide (SEQ ID NO: 10)

Chem. 130

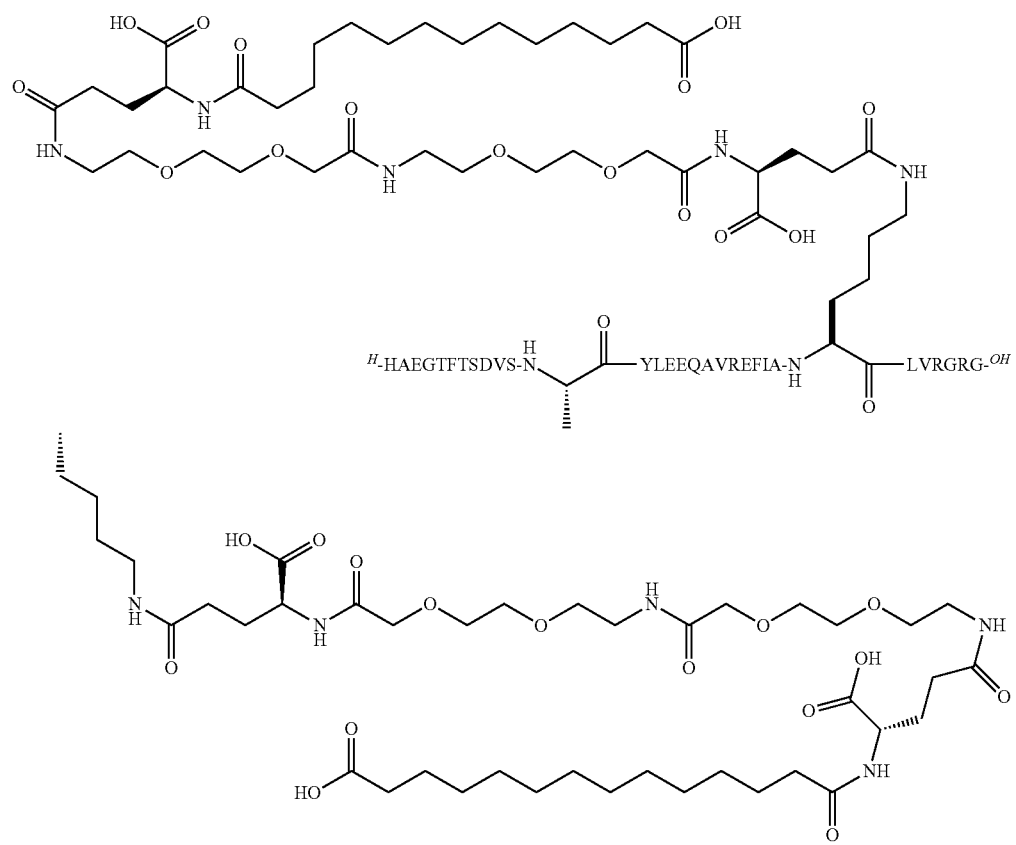

Preparation Method: SPPS_L; SC_L
LCMS: Method: LCMS_4: Rt=2.05 min; m/3: 1691; m/4: 1268; m/5: 1014
UPLC: Method: B2_1: Rt=12.26 min
UPLC: Method: 05_B7_1: Rt=8.18 min Example 112

$N^{\epsilon 18}$-[2-[2-[2-[[2-[2-[2-[[(4S)-4-carboxy-4-(13-carboxytridecanoylamino)butanoyl]amino]ethoxy]ethoxy]acetyl]amino]ethoxy]ethoxy]acetyl], $N^{\epsilon 31}$-[2-[2-[2-[[2-[2-[2-[[(4S)-4-carboxy-4-(13-carboxytridecanoylamino)butanoyl]amino]ethoxy]ethoxy]acetyl]amino]ethoxy]ethoxy]acetyl]-[Aib$^8$,Lys$^{18}$,Val$^{25}$,Arg$^{26}$,Lys$^{31}$,Arg$^{34}$]-GLP-1-(7-37)-peptide (SEQ ID NO: 58)

Chem. 131
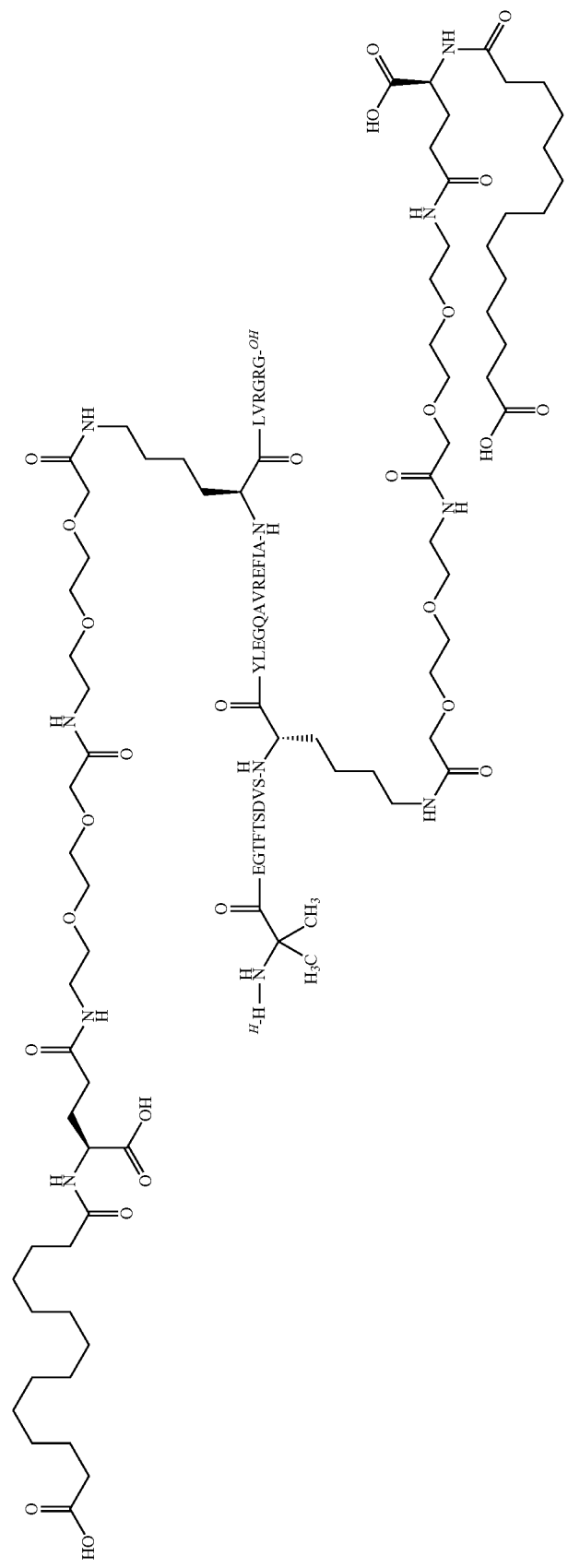

Preparation Method: SPPS_P; SC_L
LCMS: Method: LCMS_4: Rt=2.12 min; m/3: 1586; m/4: 1189; m/5: 951
UPLC Method: B2_1: Rt=14.31 min
UPLC Method: 05_B7_1: Rt=8.82 min

Example 113

$N^{\epsilon 18}$-[2-[2-[2-[[2-[2-[2-[[(4S)-4-carboxy-4-[12-[[(4S)-4-carboxy-4-(4-phenylbutanoylamino)butanoyl]amino]dodecanoylamino]butanoyl]amino]ethoxy]ethoxy]acetyl]amino]ethoxy]ethoxy]acetyl], $N^{\epsilon 26}$-[2-[2-[2-[[2-[2-[2-[[(4S)-4-carboxy-4-[12-[[(4S)-4-carboxy-4-(4-phenylbutanoylamino)butanoyl]amino]dodecanoylamino]butanoyl]amino]ethoxy]ethoxy]acetyl]amino]ethoxy]ethoxy]acetyl]-[Aib$^8$,Lys$^{18}$,Glu$^{22}$,Gln$^{34}$]-GLP-1-(7-37)-peptide (SEQ ID NO: 7)

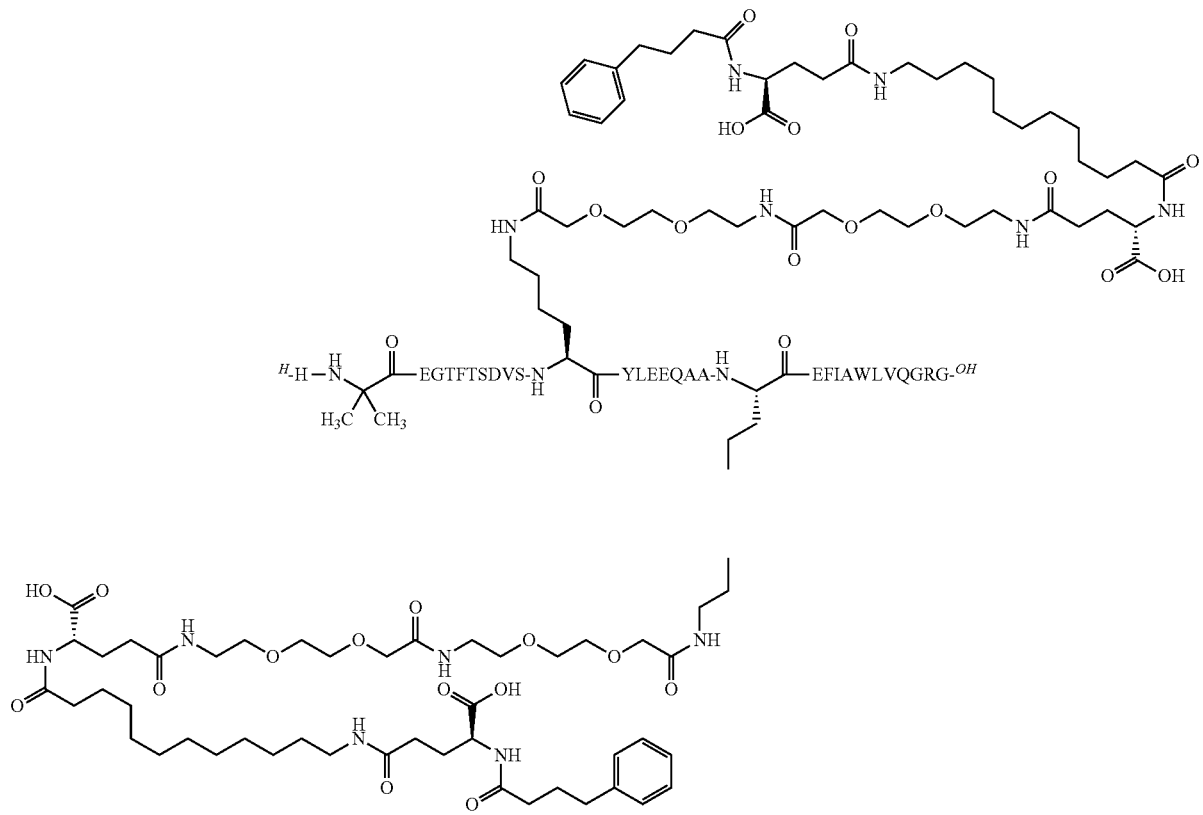

Chem. 132

Preparation Method: SPPS_L: SC_L: CP_M1
LCMS: Method: LCMS_4: Rt=2.46 min, m/z: 5267.0
UPLC Method: B4_1: Rt=9.10 min
UPLC Method: 05_B9_1: Rt=8.12 min

Example 114

$N^{\epsilon 18}$-[(4S)-4-carboxy-4-[[2-[2-[2-[[2-[2-[2-[[(4S)-4-carboxy-4-[10-(4-carboxyphenoxy)decanoylamino]butanoyl]amino]ethoxy]ethoxy]acetyl]amino]ethoxy]ethoxy]acetyl]amino]butanoyl], $N^{\epsilon 26}$-[(4S)-4-carboxy-4-[[2-[2-[2-[[2-[2-[2-[[(4S)-4-carboxy-4-[10-(4-carboxyphenoxy)decanoylamino]butanoyl]amino]ethoxy]ethoxy]acetyl]amino]ethoxy]ethoxy]acetyl]amino]butanoyl]-[Aib$^8$,Lys$^{18}$,Glu$^{22}$,Gln$^{34}$]-GLP-1-(7-37)-peptide (SEQ ID NO: 7)

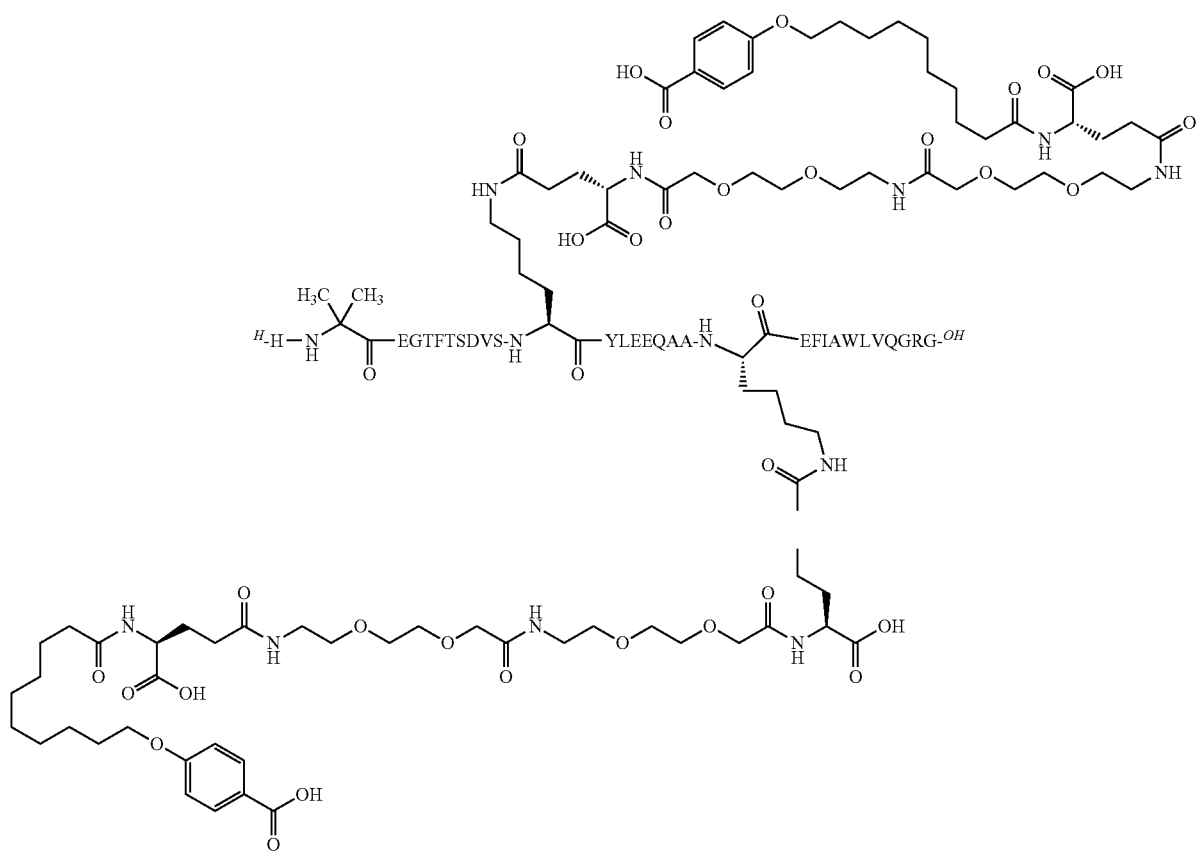

Chem. 133

Preparation Method: SPPS_L: SC_L: CP_M1
LCMS: Method LCMS_4: Rt=2.37 min, m/z: 5160.6
UPLC Method: B4_1: Rt=8.74 min
UPLC Method: 05_B9_1: Rt=8.05 min

Example 115

$N^{\epsilon 18}$-[(4S)-4-carboxy-4-[[2-[2-[2-[[2-[2-[2-[10-(4-carboxyphenoxy)decanoylamino]ethoxy]ethoxy]acetyl]amino]ethoxy]ethoxy]acetyl]amino]butanoyl], $N^{\epsilon 26}$[(4S)-4-carboxy-4-[[2-[2-[2-[[2-[2-[2-[10-(4-carboxyphenoxy)decanoylamino]ethoxy]ethoxy]acetyl]amino]ethoxy]acetyl]amino]butanoyl]-[Aib$^8$,Lys$^{18}$,Arg$^{34}$]-GLP-1-(7-37)-peptide (SEQ ID NO: 55)

Chem. 134

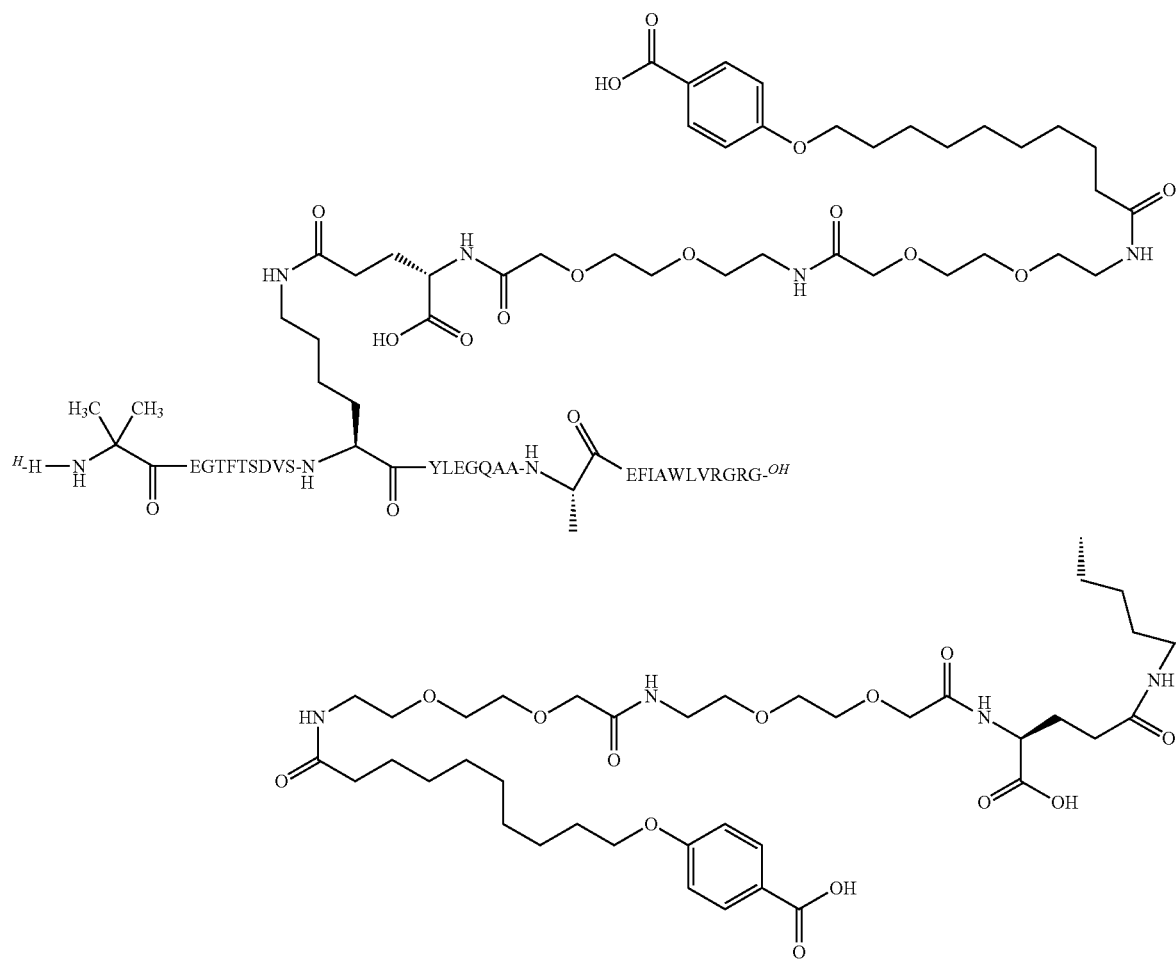

Preparation Method: SPPS_L: SC_L: CP_M1
LCMS: Method LCMS_4: Rt=2.34 min, m/z: 4857.8
UPLC Method: B4_1: Rt=10.0 min
UPLC Method: 05_B9_1: Rt=8.85 min Example 116
$N^{\epsilon 18}$-[(4S)-4-carboxy-4-[[2-[2-[2-[2-[[2-[2-(13-carboxytridecanoylamino)ethoxy]ethoxy]acetyl]amino]ethoxy]ethoxy]acetyl]amino]butanoyl]$N^{\epsilon 31}$-[(4S)-4-carboxy-4-[[2-[2-[2-[[2-[2-(13-carboxytridecanoylamino)ethoxy]ethoxy]acetyl]amino]ethoxy]ethoxy]acetyl]amino]butanoyl]-[$Lys^{18}$,$Glu^{22}$, $Arg^{26}$,$Lys^{31}$,$Arg^{34}$]-GLP-1-(7-37)-peptide (SEQ ID NO: 50)

Chem. 135
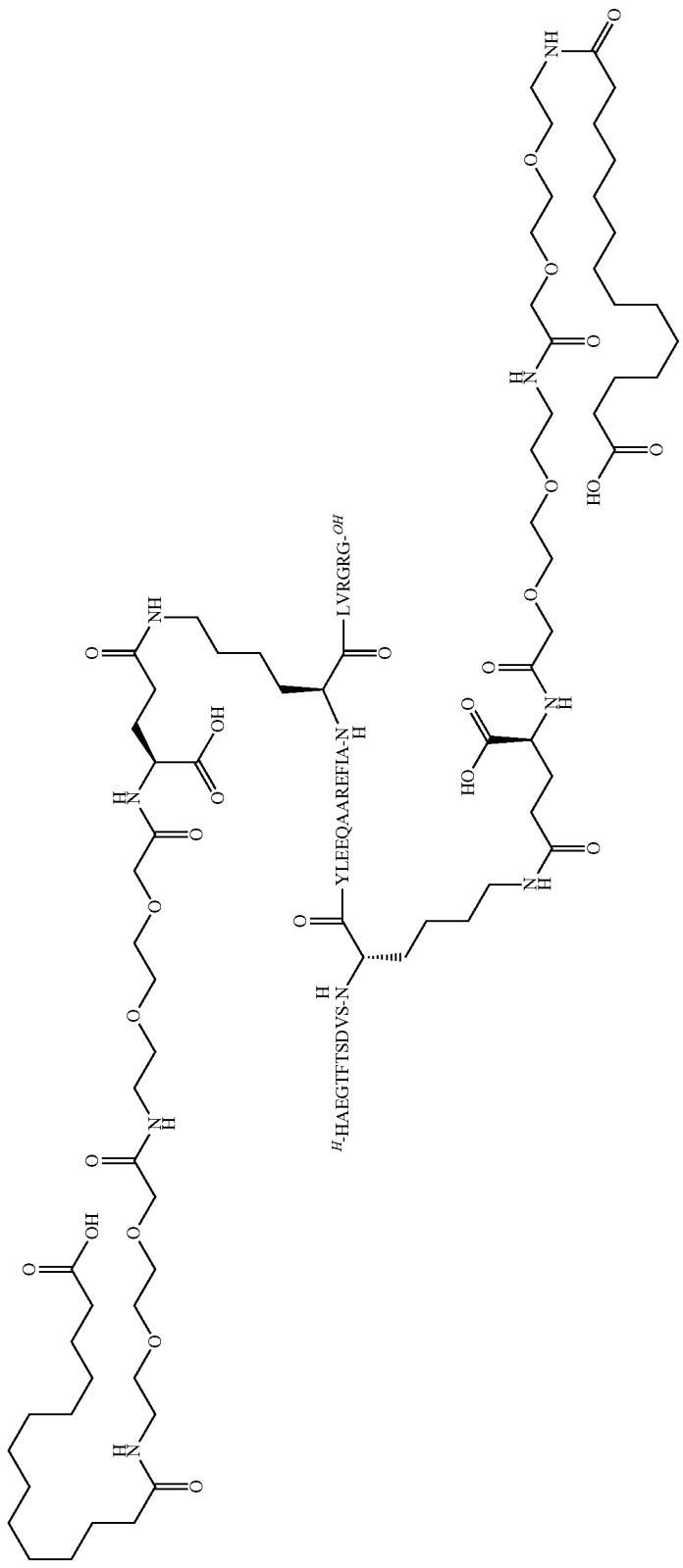

Preparation Method: SPPS_L: SC_L: CP_M1
LCMS: Method LCMS_4: Rt=2.13 min, m/z: 4785.9
UPLC Method: B4_1: Rt=9.09 min
UPLC Method: 05_B9_1: Rt=7.30 min Example 117

$N^{\epsilon 18}$-[2-[2-[2-[[2-[2-[2-[[(4S)-4-amino-4-carboxybutanoyl]amino]ethoxy]ethoxy]acetyl]amino]ethoxy]ethoxy]acetyl], $N^{\epsilon 27}$-[2-[2-[2-[[2-[2-[2-[[(4S)-4-amino-4-carboxybutanoyl]amino]ethoxy]ethoxy]acetyl]amino]ethoxy]ethoxy]acetyl]-[Aib$^8$,Lys$^{18}$,Val$^{26}$,Lys$^{27}$,Arg$^{34}$]-GLP-1-(7-37)-peptide (SEQ ID NO: 6)

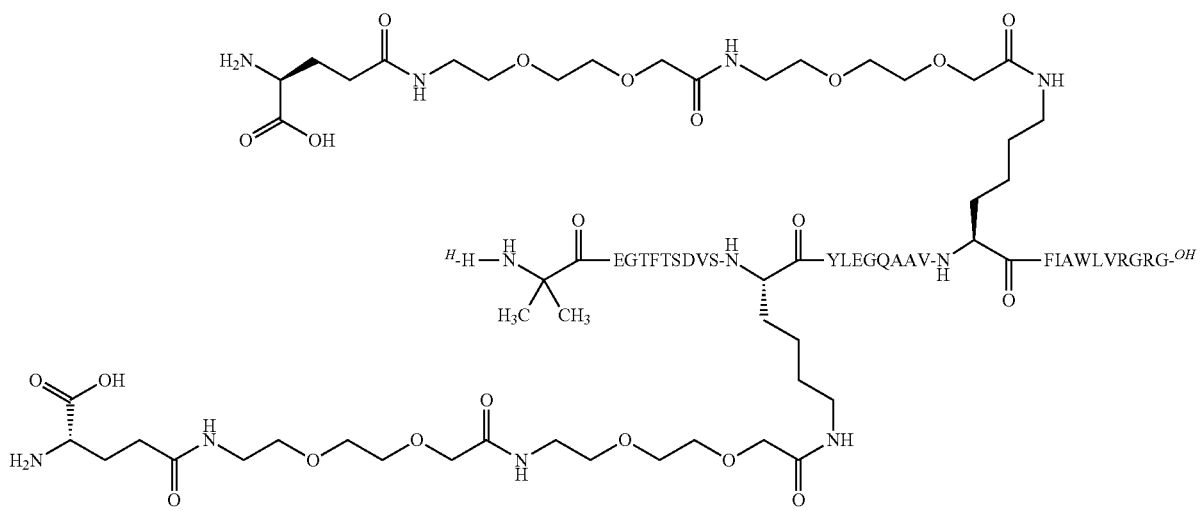

Chem. 136

Preparation Methods: SPPS_L; SC_L; CP_M1

LCMS: Method LCMS_4: Rt=1.90: m/z: m/3 1416; m/4 1062; m/5 850; m/6 708

UPLC method: B4_1: Rt=7.19 min.

This compound is an intermediate product in the preparation of the compound of Example 68 (Chem. 87).

Example 118

$N^{\epsilon 18}$-[2-[2-[2-[[2-[2-[2-[[(4S)-4-carboxy-4-(13-carboxytridecanoylamino)butanoyl]amino]ethoxy]ethoxy]acetyl]amino]ethoxy]ethoxy]acetyl],$N^{\epsilon 27}$-[2-[2-[2-[[2-[2-[2-[[(4S)-4-carboxy-4-(13-carboxytridecanoylamino)butanoyl]amino]ethoxy]ethoxy]acetyl]amino]ethoxy]ethoxy]acetyl]-[Lys$^{18}$,Glu$^{22}$,Val$^{25}$,Arg$^{26}$,Lys$^{27}$,His$^{31}$,Gln$^{34}$]-GLP-1-(7-37)-peptide (SEQ ID NO: 59)

Chem. 161

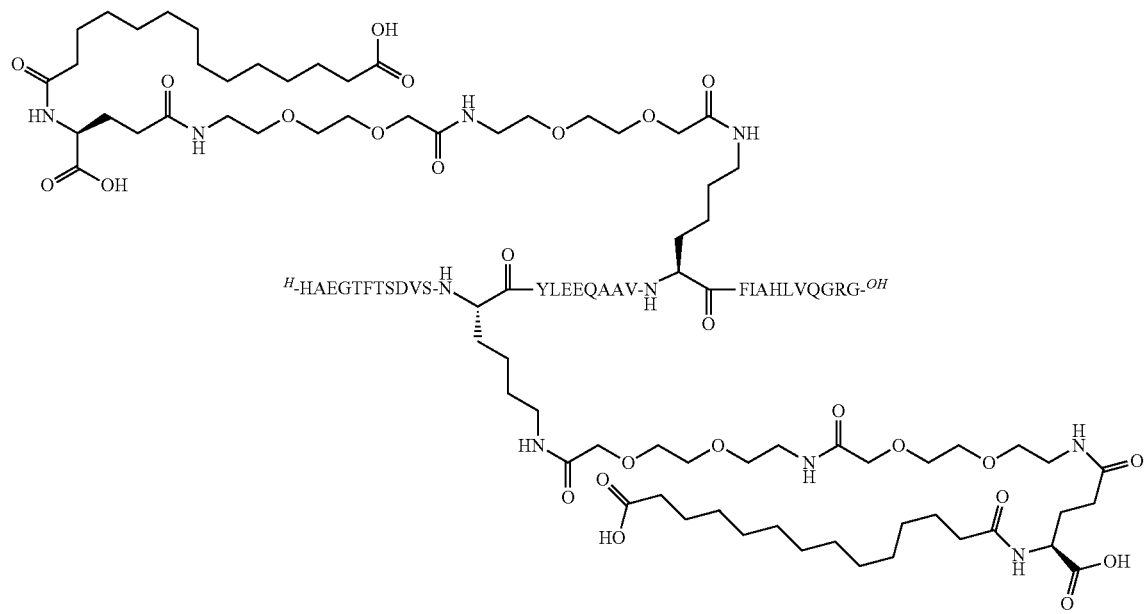

Preparation Methods: SPPS_L; SC_L; CP_M1
LCMS method: LCMS_4: Rt=2.08 min; m/3=1598; m/4=1199; m/5=959
UPLC method: B2_1: Rt=12.20 min
UPLC method: 05_B9_1: Rt=7.50 min Example 119
$N^{\varepsilon18}$-[2-[2-[2-[[2-[2-[2-[[(4S)-4-carboxy-4-(13-carboxytridecanoylamino)butanoyl]amino]ethoxy]ethoxy]acetyl]amino]ethoxy]ethoxy]acetyl], $N^{\varepsilon27}$-[2-[2-[2-[[2-[2-[2-[[(4S)-4-carboxy-4-(13-carboxytridecanoylamino)butanoyl]amino]ethoxy]ethoxy]acetyl]amino]ethoxy]ethoxy]acetyl]-[Lys$^{18}$,Glu$^{22}$,His$^{26}$,Lys$^{27}$,His$^{31}$,Gln$^{34}$]-GLP-1-(7-37)-peptide (SEQ ID NO: 60)

Chem. 162
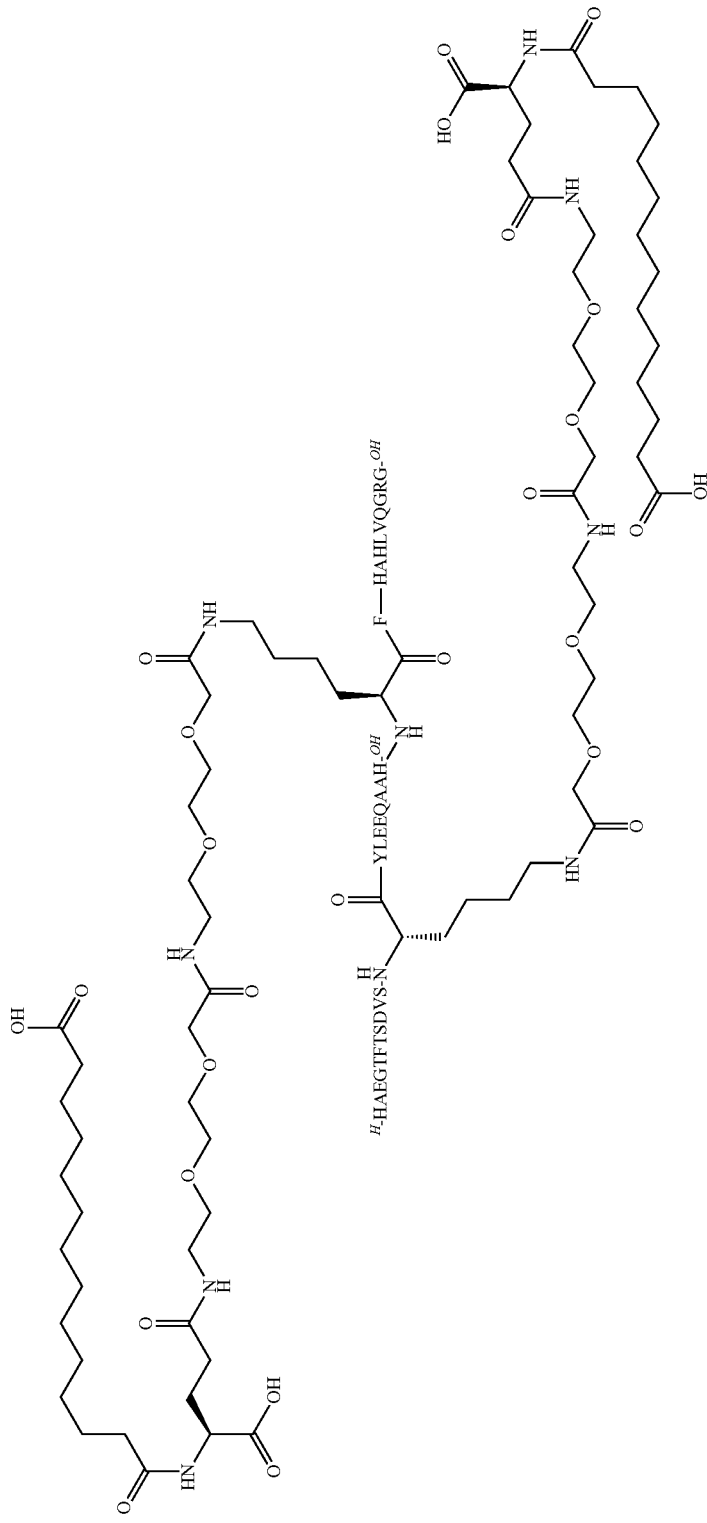

Preparation Methods: SPPS_L; SC_L; CP_M1

LCMS method: LCMS_4: Rt=1.87 min; m/3=1583; m/4=1187; m/5=949 (1A)

UPLC method: B2_1: Rt=11.74 min

UPLC method: 04_A7_1: Rt=5.41 min

Example 120

$N^{\epsilon 18}$-[2-[2-[2-[[2-[2-[2-[[(4S)-4-carboxy-4-[[2-[4-(4-fluorophenoxy)phenyl]acetyl]amino]butanoyl]amino]ethoxy]ethoxy]acetyl]amino]ethoxy]ethoxy]acetyl], $N^{22}$-[2-[2-[2-[[2-[2-[2-[[(4S)-4-carboxy-4-[[2-[4-(4-fluorophenoxy)phenyl]acetyl]amino]butanoyl]amino]ethoxy]ethoxy]acetyl]amino]ethoxy]ethoxy]acetyl]-[Lys$^{18}$,Lys$^{22}$,Arg$^{26}$,Gln$^{34}$]-GLP-1-(7-37)-peptide (SEQ ID NO: 61)

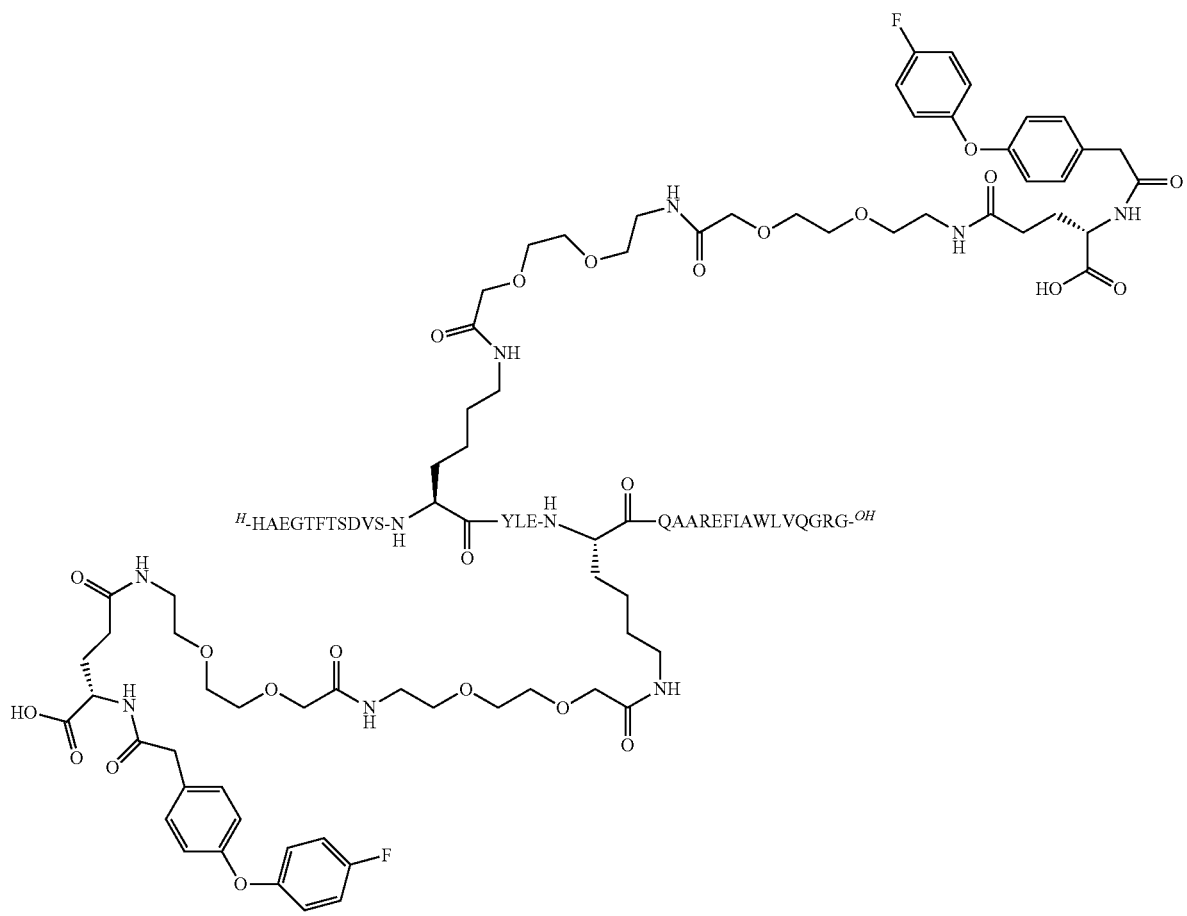

Chem. 163

Preparation Method: SPPS_L; SC_L; CP_L1

LCMS method: LCMS_4: Rt=2.15 min; m/5=959; m/4=1198; m/3=1597

UPLC method: B4_1: Rt=8.53 min

UPLC method: 04_A6_1: Rt=6.50 min

Example 121

$N^{\epsilon 18}$-[2-[2-[2-[[2-[2-[2-[[(4S)-4-carboxy-4-[4-(4-chlorophenyl)butanoylamino]butanoyl]amino]ethoxy]ethoxy]acetyl]amino]ethoxy]ethoxy]acetyl], $N^{\epsilon 26}$-[2-[2-[2-[[2-[2-[2-[[(4S)-4-carboxy-4-[4-(4-chlorophenyl)butanoylamino]butanoyl]amino]ethoxy]ethoxy]acetyl]amino]ethoxy]ethoxy]acetyl]-[Aib$^8$,Lys$^{18}$,Glu$^{22}$,Gln$^{34}$]-GLP-1-(7-37)-peptide (SEQ ID NO: 7)

Chem. 164
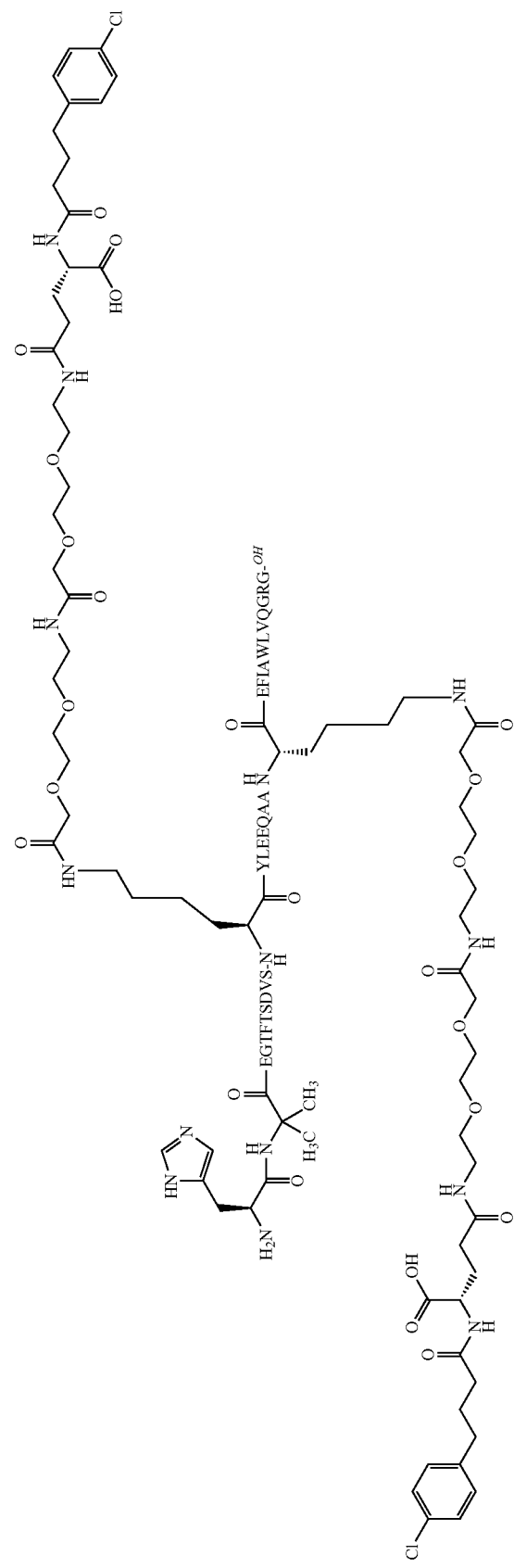

LCMS: Method: LCMS_4: Rt=2.27 min; m/4=1171; m3=1561
Preparation Method: SPPS_P; SC_M1; CP_M1
UPLC method B4_1: Rt=8.37 min
UPLC method 05_B5_1: Rt=4.61 min Example 122

$N^{\epsilon 18}$-[2-[2-[2-[[2-[2-[2-[[(4S)-4-carboxy-4-[4-(4-nitrophenyl)butanoylamino]butanoyl]amino]ethoxy]ethoxy]acetyl]amino]ethoxy]ethoxy]acetyl], $N^{\epsilon 26}$-[2-[2-[2-[[2-[2-[2-[[(4S)-4-carboxy-4-[4-(4-nitrophenyl)butanoylamino]butanoyl]amino]ethoxy]ethoxy]acetyl]amino]ethoxy]ethoxy]acetyl]-[Aib$^8$,Lys$^{18}$,Glu$^{22}$,Gln$^{34}$]-GLP-1-(7-37)-peptide (SEQ ID NO: 7)

Chem. 165
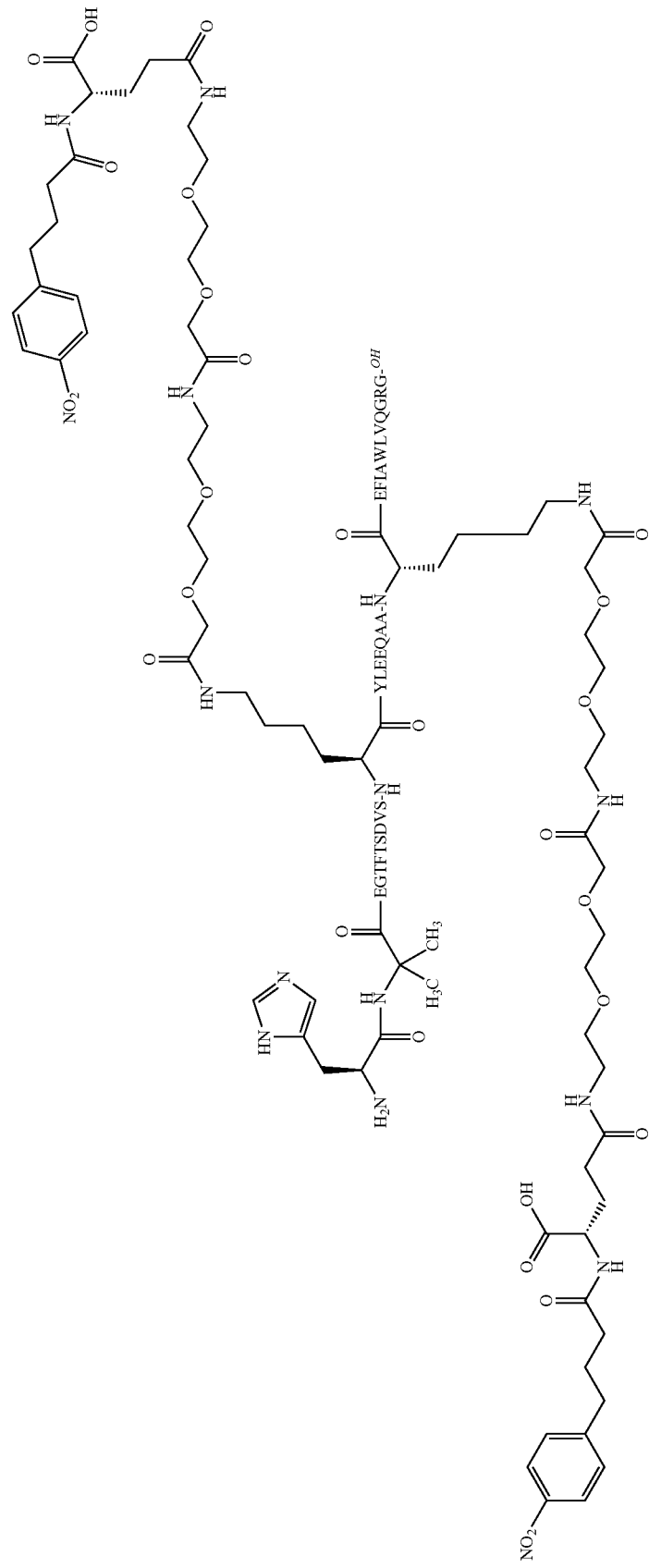

Preparation Method: SPPS_P; SC_M1; CP_M1
LCMS: Method: LCMS_4: Rt=2.17 min; m/5=941; m4=1176; m/3=1568
UPLC method B4_1: Rt=8.24 min
UPLC method 05_B5_1: Rt=4.90 min

Example 123

$N^{\epsilon 18}$-[2-[2-[2-[[2-[2-[2-[[(4S)-4-carboxy-4-(6-phenylhexanoylamino)butanoyl]amino]ethoxy]ethoxy]acetyl]amino]ethoxy]ethoxy]acetyl], $N^{\epsilon 26}$-[2-[2-[2-[[2-[2-[2-[[(4S)-4-carboxy-4-(6-phenylhexanoylamino)butanoyl]amino]ethoxy]ethoxy]acetyl]amino]ethoxy]ethoxy]acetyl]-[Aib$^8$,Lys$^{18}$,Glu$^{22}$,Gln$^{34}$]-GLP-1-(7-37)-peptide (SEQ ID NO: 7)

Chem. 166
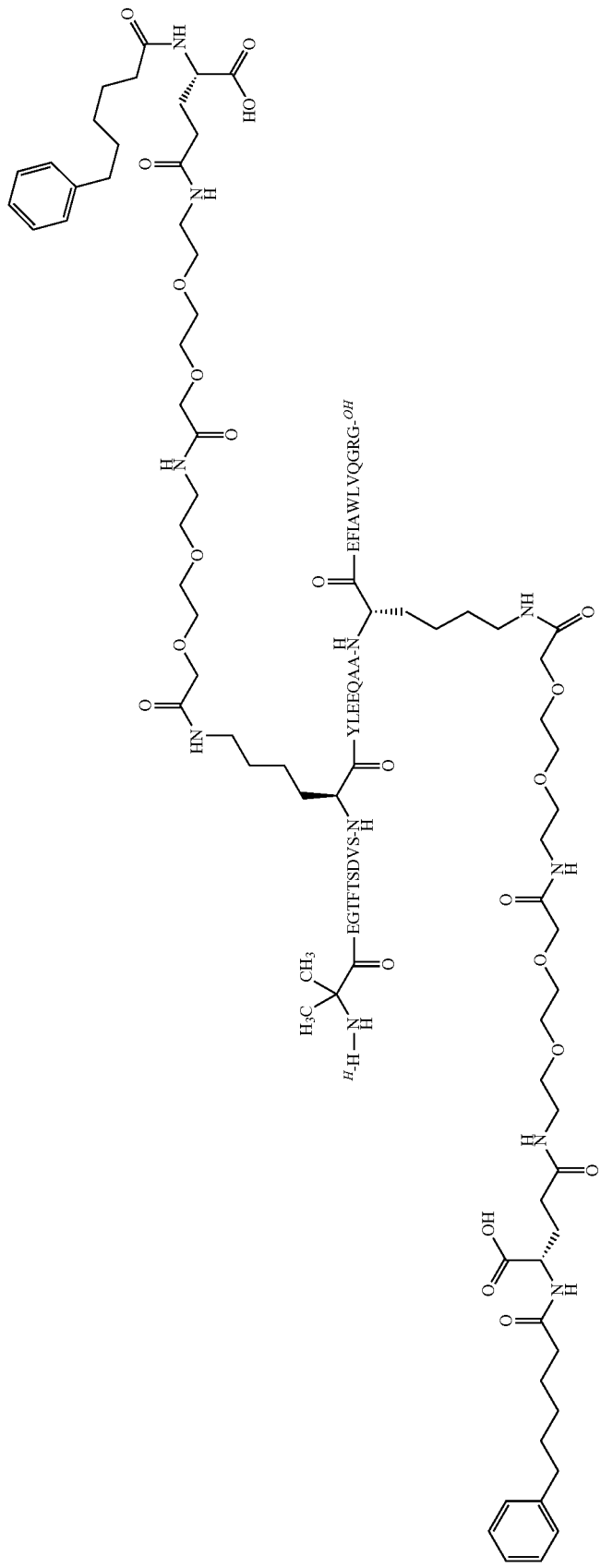

Preparation Method: SPPS_L; SC_L; CP_M1
LCMS: Method: LCMS_4: Rt: 2.31 min; m/3: 1557; m/4: 1168; m/5: 935
UPLC Method: B4_1: Rt=8.86 min
UPLC Method: 04_A6_1: Rt=5.47 min Example 124

$N^{\epsilon 18}$-[2-[2-[2-[[2-[2-[2-[[(4S)-4-carboxy-4-(11-carboxyundecanoylamino)butanoyl]amino]ethoxy]ethoxy]acetyl]amino]ethoxy]ethoxy]acetyl], $N^{\epsilon 31}$-[2-[2-[2-[[2-[2-[2-[[(4S)-4-carboxy-4-(11-carboxyundecanoylamino)butanoyl]amino]ethoxy]ethoxy]acetyl]amino]ethoxy]ethoxy]acetyl]-[Lys$^{18}$,Glu$^{22}$,Val$^{25}$,Arg$^{26}$,Lys$^{31}$,Arg$^{34}$]-GLP-1-(7-37)-peptide (SEQ ID NO: 10)

Chem. 167
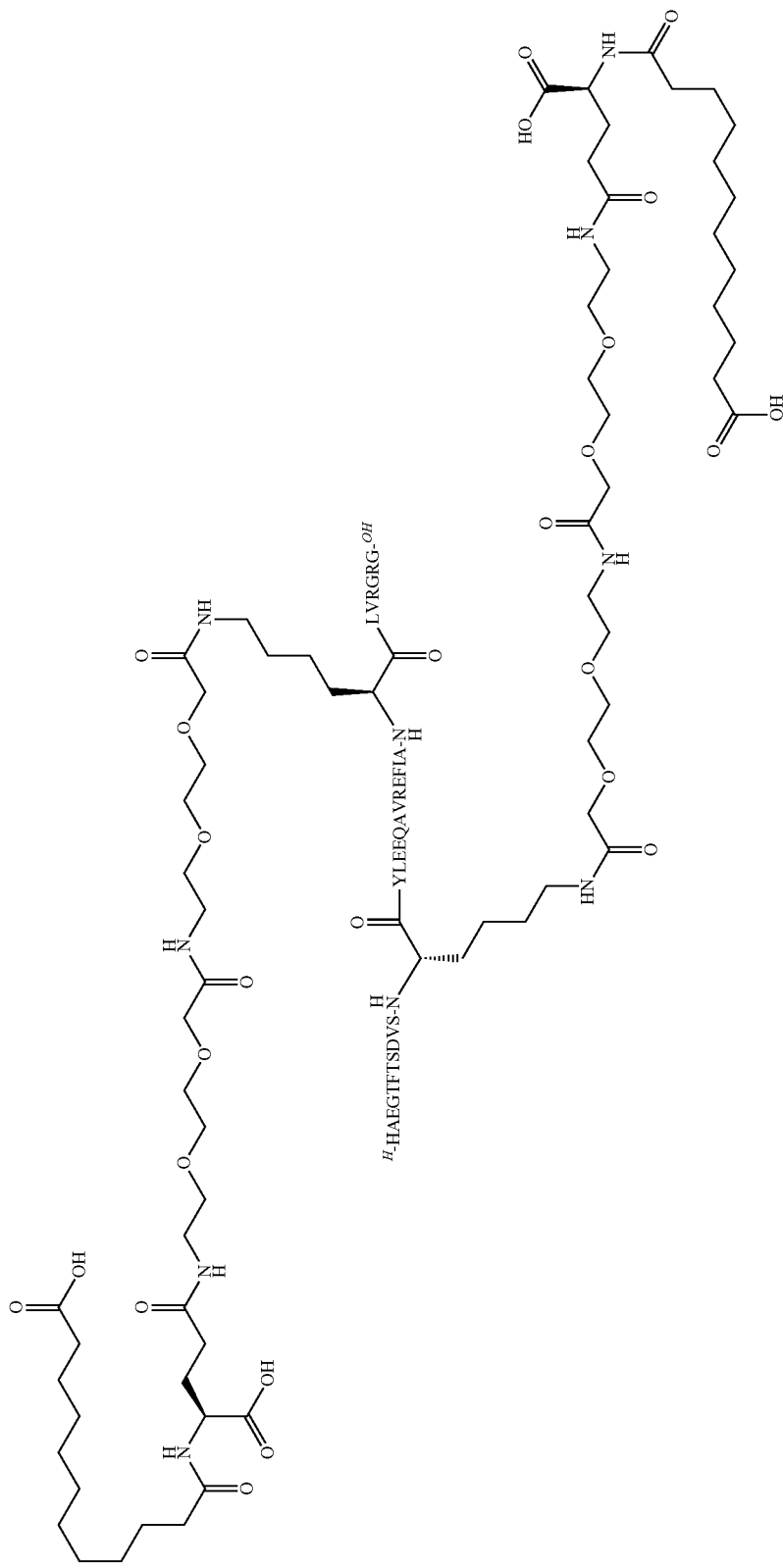

Preparation Method: SPPS_P; SC_M1; CP_M1
LCMS: Method: LCMS_AP: Rt: 8.51 min; m/3: 1587; m/4: 1190
UPLC Method: AP_B4_1: Rt=8.04 min

Example 125

$N^{\epsilon 18}$-[2-[2-[2-[[2-[2-[2-[[(4S)-4-carboxy-4-[[2-[2-(trifluoromethyl)phenyl]acetyl]amino]butanoyl]amino]ethoxy]ethoxy]acetyl]amino]ethoxy]ethoxy]acetyl], $N^{22}$-[2-[2-[2-[[2-[2-[2-[[(4S)-4-carboxy-4-[[2-[2-(trifluoromethyl)phenyl]acetyl]amino]butanoyl]amino]ethoxy]ethoxy]acetyl]amino]ethoxy]ethoxy]acetyl]-[Lys$^{18}$,Lys$^{22}$,Arg$^{26}$,Gln$^{34}$]-GLP-1-(7-37)-peptide (SEQ ID NO: 61)

Chem. 168
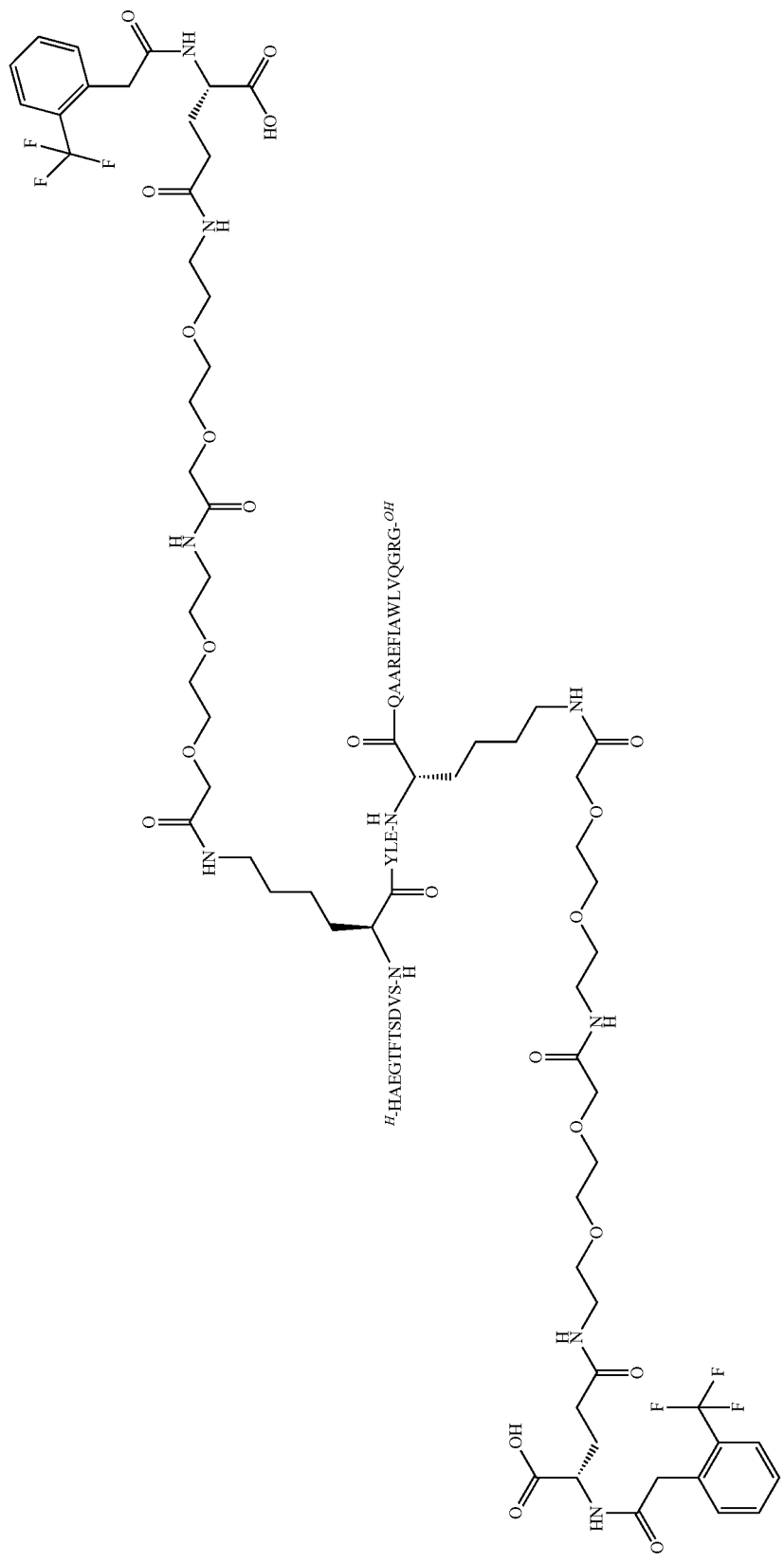

Preparation Method: SPPS_L; SC_L; CP_L1
LCMS method: LCMS_4: Rt=2.01 min; m/5=942; m/4=1177; m/3=1570
UPLC method: B4_1: Rt=7.94 min
UPLC method: 04_A6_1: Rt=5.27 min Example 126

$N^{\epsilon 18}$-[2-[2-[2-[[2-[2-[2-[[(4S)-4-carboxy-4-[[(4S)-4-carboxy-4-(13-carboxytridecanoylamino)butanoyl]amino]butanoyl]amino]ethoxy]ethoxy]acetyl]amino]ethoxy]ethoxy]acetyl], $N^{22}$-[2-[2-[2-[[2-[2-[2-[[(4S)-4-carboxy-4-[[(4S)-4-carboxy-4-(13-carboxytridecanoylamino)butanoyl]amino]butanoyl]amino]ethoxy]ethoxy]acetyl]amino]ethoxy]ethoxy]acetyl]-[Lys$^{18}$,Lys$^{22}$,Arg$^{26}$,Gln$^{34}$]-GLP-1-(7-37)-peptide (SEQ ID NO: 61)

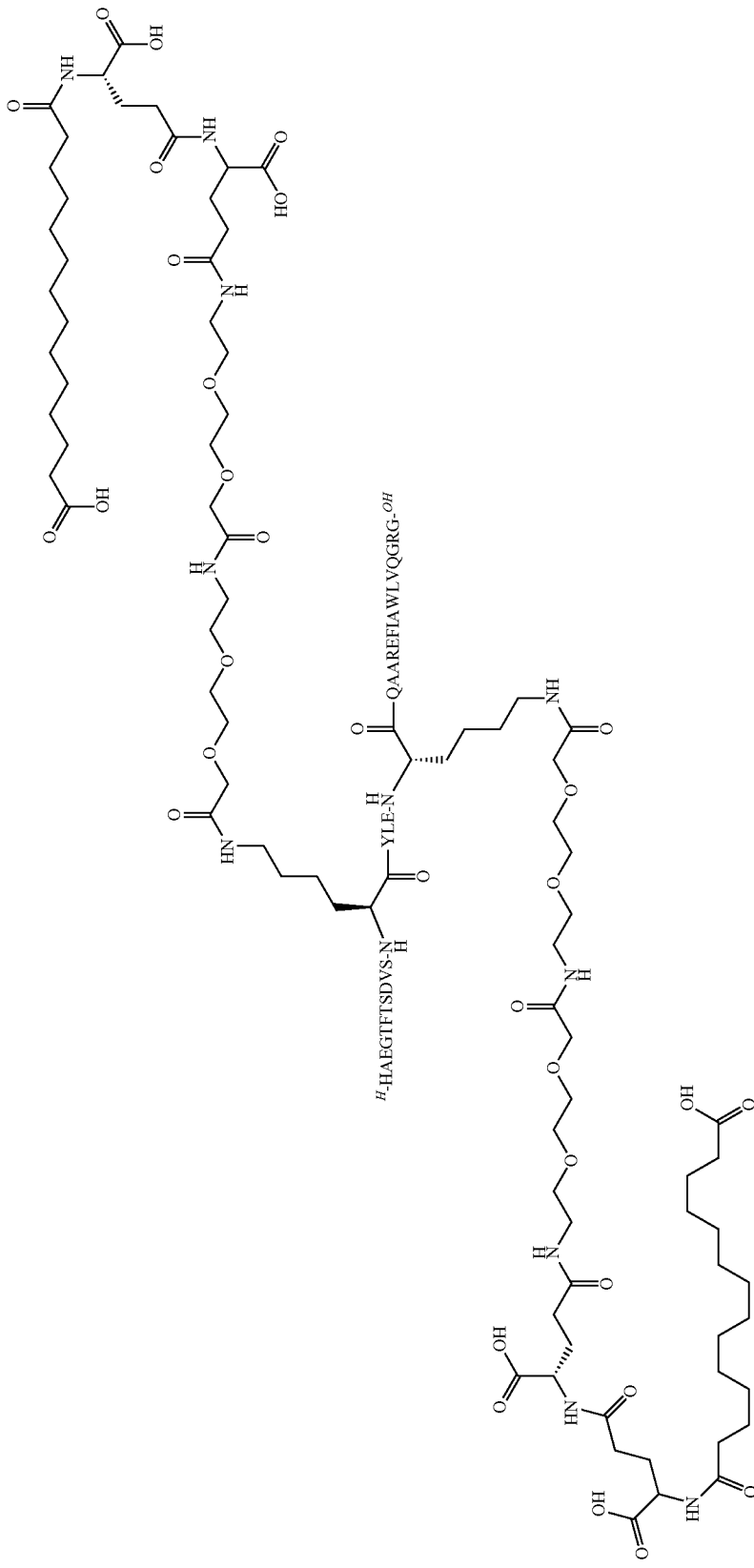
Chem. 169

Preparation Method: SPPS_L; SC_L; CP_L1
LCMS method: LCMS_4: Rt=2.20 min; m/5=1016; m/4=1269; m/3=1692
UPLC method: B4_1: Rt=8.49 min
UPLC method: 05_B5_1: Rt=5.64 min Example 127

$N^{\epsilon18}$-[2-[2-[2-[[2-[2-[2-[[(4S)-4-carboxy-4-[8-[[(4S)-4-carboxy-4-(6-phenylhexanoylamino)butanoyl]amino]octanoylamino]butanoyl]amino]ethoxy]ethoxy]acetyl]amino]ethoxy]ethoxy]acetyl], $N^{\epsilon26}$-[2-[2-[2-[[2-[2-[2-[[(4S)-4-carboxy-4-[8-[[(4S)-4-carboxy-4-(6-phenylhexanoylamino)butanoyl]amino]octanoylamino]butanoyl]amino]ethoxy]ethoxy]acetyl]amino]ethoxy]ethoxy]acetyl]-[Aib$^8$,Lys$^{18}$,Glu$^{22}$,Gln$^{34}$]-GLP-1-(7-37)-peptide (SEQ ID NO: 7)

Chem. 170
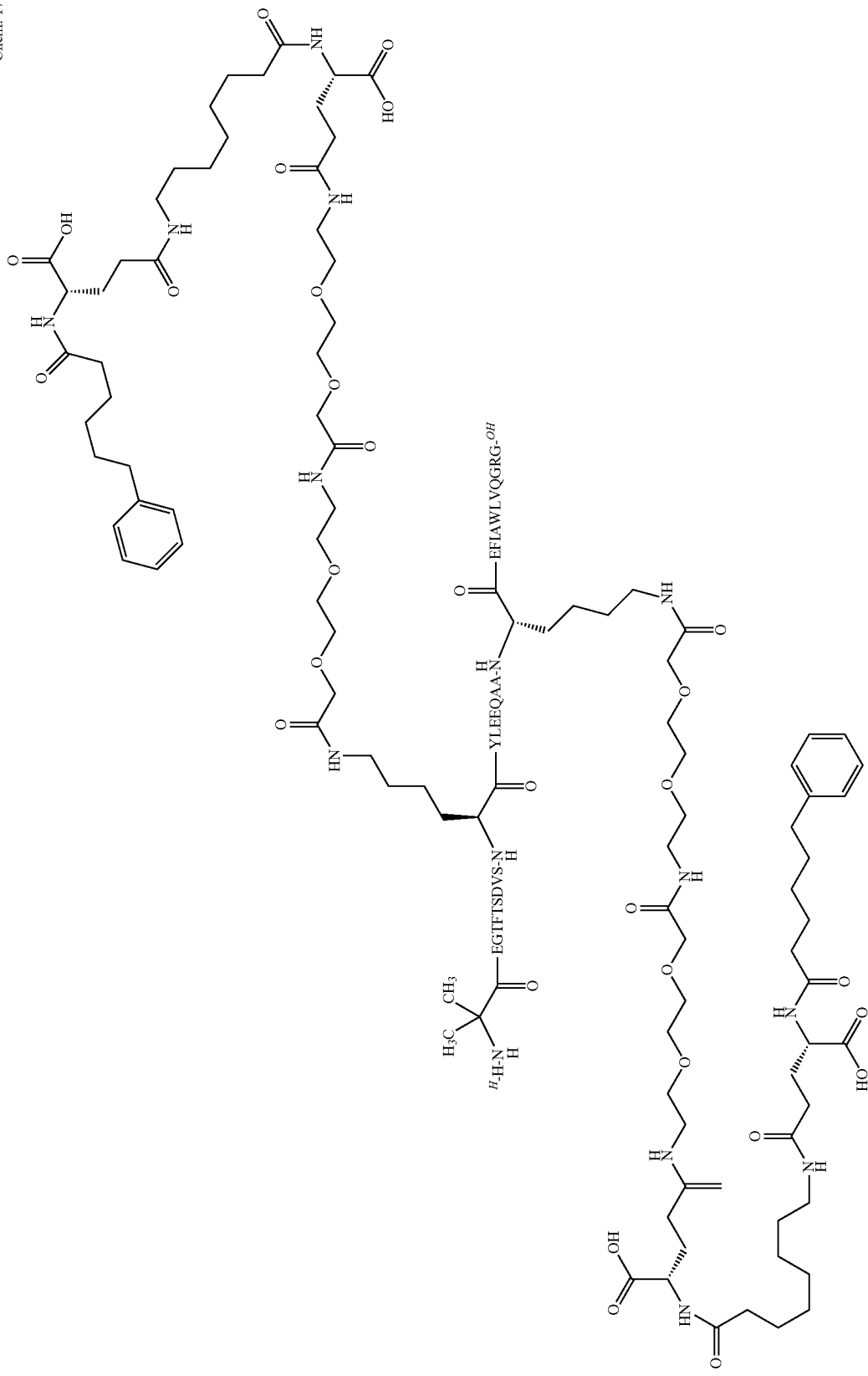

Preparation Method: SPPS_P; SC_M1; CP_M1
LCMS: Method: LCMS_4: Rt: 2.31 min; m/5=1043; m/4=1303; m/3=1737
UPLC Method: B4_1: Rt=10.84 min
UPLC Method: 05_B9_1: Rt=7.90 min Example 128

$N^{\epsilon 18}$-[2-[2-[2-[[2-[2-[2-[[(4S)-4-carboxy-4-[12-[[(4S)-4-carboxy-4-[(2-phenylacetyl)amino]butanoyl]amino]dodecanoylamino]butanoyl]amino]ethoxy]ethoxy]acetyl]amino]ethoxy]ethoxy]acetyl], $N^{\epsilon 26}$-[2-[2-[2-[[2-[2-[2-[[(4S)-4-carboxy-4-[12-[[(4S)-4-carboxy-4-[(2-phenylacetyl)amino]butanoyl]amino]dodecanoylamino]butanoyl]amino]ethoxy]ethoxy]acetyl]amino]ethoxy]ethoxy]acetyl]-[Aib$^8$,Lys$^{18}$,Glu$^{22}$,Gln$^{34}$]-GLP-1-(7-37)-peptide (SEQ ID NO: 7)

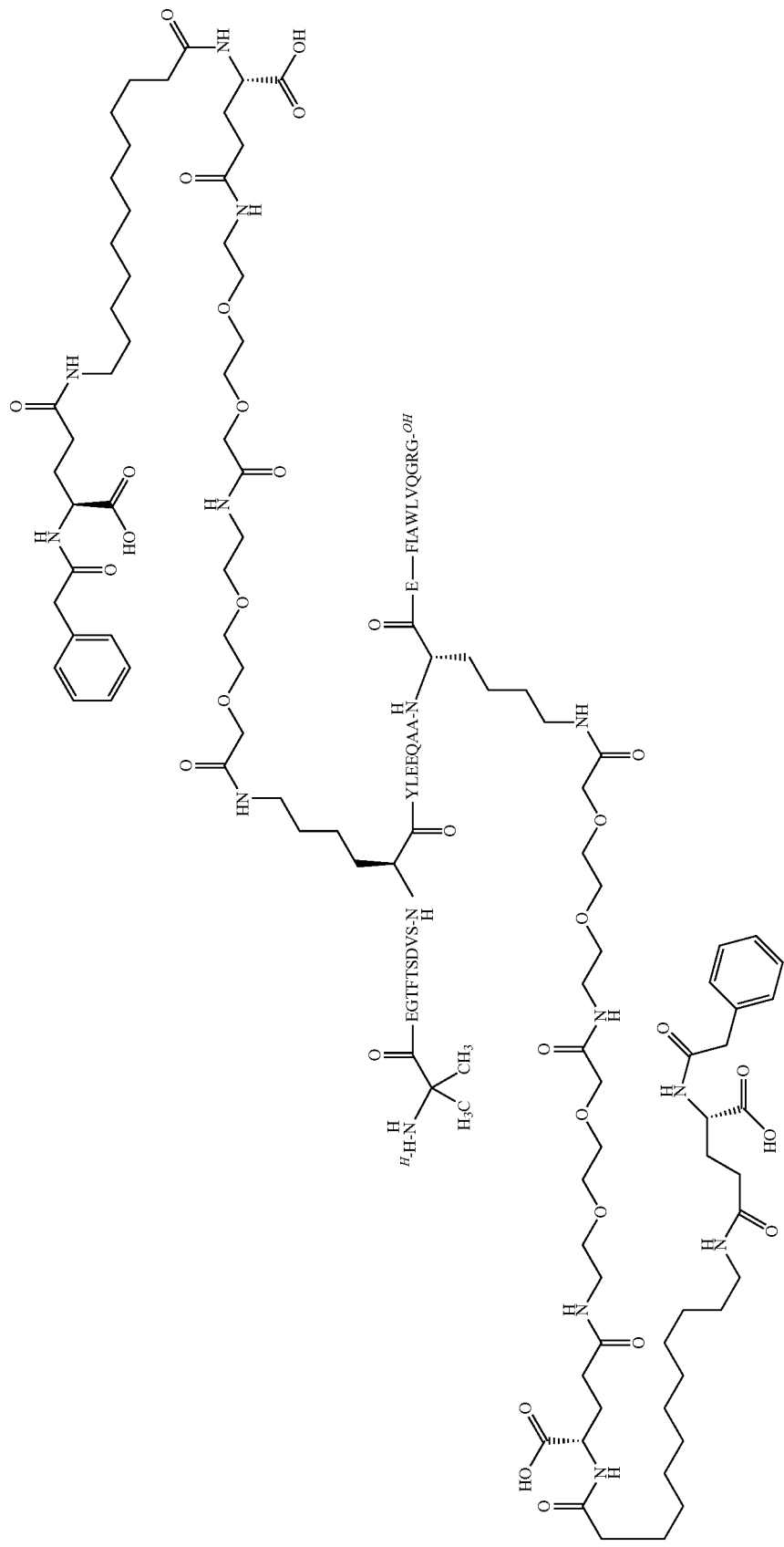
Chem. 171

Preparation Method: SPPS_C; SC_M1; CP_M1
LCMS: Method: LCMS_4: Rt=2.34 min; m/5=1043; m/4=1303; m/3=1738
UPLC Method B4_1: Rt=8.68 min
UPLC Method 05_B9_1: Rt=7.54 min Example 129

$N^{\epsilon18}$-[2-[2-[2-[[2-[2-[2-[[(4S)-4-carboxy-4-[6-[[(4S)-4-carboxy-4-(6-phenylhexanoylamino)butanoyl]amino]hexanoylamino]butanoyl]amino]ethoxy]ethoxy]acetyl]amino]ethoxy]ethoxy]acetyl], $N^{\epsilon26}$-[2-[2-[2-[[2-[2-[2-[[(4S)-4-carboxy-4-[6-[[(4S)-4-carboxy-4-(6-phenylhexanoylamino)butanoyl]amino]hexanoylamino]butanoyl]amino]ethoxy]ethoxy]acetyl]amino]ethoxy]ethoxy]acetyl]-[Lys$^{18}$,Arg$^{34}$]-GLP-1-(7-37)-peptide (SEQ ID NO: 57)

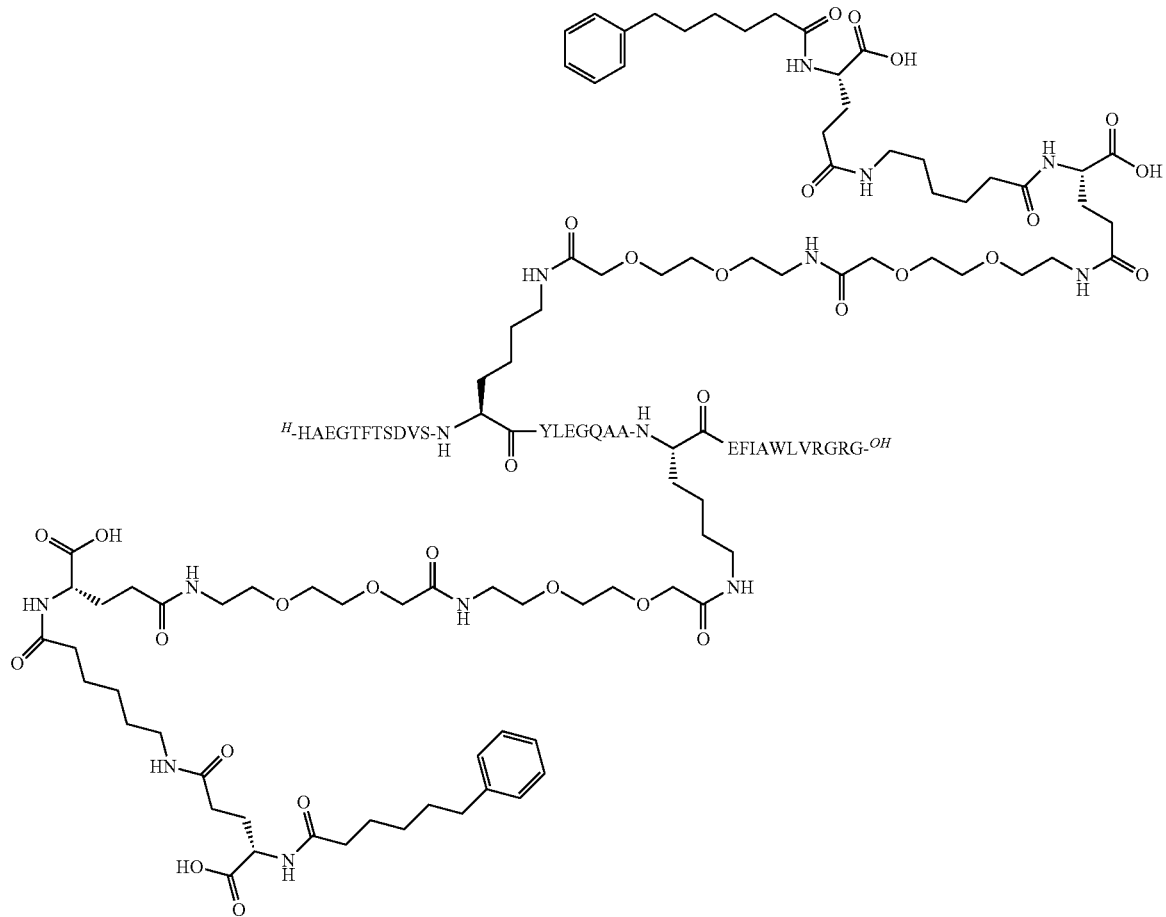

Chem. 172

Preparation Method: SPPS_P; SC_M1; CP_M1
LCMS: Method: LCMS_4: Rt=2.31 min; m/5=1019; m/4=1274; m/3=1699
UPLC Method B4_1: Rt=9.91 min
UPLC Method 05_B9_1: Rt=7.25 min Example 130

$N^{\epsilon18}$-[2-[2-[2-[[2-[2-[2-[[2-[2-[2-[[2-[2-[2-[[(4S)-4-carboxy-4-(13-carboxytridecanoylamino)butanoyl]amino]ethoxy]ethoxy]acetyl]amino]ethoxy]ethoxy]acetyl]amino]ethoxy]ethoxy]acetyl]amino]ethoxy]ethoxy]acetyl], $N^{\epsilon31}$-[2-[2-[2-[[2-[2-[2-[[2-[2-[2-[[2-[2-[2-[[(4S)-4-carboxy-4-(13-carboxytridecanoylamino)butanoyl]amino]ethoxy]ethoxy]acetyl]amino]ethoxy]ethoxy]acetyl]amino]ethoxy]ethoxy]acetyl]amino]ethoxy]ethoxy]acetyl]-[Aib$^8$,Lys$^{18}$,Glu$^{22}$,Val$^{25}$,Arg$^{26}$,Lys$^{31}$,Arg$^{34}$]-GLP-1-(7-37)-peptide (SEQ ID NO: 12)

Chem. 173
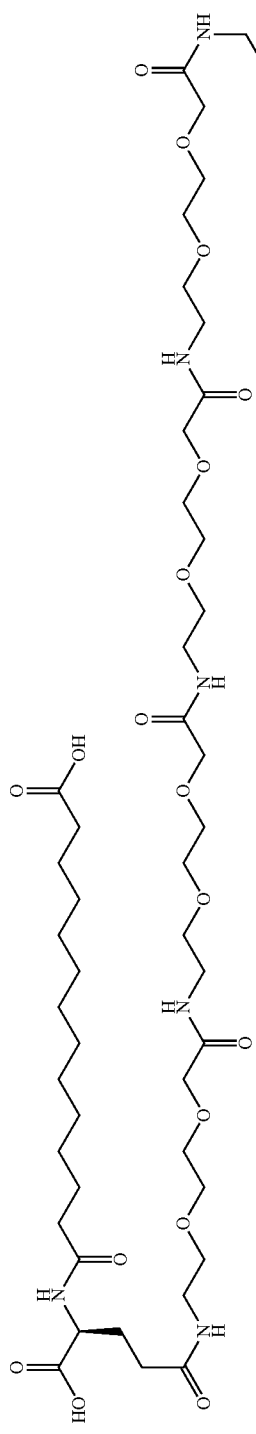
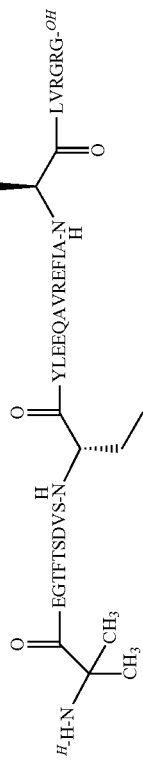
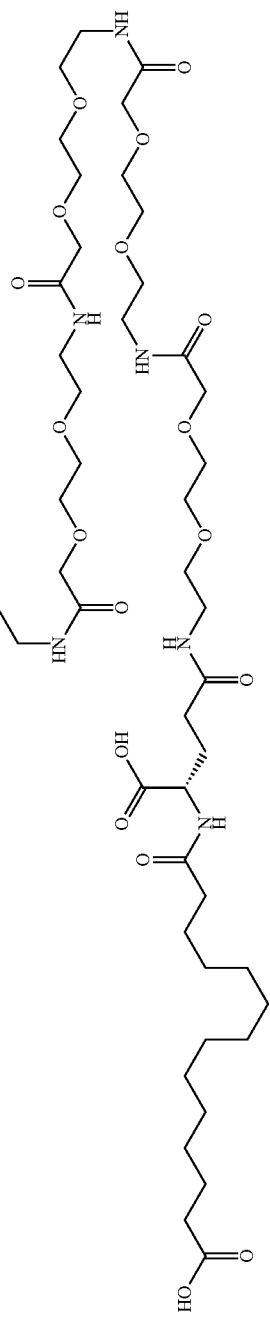

Preparation Method: SPPS_P; SC_P; CP_M1
LCMS method: LCMS_4: Rt=2.22 min; m/5=1083; m/4=1353; m/3=1804
UPLC method: B4_1: Rt=7.92 min
UPLC method: 05_B5_1: Rt=4.57 min Example 131

$N^{\epsilon 18}$-[2-[2-[2-[[2-[2-[[2-[2-[2-[[2-[2-[2-[[2-[2-[[2-[2-[[(4S)-4-carboxy-4-(13-carboxytridecanoylamino)butanoyl]amino]ethoxy]ethoxy]acetyl]amino]ethoxy]ethoxy]acetyl]amino]ethoxy]ethoxy]acetyl]amino]ethoxy]ethoxy]acetyl], $N^{\epsilon 31}$-[2-[2-[2-[[2-[2-[2-[[2-[2-[2-[[2-[2-[2-[[2-[2-[2-[[(4S)-4-carboxy-4-(13-carboxytridecanoylamino)butanoyl]amino]ethoxy]ethoxy]acetyl]amino]ethoxy]ethoxy]acetyl]amino]ethoxy]ethoxy]acetyl]amino]ethoxy]ethoxy]acetyl]amino]ethoxy]ethoxy]acetyl]-[Aib$^8$,Lys$^{18}$,Glu$^{22}$,Val$^{25}$,Arg$^{26}$,Lys$^{31}$,Arg$^{34}$]-GLP-1-(7-37)-peptide (SEQ ID NO: 12)

Chem. 174

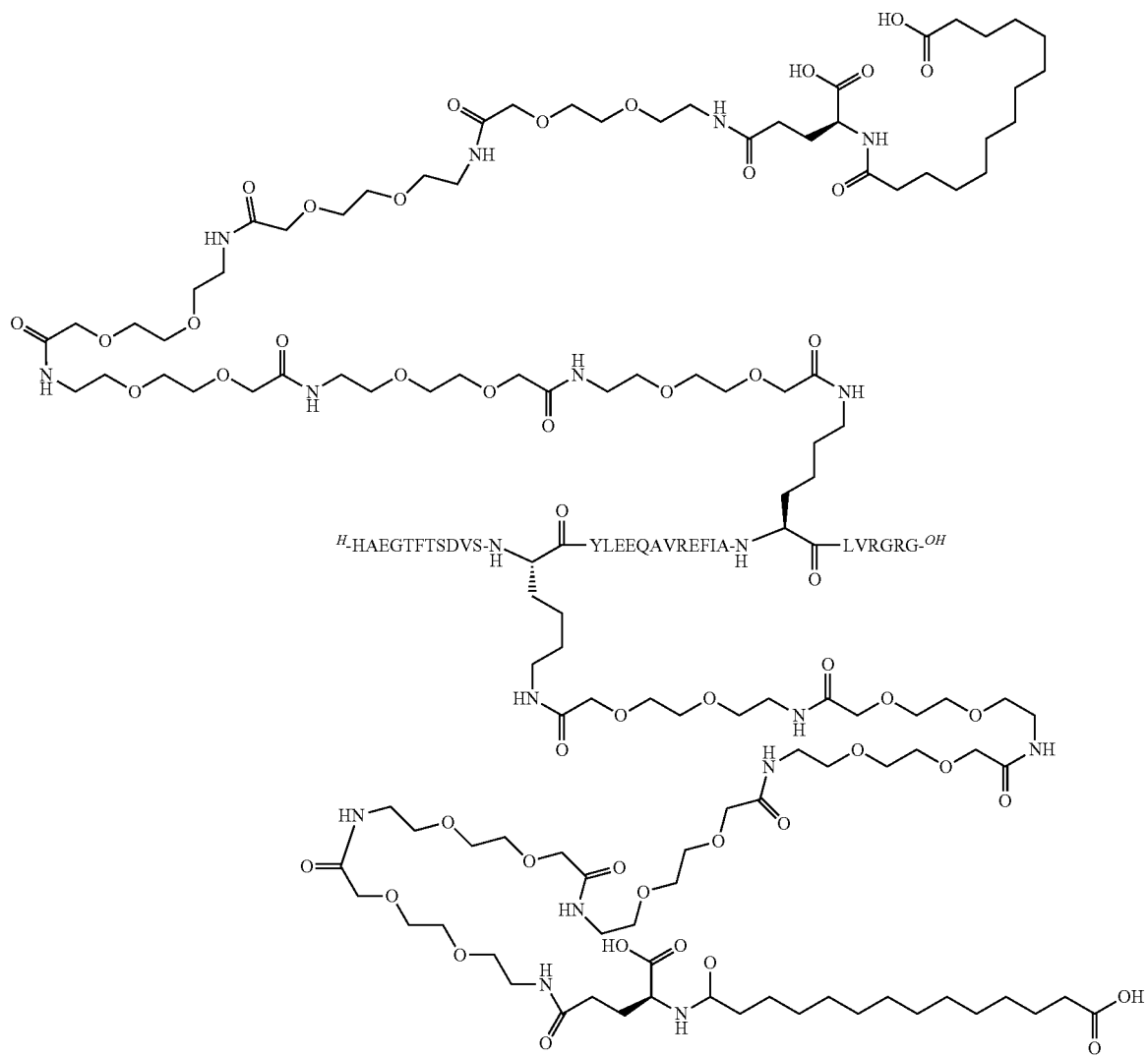

Preparation Method: SPPS_P; SC_P; CP_M1
LCMS method: LCMS_4: Rt=2.20 min; m/6=999; m/5=1199; m/4=1498; m/3=1997
UPLC method: B2_1: Rt=11.95 min
UPLC method: 05_B5_1: Rt=4.62 min Example 132

$N^{\epsilon 18}$-[2-[2-[2-[[2-[2-[2-[[(4S)-4-carboxy-4-[10-(4-carboxyphenoxy)decanoylamino]butanoyl]amino]ethoxy]ethoxy]acetyl]amino]ethoxy]ethoxy]acetyl], $N^{\epsilon 26}$-[2-[2-[2-[[2-[2-[2-[[(4S)-4-carboxy-4-[10-(4-carboxyphenoxy)decanoylamino]butanoyl]amino]ethoxy]ethoxy]acetyl]amino]ethoxy]ethoxy]acetyl]-[Aib$^{8}$,Lys8,Glu$^{22}$,Gln$^{34}$]-GLP-1-(7-37)-peptide amide (SEQ ID NO: 7)

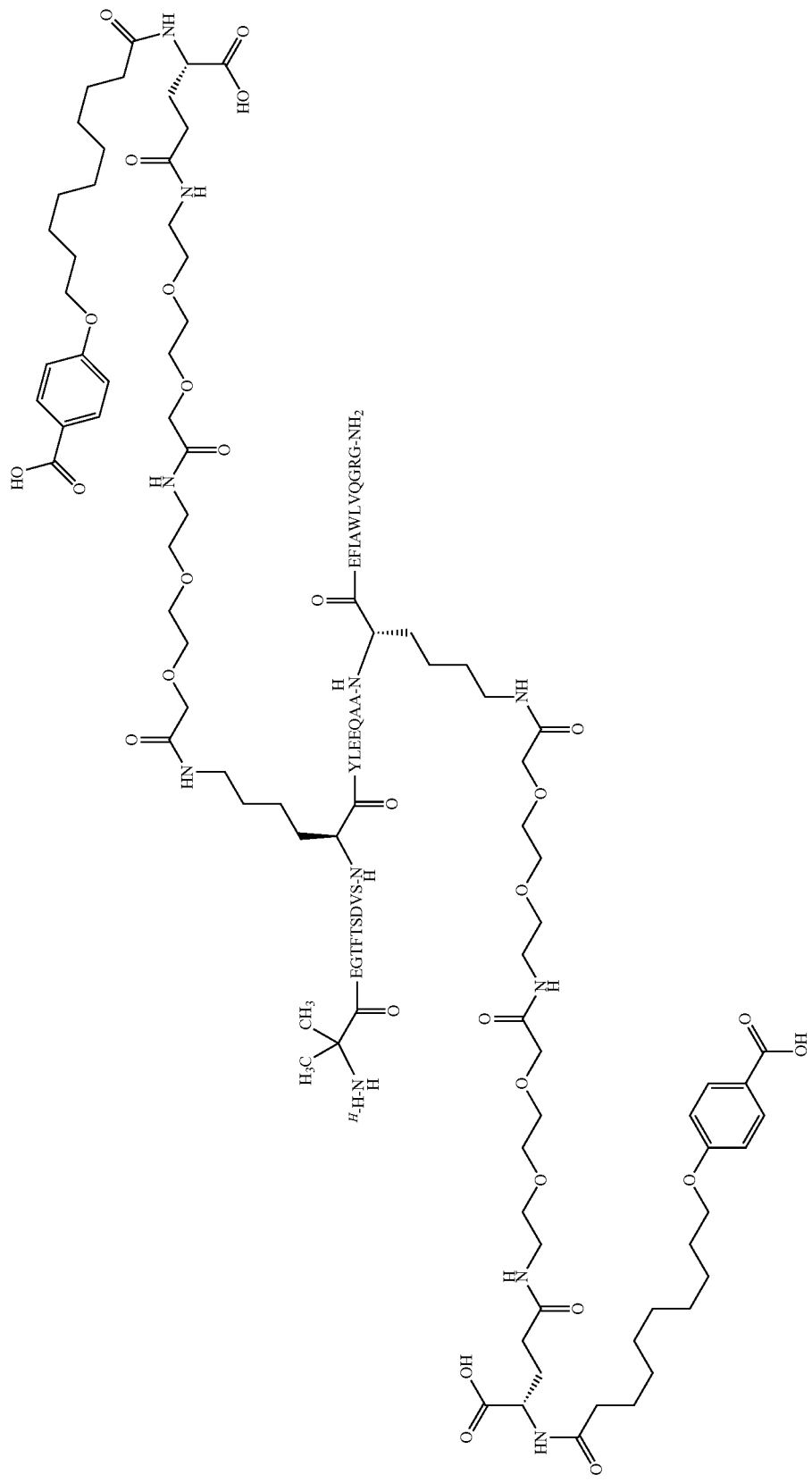

Preparation Method: SPPS_P; SC_M1; CP_M1
The theoretical molecular mass of 4901 Da was confirmed by method: MALDI_MS: m/z: 4899
UPLC Method: B2_1: Et=13.47 min
UPLC Method: 04_A6_1: Rt=5.15 min

Example 133

$N^{\epsilon 18}$-[2-[2-[2-[[2-[2-[2-[[(4S)-4-carboxy-4-(13-carboxytridecanoylamino)butanoyl]amino]ethoxy]ethoxy]acetyl]amino]ethoxy]ethoxy]acetyl],$N^{\epsilon 31}$-[2-[2-[2-[[2-[2-[2-[[(4S)-4-carboxy-4-(13-carboxytridecanoylamino)butanoyl]amino]ethoxy]ethoxy]acetyl]amino]ethoxy]ethoxy]acetyl]-[Lys18,Glu22,Val25,Arg26,Lys31,Arg34]-GLP-1-(7-37)-peptide amide (SEQ ID NO: 10)

Chem. 176
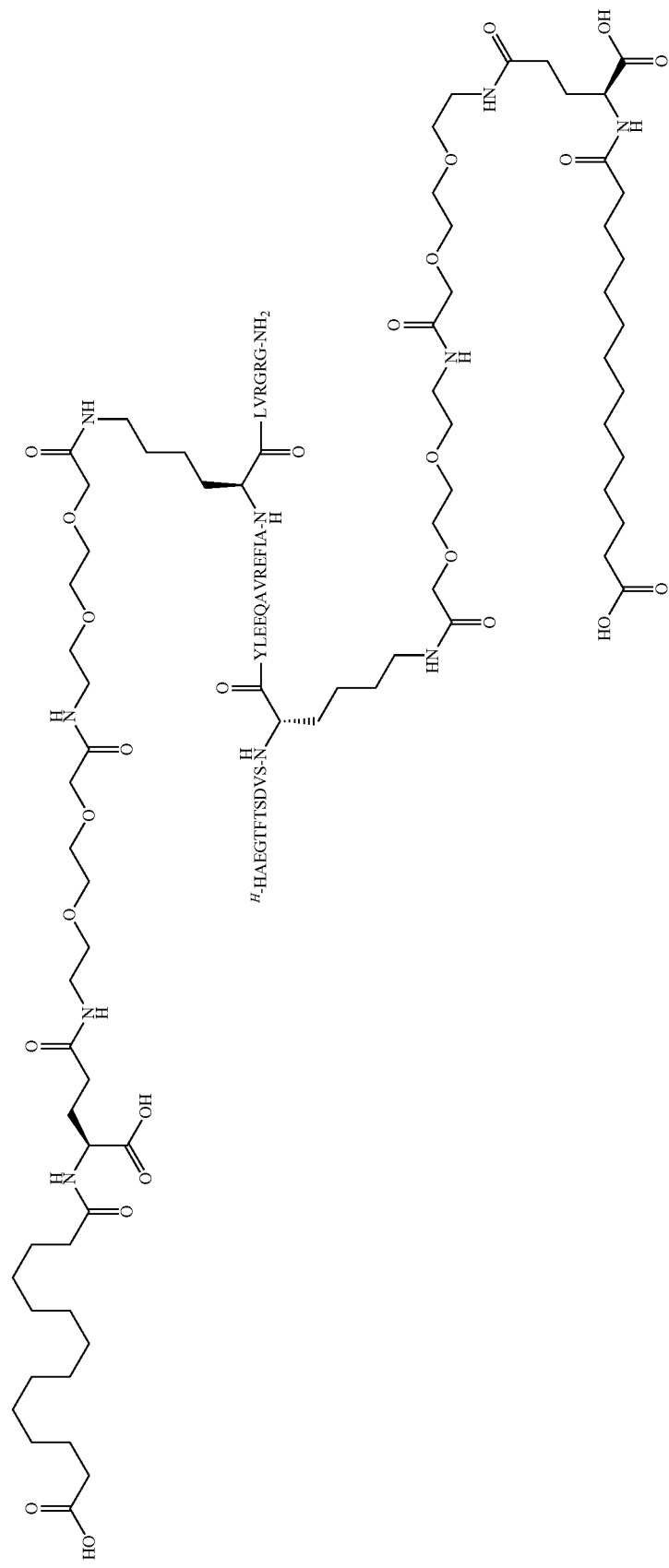

Preparation Method: SPPS_P; SC_M1; CP_M1
The theoretical molecular mass of 4813.5 Da was confirmed by method: MALDI_MS: m/z: 4813
UPLC Method: B2_1: Rt=12.42 min
UPLC Method: 04_A6_1: Rt=5.18 min Example 134

$N^{\epsilon18}$-[2-[2-[2-[[2-[2-[2-[[(4S)-4-carboxy-4-[[(4S)-4-carboxy-4-(15-carboxypentadecanoylamino)butanoyl]amino]butanoyl]amino]ethoxy]ethoxy]acetyl]amino]ethoxy]ethoxy]acetyl], $N^{\epsilon31}$-[2-[2-[2-[[2-[2-[2-[[(4S)-4-carboxy-4-[[(4S)-4-carboxy-4-(15-carboxypentadecanoylamino)butanoyl]amino]butanoyl]amino]ethoxy]ethoxy]acetyl]amino]ethoxy]ethoxy]acetyl]-[Aib$^8$,Lys$^{18}$,Glu$^{22}$,Val$^{25}$,Arg$^{26}$,Lys$^{31}$,Arg$^{34}$]-GLP-1-(7-37)-peptide (SEQ ID NO: 12)

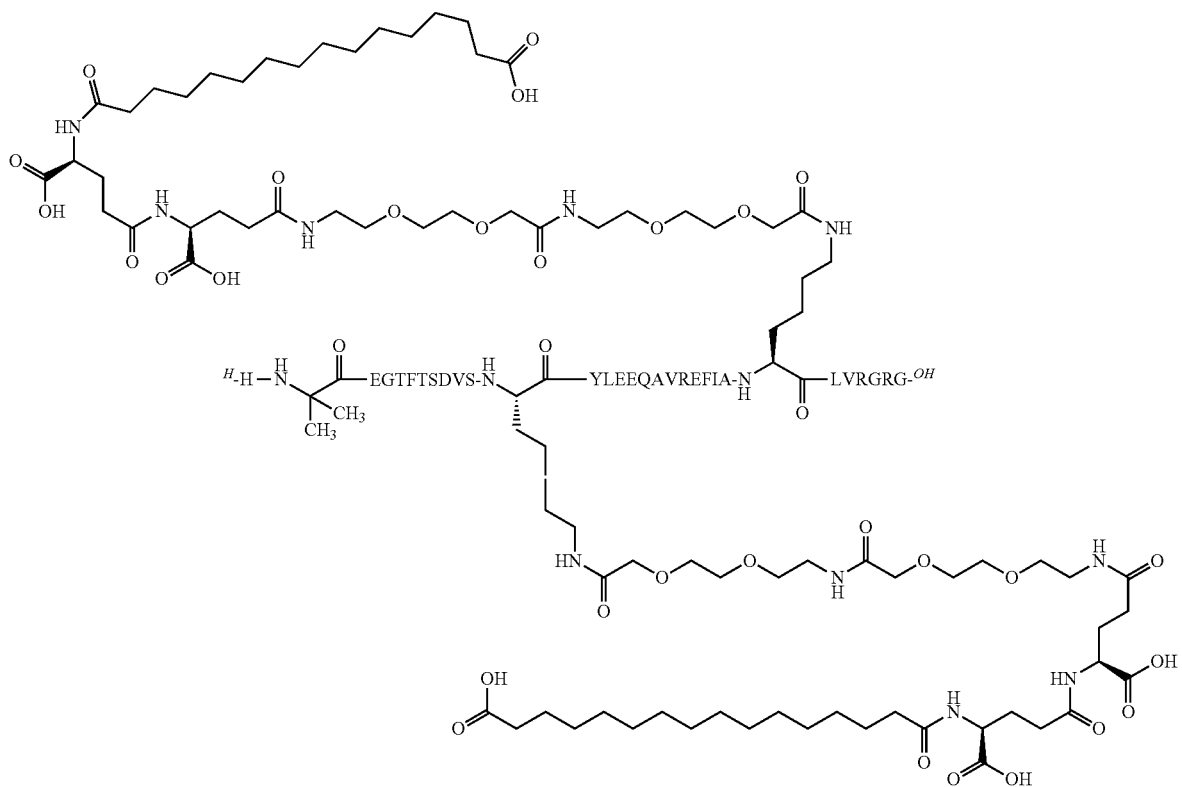

Chem. 177

Preparation Method: SPPS_P; SC_P; CP_M1
LCMS: Method LCMS_4: Rt=3.1 min; m/5=1029; m/4=1286; m/3=1715
UPLC: Method: B4_1: Rt=8.7 min Example 135

$N^{\epsilon18}$-[2-[2-[2-[[2-[2-[2-[[2-[2-[2-[[2-[2-[2-[[(4S)-4-carboxy-4-(15-carboxypentadecanoylamino)butanoyl]amino]ethoxy]ethoxy]acetyl]amino]ethoxy]ethoxy]acetyl]amino]ethoxy]ethoxy]acetyl]amino]ethoxy]ethoxy]acetyl], $N^{\epsilon31}$-[2-[2-[2-[[2-[2-[2-[[2-[2-[2-[[2-[2-[2-[[(4S)-4-carboxy-4-(15-carboxypentadecanoylamino)butanoyl]amino]ethoxy]ethoxy]acetyl]amino]ethoxy]ethoxy]acetyl]amino]ethoxy]ethoxy]acetyl]amino]ethoxy]ethoxy]acetyl]-[Aib$^8$,Lys$^{18}$,Glu$^{22}$,Val$^{25}$,Arg$^{26}$,Lys$^{31}$,Arg$^{34}$]-GLP-1-(7-37)-peptide amide (SEQ ID NO: 12)

Chem. 178

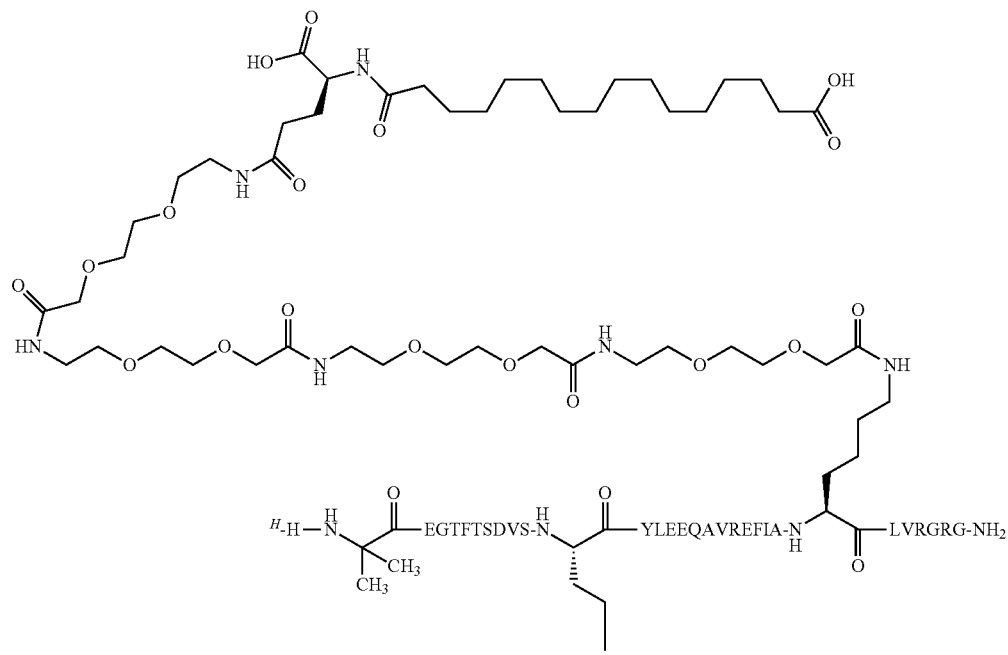

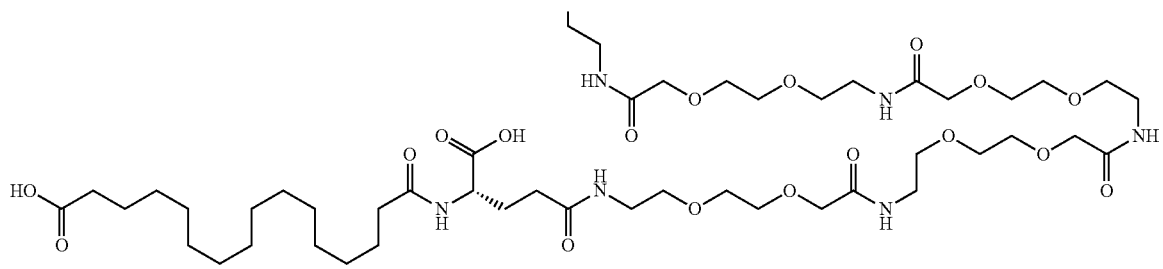

Preparation Method: SPPS_P; SC_P; CP_M1

The theoretical molecular mass of 5463 Da was confirmed by Method: Maldi_MS: m/z 5463

UPLC: Method: 10_B29_1, Rt=10.7 min
UPLC: Method: 04_A6_1, Rt=5.9 min

Example 136

$N^{\epsilon 18}$-[2-[2-[2-[[2-[2-[2-[[(4S)-4-carboxy-4-[10-(4-carboxyphenoxy)decanoylamino]butanoyl]amino]ethoxy]ethoxy]acetyl]amino]ethoxy]ethoxy]acetyl], $N^{\epsilon 26}$-[2-[2-[2-[[2-[2-[2-[[(4S)-4-carboxy-4-[10-(4-carboxyphenoxy)decanoylamino]butanoyl]amino]ethoxy]ethoxy]acetyl]amino]ethoxy]ethoxy]acetyl]-[Imp$^7$,Lys$^{18}$,Glu$^{22}$,Gln$^{34}$]-GLP-1-(7-37)-peptide (SEQ ID NO: 62)

Chem. 179

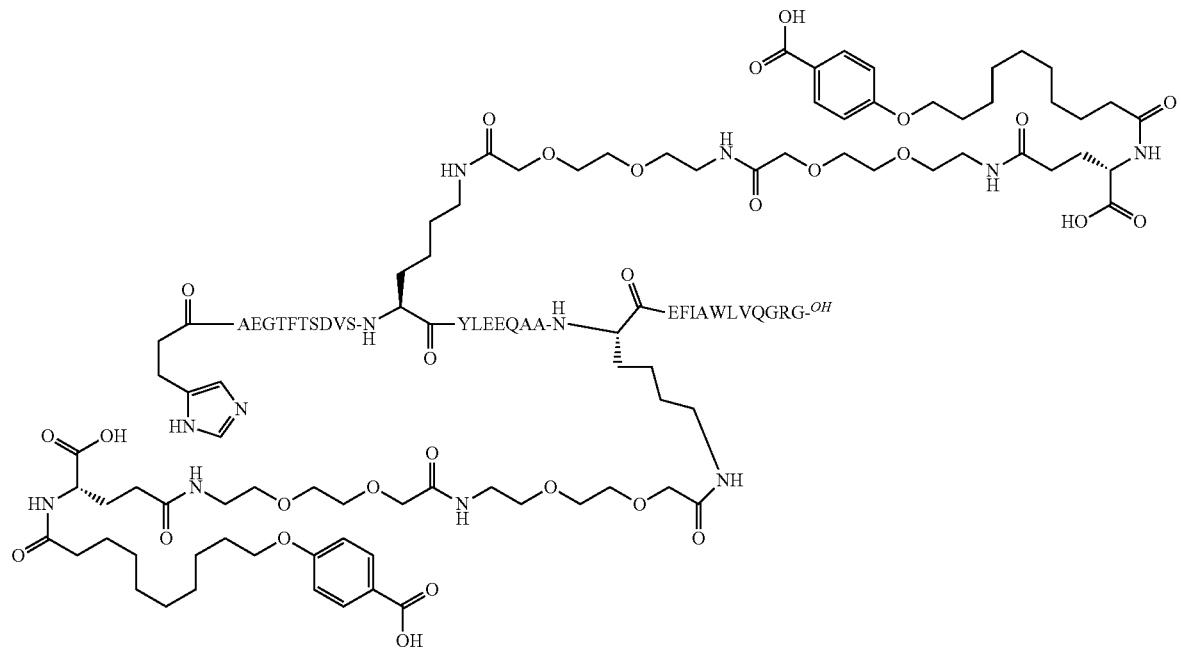

Preparation Method: SPPS_P; SC_M1; CP_M1
LCMS: Method LCMS_4: Rt=2.37 min; m/4=1219; m/3=1625
UPLC Method B41: Rt=9.16 min
UPLC Method 04_A6_1: Rt=4.5 min Example 137

$N^{\epsilon 18}$-[2-[2-[2-[[2-[2-[2-[[2-[2-[2-[[2-[2-[2-[[(4S)-4-carboxy-4-(13-carboxytridecanoylamino)butanoyl]amino]ethoxy]ethoxy]acetyl]amino]ethoxy]ethoxy]acetyl]amino]ethoxy]ethoxy]acetyl]amino]ethoxy]ethoxy]acetyl], $N^{\epsilon 31}$-[2-[2-[2-[[2-[2-[2-[[2-[2-[2-[[2-[2-[2-[[(4S)-4-carboxy-4-(13-carboxytridecanoylamino)butanoyl]amino]ethoxy]ethoxy]acetyl]amino]ethoxy]ethoxy]acetyl]amino]ethoxy]ethoxy]acetyl]amino]ethoxy]ethoxy]acetyl]-[Aib$^8$,Lys$^{18}$,Glu$^{22}$,Val$^{25}$,Arg$^{26}$,Lys$^{31}$,Arg$^{34}$]-GLP-1-(7-37)-peptide (SEQ ID NO: 12)

Chem. 180
411 412
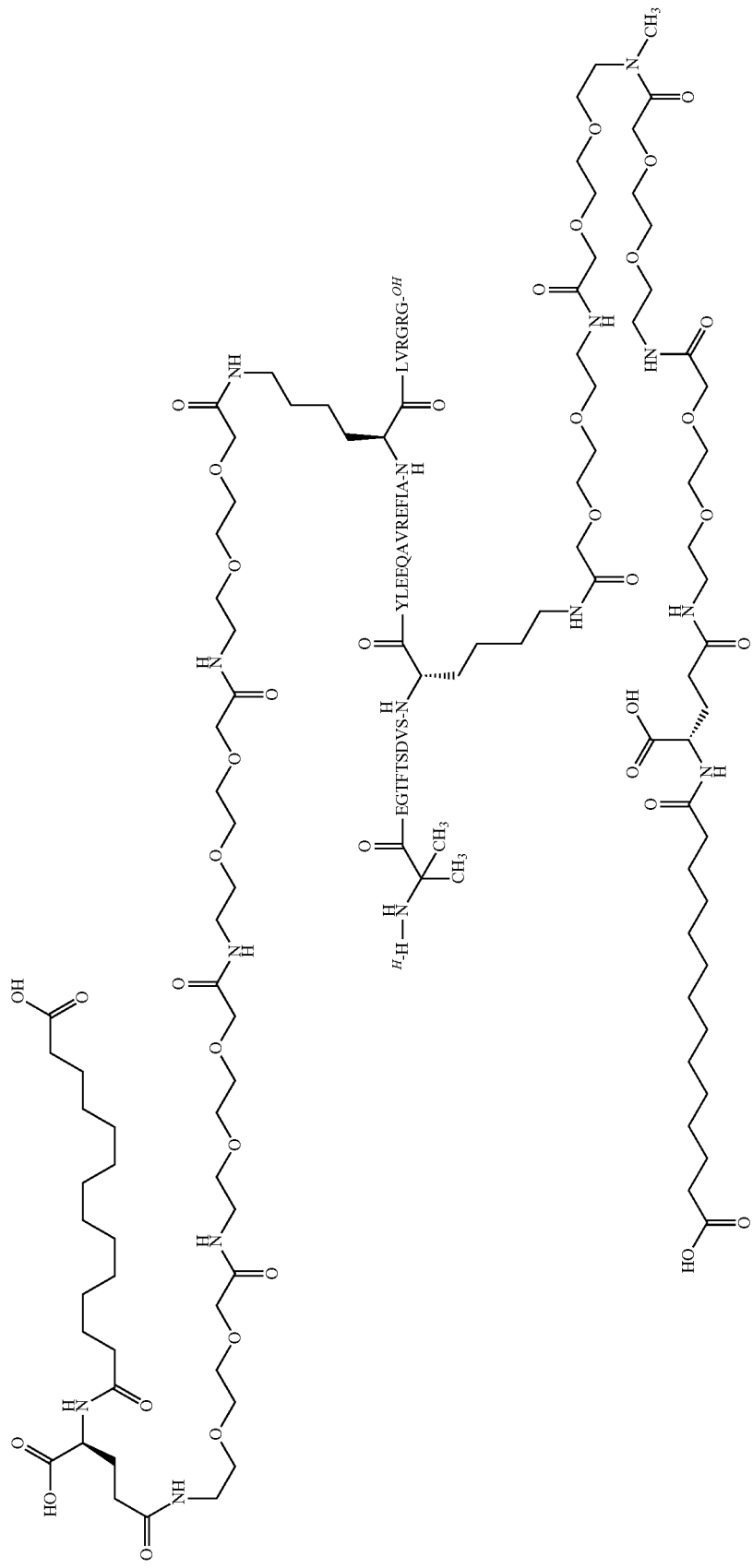

Preparation Method: SPPS_P; SC_P; CP_M1
The theoretical molecular mass of 5409 Da was confirmed by Method: Maldi_MS: m/z 5408
UPLC: Method 10_B29_1: Rt=8.6 min
UPLC: Method 04_A6_1: Rt=5.2 min Example 138

$N^{\epsilon 18}$-[2-[2-[2-[[2-[2-[2-[[(4S)-4-carboxy-4-(15-carboxypentadecanoylamino)butanoyl]amino]ethoxy]ethoxy]acetyl]amino]ethoxy]ethoxy]acetyl], $N^{\epsilon 26}$-[2-[2-[2-[[2-[2-[2-[[(4S)-4-carboxy-4-(15-carboxypentadecanoylamino)butanoyl]amino]ethoxy]ethoxy]acetyl]amino]ethoxy]ethoxy]acetyl]-[Aib$^8$,Lys$^{18}$,Glu$^{22}$,Arg$^{34}$]-GLP-1-(7-35)-peptide (SEQ ID NO: 53)

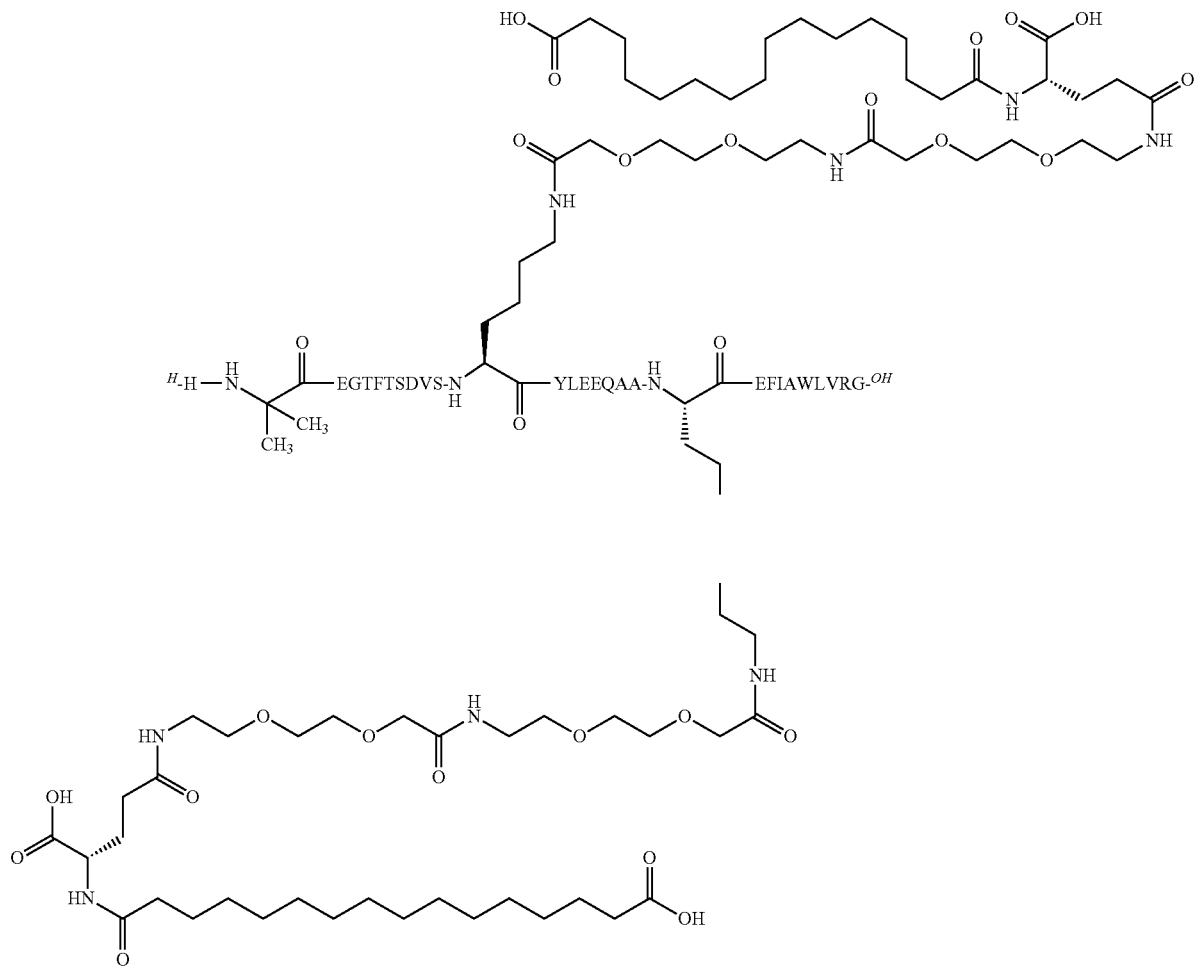

Chem. 181

Preparation Method: SPPS_P; SC_P; CP_M1
The theoretical molecular mass of 4673 Da was confirmed by Method: Maldi_MS: m/z 4673
UPLC: Method 10_B29_1: Rt=15.7 min
UPLC: Method 04_A6_1: Rt=4.6 min

Example 139

N^ε18^-[2-[2-[2-[[2-[2-[2-[[(4S)-4-carboxy-4-[0-(4-carboxy-phenoxy)decanoylamino]butanoyl]amino]ethoxy]ethoxy]acetyl]amino]ethoxy]ethoxy]acetyl], N^ε26^-[2-[2-[2-[[2-[2-[2-[[(4S)-4-carboxy-4-[10-(4-carboxyphenoxy)decanoylamino]butanoyl]amino]ethoxy]ethoxy]acetyl]amino]ethoxy]ethoxy]acetyl]-[Aib8,Leu12,Lys18,Gln34]-GLP-1-(7-37)-peptide (SEQ ID NO: 63)

Chem. 182

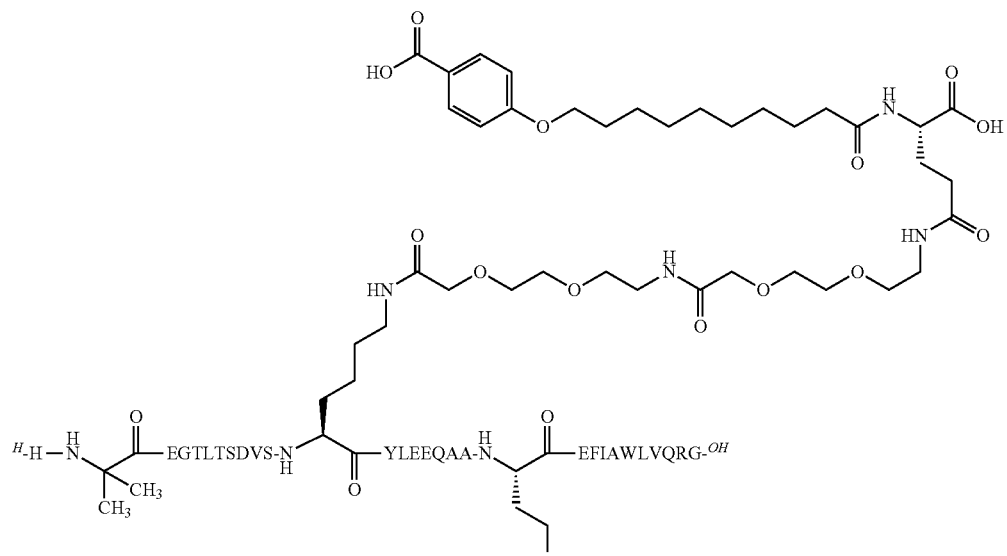

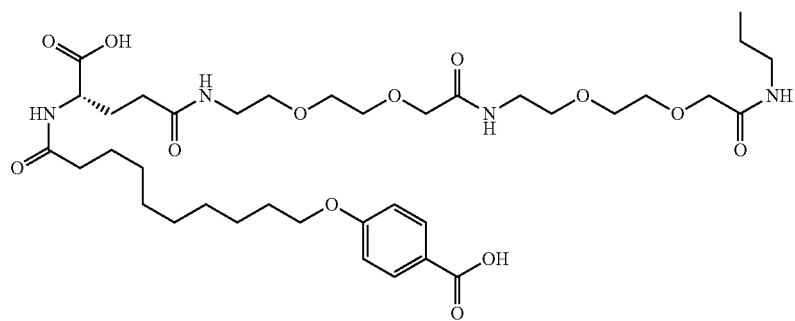

Preparation Method: SPPS_P; SC_P; CP_M1

The theoretical molecular mass of 4796 Da was confirmed by Method: Maldi_MS: m/z 4796

UPLC: Method 10_B31_1: Rt=16.6 min

UPLC: Method 04_A6_1: Rt=5.6 min

Example 140

$N^{\epsilon 18}$-[2-[2-[2-[[2-[2-[2-[[(4S)-4-carboxy-4-[10-(4-carboxyphenoxy)decanoylamino]butanoyl]amino]ethoxy]ethoxy]acetyl]amino]ethoxy]ethoxy]acetyl], $N^{\epsilon 26}$-[2-[2-[2-[[2-[2-[2-[[(4S)-4-carboxy-4-[10-(4-carboxyphenoxy)decanoylamino]butanoyl]amino]ethoxy]ethoxy]acetyl]amino]ethoxy]ethoxy]acetyl]-[Aib$^8$,Lys$^{18}$,Glu$^{22}$,Arg$^{34}$]-GLP-1-(7-35)-peptide (SEQ ID NO: 53)

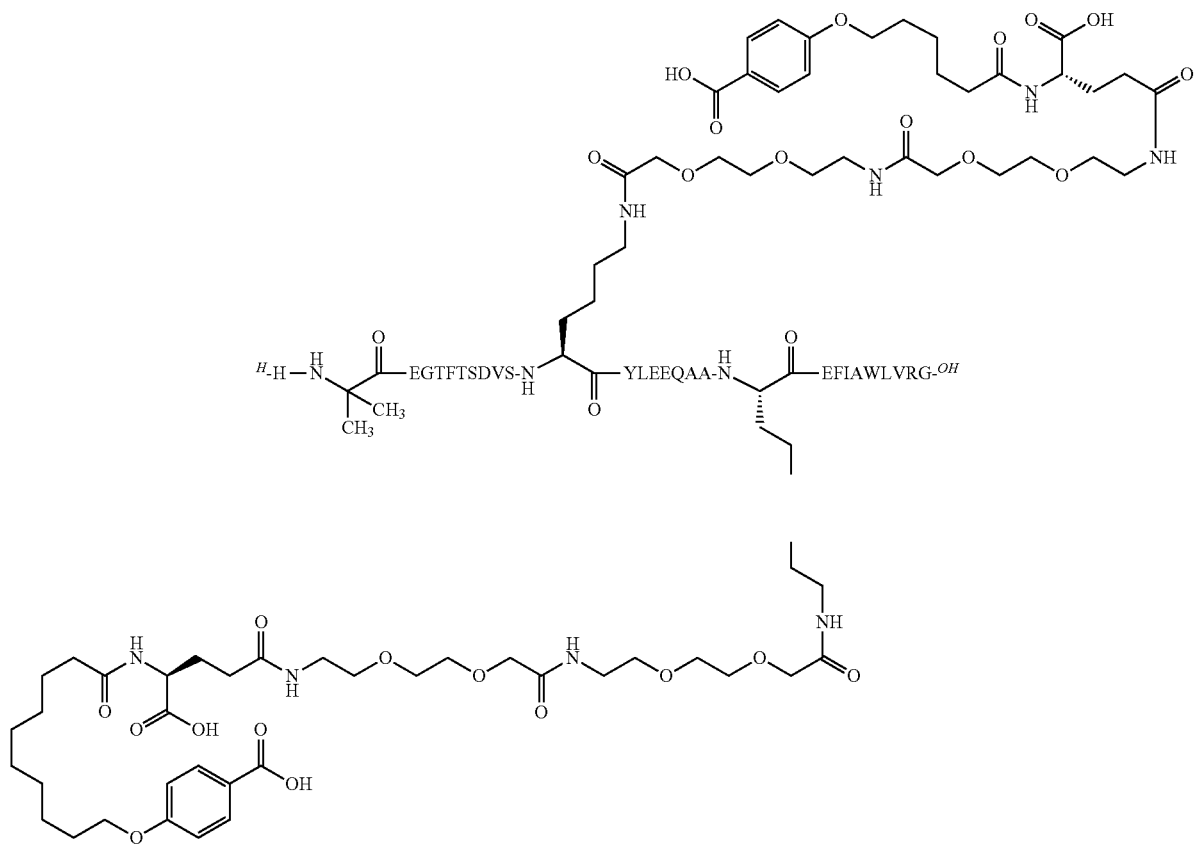

Chem. 183

Preparation Method: SPPS_P; SC_P; CP_M1

The theoretical molecular mass of 4717 Da was confirmed by Method: Maldi_MS: m/z 4716

UPLC: Method 10_B31_1: Rt=18.0 min
UPLC: Method 04_A6_1: Rt=4.6 min

Example 141

$N^{\epsilon 18}$-[2-[2-[2-[[2-[2-[2-[[(4S)-4-carboxy-4-(13-carboxytridecanoylamino)butanoyl]amino]ethoxy]ethoxy]acetyl]amino]ethoxy]ethoxy]acetyl], $N^{\epsilon 26}$-[2-[2-[2-[[2-[2-[2-[[(4S)-4-carboxy-4-(13-carboxytridecanoylamino)butanoyl]amino]ethoxy]ethoxy]acetyl]amino]ethoxy]acetyl]-[Aib$^8$,Lys$^{18}$,Gln$^{34}$]-GLP-1-(7-37)-peptide (SEQ ID NO: 54)

Chem. 189

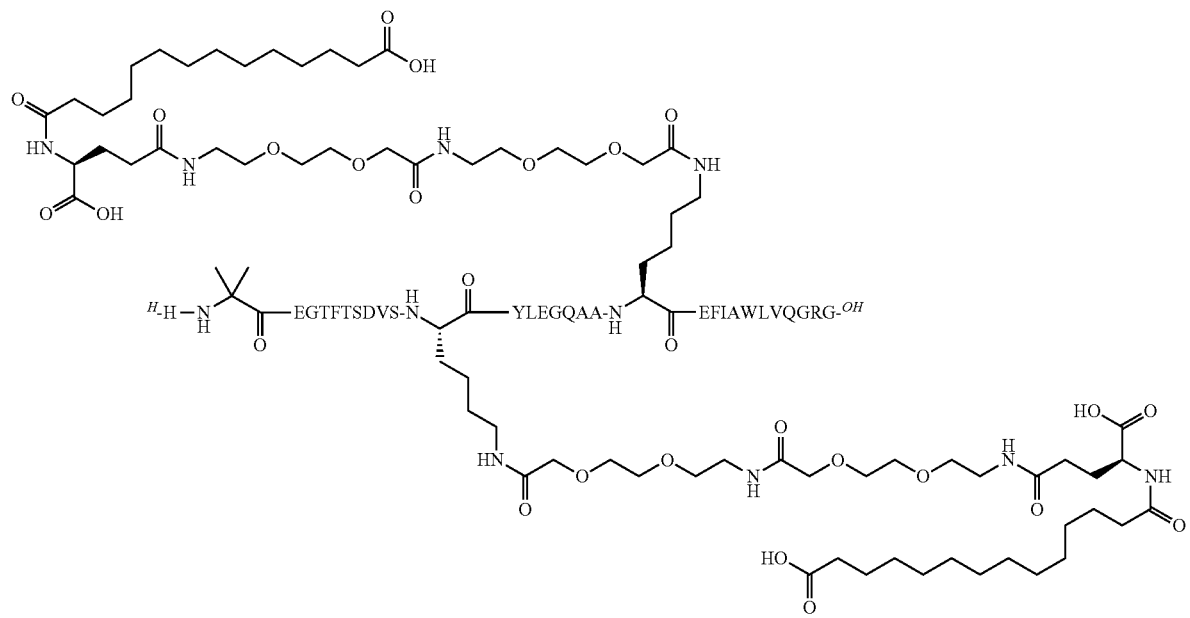

Preparation Method: SPPS_L; SC_L; CP_M1
UPLC method: B2_1; Rt=13.70 min
UPLC method: 04_A6_1: Rt=6.23 min
LCMS method: LCMS_4: Rt=3.08 min; m/3=1577; m/4=1183; m/5=947

Example 142

$N^{\epsilon 18}$-[2-[2-[2-[[2-[2-[2-[[(4S)-4-carboxy-4-[10-(4-carboxyphenoxy)decanoylamino]butanoyl]amino]ethoxy]ethoxy]acetyl]amino]ethoxy]ethoxy]acetyl], $N^{\epsilon 26}$-[2-[2-[2-[[2-[2-[2-[[(4S)-4-carboxy-4-[10-(4-carboxyphenoxy)decanoylamino]butanoyl]amino]ethoxy]ethoxy]acetyl]amino]ethoxy]ethoxy]acetyl]-[Aib$^8$,Lys$^{18}$,His$^{34}$]-GLP-1-(7-37)-peptide (SEQ ID NO: 64)

Chem. 190
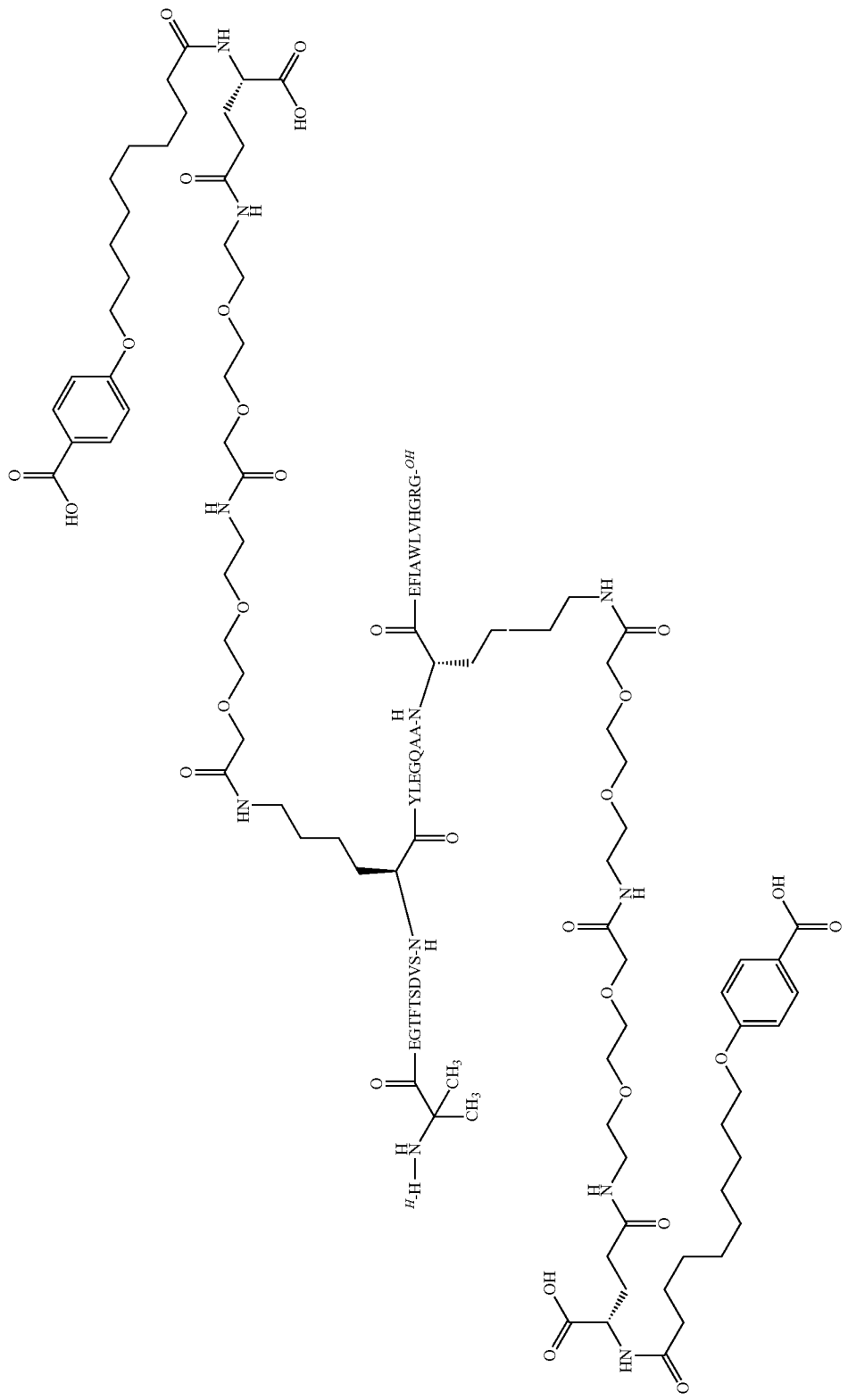

Preparation Method: SPPS_P; SC_P; CP_M1
UPLC method: 10_B31_1; Rt=16.5 min
UPLC method: 04_A6_1; Rt=5.2 min
The theoretical molecular mass of 4839 Da was confirmed by Method: Maldi_MS: m/z 4837

Example 143

$N^{\epsilon 18}$-[2-[2-[2-[[2-[2-[2-[[(4S)-4-carboxy-4-(15-carboxy-pentadecanoylamino)butanoyl]amino]ethoxy]ethoxy]acetyl]amino]ethoxy]ethoxy]acetyl], $N^{\epsilon 26}$-[2-[2-[2-[[2-[2-[2-[[(4S)-4-carboxy-4-(15-carboxypentadecanoylamino)butanoyl]amino]ethoxy]ethoxy]acetyl]amino]ethoxy]ethoxy]acetyl]-[Aib$^8$,Lys$^{18}$,Glu$^{22}$,Gln$^{34}$]-GLP-1-(7-37)-peptide (SEQ ID NO: 7)

Chem. 191
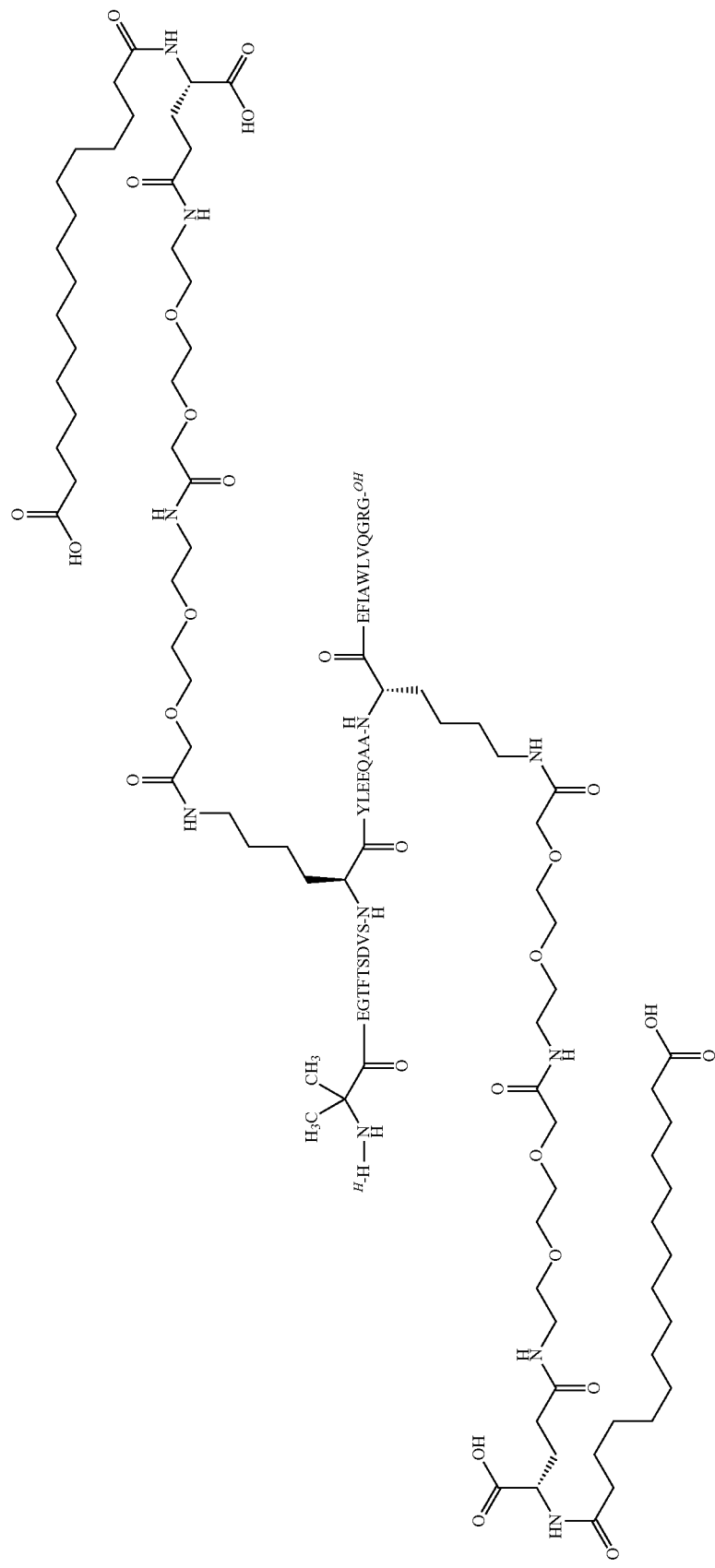

Preparation Method: SPPS_L; SC_L; CP_M1
UPLC method: B4_1; Rt=9.56 min
UPLC method: 08_B29_1; Rt=9.15 min
LCMS method: LCMS_4: Rt=2.48 min m/z=4859; m/3=1620; m/4=1215; m/5=972; m/6=810; m/7=695

Example 144

$N^{\epsilon 18}$-[2-[2-[2-[[2-[2-[2-[[2-[2-[2-[[2-[2-[2-[[2-[2-[2-[[2-[2-[2-[[(4S)-4-carboxy-4-(13-carboxytridecanoylamino)butanoyl]amino]ethoxy]ethoxy]acetyl]amino]ethoxy]ethoxy]acetyl]amino]ethoxy]ethoxy]acetyl]amino]ethoxy]ethoxy]acetyl]amino]ethoxy]ethoxy]acetyl]amino]ethoxy]ethoxy]acetyl], N β-[2-[2-[2-[[2-[2-[2-[[2-[2-[2-[[2-[2-[2-[[2-[2-[2-[[(4S)-4-carboxy-4-(13-carboxytridecanoylamino)butanoyl]amino]ethoxy]ethoxy]acetyl]amino]ethoxy]ethoxy]acetyl]amino]ethoxy]ethoxy]acetyl]amino]ethoxy]ethoxy]acetyl]amino]ethoxy]ethoxy]acetyl]-[Aib$^8$,Lys$^{18}$,Glu$^{22}$,Val$^{25}$,Arg$^{26}$,Lys$^{31}$,Arg$^{34}$]-GLP-1-(7-37)-peptide (SEQ ID NO: 12)

Chem. 192

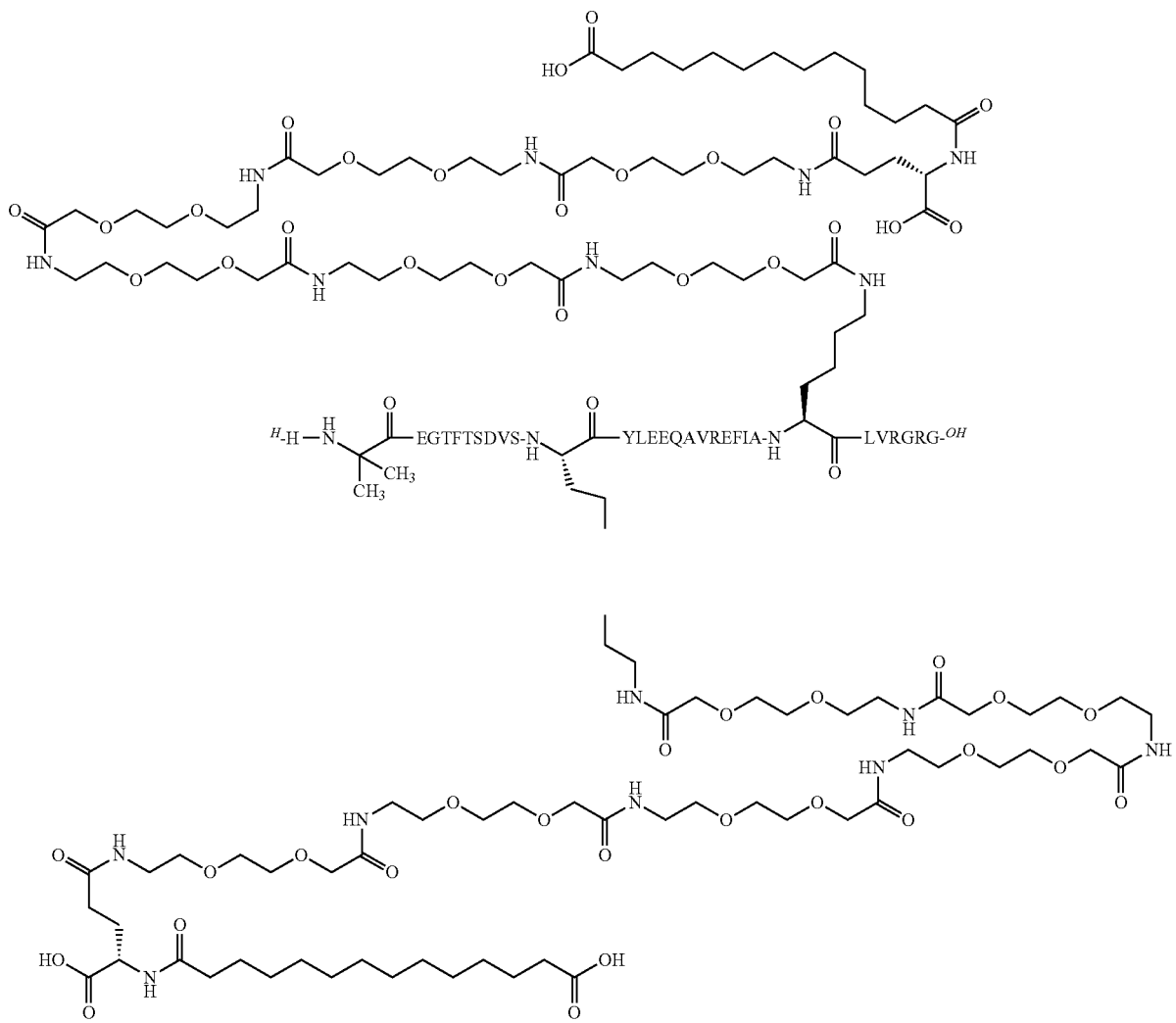

Preparation Method: SPPS_L; SC_L; CP_M1
UPLC Method: B4_1; Rt=7.78 min
UPLC Method: 04_A6_1; Rt=5.01 min
UPLC Method: 10_B29_1; Rt=8.31 min
LC-MS Method: LCMS_4; RT=2.01 min; m/4: 1498; m/5: 1199

Example 14

$N^{\epsilon 18}$-[2-[2-[2-[[(4S)-4-carboxy-4-[2-[[2-[2-(13-carboxytridecanoylamino)ethoxy]ethoxy]acetyl]amino]butanoyl]amino]ethoxy]ethoxy]acetyl]$N^{\epsilon 31}$-[2-[2-[2-[[(4S)-4-carboxy-4-[[2-[2-[2-(13-carboxytridecanoylamino)ethoxy]ethoxy]acetyl]amino]butanoyl]amino]ethoxy]ethoxy]acetyl]-[Aib$^8$,Lys$^{18}$,Glu$^{22}$,Val$^{25}$,Arg$^{26}$,Lys$^{31}$,Arg$^{34}$]-GLP-1-(7-37)-peptide (SEQ ID NO: 12)

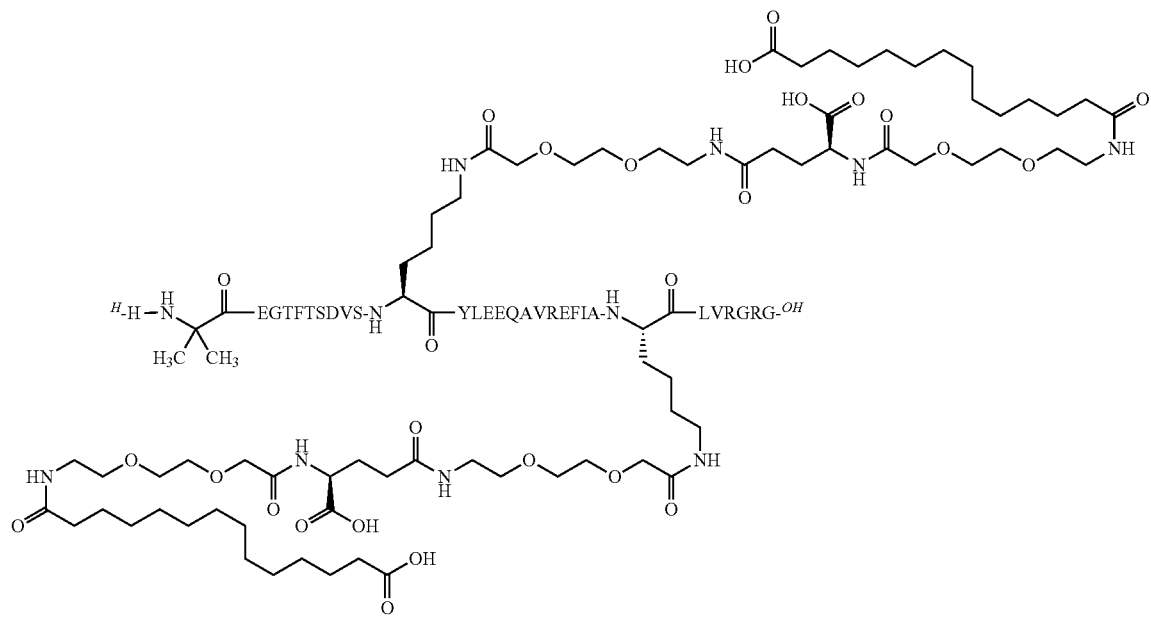

Chem. 193

Preparation Method: SPPS_A; SC_A; CP_M1

UPLC Method: 10_B29_1: Rt=10.56 min

UPLC method: B4_1: Rt=8.35 min

UPLC Method: 04_A6_1: Rt=5.37 min

LCMS method: LCMS_4: Rt=2.12 min; m/3=1611; m/4=1208; m/5=967

Example 146

$N^{\epsilon 18}$-[2-[2-[2-[[(4S)-4-carboxy-4-[2-[[2-[2-(15-carboxypentadecanoylamino)ethoxy]ethoxy]acetyl]amino]butanoyl]amino]ethoxy]ethoxy]acetyl], $N^{\epsilon 31}$-[2-[2-[2-[[(4S)-4-carboxy-4-[[2-[2-[2-(15-carboxypentadecanoylamino)ethoxy]ethoxy]acetyl]amino]butanoyl]amino]ethoxy]ethoxy]acetyl]-[Aib$^8$, Lys$^{18}$,Glu$^{22}$,Val$^{25}$,Arg$^{26}$,Lys$^{31}$,Arg$^{34}$]-GLP-1-(7-37)-peptide (SEQ ID NO: 12)

Chem. 194

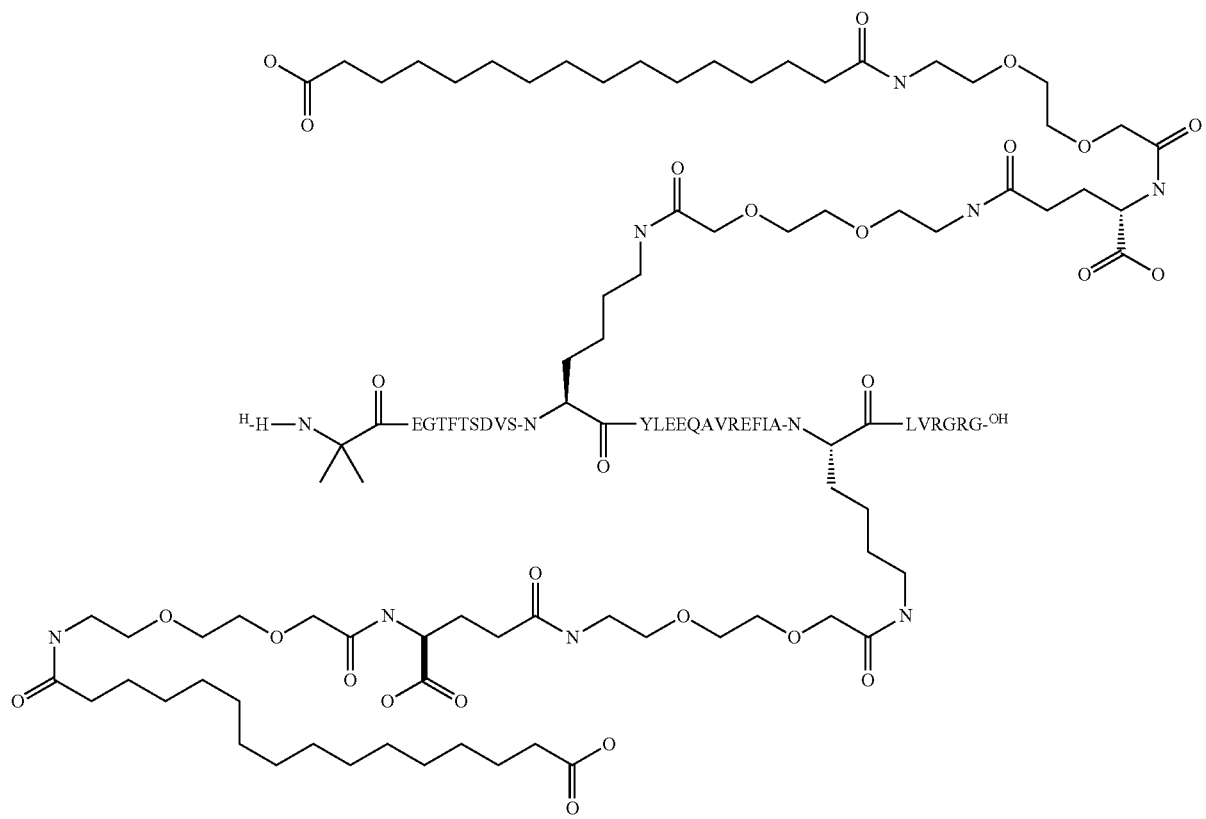

Preparation Method: SPPS_A; SC_A; CP_M1

UPLC Method: 10_B29_1: Rt=13.63 min

UPLC Method: B4_1: Rt=9.02 min

UPLC Method: 04_A9_1: Rt=13.76 min

LCMS method: LCMS_4: Rt=2.27 min; m/3=1629; m/4=1222; m/5=978

Example 147

$N^{\epsilon 18}$-[2-[2-[2-[[2-[2-[2-[[(4S)-4-carboxy-4-(15-carboxy-pentadecanoylamino)butanoyl]amino]ethoxy]ethoxy]acetyl]amino]ethoxy]ethoxy]acetyl], $N^{\epsilon 27}$-[2-[2-[2-[[2-[2-[2-[[(4S)-4-carboxy-4-(15-carboxypentadecanoylamino)butanoyl]amino]ethoxy]ethoxy]acetyl]amino]ethoxy]ethoxy]acetyl]-[Imp$^7$,Lys$^{18}$, Glu$^{22}$,Arg$^{26}$,Lys$^{27}$,Gln$^{34}$]-GLP-1-(7-37)-peptide (SEQ ID NO: 65)

Chem. 195

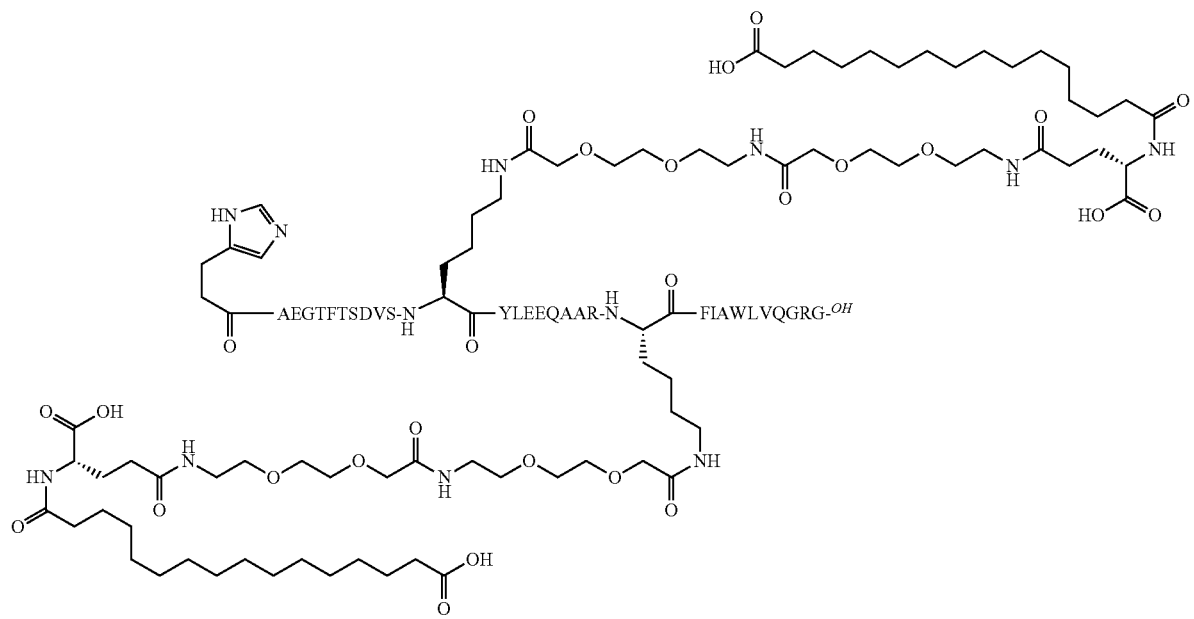

Preparation Method: SPPS_L; SC_L; CP_M1
UPLC Method: B4_1: Rt=9.3 min
UPLC Method: 04_A6_1: Rt=6.5 min
LCMS Method: LCMS_4: Rt=2.52 min; m/3: 1619; m/4: 1215

Biological Methods

Example 148: In Vitro Potency

The purpose of this example is to test the activity, or potency, of the GLP-1 derivatives in vitro.

The potencies of the GLP-1 derivatives of Examples 1-79, 81-116, and 118-146 were determined as described below, i.e. as the stimulation of the formation of cyclic AMP (cAMP) in a medium containing membranes expressing the human GLP-1 receptor.

Principle

Purified plasma membranes from a stable transfected cell line, BHK467-12A (tk-ts13), expressing the human GLP-1 receptor were stimulated with the GLP-1 derivative in question, and the potency of cAMP production was measured using the AlphaScreen™ cAMP Assay Kit from Perkin Elmer Life Sciences. The basic principle of The AlphaScreen Assay is a competition between endogenous cAMP and exogenously added biotin-cAMP. The capture of cAMP is achieved by using a specific antibody conjugated to acceptor beads.

Cell Culture and Preparation of Membranes

A stable transfected cell line and a high expressing clone were selected for screening. The cells were grown at 5% $CO_2$ in DMEM, 10% FCS, 1% Pen/Strep (Penicillin/Streptomycin) and 1.0 mg/ml of the selection marker G418.

Cells at approximate 80% confluence were washed 2× with PBS and harvested with Versene (aqueous solution of the tetrasodium salt of ethylenediaminetetraacetic acid), centrifuged 5 min at 1000 rpm and the supernatant removed. The additional steps were all made on ice. The cell pellet was homogenised by the Ultrathurax for 20-30 sec. in 10 ml of Buffer 1 (20 mM Na-HEPES, 10 mM EDTA, pH=7.4), centrifuged 15 min at 20,000 rpm and the pellet resuspended in 10 ml of Buffer 2 (20 mM Na-HEPES, 0.1 mM EDTA, pH=7.4). The suspension was homogenised for 20-30 sec and centrifuged 15 min at 20,000 rpm. Suspension in Buffer 2, homogenisation and centrifugation was repeated once and the membranes were resuspended in Buffer 2. The protein concentration was determined and the membranes stored at −80° C. until use.

The assay was performed in %-area 96-well plates, flat bottom (Costar cat. no: 3693). The final volume per well was 50 µl.

Solutions and Reagents

AlphaScreen cAMP Assay Kit from Perkin Elmer Life Sciences (cat. No: 6760625M); containing Anti-cAMP Acceptor beads (10 U/µl), Streptavidin Donor beads (10 U/µl) and Biotinylated-cAMP (133 U/µl).

AlphaScreen Buffer, pH=7.4: 50 mM TRIS-HCl (Sigma, cat. no: T3253); 5 mM HEPES (Sigma, cat. no: $H_{3375}$); 10 mM $MgCl_2$, $6H_2O$ (Merck, cat. no: 5833); 150 mM NaCl (Sigma, cat. no: S9625); 0.01% Tween (Merck, cat. no: 822184). The following was added to the AlphaScreen Buffer prior to use (final concentrations indicated): BSA (Sigma, cat. no. A7906): 0.1%; IBMX (Sigma, cat. no. 15879): 0.5 mM; ATP (Sigma, cat. no. A7699): 1 mM; GTP (Sigma, cat. no. G8877): 1 uM.

cAMP standard (dilution factor in assay=5): cAMP Solution: 5 µL of a 5 mM cAMP-stock+495 µL AlphaScreen Buffer.

Suitable dilution series in AlphaScreen Buffer were prepared of the cAMP standard as well as the GLP-1 derivative to be tested, e.g. the following eight concentrations of the GLP-1 compound: $10^{-7}$, $10^{-8}$, $10^{-9}$, $10^{-10}$, $10^{-11}$, $10^{-12}$, $10^{-13}$ and $10^{-14}$M, and a series from, e.g., $10^{-6}$ to $3\times10^{-11}$ of cAMP.

Membrane/Acceptor Beads

Use hGLP-1/BHK 467-12A membranes; 3 µg/well corresponding to 0.6 mg/ml (the amount of membranes used pr. well may vary)

"No membranes": Acceptor Beads (2 units/well final) in AlphaScreen buffer

"3 µg/well membranes": membranes+Acceptor Beads (2 units/well final) in AlphaScreen buffer Add 10 µl "No membranes" to the cAMP standard (per well in duplicates) and the positive and negative controls Add 10 µl "3 µg/well membranes" to the GLP-1 derivatives (per well in duplicates/triplicates)

Pos. Control: 10 µl "no membranes"+10 µl AlphaScreen Buffer

Neg. Control: 10 µl "no membranes"+10 µl cAMP Stock Solution (50 pM)

As the beads are sensitive to direct light, any handling was in the dark (as dark as possible), or in green light. All dilutions were made on ice.

Procedure

1. Make the AlphaScreen Buffer.
2. Dissolve and dilute the GLP-1 derivatives/cAMP standard in AlphaScreen Buffer.
3. Make the Donor Beads solution (by mixing streptavidin donor beads (2 units/well) and biotynylated cAMP (1.2 units/well) and incubate 20-30 min. in the dark at RT.
4. Add the cAMP/GLP-1 derivatives to the plate: 10 µl per well.
5. Prepare membrane/Acceptor Beads solution and add this to the plates: 10 µl per well.
6. Add the Donor Beads: 30 µl per well.
7. Wrap the plate in aluminium foil and incubate on the shaker for 3 hours (very slowly) at RT.
8. Count on AlphaScreen—each plate pre incubates in the AlphaScreen for 3 minutes before counting.

Results

The $EC_{50}$ [nM] values were calculated using the GraphPad Prism software (version 5).

The potency of all derivatives in vitro was confirmed. 138 derivatives had an in vitro potency corresponding to an $EC_{50}$ of 2000 pM or below; 131 derivatives were even more potent having an $EC_{50}$ below 1200 pM; 110 derivatives had a still further improved potency corresponding to an $EC_{50}$ at at 500 pM or below; 78 derivatives were very potent corresponding to an $EC_{50}$ at 200 pM or below; and 52 derivatives had a very good potency corresponding to an $EC_{50}$ of 100 pM or below.

For comparison, compound no. 13 in Table 1 of Journal of Medicinal Chemistry (2000), vol. 43, no. 9, p. 1664-669 (GLP-1(7-37) acylated at $K^{26,34}$ with bis-C12-diacid) had an in vitro potency corresponding to an $EC_{50}$ of 1200 pM.

If desired, the fold variation in relation to GLP-1 may be calculated as $EC_{50}$ (GLP-1)/$EC_{50}$ (analogue)–3693.2.

Example 149: GLP-1 Receptor Binding

The purpose of this experiment is to investigate the binding to the GLP-1 receptor of the GLP-1 derivatives, and how the binding is potentially influenced by the presence of albumin. This is done in an in vitro experiment as described below.

The binding affinity of the GLP-1 derivatives of Examples 1-116 and 118-147 to the human GLP-1 receptor was measured by way of their ability displace of $^{125}$I-GLP-1 from the receptor. In order to test the binding of the derivatives to the receptor in the presence of albumin, the assay was performed with a low concentration of albumin (0.005%–corresponding to the residual amount thereof in the tracer), as well as with a high concentration of albumin (2.0% added). A shift in the binding affinity, $IC_{50}$, is an indication that the derivative in question binds to albumin, and thereby a prediction of a potential protracted pharmacokinetic profile of the derivative in question in animal models.

Conditions
 Species (in vitro): Hamster
 Biological End Point: Receptor Binding
 Assay Method: SPA
 Receptor: GLP-1 receptor
 Cell Line: BHK tk-ts13

Cell Culture and Preparation of Membranes

A stable transfected cell line and a high expressing clone were selected for screening. The cells were grown at 5% $CO_2$ in DMEM, 10% FCS, 1% Pen/Strep (Penicillin/Streptomycin) and 1.0 mg/ml of the selection marker G418.

Cells at approximate 80% confluence were washed 2× with PBS and harvested with Versene (aqueous solution of the tetrasodium salt of ethylenediaminetetraacetic acid), centrifuged 5 min at 1000 rpm and the supernatant removed. The additional steps were all made on ice. The cell pellet was homogenised by the Ultrathurax for 20-30 sec. in a suitable amount of Buffer 1 (20 mM Na-HEPES, 10 mM EDTA, pH=7.4) but e.g. 10-20 ml, centrifuged 15 min at 20,000 rpm and the pellet resuspended in a suitable amount of Buffer 2 (20 mM Na-HEPES, 0.1 mM EDTA, pH=7.4) but e.g. 10-20 ml. The suspension was homogenised for 20-30 sec and centrifuged 15 min at 20,000 rpm. Suspension in Buffer 2, homogenisation and centrifugation was repeated once more and the membranes were resuspended in Buffer 2. The protein concentration was determined and the membranes stored at −80° C. until use.

SPA Binding Assay:

Test compounds, membranes, SPA-particles and $[^{125}I]$-GLP-1 (7-36)$NH_2$ were diluted in assay buffer. 25 ul (microliter) of test compounds are added to Optiplate. HSA ("high albumin" experiment containing 2% HSA), or buffer ("low albumin" experiment containing 0.005% HSA), was added (50 ul). 5-10 µg protein/sample was added (50 ul) corresponding to 0.1-0.2 mg protein/ml (to be preferably optimised for each membrane preparation). SPA-particles (Wheatgerm agglutinin SPA beads, Perkin Elmer, #RPNQ0001) were added in an amount of 0.5 mg/well (50 ul). The incubation was started with $[^{125}I]$-GLP-1 (7-36)$NH_2$ (final concentration 0.06 nM corresponding to 49.880 DPM, 25 ul). The plates were sealed with PlateSealer and incubated for 120 minutes at 30° C. while shaking. The plates were centrifuged (1500 rpm, 10 min) and counted in Topcounter.

Assay Buffer:
 50 mM HEPES
 5 mM EGTA
 5 mM MgCl2
 0.005% Tween 20
 pH 7.4
 HSA was SIGMA A1653.

Calculations

The $IC_{50}$ value was read from the curve as the concentration which displaces 50% of $^{125}$I-GLP-1 from the receptor, and the ratio of [($IC_{50}$/nM) high HSA]/[($IC_{50}$/nM) low HSA] was determined.

Generally, the binding to the GLP-1 receptor at low albumin concentration should be as good as possible, corresponding to a low $IC_{50}$ value.

The $IC_{50}$ value at high albumin concentration is a measure of the influence of albumin on the binding of the derivative to the GLP-1 receptor. As is known, the GLP-1 derivatives also bind to albumin. This is a generally desirable effect, which extends their lifetime in plasma. Therefore, the $IC_{50}$ value at high albumin will generally be higher than the $IC_{50}$ value at low albumin, corresponding to a reduced binding to the GLP-1 receptor, caused by albumin binding competing with the binding to the GLP-1 receptor.

A high ratio ($IC_{50}$ value (high albumin)/$IC_{50}$ value (low albumin)) may therefore be taken as an indication that the derivative in question binds well to albumin (may have a long half-life), and also per se binds well to the GLP-1 receptor (the $IC_{50}$ value (high albumin) is high, and the $IC_{50}$ value (low albumin) is low).

Results

The following results were obtained, where "ratio" refers to [($IC_{50}$/nM) high HSA]/[($IC_{50}$/nM) low HSA]):

All derivatives had a ratio above 1.0; 116 derivatives were above 10; 86 derivatives were above 50; 56 derivatives were above 100; 17 derivatives above 500; and 7 derivatives had a ratio above 1000.

Furthermore as regards $IC_{50}$ (low albumin), all derivatives had an $IC_{50}$ (low albumin) below 1000 nM; 144 derivatives were below 500 nM; 137 derivatives were below 100 nM; 126 derivatives were below 50 nM; 95 derivatives were below 10 nM; 70 derivatives were below 5.0 nM; 34 derivatives were below 1.0 nM; and 21 derivatives were below 0.50 nM.

Finally as regards $IC_{50}$ (high albumin), 110 derivatives had an $IC_{50}$ (high albumin) below 1000 nM; 79 derivatives were below 500 nM; and 28 derivatives were below 100 nM.

Example 150: Estimate of Oral Bioavailability

The purpose of this experiment is to estimate the oral bioavailability of the GLP-1 derivatives.

To this end, the exposure in plasma after direct injection into the intestinal lumen of the GLP-1 derivatives of Examples 2-3, 10, 17, 19-20, 26, 28-29, 31, 34-35, 38-39, 41-53, 55-64, 67, 70, 74-80, 82-86, 88, 90, 92-95, 98, 100, 106, and 118-123 was studied in vivo in rats, as described in the following.

The GLP-1 derivatives were tested in a concentration of 1000 uM in a solution of 55 mg/ml sodium caprate.

32 male Sprague Dawley rats with a body weight upon arrival of approximately 240 g were obtained from Taconic (Denmark) and assigned to the different treatments by simple randomisation, 4 rats per group. The rats were fasted for approximately 18 hours before the experiment and taken into general anaesthesia (Hypnorm/Dormicum).

The GLP-1 derivatives were administered in the jejunum either in the proximal part (10 cm distal for the duodenum) or in the mid-intestine (50 cm proximal for the cecum). A PE50-catheter, 10 cm long was inserted into the jejunum, forwarded at least 1.5 cm into the jejunum, and secured before dosing by ligature around the gut and the catheter with 3/0 suture distal to tip to prevent leak or catheter displacement. Catheter was placed without syringe and needle and 2 ml saline was administered into abdomen before closing the incision with wound clips.

100 μl of the respective GLP-1 derivative was injected into the jejunal lumen through the catheter with a 1 ml syringe. Subsequently, 200 μl of air was pushed into the jejunal lumen with another syringe to "flush" the catheter. This syringe was leaved connected to the catheter to prevent flow back into the catheter.

Blood samples (200 ul) were collected at desired intervals (usually at times 0, 10, 30, 60, 120 and 240 min) into EDTA tubes from the tail vein and centrifuged 5 minutes, 10000G, at 4° C. within 20 minutes. Plasma (75 ul) was separated to Micronic tubes, immediately frozen, and kept at −20° C. until analyzed for plasma concentration of the respective GLP-1 derivative with LOCI (Luminescent Oxygen Channeling Immunoassay), generally as described for the determination of insulin by Poulsen and Jensen in Journal of Biomolecular Screening 2007, vol. 12, p. 240-247. The donor beads were coated with streptavidin, while acceptor beads were conjugated with a monoclonal antibody recognising a mid-/C-terminal epitope of the peptide. Another monoclonal antibody, specific for the N-terminus, was biotinylated. The three reactants were combined with the analyte and formed a two-sited immuno-complex. Illumination of the complex released singlet oxygen atoms from the donor beads, which were channeled into the acceptor beads and triggered chemiluminescence which was measured in an Envision plate reader. The amount of light was proportional to the concentration of the compound.

After the blood sampling the rats were sacrificed under anaesthesia and the abdomen was opened to verify correct catheter placement.

The mean (n=4) plasma concentrations (μmol/l) were determined as a function of time. The ratio of plasma concentration (μmol/l) divided by the concentration of the dosing solution (μmol/l) was calculated for each treatment, and the results for t=30 min (30 minutes after the injection of the compound in the jejunum) were assessed (dose-corrected exposure at 30 min) as a surrogate measure of intestinal bioavailability. The dose-corrected exposure is expected to correlate with the actual bioavailability.

The following results were obtained, where dose-corrected exposure at 30 min refers to (the plasma concentration 30 minutes after injection of the compound in the jejunum (pM)), divided by (the concentration of the compound in the dosing solution (μM)): All but three derivatives had a dose-corrected exposure at 30 min of above 45; 64 derivatives were above 50; 49 derivatives were above 100; 25 derivatives were above 150; 13 derivatives were above 200; and 2 derivatives were above 250.

For comparison, compound no. 13 in Table 1 of Journal of Medicinal Chemistry (2000), vol. 43, no. 9, p. 1664-669 (GLP-1(7-37) acylated at $K^{26,34}$ with bis-C12-diacid) had a dose-corrected exposure at 30 min of below 45, and the dose-corrected exposure at 30 min for semaglutide was in the same range of below 45.

Example 151: Effect on Blood Glucose and Body Weight

The purpose of the study is to verify the effect of the GLP-1 derivatives on blood glucose (BG) and body weight (BW) in a diabetic setting.

The GLP-1 derivatives of Examples 2 and 5 were tested in a dose-response study in an obese, diabetic mouse model (db/db mice) as described in the following.

Fifty db/db mice (Taconic, Denmark), fed from birth with the diet NIH31 (NIH 31M Rodent Diet, commercially available from Taconic Farms, Inc., US, see www.taconic.com), were enrolled for the study at the age of 7-9 weeks The mice were given free access to standard chow (e.g. Altromin 1324, Brogaarden, Gentofte, Denmark) and tap water and kept at 24° C. After 1-2 weeks of acclimatisation, the basal blood glucose was assessed twice on two consecutive days (i.e. at 9 am). The 8 mice with the lowest blood glucose values were excluded from the experiments. Based on the mean blood glucose values, the remaining 42 mice were selected for further experimentation and allocated to 7 groups (n=6) with matching blood glucose levels. The mice were used in experiments with duration of 5 days for up to 4 times. After the last experiment the mice were euthanised.

The seven groups received treatment as follows:
1: Vehicle, s.c.
2: GLP-1 derivative, 0.3 nmol/kg, s.c.
3: GLP-1 derivative, 1.0 nmol/kg, s.c.
4: GLP-1 derivative, 3.0 nmol/kg, s.c.
5: GLP-1 derivative, 10 nmol/kg, s.c.
6: GLP-1 derivative, 30 nmol/kg, s.c.
7: GLP-1 derivative, 100 nmol/kg, s.c.
Vehicle: 50 mM sodium phosphate, 145 mM sodium chloride, 0.05% tween 80, pH 7.4.

The GLP-1 derivative was dissolved in the vehicle, to concentrations of 0.05, 0.17, 0.5, 1.7, 5.0 and 17.0 nmol/ml. Animals were dosed s.c. with a dose-volume of 6 ml/kg (i.e. 300 µl per 50 g mouse).

On the day of dosing, blood glucose was assessed at time −½ h (8.30 am), where after the mice were weighed. The GLP-1 derivative was dosed at approximately 9 am (time 0). On the day of dosing, blood glucose was assessed at times 1, 2, 4 and 8 h (10 am, 11 am, 1 µm and 5 µm).

On the following days, the blood glucose was assessed at time 24, 48, 72, and 96 h after dosing (i.e. at 9 am on day 2, 3, 4, 5). On each day, the mice were weighed following blood glucose sampling.

The mice were weighed individually on a digital weight.

Samples for the measurement of blood glucose were obtained from the tail tip capillary of conscious mice. Blood, 10 µl, was collected into heparinised capillaries and transferred to 500 µl glucose buffer (EKF system solution, Eppendorf, Germany). The glucose concentration was measured using the glucose oxidase method (glucose analyser Biosen 5040, EKF Diagnostic, GmbH, Barleben, Germany). The samples were kept at room temperature for up to 1 h until analysis. If analysis had to be postponed, samples were kept at 4° C. for a maximum of 24 h.

$ED_{50}$ is the dose giving rise to half-maximal effect in nmol/kg. This value is calculated on the basis of the ability of the derivatives to lower body weight as well as the ability to lower blood glucose, as explained below.

$ED_{50}$ for body weight is calculated as the dose giving rise to half-maximum effect on delta BW 24 hours following the subcutaneous administration of the derivative. For example, if the maximum decrease in body weight after 24 hours is 4.0 g, then $ED_{50}$ bodyweight would be that dose in nmol/kg which gives rise to a decrease in body weight after 24 hours of 2.0 g.

This dose ($ED_{50}$ body weight) may be read from the dose-response curve.

$ED_{50}$ for blood glucose is calculated as the dose giving rise to half-maximum effect on AUC delta BG 8 hours following the subcutaneous administration of the analogue.

The $ED_{50}$ value may only be calculated if a proper sigmoidal dose-response relationship exists with a clear definition of the maximum response. Thus, if this would not be the case the derivative in question is re-tested in a different range of doses until the sigmoidal dose-response relationship is obtained.

The following results were obtained:

The tested derivatives had the expected effect on blood glucose as well as on body weight (a lowering in both cases). Furthermore, a sigmoidal dose-response curve was obtained enabling the calculation of the $ED_{50}$ values for blood glucose and body weight, respectively, as explained above.

Example 152: Half-Life in Minipigs

The purpose of this study is to determine the protraction in vivo of the GLP-1 derivatives after i.v. administration to minipigs, i.e. the prolongation of their time of action. This is done in a pharmacokinetic (PK) study, where the terminal half-life of the derivative in question is determined. By terminal half-life is generally meant the period of time it takes to halve a certain plasma concentration, measured after the initial distribution phase.

Male Göttingen minipigs (Ellegaard Göttingen Minipigs A/S, Dalmose, Denmark), approximately 7-14 months of age and weighing from approximately 16-35 kg, were used in the studies. The minipigs were housed individually and fed restrictedly once or twice daily with SDS minipig diet (Special Diets Services, Essex, UK). After at least 2 weeks of acclimatisation two permanent central venous catheters were implanted in vena cava caudalis or cranialis in each animal. The animals were allowed 1 week recovery after the surgery, and were then used for repeated pharmacokinetic studies with a suitable wash-out period between dosings.

The animals were fasted for approximately 18 h before dosing and for at least 4 h after dosing, but had ad libitum access to water during the whole period.

The GLP-1 derivatives of Examples 2, 10, 17, 20, 23, 28-29, 43-44, 74-76, 82, 84-86, 90, 92, and 118 were dissolved in 50 mM sodium phosphate, 145 mM sodium chloride, 0.05% tween 80, pH 7.4 to a concentration of usually from 20-60 nmol/ml. Intravenous injections (the volume corresponding to usually 1-2 nmol/kg) of the compounds were given through one catheter, and blood was sampled at predefined time points for up till 13 days post dosing (preferably through the other catheter). Blood samples were collected in EDTA buffer (8 mM) and then centrifuged at 4° C. and 1942G for 10 minutes. Plasma was pippetted into Micronic tubes on dry ice, and kept at −20° C. until analyzed for plasma concentration of the respective GLP-1 compound using ELISA or a similar antibody based assay or LC-MS. Individual plasma concentration-time profiles were analyzed by a non-compartmental model in WinNonlin v. 5.0 (Pharsight Inc., Mountain View, Calif., USA), and the resulting terminal half-lives (harmonic mean) determined.

The following results were obtained: All derivatives had a terminal half-life of above 8 hours; 18 derivatives above 10 hours; 16 derivatives above 20 hours; 10 derivatives above hours; 6 derivatives above 60 hours; and 2 derivatives above 80 hours.

Example 153: Effect on Food Intake

The purpose of this experiment is to investigate the effect of GLP-1 derivatives on food intake in pigs. This is done in a pharmacodynamic (PD) study as described below, in which food intake is measured 1, 2, 3, and 4 days after administration of a single dose of the GLP-1 derivative, as compared to a vehicle-treated control group.

Female Landrace Yorkshire Duroc (LYD) pigs, approximately 3 months of age, weighing approximately 30-35 kg were used (n=3-4 per group). The animals were housed in a group for 1-2 weeks during acclimatisation to the animal facilities. During the experimental period the animals were placed in individual pens from Monday morning to Friday afternoon for measurement of individual food intake. The animals were fed ad libitum with pig fodder (Svinefoder, Antonio) at all times both during the acclimatisation and the experimental period. Food intake was monitored on line by logging the weight of fodder every 15 minutes. The system used was Mpigwin (Ellegaard Systems, Faaborg, Denmark).

The GLP-1 derivatives were dissolved in a phosphate buffer (50 mM phosphate, 0.05% tween 80, pH 8) at concentrations of 12, 40, 120, 400 or 1200 nmol/ml corresponding to doses of 0.3, 1, 3, 10 or 30 nmol/kg. The phosphate buffer served as vehicle. Animals were dosed with a single subcutaneous dose of the GLP-1 derivative or vehicle (dose volume 0.025 ml/kg) on the morning of day 1, and food intake was measured for 4 days after dosing. On the last day of each study, 4 days after dosing, a blood sample for measurement of plasma exposure of the GLP-1 derivative was taken from the heart in anaesthetised animals. The animals were thereafter euthanised with an intra-cardial overdose of pentobarbitone. Plasma content of the GLP-1 derivatives was analysed using ELISA or a similar antibody based assay.

Food intake was calculated as mean±SEM 24 h food intake on the 4 days.

Statistical comparisons of the 24 hour food intake in the vehicle vs. GLP-1 derivative group on the 4 days were done using one-way or two-way-ANOVA repeated measures, followed by Bonferroni post-test.

The derivatives of Examples 2-3, 5, 43-45, 48, 52, 66, 61, 74-78, 80, 82, 86, and 92 were tested as described above in a dosage of 3 nM/kg. For thirteen derivatives the food intake was reduced as compared to the vehicle-treated group on day 1 (0-24 h). For eight derivatives, the food intake was reduced on day 2 (24-48 h). The food intake was reduced on day 3 (48-72 h) for six derivatives. On day 4 (72-96 h), the food intake was reduced for four derivatives (only fifteen were tested on that day). As expected, the food intake reducing effect of the derivatives diminished from day to day in the study period, depending on the terminal half-life of the derivative.

Example 154: Half-Life in Rat—PK Rat

The purpose of this Example is to investigate half-life in vivo in rat.

In vivo pharmacokinetic studies in rats were performed with the GLP-1 derivatives of Examples 5, 17, 20, 23, 28, 29, 34, 39, 43-45, 47, 52, 55, 59, 61, 71, 74-77, 80, 82, 84, 86, 90, 92, 101, 114, 118, 137, 143, and 144 as described in the following.

Male Sprague Dawley rats of same age with a body weight from 400 to 600 g were obtained from Taconic (Denmark) and assigned to the treatments by simple randomisation on body weight, approximately 3-6 rats per group, so that all animals in each group were of similar body weight.

The GLP-1 derivatives (approximately 6 nmole/ml) were dissolved in 50 mM sodium phosphate, 145 mM sodium chloride, 0.05% tween 80, pH 7.4. Intravenous injections (1.0 ml/kg) of the compounds were given through a catheter implanted in the right jugular vein. Blood was sampled from vena sublingualis for 5 days post dosing. Blood samples (200 µl) were collected in EDTA buffer (8 mM) and then centrifuged at 4° C. and 10000G for 5 minutes. Plasma samples were kept at −20° C. until analyzed for plasma concentration of the respective GLP-1 compound.

The plasma concentrations of the GLP-1 compounds were determined using a Luminescence Oxygen Channeling Immunoasssay (LOCI), generally as described for the determination of insulin by Poulsen and Jensen in Journal of Biomolecular Screening 2007, vol. 12, p. 240-247. The donor beads were coated with streptavidin, while acceptor beads were conjugated with a monoclonal antibody recognising a mid-/C-terminal epitope of the peptide. Another monoclonal antibody, specific for the N-terminus, was biotinylated. The three reactants were combined with the analyte and formed a two-sited immuno-complex. Illumination of the complex released singlet oxygen atoms from the donor beads, which were channeled into the acceptor beads and triggered chemiluminescence which was measured in an Envision plate reader. The amount of light was proportional to the concentration of the compound.

Plasma concentration-time profiles were analyzed using WinNonlin (ver. 5.0, Pharsight Inc., Mountain View, Calif., USA), and the half-life ($T_{1/2}$) calculated using individual plasma concentration-time profiles from each animal.

Of the tested derivatives 31 had a half-life of 7 hours or above, 23 had a half-life of hours or above, 14 had a half-life of 20 hours or above, 9 a half-life of 25 hours or above, and three had a half-life of 30 hours or above.

While certain features of the invention have been illustrated and described herein, many modifications, substitutions, changes, and equivalents will now occur to those of ordinary skill in the art. It is, therefore, to be understood that the appended claims are intended to cover all such modifications and changes as fall within the true spirit of the invention.

The invention claimed is:

1. A derivative of a GLP-1 analogue,
which analogue comprises a first K residue at a position corresponding to position 18 of GLP-1(7-37) (SEQ ID NO: 1), a second K residue at a position corresponding to position 22, 26, 27, 30, 31, 34, or 37 of GLP-1(7-37) (SEQ ID NO: 1), and a maximum of twelve amino acid changes as compared to GLP-1(7-37),
which derivative comprises two protracting moieties attached to said first and second K residue, respectively, via a linker, wherein
the protracting moiety is selected from Chem. 2, Chem. 1, and Chem. 3:

$$HOOC-C_6H_4-O-(CH_2)_y-CO-*$$  Chem. 2:

$$HOOC-(CH_2)_x-CO-*$$  Chem. 1:

$$R^2-C_6H_4-(CH_2)_z-CO-*,$$  Chem. 3:

in which x is an integer in the range of 6-18, y is an integer in the range of 3-17, z is an integer in the range of 1-5, and $R^2$ is a group having a molar mass not higher than 150 Da; and
the linker comprises

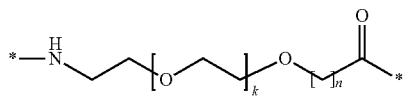

Chem. 4 wherein k is an integer in the range of 1-5, and n is an integer in the range of 1-5;
or a pharmaceutically acceptable salt, amide, or ester thereof.

2. The derivative of claim 1, wherein the protracting moiety is selected from Chem. 1 and Chem. 2.

3. The derivative of claim 1, wherein the second K residue is at positions 22, 27, 30, 31, or 37.

4. The derivative of claim 1, wherein the analogue comprises a GLP-1 analogue of Formula I:

$Xaa_7$-$Xaa_8$-Glu-Gly-Thr-$Xaa_{12}$-Thr-Ser-Asp-$Xaa_{16}$-Ser-Lys-$Xaa_{19}$-$Xaa_{20}$-Glu-$Xaa_{22}$-$Xaa_{23}$-Ala-$Xaa_{25}$-$Xaa_{26}$-$Xaa_{27}$-Phe-Ile-$Xaa_{30}$-$Xaa_{31}$-Leu-$Xaa_{33}$-$Xaa_{34}$-$Xaa_{35}$-$Xaa_{36}$-$Xaa_{37}$-$Xaa_{38}$, wherein  Formula I:

$Xaa_7$ is L-histidine, imidazopropionyl, α-hydroxy-histidine, D-histidine, desamino-histidine, 2-amino-histidine, β-hydroxy-histidine, homohistidine, $N^\alpha$-acetyl-histidine, $N^\alpha$-formyl-histidine, α-fluoromethyl-histidine, α-methyl-histidine, β-pyridylalanine, 2-pyridylalanine, or 4-pyridylalanine;

$Xaa_8$ is Ala, Gly, Val, Leu, Ile, Thr, Ser, Aib, (1-aminocyclopropyl) carboxylic acid, (1-aminocyclobutyl) carboxylic acid, (1-aminocyclopentyl) carboxylic acid, (1-aminocyclohexyl) carboxylic acid, (1-aminocycloheptyl) carboxylic acid, or (1-aminocyclooctyl) carboxylic acid;

$Xaa_{12}$- is Phe or Leu;
$Xaa_{16}$ is Val or Leu;
$Xaa_{19}$ is Tyr or Gln;
$Xaa_{20}$ is Leu or Met;
$Xaa_{22}$ is Gly, Glu, Lys, or Aib;
$Xaa_{23}$ is Gln, Glu, or Arg;
$Xaa_{25}$ is Ala or Val;
$Xaa_{26}$ is Val, His, Lys, or Arg;
$Xaa_{27}$ is Glu, His, Leu, or Lys;
$Xaa_{30}$ is Ala, Glu, Lys, or Arg;
$Xaa_{31}$ is Trp, Lys, or His
$Xaa_{33}$ is Val or Lys;
$Xaa_{34}$ is Lys, Glu, Asn, Gly, Gln, Arg, His, or absent;
$Xaa_{35}$ is Gly, Aib, or absent;
$Xaa_{36}$ is Arg, Gly, or absent;
$Xaa_{37}$ is Gly, Ala, Glu, Pro, Lys, Arg, or absent; and
$Xaa_{38}$ is Ser, Gly, Ala, Glu, Pro, Arg, or absent.

5. The derivative of claim 1, wherein x is 10, 12, 14, or 16.

6. The derivative of claim 1, wherein y is 7, 8 or 9.
7. The derivative of claim 1, wherein the analogue is modified so as to comprise a C-terminal amide.
8. The derivative of claim 1, wherein the analogue has a C-terminal carboxylic acid.
9. A compound selected from the following:
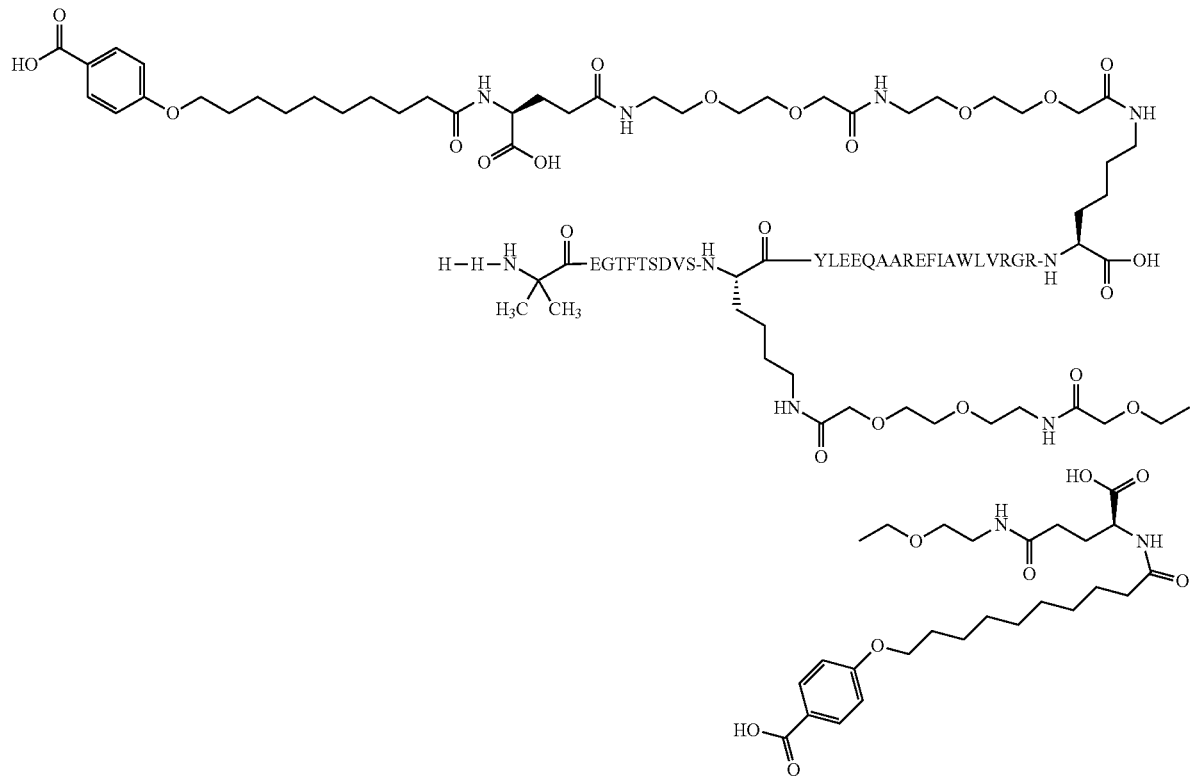
where the amino acid sequence is that of SEQ ID NO: 13,
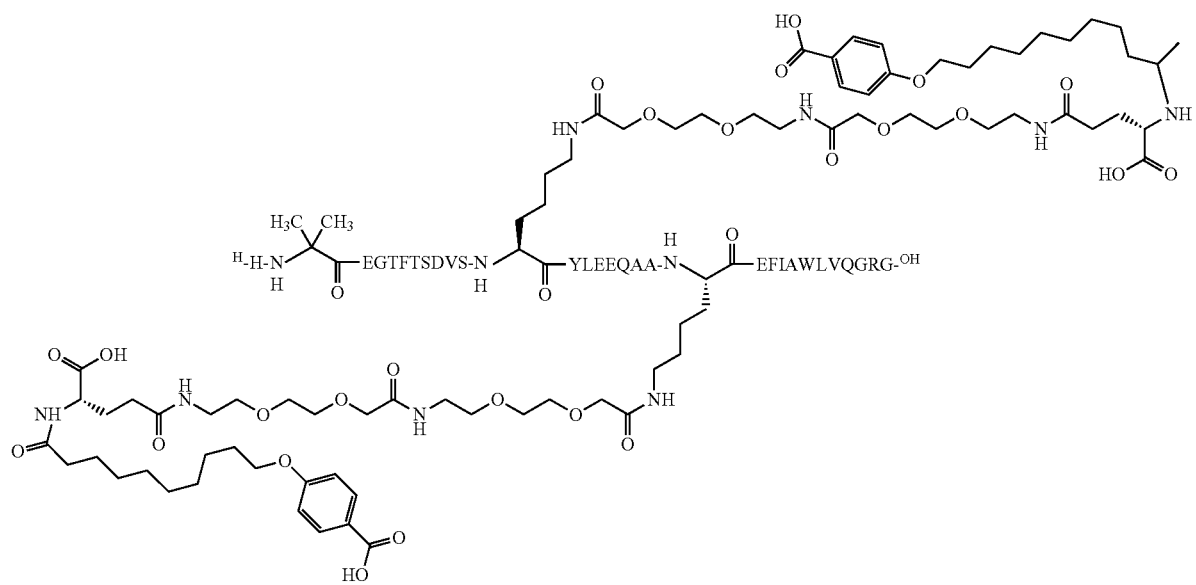
where the amino acid sequence is that of SEQ ID NO: 7, Chem. 22
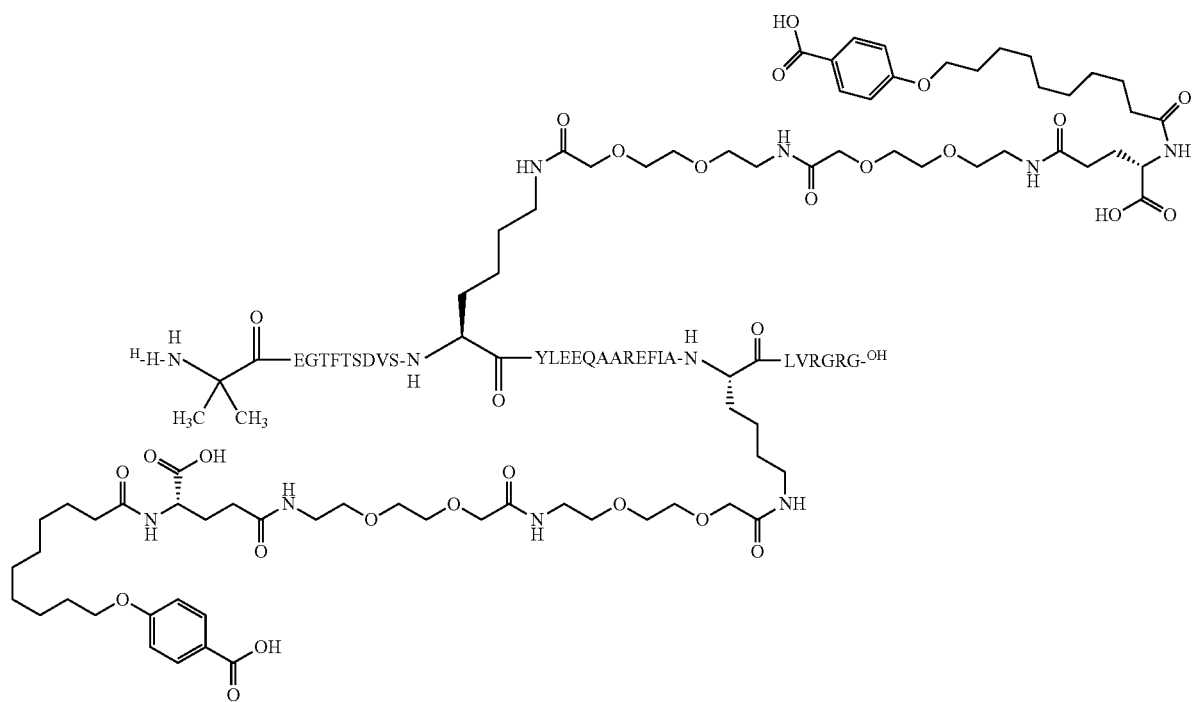
where the amino acid sequence is that of SEQ ID NO: 8,
Chem. 23
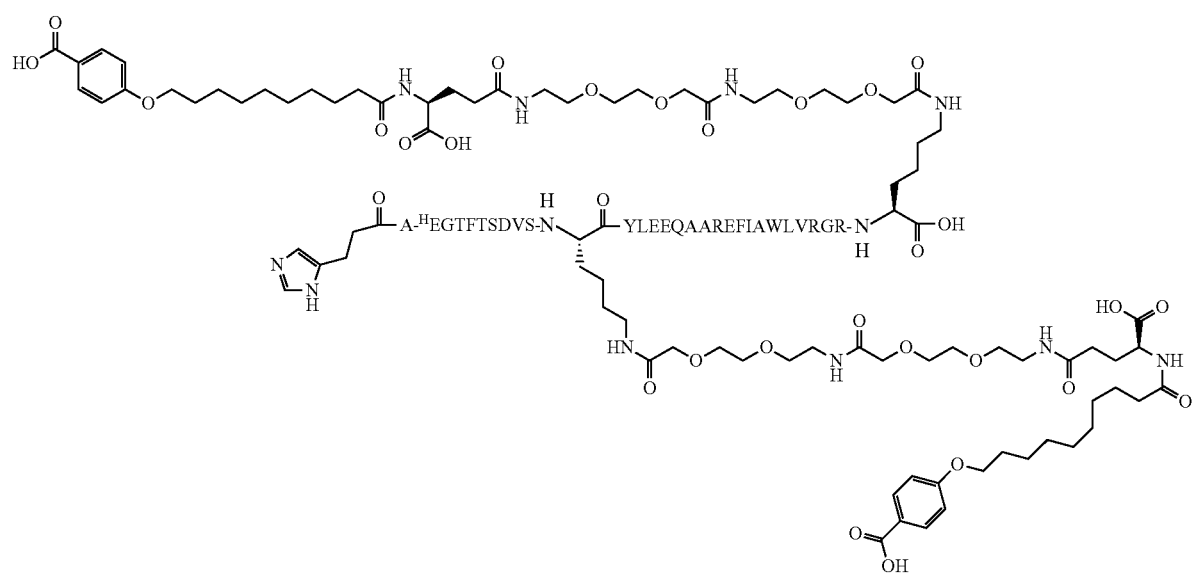
where the amino acid sequence is that of SEQ ID NO: 14,

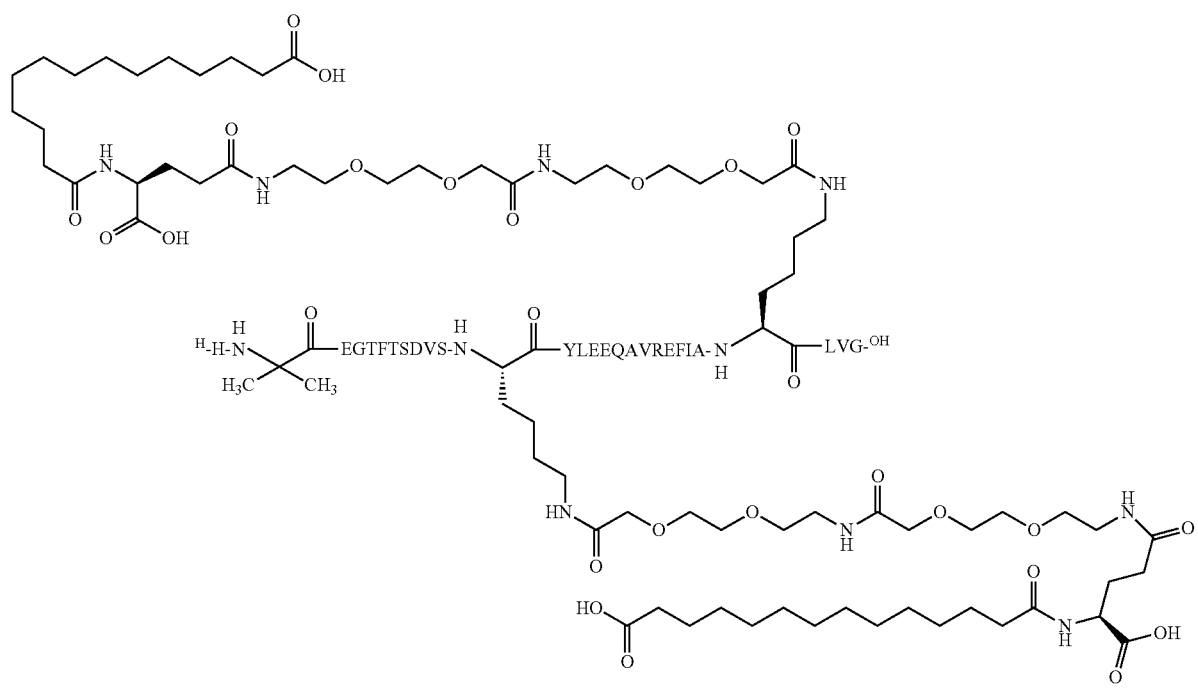
where the amino acid sequence is that of SEQ ID NO: 9,
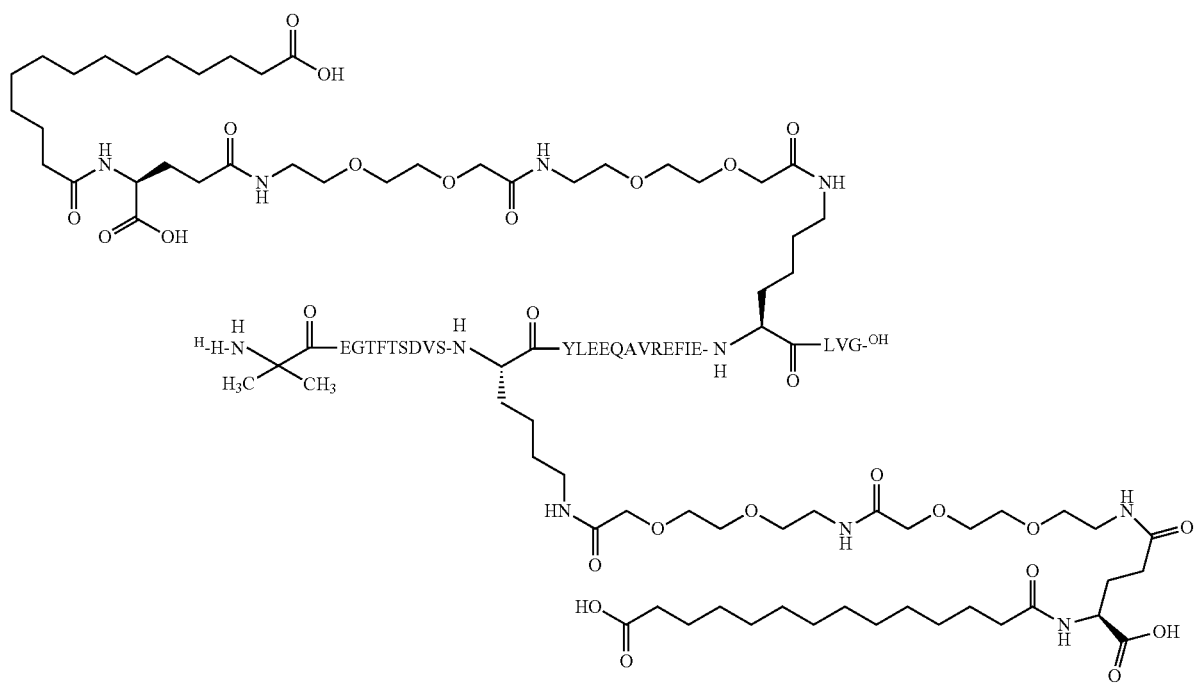
where the amino acid sequence is that of SEQ ID NO: 15, Chem. 26
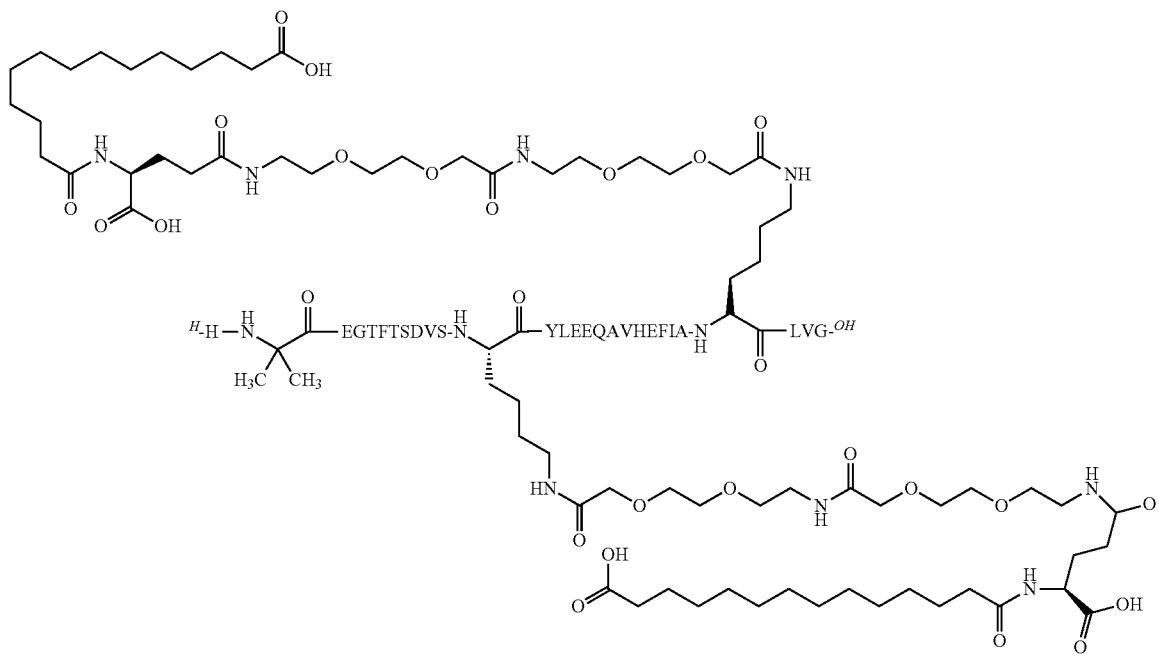
where the amino acid sequence is that of SEQ ID NO: 16, Chem. 27
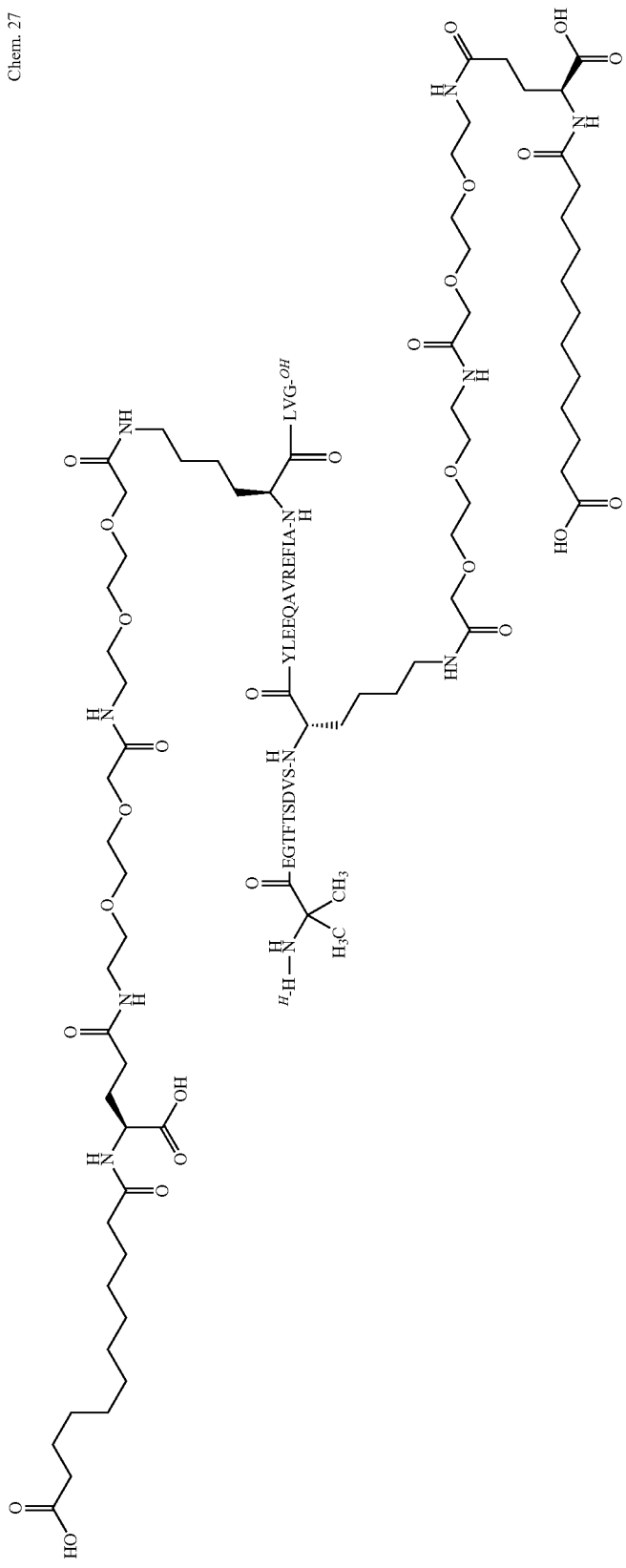

where the amino acid sequence is that of SEQ ID NO: 9,

Chem. 28
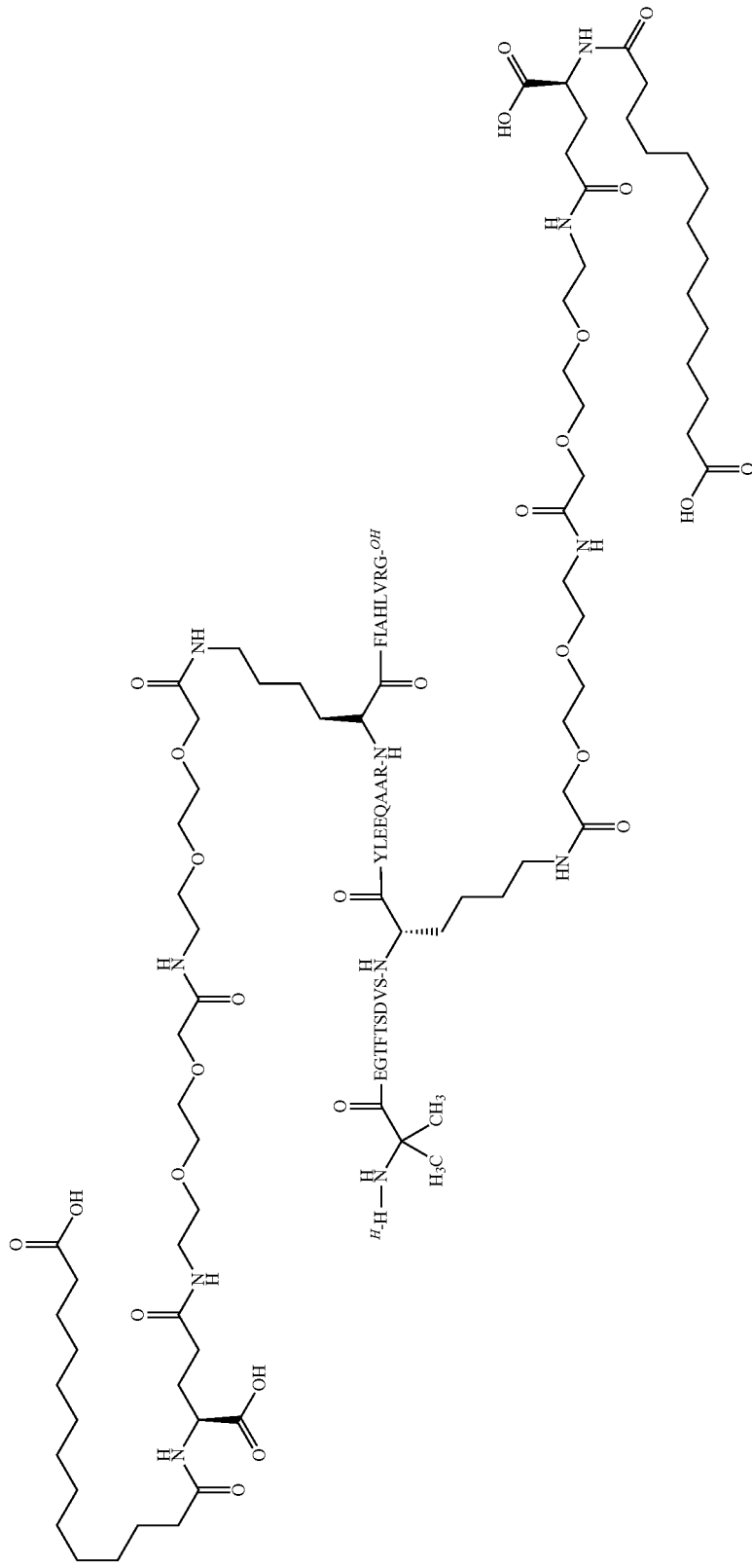

where the amino acid sequence is that of SEQ ID NO: 17,

Chem. 29
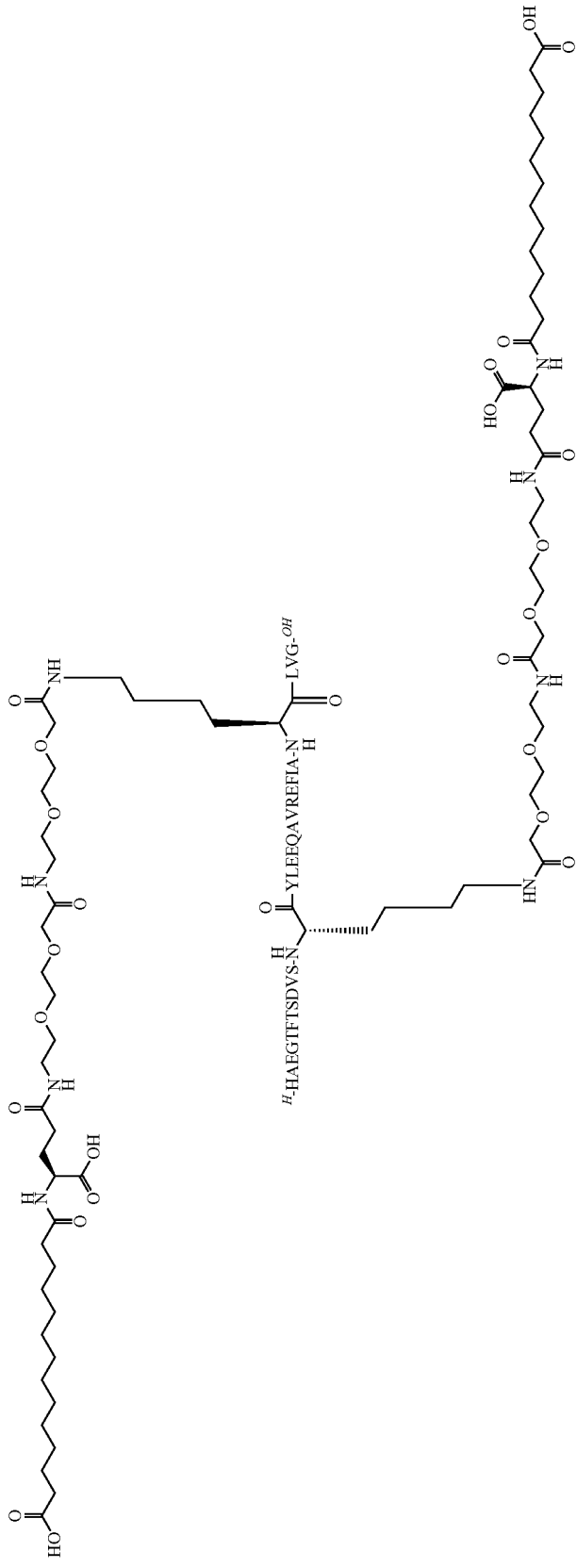

where the amino acid sequence is that of SEQ ID NO: 18,
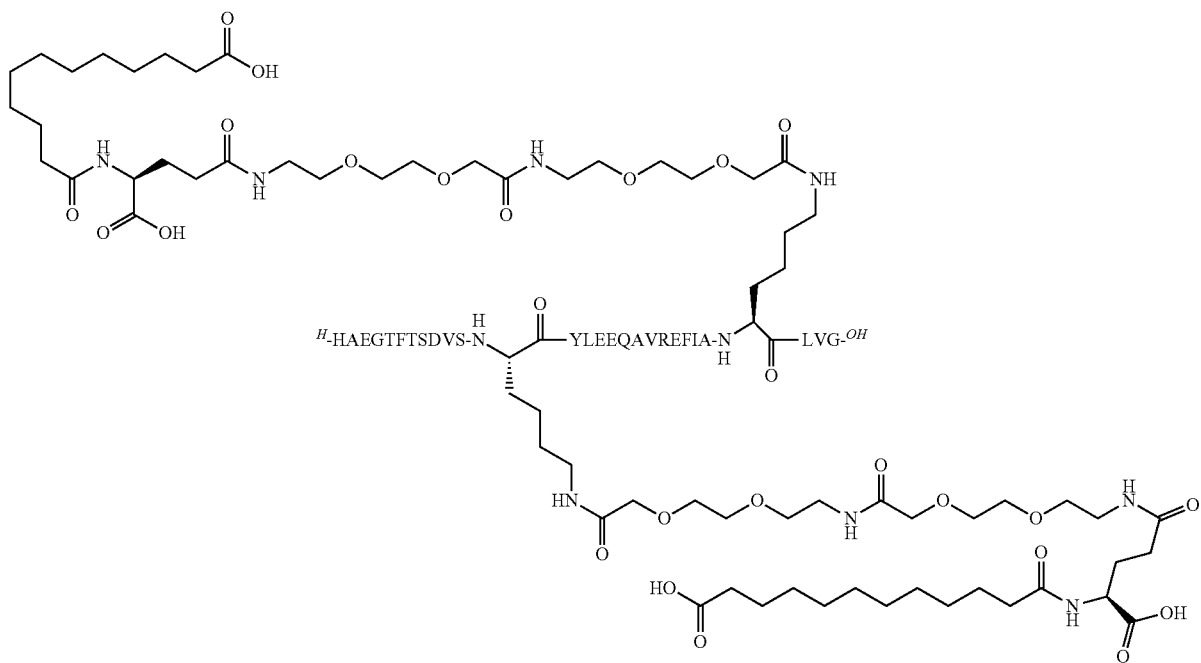
Chem. 30
where the amino acid sequence is that of SEQ ID NO: 18,

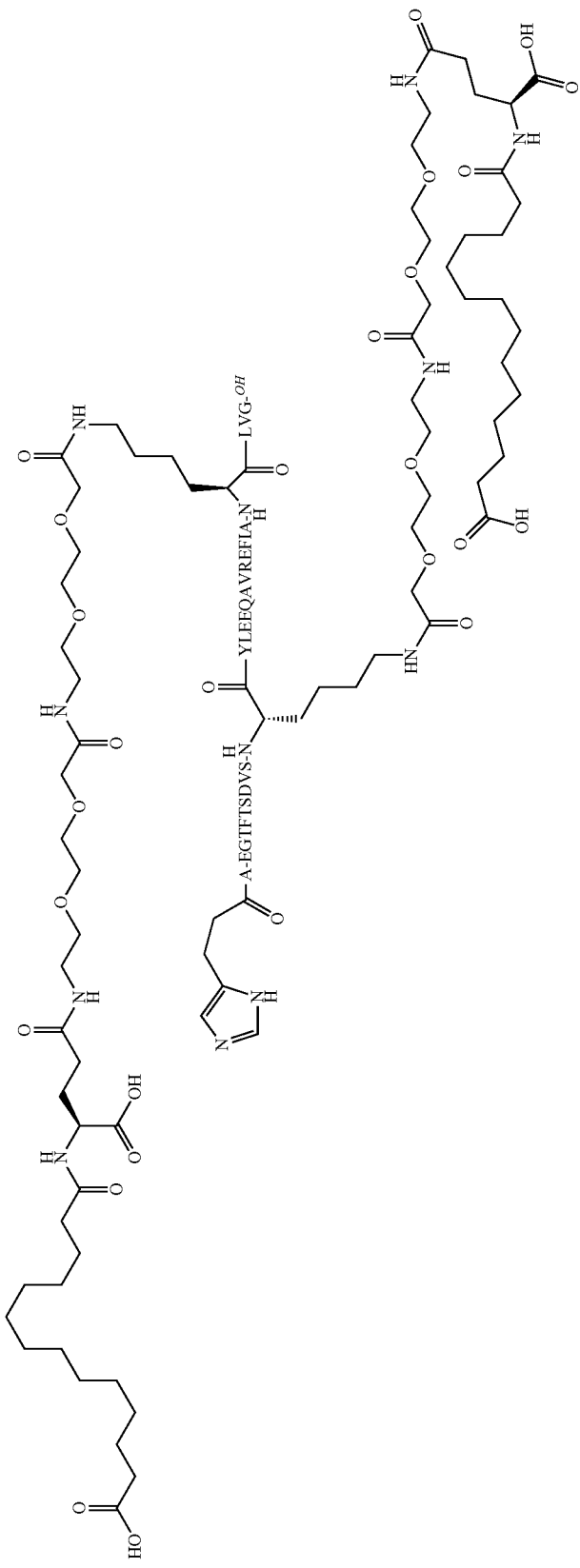
Chem. 31 where the amino acid sequence is that of SEQ ID NO: 19,

Chem. 32
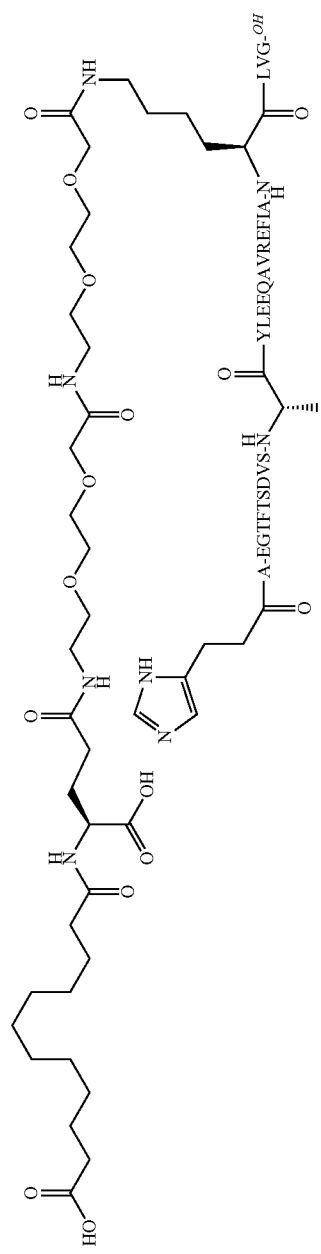
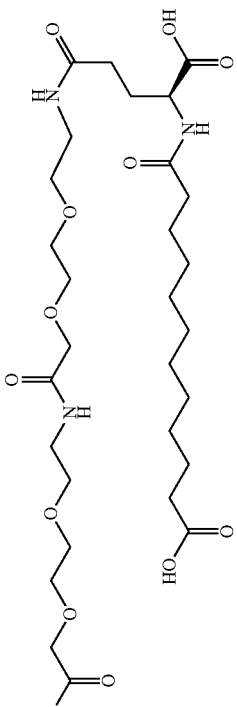

where the amino acid sequence is that of SEQ ID NO: 19,
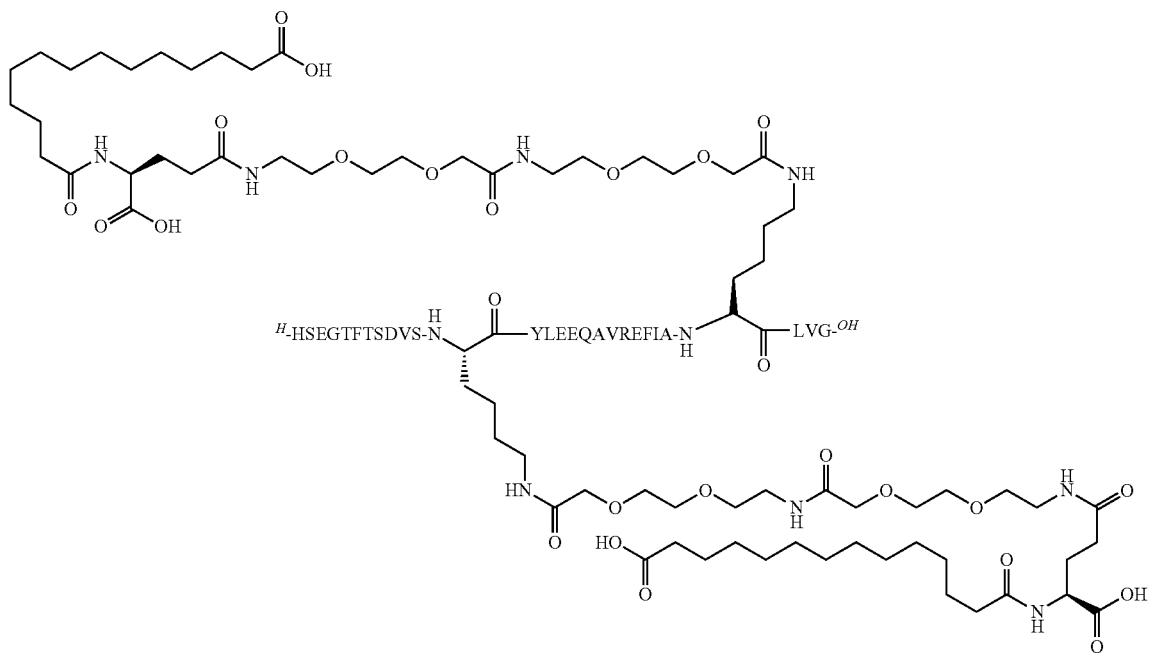
Chem. 33
where the amino acid sequence is that of SEQ ID NO: 20, Chem. 34
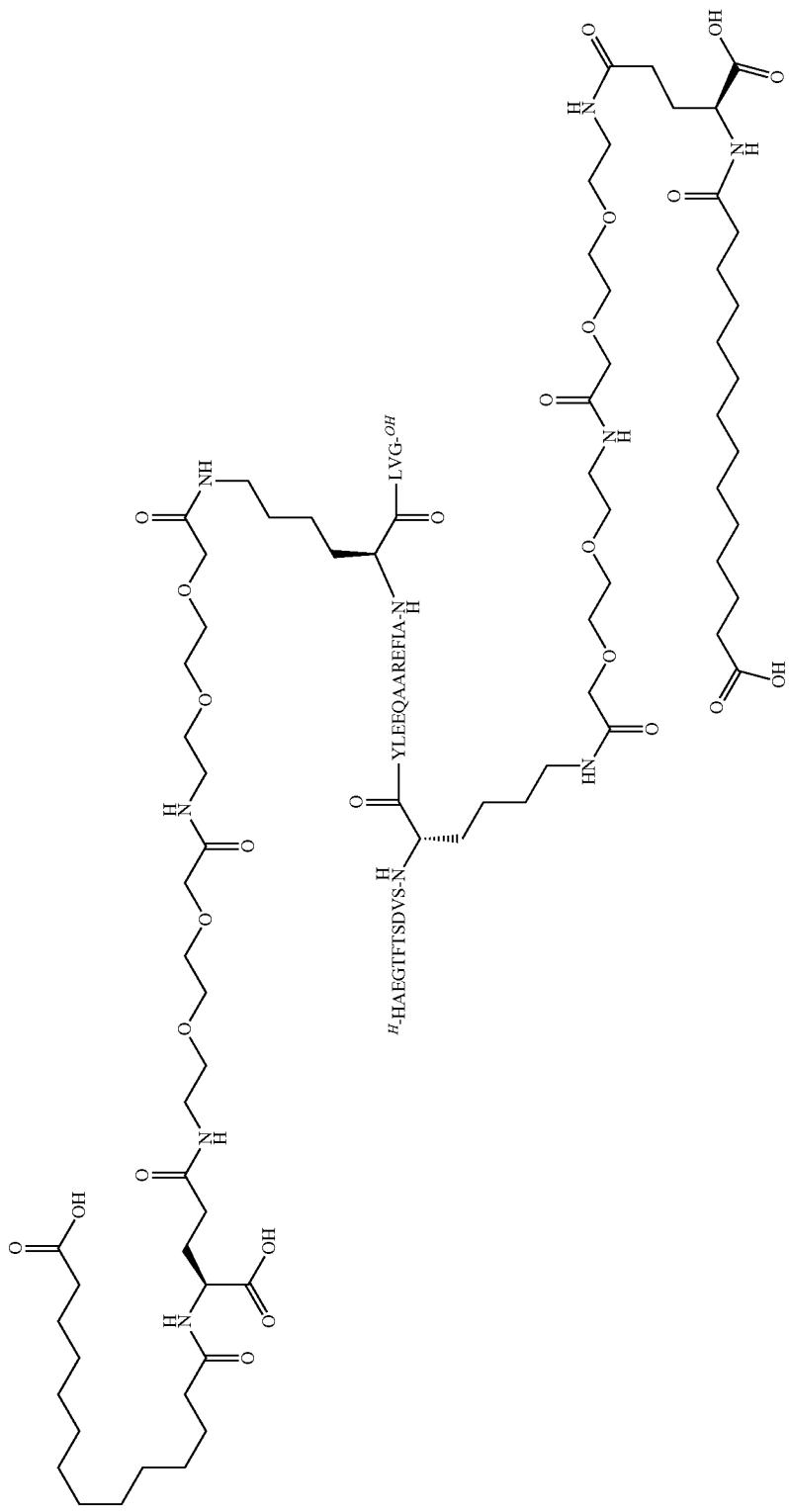

where the amino acid sequence is that of SEQ ID NO: 21,
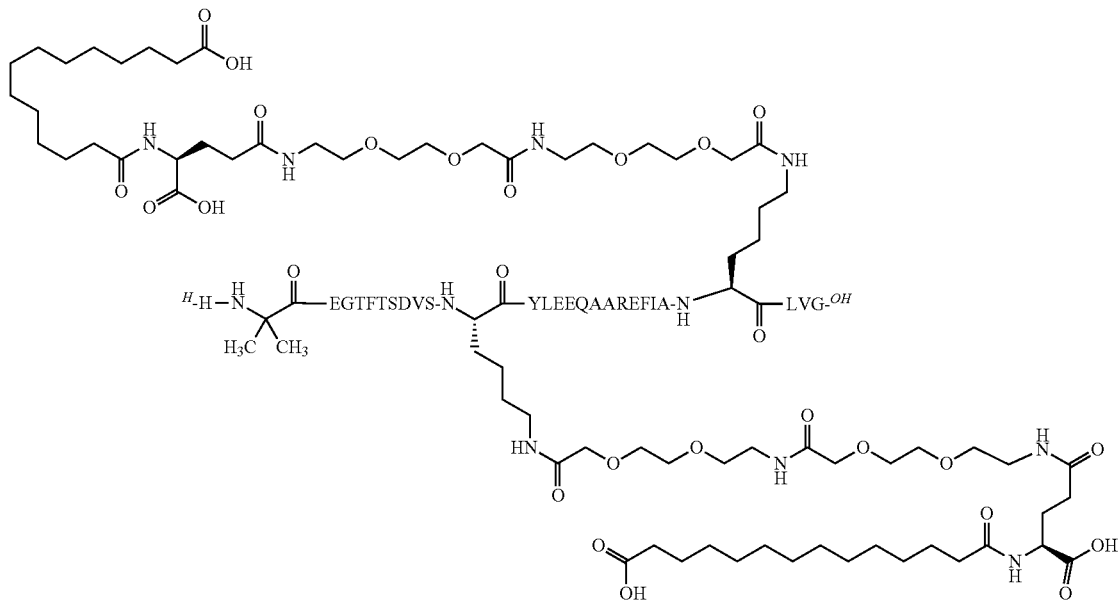
Chem. 35
where the amino acid sequence is that of SEQ ID NO: 22,
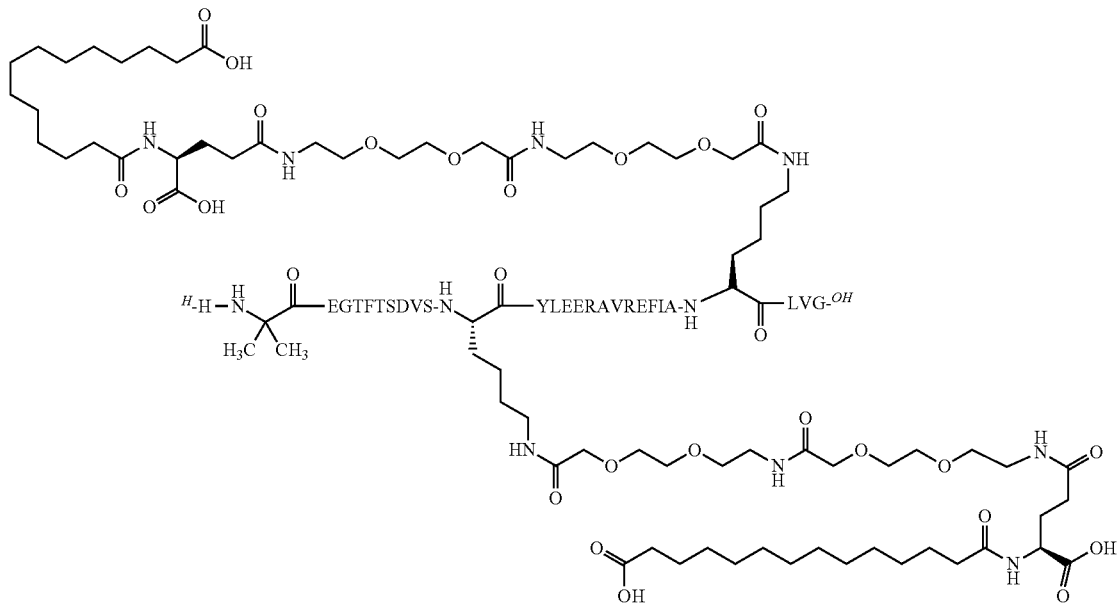
Chem. 36
where the amino acid sequence is that of SEQ ID NO: 23, Chem 37
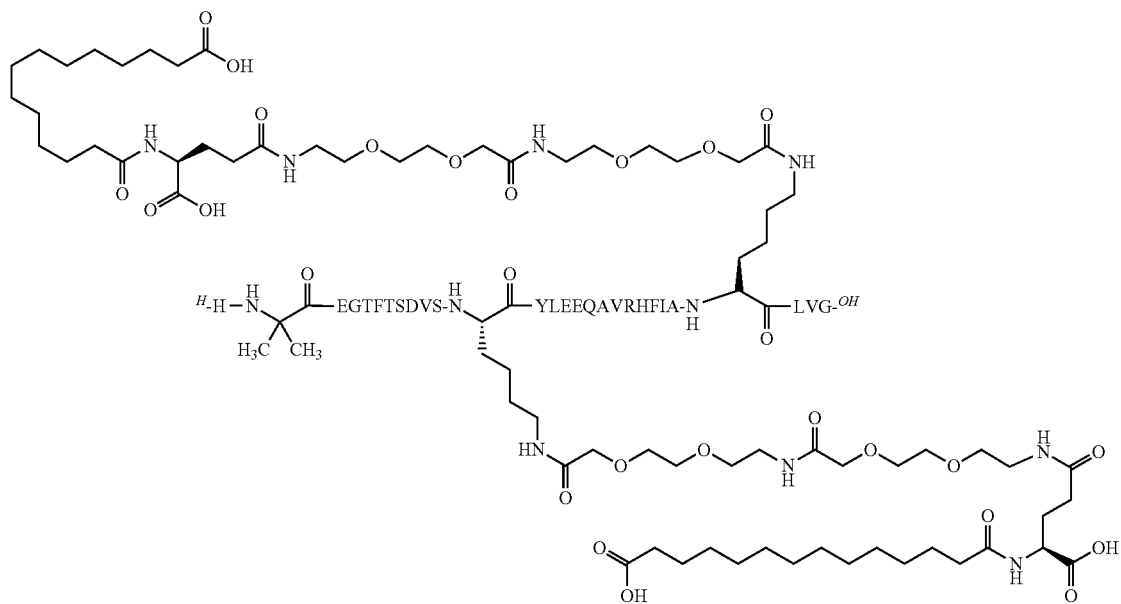
where the amino acid sequence is that of SEQ ID NO: 24, Chem. 38
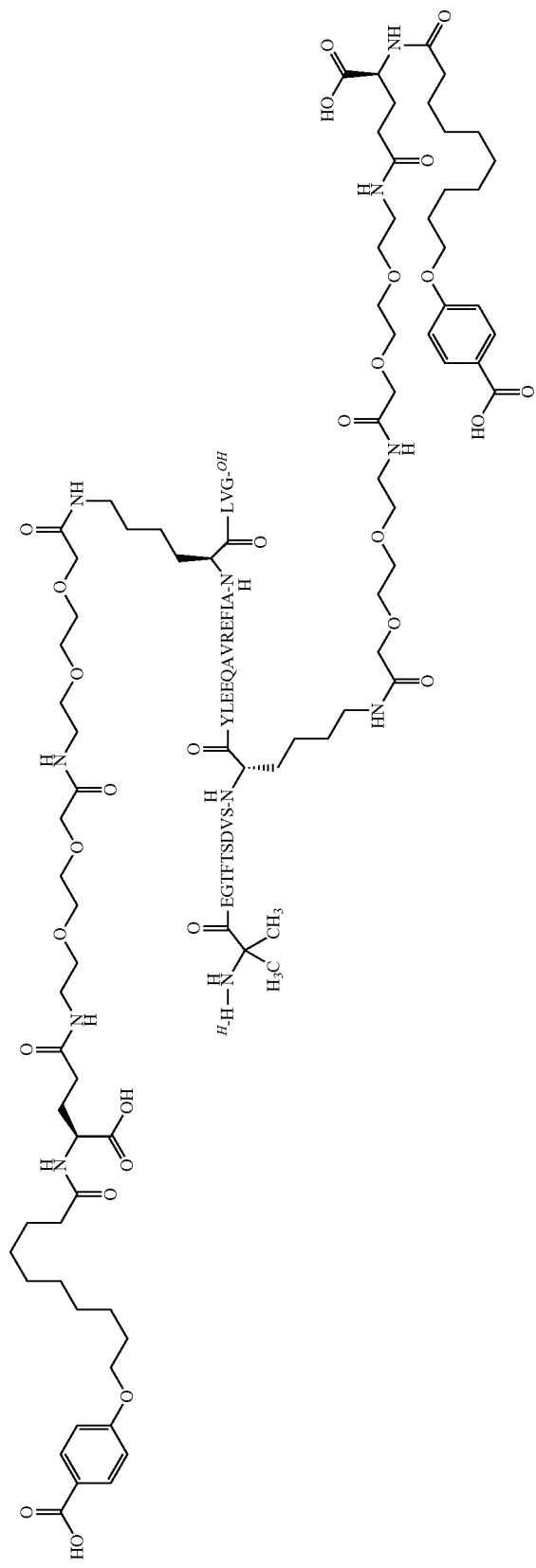

where the amino acid sequence is that of SEQ ID NO: 9,
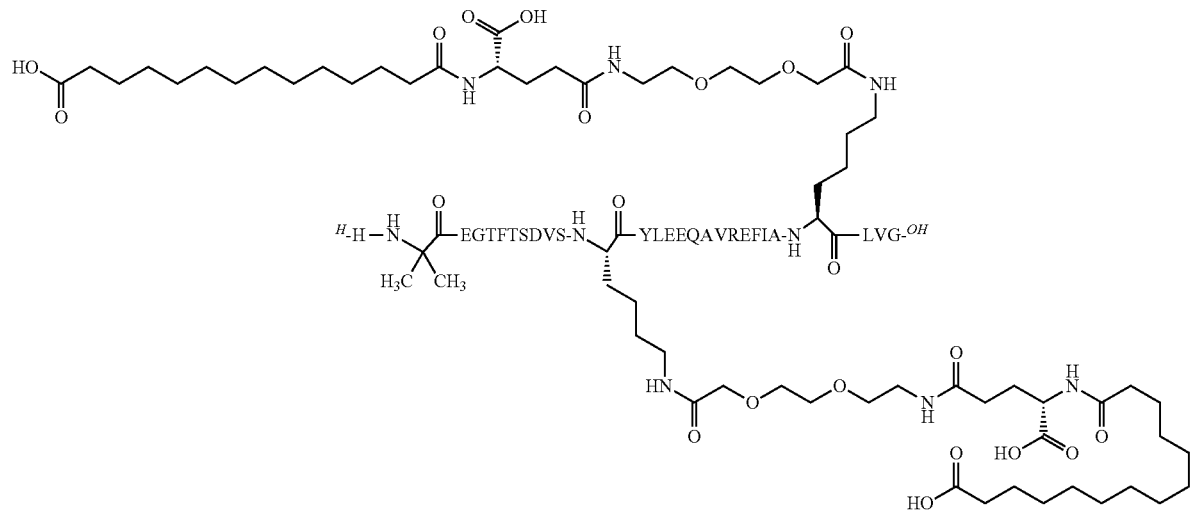
Chem. 39
where the amino acid sequence is that of SEQ ID NO: 9,
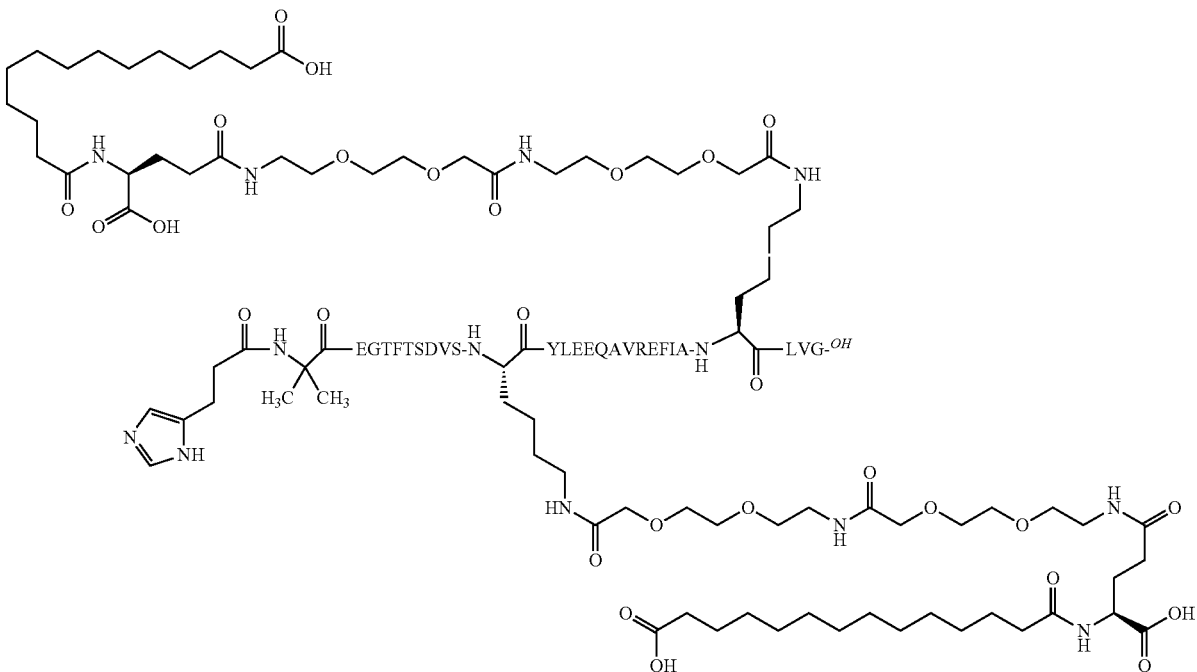
Chem. 40
where the amino acid sequence is that of SEQ ID NO: 25, Chem. 41
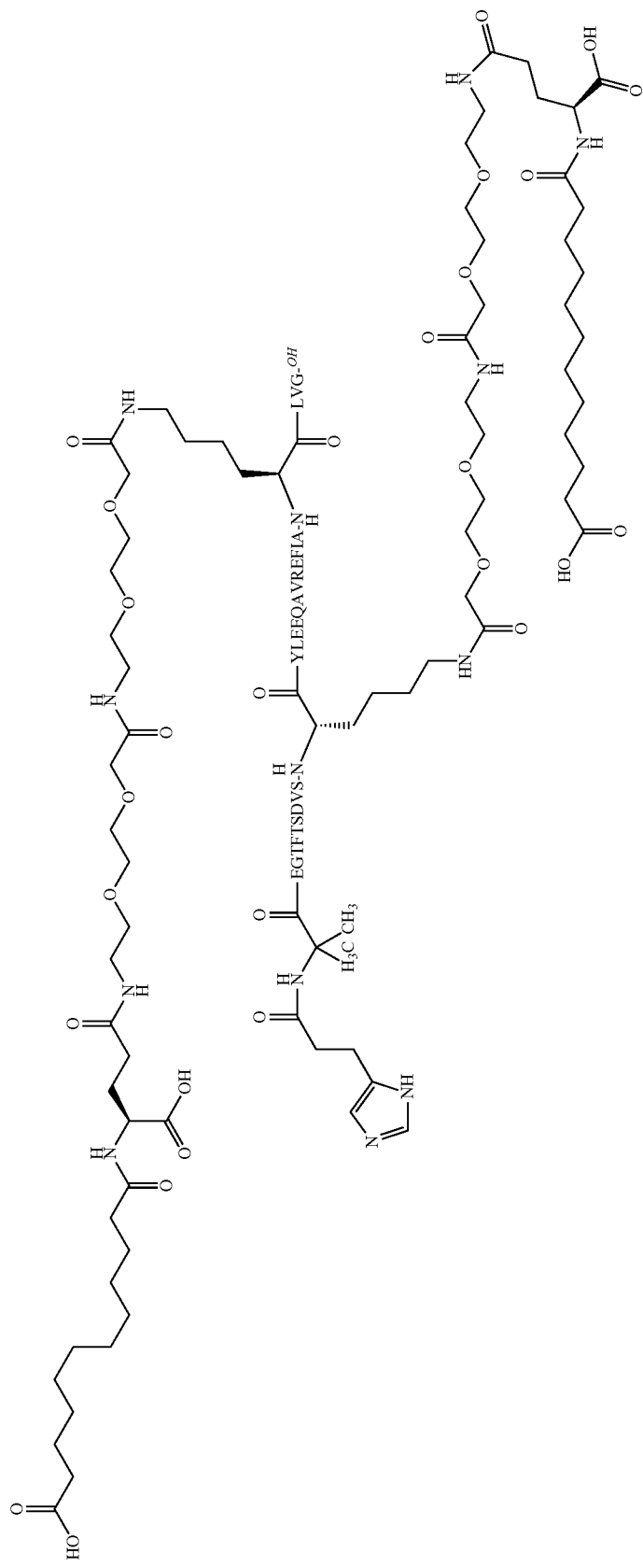

where the amino acid sequence is that of SEQ ID NO: 25,

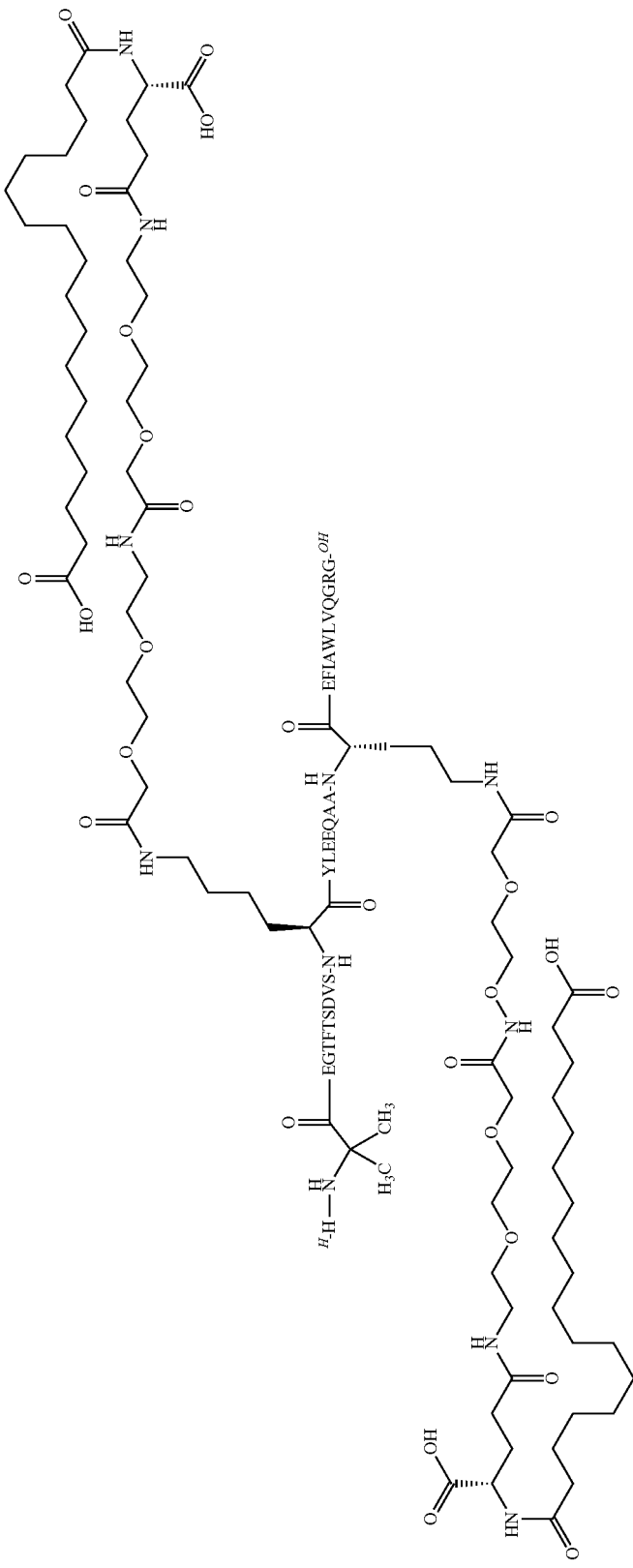
Chem. 42 where the amino acid sequence is that of SEQ ID NO: 7,
Chem. 43
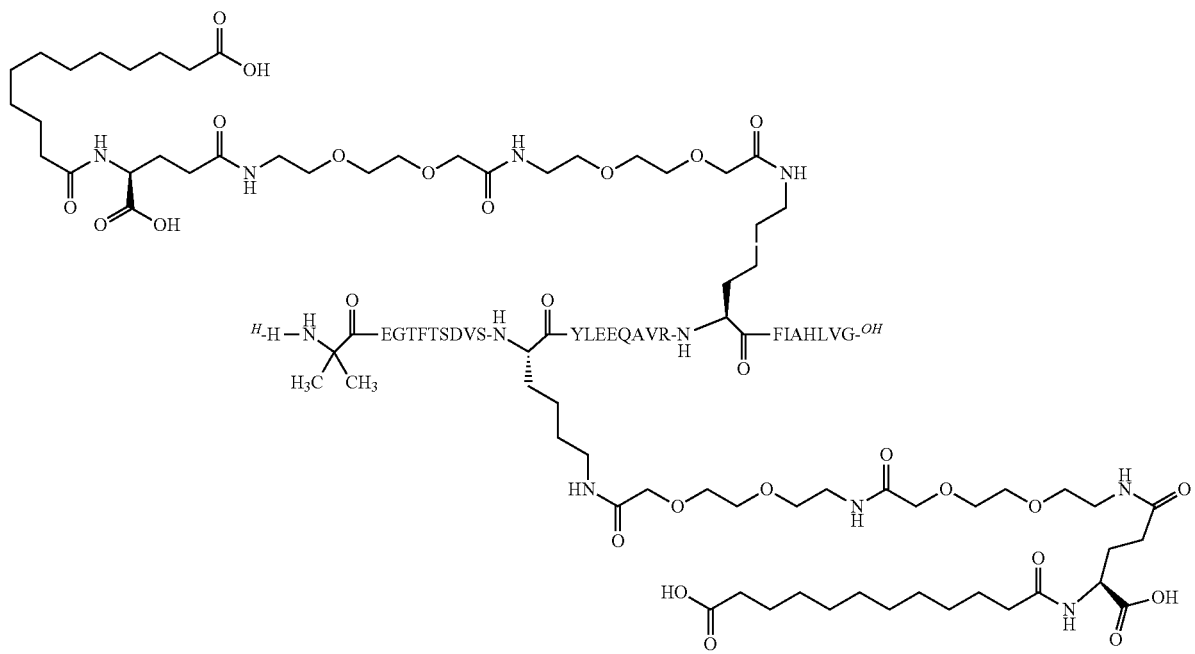
where the amino acid sequence is that of SEQ ID NO: 26,
Chem. 44
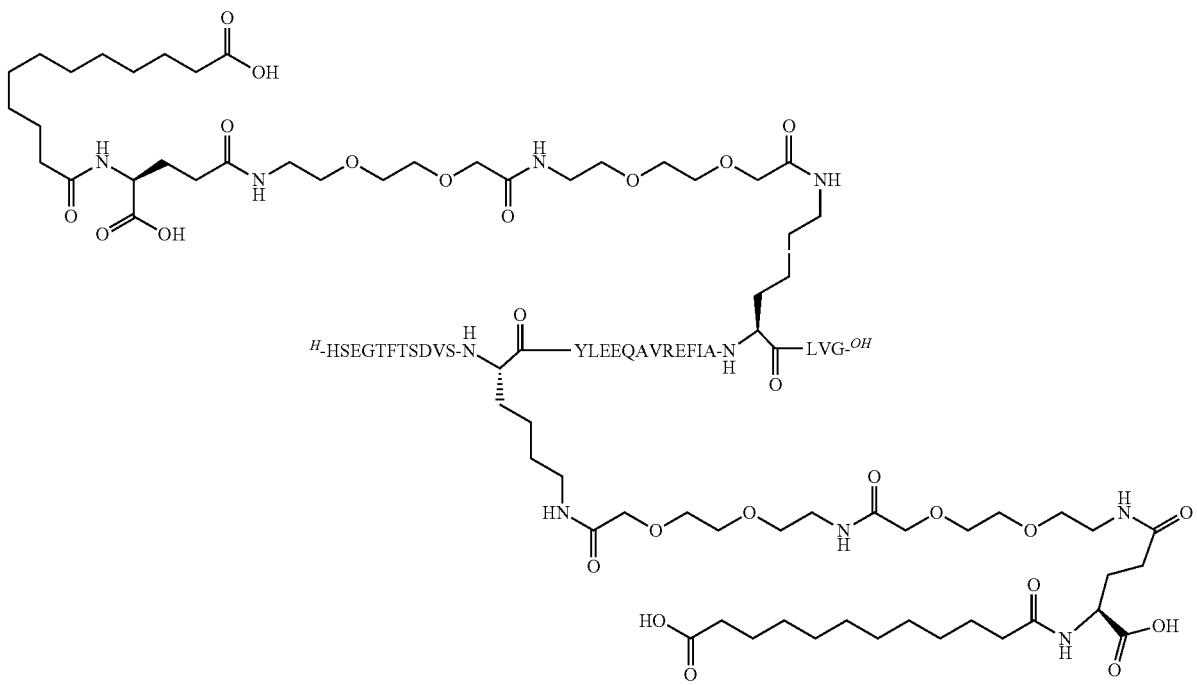
where the amino acid sequence is that of SEQ ID NO: 20, Chem. 45
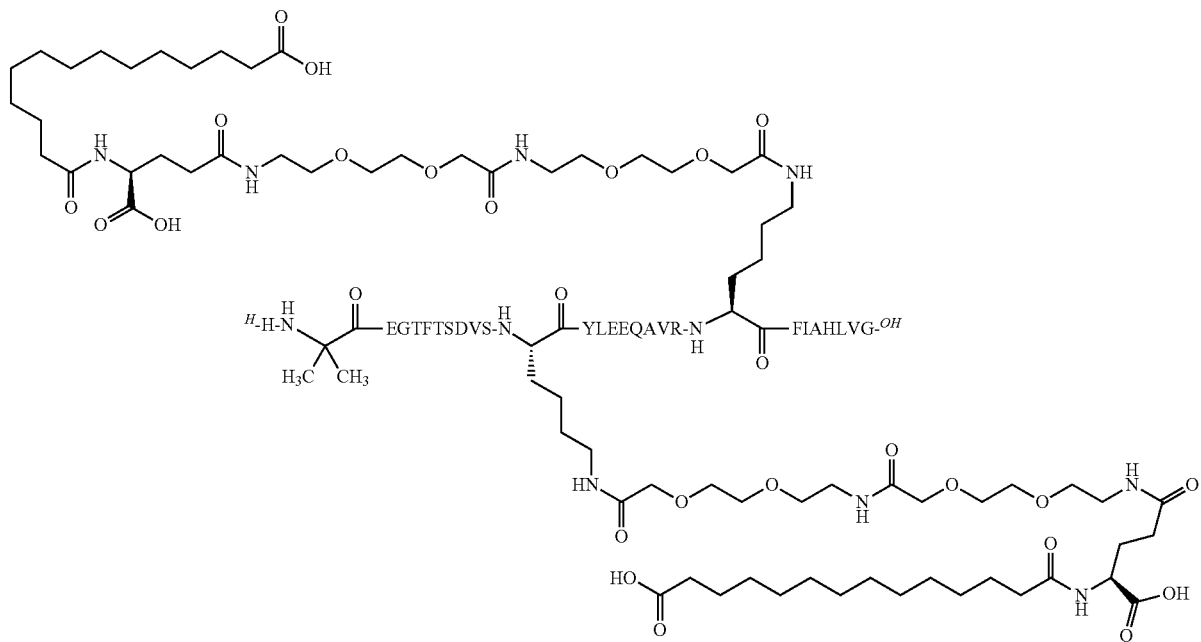
where the amino acid sequence is that of SEQ ID NO: 26,
Chem. 46
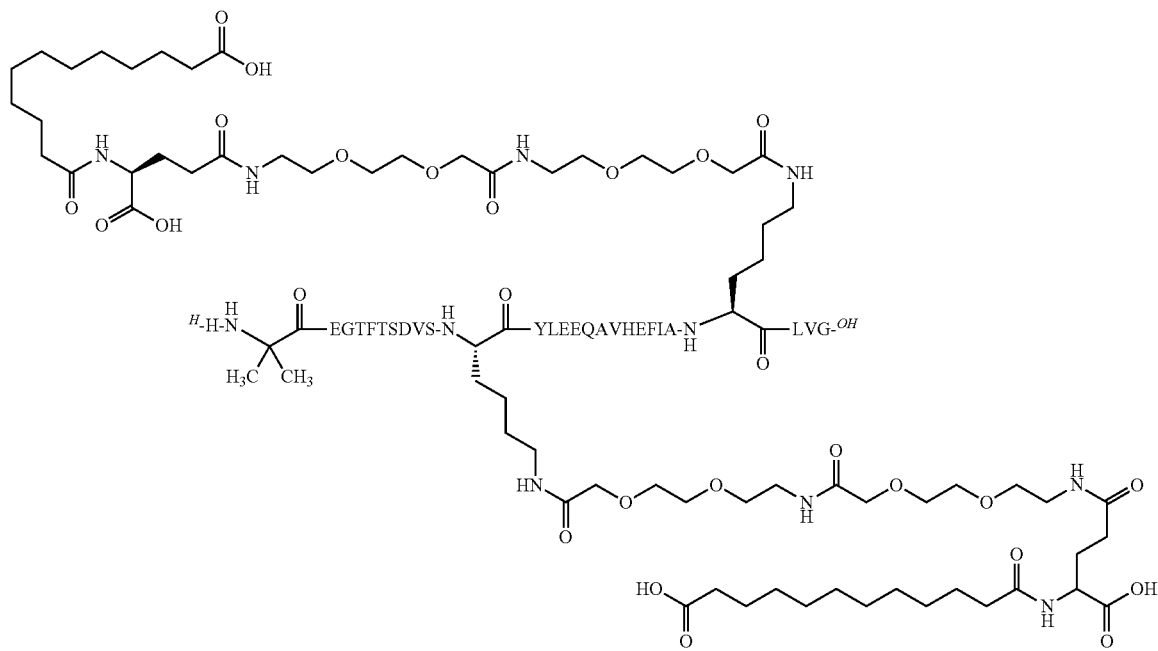
where the amino acid sequence is that of the SEQ ID NO: 16,

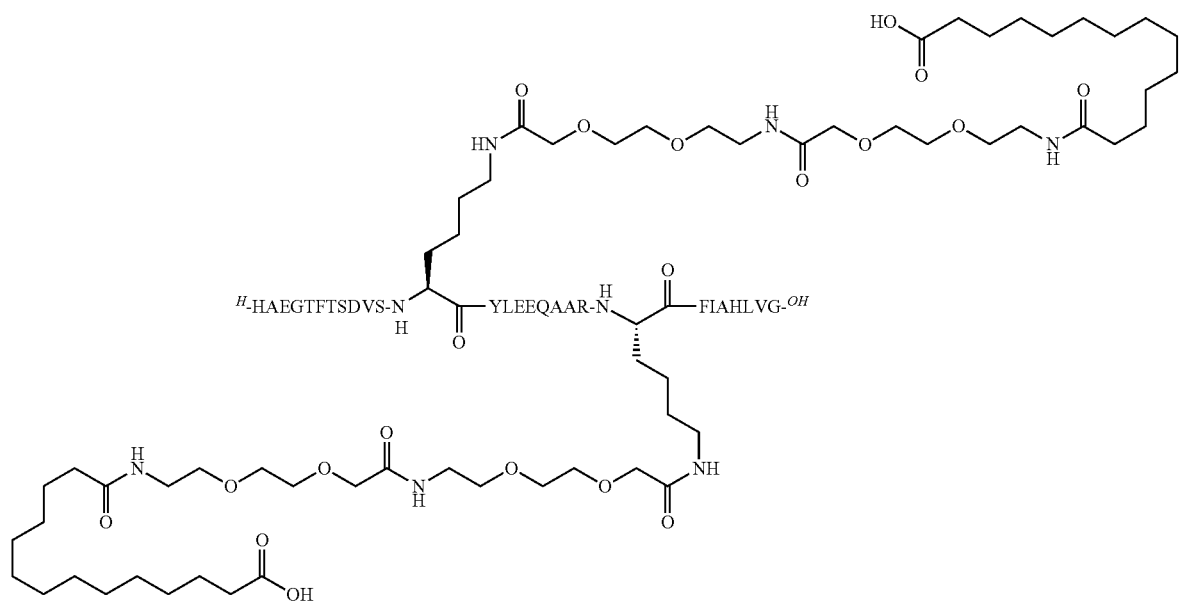
Chem. 47
where the amino acid sequence is that of SEQ ID NO: 27,

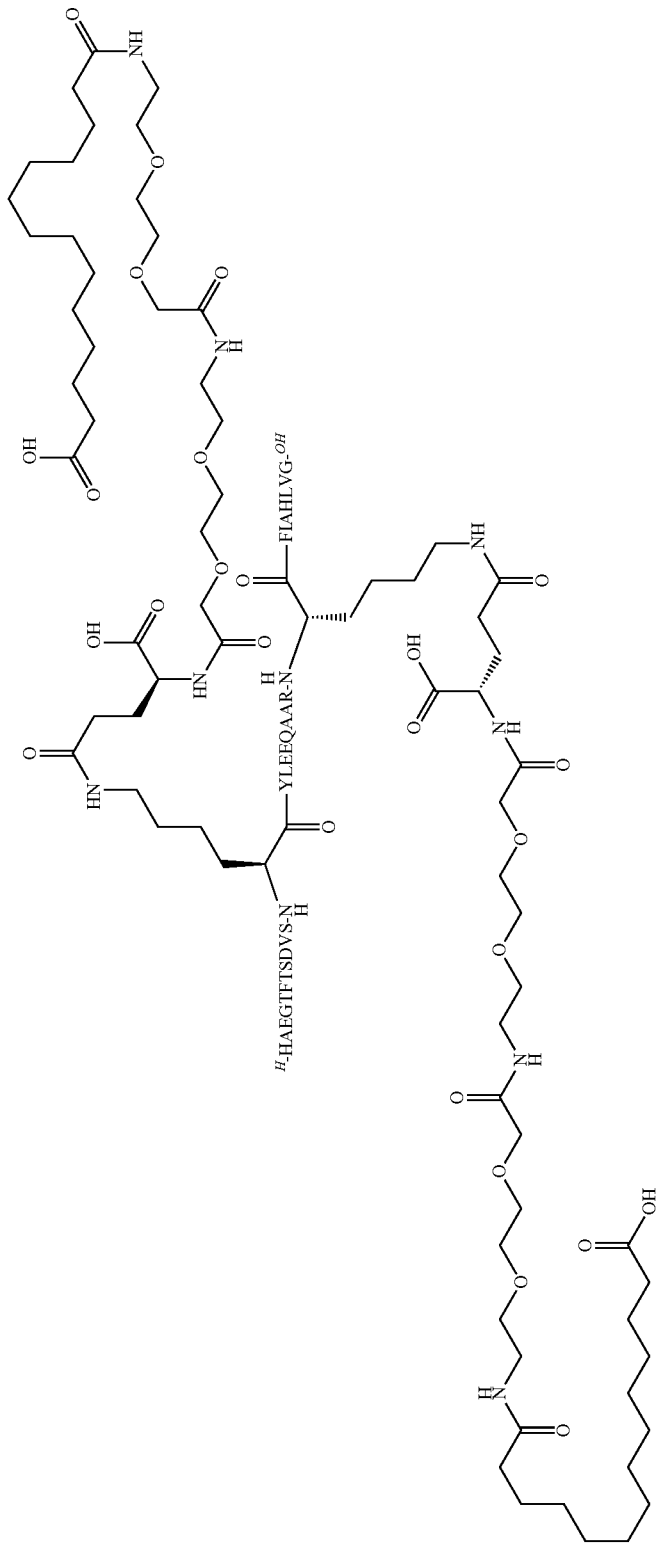
Chem. 48 where the amino acid sequence is that of SEQ ID NO: 27,

Chem. 49
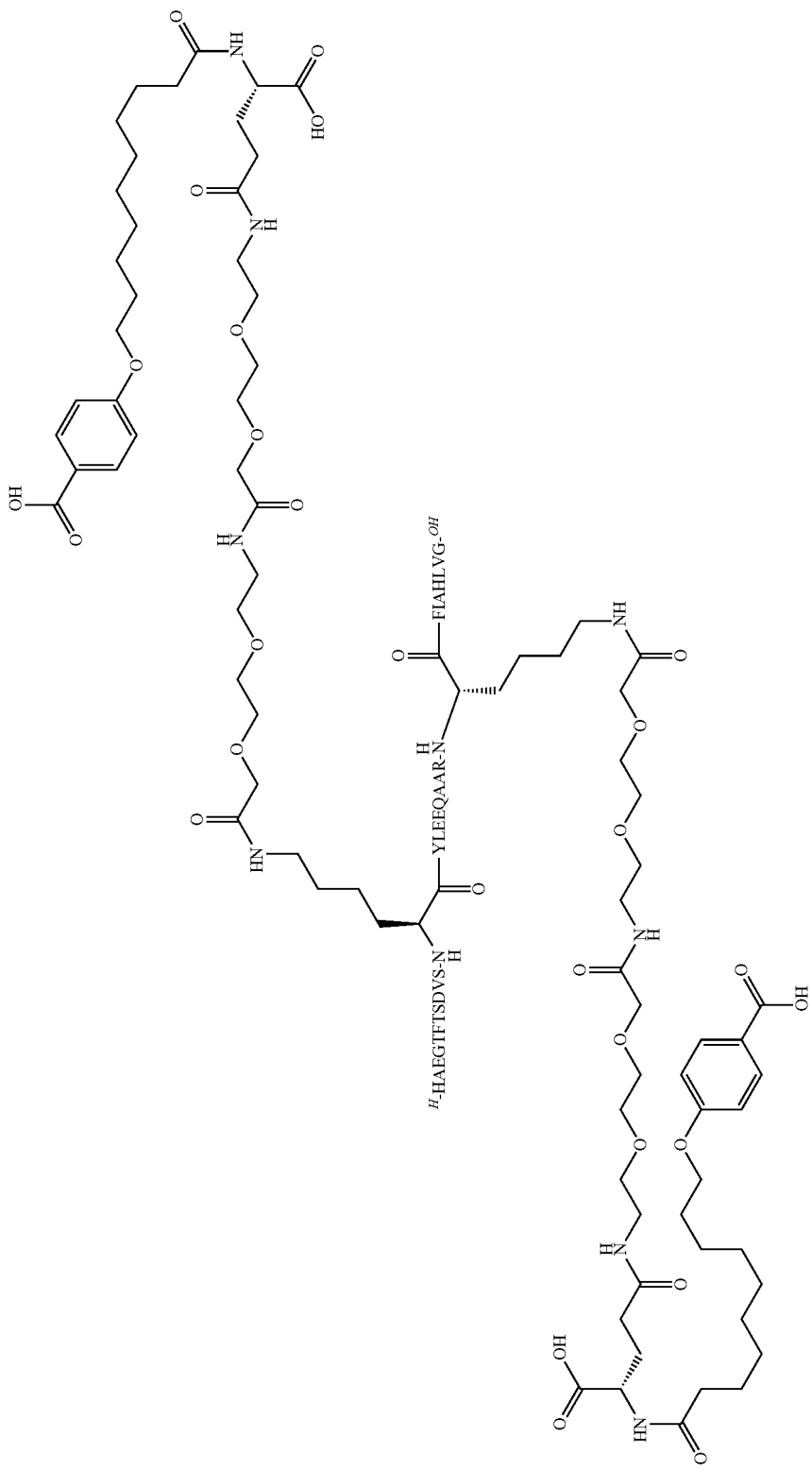

where the the amino acid sequence is that of SEQ ID NO: 27,
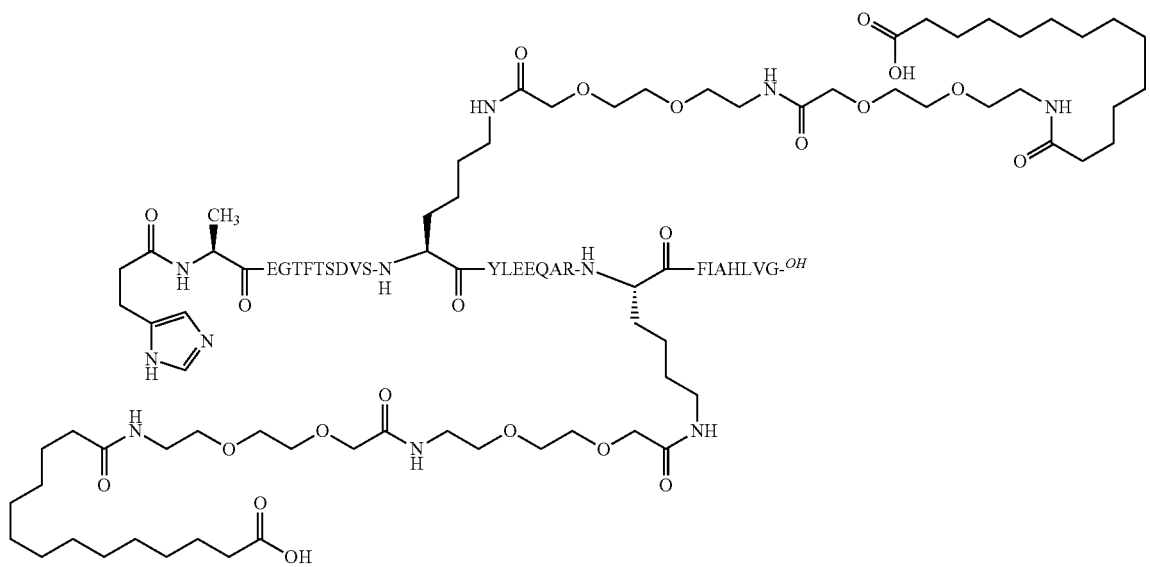
Chem. 50
where the amino acid sequence is that of SEQ ID NO: 28,
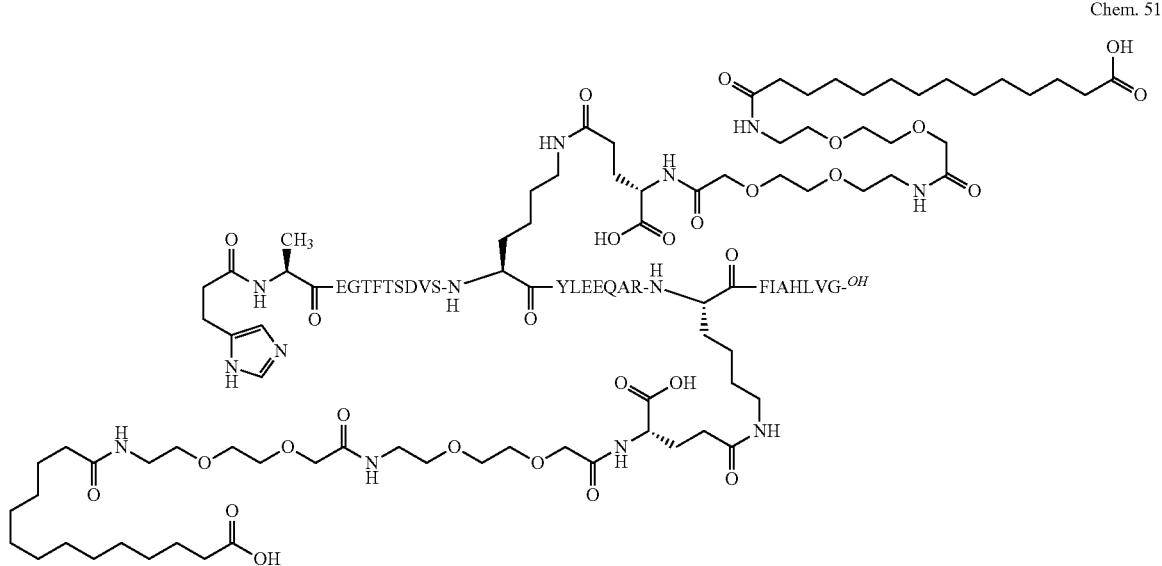
Chem. 51
where the amino acid sequence is that of SEQ ID NO: 28,

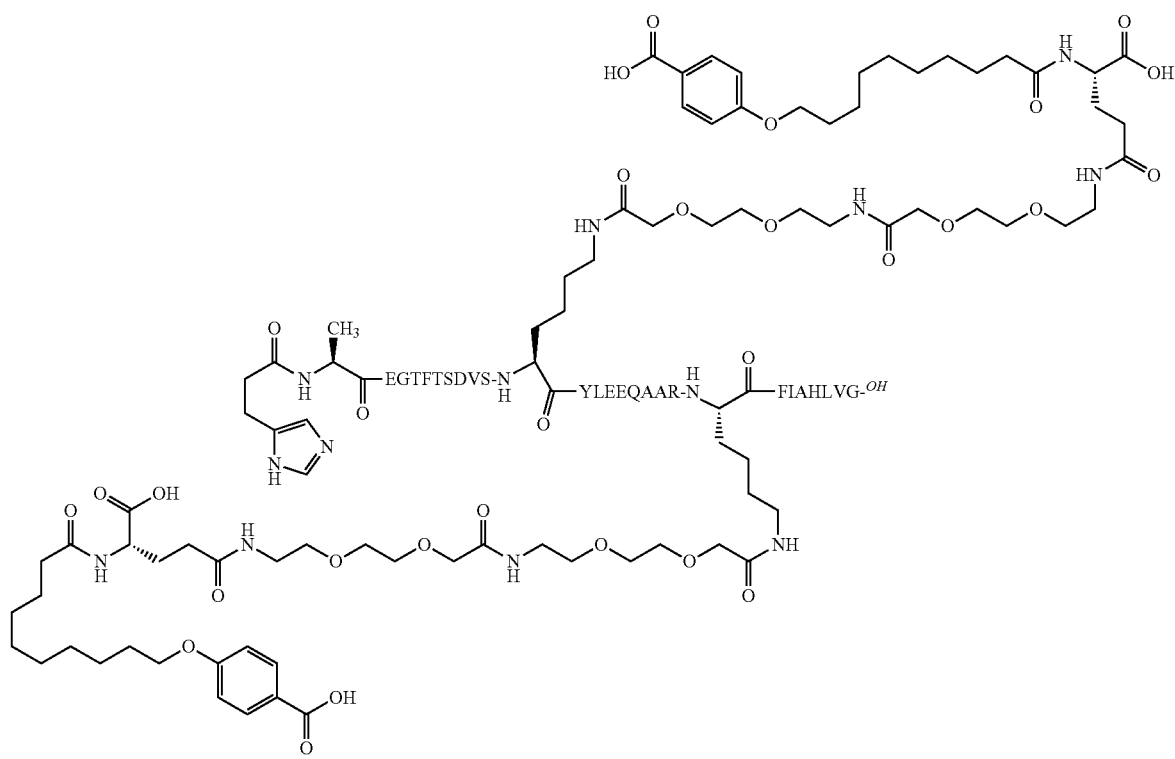
where the amino acid sequence is that of SEQ ID NO: 28,
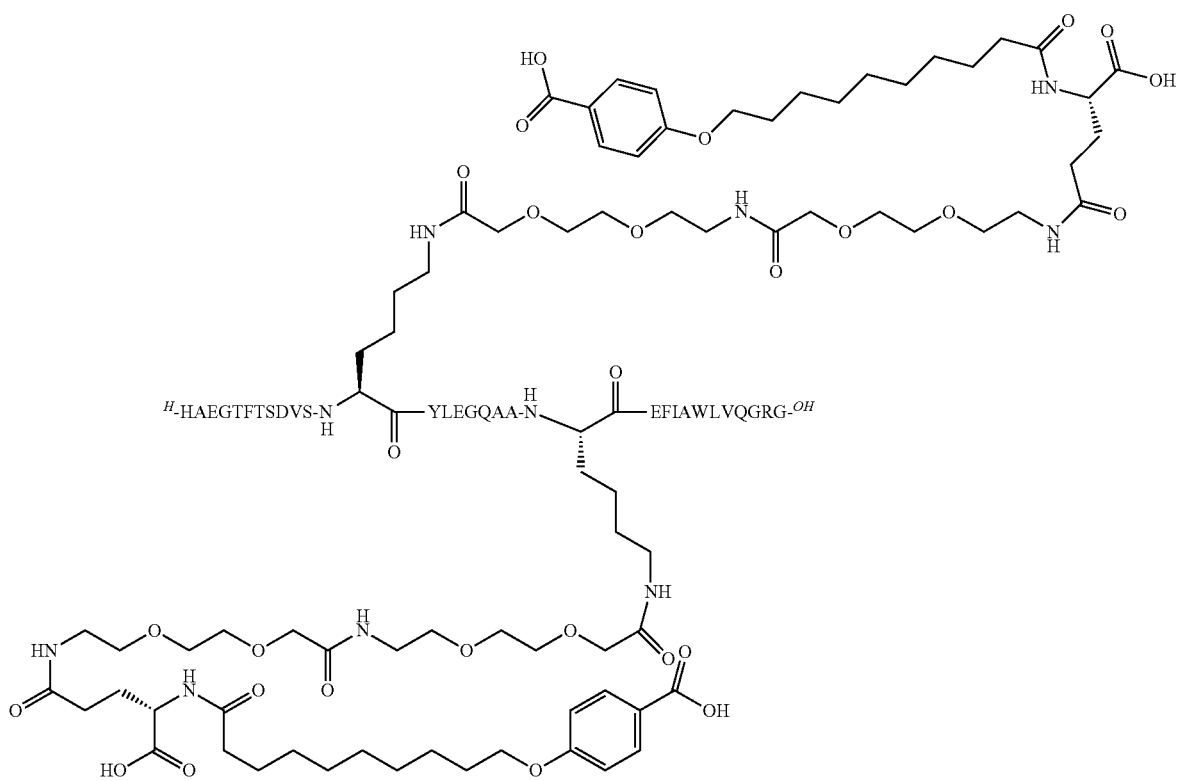
where the amino acid sequence is that of SEQ ID NO: 29, Chem. 54
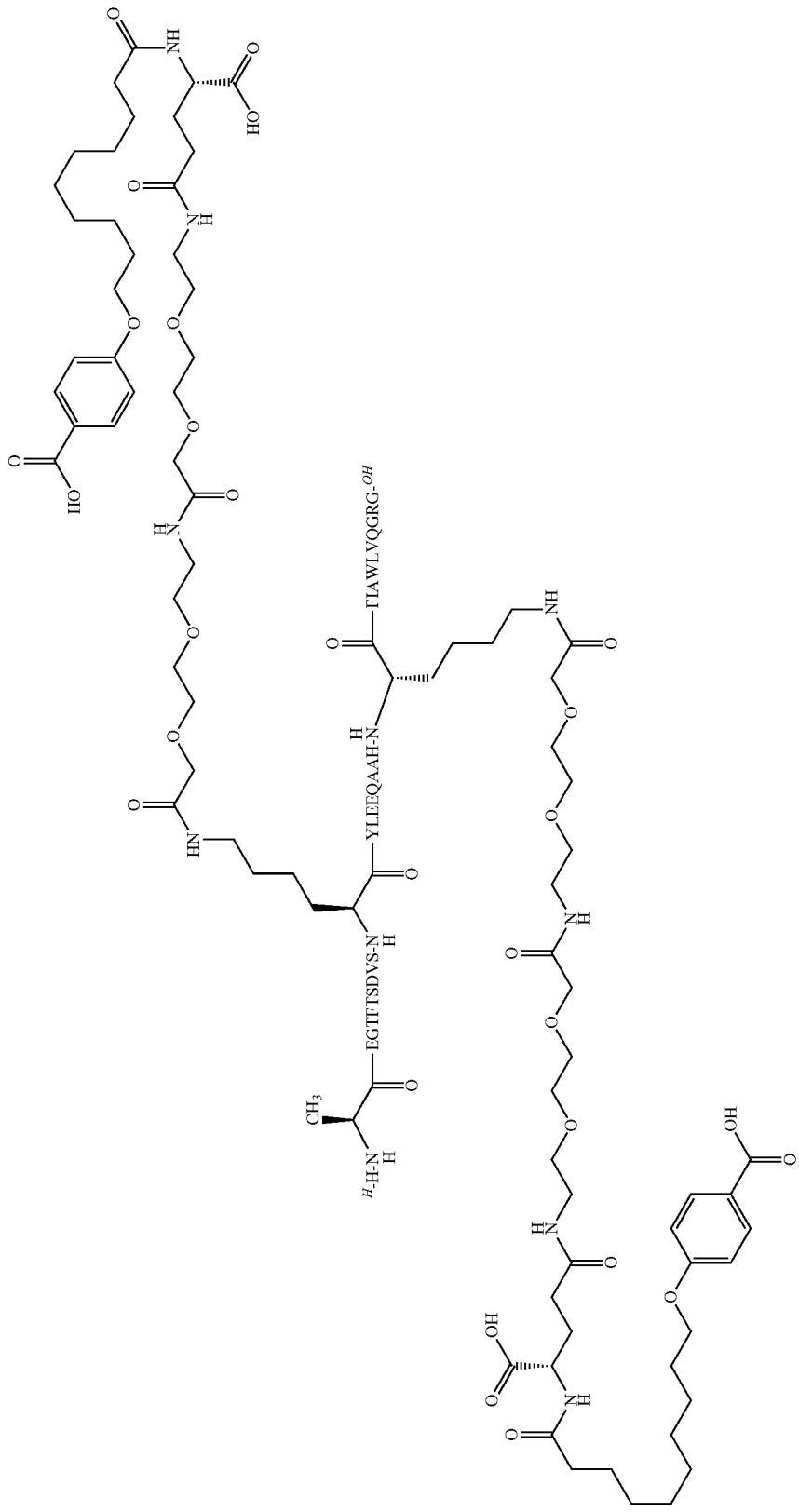

where the amino acid sequence is that of SEQ ID NO: 30,

Chem. 55
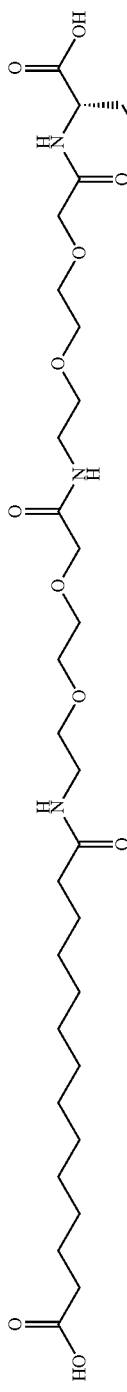
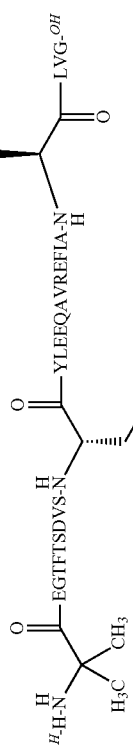
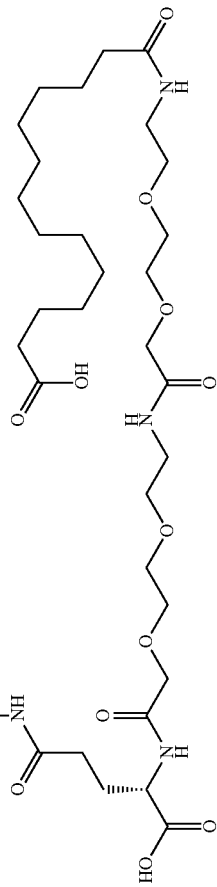

where the amino acid sequence is that of SEQ ID NO: 9,

Chem. 56
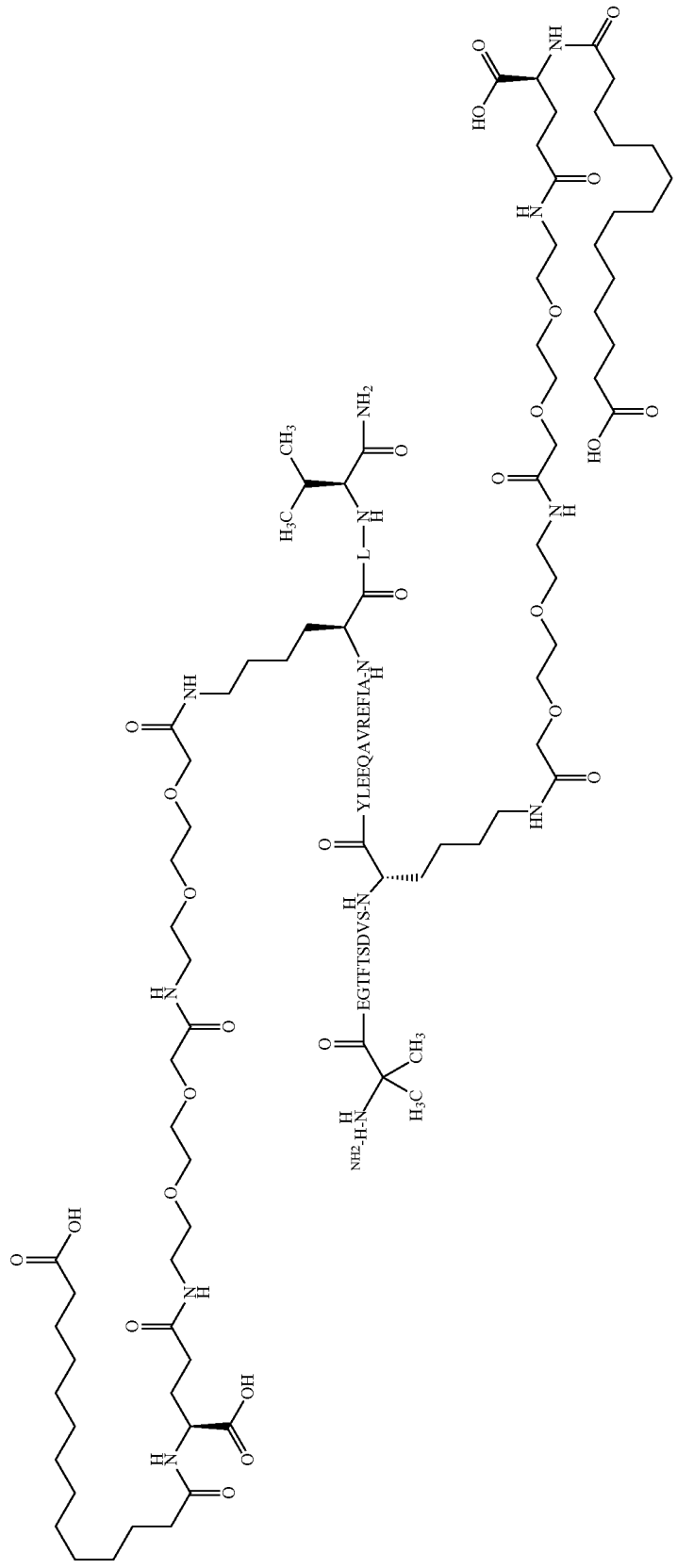

where the amino acid sequence is that of SEQ ID NO: 31,

Chem. 57
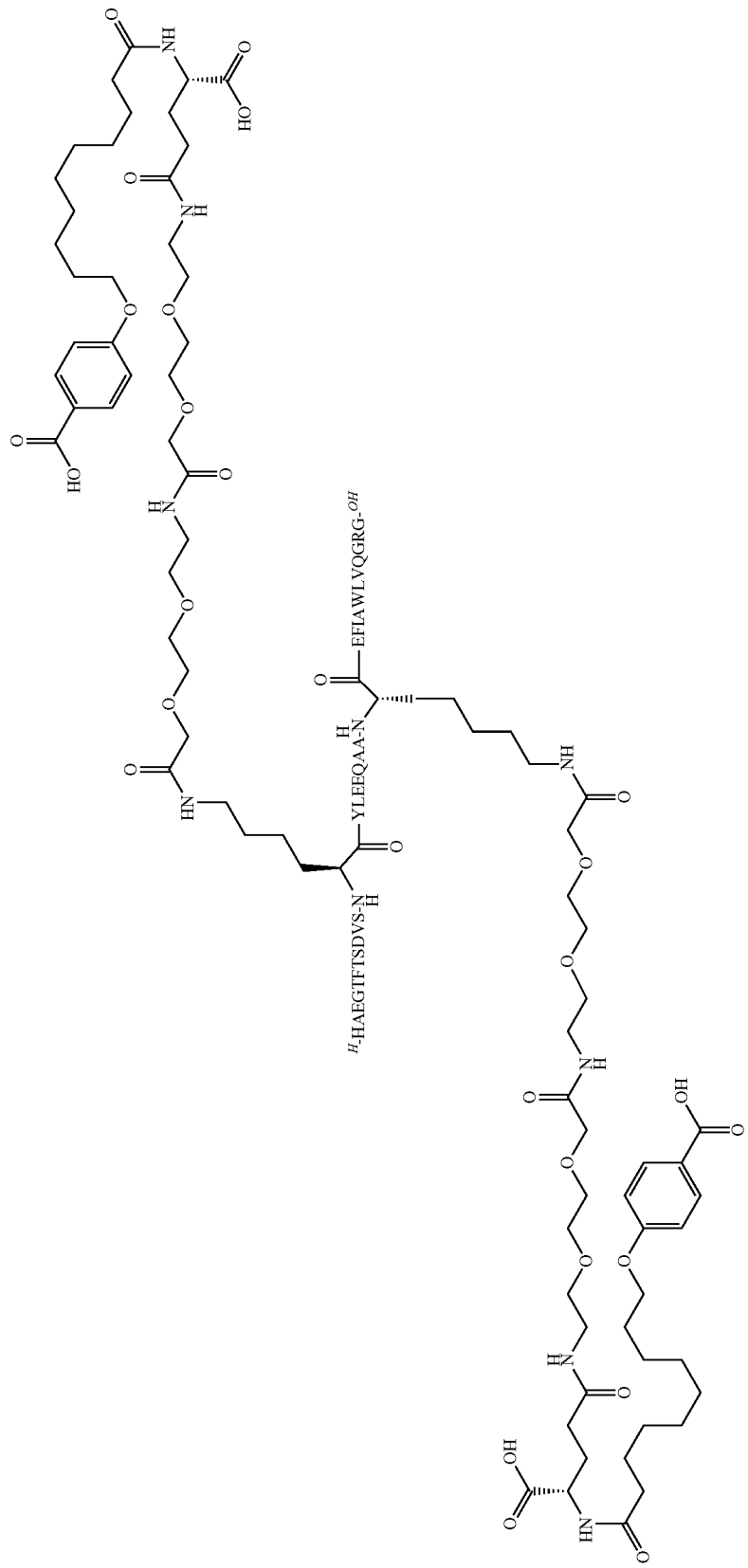

where the amino acid sequence is that of SEQ ID NO: 32,

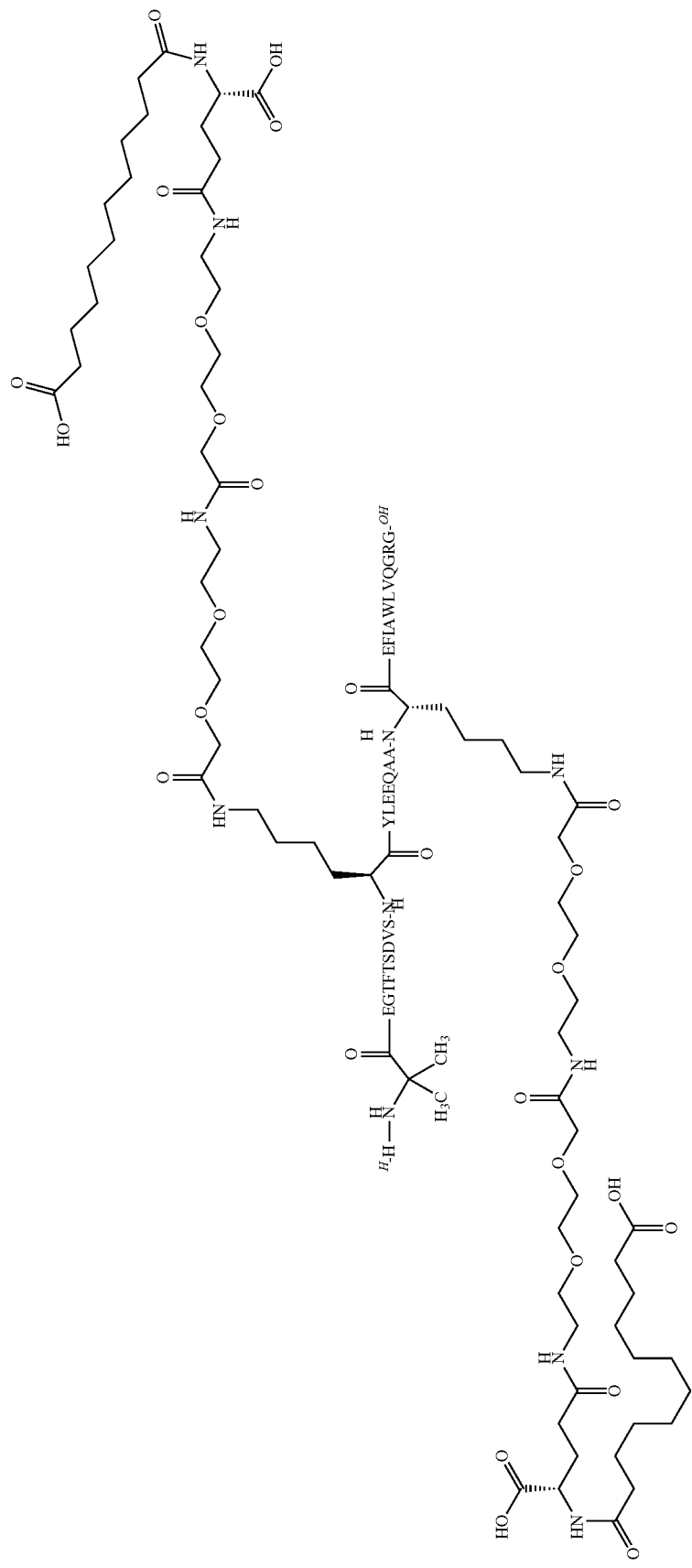
Chem. 58 where the amino acid sequence is that of SEQ ID NO: 7,
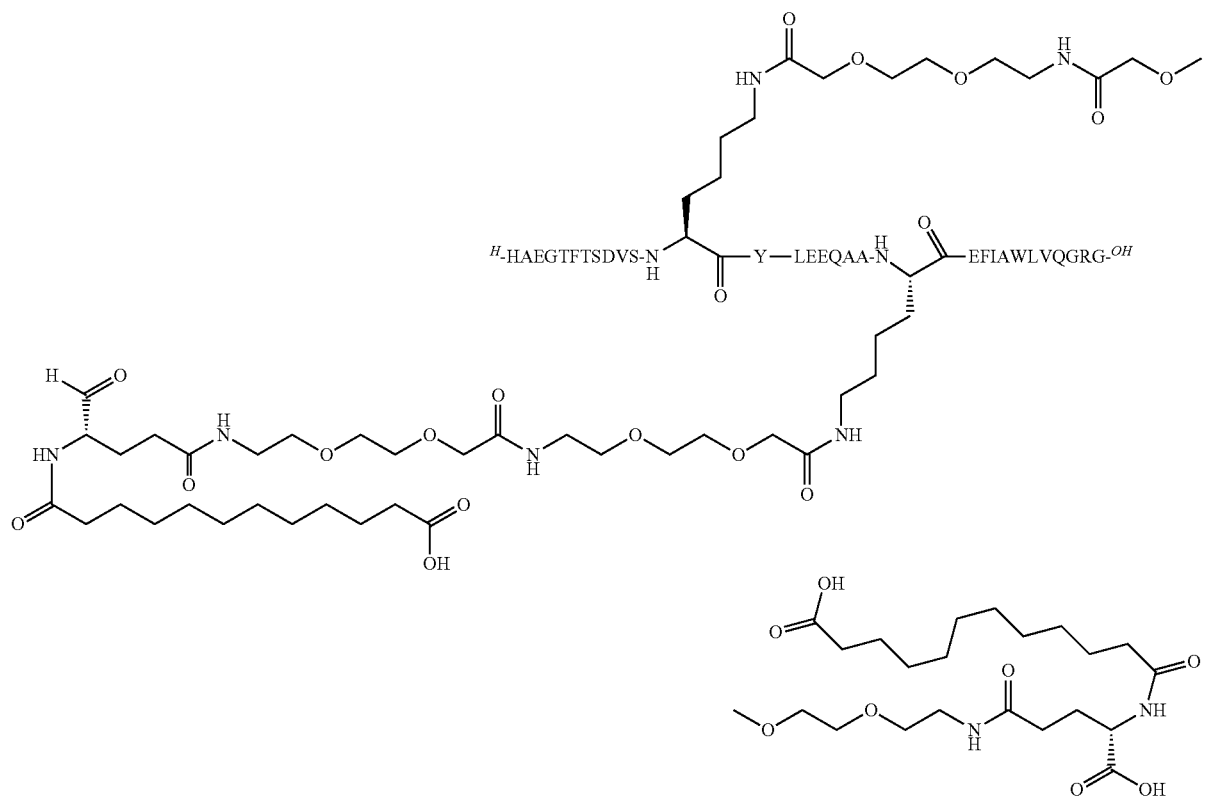
where the amino acid sequence is that of SEQ ID NO: 32,
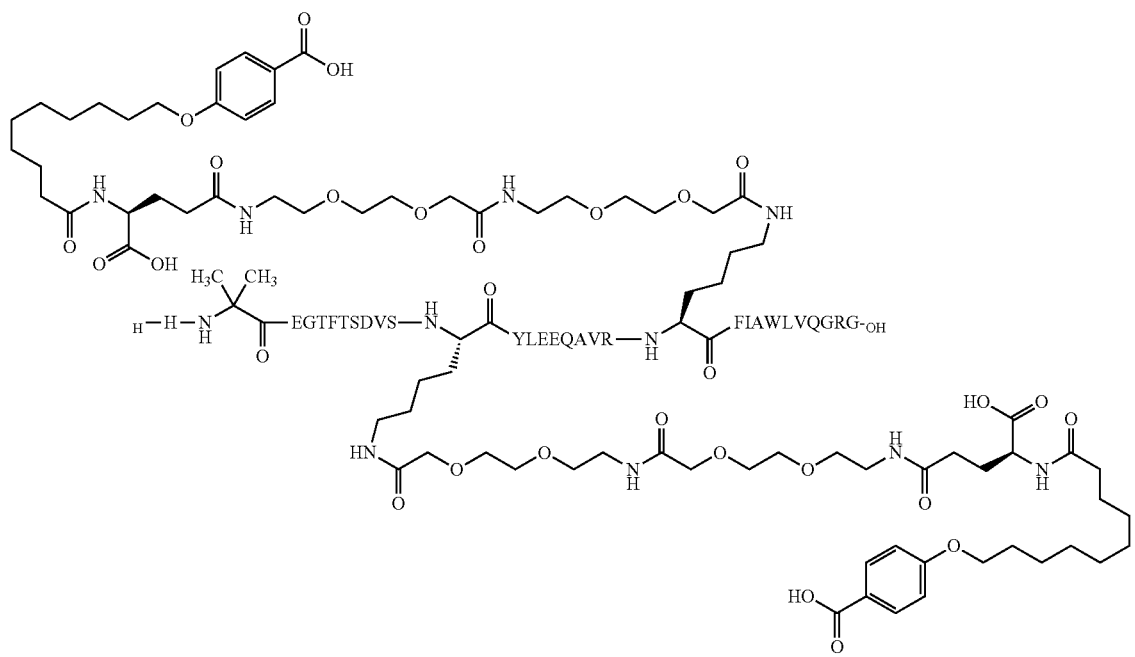
where the amino acid sequence is that of SEQ ID NO: 33, Chem. 61
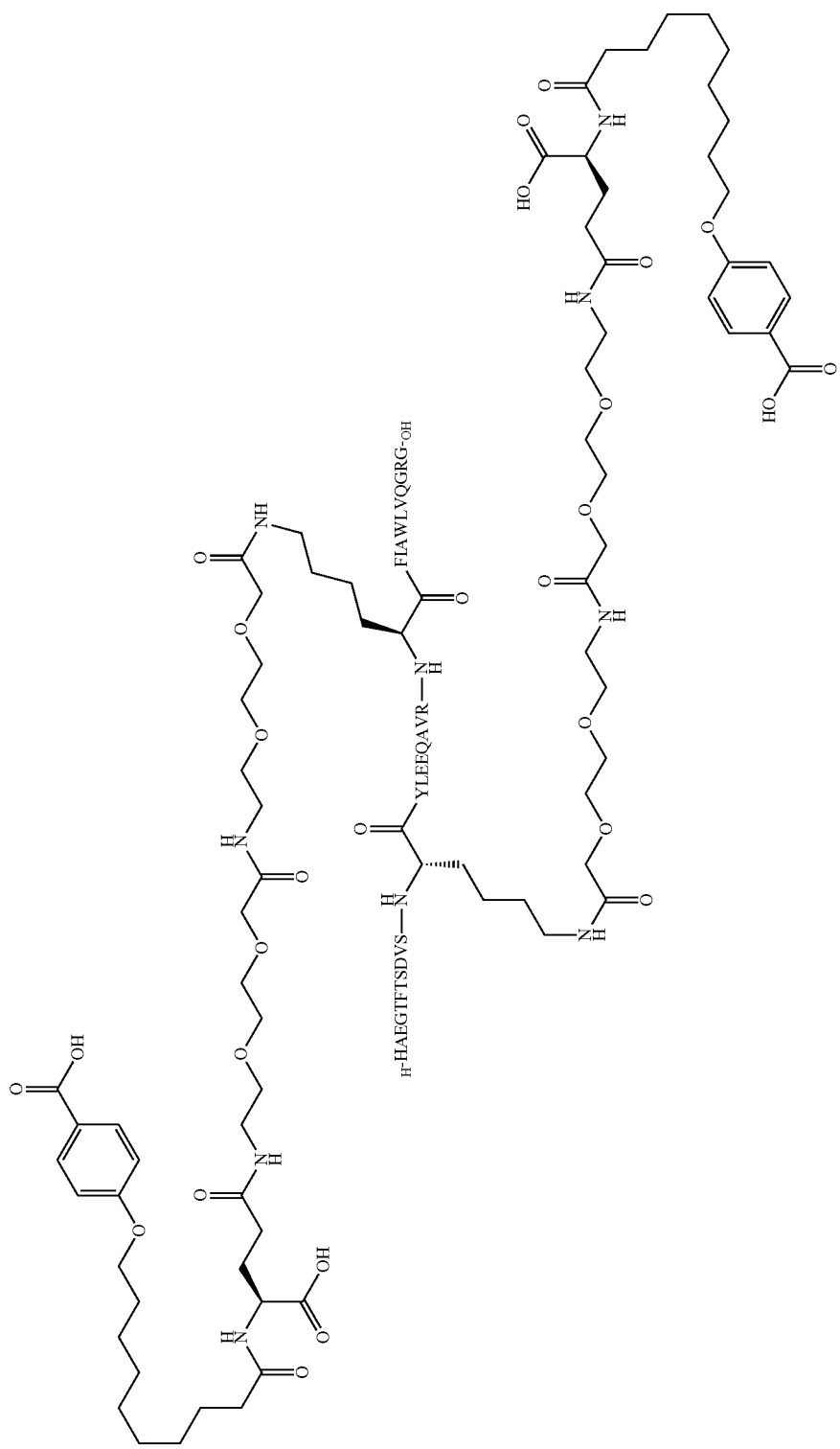

where the amino acid sequence is that of SEQ ID NO: 34,

Chem. 62
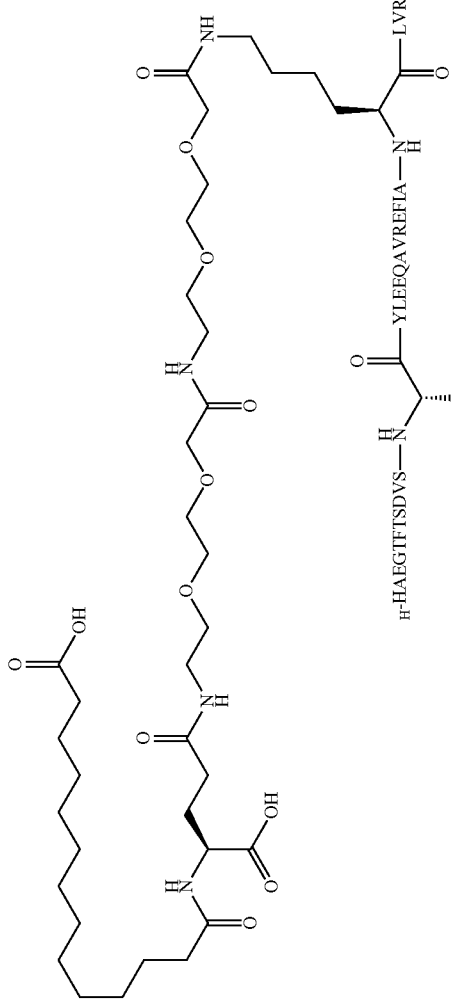
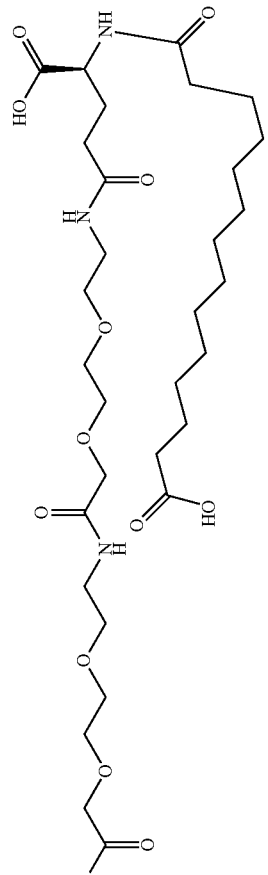

where the amino acid sequence is that of SEQ ID NO: 10,
Chem. 63
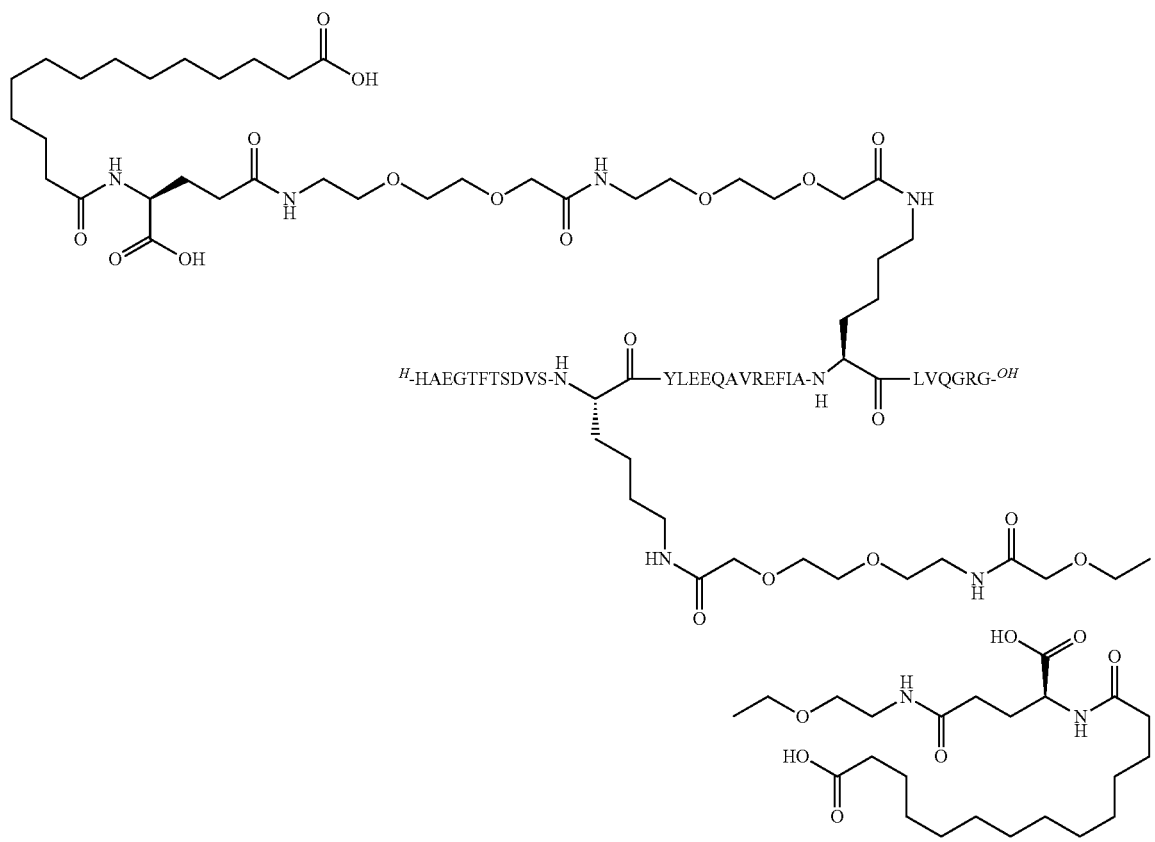
where the amino acid sequence is that of SEQ ID NO: 11,
Chem. 64
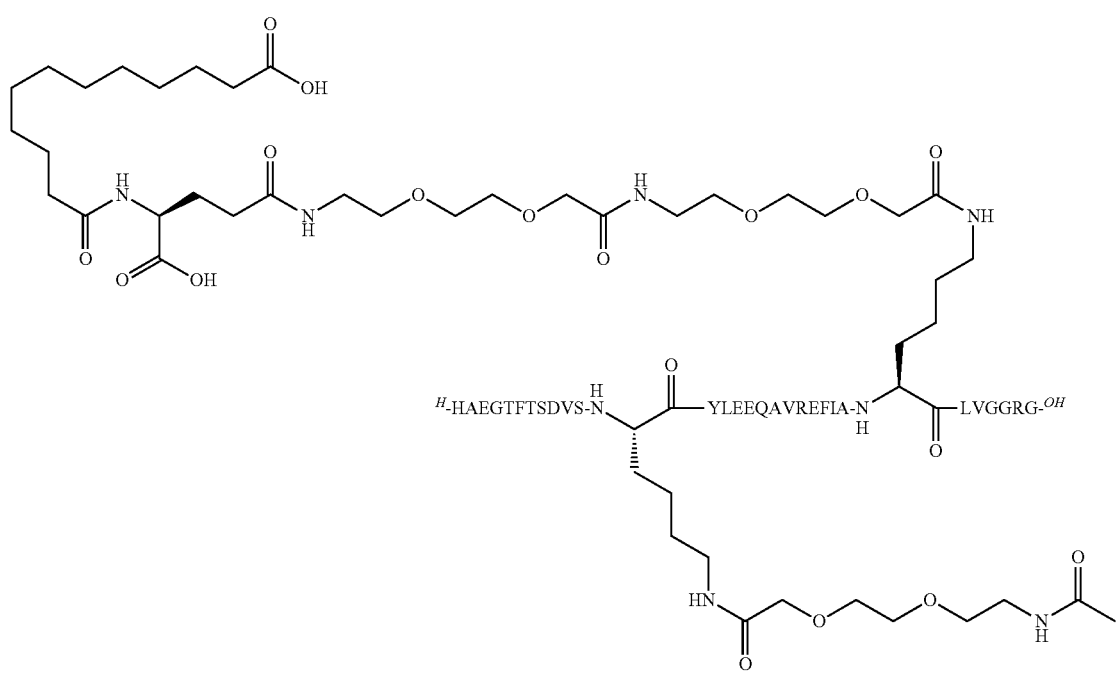

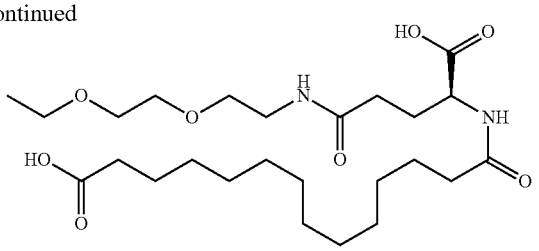
where the amino acid sequence is that of SEQ ID NO: 18,

Chem. 65
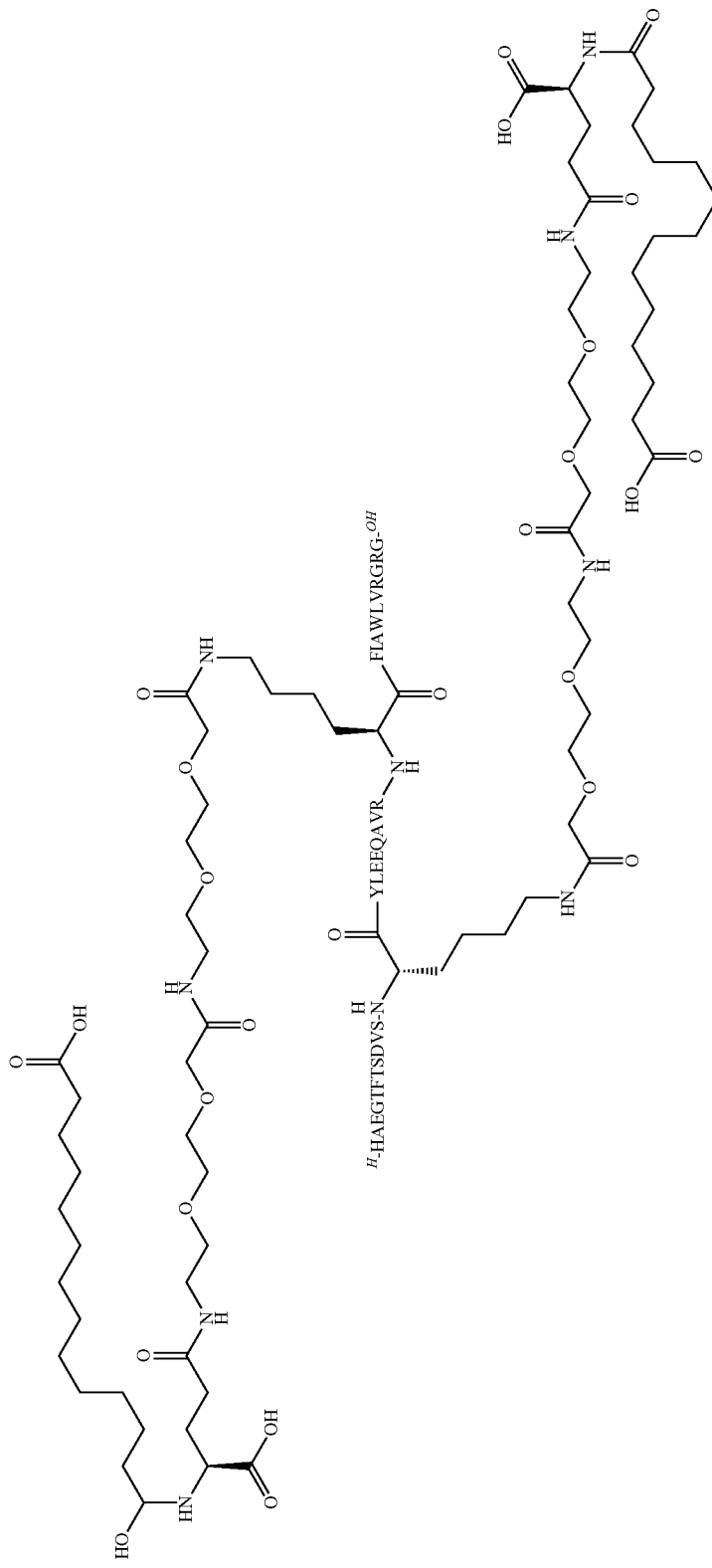

where the amino acid sequence is that of SEQ ID NO: 35,

Chem. 66
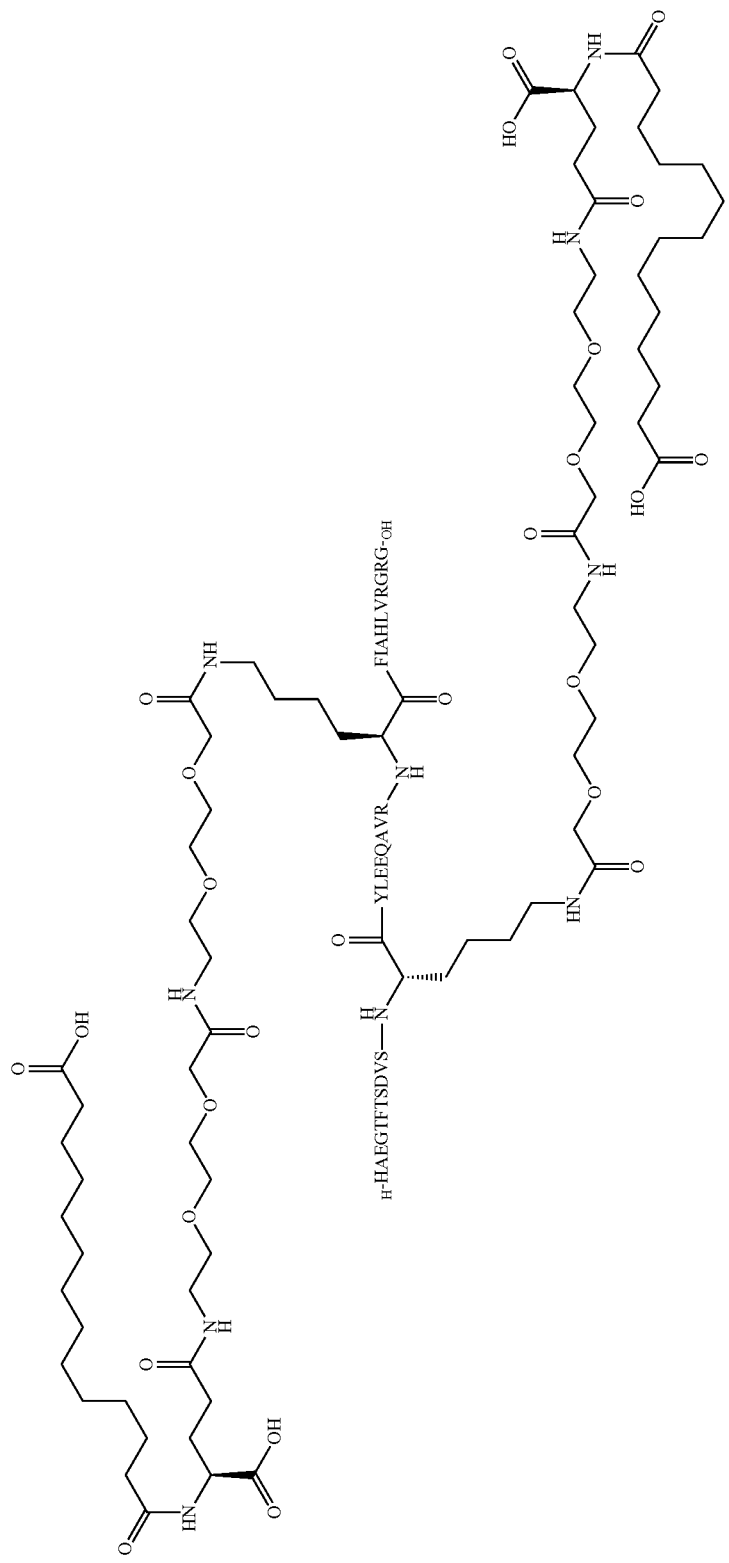

where the amino acid sequence is that of SEQ ID NO: 36,

Chem. 67
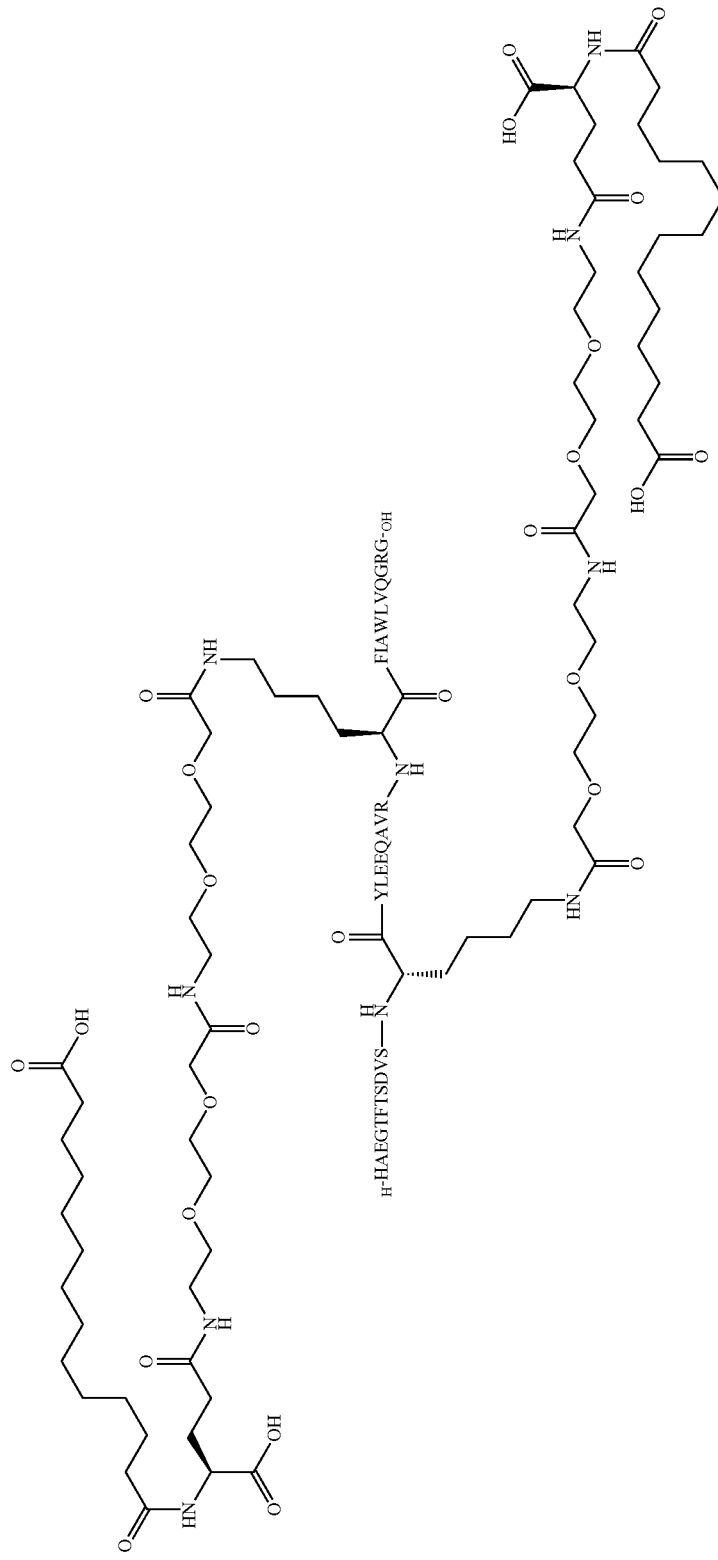

where the amino acid sequence is that of SEQ ID NO: 34,

Chem. 68
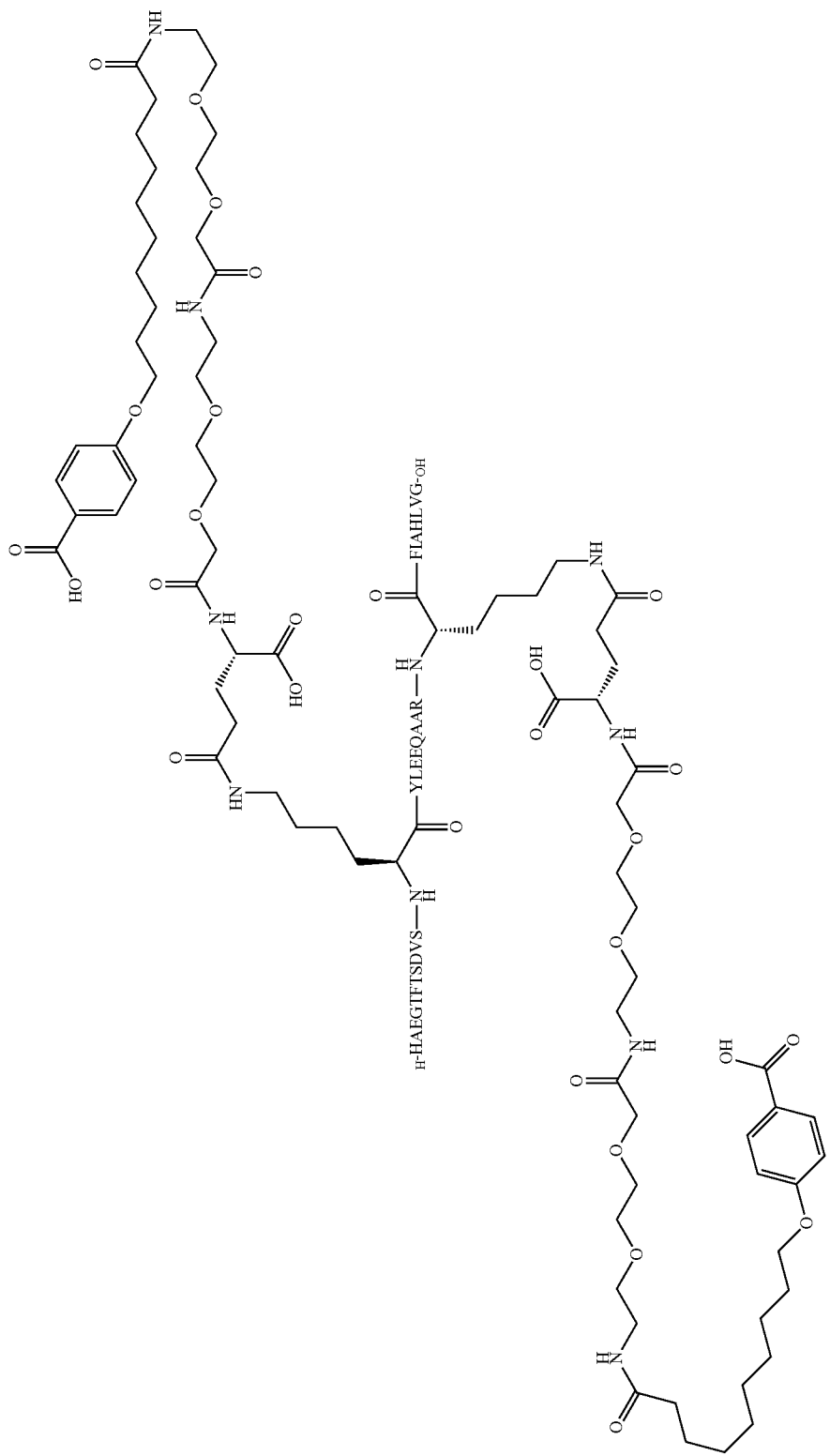

where the amino acid sequence is that of SEQ ID NO: 27,

Chem. 69
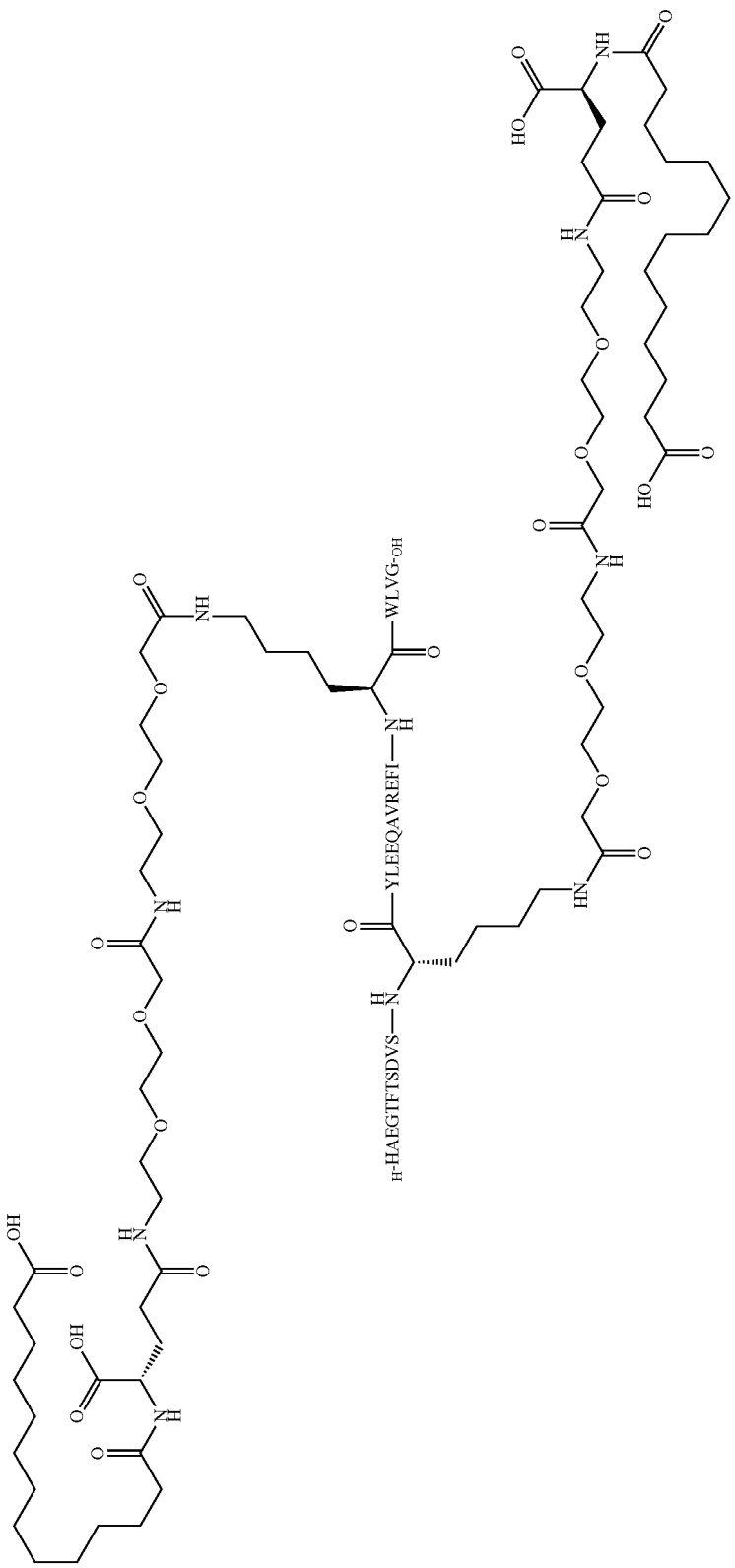

where the amino acid sequence is that of SEQ ID NO: 37,

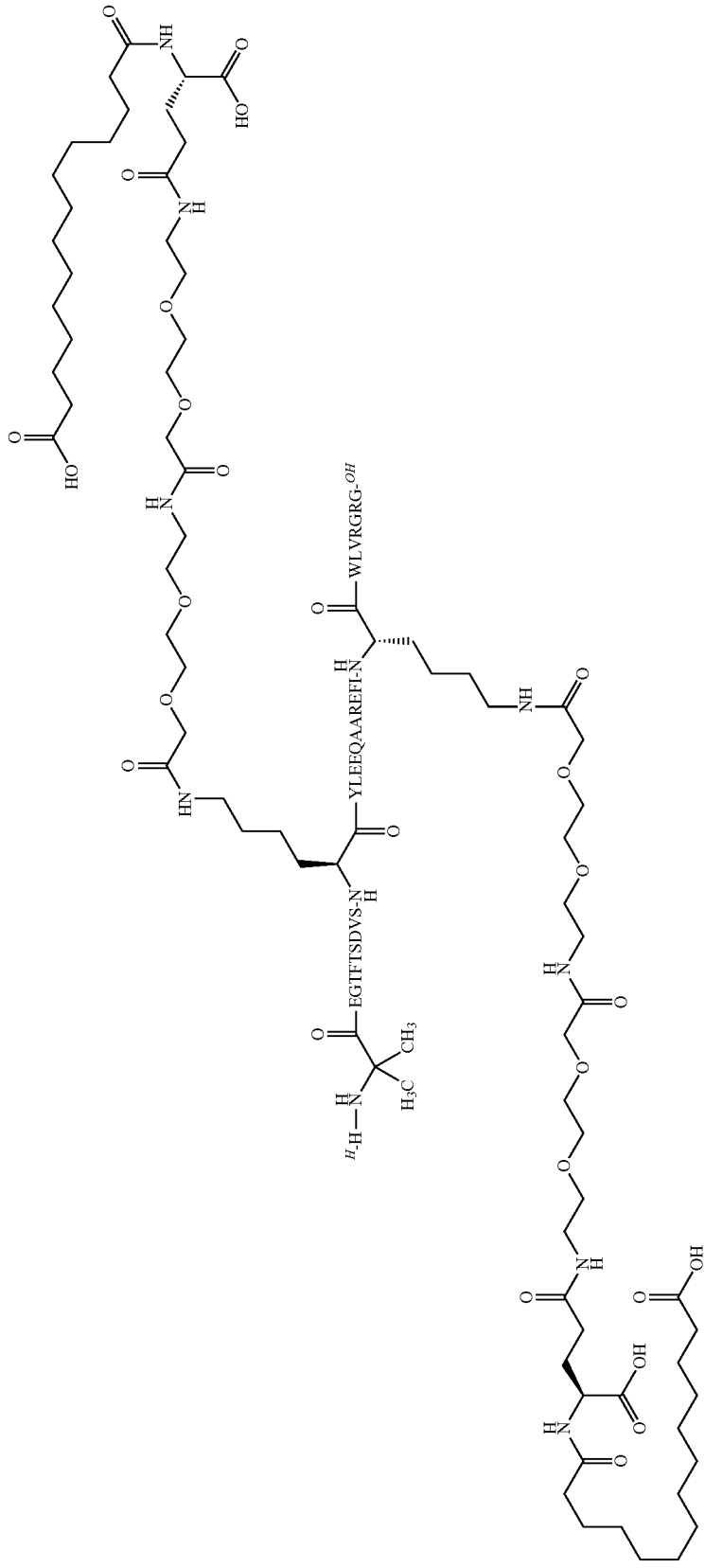
Chem. 70 where the amino acid sequence is that of SEQ ID NO: 38,
Chem. 71
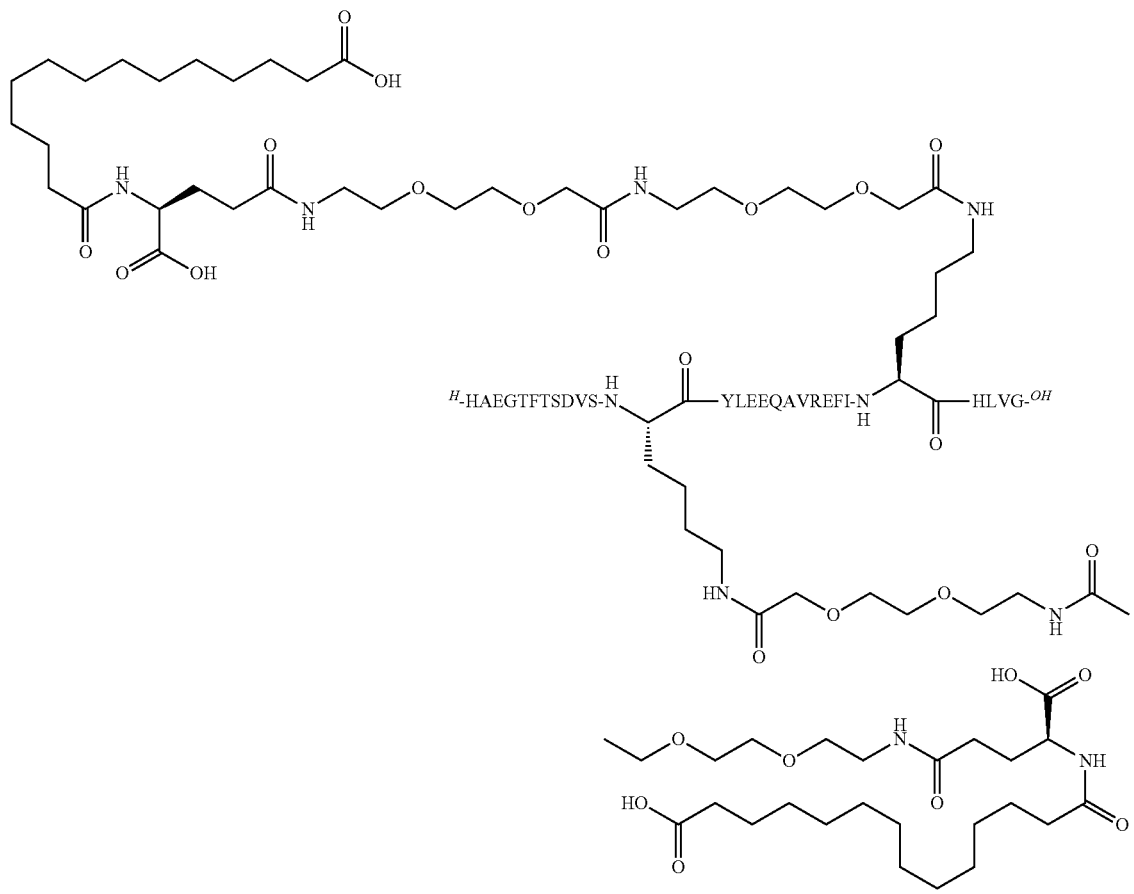
where the amino acid sequence is that of SEQ ID NO: 39,
Chem. 72
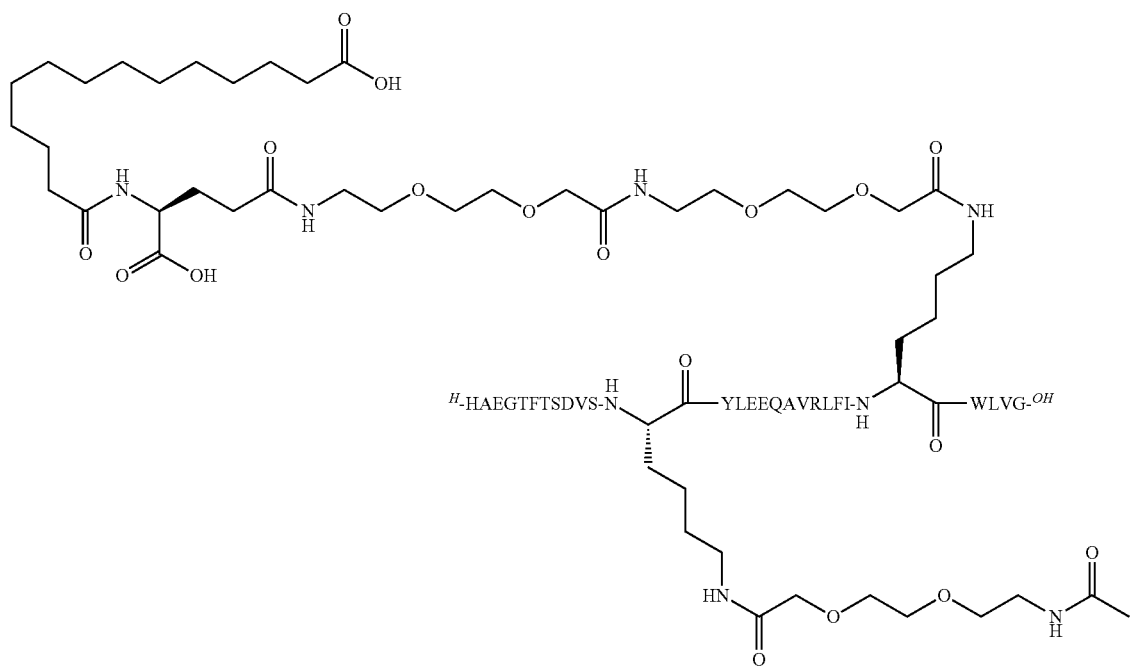

-continued
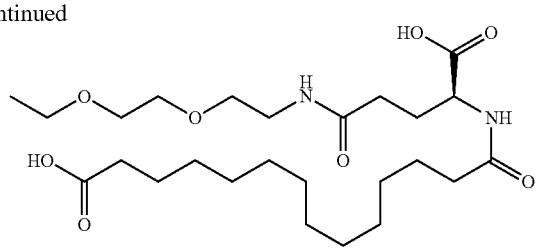
where the amino acid sequence is that of SEQ ID NO: 40,

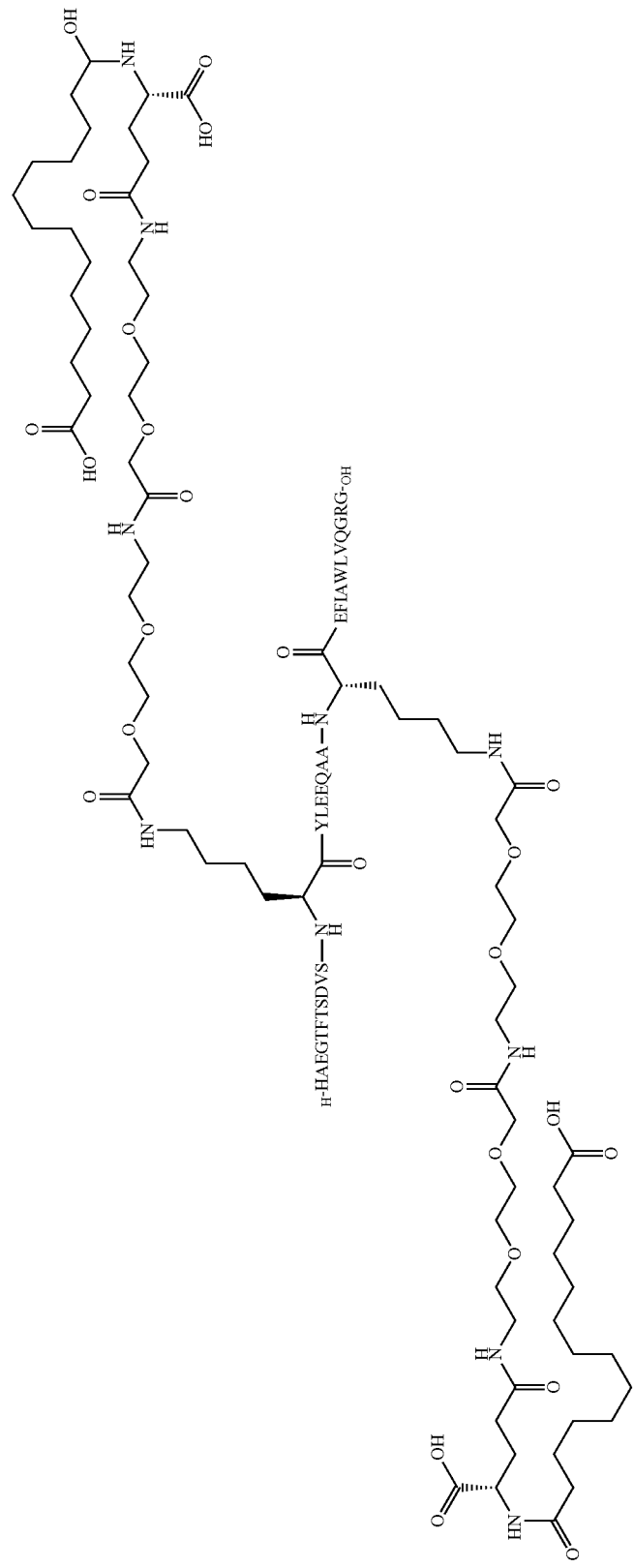
Chem. 73 where the amino acid sequence is that of SEQ ID NO:32,

Chem. 74
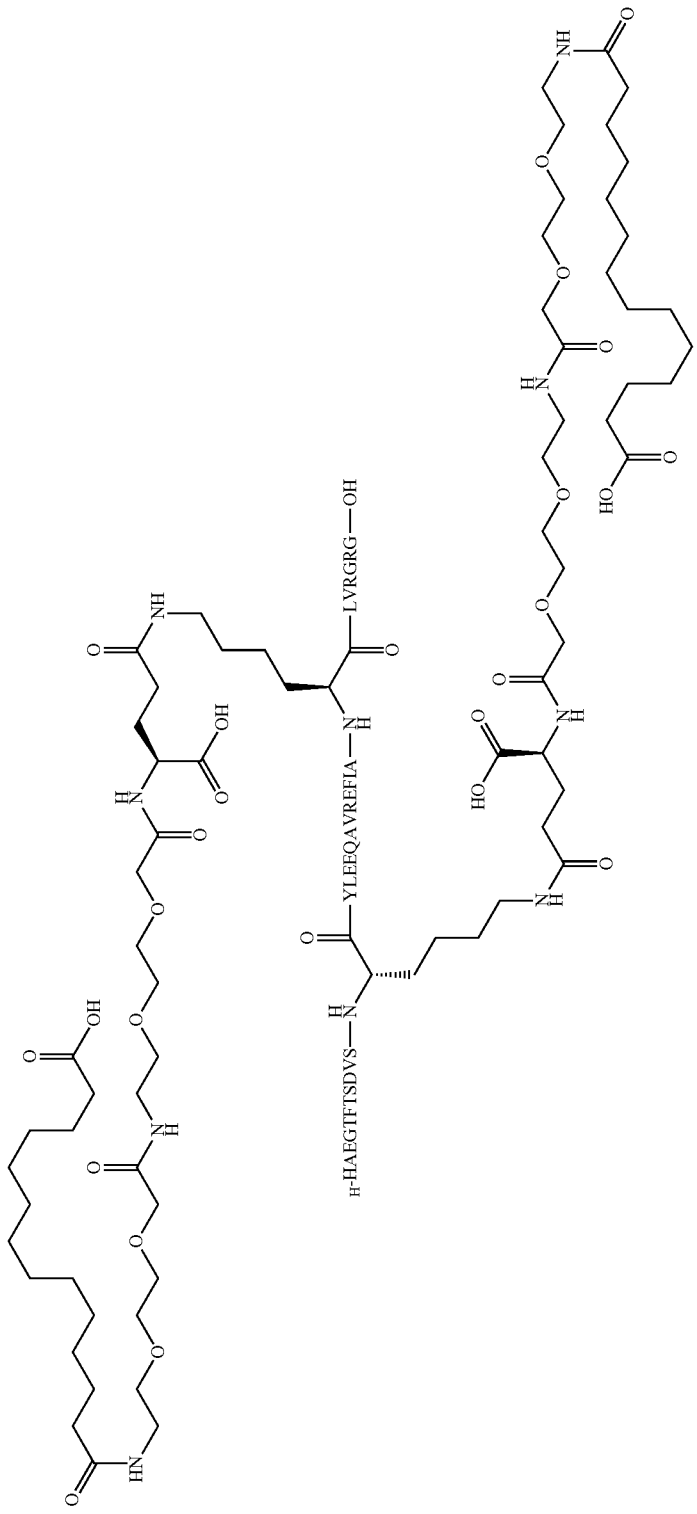

where the amino acid sequence is that of SEQ ID NO: 10,
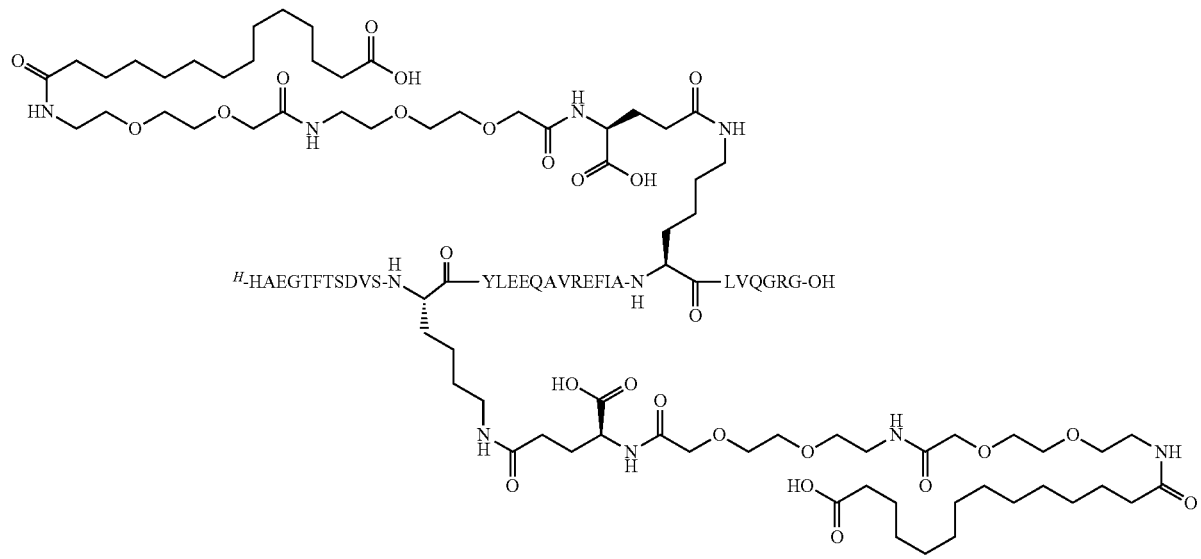
Chem. 75
where the amino acid sequence is that of SEQ ID NO: 11,
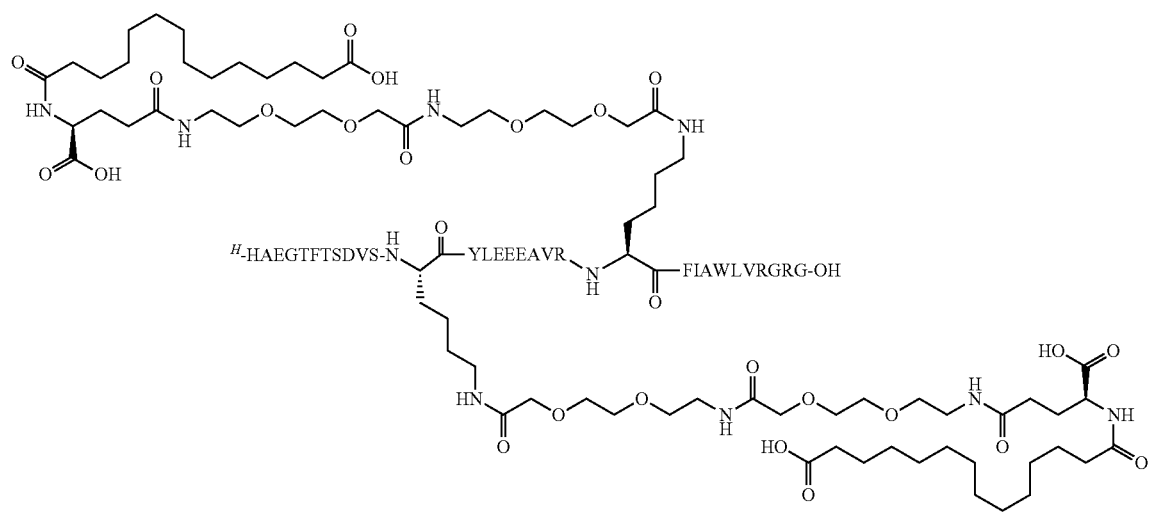
Chem. 76
where the amino acid sequence is that of SEQ ID NO: 41, Chem. 77
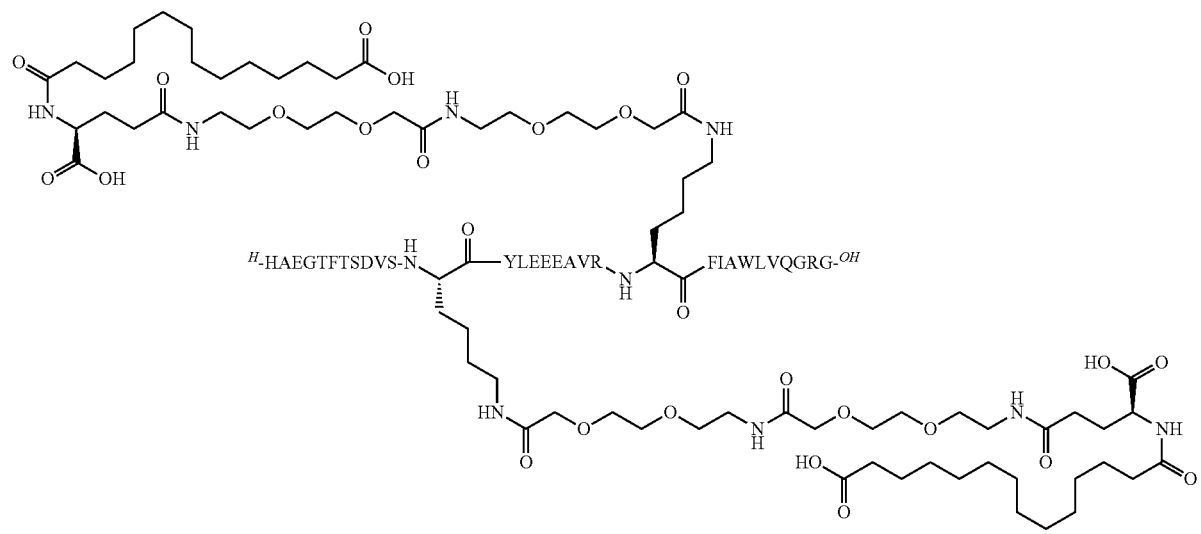
where the amino acid sequence is that of SEQ ID NO: 42,
Chem. 78
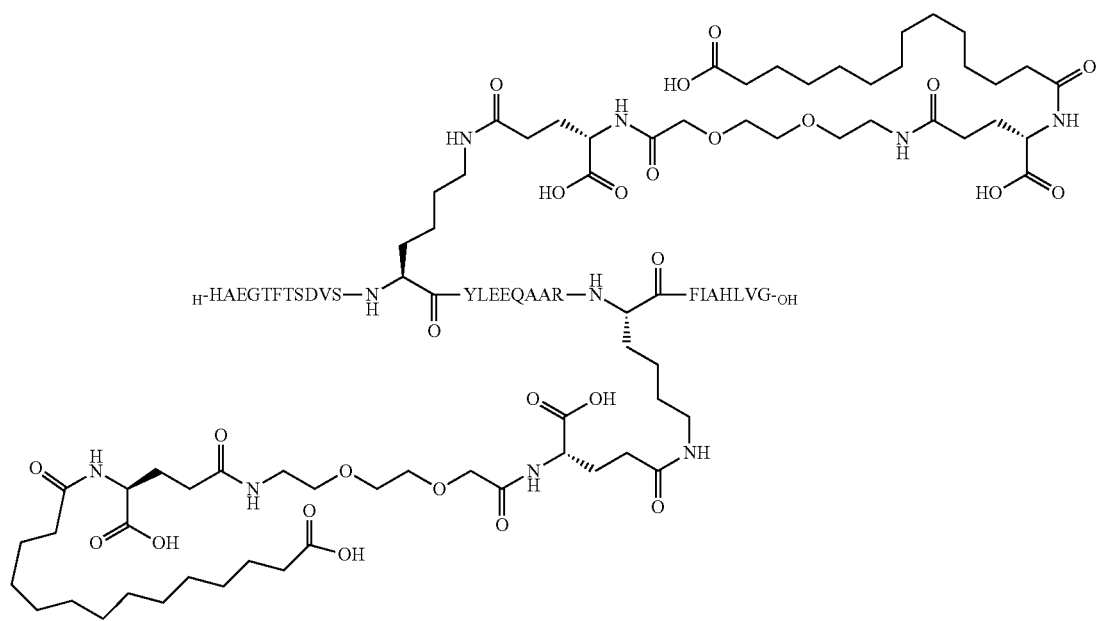
where the amino acid sequence is that of SEQ ID NO: 27, Chem. 79
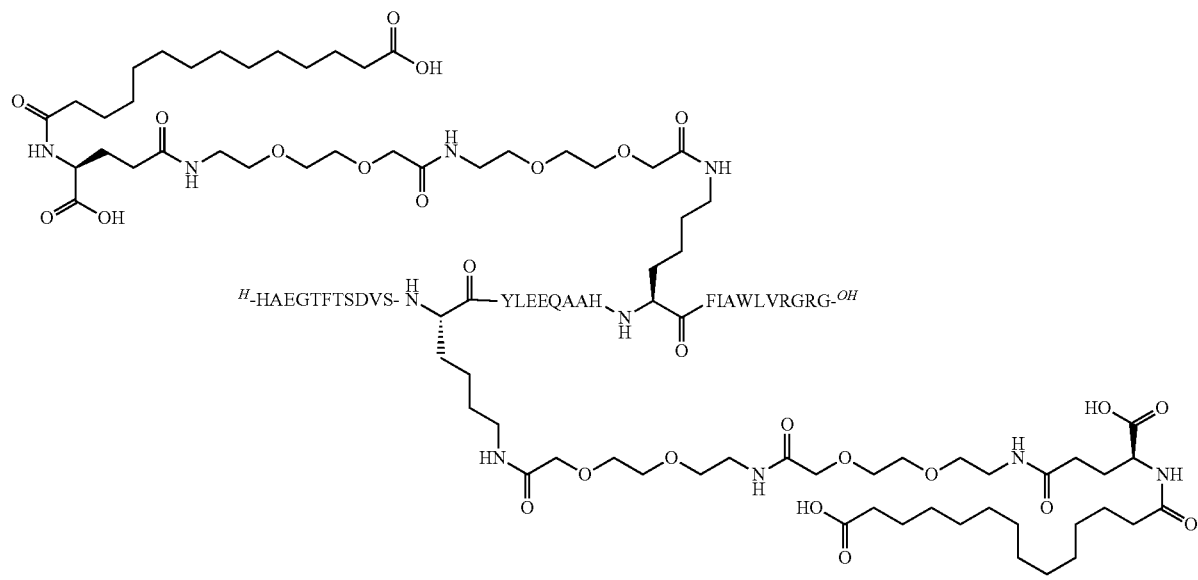
where the amino acid sequence is that of SEQ ID NO: 43,
Chem. 80
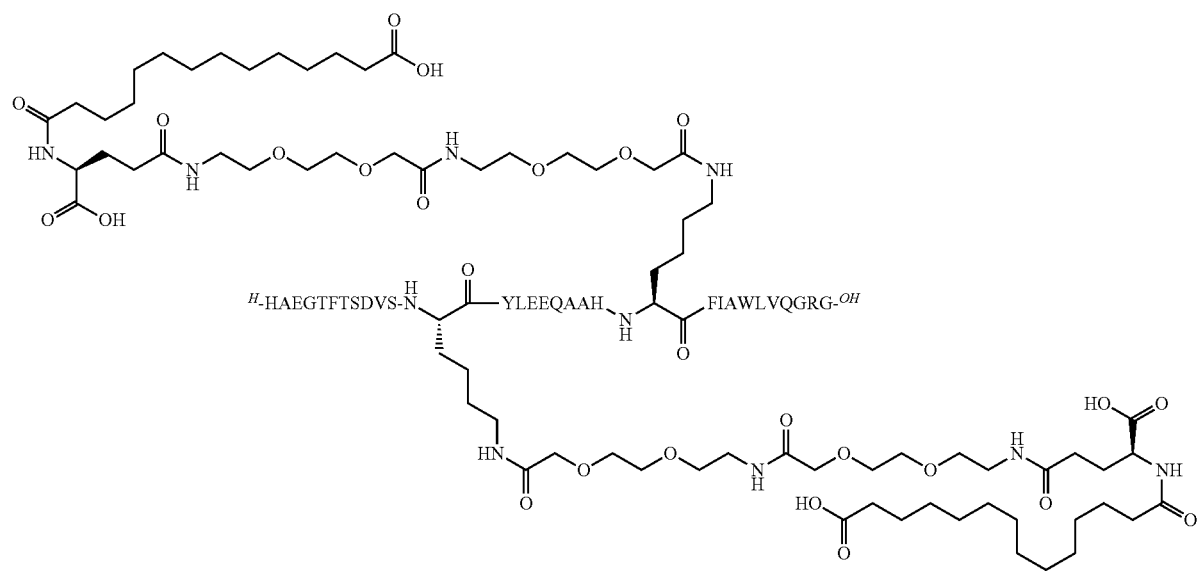
where the amino acid sequence is that of SEQ ID NO: 30, Chem. 81
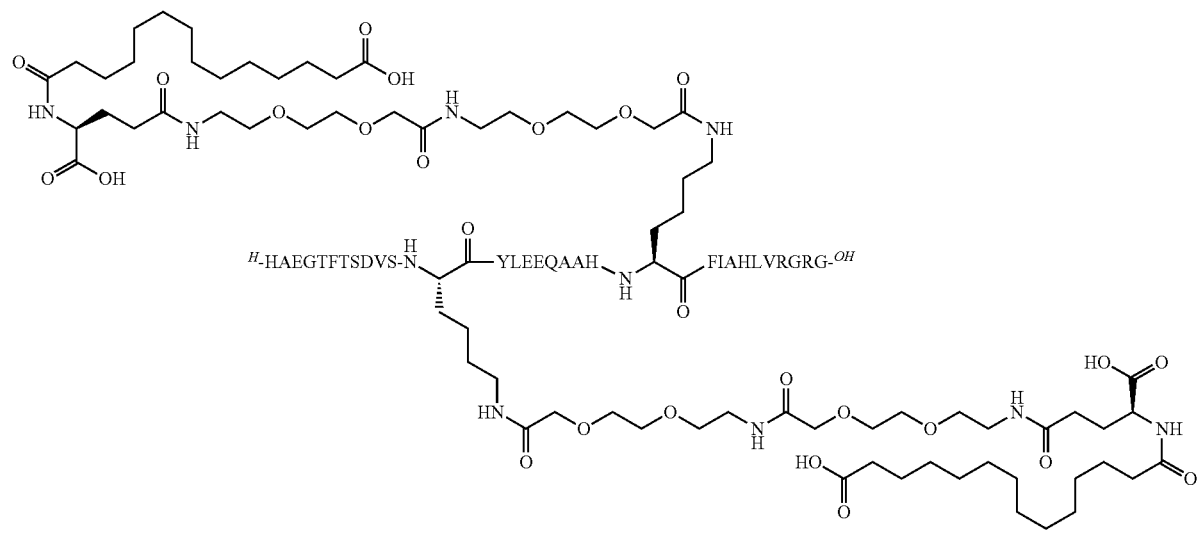
where the amino acid sequence is that of SEQ ID NO: 44,
Chem. 82
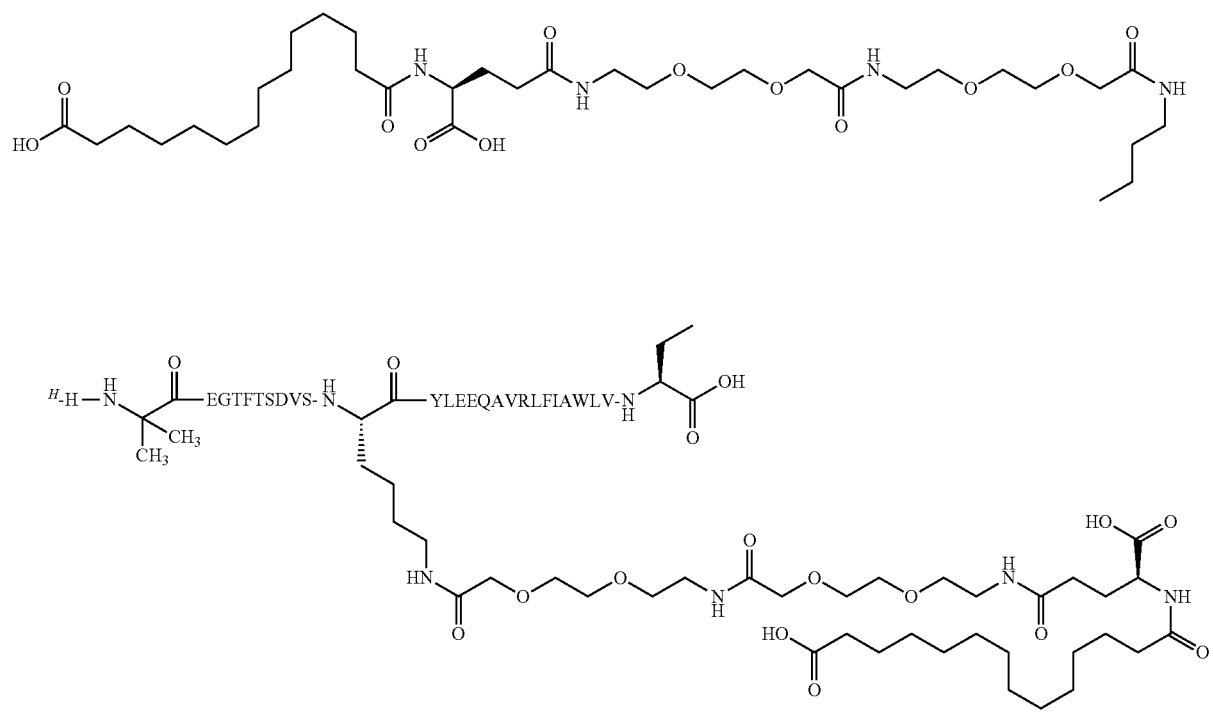
where the amino acid sequence is that of SEQ ID NO: 45, Chem. 83
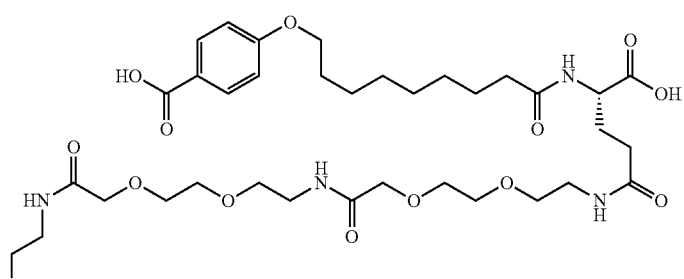
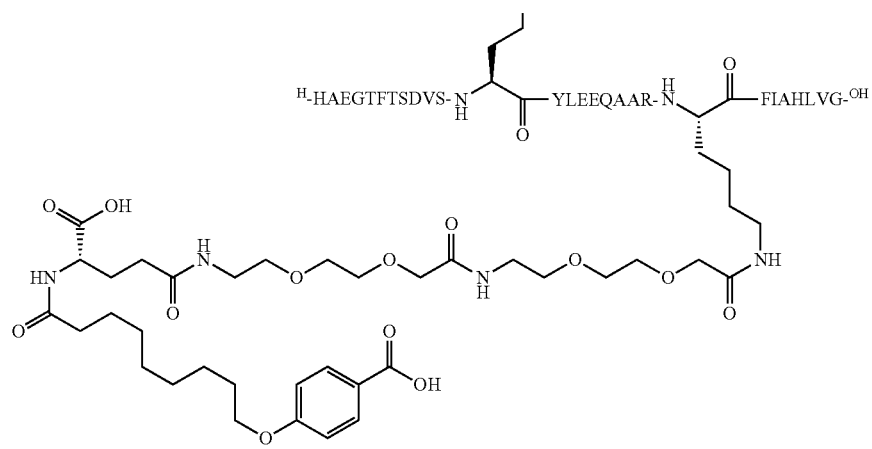
where the amino acid sequence is that of SEQ ID NO: 27,
Chem. 84
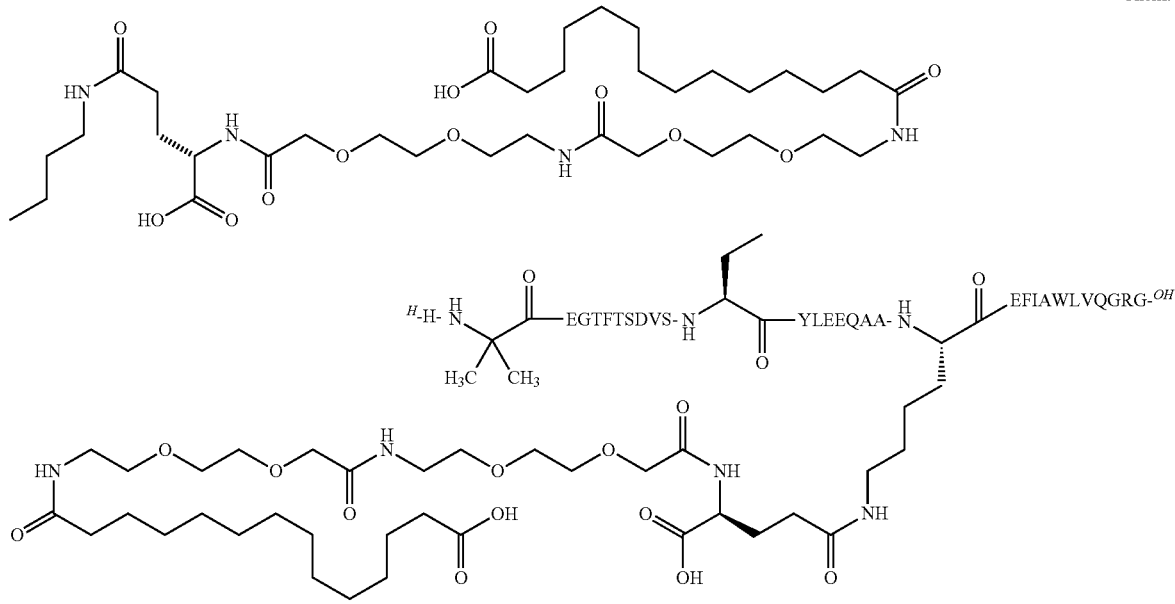
where the amino acid sequence is that of SEQ ID NO: 7,

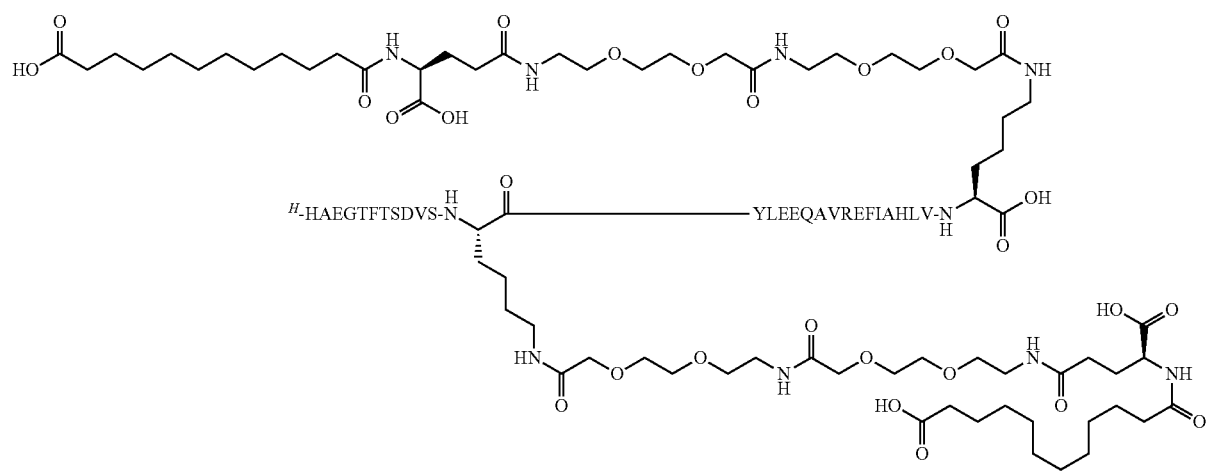
where the amino acid sequence is that of SEQ ID NO: 46,
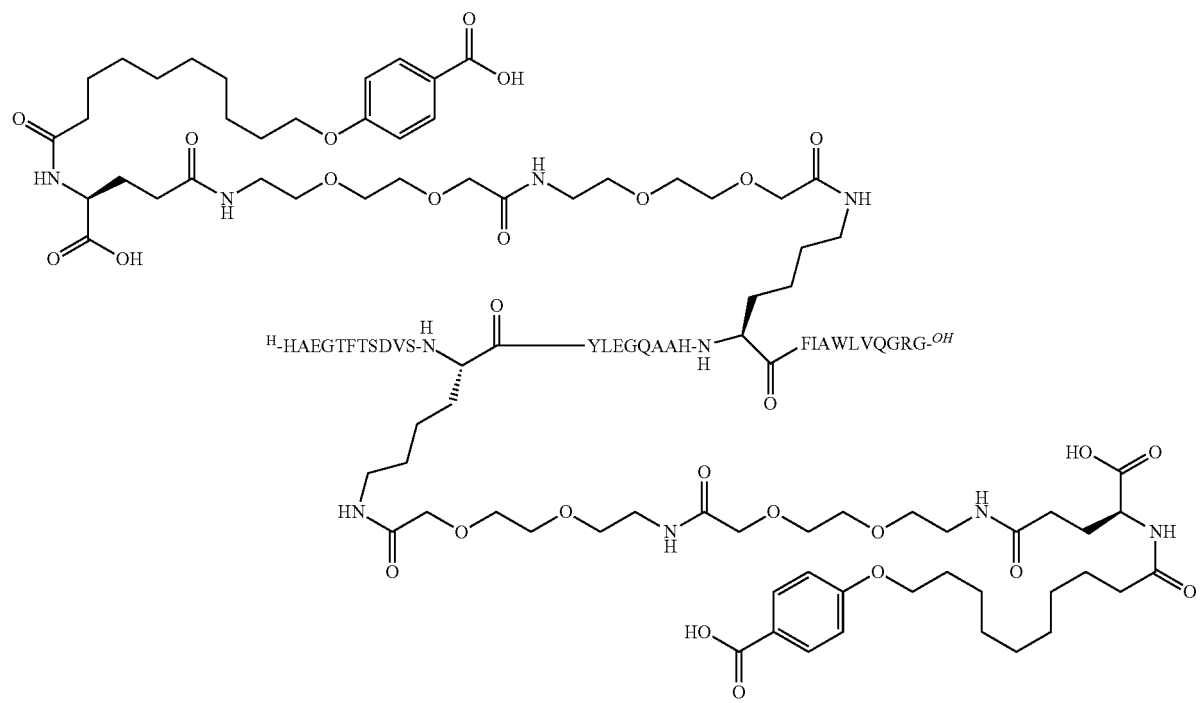
where the amino acid sequence is that of SEQ ID NO: 47, Chem. 87
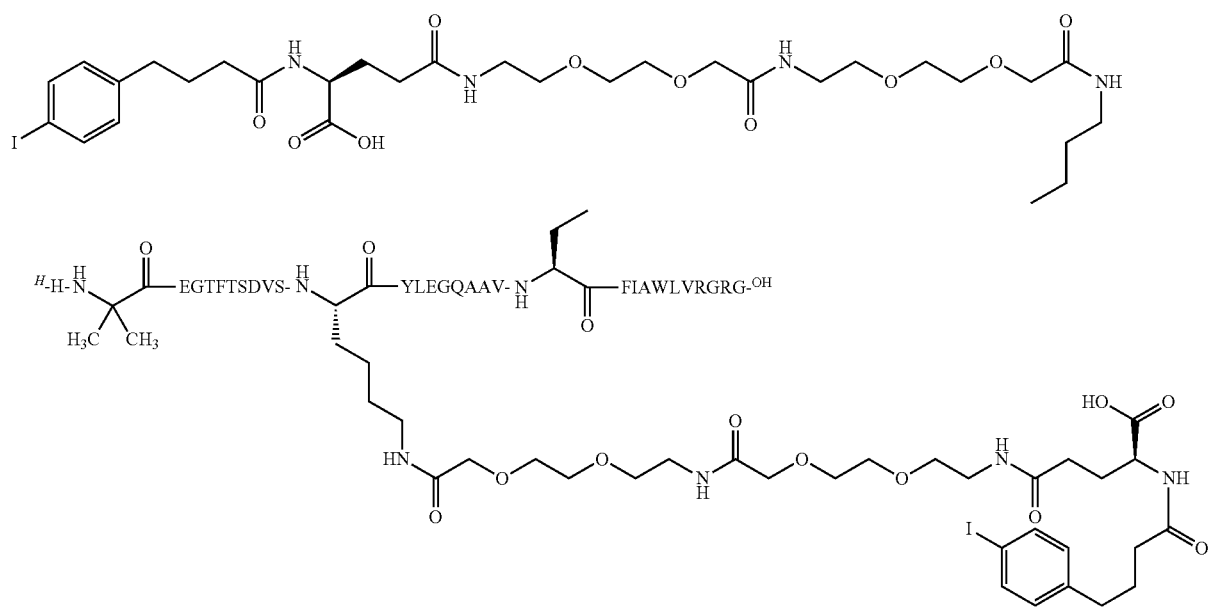
where the amino acid sequence is that of SEQ ID NO: 6,
Chem. 88
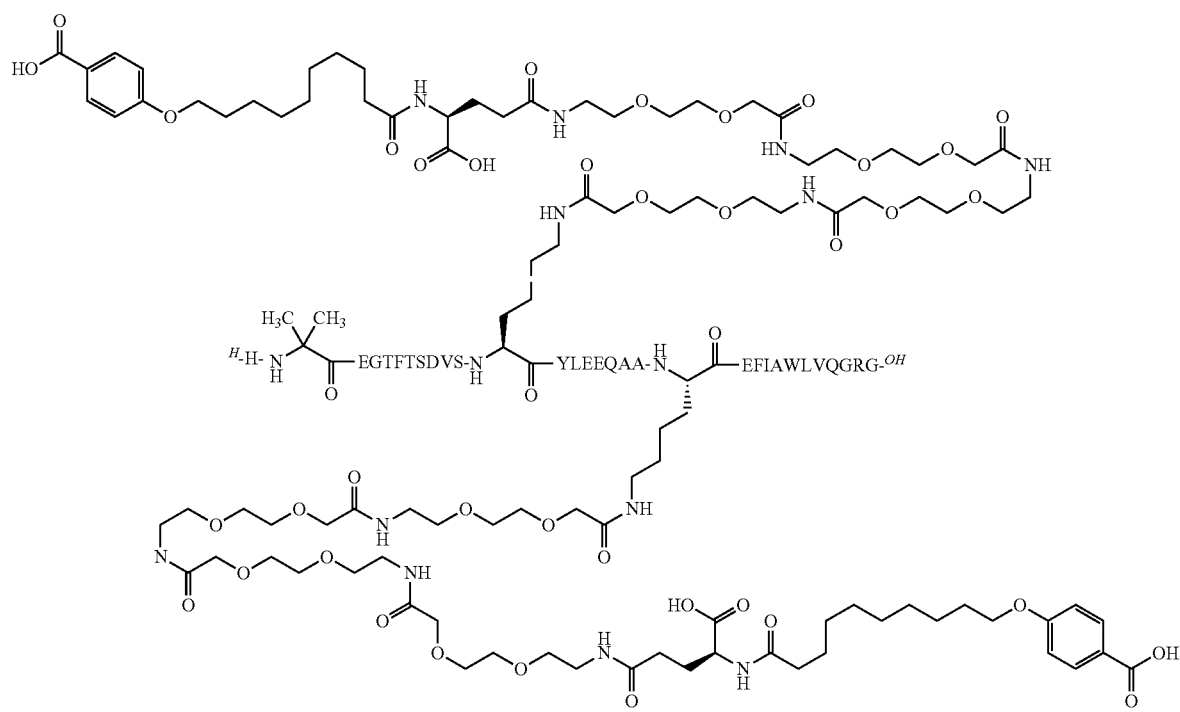
where the amino acid sequence is that of SEQ ID NO: 7, Chem. 89
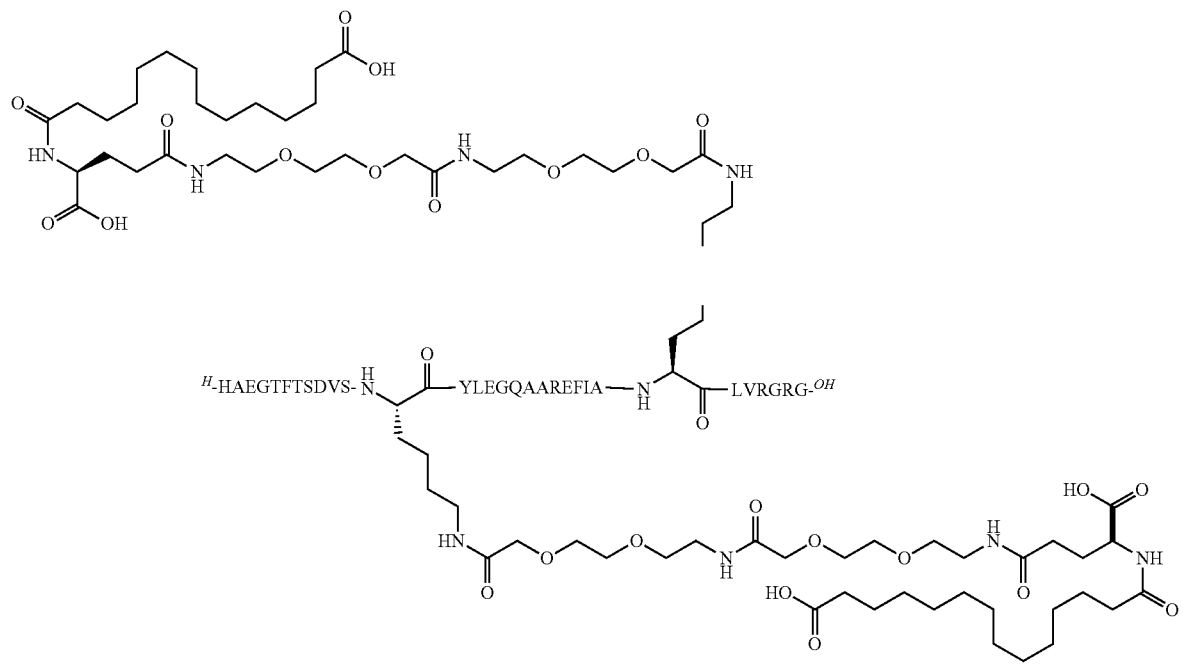
where the amino acid sequence is that of SEQ ID NO: 48,
Chem. 90
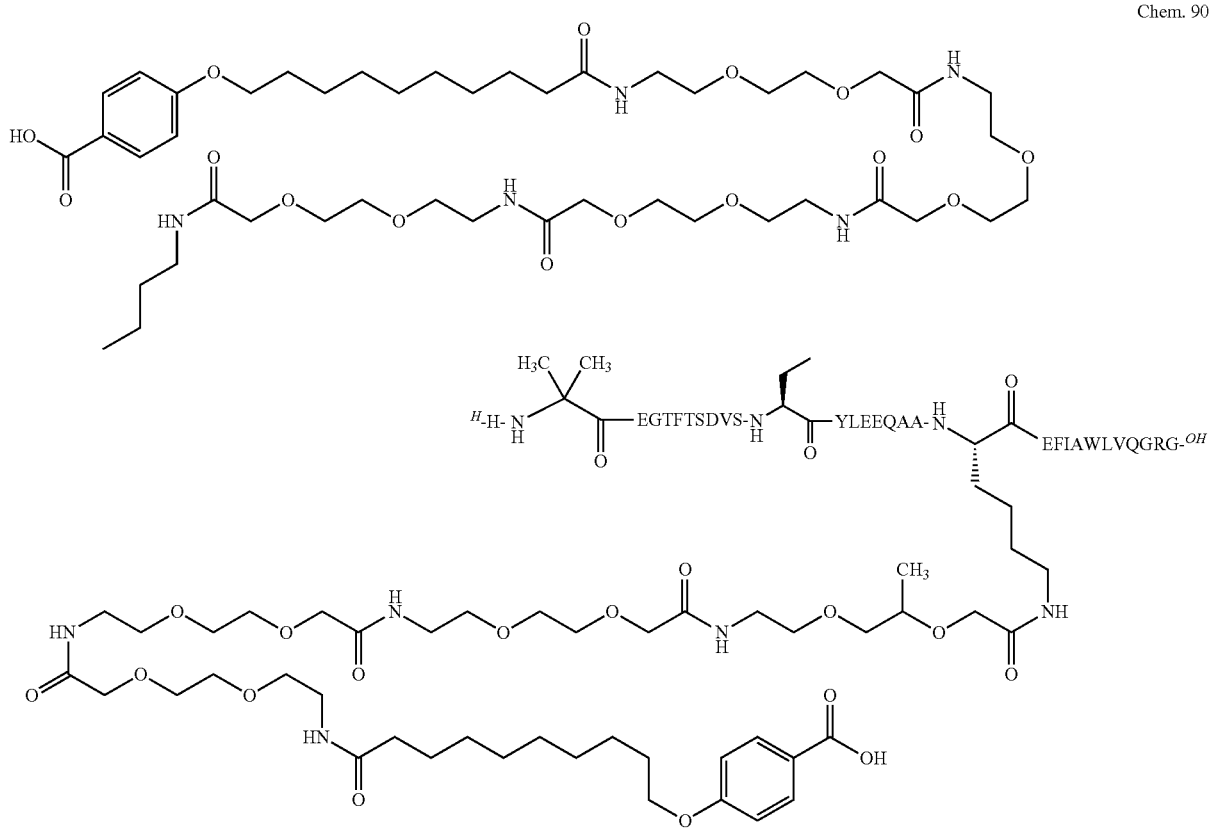
where the amino acid sequence is that of SEQ ID NO: 7, Chem. 91
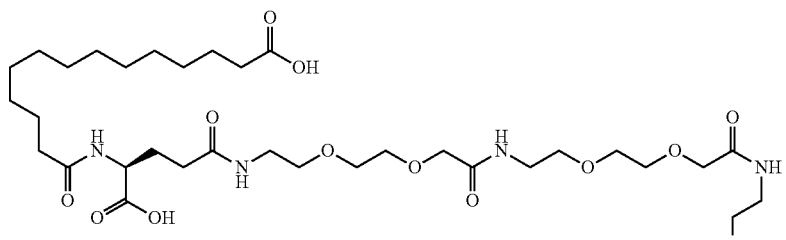
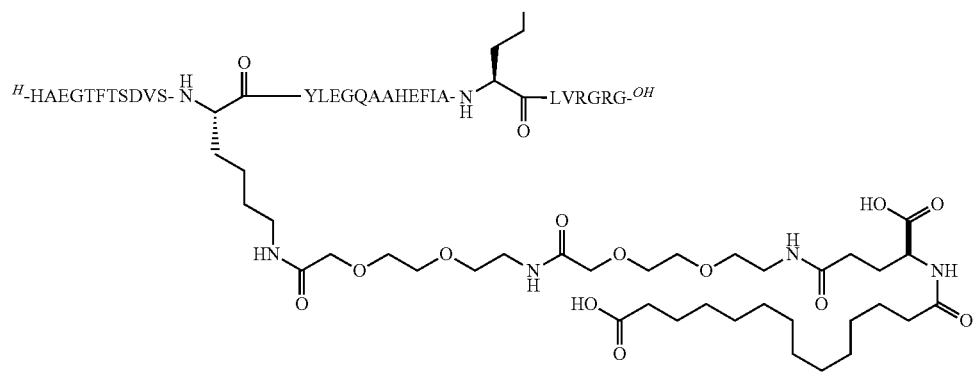
where the amino acid sequence is that of SEQ ID NO: 48,
Chem. 92
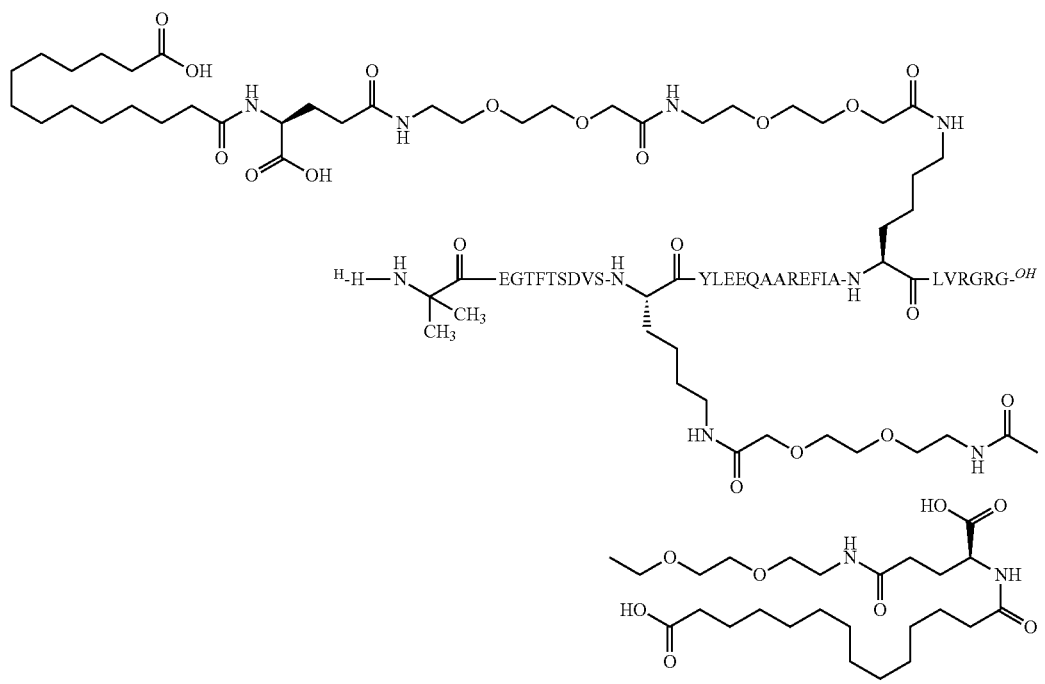
where the amino acid sequence is that of SEQ ID NO: 8, Chem. 93
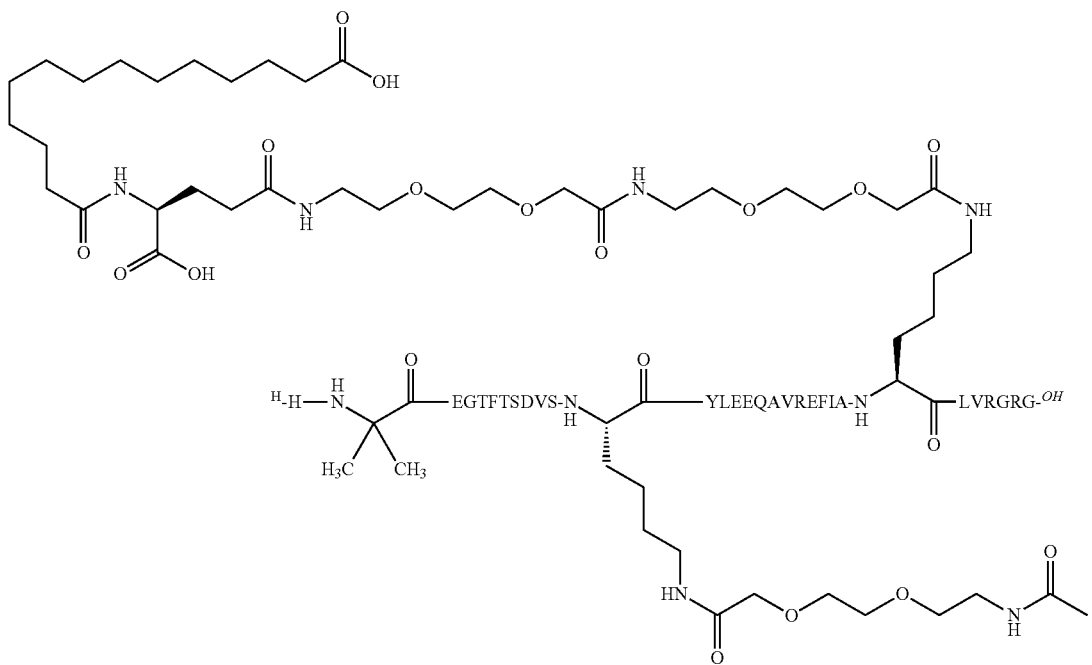
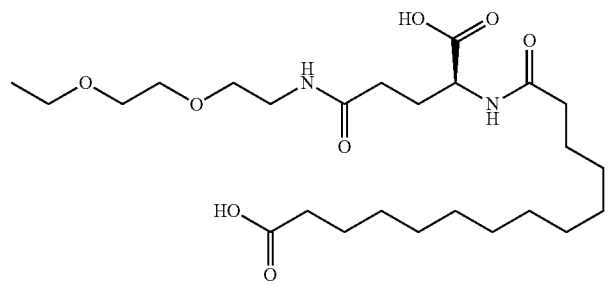
where the amino acid sequence is that of SEQ ID NO: 12,
Chem. 94
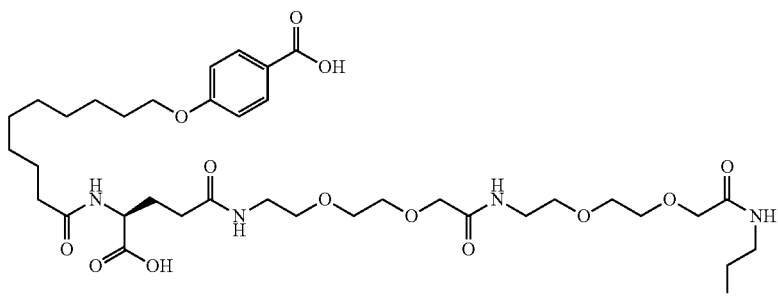

-continued
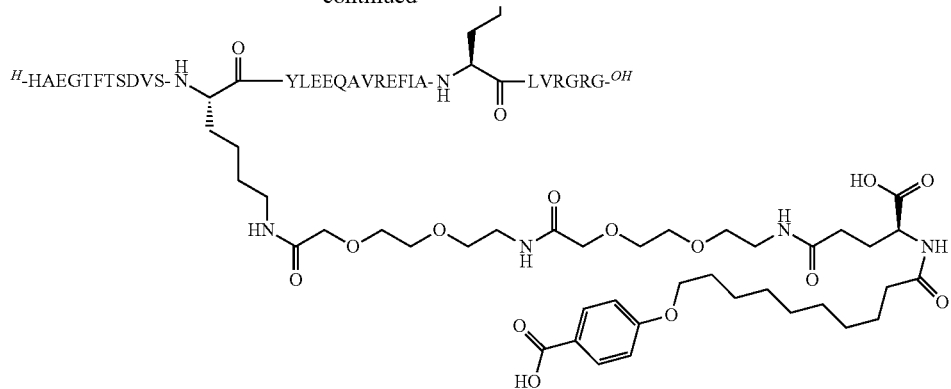
where the amino acid sequence is that of SEQ ID NO: 10,
Chem. 95
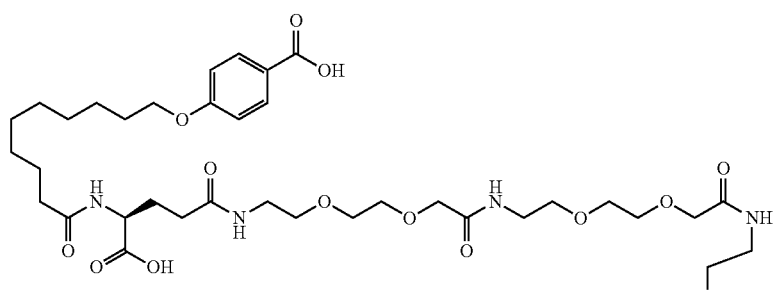
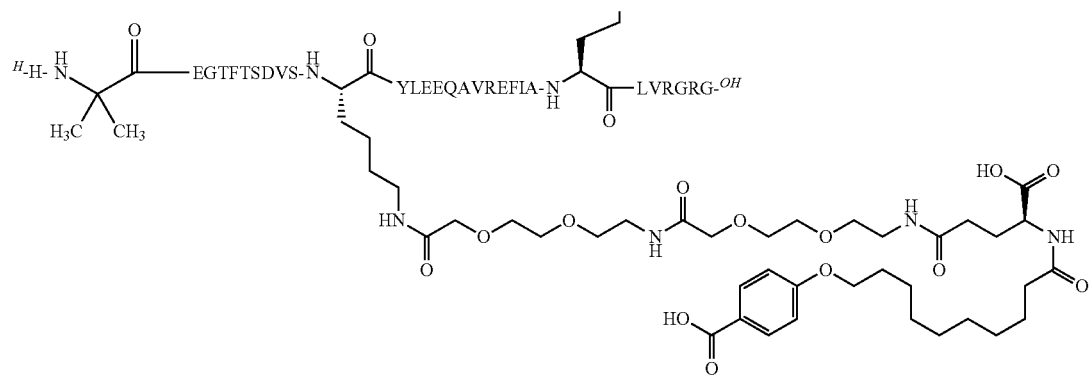
where the amino acid sequence is that of SEQ ID NO: 12, Chem. 96
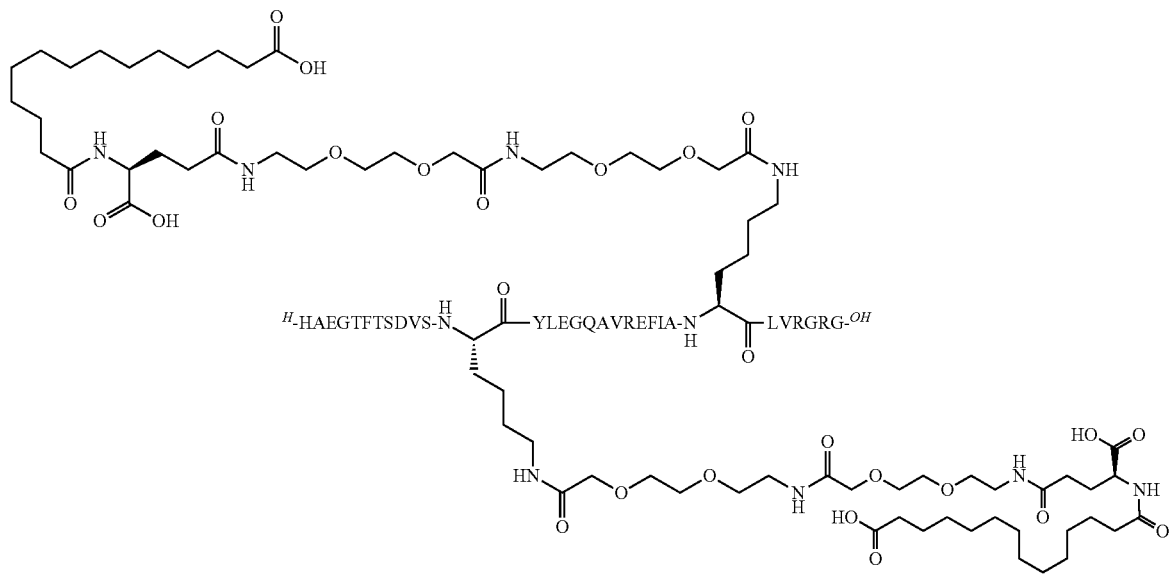
where the amino acid sequence is that of SEQ ID NO: 49,
Chem. 97
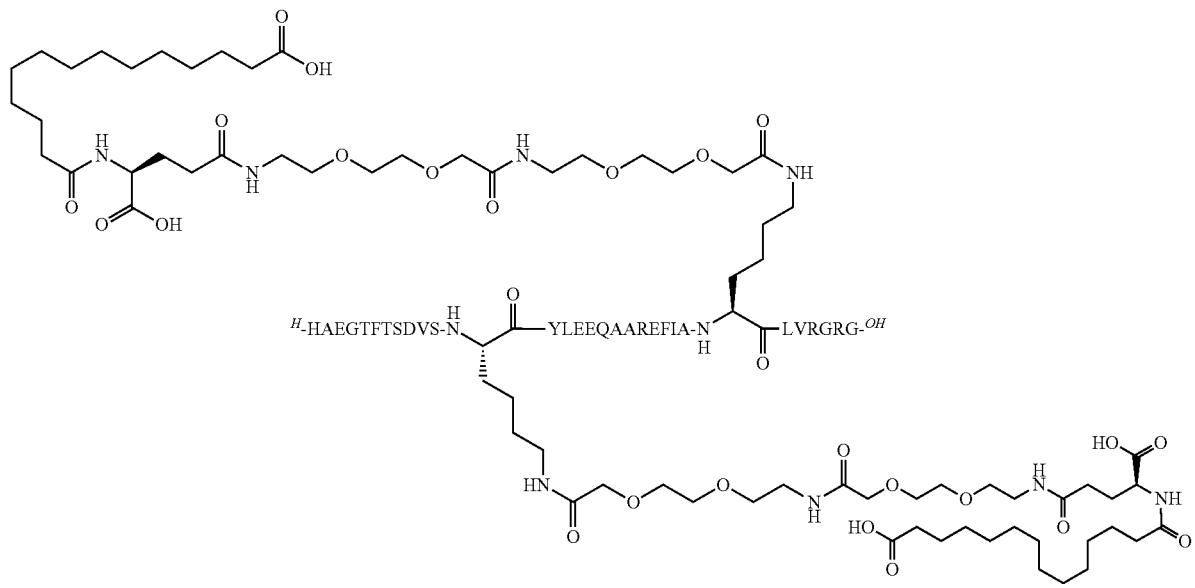
where the amino acid sequence is that of SEQ ID NO: 50,

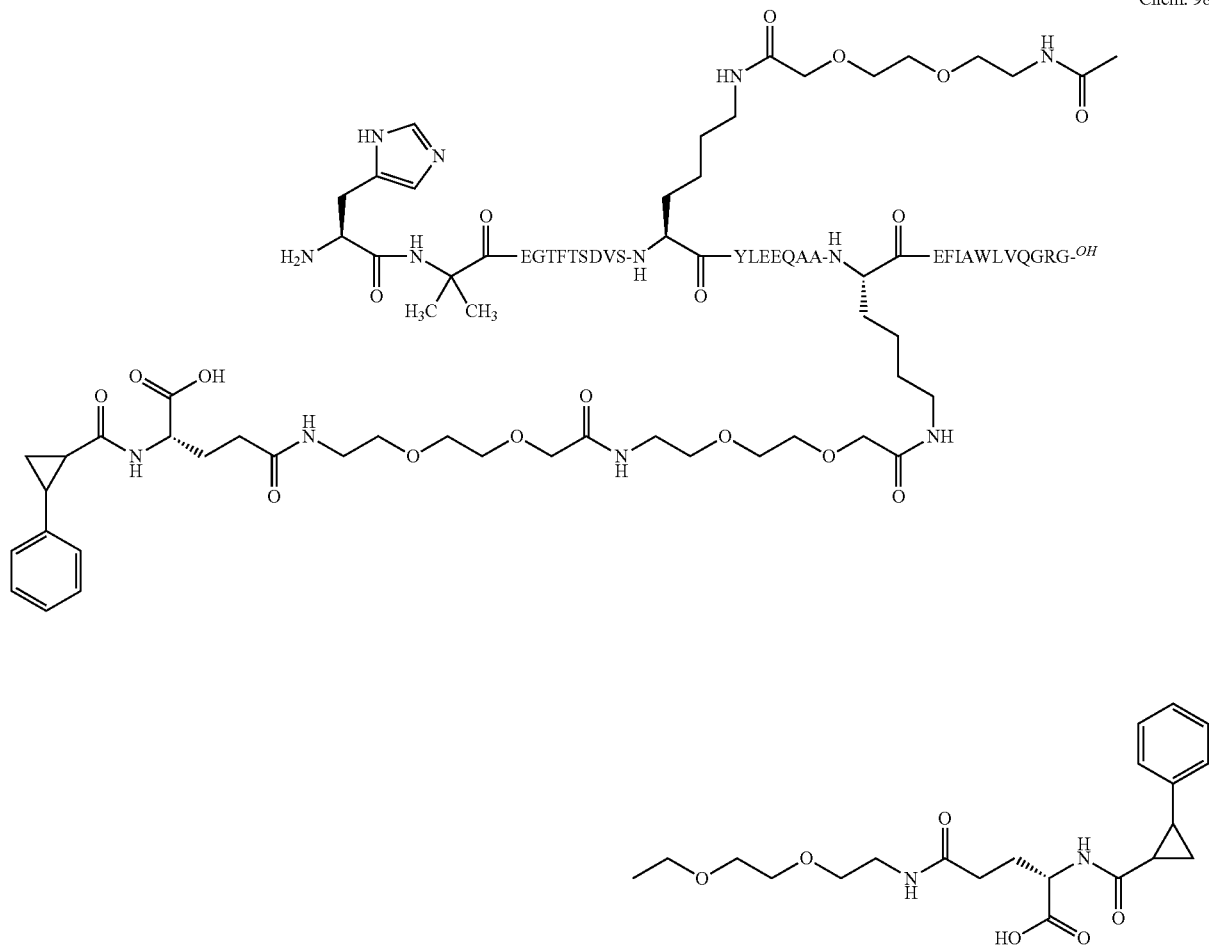
Chem. 98
where the amino acid sequence is that of SEQ ID NO: 7,
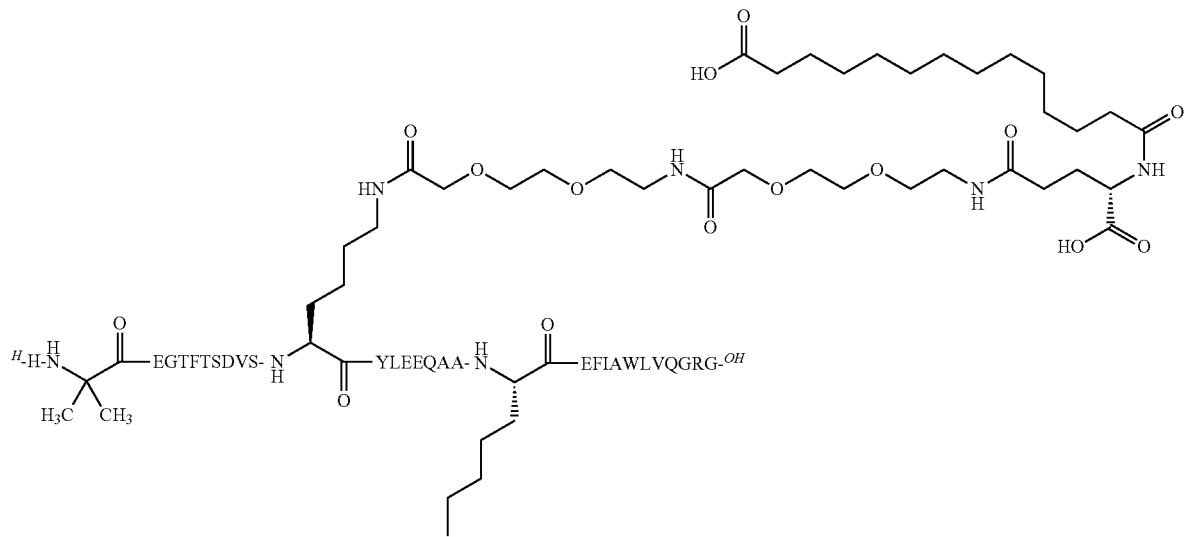
Chem. 99

-continued
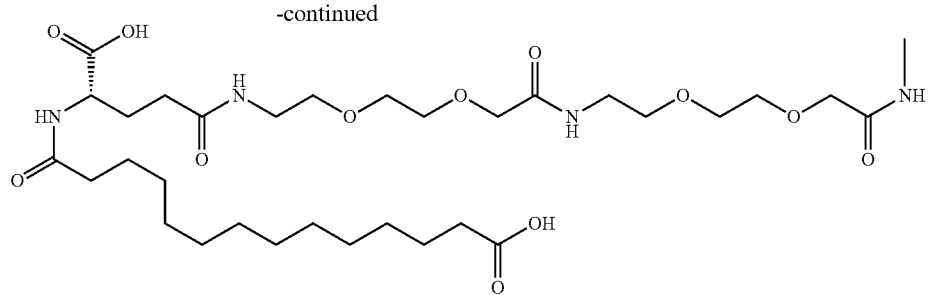
where the amino acid sequence is that of SEQ ID NO: 7,
Chem. 100
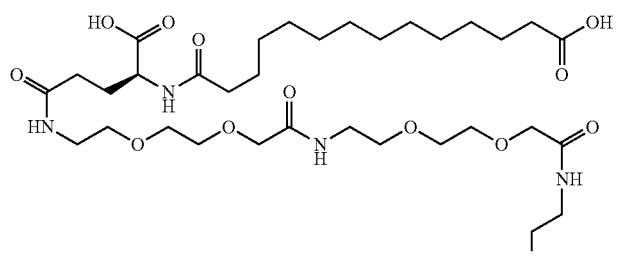
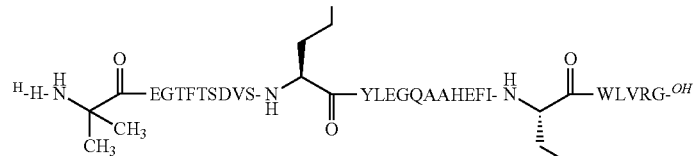
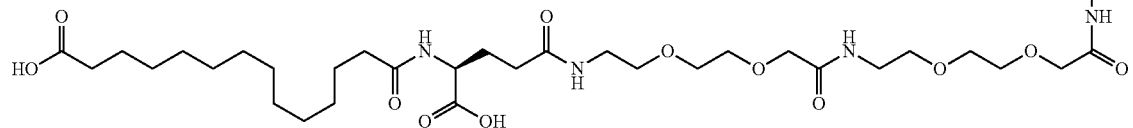
where the amino acid sequence is that of SEQ ID NO: 51,
Chem. 101
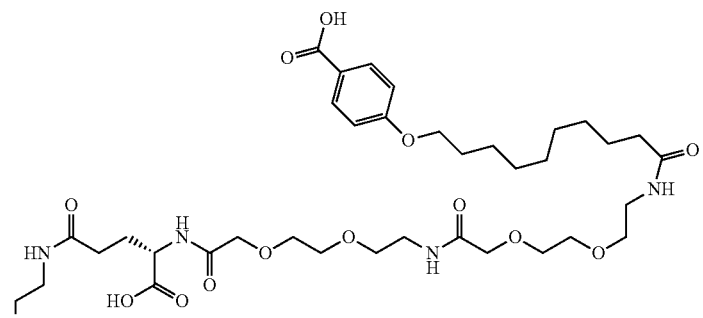

-continued
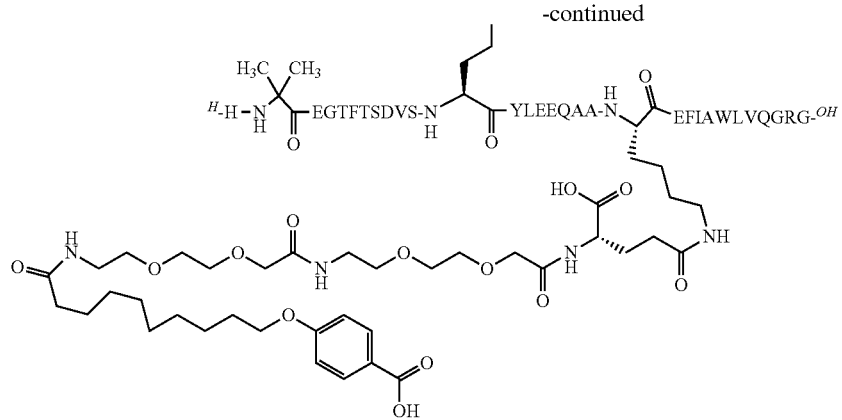
where the amino acid sequence is that of SEQ ID NO: 7,

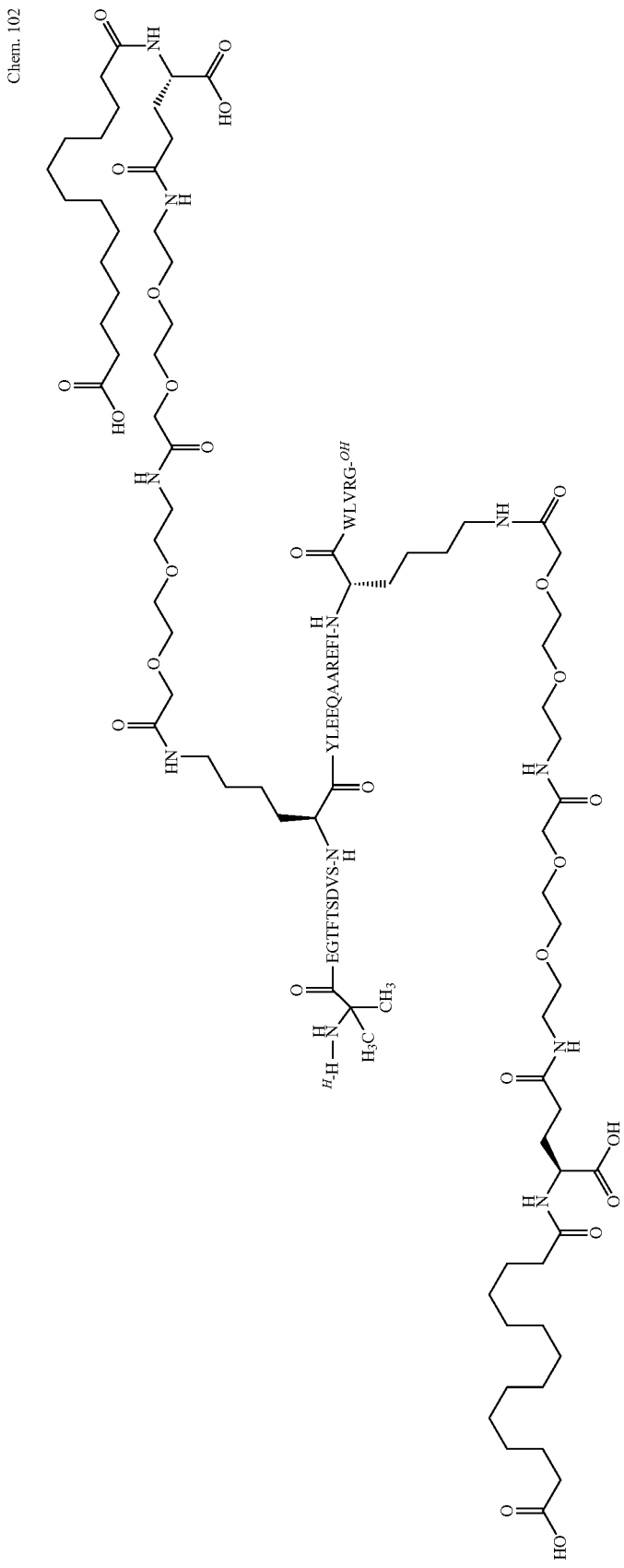

where the amino acid sequence is that of SEQ ID NO: 38,
Chem. 103
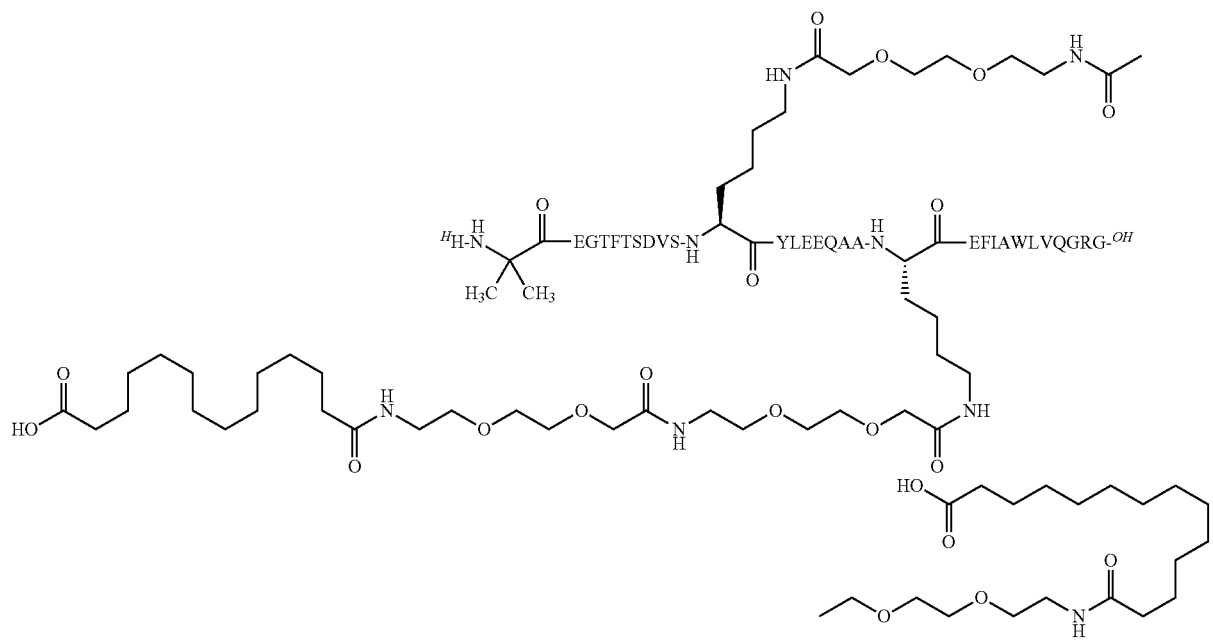
where the amino acid sequence is that of SEQ ID NO: 7,
Chem. 104
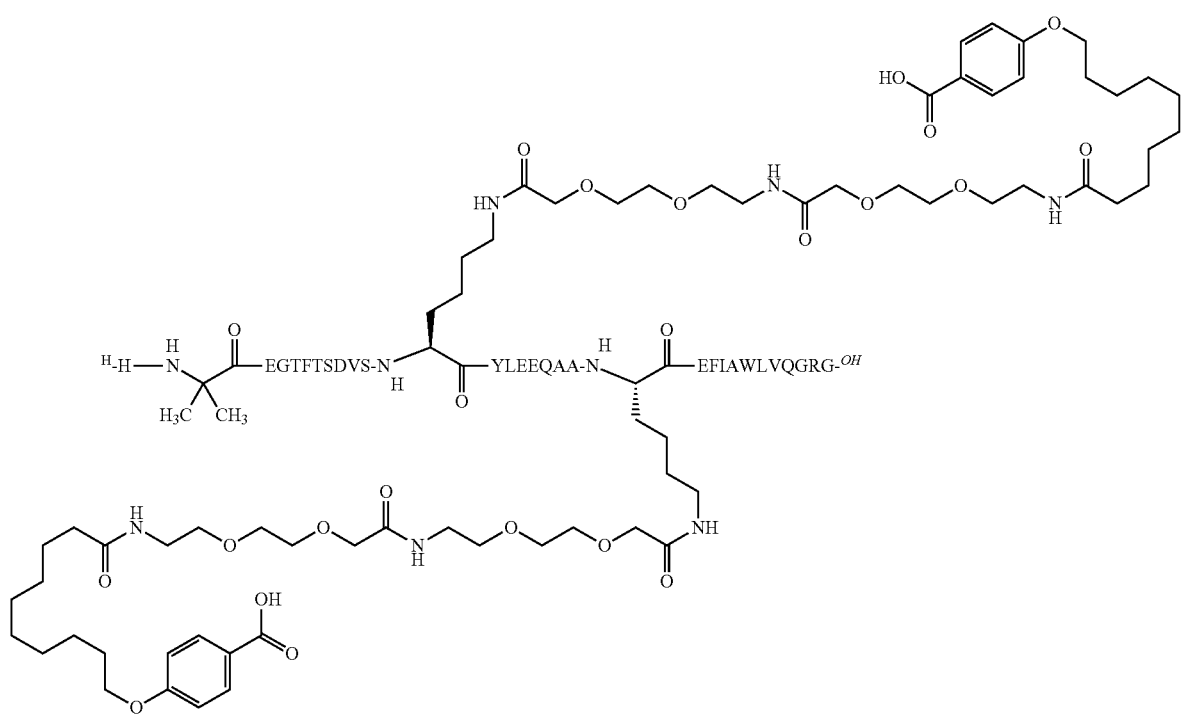
where the amino acid sequence is that of SEQ ID NO: 52, Chem. 105
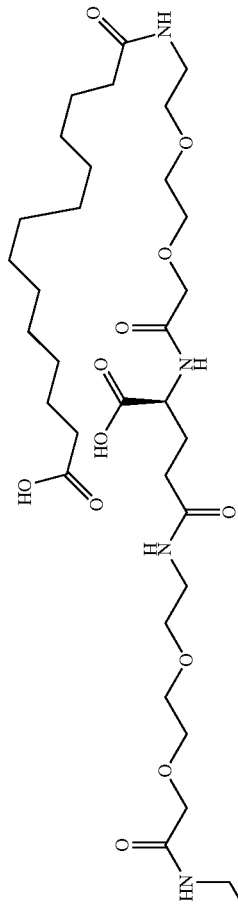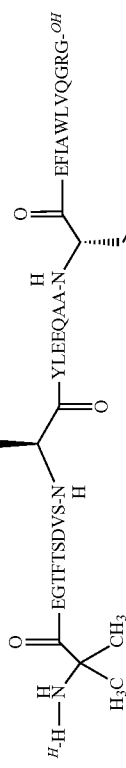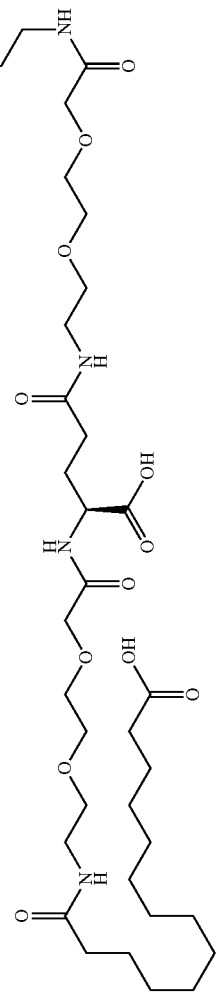

where the amino acid sequence is that of SEQ ID NO: 7,
Chem. 106
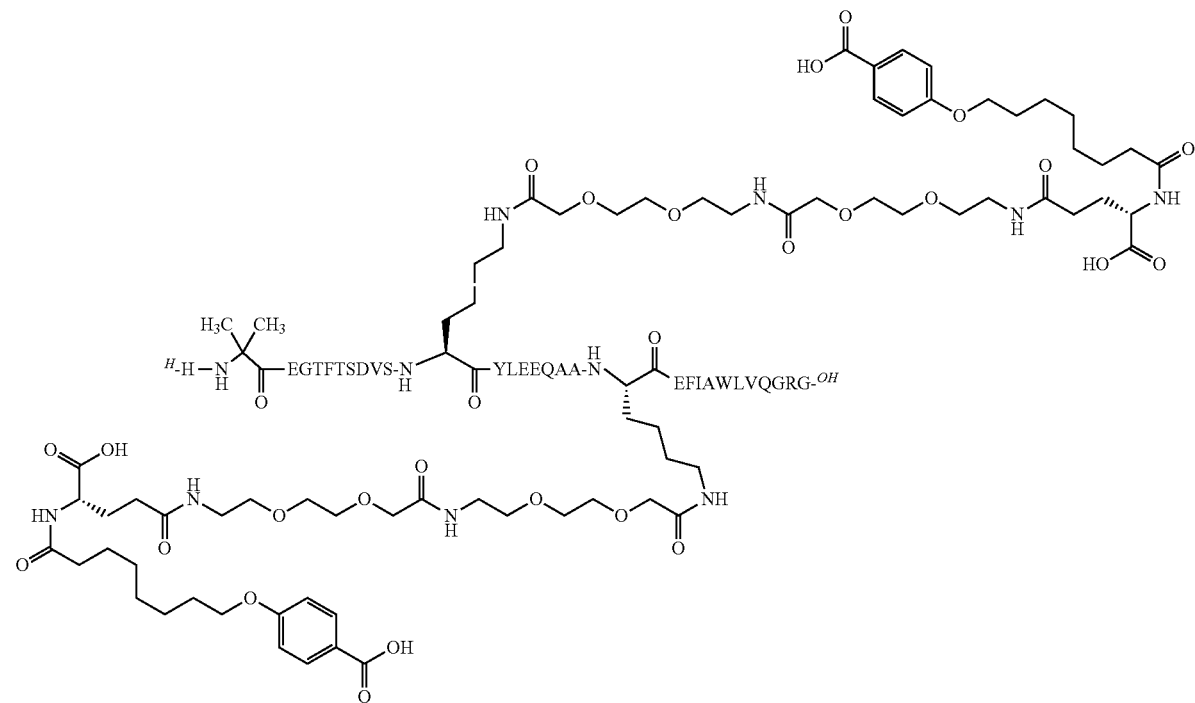
where the amino acid sequence is that of SEQ ID NO: 7,
Chem. 107
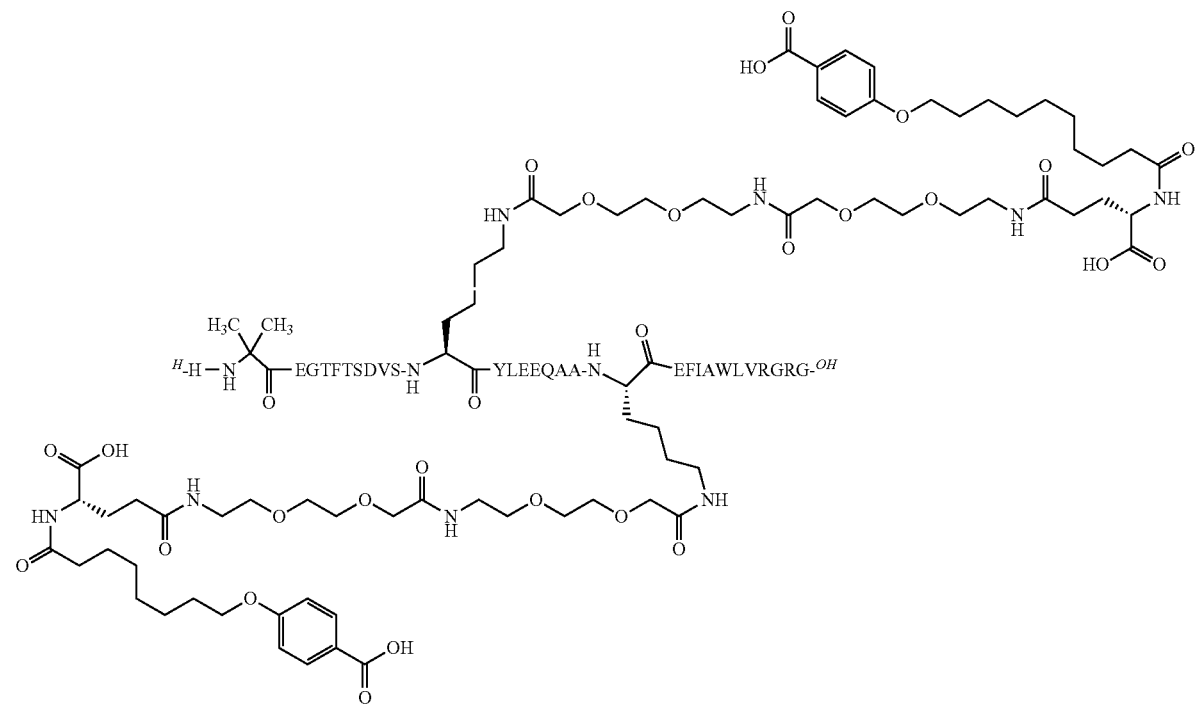
where the amino acid sequence is that of SEQ ID NO: 53,

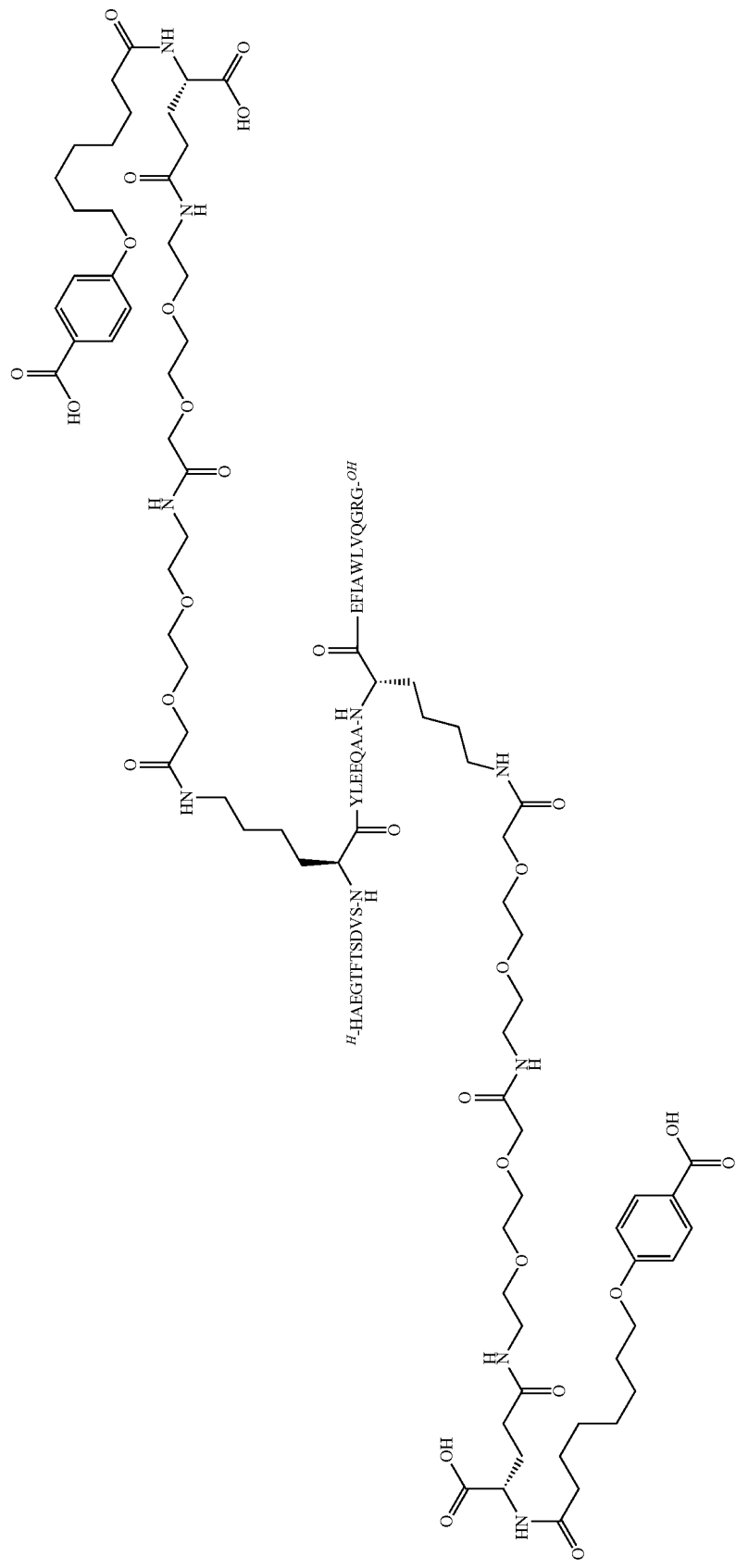

where the amino acid sequence is that of SEQ ID NO: 32,

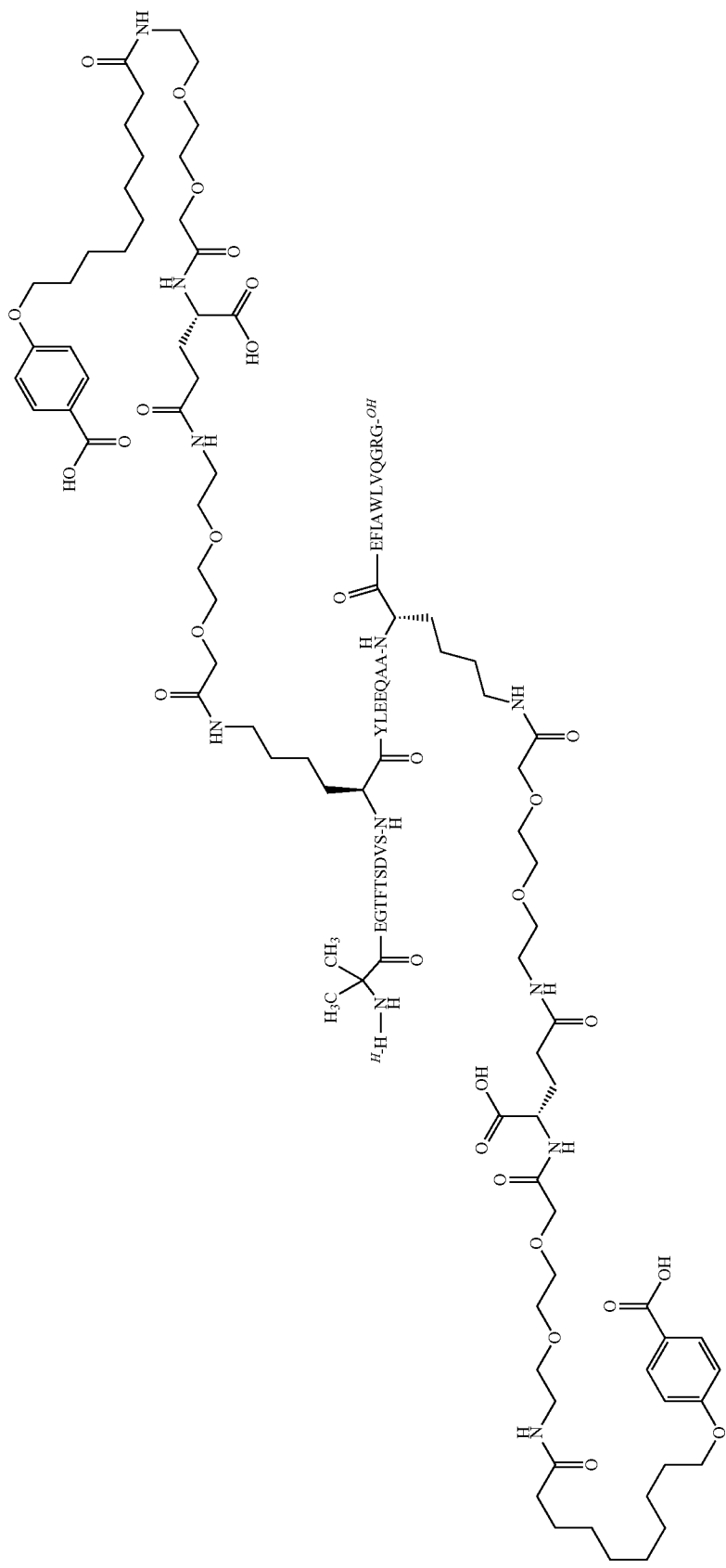

where the amino acid sequence is that of SEQ ID NO: 7,

Chem. 110
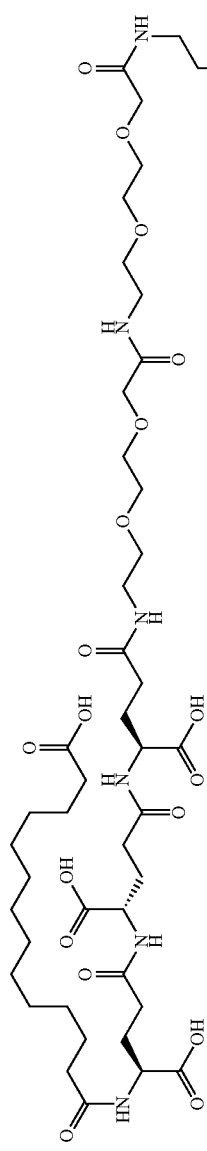
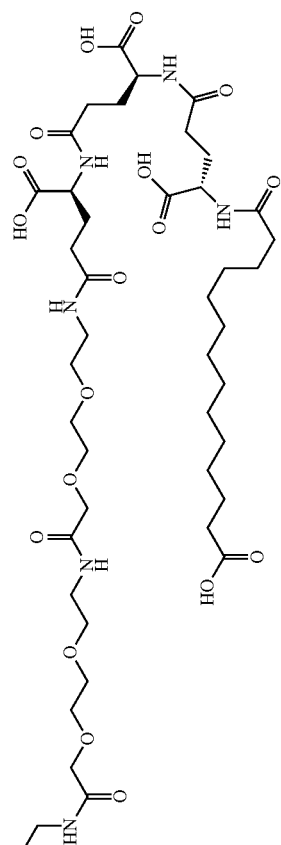

where the amino acid sequence is that of SEQ ID NO: 48,
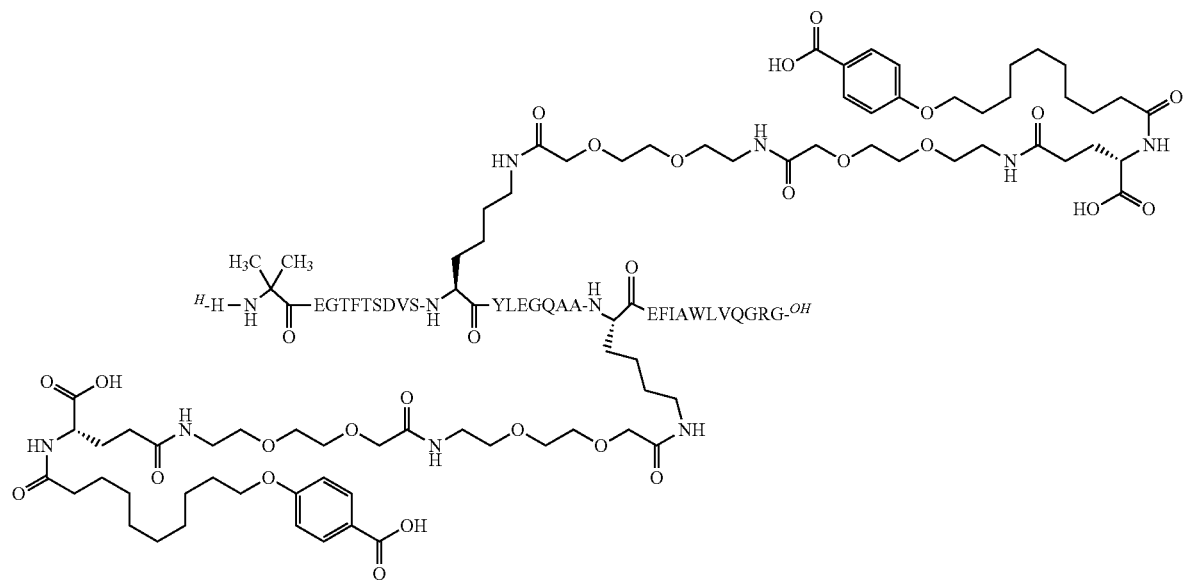
Chem. 111
where the amino acid sequence is that of SEQ ID NO: 54,
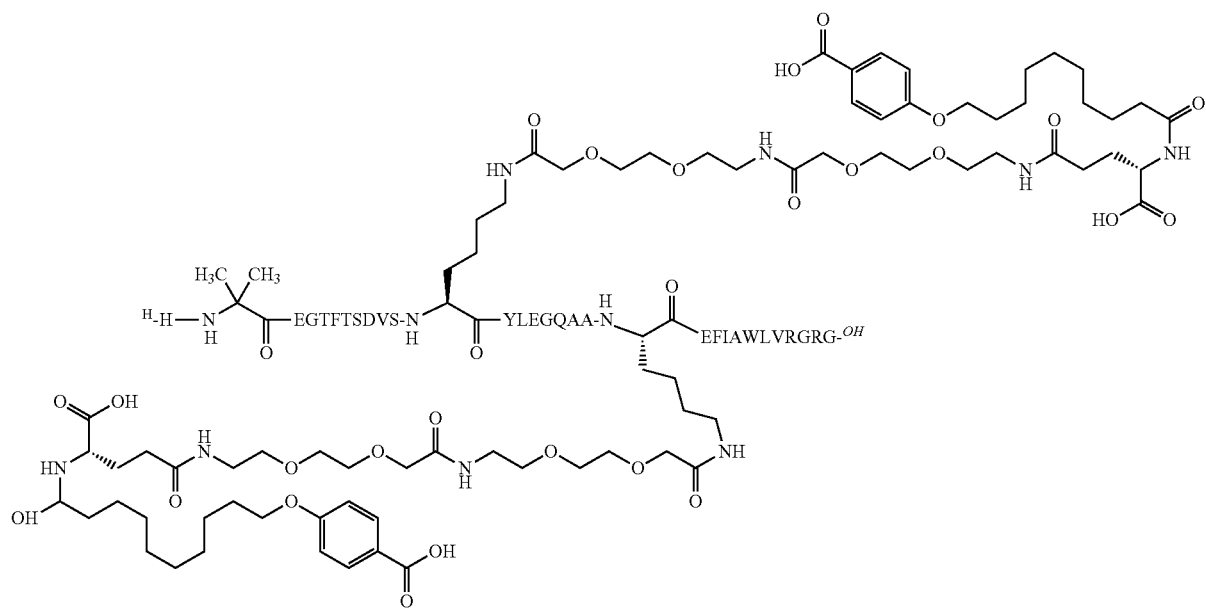
Chem. 112
where the amino acid sequence is that of SEQ ID NO: 55, Chem. 113
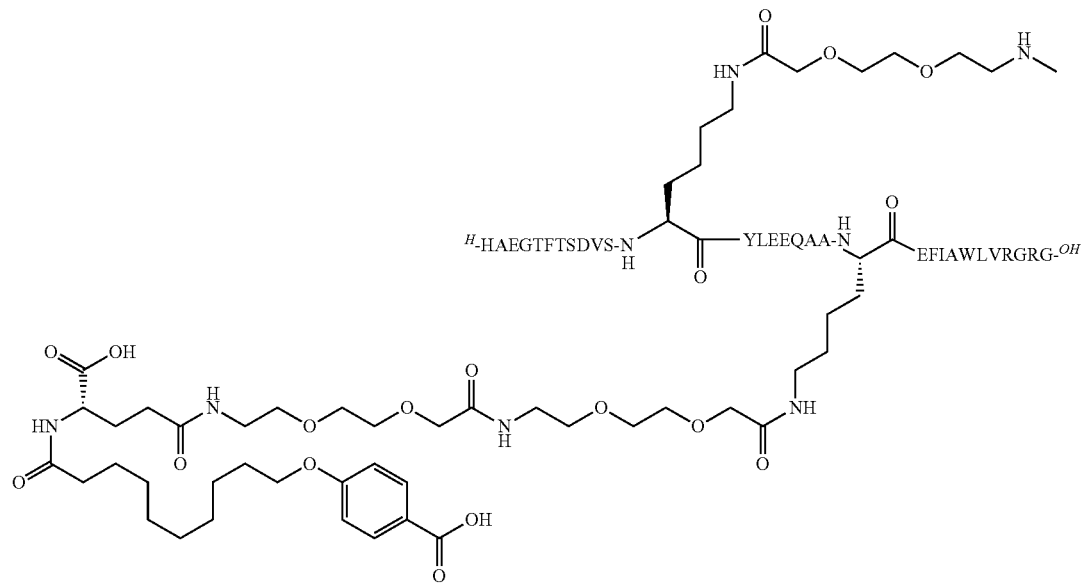
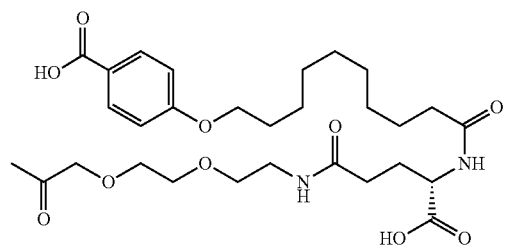
where the amino acid sequence is that of SEQ ID NO: 56,
Chem. 114
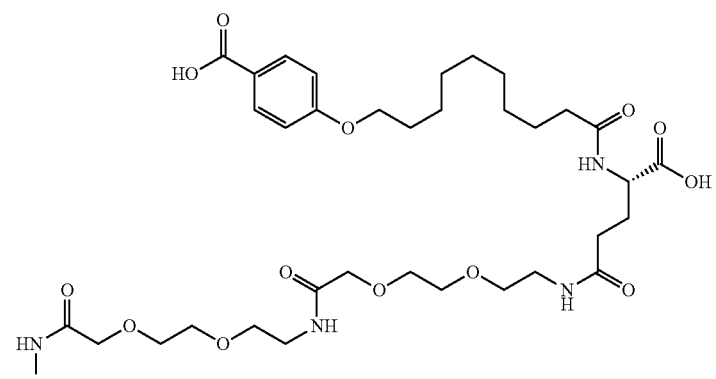

-continued
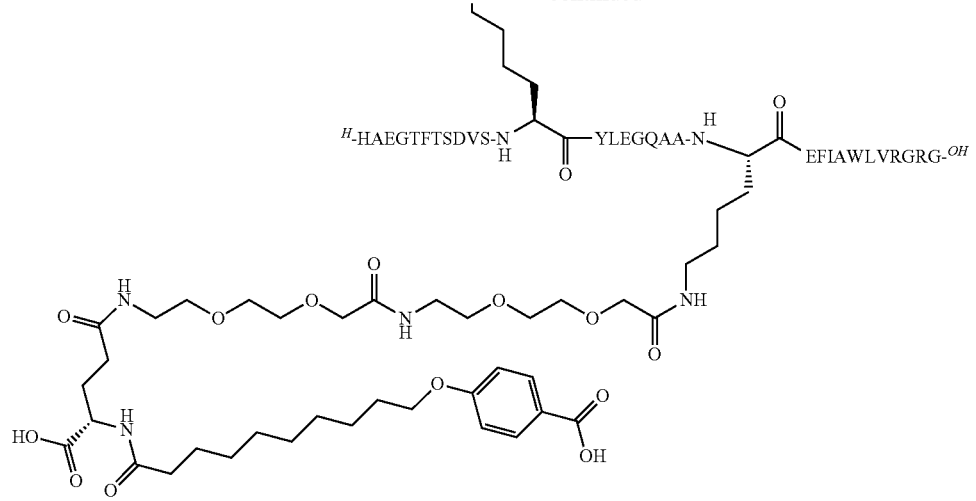
where the amino acid sequence is that of SEQ ID NO: 57,

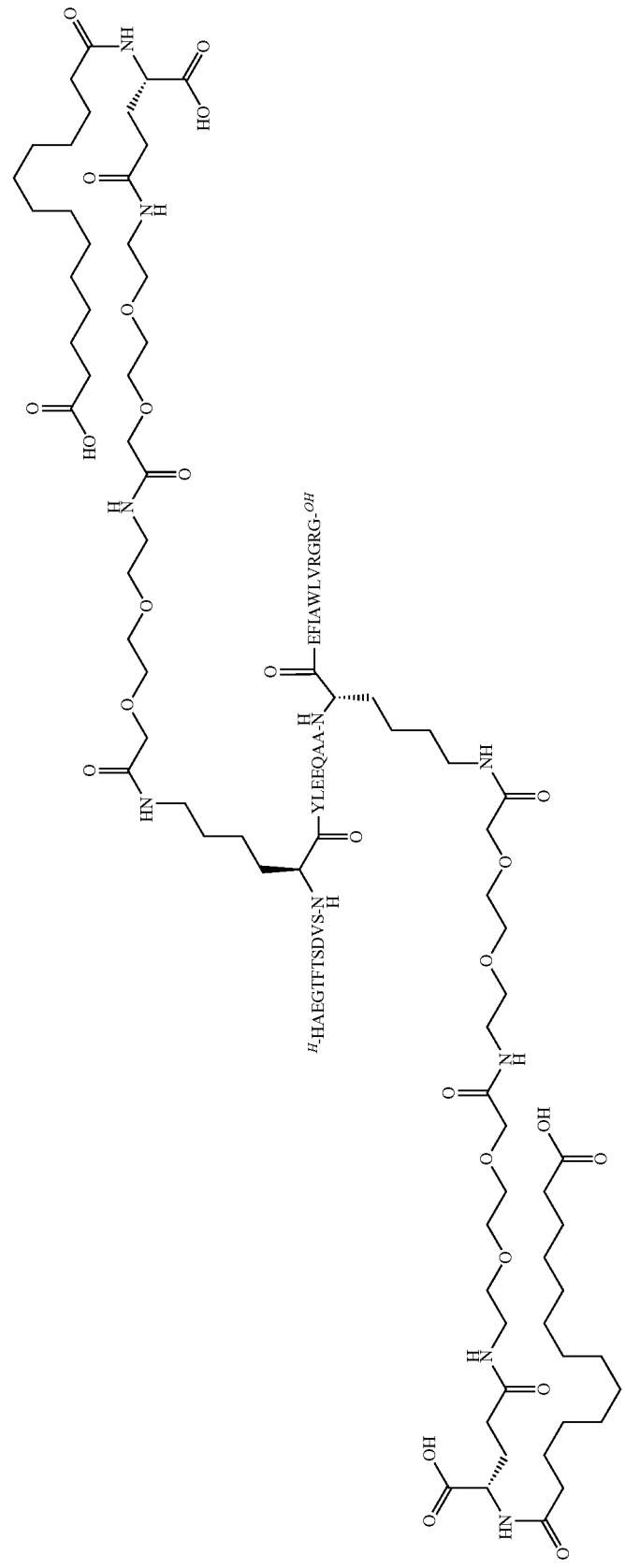

where the amino acid sequence is that of SEQ ID NO: 56,

Chem. 116
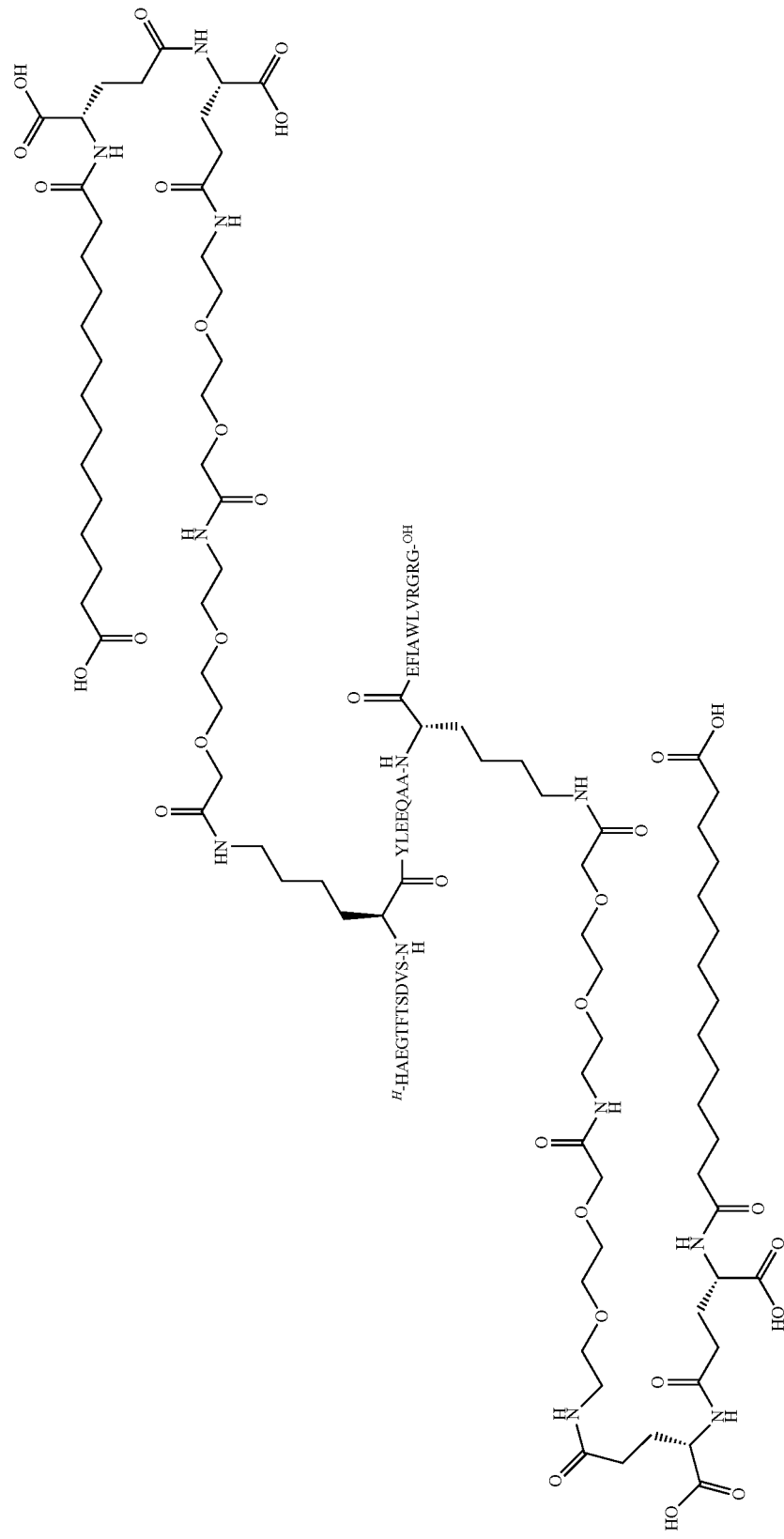

where the amino acid sequence is that of SEQ ID NO: 56,

Chem. 117
663
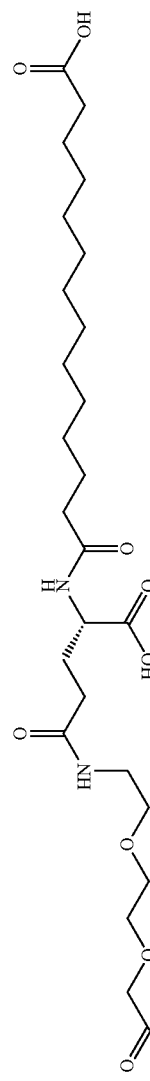
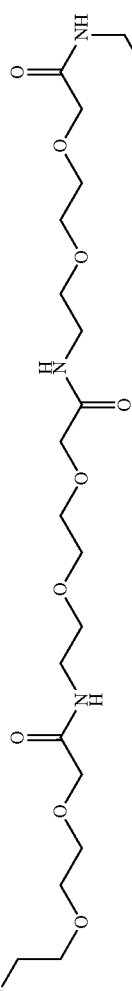
664
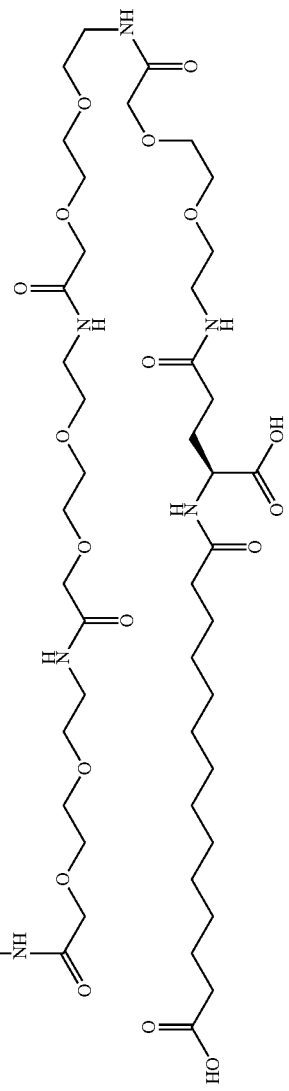

where the amino acid sequence is that of SEQ ID NO: 10,

Chem. 118
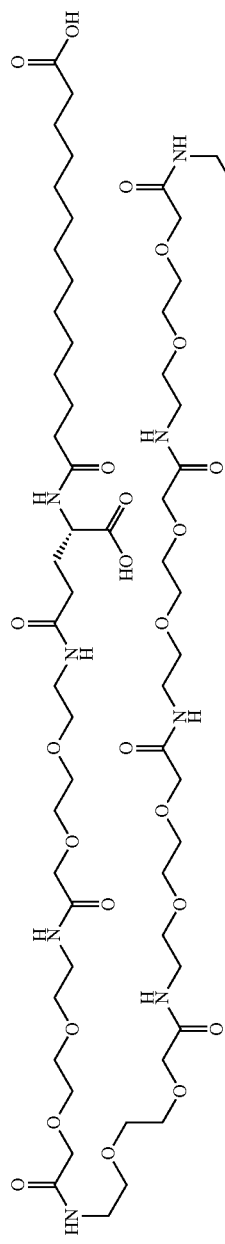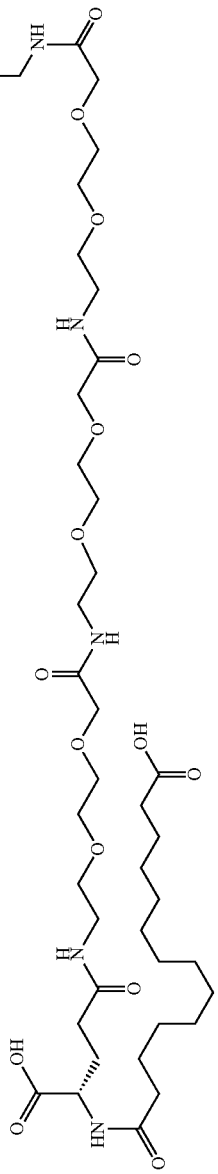

where the amino acid sequence is that of SEQ ID NO: 10,
Chem. 119
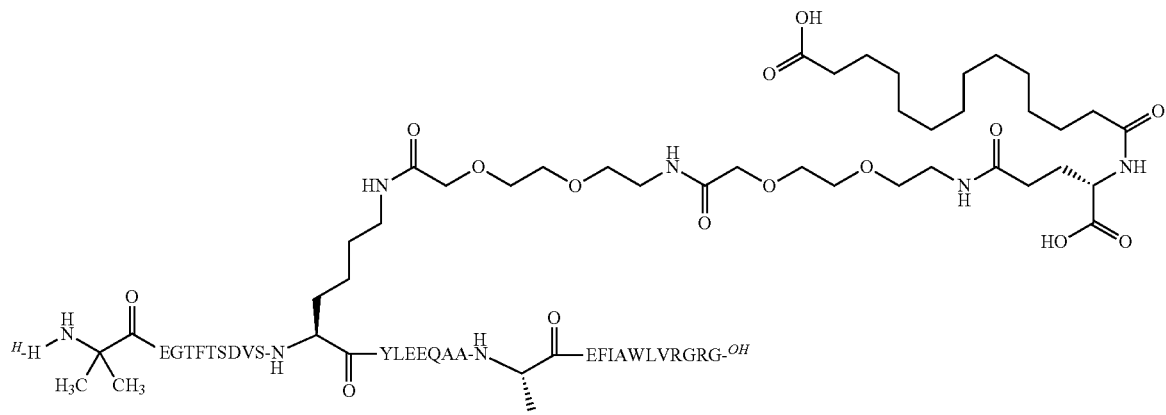
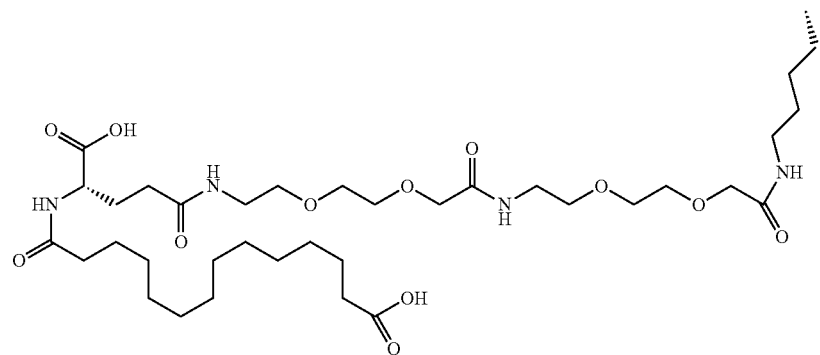
where the amino acid sequence is that of SEQ ID NO: 53,
Chem. 120
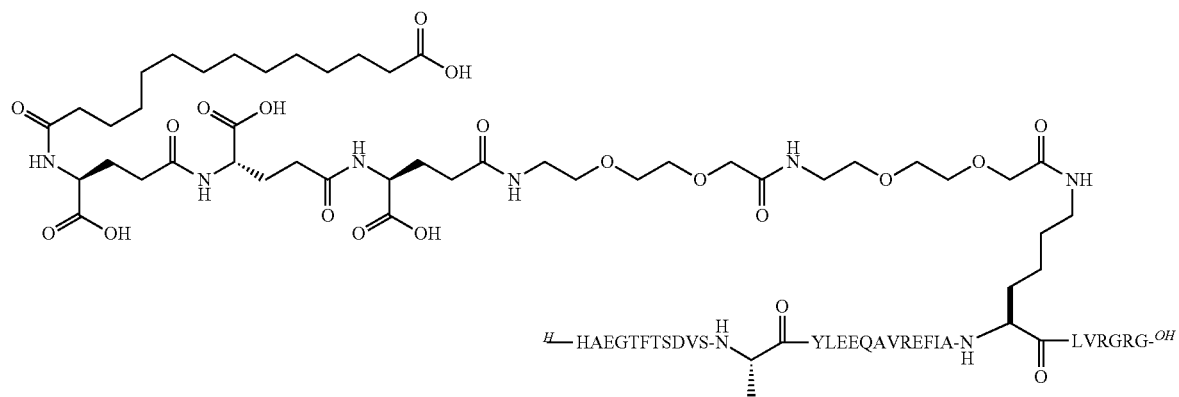

-continued
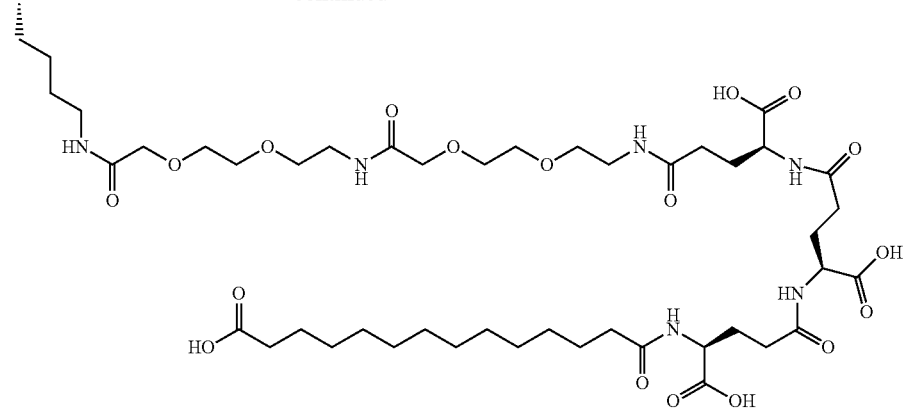
where the amino acid sequence is that of SEQ ID NO: 10,
Chem. 85
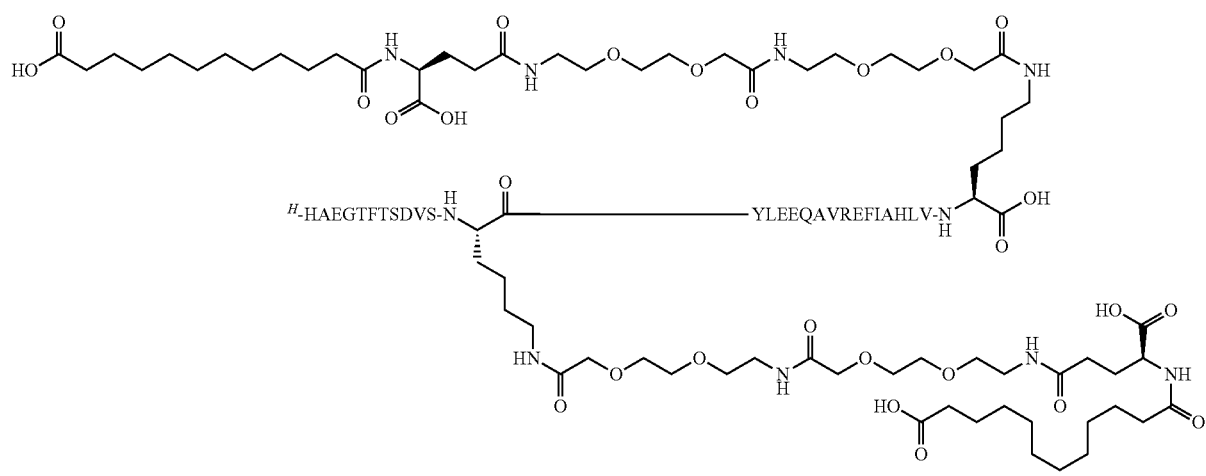
where the amino acid sequence is that of SEQ ID NO: 12,
Chem. 122
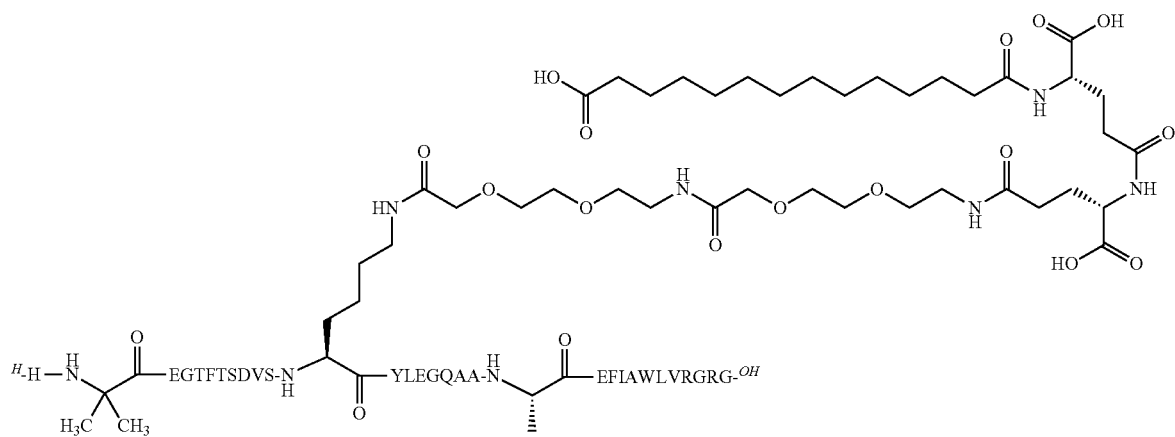

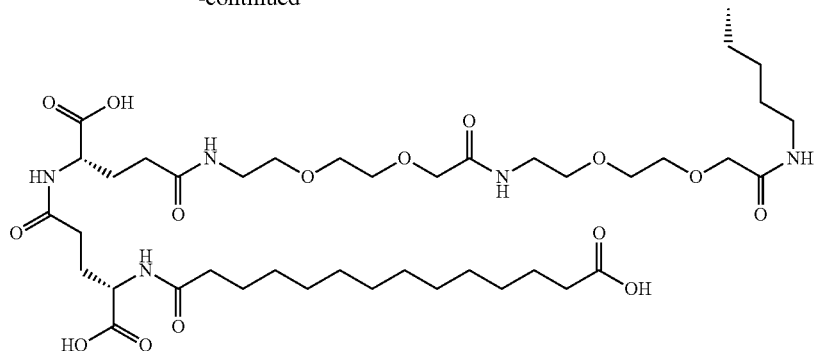
where the amino acid sequence is that of SEQ ID NO: 55,
Chem. 123
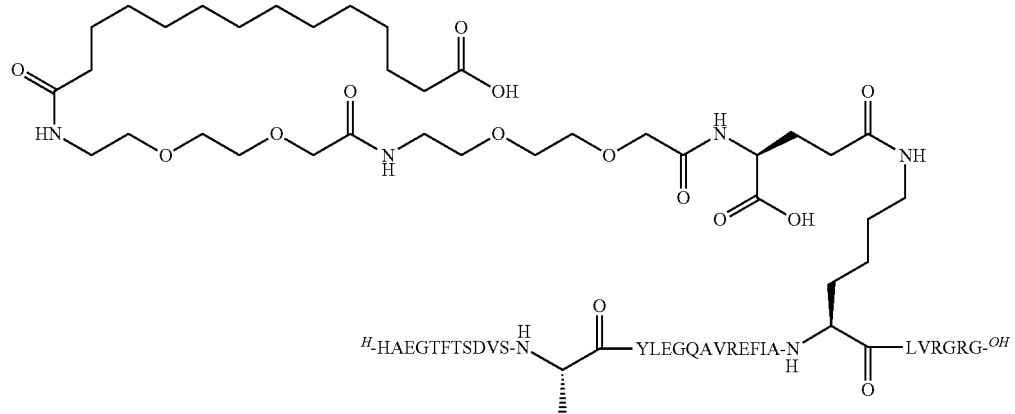
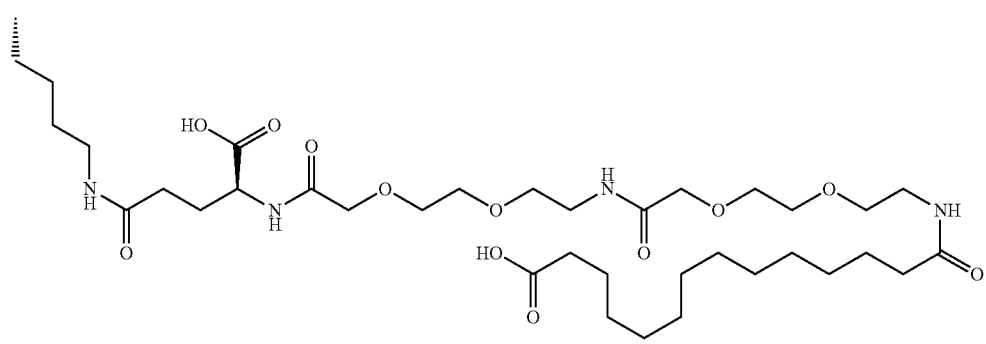
where the amino acid sequence is that of SEQ ID NO: 49, Chem. 124
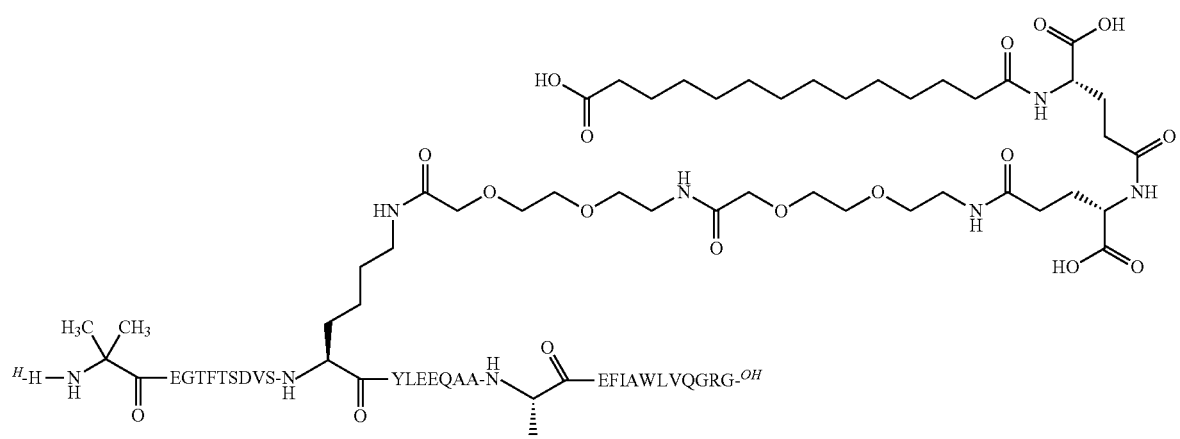
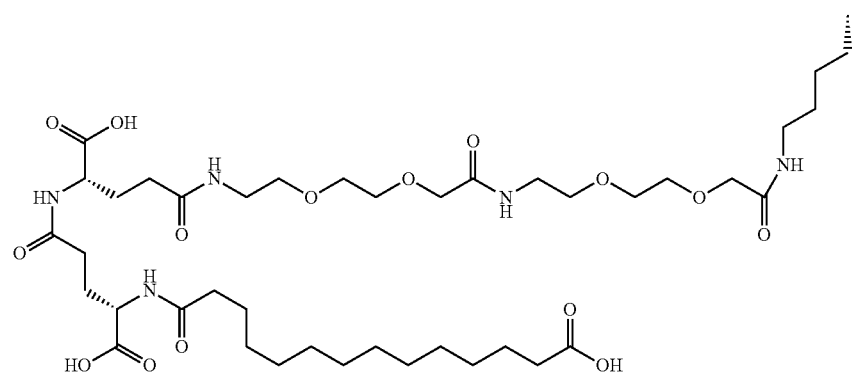
where the amino acid sequence is that of SEQ ID NO: 7,
Chem. 125
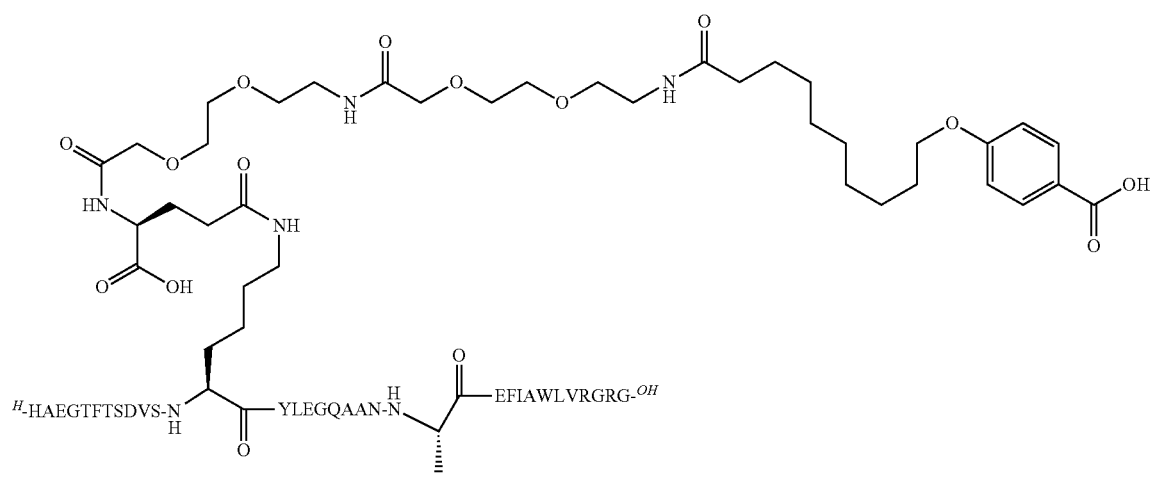

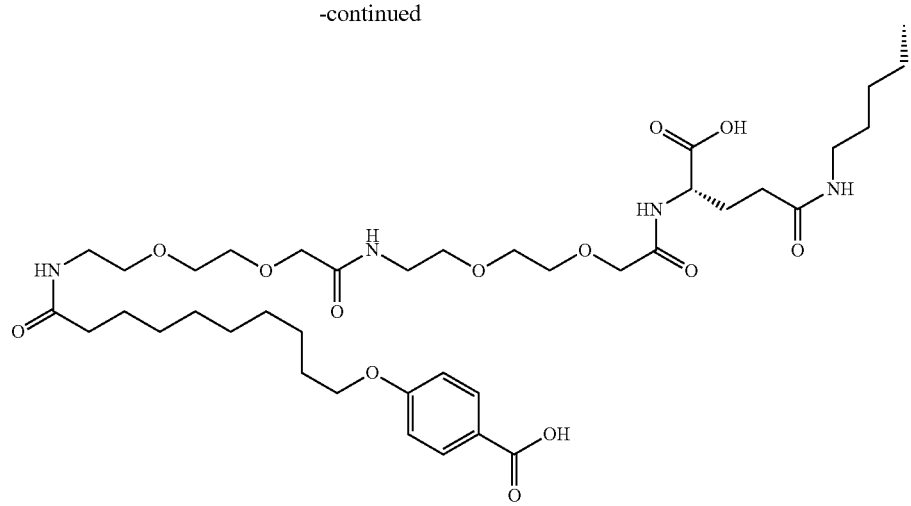
where the amino acid sequence is that of SEQ ID NO: 57,
Chem. 126
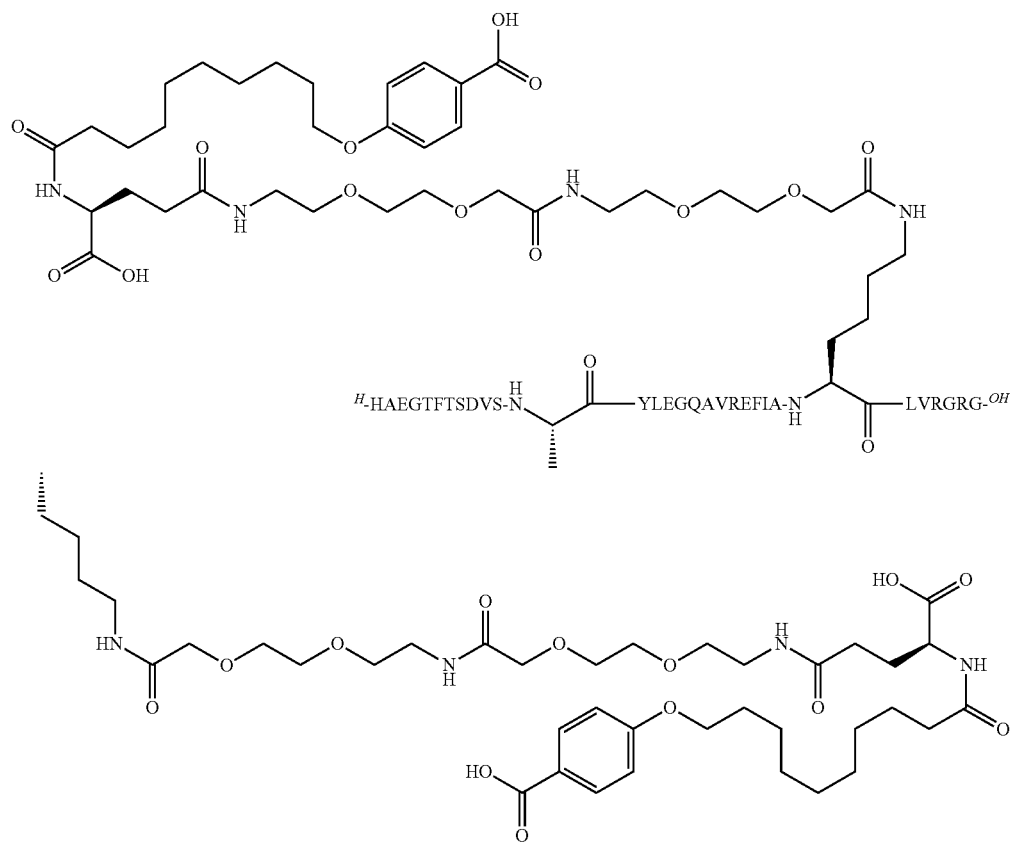
where the amino acid sequence is that of SEQ ID NO: 49,

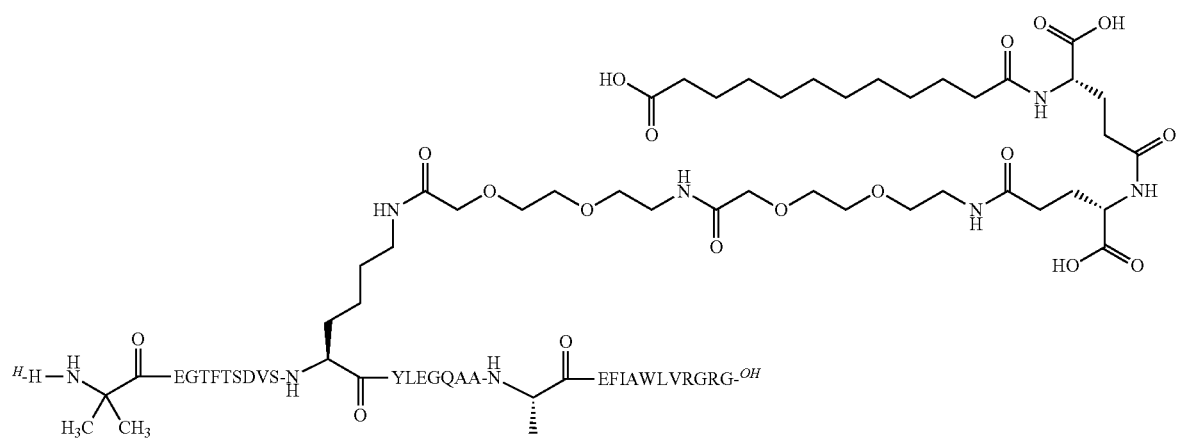
Chem. 127
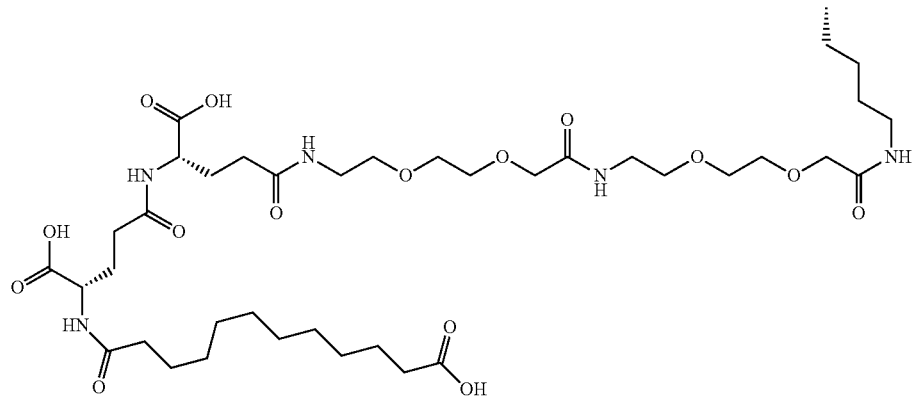
where the amino acid sequence is that of SEQ ID NO: 55,
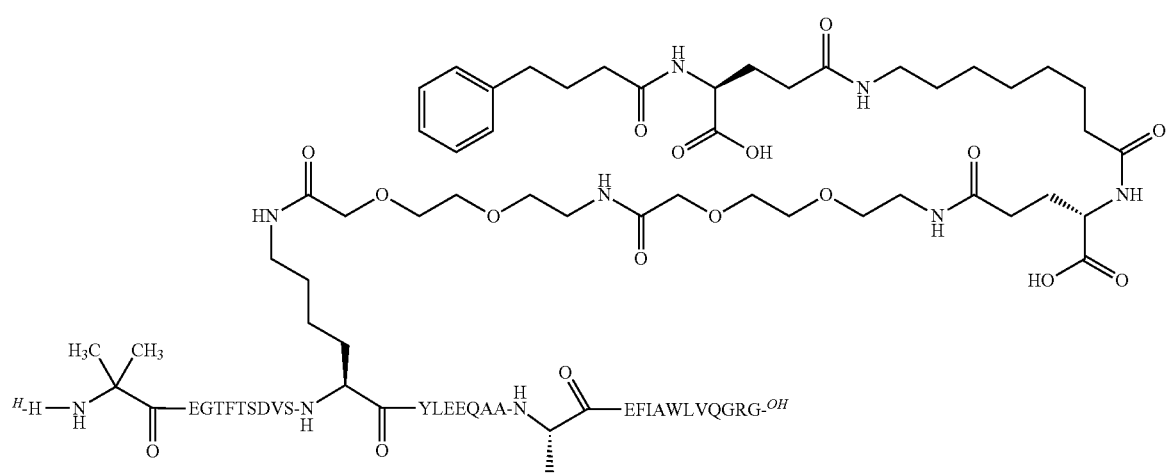
Chem. 128

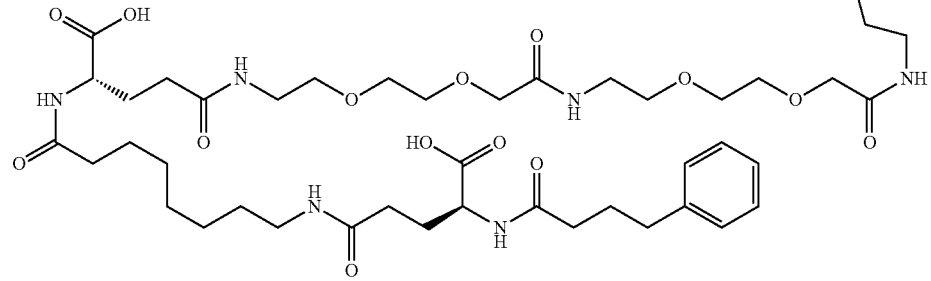
where the amino acid sequence is that of SEQ ID NO: 7,
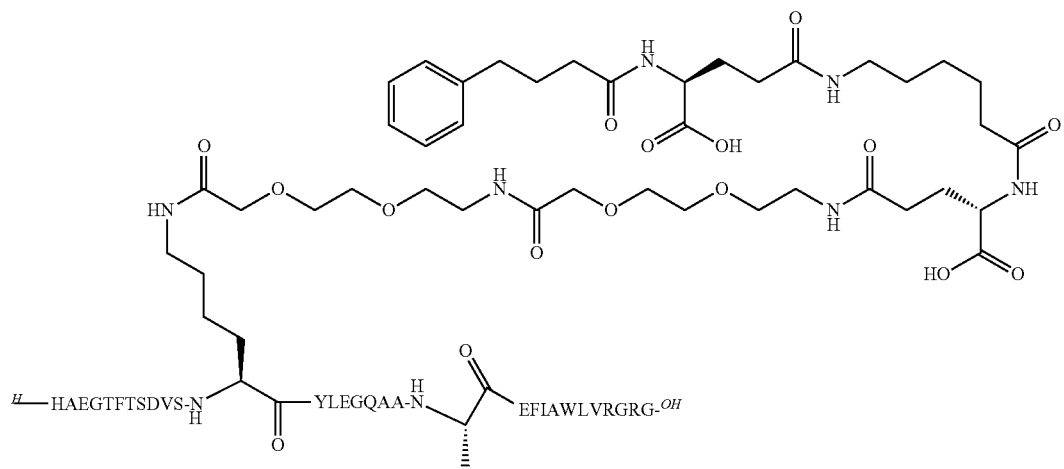
Chem. 129
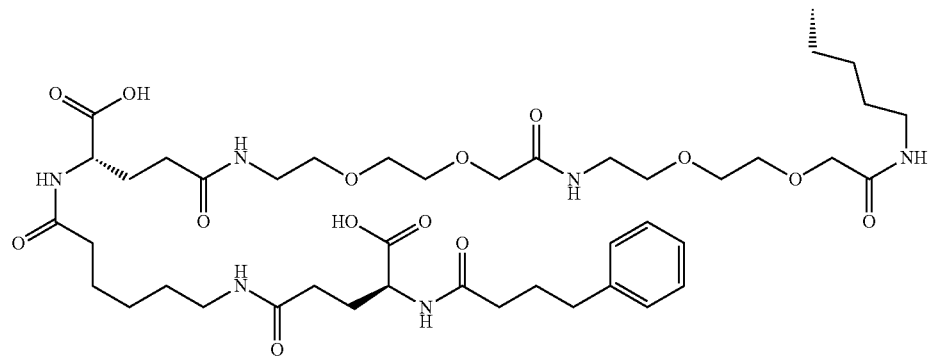
where the amino acid sequence is that of SEQ ID NO: 57,

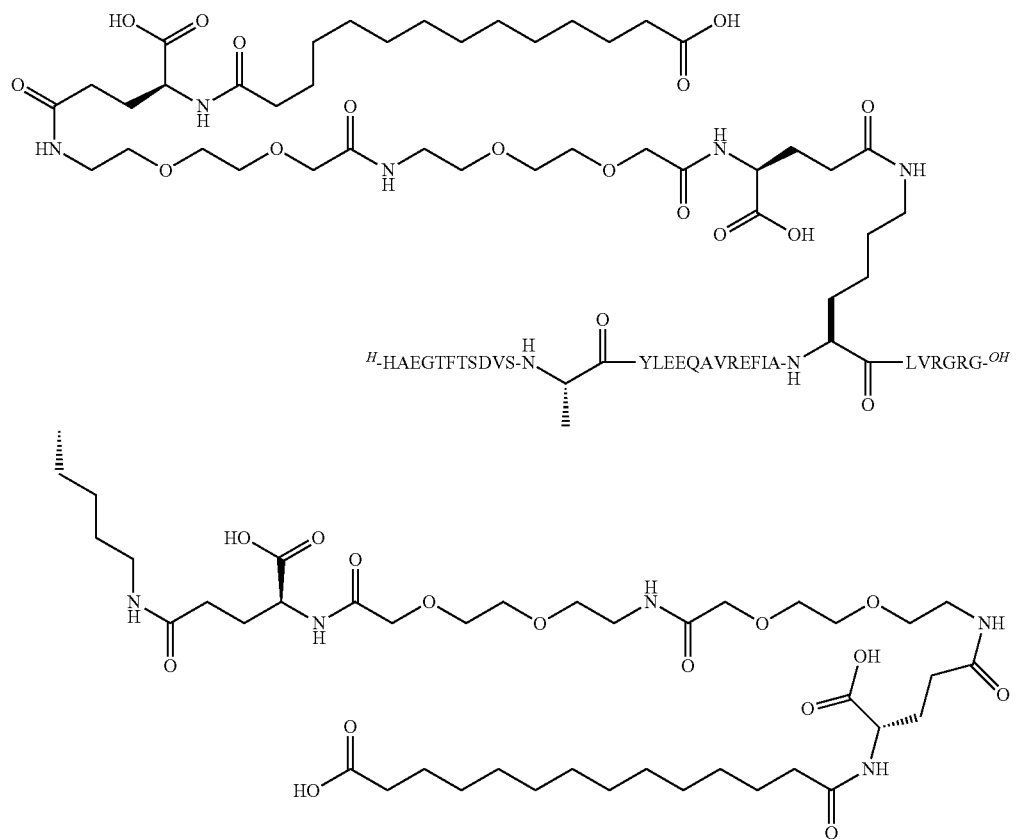
Chem. 130
where the amino acid sequence is that of SEQ ID NO: 10,

Chem. 131
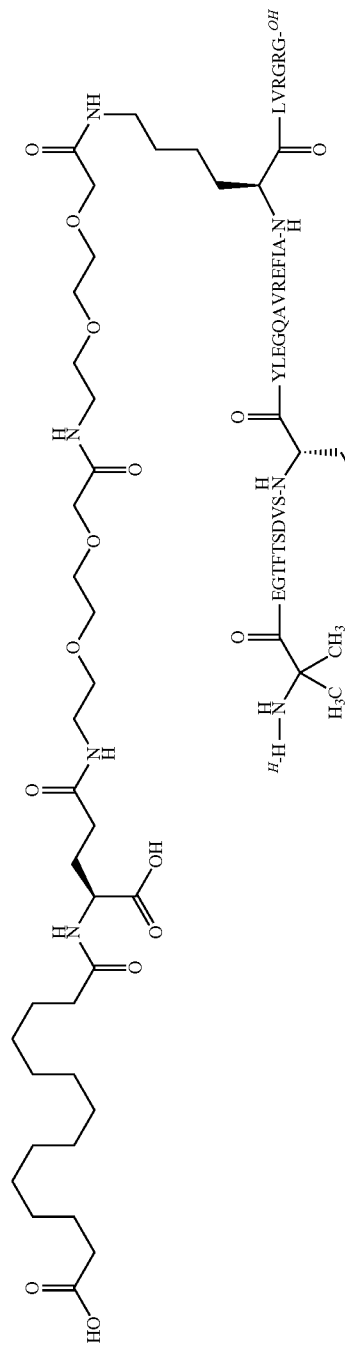
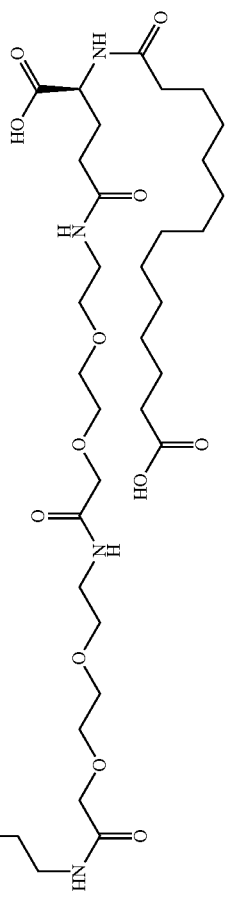

where the amino acid sequence is that of SEQ ID NO: 58,
Chem. 132
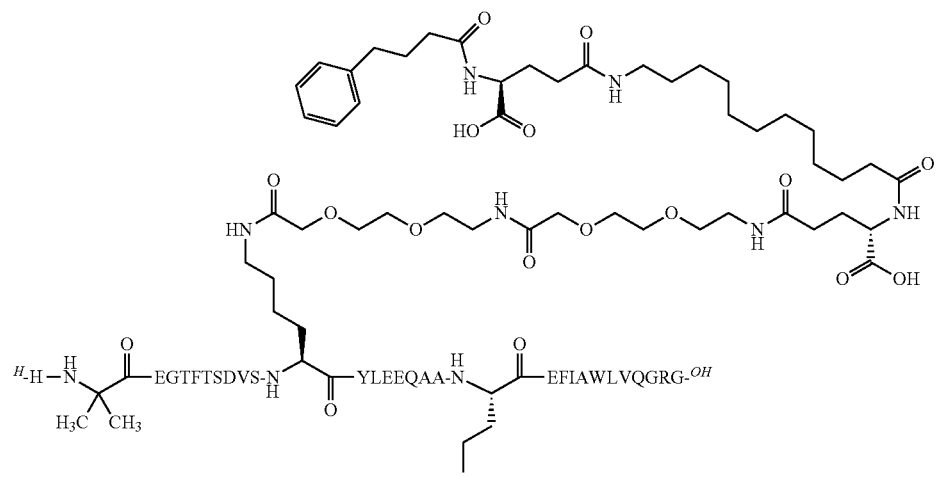
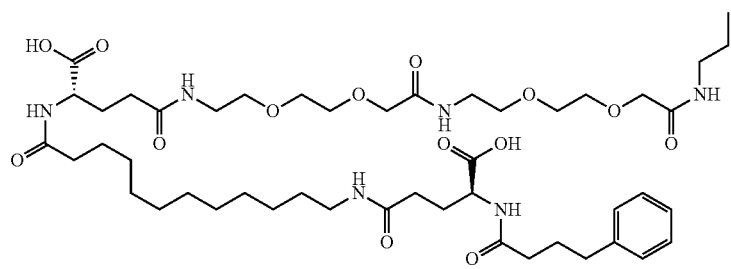
where the amino acid sequence is that of SEQ ID NO: 7,
Chem. 133
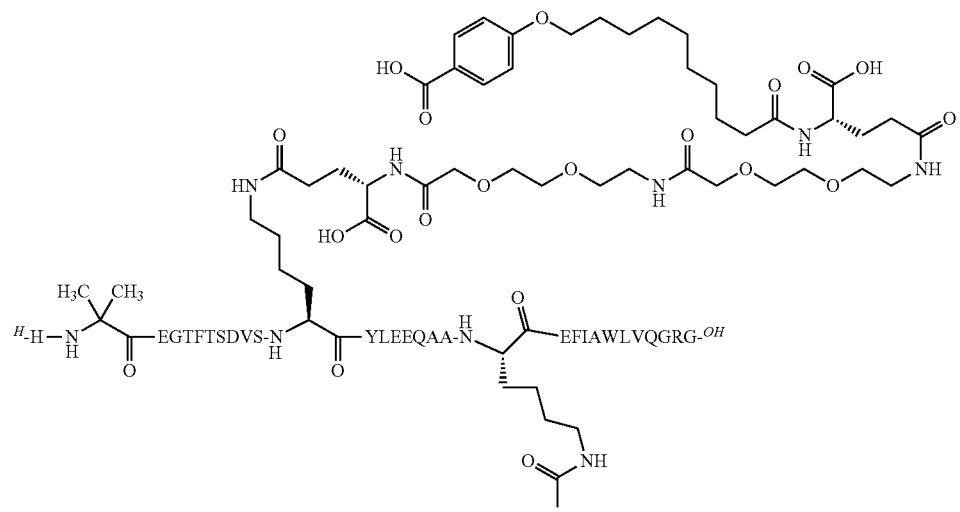

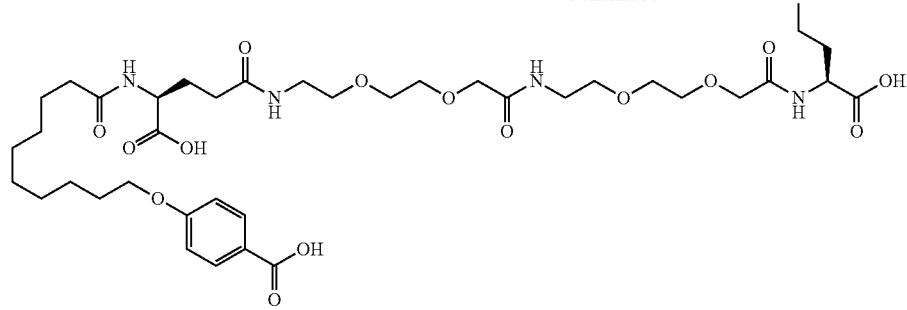
where the amino acid sequence is that of SEQ ID NO: 7,
Chem. 134
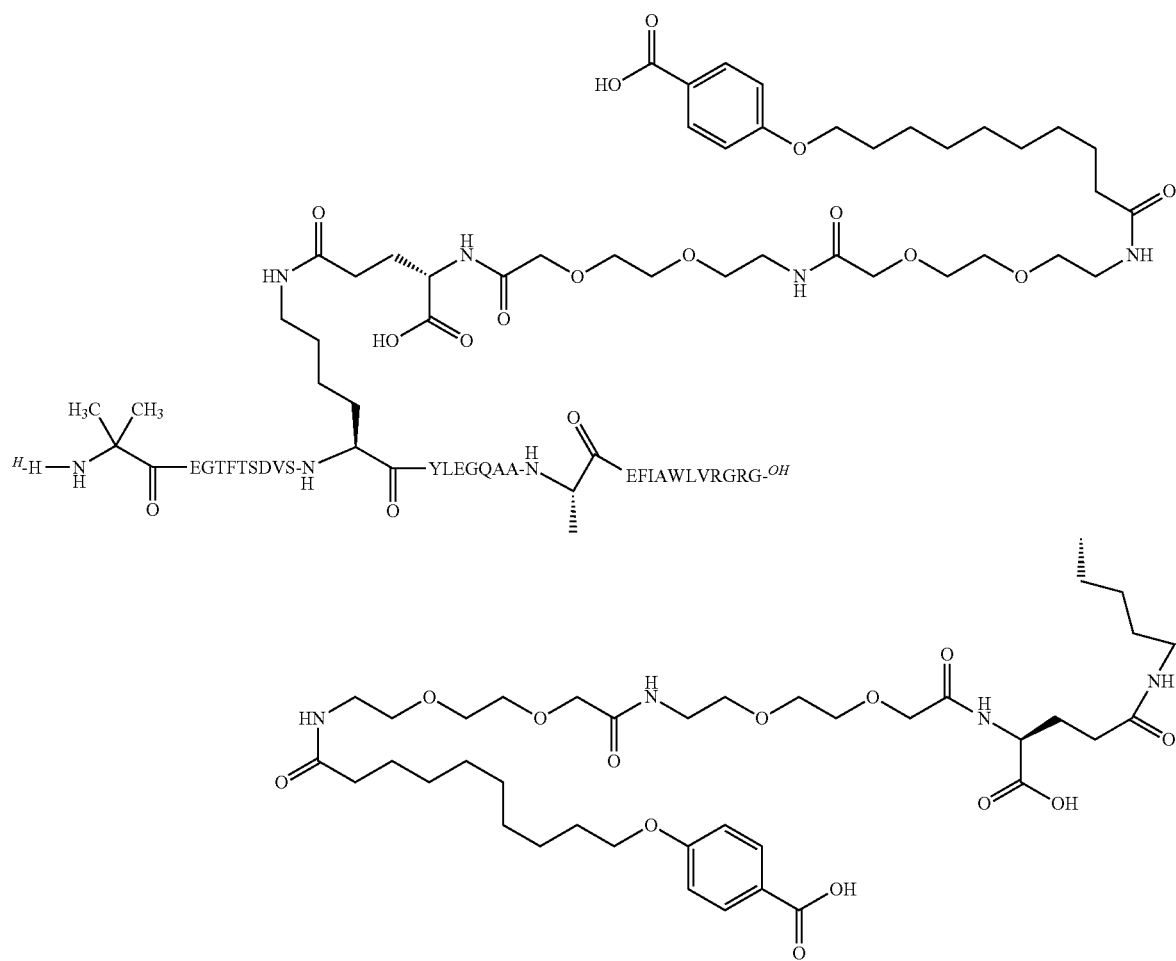
where the amino acid sequence is that of SEQ ID NO: 55, Chem. 135
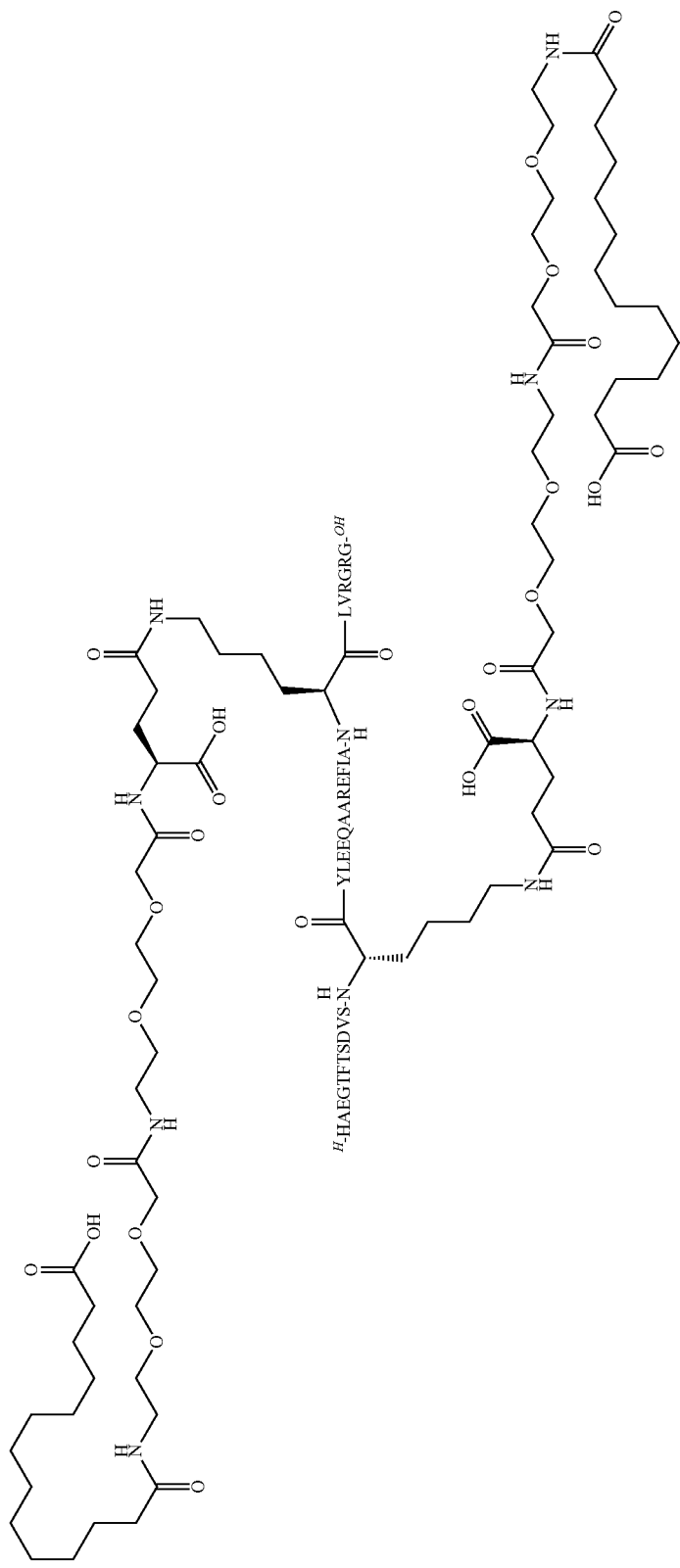

where the amino acid sequence is that of SEQ ID NO: 50,
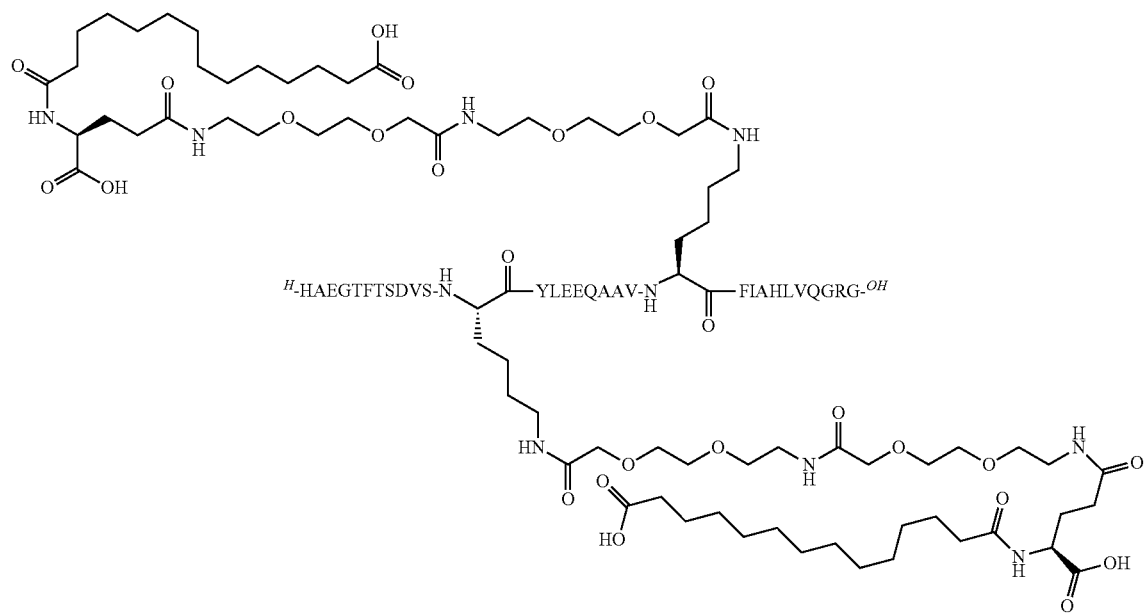
Chem. 161
where the amino acid sequence is that of SEQ ID NO: 59, Chem. 162
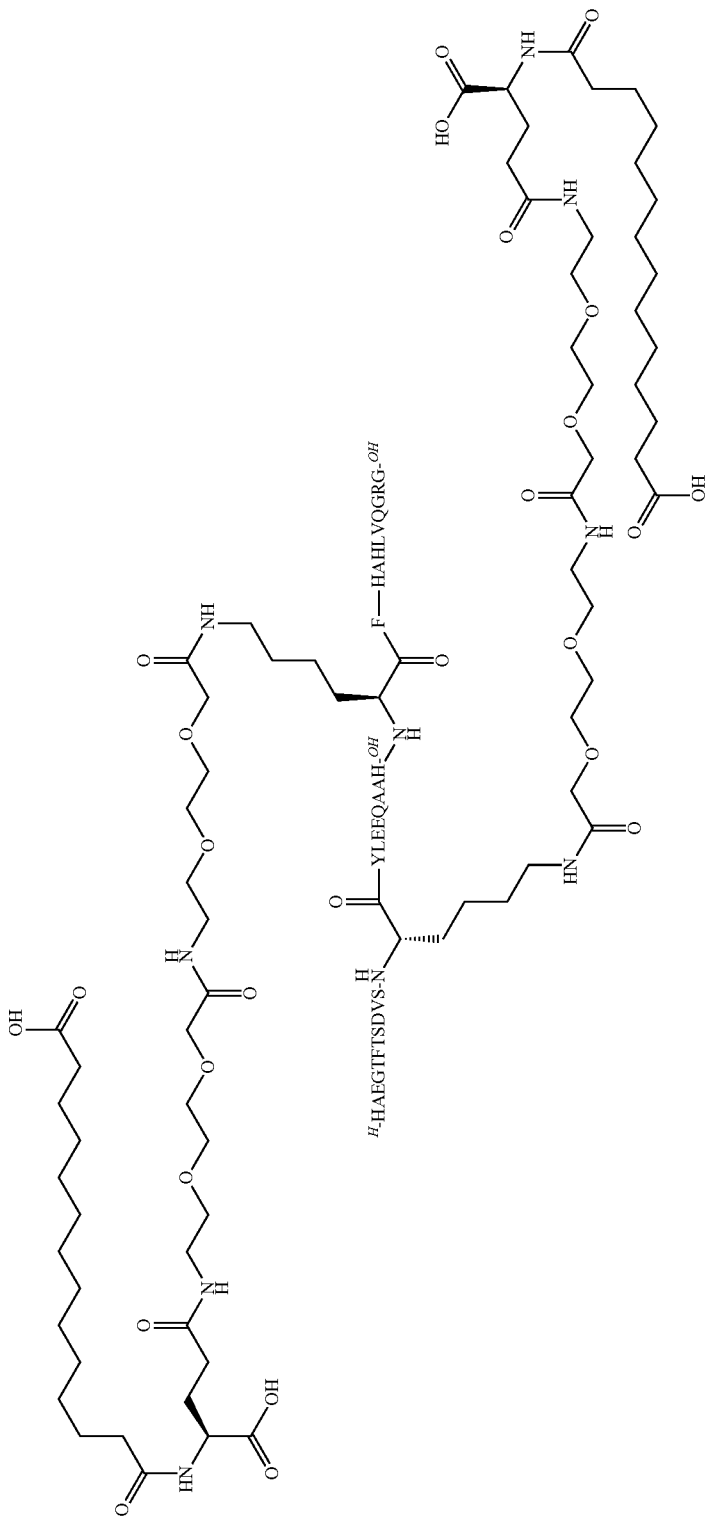

where the amino acid sequence is that of SEQ ID NO: 60,
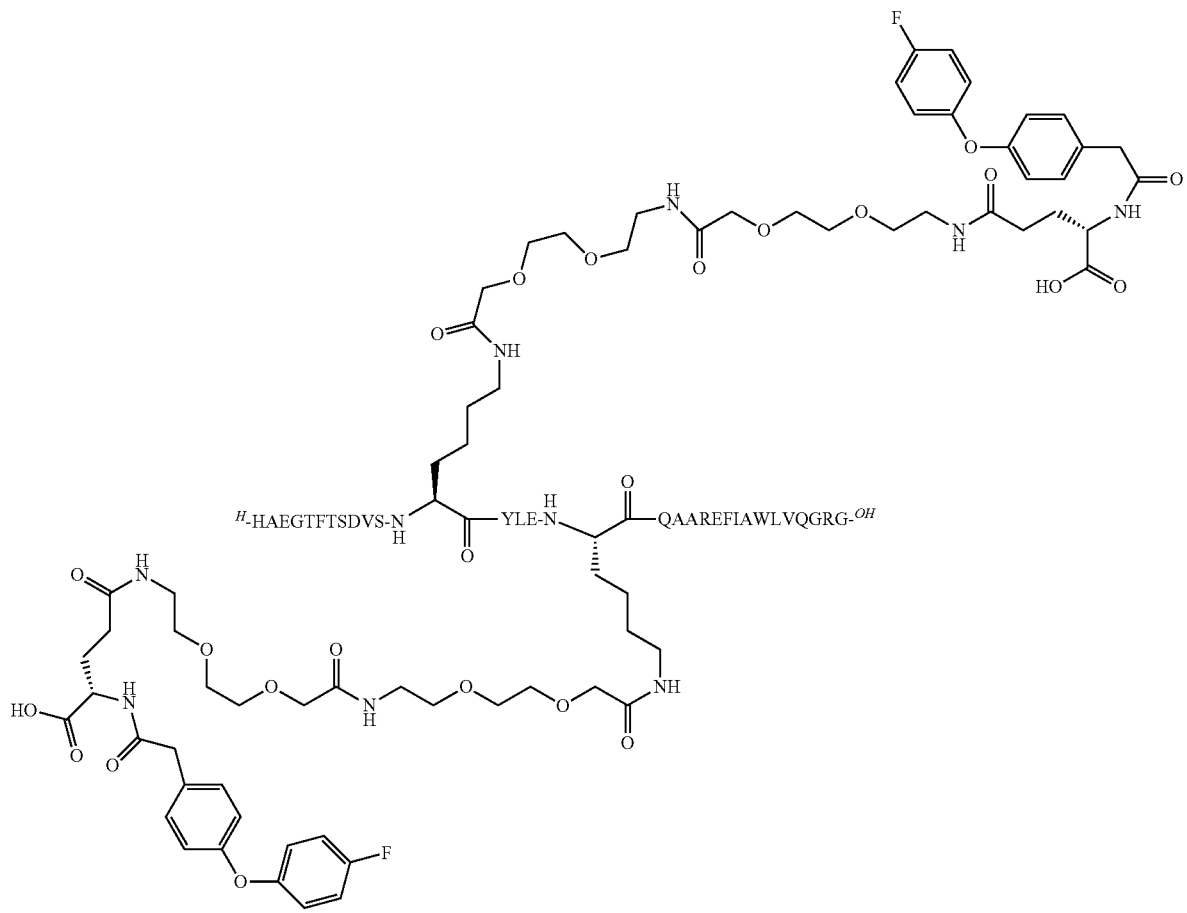
Chem. 163
where the amino acid sequence is that of SEQ ID NO: 61,

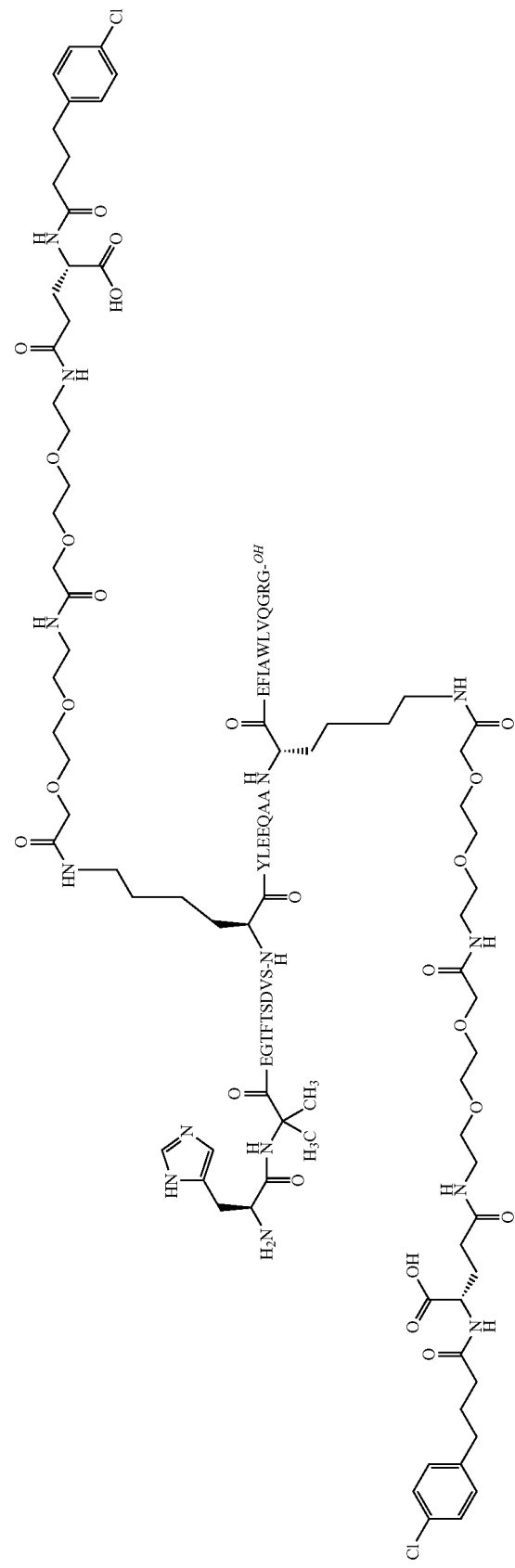
Chem. 164 where the amino acid sequence is that of SEQ ID NO: 7,

Chem. 165
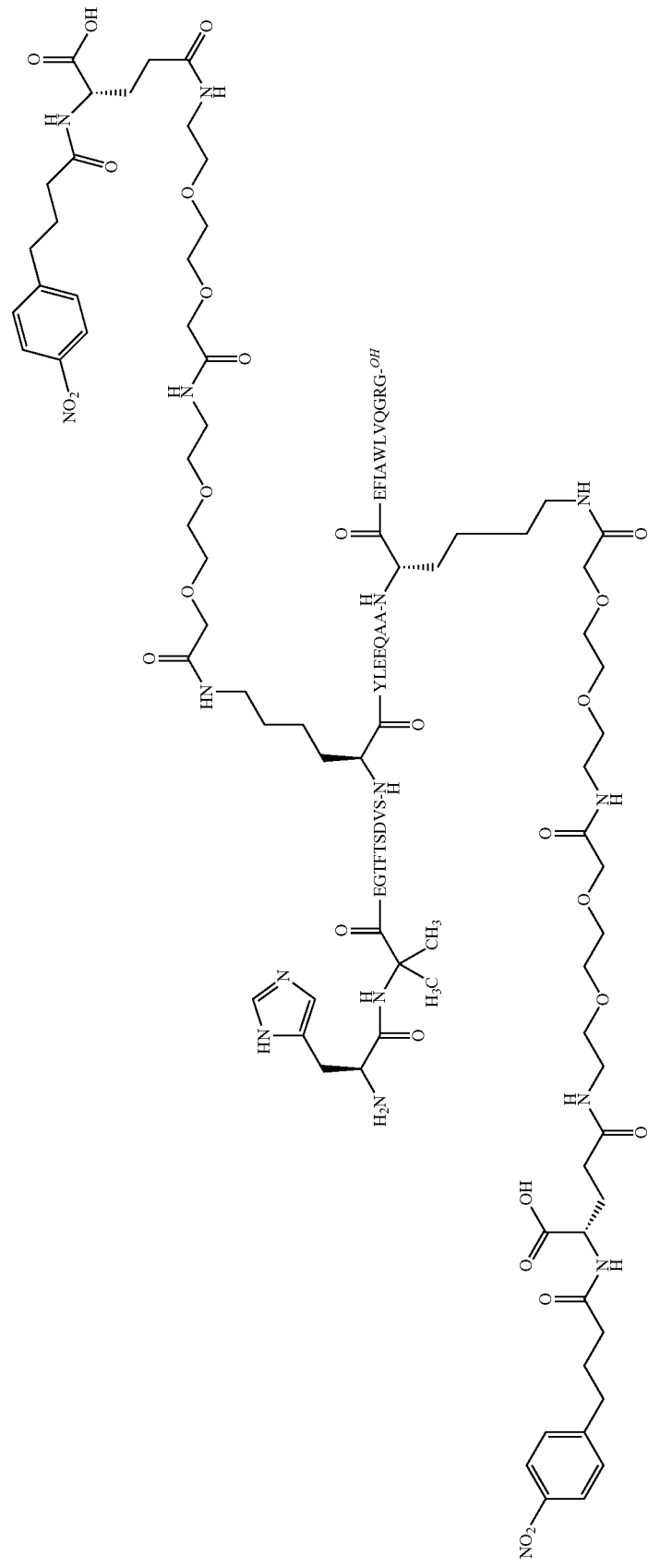

where the amino acid sequence is that of SEQ ID NO: 7,

Chem. 166
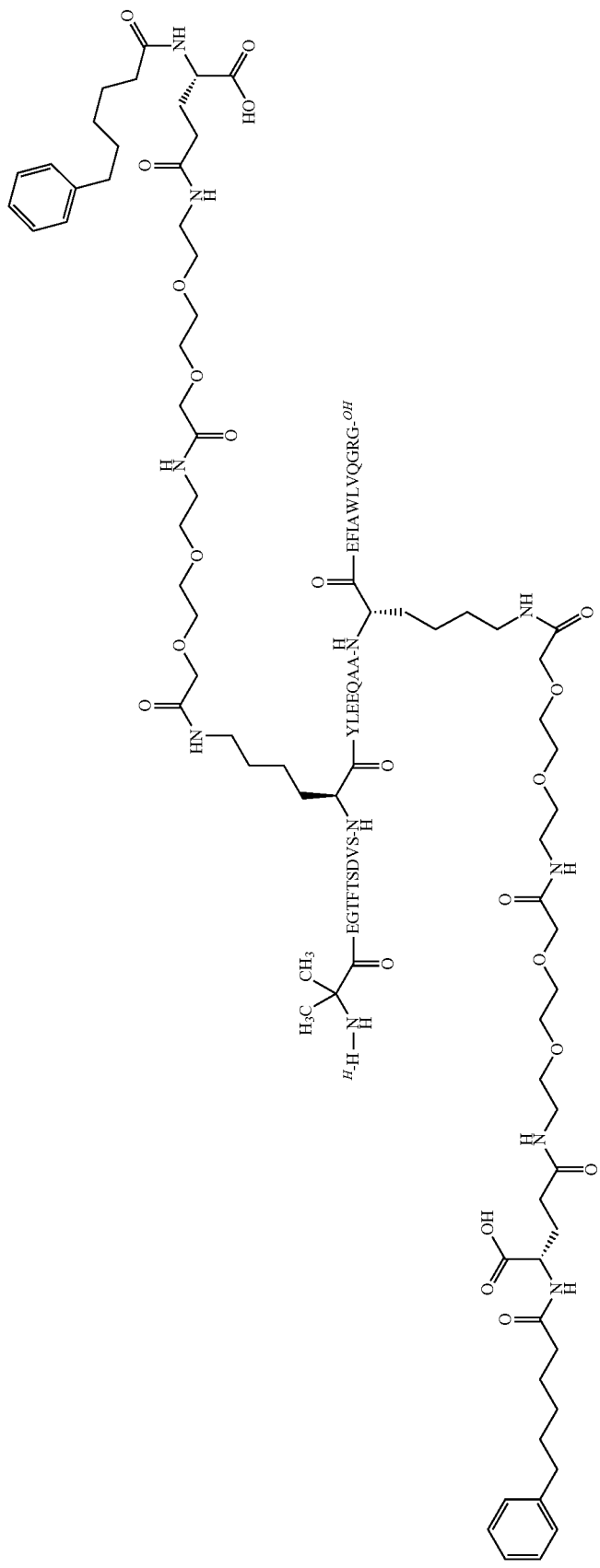

where the amino acid sequence is that of SEQ ID NO: 7,

Chem. 167
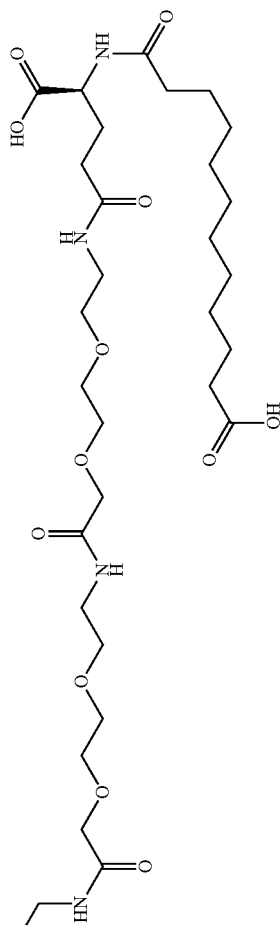
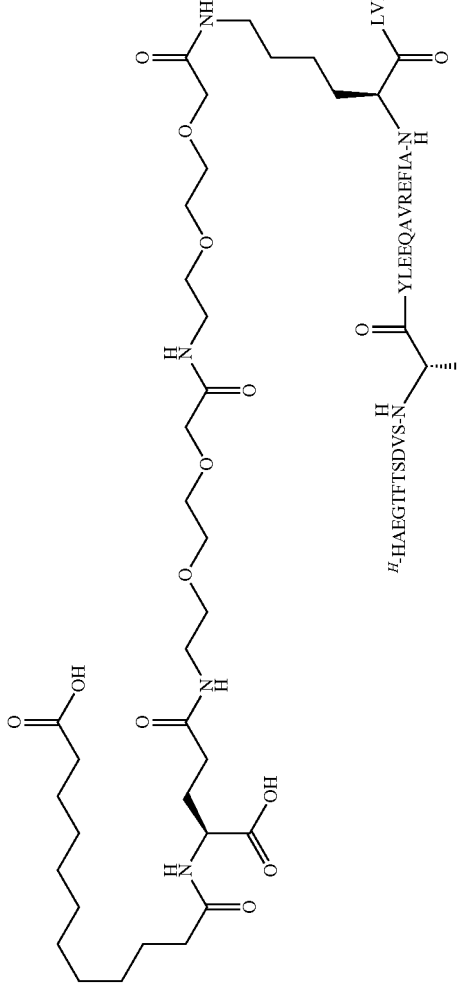

where the amino acid sequence is that of SEQ ID NO: 10,

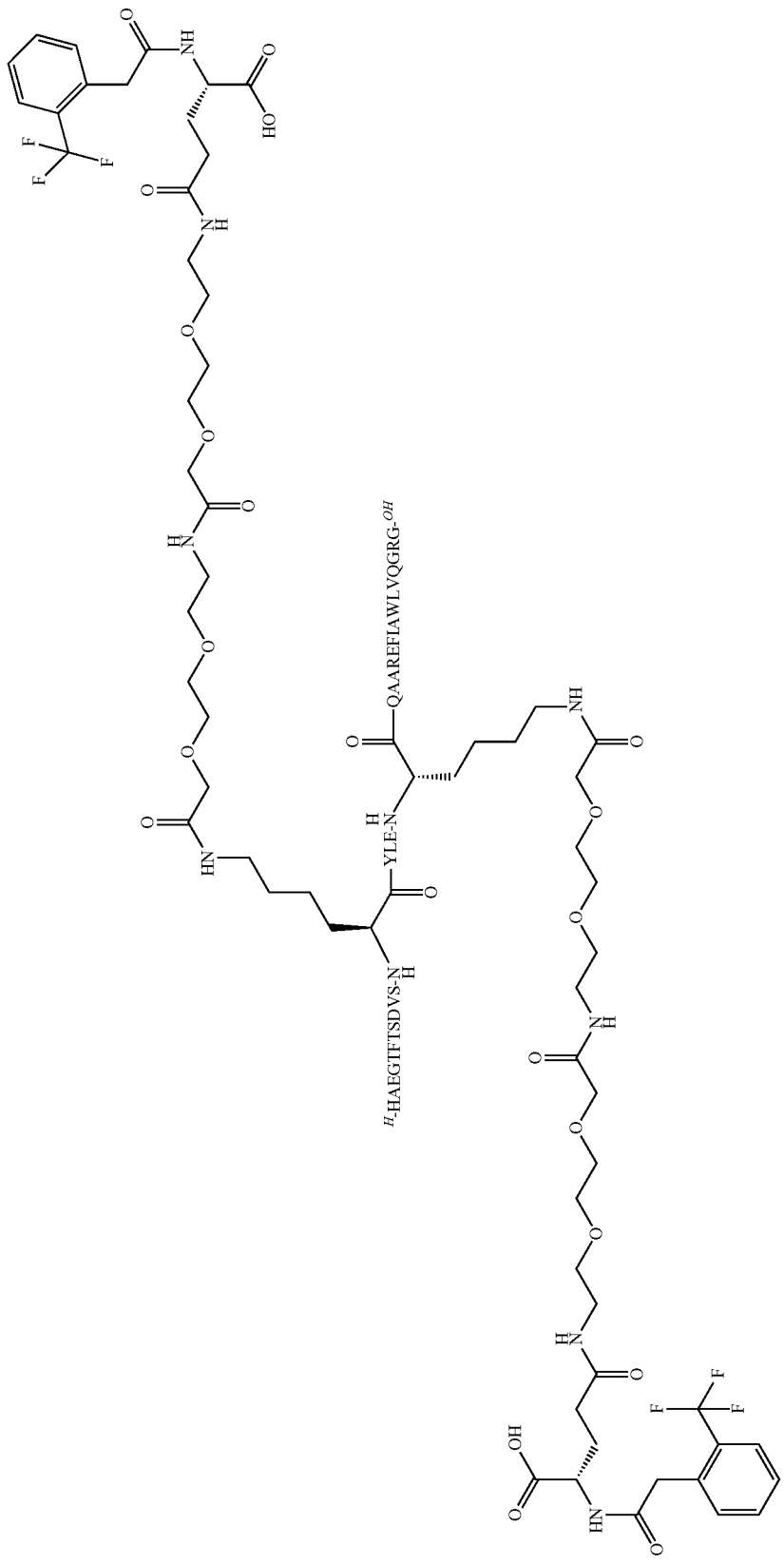
Chem. 168 where the amino acid sequence is that of SEQ ID NO: 61,

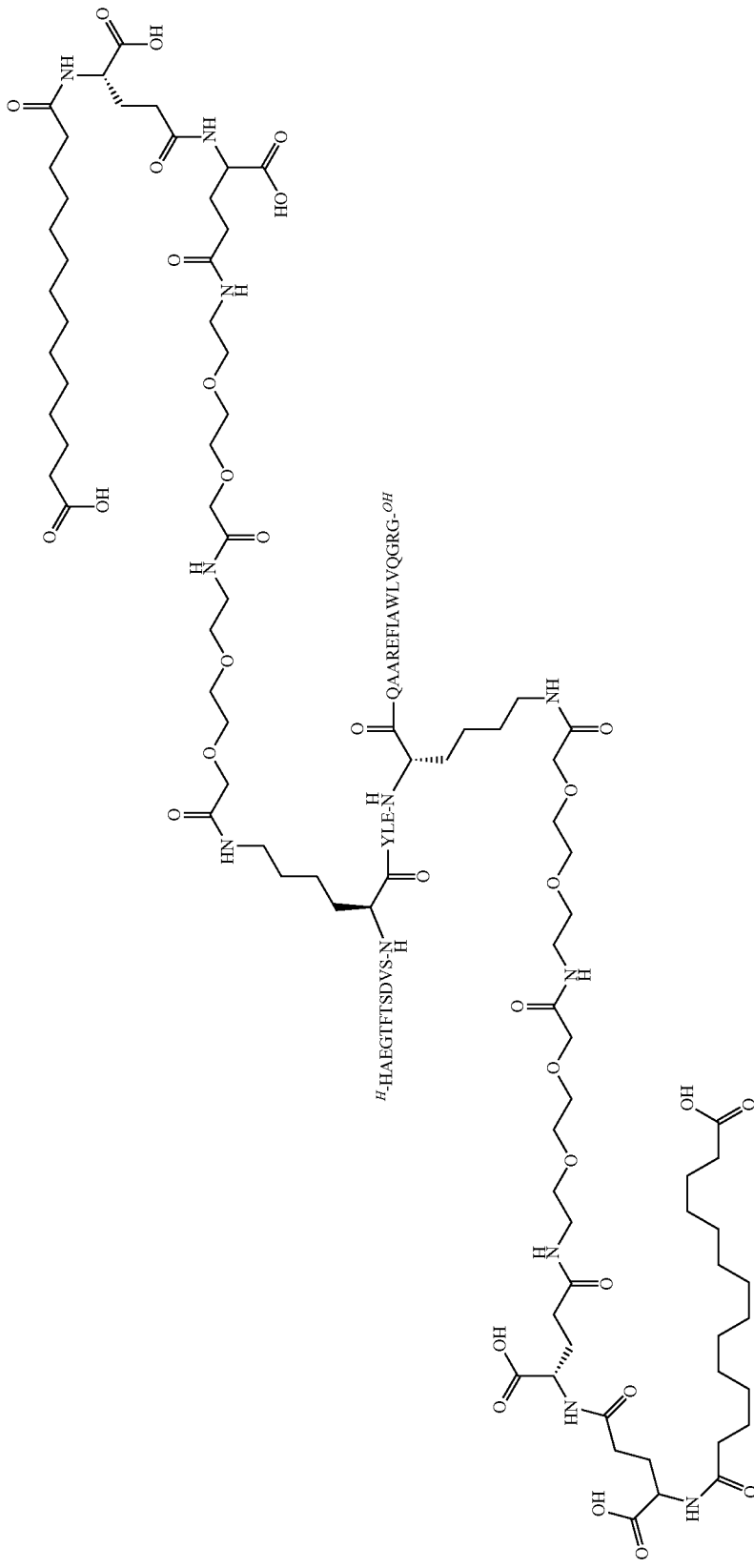
Chem. 169 where the amino acid sequence is that of SEQ ID NO: 61,

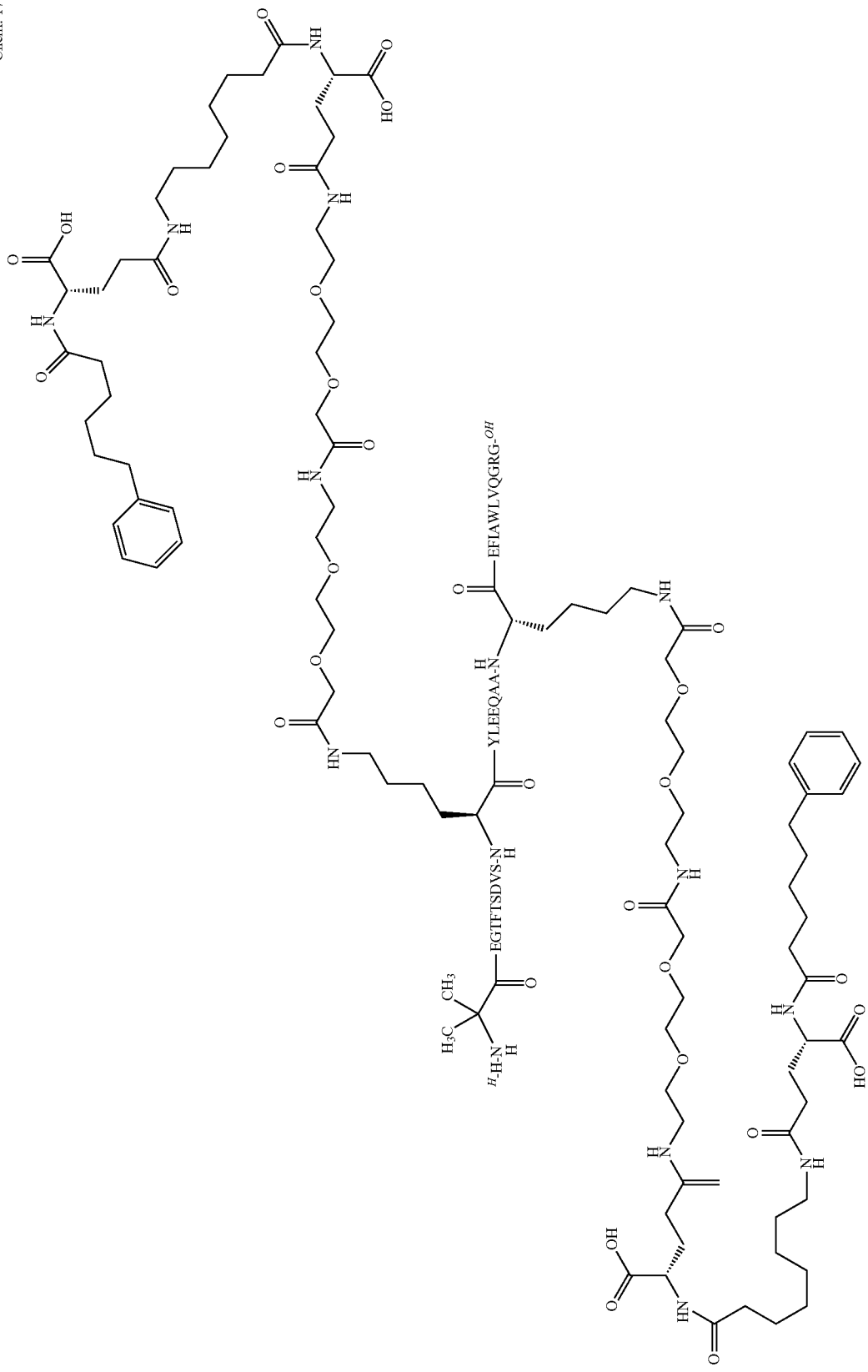
Chem. 170 where the amino acid sequence is that of SEQ ID NO: 7,

Chem. 171
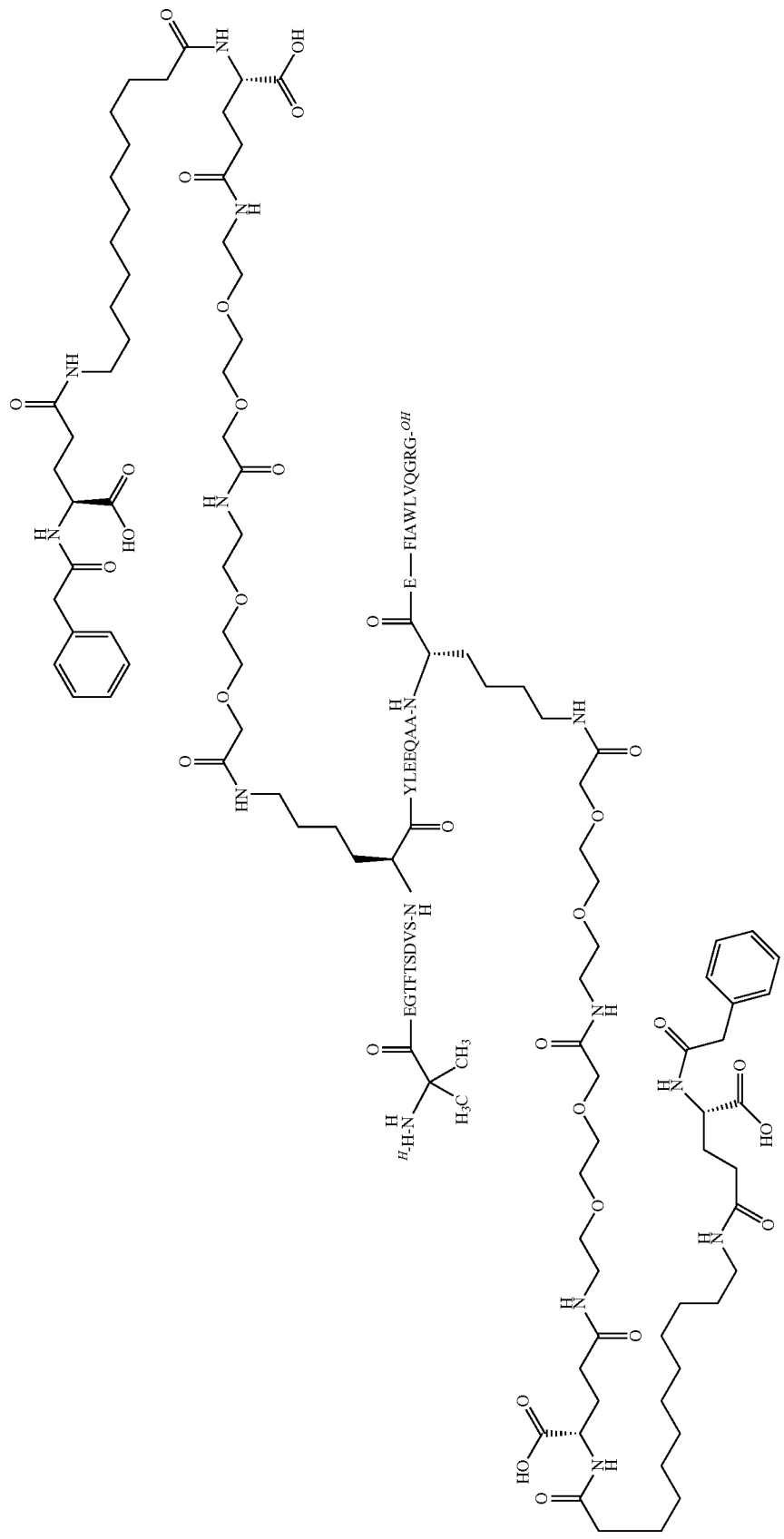

where the amino acid sequence is that of SEQ ID NO: 7,
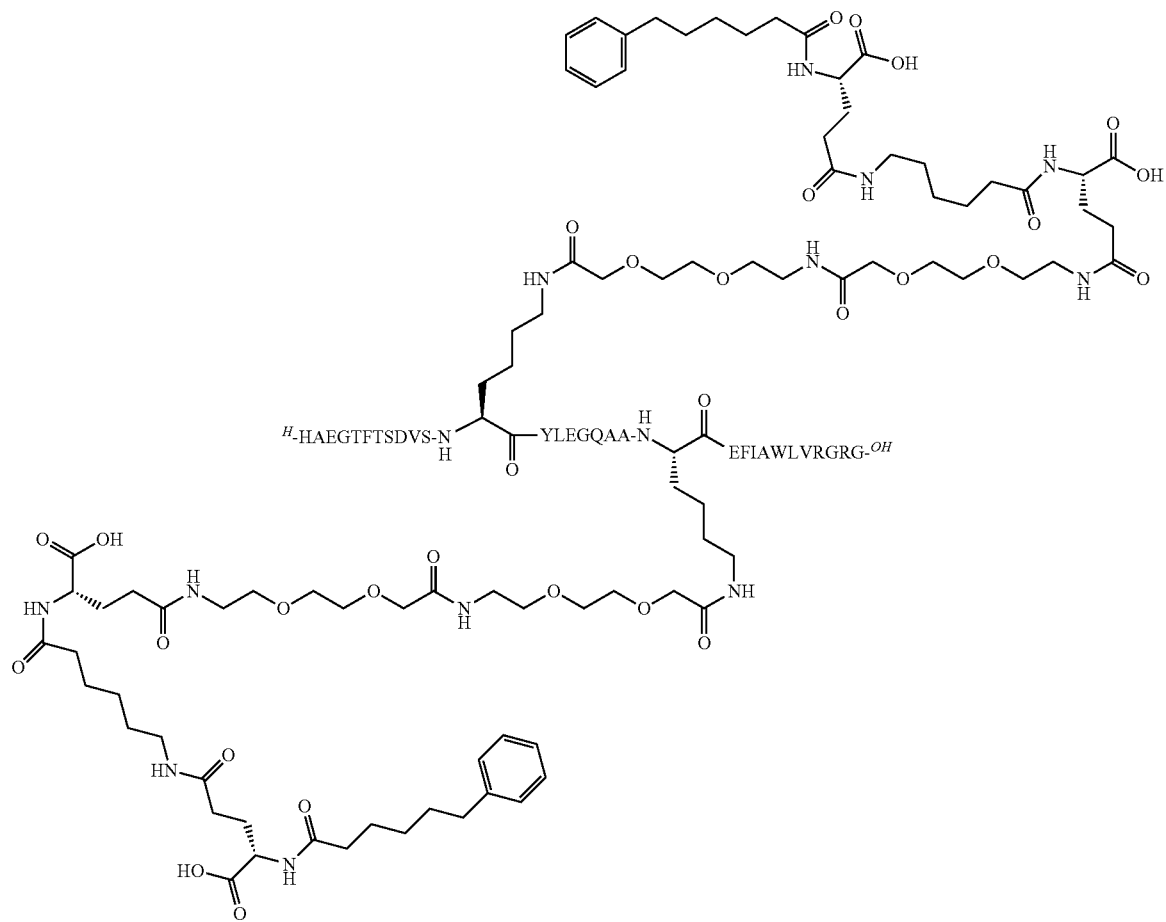
Chem. 172
where the amino acid sequence is that of SEQ ID NO: 57, Chem. 173
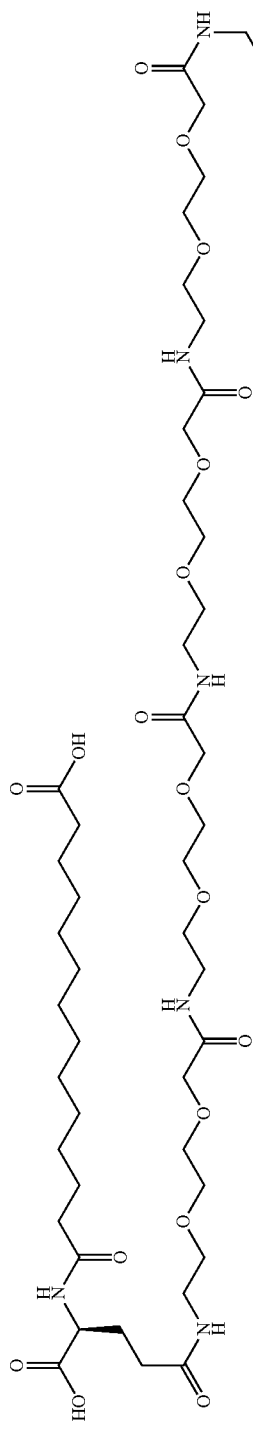
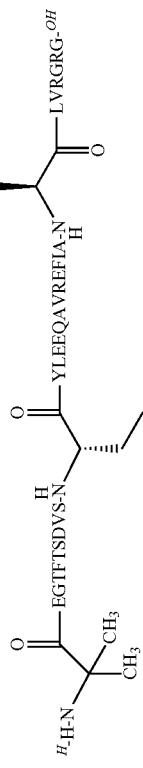
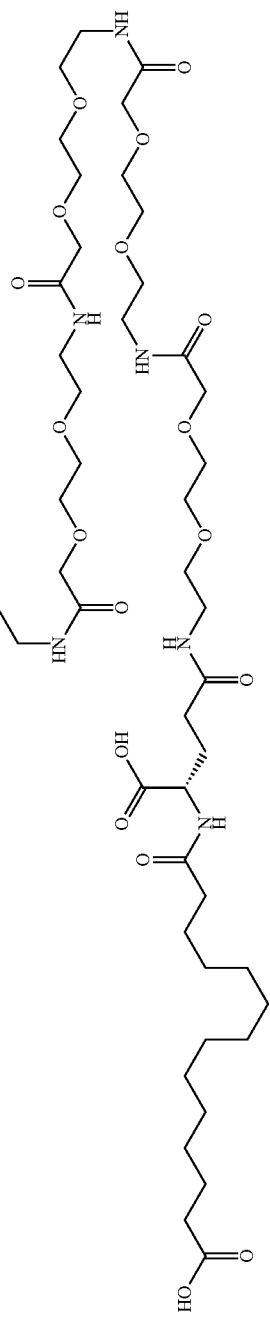

where the amino acid sequence is that of SEQ ID NO: 12,
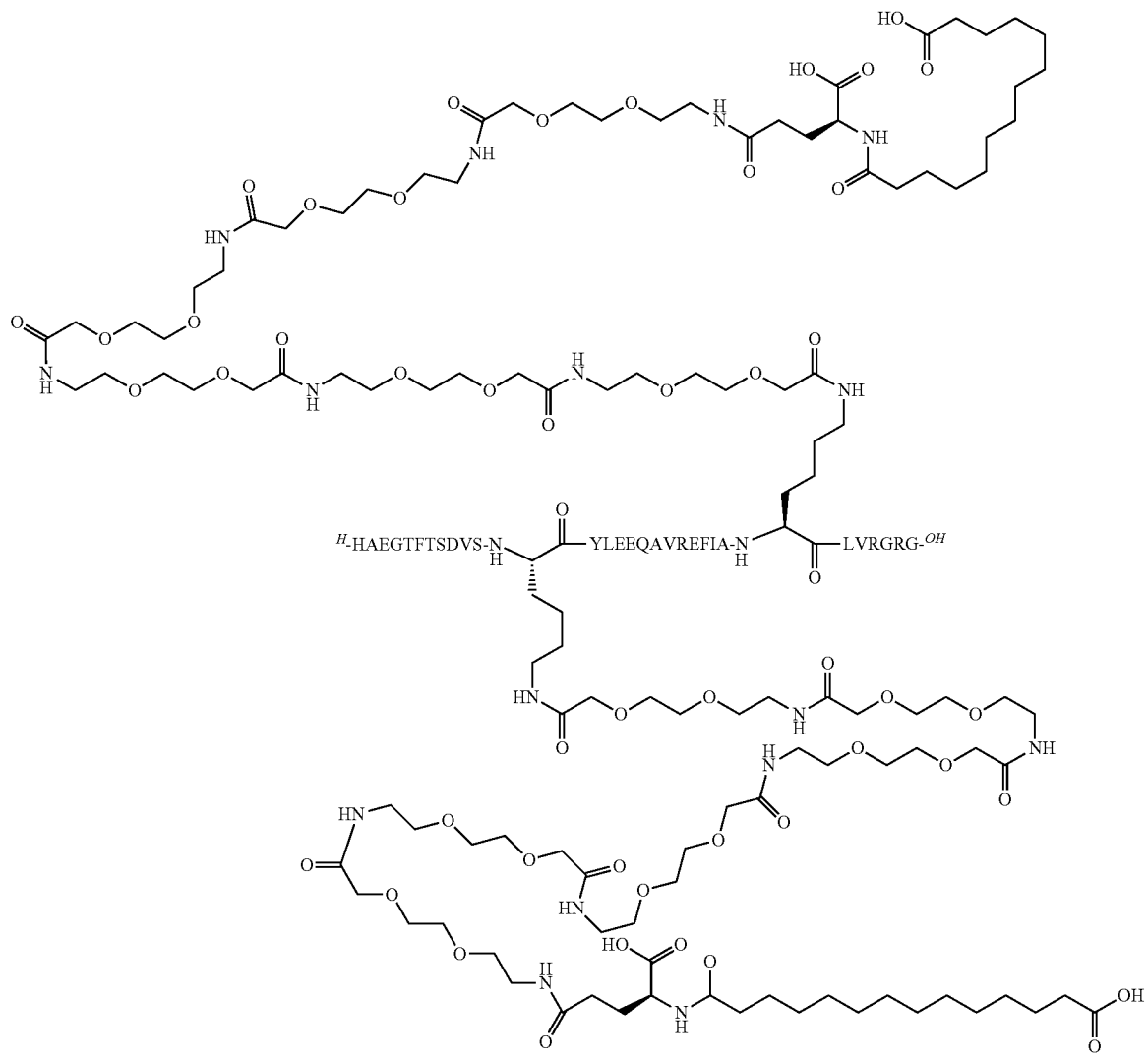
Chem. 174
where the amino acid sequence is that of SEQ ID NO: 12,

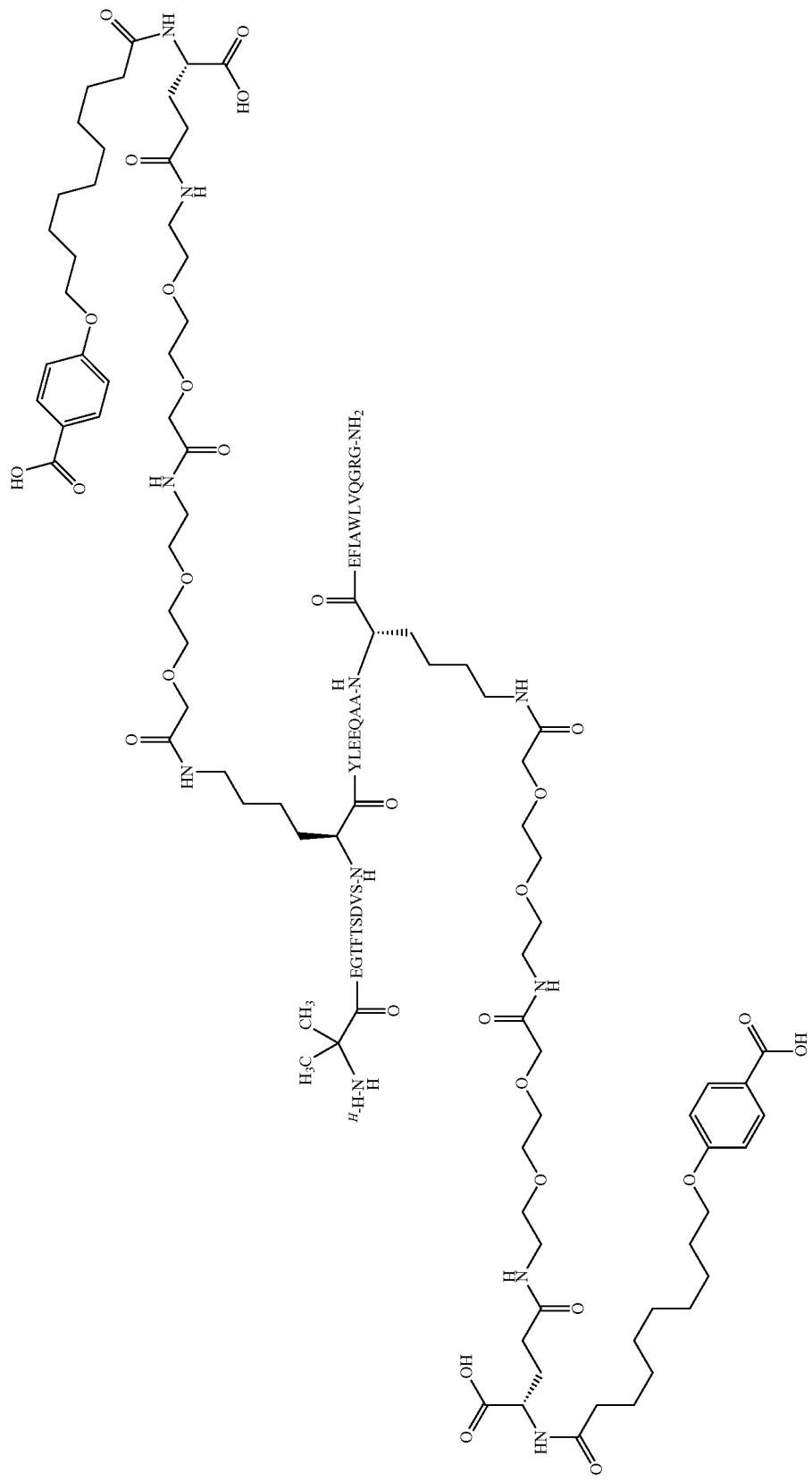

where the amino acid sequence is that of SE NO: 7,
Chem. 176
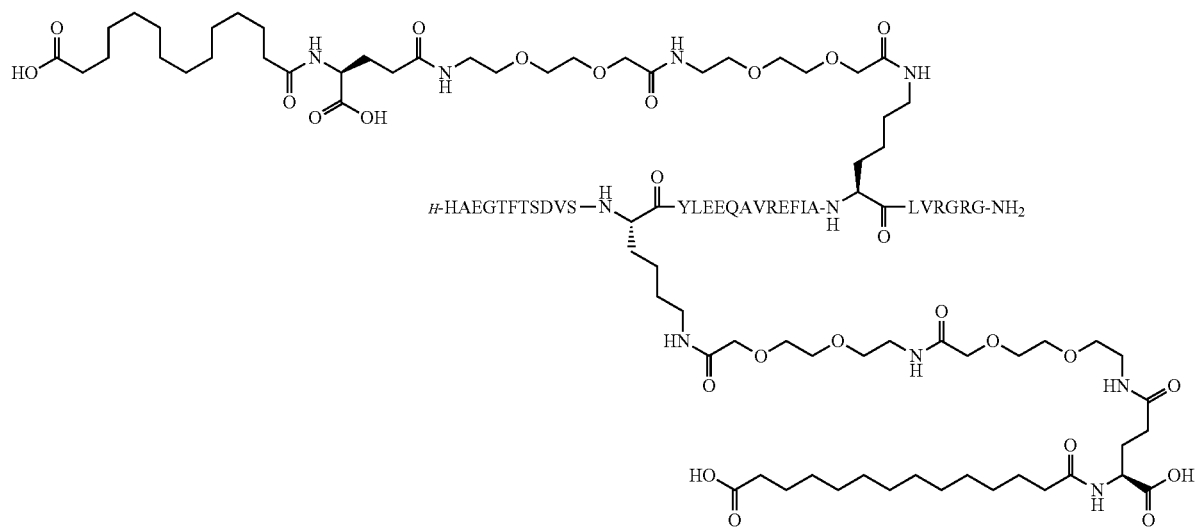
where the amino acid sequence is that of SEQ ID NO: 10,
Chem. 177
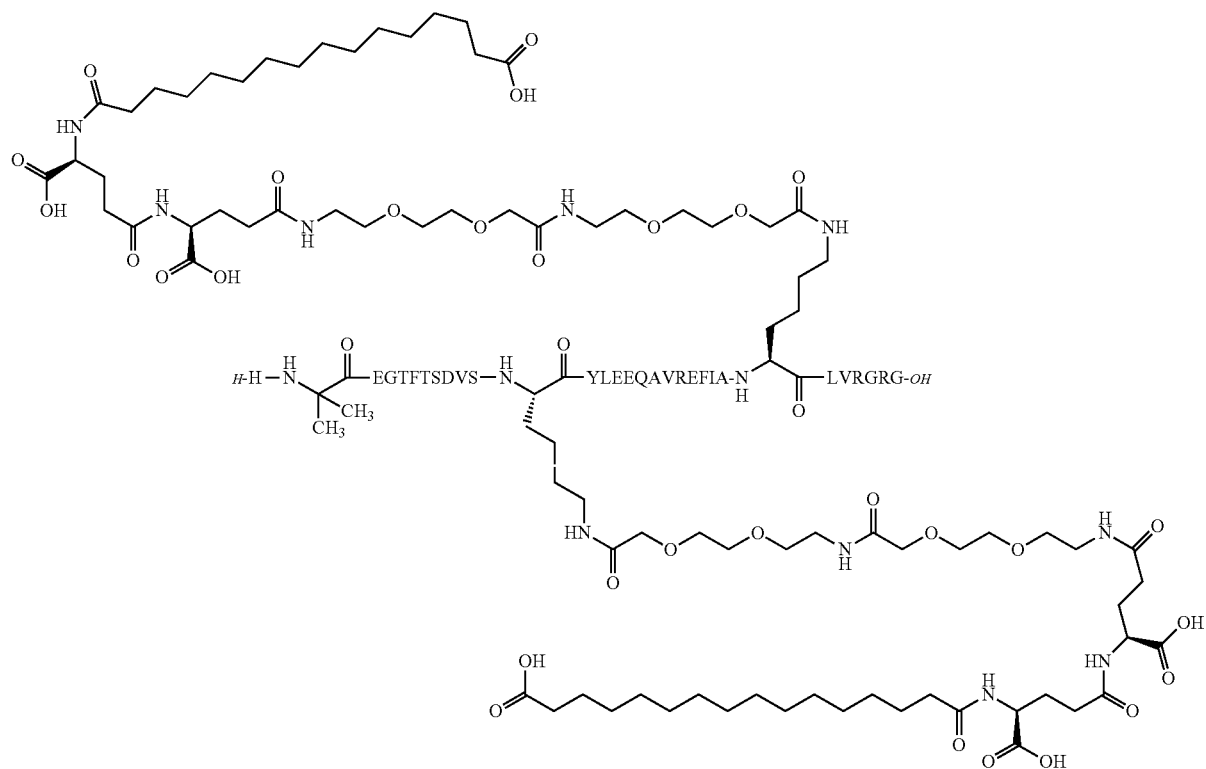
where the amino acid sequence is that of SEQ ID NO: 12, Chem. 178
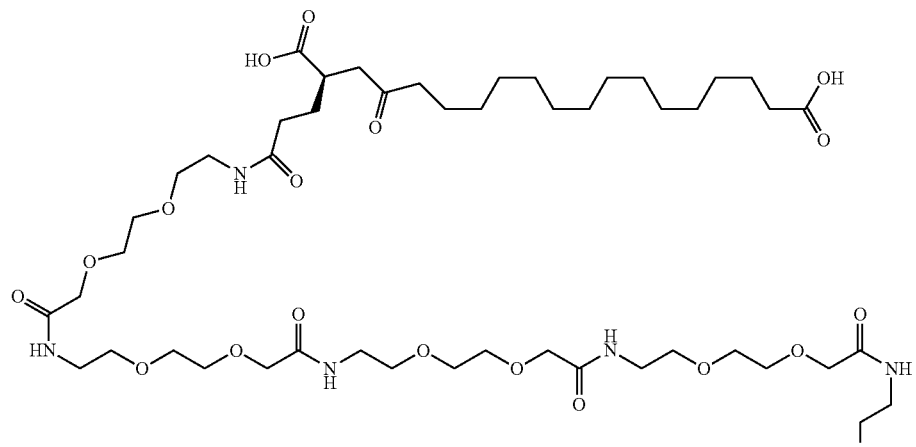
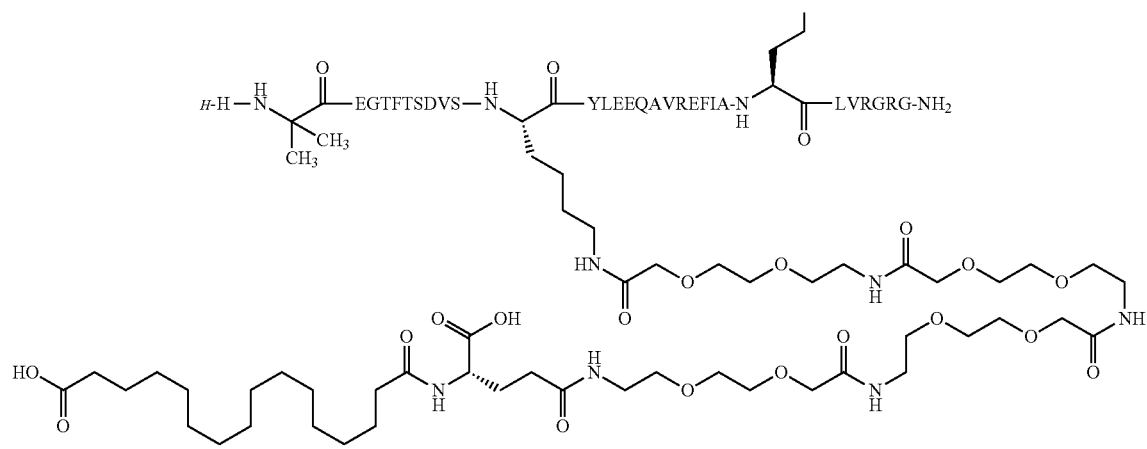
where the amino acid sequence is that of SEQ ID NO: 12,
Chem. 179
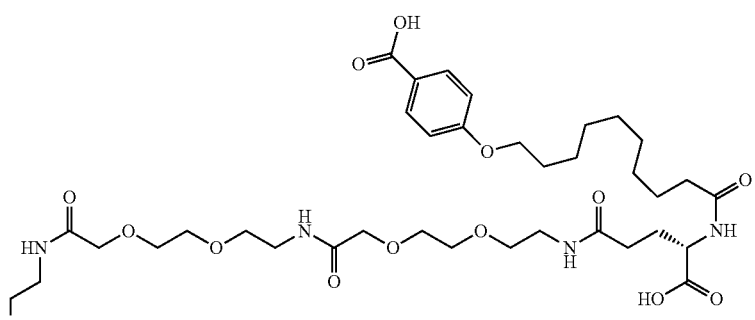

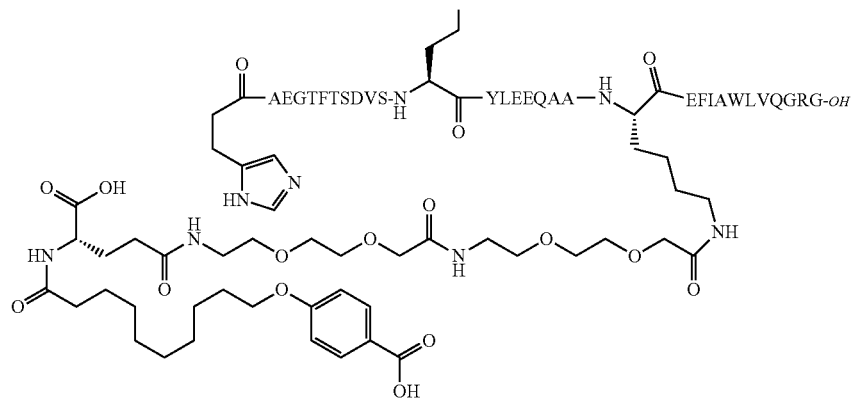
where the amino acid sequence is that of SEQ ID NO: 62,
Chem. 180
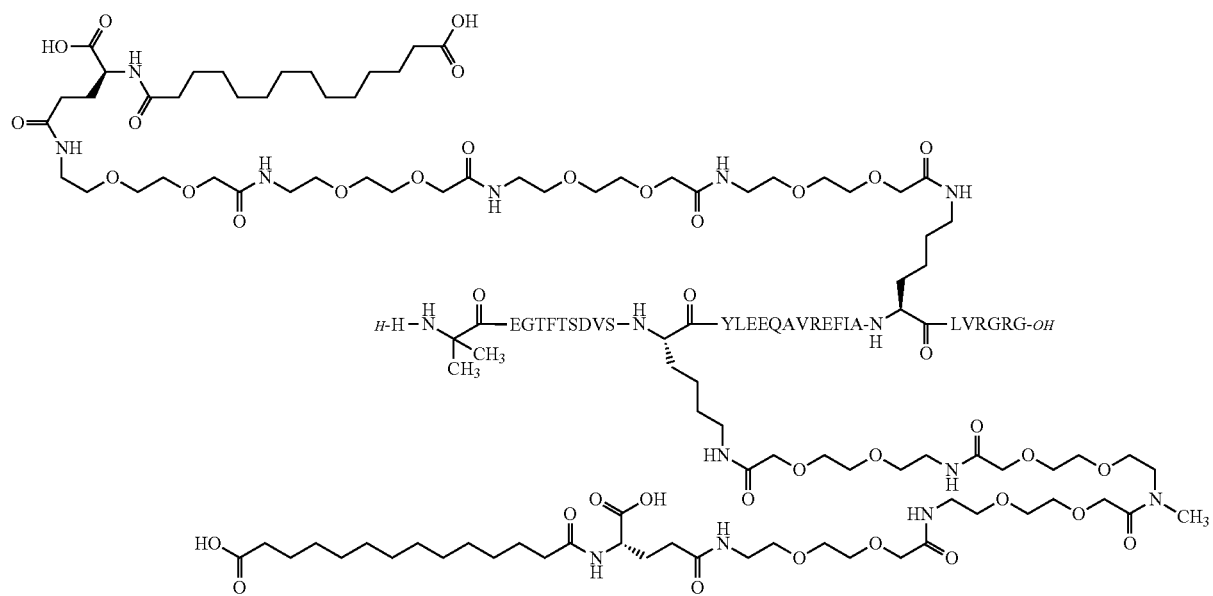
where the amino acid sequence is that of SEQ ID NO: 12, Chem. 181
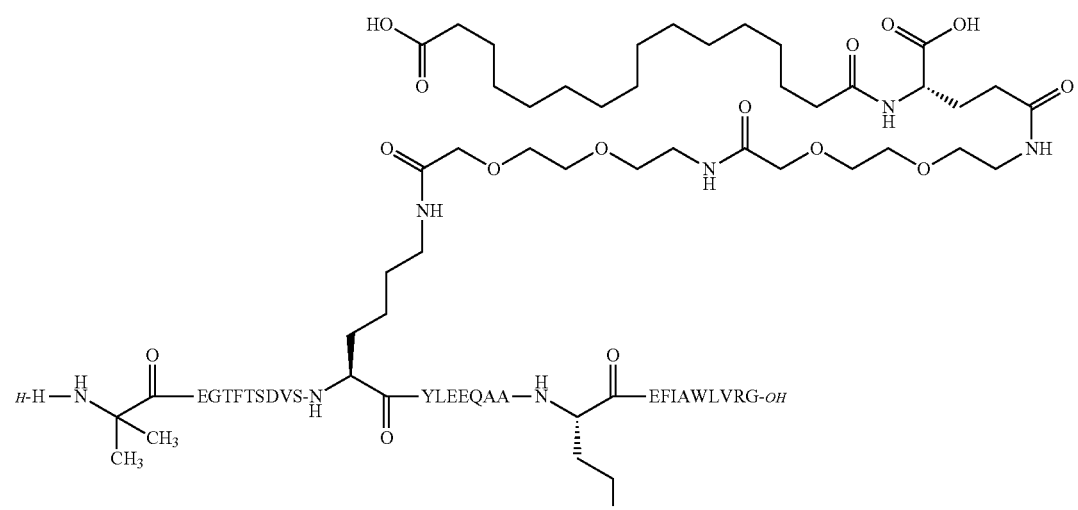
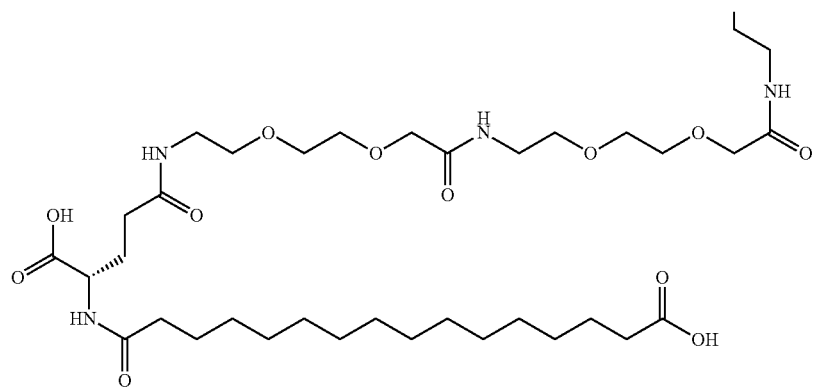
where the amino acid sequence is that of SEQ ID NO: 53,
Chem. 182
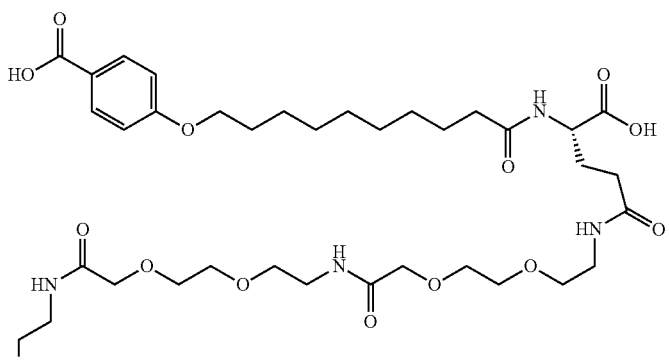

-continued
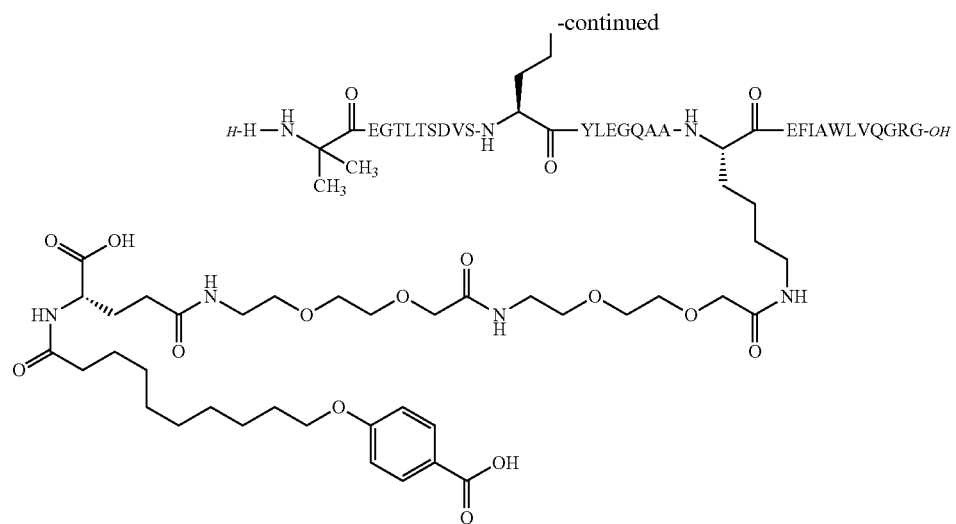
where the amino acid sequence is that of SEQ ID NO: 63,
Chem. 183
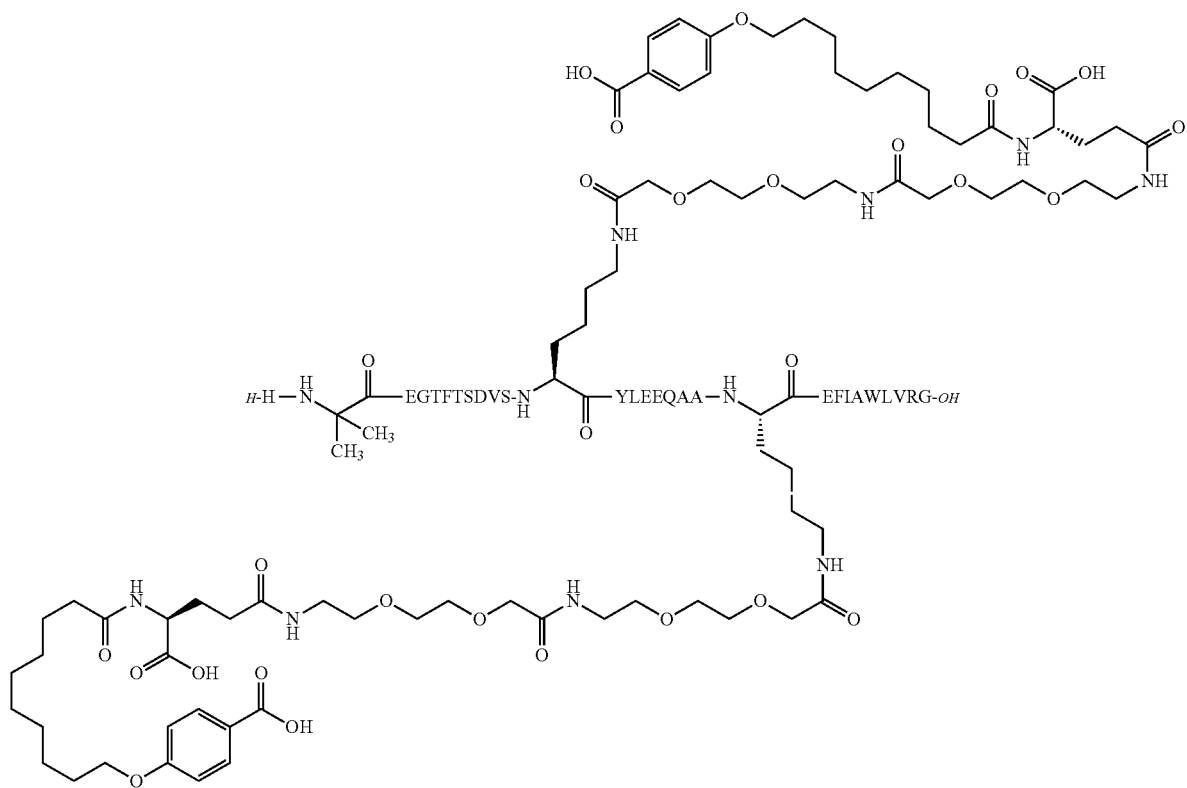
where the amino acid sequence is that of SEQ ID NO: 53, Chem. 189
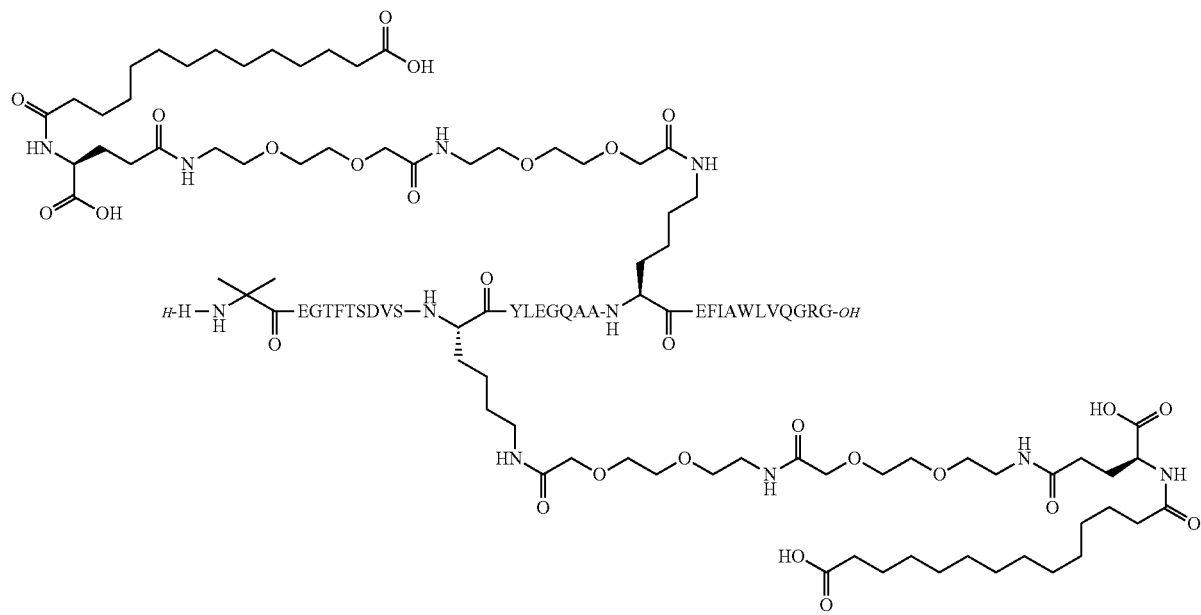
where the amino acid sequence is that of SEQ ID NO: 54,
Chem. 190
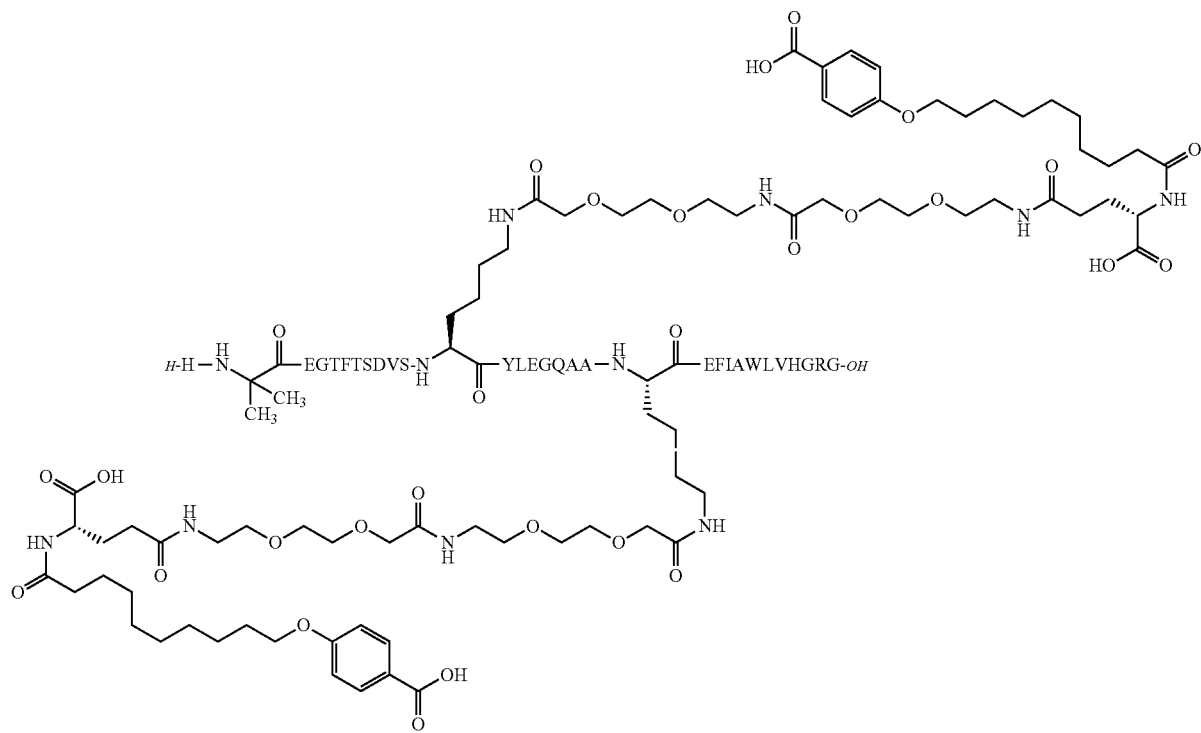
where the amino acid sequence is that of SEQ ID NO: 64,

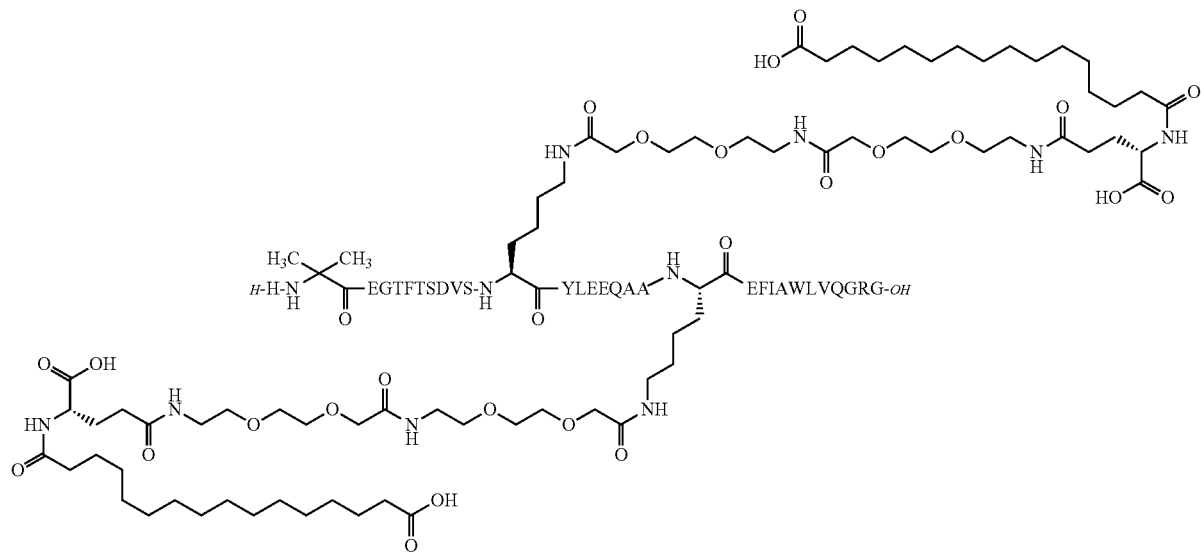
Chem. 191
where the amino acid sequence is that of SEQ ID NO: 7,
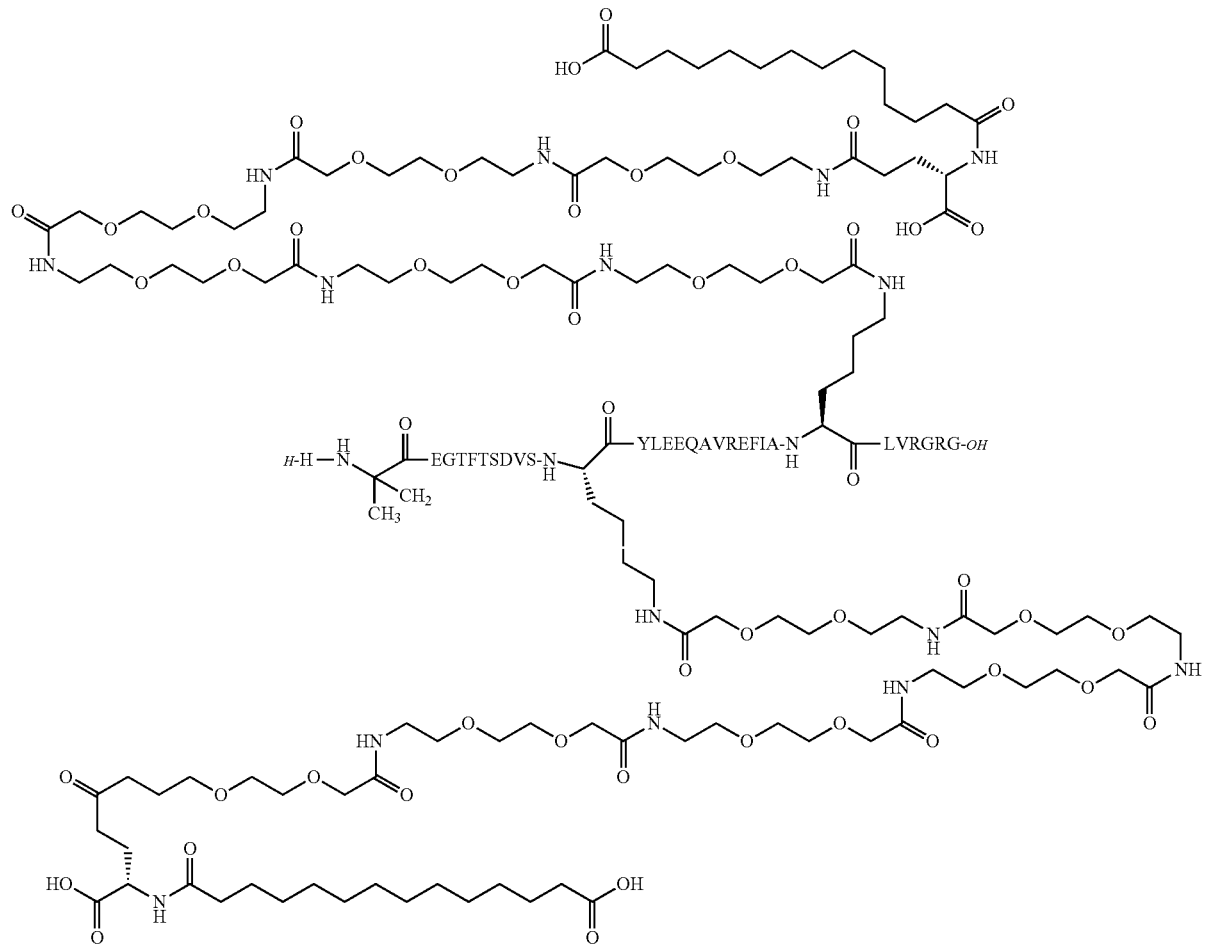
Chem. 192
where the amino acid sequence is that of SEQ ID NO: 12, Chem. 193
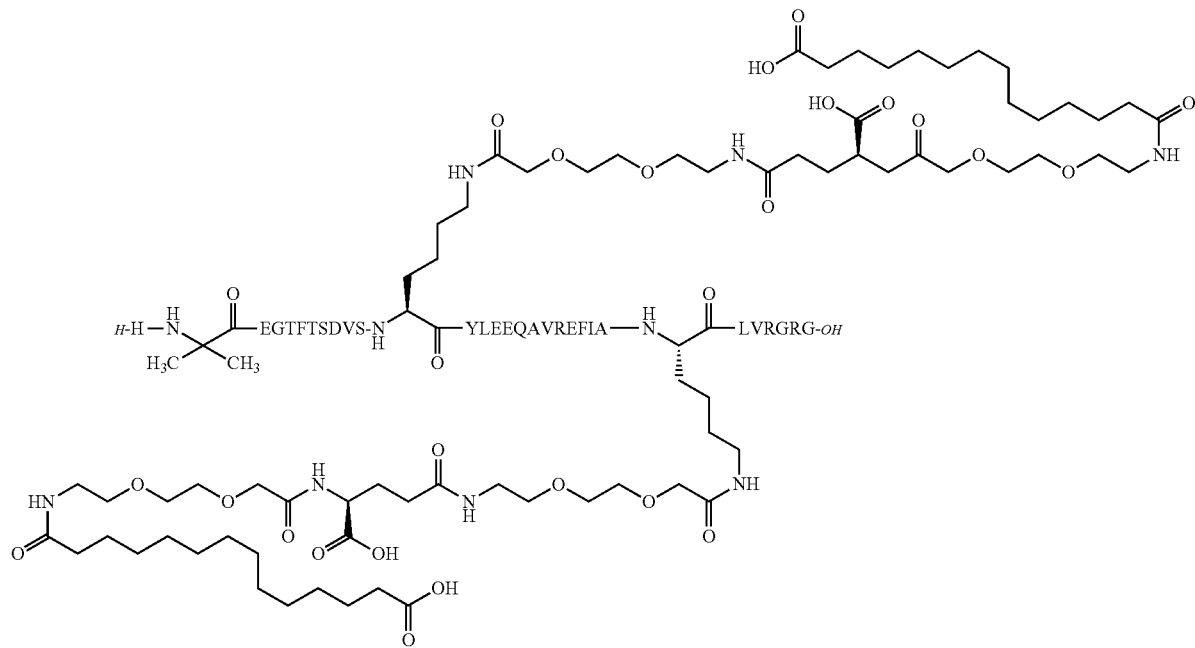
where the amino acid sequence is that of SEQ ID NO: 12,
Chem. 194
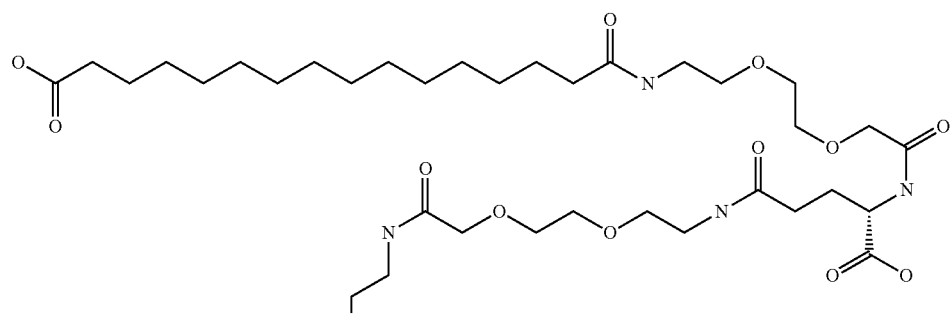

-continued

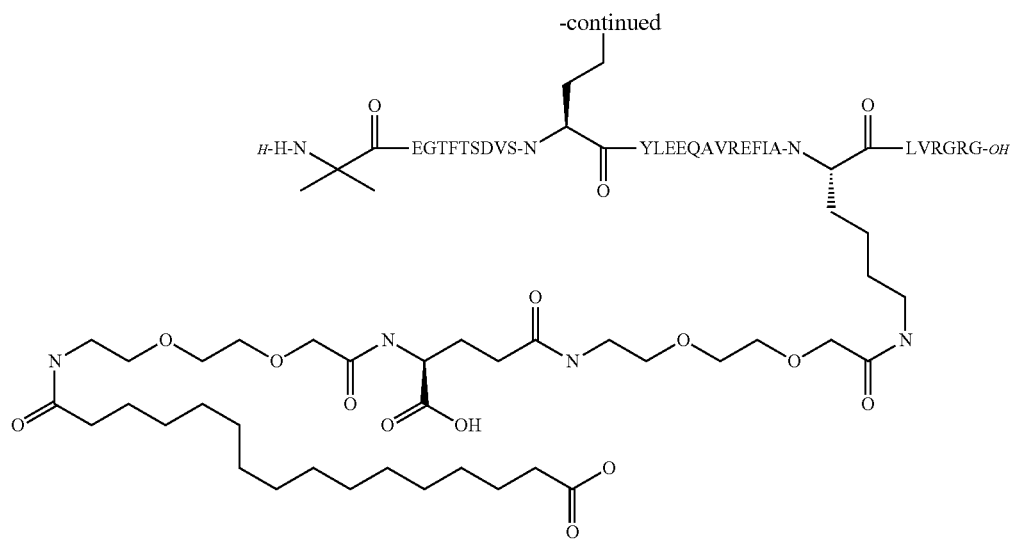

where the amino acid sequence is that of SEQ ID NO: 12, and

Chem. 195

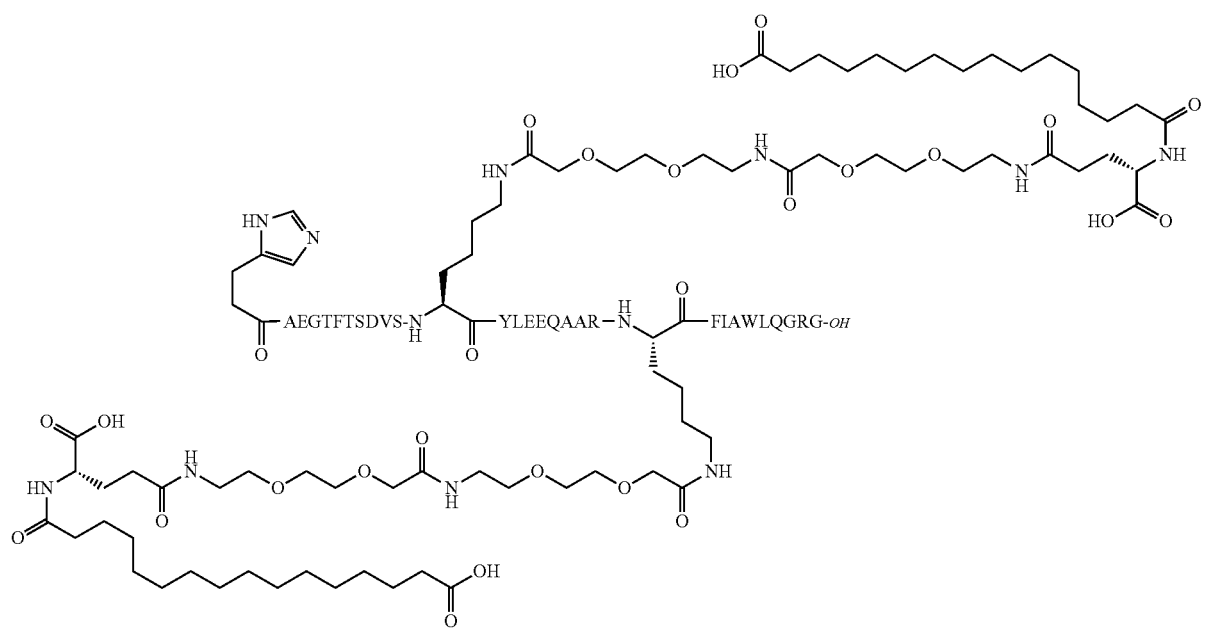

wherein the amino acid sequence is that of SEQ ID NO: 65; or a pharmaceutically acceptable salt, amide, or ester thereof.

10. A method for treating all forms of diabetes, reducing the likelihood of type II diabetes and treating diabetes related conditions, wherein the diabetes related conditions are obesity, cardiovascular diseases, gastrointestinal diseases, and/or polycystic ovary syndrome; and/or for improving lipid parameters, improving β-cell function, and/or for delaying or inhibiting diabetic disease progression—by administering a pharmaceutically active amount of a derivative according to claim 1.

11. The derivative of claim 1, wherein x is 12 or 14.
12. The derivative of claim 1, wherein y is 9.
13. A pharmaceutical composition comprising: a pharmaceutically acceptable carrier and a derivative of claim 1 or a pharmaceutically acceptable salt thereof.
14. A pharmaceutical composition comprising: a pharmaceutically acceptable carrier and a derivative of claim 9 or a pharmaceutically acceptable salt thereof.
15. The derivative of claim 5, wherein Xaa8 is Aib.
16. The derivative of claim 15, wherein Xaa22 is Glu.

* * * * *